(12) United States Patent
Anderskewitz et al.

(10) Patent No.: US 9,713,606 B2
(45) Date of Patent: *Jul. 25, 2017

(54) METHODS FOR TREATING PULMONARY EMPHYSEMA USING SUBSTITUTED 2-AZA-BICYCLO[2.2.1]HEPTANE-3-CARBOXYLIC ACID (BENZYL-CYANO-METHYL)-AMIDES INHIBITORS OF CATHEPSIN C

(71) Applicant: Boehringer Ingelheim International GmbH, Ingelheim am Rhein (DE)

(72) Inventors: Ralf Anderskewitz, Laupheim (DE); Florian Binder, Maselheim (DE); Matthias Grauert, Biberach an der Riss (DE); Marc Grundl, Biberach an der Riss (DE); Peter Wilhelm Haebel, Mittelbiberach (DE); Thorsten Oost, Biberach an der Riss (DE); Alexander Pautsch, Biberach an der Riss (DE); Stefan Peters, Biberach an der Riss (DE); Viktor Vintonyak, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/955,379

(22) Filed: Dec. 1, 2015

(65) Prior Publication Data

US 2016/0081982 A1 Mar. 24, 2016

Related U.S. Application Data

(63) Continuation of application No. 14/574,573, filed on Dec. 18, 2014, now abandoned, which is a (Continued)

(30) Foreign Application Priority Data

Mar. 14, 2013 (EP) .................................. 13159240
May 31, 2013 (EP) .................................. 13170005

(51) Int. Cl.
| | |
|---|---|
| *A61K 31/551* | (2006.01) |
| *A61K 31/5383* | (2006.01) |
| *A61K 31/496* | (2006.01) |
| *A61K 31/438* | (2006.01) |
| *A61K 31/403* | (2006.01) |
| *C07D 209/52* | (2006.01) |
| *A61K 31/4035* | (2006.01) |

(Continued)

(52) U.S. Cl.
CPC .......... *A61K 31/403* (2013.01); *A61K 31/397* (2013.01); *A61K 31/404* (2013.01); *A61K 31/4035* (2013.01); *A61K 31/4045* (2013.01); *A61K 31/416* (2013.01); *A61K 31/4155* (2013.01); *A61K 31/4192* (2013.01); *A61K 31/423* (2013.01); *A61K 31/438* (2013.01); *A61K 31/473* (2013.01); *A61K 31/496* (2013.01); *A61K 31/5383* (2013.01); *A61K 31/551* (2013.01); *A61K 45/06* (2013.01); *C07D 209/52* (2013.01); *C07D 401/10* (2013.01); *C07D 401/12* (2013.01); *C07D 403/12* (2013.01); *C07D 403/14* (2013.01); *C07D 405/12* (2013.01); *C07D 409/12* (2013.01); *C07D 413/14* (2013.01); *C07D 417/12* (2013.01); *C07D 471/08* (2013.01); *C07D 487/10* (2013.01); *C07D 498/04* (2013.01)

(58) Field of Classification Search
CPC .............. A61K 31/551; A61K 31/5383; A61K 31/496; A61K 31/438
USPC .................... 514/210.18, 219, 249, 301, 304
See application file for complete search history.

(56) References Cited

U.S. PATENT DOCUMENTS

| | | | |
|---|---|---|---|
| 4,125,727 | A | 11/1978 | Los |
| 7,012,075 | B2 | 3/2006 | Prasit et al. |

(Continued)

FOREIGN PATENT DOCUMENTS

| | | |
|---|---|---|
| GE | 20012487 | 4/2001 |
| WO | 9105282 A1 | 4/1991 |

(Continued)

OTHER PUBLICATIONS

Abstract in English for WO 2009/047829, publication date Apr. 16, 2009.

(Continued)

*Primary Examiner* — Niloofar Rahmani
(74) *Attorney, Agent, or Firm* — Paula K. Wittmayer; Usha R. Patel

(57) ABSTRACT

This invention relates to 2-Aza-bicyclo[2.2.1]heptane-3-carboxylic acid (benzyl-cyano-methyl)-amides of formula 1

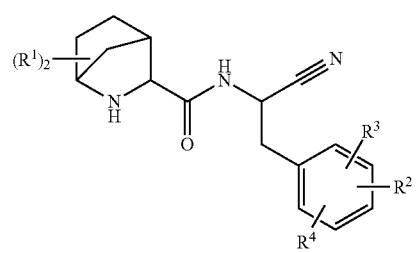

and their use as inhibitors of Cathepsin C, pharmaceutical compositions containing the same, and methods of using the same as agents for treatment and/or prevention of diseases connected with dipeptidyl peptidase I activity, e.g. respiratory diseases.

25 Claims, No Drawings

Related U.S. Application Data continuation of application No. 14/205,861, filed on Mar. 12, 2014, now Pat. No. 8,987,249.

(51) Int. Cl.

| | |
|---|---|
| A61K 31/4045 | (2006.01) |
| A61K 31/4155 | (2006.01) |
| A61K 31/4192 | (2006.01) |
| A61K 45/06 | (2006.01) |
| C07D 401/12 | (2006.01) |
| C07D 403/12 | (2006.01) |
| C07D 403/14 | (2006.01) |
| C07D 405/12 | (2006.01) |
| C07D 487/10 | (2006.01) |
| C07D 498/04 | (2006.01) |
| C07D 471/08 | (2006.01) |
| A61K 31/397 | (2006.01) |
| A61K 31/404 | (2006.01) |
| A61K 31/416 | (2006.01) |
| A61K 31/473 | (2006.01) |
| C07D 401/10 | (2006.01) |
| C07D 409/12 | (2006.01) |
| C07D 413/14 | (2006.01) |
| C07D 417/12 | (2006.01) |
| A61K 31/423 | (2006.01) |

(56) References Cited

U.S. PATENT DOCUMENTS

| | | |
|---|---|---|
| 7,902,181 B2 | 3/2011 | Furber et al. |
| 8,859,774 B2 | 10/2014 | Hunt et al. |
| 8,933,236 B2 | 1/2015 | Chowdhury et al. |
| 8,952,151 B2 | 2/2015 | Chen et al. |
| 8,987,249 B2 | 3/2015 | Anderskewitz et al. |
| 9,006,242 B2 | 4/2015 | Kuntz et al. |
| 9,056,874 B2 | 6/2015 | Adams et al. |
| 9,066,946 B2 | 6/2015 | Vaca et al. |
| 9,145,387 B2 | 9/2015 | Haq et al. |
| 9,156,824 B2 | 10/2015 | Dally et al. |
| 9,180,169 B2 | 11/2015 | Tolborg et al. |
| 9,181,271 B2 | 11/2015 | Li et al. |
| 9,233,974 B2 | 1/2016 | Link et al. |
| 9,242,969 B2 | 1/2016 | Barsani et al. |
| 9,290,476 B2 | 3/2016 | Leonard et al. |
| 9,375,418 B2 | 6/2016 | Schmidt et al. |
| 9,428,452 B2 | 8/2016 | Birault et al. |
| 9,434,719 B2 | 9/2016 | Caferre et al. |
| 9,434,761 B2 | 9/2016 | Mcminn et al. |
| 9,532,992 B2 | 1/2017 | Kuntz et al. |
| 2006/0223846 A1 | 10/2006 | Dyatkin et al. |
| 2013/0172327 A1 | 7/2013 | Grundl et al. |
| 2014/0213554 A1 | 7/2014 | Wu et al. |
| 2016/0001608 A1 | 1/2016 | Abdallah et al. |
| 2016/0060266 A1 | 3/2016 | Kumar et al. |
| 2016/0102094 A1 | 4/2016 | Breslin et al. |
| 2017/0008891 A1 | 1/2017 | Tao et al. |

FOREIGN PATENT DOCUMENTS

| | | |
|---|---|---|
| WO | 0202556 A2 | 1/2002 |
| WO | 02069901 A2 | 9/2002 |
| WO | 03080046 A1 | 10/2003 |
| WO | 2004110988 A1 | 12/2004 |
| WO | 2005042533 A2 | 5/2005 |
| WO | 2009047829 A1 | 4/2009 |
| WO | 2009074829 A1 | 6/2009 |
| WO | 2010128324 A1 | 11/2010 |
| WO | 2010142985 A1 | 12/2010 |
| WO | 2012119941 A1 | 9/2012 |
| WO | 2013041497 A1 | 3/2013 |

OTHER PUBLICATIONS

Adkison, A.M. et al., "Dipeptidyl peptidase I activates neutrophil-derived serine proteases and regulates the development of acute experimental arthritis." The Journal of Clinical Investigation, 2002, vol. 109, No. 3, pp. 363-371.

Akk, A.M. et al., "Dipeptidyl Peptidase I-Dependent Neutrophil Recruitment Modulates the Inflammatory Response to Sendai Virus Infection." The Journal of Immunology, 2008, vol. 180, pp. 3535-3542.

Bondebjerg, J. et al., "Dipeptidyl nitriles as human dipeptidyl peptidase I inhibitors." Bioorganic & Medicinal Chemistry Letters, 2006, vol. 16, No. 13, pp. 3614-3617.

Farberman, M.M. et al., "Airway proteins involved in bacterial clearance susceptible to cathepsin G proteolysis." European Respiratory Journal, 2010, vol. 35, No. 2, pp. 410-417.

Guay, D. et al., "Design and synthesis of dipeptidyl nitriles as potent, selective, and reversible inhibitors of cathespin C." Bioorganic & Medicinal Chemistry Letters, 2009, vol. 19, No. 18, pp. 5392-5396.

Guyot, N. et al., "Deficiency in All Three Neutrophil Serine Proteases Protects Mice Against Cigarette Smoke-Induced Emphysema." American Journal of Respiratory and Critical Care Medicine, 2010, vol. 181, p. A5128.

Henriksen, P.A. et al., "Human neutrophil elastase: Mediator and therapeutic target in atherosclerosis." The International Journal of Biochemistry & Cell Biology, 2008, vol. 40, pp. 1095-1100.

Herias, M. et al., "Abstract 5871: Leukocyte Cathepsin C Deficiency Attenuates Atherosclerosis in LDL Receptor Deficient Mice." Circulation, 2009, vol. 120, p. 1166.

Hu, Y. et al., "Dipeptidyl Peptidase I Regulates the Development of Collagen-Induced Arthritis." Arthritis & Rheumatism, 2005, vol. 52, No. 8, pp. 2553-2558.

International Search Report for PCT/EP2014/054794 mailing date Apr. 2, 2014.

Joosten, L.A. et al., "Inflammatory Arthritis in Caspase 1 Gene-Deficient Mice." Arthritis & Rheumatism, 2009, vol. 60, No. 12, pp. 3651-3662.

Koga, H. et al., "Inhibition of neutrophil elastase attenuates airway hyperresponsiveness and inflammation in a mouse model of secondary allergen challenge: neutrophil elastase inhibition attenuates allergic airway responses." Respiratory Research, 2013, vol. 14, No. 8, pp. 1-13.

Kotlowski, R. et al., "Population-Based Case-Control Study of Alpha 1-Antitrypsin and SLC11A1 in Crohn's Disease and Ulcerative Colitis." Inflammatory Bowel Disease, 2008, vol. 14, No. 8, pp. 1112-1117.

Laprise, C. et al., "Functional classes of bronchial mucosa genes that are differentially expressed in asthma." BMC Genomics, 2004, vol. 5, No. 21, pp. 1-10.

Liu, H. et al., "Neutrophil elastase and elastase-rich cystic fibrosis sputum degranulate human eosinophils in vitro." American Physiological Scoiety, 1999, vol. 276, pp. L28-L34.

Milner, J.M. et al., "Emerging Roles of Serine Proteinases in Tissue Turnover in Arthritis." Arthritis & Rheumatism, 2008, vol. 58, No. 12, pp. 3644-3656.

Morohoshi, Y. et al., "Inhibition of neutrophil elastase prevents the development of murine dextran sulfate sodium-induced colitis." Journal of Gastroenterology, 2006, vol. 41, pp. 318-324.

Motta, Jean-Paul et al., "Modifying the Protease, Antiprotease Pattern by Elafin Overexpression Protects Mice From Colitis." Gastroenterology, 2011, vol. 140, pp. 1272-1282.

Schmid, M. et al., "Attenuated induction of epithelial and leukocyte serine antiproteases elafin and secretory leukocyte protease inhibitor in Crohn's disease." Journal of Leukocyte Biology, 2007, vol. 81, pp. 907-915.

Sedor, J. et al., "Cathepsin-G Interferes with Clearance of Pseudomonas aeruginosa from Mouse Lungs." Pediatric Research, 2007, vol. 61, No. 1, pp. 26-31.

Shapiro, S.D. et al., "Neutrophil Elastase Contributes to Cigarette Smoke-Induced Emphysema in Mice." American Journal of Pathology, 2003, vol. 163, No. 6, pp. 2329-2335.

(56) References Cited

OTHER PUBLICATIONS

Wright, J.L. et al., "Synthetic Serine Elastase Inhibitor Reduces Cigarette Smoke-Induced Emphysema in Guinea Pigs." Ameican Journal of Respiratory and Critical Care Medicine, 2002, vol. 166, pp. 954-960.
Yuyama, N. et al., "Analysis of Novel Disease-Related Genes in Bronchial Asthma." Cytokine, 2002, vol. 19, No. 6, pp. 287-296.
Abstract in English for GE 20012487, publication date Apr. 10, 2001.

METHODS FOR TREATING PULMONARY EMPHYSEMA USING SUBSTITUTED 2-AZA-BICYCLO[2.2.1]HEPTANE-3-CARBOXYLIC ACID (BENZYL-CYANO-METHYL)-AMIDES INHIBITORS OF CATHEPSIN C

FIELD OF INVENTION

This invention relates to substituted 2-Aza-bicyclo[2.2.1]heptane-3-carboxylic acid (benzyl-cyano-methyl)-amides of formula 1

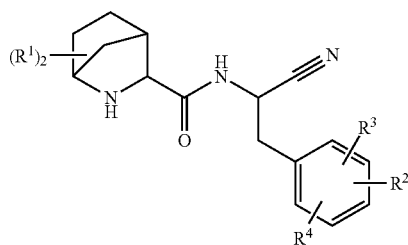

and their use as inhibitors of Cathepsin C, pharmaceutical compositions containing the same, and methods of using the same as agents for treatment and/or prevention of diseases connected with dipeptidyl peptidase I activity, e.g. respiratory diseases.

BACKGROUND INFORMATION

WO2004110988 discloses peptidyl nitrile inhibitors as dipeptidyl-peptidase I (DPPI) inhibitors for the treatment of a series of diseases.

WO2009074829 and WO2010142985 also disclose peptidyl nitrile inhibitors as dipeptidyl-peptidase I (DPPI) inhibitors for the treatment asthma, COPD or allergic rhinitis.

BRIEF SUMMARY OF THE INVENTION

Dipeptidyl-aminopeptidase I (DPPI or Cathepsin C; EC3.4.141), is a lysosomal cysteine protease capable of removing dipeptides from the amino terminus of protein substrates. DPPI was first discovered by Gutman and Fruton in 1948 (J. Biol. Chem 174: 851-858, 1948). The cDNA of the human enzyme has been described in 1995 (Paris et al.; FEBS Lett 369: 326-330, 1995). The DPPI protein is processed into a mature proteolytically active enzyme consisting of a heavy chain, a light chain, and a propeptide that remains associated with the active enzyme (Wolters et al.; J. Biol. Chem. 273: 15514-15520, 1998). Whereas the other cysteine Cathepsins (e.g. B, H, K, L and S) are monomers, DPPI is a 200-kD tetramer with 4 identical subunits, each composed of the 3 different polypeptide chains. DPPI is constitutively expressed in many tissues with highest levels in lung, kidney, liver and spleen (Kominami et al.; Biol. Chem. Hoppe Seyler 373: 367-373, 1992). Consistent with its role in the activation of serine proteases from hematopoetic cells, DPPI is also relatively highly expressed in neutrophils, cytotoxic lymphocytes, natural killer cells, alveolar macrophages and mast cells. Recent data from DPPI deficient mice suggest that, besides being an important enzyme in lysosomal protein degradation, DPPI also functions as the key enzyme in the activation of granule serine proteases in cytotoxic T lymphocytes and natural killer cells (granzymes A and B; Pham et al.; Proc. Nat. Acad. Sci 96: 8627-8632, 1999), mast cells (chymase and tryptase; Wolter et al.; J Biol. Chem. 276: 18551-18556, 2001), and neutrophils (Cathepsin G, elastase and proteinase 3; Adkison et al.; J Clin. Invest. 109: 363.371, 2002). Once activated, these proteases are capable of degrading various extracellular matrix components, which can lead to tissue damage and chronic inflammation.

Thus, inhibitors of Cathepsin C could potentially be useful therapeutics for the treatment of neutrophil-dominated inflammatory diseases such as chronic obstructive pulmonary disease (COPD), pulmonary emphysema, asthma, multiple sclerosis, and cystic fibrosis (Guay et al.; Curr. Topics Med. Chem. 10: 708-716, 2010; Laine and Busch-Petersen; Expert Opin. Ther. Patents 20: 497-506, 2010). Rheumatoid arthritis is also another chronic inflammatory disease where DPPI appears to play a role. Neutrophils are recruited to the site of joint inflammation and release Cathepsin G, elastase and proteinase 3, proteases which are believed to be responsible for cartilage destruction associated with rheumatoid arthritis. Indeed, DPPI deficient mice were protected against acute arthritis induced by passive transfer of monoclonal antibodies against type II collagen (Adkison et al.; J Clin. Invest. 109: 363.371, 2002).

In light of the role DPPI plays in activating certain pro-inflammatory serine proteases, it seems desirable to prepare compounds that inhibit its activity, which thereby inhibit downstream serine protease activity. It has been surprisingly found that the bicyclic compounds of the present invention possess potent Cathepsin C activity, high selectivity against other Cathepsins, e.g. Cathepsin K, and in general desirable pharmacokinetic properties.

DETAILED DESCRIPTION OF THE INVENTION

A compound of formula 1

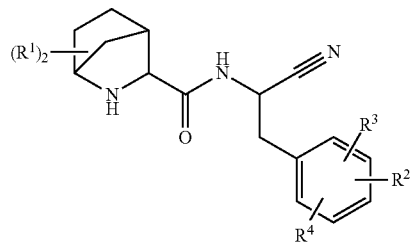

wherein
$R^1$ is independently selected from H, $C_{1-6}$-alkyl-, halogen, HO—, $C_{1-6}$-alkyl-O—, $H_2N$—, $C_{1-6}$-alkyl-HN— and $(C_{1-6}$-alkyl$)_2N$—, $C_{1-6}$-alkyl-C(O)HN—;
or two $R^1$ are together $C_{1-4}$-alkylene;
$R^2$ is selected from
$R^{2.1}$;
aryl-; optionally substituted with one, two or three residues independently selected from $R^{2.1}$; optionally substituted with one $R^{2.3}$;
$C_{5-10}$-heteroaryl-; containing one, two, three or four heteroatoms independently selected from S, S(O), S(O)$_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$; wherein a carbon atom of the ring is optionally substituted with one $R^{2.3}$; a nitrogen atom of the ring is optionally substituted with one $R^{2.4}$; and $C_{5-10}$-heterocyclyl-; containing one, two, three or four heteroatoms independently selected from S, S(O), S(O)$_2$, O and N, wherein the ring is fully or partially saturated, wherein carbon atoms of the ring are optionally and independently from each other substituted with one, two or three or four $R^{2.1}$; wherein nitrogen atoms of the ring are optionally and independently from each other substituted with one, two or three $R^{2.2}$; wherein a carbon atom of the ring is optionally substituted with one $R^{2.3}$ or one $R^{2.5}$; a nitrogen atom of the ring is optionally substituted with one $R^{2.4}$ or $R^2$ and $R^4$ are together with two adjacent carbon atoms of the phenyl ring a 5- or 6-membered aryl or heteroaryl, containing one, two or three heteroatoms independently selected from S, S(O), S(O)$_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$;

$R^{2.1}$ is independently selected from among H, halogen, NC—, O=, HO—, H-A-, H-A-$C_{1-6}$-alkylene-, $C_{1-6}$-alkyl-A-, $C_{1-6}$-haloalkyl-A-, $R^{2.1.1}$—$C_{1-6}$-alkylene-A-, $C_{1-6}$-alkyl-A-$C_{1-6}$-alkylene-, $C_{3-8}$-cycloalkyl-A-$C_{1-6}$-alkylene-, $C_{1-6}$-haloalkyl-A-$C_{1-6}$-alkylene-, $R^{2.1.1}$—$C_{1-6}$-alkylene-A-$C_{1-6}$-alkylene-, $R^{2.1.1}$-A-$C_{1-6}$-alkylene-, HO—$C_{1-6}$-alkylene-A-, HO—$C_{1-6}$-alkylene-A-$C_{1-6}$-alkylene-, $C_{1-6}$-alkyl-O—$C_{1-6}$-alkylene-A- and $C_{1-6}$-alkyl-O—$C_{1-6}$-alkylene-A-$C_{1-6}$-alkylene-;

$R^{2.1.1}$ is independently selected from
  aryl-; optionally substituted independently from each other with one, two or three $R^{2.1.1.1}$;
  $C_{5-10}$-heteroaryl-; containing one, two, three or four heteroatoms independently selected from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;
  $C_{5-10}$-heterocyclyl-; containing one, two, three or four heteroatoms independently selected from S, S(O), S(O)$_2$, O and N, wherein the ring is fully or partially saturated, wherein carbon atoms of the ring are optionally and independently from each other substituted with one, two or three or four $R^{2.1.1.1}$; wherein nitrogen atoms of the ring are optionally and independently from each other substituted with one, two or three $R^{2.1.1.2}$;

$R^{2.1.1.1}$ is independently selected from among halogen, HO—, O=, $C_{1-6}$-alkyl-, $C_{1-6}$-alkyl-O—, $C_{1-6}$-haloalkyl-, $C_{1-6}$-haloalkyl-O— and $C_{3-8}$-cycloalkyl-;

$R^{2.1.1.2}$ is independently selected from among O=, $C_{1-6}$-alkyl-, $C_{1-6}$-haloalkyl-; $C_{3-8}$ cycloalkyl, $C_{1-6}$-alkyl-O—$C_{1-6}$-alkyl-, H(O)C—, $C_{1-6}$-alkyl-(O)C—, tetrahydrofuranylmethyl- and tetrahydropyranylmethyl-;

$R^{2.2}$ is independently selected from among H-A-$C_{1-6}$-alkylene-, $C_{1-6}$-alkyl-A-$C_{1-6}$-alkylene-, $C_{3-8}$-cycloalkyl-A-$C_{1-6}$-alkylene-, $C_{1-6}$-haloalkyl-A-$C_{1-6}$-alkylene-, $R^{2.1.1}$-A-$C_{1-6}$-alkylene-, $C_{1-6}$-alkyl-S(O)$_2$—, $C_{1-6}$-alkyl-C(O)— and $R^{2.1.1}$-A-;

$R^{2.3}$ and $R^4$ are together selected from among —O—, —S—, —N($R^{2.3.1}$)—, —C(O)N($R^{2.3.1}$)—, —N($R^{2.3.1}$)C(O)—, —S(O)$_2$N($R^{2.3.1}$)—, —N($R^{2.3.1}$)S(O)$_2$—, —C(O)O—, —OC(O)—, —C(O)—, —S(O)—, —S(O)$_2$—, $R^{2.3}$, $R^{2.3}$, —C($R^{2.3.2}$)=C($R^{2.3.2}$)—, —C=N—, —N=C—, —C($R^{2.3.2}$)$_2$—O—, —O—C($R^{2.3.2}$)$_2$—, —C($R^{2.3.2}$)$_2$N($R^{2.3.1}$)—, —N($R^{2.3.1}$)C($R^{2.3.2}$)$_2$— and —$C_{1-4}$-alkylene-;

$R^{2.3.1}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and, ($C_{1-4}$-alkyl)$_2$N—$C_{1-4}$-alkylene-;

$R^{2.3.2}$ is independently selected from among H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.4}$ and $R^4$ are together selected from among —N($R^{2.4.1}$)—, —C(O)N($R^{2.4.1}$)—, —N($R^{2.4.1}$)C(O)—, —S(O)$_2$N($R^{2.4.1}$)—, —N($R^{2.4.1}$)S(O)$_2$—, —C(O)—, —S(O)—, —S(O)$_2$—, —C($R^{2.4.2}$)=C($R^{2.4.2}$)—, —C=N—, —N=C—, —C($R^{2.4.2}$)$_2$N($R^{2.4.1}$)—, —N($R^{2.4.1}$)C($R^{2.4.2}$)$_2$— and —$C_{1-4}$-alkylene-; and $R^{2.4.1}$ is independently selected from H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene-, ($C_{1-4}$-alkyl)$_2$N—$C_{1-4}$-alkylene-;

$R^{2.4.2}$ is independently selected from H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.5}$ and $R^4$ are together selected from —C($R^{2.5.1}$)=, =C($R^{2.5.1}$)— and —N=; and $R^{2.5.1}$ is independently selected from H, $C_{1-6}$-alkyl-, $C_{1-6}$-haloalkyl-; $C_{3-8}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^3$ is H or F;

$R^4$ is independently selected from F, Cl, phenyl-H$_2$C—O—, HO—, $C_{1-6}$-alkyl-, $C_{1-6}$-haloalkyl-, $C_{3-8}$-cycloalkyl-, $C_{1-6}$-alkyl-O—, $C_{1-6}$-haloalkyl-O—, $C_{1-6}$-alkyl-HN—, ($C_{1-6}$-alkyl)$_2$-HN—, $C_{1-6}$-alkyl-HN—$C_{1-4}$-alkylene- and ($C_{1-6}$-alkyl)$_2$-HN—$C_{1-4}$-alkylene-;

A is a bond or independently selected
  from —O—, —S—, —N($R^5$)—, —C(O)N($R^5$)—, —N($R^5$)C(O)—, —S(O)$_2$N($R^5$)—, —N($R^5$)S(O)$_2$—, —S(O)(=N$R^5$)—N($R^5$)—, —N($R^5$)(N$R^5$=) S(O)—, —S(=N$R^5$)$_2$—N($R^5$)—, —N($R^5$)(N$R^5$=)$_2$S—, —C($R^5$)=C($R^5$)—, —C≡C—, —C(O)O—, —OC(O)—, —C(O)—, —S(O)—, —S(O)$_2$—, —S(=N$R^5$)—, —S(O)(=N$R^5$)—, —S(=N$R^5$)$_2$—, —($R^5$)(O)S=N—, —($R^5$N=)(O)S— and —N=(O)($R^5$)S—;

$R^5$ is independently selected from H, $C_{1-6}$-alkyl- and NC—; or a salt thereof.

Preferred Embodiments

Preferred are the above compounds of formula 1, wherein $R^1$ is $R^{1.a}$ and $R^{1.a}$ is independently selected from H, $C_{1-4}$-alkyl-, F and HO—.

Preferred are the above compounds of formula 1, wherein $R^1$ is $R^{1.b}$ and $R^{1.b}$ is H.

Preferred are the above compounds of formula 1, wherein $R^1$ is $R^{1.c}$ and two $R^{1.c}$ are together —$CH_2$—.

Preferred are the above compounds of formula 1, wherein $R^2$ is $R^{2.a}$ and $R^{2.a}$ is $R^{2.1}$.

Preferred are the above compounds of formula 1, wherein $R^2$ is $R^{2.b}$ and $R^{2.b}$ is $R^{2.1.a}$.

Preferred are the above compounds of formula 1, wherein $R^2$ is $R^{2.c}$ and $R^{2.c}$ is aryl-; optionally substituted with one, two or three residues independently selected from $R^{2.1}$; optionally substituted with one $R^{2.3}$.

Preferred are the above compounds of formula 1, wherein $R^2$ is $R^{2.d}$ and $R^{2.d}$ is phenyl; optionally substituted with one, two or three residues independently selected from $R^{2.1}$; optionally substituted with one $R^{2.3}$.

Preferred are the above compounds of formula 1, wherein $R^2$ is $R^{2.d}$ and $R^{2.d}$ is phenyl; optionally substituted with one, two or three residues independently selected from $R^{2.1}$ and $R^{2.1}$ is $R^{2.1.a}$ and $R^{2.1.a}$ is selected from H, halogen, NC—, O═, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from
  aryl-, optionally substituted independently from each other with one, two or three residues independently selected from $R^{2.1.1.1}$;
  $C_{5-10}$-heteroaryl-, containing one, two, three or four heteroatoms selected independently from S, S(O), $S(O)_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;
  $C_{5-10}$-heterocyclyl-, containing one, two, three or four heteroatoms selected independently from S, S(O), $S(O)_2$, O and N, and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from halogen, HO—, O═, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from O═, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl.

Preferred are the above compounds of formula 1, wherein $R^2$ is $R^{2.g}$ and $R^{2.g}$ is selected from

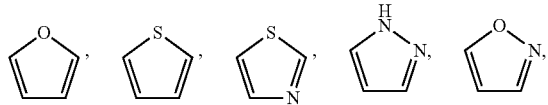

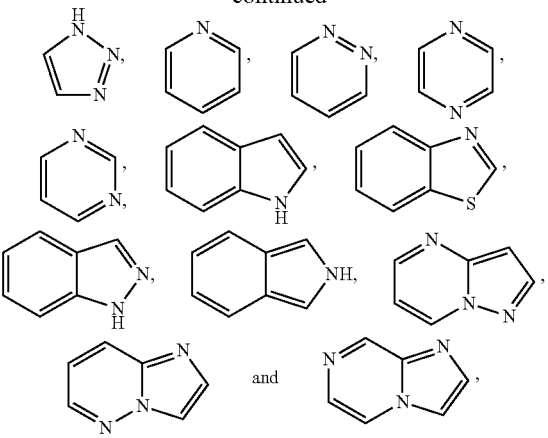

and wherein carbon atoms of the ring are optionally and independently from each other substituted with one, two or three $R^{2.1}$; wherein possibly available nitrogen atoms of the ring are optionally and independently from each other substituted with $R^{2.2}$; and $R^{2.1}$ is $R^{2.1.a}$ and $R^{2.1.a}$ is selected from H, halogen, NC—, O═, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from
  aryl-, optionally substituted independently from each other with one, two or three residues independently selected from $R^{2.1.1.1}$;
  $C_{5-10}$-heteroaryl-, containing one, two, three or four heteroatoms selected independently from S, S(O), $S(O)_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and
  $C_{5-10}$-heterocyclyl-, containing one, two, three or four heteroatoms selected independently from S, S(O), $S(O)_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from halogen, HO—, O═, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from O═, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $R^{2.1.1}$-A-, $C_{1-4}$-alkyl-$S(O)_2$— and $C_{1-4}$-alkyl-C(O)—, $R^{2.1.1}$-A-.

Preferred are the above compounds of formula 1, wherein $R^2$ is $R^{2.e}$ and $R^{2.e}$ is $C_{5\,or\,6}$-heteroaryl-, containing one, two, three or four heteroatoms independently selected from S, S(O), S(O)$_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$; wherein a carbon atom of the ring is optionally substituted with one $R^{2.3}$; a nitrogen atom of the ring is optionally substituted with one $R^{2.4}$.

Preferred are the above compounds of formula 1, wherein $R^2$ is $R^{2.f}$ and $R^{2.f}$ is bicyclic $C_{7-10}$-heteroaryl-, each containing one, two, three or four heteroatoms independently selected from S, S(O), S(O)$_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$; wherein a carbon atom of the ring is optionally substituted with one $R^{2.3}$; a nitrogen atom of the ring is optionally substituted with one $R^{2.4}$.

Preferred are the above compounds of formula 1, wherein $R^2$ is $R^{2.g}$ and $R^{2.g}$ is selected from

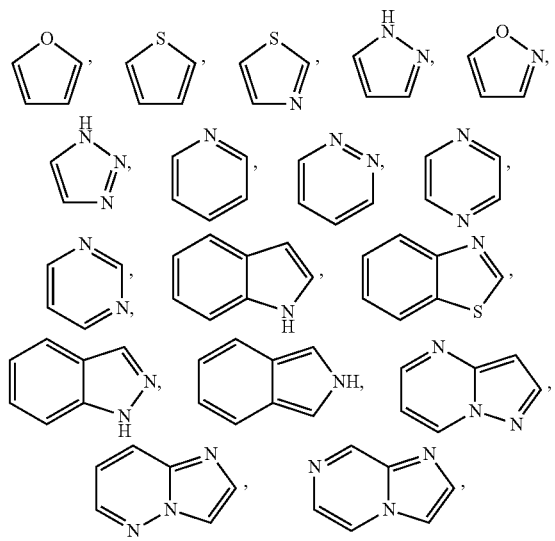

wherein carbon atoms of the ring are optionally and independently from each other substituted with one, two or three $R^{2.1}$; wherein possibly available nitrogen atoms of the ring are optionally and independently from each other substituted with $R^{2.2}$; wherein a carbon atom of the ring is optionally substituted with one $R^{2.3}$; a nitrogen atom of the ring is optionally substituted with one $R^{2.4}$.

Preferred are the above compounds of formula 1, wherein $R^2$ is $R^{2.h}$ and $R^{2.h}$ is selected from pyrazole, thiophene and furane, wherein carbon atoms of the ring are optionally and independently substituted with one, two or three $R^{2.1}$; wherein possibly available nitrogen atoms of the ring are optionally and independently from each other substituted with $R^{2.2}$; wherein a carbon atom of the ring is optionally substituted with one $R^{2.3}$; a nitrogen atom of the ring is optionally substituted with one $R^{2.4}$.

Preferred are the above compounds of formula 1, wherein $R^2$ is $R^{2.i}$ and $R^{2.i}$ is selected from $C_6$-heterocyclyl- and $C_{7-10}$-heterocyclyl-, each containing one, two, three or four heteroatoms independently selected from S, O and N and the ring is fully or partially saturated, wherein carbon atoms of the ring are optionally and independently from each other substituted with one, two or three $R^{2.1}$; wherein nitrogen atoms of the ring are optionally and independently from each other substituted with one, two or three $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2.j}$ and $R^{2.j}$ is selected from

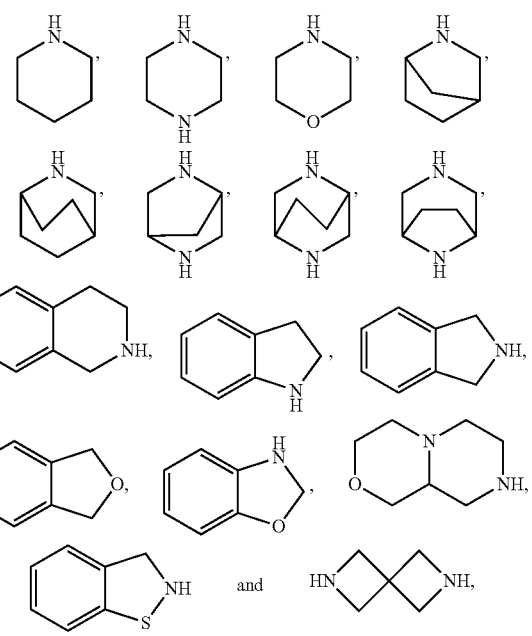

wherein carbon atoms of the ring are optionally and independently from each other substituted with one, two or three $R^{2.1}$; wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2.j}$ and $R^{2.j}$ is selected from

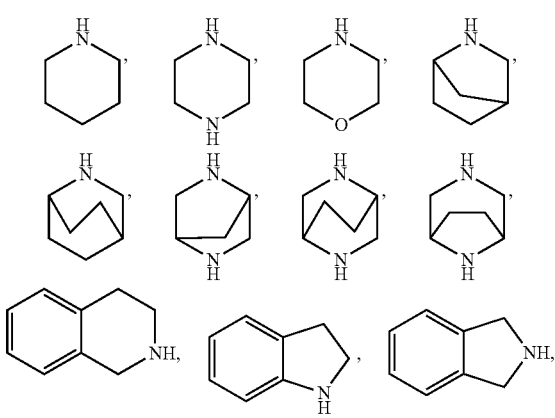

-continued

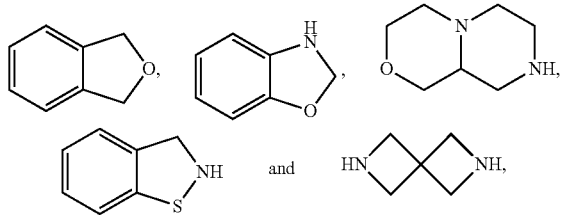

wherein carbon atoms of the ring are optionally and independently from each other substituted with one, two or three $R^{2.1}$; wherein possibly available nitrogen atoms of the ring are optionally and independently from each other substituted with $R^{2.2}$; and $R^{2.1}$ is $R^{2.1.a}$ and $R^{2.1.a}$ is selected from H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from
  aryl-, optionally substituted independently from each other with one, two or three residues independently selected from $R^{2.1.1.1}$;
  $C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and
  $C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$ alkylene-, $C_{1-4}$-alkyl-S(O)$_2$— and $C_{1-4}$-alkyl-C(O)—, $R^{2.1.1}$-A-.

Preferred are the above compounds of formula 1, wherein $R^2$ is $R^{2.k}$ and $R^{2.k}$ is selected from

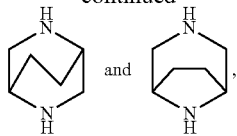

-continued

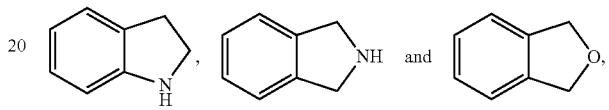

wherein carbon atoms of the ring are optionally and independently from each other substituted with one, two or three $R^{2.1}$; wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2.1}$ and $R^{2.1}$ is selected from

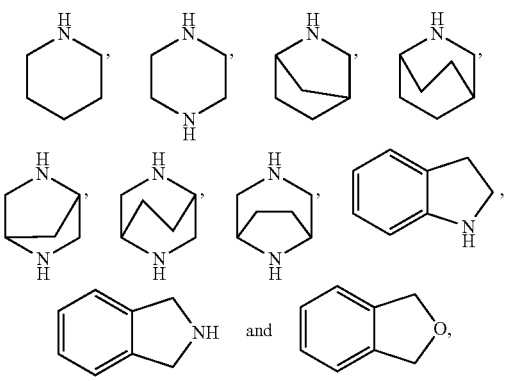

wherein carbon atoms of the ring are optionally and independently from each other substituted with one, two, three or four $R^{2.1}$; wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2.m}$ and $R^{2.m}$ is together with $R^4$ and two adjacent carbon atoms of the phenyl ring a 5- or 6-membered aryl or heteroaryl, containing one, two or three heteroatoms independently selected from S, S(O), S(O)$_2$, O and N, preferably pyrazole, naphthene, wherein carbon atoms of the ring are optionally and independently from each other substituted with one, two or three $R^{2.1}$, wherein possibly available nitrogen atoms of the ring are optionally and independently from each other substituted with one, two or three $R^{2.2}$.

Preferred are the above compounds of formula 1, wherein $R^2$ is $R^{2.n}$ and $R^{2.n}$ is selected from aryl-, pyrazole, thiophene and furane; wherein carbon atoms of the ring are optionally and independently from each other substituted with one, two, three or four $R^{2.1}$; wherein possibly available nitrogen atoms of the ring are optionally and independently from each other substituted with $R^{2.2}$; wherein a carbon atom of the ring is optionally substituted with one $R^{2.3}$; a nitrogen atom of the ring is optionally substituted with one $R^{2.4}$; or $R^{2.n}$ is selected from wherein carbon atoms of the ring are optionally and independently from each other substituted with one, two, three or four $R^{2.1}$; wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^{2,p}$ is $R^{2,p}$ and $R^{2,p}$ is selected from aryl-, pyrazole, thiophene and furane; wherein carbon atoms of the ring are optionally and independently from each other substituted with one, two, three or four $R^{2.1}$; wherein possibly available nitrogen atoms of the ring are optionally and independently from each other substituted with $R^{2.2}$; wherein a carbon atom of the ring is optionally substituted with one $R^{2.3}$; a nitrogen atom of the ring is optionally substituted with one $R^{2.4}$.

Preferred are the above compounds of formula 1, wherein $R^2$ is $R^{2,p}$ and $R^{2,p}$ is selected from wherein carbon atoms of the ring are optionally and independently from each other substituted with one, two, three or four $R^{2.1}$; wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$.

Preferred are the above compounds of formula 1, wherein $R^2$ is $R^{2,q}$ and $R^{2,q}$ is selected from among the substituents (a1) to (q1)

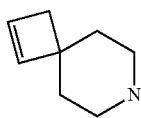

(q1)

wherein carbon atoms of the ring are optionally and independently from each other substituted with one, two, three or four $R^{2.1}$; wherein possibly available nitrogen atoms of the ring are optionally and independently from each other are substituted with $R^{2.2}$;

Particularly preferred $R^{2-q}$ is substituent (a1) or (c1), wherein carbon atoms of the ring are optionally and independently from each other substituted with one, two, three or four $R^{2.1}$; wherein possibly available nitrogen atoms of the ring are optionally and independently from each other are substituted with $R^{2.2}$.

Particularly preferred $R^{2-q}$ denotes a substituent selected from the group (a1) to (q1), wherein carbon atoms of the ring are optionally and independently from each other substituted with a group selected from among =O, Me, MeSO$_2$—, Me-piperazinyl-SO$_2$—, morpholinyl, —CN and F, and possibly available nitrogen atoms of the ring are optionally and independently from each other substituted with Me$_2$N—CH$_2$—CH$_2$—, F$_2$CH—CH$_2$—, —CH$_3$ and tetrahydrofuranyl.

Preferred are the above compounds of formula 1, wherein $R^2$ is $R^{2.s}$ and $R^{2.s}$ is Phenyl-$R^{2.3}$, wherein the phenyl ring is optionally substituted with one or two residues $R^{2.1}$, wherein $R^{2.1}$ is $R^{2.1.a}$ and $R^{2.1.a}$ is selected from H, halogen, NC—, O=, HO—, H-A-, H-A-C$_{1-4}$-alkylene-, $R^{2.1.1}$-A, C$_{1-4}$-alkyl-A-, C$_{3-6}$-cycloalkyl-A-, C$_{1-4}$-haloalkyl-A-, $R^{2.1.1}$—C$_{1-4}$-alkylene-A-, C$_{1-4}$-alkyl-A-C$_{1-4}$-alkylene-, C$_{3-6}$-cycloalkyl-A-C$_{1-4}$-alkylene-, C$_{1-4}$-haloalkyl-A-C$_{1-4}$-alkylene-, $R^{2.1.1}$—C$_{1-4}$-alkylene-A-C$_{1-4}$-alkylene-, $R^{2.1.1}$-A-C$_{1-4}$-alkylene-, HO—C$_{1-4}$-alkylene-A-, HO—C$_{1-4}$-alkylene-A-C$_{1-4}$-alkylene-, C$_{1-4}$-alkyl-O—C$_{1-4}$-alkylene-A- and C$_{1-4}$-alkyl-O—C$_{1-4}$-alkylene-A-C$_{1-4}$-alkylene-; and $R^{2.1.1}$ is $R^{2.1.1.a}$ and $R^{2.1.1.a}$ is selected from aryl-, optionally substituted independently from each other with one, two or three residues independently selected from $R^{2.1.1.1}$;

C$_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;

C$_{5-10}$-heterocyclyl-, containing one, two, three or four heteroatoms selected independently from S, S(O), S(O)$_2$, O and N, and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from halogen, HO—, O=, C$_{1-4}$-alkyl-, C$_{1-4}$-alkyl-O—, C$_{1-4}$-haloalkyl-, C$_{1-4}$-haloalkyl-O— and C$_{3-6}$-cycloalkyl-; and $R^{2.1.1.2}$ is independently selected from O=, C$_{1-4}$-alkyl-, C$_{1-4}$-haloalkyl-; C$_{3-6}$-cycloalkyl-, C$_{1-4}$-alkyl-O—C$_{1-4}$-alkyl-, H(O)C—, C$_{1-4}$-alkyl-(O)C—, tetrahydrofuranylmethyl- and tetrahydropyranylmethyl.

and $R^{2.s}$ and $R^4$ together denote a group (r1),

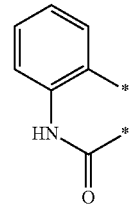

(r1)

wherein the N-atom is optionally substituted with —$R^{2.2}$, wherein $R^{2.2}$ is independently selected from H-A-C$_{1-6}$-alkylene-, C$_{3-8}$-cycloalkyl-, C$_{1-6}$-alkyl-A-C$_{1-6}$-alkylene-, C$_{3-8}$-cycloalkyl-A-C$_{1-6}$-alkylene-, C$_{1-6}$-haloalkyl-A-C$_{1-6}$-alkylene-, $R^{2.1.1}$-A-C$_{1-6}$-alkylene-, C$_{1-6}$-alkyl-S(O)$_2$, C$_{1-6}$-alkyl-C(O)— and $R^{2.1.1}$-A-.

Particularly preferred are the above compounds of formula 1, wherein $R^2$ is $R^{2.s}$ and $R^{2.s}$ is Phenyl-$R^{2.3}$, wherein the phenyl ring is optionally substituted with one or two residues independently selected from F and —CN, and $R^{2.s}$ and $R^4$ together denote a group (r1), wherein the N-atom is optionally substituted with —CH$_3$,

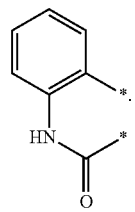

(r1)

Particularly preferred are the above compounds of formula 1, wherein $R^1$ is H, $R^3$ is H or F, preferably F, and $R^2$ is $R^{2.s}$ and $R^{2.s}$ is Phenyl-$R^{2.3}$, wherein the phenyl ring is optionally substituted with one or two residues independently selected from F and —CN, and $R^{2.s}$ and $R^4$ together denote a group (r1), wherein the N-atom is optionally substituted with —CH$_3$;

Particularly preferred are the above compounds of formula 1, wherein $R^{2.s}$ and $R^4$ together denote a group (r1), optionally substituted as described above, in meta and para position of the phenyl ring.

Preferred are the above compounds of formula 1, wherein $R^2$ is $R^{2.r}$ and $R^{2.r}$ is selected from among the substituents (a2) to (w2) or $R^2$ together with $R^4$ denotes a group selected from among (a3) to (e3).

(u2)
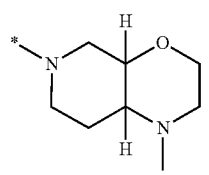

(v2)
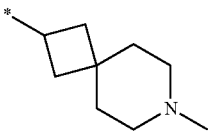

(w2)
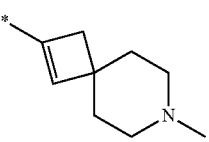

(a3)
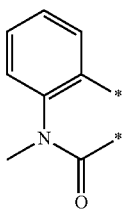

(b3)
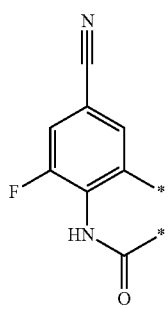

(c3)
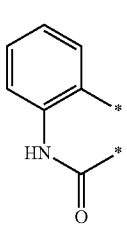

(d3)
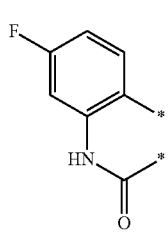

(e3)
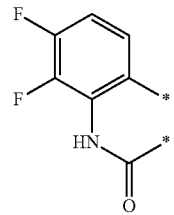

Particularly preferred $R^{2.r}$ is substituent (a2) or (c2).

Particularly preferred $R^2$ is substituted Phenyl-$R^{2.3}$ wherein $R^2$ together with $R^4$ denotes a group selected from among (a3), (b3), (c3), (d3) and (e3).

Preferred are the above compounds of formula 1, wherein $R^{2.1}$ is $R^{2.1.a}$ and $R^{2.1.a}$ is selected from H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-.

Preferred are the above compounds of formula 1, wherein $R^{2.1.1}$ is $R^{2.1.1.a}$ and $R^{2.1.1.a}$ is selected from aryl-, optionally substituted independently from each other with one, two or three residues independently selected from $R^{2.1.1.1}$;

$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$ and $C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other are substituted with one, two or three $R^{2.1.1.2}$; and $R^{2.1.1.1}$ is independently selected from halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl.

Preferred are the above compounds of formula 1, wherein $R^{2.1.1}$ is $R^{2.1.1.b}$ and $R^{2.1.1.b}$ is phenyl or selected from

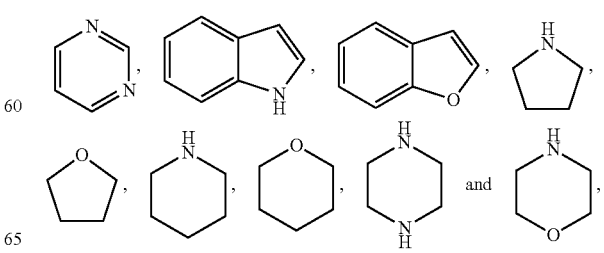

wherein carbon atoms of the ring are optionally and independently from each other substituted with one, two or three $R^{2.1.1.1}$ wherein possibly available nitrogen atoms of the ring are optionally and independently from each other substituted with $R^{2.1.1.2}$; and $R^{2.1.1.1}$ is independently selected from halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranyl-methyl- and tetrahydropyranylmethyl.

Preferred are the above compounds of formula 1, wherein $R^{2.1.1}$ is $R^{2.1.1.c}$ and $R^{2.1.1.c}$ is phenyl or selected from

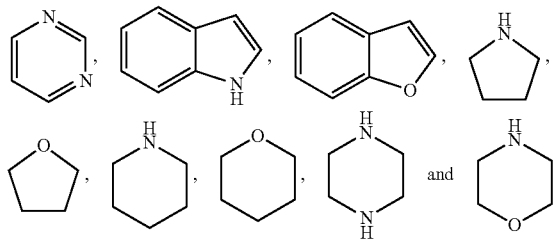

wherein carbon atoms of the ring are optionally and independently from each other substituted with one, two or three $R^{2.1.1.1}$, wherein possibly available nitrogen atoms of the ring are optionally and independently from each other substituted with $R^{2.1.1.2}$; and $R^{2.1.1.1}$ is independently selected from F, Cl, Me, MeO— and cyclopropyl-; and $R^{2.1.1.2}$ is independently selected from Me, tetrahydrofuranylmethyl- and tetrahydropyranylmethyl.

Preferred are the above compounds of formula 1, wherein $R^{2.1.2}$ is $R^{2.1.2.a}$ and $R^{2.1.2.a}$ is selected from H, NC—, $C_{1-4}$-alkyl-, $C_{1-4}$-haloalkyl-, $C_{3-6}$-cycloalkyl-, HO—$C_{1-4}$-alkylene- and ($C_{1-4}$-alkyl)-O—$C_{1-4}$-alkylene-.

Preferred are the above compounds of formula 1, wherein $R^{2.1.2}$ is $R^{2.1.2.b}$ and $R^{2.1.2.b}$ is selected from H, and $C_{1-4}$-alkyl-, and $C_{3-6}$-cycloalkyl-;

Preferred are the above compounds of formula 1, wherein $R^{2.2}$ is $R^{2.2.a}$ and $R^{2.2.a}$ is independently selected from H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$— and $C_{1-4}$-alkyl-C(O)—, $R^{2.1.1}$-A-;

Preferred are the above compounds of formula 1, wherein $R^{2.2}$ is $R^{2.2.b}$ and $R^{2.2.b}$ is together with $R^4$ selected from —C(O)—, —S(O)—, —S(O)$_2$—, —C($R^{2.1.1}$)=C($R^{2.1.2}$) and —$C_{1-4}$-alkylene-;

Preferred are the above compounds of formula 1, wherein $R^{2.3}$ is together with $R^4$ a group $R^{2.3.a}$ and $R^{2.3.a}$ is selected
from —O—, —S—, —N($R^{2.3.1}$)—, —C(O)N($R^{2.3.1}$)—, —N($R^{2.3.1}$)C(O)—, —S(O)$_2$N($R^{2.3.1}$)—, —N($R^{2.3.1}$)S(O)$_2$—, —C(O)O—, —OC(O)—, —C(O)—, —S(O)—, —S(O)$_2$—, —C($R^{2.3.2}$)=C($R^{2.3.2}$)—, —C($R^{2.3.2}$)$_2$—O—, —O—C($R^{2.3.2}$)$_2$—, —C($R^{2.3.2}$)$_2$N($R^{2.3.1}$)—, —N($R^{2.3.1}$)C($R^{2.3.2}$)$_2$— and —$C_{1-4}$-alkylene-; and $R^{2.3.1}$ is independently selected from H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.3.2}$ is independently selected from H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-.

Preferred are the above compounds of formula 1, wherein $R^{2.4}$ is together with $R^4$ a group $R^{2.4.a}$ and
$R^{2.4.a}$ is selected
from —N($R^{2.4.1}$)—, —C(O)N($R^{2.4.1}$)—, —N($R^{2.4.1}$)C(O)—, —S(O)$_2$N($R^{2.4.1}$)—, —N($R^{2.4.1}$)S(O)$_2$—, —C(O)—, —S(O)—, —S(O)$_2$—, —C($R^{2.4.2}$)=C($R^{2.4.2}$)—, —C=N—, —N=C—, —C($R^{2.4.2}$)$_2$N($R^{2.4.1}$)—, —N($R^{2.4.1}$)C($R^{2.4.2}$)$_2$— and $C_{1-4}$- alkylene; and $R^{2.4.1}$ is independently selected from H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.4.2}$ is independently selected from H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene-, ($C_{1-4}$-alkyl)$_2$N—$C_{1-4}$-alkylene-.

Preferred are the above compounds of formula 1, wherein $R^{2.5}$ is together with $R^4$ a group $R^{2.5.a}$ and $R^{2.5.a}$ is selected from —C($R^{2.5.1}$)=, =C($R^{2.5.1}$)— and —N=; and
$R^{2.5.1}$ is independently selected from H, $C_{1-4}$-alkyl, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-.

Preferred are the above compounds of formula 1, wherein $R^2$ is $R^{2.m}$ and $R^{2.m}$ is together with $R^4$ and two adjacent carbon atoms of the phenyl ring a 5- or 6-membered aryl or heteroaryl, containing one, two or three heteroatoms independently selected from S, S(O), S(O)$_2$, O and N, wherein carbon atoms of the ring are optionally and independently from each other substituted with one, two or three $R^{2.1}$, wherein possibly available nitrogen atoms of the ring are optionally and independently from each other substituted with one, two or three $R^{2.2}$; and $R^{2.1}$ is $R^{2.1.a}$ and $R^{2.1.a}$ is selected from H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from
aryl-, optionally substituted independently from each other with one, two or three residues independently selected from $R^{2.1.1.1}$;
$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;
$C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from halogen, HO—, O=, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from O=, $C_{1-4}$-alkyl-, $C_{1-4}$-haloalkyl-; $C_{3-6}$-cycloalkyl-, $C_{1-4}$-alkyl-O—$C_{1-4}$-alkyl, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$— and $C_{1-4}$-alkyl-C(O)—, $R^{2.1.1}$-A-.

Preferred are the above compounds of formula 1, wherein $R^2$ is $R^{2.n}$ and $R^{2.n}$ is selected from aryl-, pyrazole, thiophene and furane; wherein carbon atoms of the ring are optionally and independently from each other substituted with one, two, three or four $R^{2.1}$; wherein possibly available nitrogen atoms of the ring are optionally and independently from each other substituted with $R^{2.2}$; wherein a carbon atom of the ring is optionally substituted with one $R^{2.3}$; a nitrogen atom of the ring is optionally substituted with one $R^{2.4}$; or $R^{2.n}$ is selected from

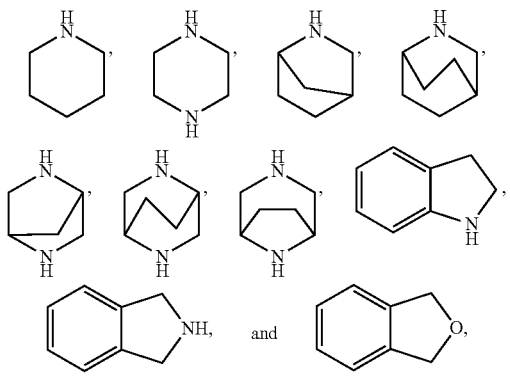

wherein carbon atoms of the ring are optionally and independently from each other substituted with one, two, three or four $R^{2.1}$; wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$; and $R^{2.1}$ is $R^{2.1.a}$ and $R^{2.1.a}$ is selected from H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$ alkylene-, $C_{3-6}$-cycloalkyl-A-$C_{1-4}$-alkylene-, $C_{1-4}$-haloalkyl-A-$C_{1-4}$ alkylene-, $R^{2.1.1}$—$C_{1-4}$-alkylene-A-$C_{1-4}$-alkylene-, $R^{2.1.1}$-A-$C_{1-4}$alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ is selected from aryl-, optionally substituted independently from each other with one, two or three residues independently selected from $R^{2.1.1.1}$;

$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from halogen, HO—, O=, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$— and $C_{1-4}$-alkyl-C(O)—, $R^{2.1.1}$-A-; and $R^{2.3}$ is together with $R^4$ a group $R^{2.3.a}$ and $R^{2.3.a}$ is selected from —O—, —S—, —N($R^{2.3.1}$)—, —C(O)N($R^{2.3.1}$)—, —N($R^{2.3.1}$)C(O)—, —S(O)$_2$N($R^{2.3.1}$)—, —N($R^{2.3.1}$)S(O)$_2$—, —C(O)O—, —OC(O)—, —C(O)—, —S(O)—, —S(O)$_2$—, —C($R^{2.3.2}$)=C($R^{2.3.2}$)—, —C=N—, —N=C—, —C($R^{2.3.2}$)$_2$—O—, —O—C($R^{2.3.2}$)$_2$—, —C($R^{2.3.2}$)$_2$N($R^{2.3.1}$)—, —N($R^{2.3.1}$)C($R^{2.3.2}$)$_2$— and —$C_{1-4}$-alkylene-; and $R^{2.3.1}$ is independently selected from H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.3.2}$ is independently selected from H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-; and $R^{2.4}$ is together with $R^4$ a group $R^{2.4.a}$ and $R^{2.4.a}$ is selected from —N($R^{2.4.1}$)—, —C(O)N($R^{2.4.1}$)—, —N($R^{2.4.1}$)C(O)—, —S(O)$_2$N($R^{2.4.1}$)—, —N($R^{2.4.1}$)S(O)$_2$—, —C(O)—, —S(O)—, —S(O)$_2$—, —C($R^{2.4.2}$)=C($R^{2.4.2}$)—, —C=N—, —N=C—, —C($R^{2.4.2}$)$_2$N($R^{2.4.1}$)—, —N($R^{2.4.1}$)C($R^{2.4.2}$)$_2$— and —$C_{1-4}$-alkylene-; and $R^{2.4.1}$ is independently selected from H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.4.2}$ is independently selected from H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-; and $R^{2.5}$ is together with $R^4$ a group $R^{2.5.a}$ and $R^{2.5.a}$ is selected from —C($R^{2.5.1}$)=, =C($R^{2.5.1}$)— and —N=; and $R^{2.5.1}$ is independently selected from H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-.

Preferred are the above compounds of formula 1, wherein
$R^1$ is $R^{1.b}$ and $R^{1.b}$ is H; or two $R^1$ are together —$CH_2$—;
$R^2$ is selected from
$R^{2.1}$;

phenyl-; optionally substituted with one or two residues independently selected from $R^{2.1}$; optionally substituted with one $R^{2.3}$;

$C_5$-heteroaryl-; containing two or three independently selected from S, O and N, wherein carbon atoms of the ring are optionally and independently from each other substituted with one $R^{2.1}$; wherein nitrogen atoms of the ring are optionally and independently from each other substituted with one $R^{2.2}$;

monocyclic $C_6$-heterocyclyl containing one or two nitrogen atoms, wherein the ring is fully or partially saturated, wherein carbon atoms of the ring are optionally and independently from each other substituted with one $R^{2.1}$; wherein nitrogen atoms of the ring are optionally and independently from each other substituted with one $R^{2.2}$; and bicyclic $C_{9 \text{ or } 10}$-heterocyclyl-; containing one, two, three or four heteroatoms independently selected from $S(O)_2$, O and N, wherein the ring is fully or partially saturated, wherein carbon atoms of the ring are optionally and independently from each other substituted with one, two or three $R^{2.1}$; wherein nitrogen atoms of the ring are optionally and independently from each other substituted with one $R^{2.2}$;

$R^{2.1}$ is independently selected from halogen, NC—, O=, H-A-, H-A-$C_{1-4}$-alkylene-, $R^{2.1.1}$-A-, $C_{1-4}$-alkyl-A-, $C_{3-6}$-cycloalkyl-A-, $R^{2.1.1}$—$C_{1-4}$-alkylene-A-, $C_{1-4}$-alkyl-A-$C_{1-4}$-alkylene-, and HO—$C_{1-4}$-alkylene-A-$C_{1-4}$-alkylene-;

$R^{2.1.1}$ is independently selected from phenyl-; and $C_{5 \text{ or } 6}$-heterocyclyl-; containing one or two heteroatoms independently selected from O and N, wherein the ring is fully or partially saturated, wherein nitrogen atoms of the ring are optionally and independently from each other substituted with one $C_{1-4}$-alkyl-;

$R^{2.2}$ is independently selected from H-A-$C_{1-4}$-alkylene-, $C_{3-6}$-cycloalkyl-, $C_{1-4}$-alkyl-A-$C_{1-4}$-alkylene-, $R^{2.1.1}$-A-$C_{1-4}$-alkylene- and $C_{1-4}$-alkyl-C(O)—;

$R^{2.3}$ and $R^4$ are together a group selected from —N($R^{2.3.1}$)—, —C(O)N($R^{2.3.2}$)— and —N($R^{2.3.1}$)C(O)—;

$R^{2.3.1}$ is independently selected from H and $H_3C$—;

$R^3$ is H or F;

$R^4$ is $R^{4.b}$ and $R^{4.b}$ is F;

A is a bond or independently selected from —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, —S(O)$_2$— and —N=(O)($R^5$)S—;

$R^5$ is independently selected from H and $C_{1-4}$-alkyl-;

or a salt thereof.

Preferred are the above compounds of formula 1, wherein $R^2$ is selected from the Table 1 $R^2$—Embodiments of the invention for $R^2$, $R^{2.1}$, $R^{2.1.1}$, $R^{2.2}$, $R^{2.3}$, $R^{2.4}$ and $R^{2.5}$ (if present):

| E# | $R^2$ | $R^{2.1}$ | $R^{2.1.1}$ | $R^{2.2}$ | $R^{2.3-5}$ |
|---|---|---|---|---|---|
| 1 | $R^{2.a}$ | $R^{2.1}$ | $R^{2.1.1.a}$ | — | — |
| 2 | $R^{2.a}$ | $R^{2.1}$ | $R^{2.1.1.b}$ | — | — |
| 3 | $R^{2.a}$ | $R^{2.1}$ | $R^{2.1.1.c}$ | — | — |
| 4 | $R^{2.b}$ | $R^{2.1.a}$ | $R^{2.1.1.a}$ | — | — |
| 5 | $R^{2.b}$ | $R^{2.1.a}$ | $R^{2.1.1.b}$ | — | — |
| 6 | $R^{2.b}$ | $R^{2.1.a}$ | $R^{2.1.1.c}$ | — | — |
| 7 | $R^{2.c}$ | $R^{2.1.a}$ | $R^{2.1.1.a}$ | — | — |
| 8 | $R^{2.c}$ | $R^{2.1.a}$ | $R^{2.1.1.b}$ | — | — |
| 9 | $R^{2.c}$ | $R^{2.1.a}$ | $R^{2.1.1.c}$ | — | — |
| 10 | $R^{2.c}$ | $R^{2.1.a}$ | $R^{2.1.1.c}$ | — | $R^{2.3.a}$ |
| 11 | $R^{2.c}$ | $R^{2.1.a}$ | $R^{2.1.1.c}$ | — | $R^{2.4.a}$ |
| 12 | $R^{2.c}$ | $R^{2.1.a}$ | $R^{2.1.1.c}$ | — | $R^{2.5.a}$ |
| 13 | $R^{2.d}$ | $R^{2.1.a}$ | $R^{2.1.1.a}$ | — | — |
| 14 | $R^{2.d}$ | $R^{2.1.a}$ | $R^{2.1.1.b}$ | — | — |
| 15 | $R^{2.d}$ | $R^{2.1.a}$ | $R^{2.1.1.c}$ | — | — |
| 16 | $R^{2.d}$ | $R^{2.1.a}$ | $R^{2.1.1.c}$ | — | $R^{2.3.a}$ |
| 17 | $R^{2.d}$ | $R^{2.1.a}$ | $R^{2.1.1.c}$ | — | $R^{2.4.a}$ |
| 18 | $R^{2.d}$ | $R^{2.1.a}$ | $R^{2.1.1.c}$ | — | $R^{2.5.a}$ |
| 19 | $R^{2.e}$ | $R^{2.1.a}$ | $R^{2.1.1.a}$ | $R^{2.2.a}$ | — |
| 20 | $R^{2.e}$ | $R^{2.1.a}$ | $R^{2.1.1.b}$ | $R^{2.2.a}$ | — |
| 21 | $R^{2.e}$ | $R^{2.1.a}$ | $R^{2.1.1.c}$ | $R^{2.2.a}$ | — |
| 22 | $R^{2.f}$ | $R^{2.1.a}$ | $R^{2.1.1.a}$ | $R^{2.2.a}$ | — |
| 23 | $R^{2.f}$ | $R^{2.1.a}$ | $R^{2.1.1.b}$ | $R^{2.2.a}$ | — |
| 24 | $R^{2.f}$ | $R^{2.1.a}$ | $R^{2.1.1.c}$ | $R^{2.2.a}$ | — |
| 25 | $R^{2.g}$ | $R^{2.1.a}$ | $R^{2.1.1.a}$ | $R^{2.2.a}$ | — |
| 26 | $R^{2.g}$ | $R^{2.1.a}$ | $R^{2.1.1.b}$ | $R^{2.2.a}$ | — |
| 27 | $R^{2.g}$ | $R^{2.1.a}$ | $R^{2.1.1.c}$ | $R^{2.2.a}$ | — |
| 28 | $R^{2.h}$ | $R^{2.1.a}$ | $R^{2.1.1.b}$ | $R^{2.2.a}$ | — |
| 29 | $R^{2.h}$ | $R^{2.1.a}$ | $R^{2.1.1.b}$ | $R^{2.2.a}$ | — |
| 30 | $R^{2.h}$ | $R^{2.1.a}$ | $R^{2.1.1.c}$ | $R^{2.2.a}$ | — |
| 31 | $R^{2.e}$ | $R^{2.1.a}$ | $R^{2.1.1.c}$ | — | $R^{2.3.a}$ |
| 32 | $R^{2.e}$ | $R^{2.1.a}$ | $R^{2.1.1.c}$ | — | $R^{2.4.a}$ |
| 33 | $R^{2.e}$ | $R^{2.1.a}$ | $R^{2.1.1.c}$ | — | $R^{2.5.a}$ |
| 34 | $R^{2.g}$ | $R^{2.1.a}$ | $R^{2.1.1.c}$ | — | $R^{2.3.a}$ |
| 35 | $R^{2.g}$ | $R^{2.1.a}$ | $R^{2.1.1.c}$ | — | $R^{2.4.a}$ |
| 36 | $R^{2.g}$ | $R^{2.1.a}$ | $R^{2.1.1.c}$ | — | $R^{2.5.a}$ |
| 37 | $R^{2.h}$ | $R^{2.1.a}$ | $R^{2.1.1.c}$ | — | $R^{2.3.a}$ |
| 38 | $R^{2.h}$ | $R^{2.1.a}$ | $R^{2.1.1.c}$ | — | $R^{2.4.a}$ |
| 39 | $R^{2.h}$ | $R^{2.1.a}$ | $R^{2.1.1.c}$ | — | $R^{2.5.a}$ |
| 40 | $R^{2.i}$ | $R^{2.1.a}$ | $R^{2.1.1.a}$ | $R^{2.2.a}$ | — |
| 41 | $R^{2.i}$ | $R^{2.1.a}$ | $R^{2.1.1.b}$ | $R^{2.2.a}$ | — |
| 42 | $R^{2.i}$ | $R^{2.1.a}$ | $R^{2.1.1.c}$ | $R^{2.2.a}$ | — |
| 43 | $R^{2.j}$ | $R^{2.1.a}$ | $R^{2.1.1.a}$ | $R^{2.2.a}$ | — |
| 44 | $R^{2.j}$ | $R^{2.1.a}$ | $R^{2.1.1.b}$ | $R^{2.2.a}$ | — |
| 45 | $R^{2.j}$ | $R^{2.1.a}$ | $R^{2.1.1.c}$ | $R^{2.2.a}$ | — |
| 46 | $R^{2.k}$ | $R^{2.1.a}$ | $R^{2.1.1.a}$ | $R^{2.2.a}$ | — |
| 47 | $R^{2.k}$ | $R^{2.1.a}$ | $R^{2.1.1.b}$ | $R^{2.2.a}$ | — |
| 48 | $R^{2.k}$ | $R^{2.1.a}$ | $R^{2.1.1.c}$ | $R^{2.2.a}$ | — |
| 49 | $R^{2.l}$ | $R^{2.1.a}$ | $R^{2.1.1.a}$ | $R^{2.2.a}$ | — |
| 50 | $R^{2.l}$ | $R^{2.1.a}$ | $R^{2.1.1.b}$ | $R^{2.2.a}$ | — |
| 51 | $R^{2.l}$ | $R^{2.1.a}$ | $R^{2.1.1.c}$ | $R^{2.2.a}$ | — |

For a better understanding of the Table 1 $R^2$—Embodiments of the invention example (E#) 21, can also be read as a group $R^2$, wherein $R^2$ is $R^{2.e}$ and $R^{2.e}$ is $C_{5 \text{ or } 6}$-heteroaryl-, containing one, two, three or four heteroatoms independently selected from S, S(O), $S(O)_2$, O and N, wherein carbon atoms of the ring are optionally and independently from each other substituted with one, two or three $R^{2.1}$; wherein nitrogen atoms of the ring are optionally and independently from each other substituted with one, two or three $R^{2.2}$; and $R^{2.1}$ is $R^{2.1.a}$ and $R^{2.1.a}$ is selected from H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.c}$ and $R^{2.1.1.c}$ is phenyl or selected from wherein carbon atoms of the ring are optionally and independently from each other substituted with one, two or three $R^{2.1.1.1}$, wherein possibly available nitrogen atoms of the ring are optionally and independently from each other substituted with $R^{2.1.1.2}$; and $R^{2.1.1.1}$ is independently selected from F, Cl, Me, MeO— and cyclopropyl-; and $R^{2.1.1.2}$ is independently selected from Me, tetrahydrofuranylmethyl- and tetrahydropyranylmethyl; and $R^{2.2}$ is $R^{2.2.a}$ and $R^{2.2.a}$ is independently selected from H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$—, $C_{1-4}$-alkyl-C(O)—, $R^{2.1.1}$-A-.

Preferred are the above compounds of formula 1, wherein $R^3$ is $R^{3.a}$ and $R^{3.a}$ is H.

Preferred are the above compounds of formula 1, wherein $R^3$ is $R^{3.b}$ and $R^{3.b}$ is F.

Preferred are the above compounds of formula 1, wherein $R^4$ is $R^{4.a}$ and $R^{4.a}$ is selected from F, Cl, phenyl-$H_2C$—O—, HO—, $C_{1-4}$-alkyl-, $C_{1-4}$-haloalkyl-, $C_{3-6}$-cycloalkyl-, $C_{1-4}$-alkyl-O— and $C_{1-4}$-haloalkyl-O—.

Preferred are the above compounds of formula 1, wherein $R^4$ is $R^{4.b}$ and $R^{4.b}$ is F; preferably in ortho position.

Preferred are the above compounds of formula 1, wherein A is $A^a$ and $A^a$ is a bond or independently selected from —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, —S(O)$_2$—, —($R^5$)(O)S=N—, —($R^5$N=)(O)S— and —N=(O)($R^5$)S— and $R^5$ is $R^{5.a}$ and $R^{5.a}$ is independently selected from H, $C_{1-4}$-alkyl- and NC—.

Preferred is a compound of formula 1, wherein $R^1$ is independently selected from H, $C_{1-4}$-alkyl-, halogen, HO—, $C_{1-4}$-alkyl-O—, $H_2N$—, $C_{1-6}$-alkyl-HN—, ($C_{1-6}$-alkyl)$_2$N- and $C_{1-6}$-alkyl-C(O)HN—;

or two $R^1$ are together $C_{1-4}$-alkylene;

$R^2$ is selected of the examples of the Table 1 $R^2$—Embodiments of the invention; preferably examples (E#) 7-51, preferably one of the groups selected from 7, 8, 9, 10, 11, 12, 13, 14, 15, 16, 17, 18 or 19, 20, 21, 22, 23, 24, 25, 26, 27, 28, 29, 30, 31, 32, 33, 34, 35, 36, 37, 38, 39 or 40, 41, 42, 43, 44, 45, 45, 46, 47, 48, 49, 50, 51;

$R^3$ is H or F;

$R^4$ is independently selected from F, Cl, phenyl-$H_2C$—O—, HO—, $C_{1-6}$-alkyl-, $C_{1-6}$-haloalkyl-, $C_{3-8}$-cycloalkyl-, $C_{1-6}$-alkyl-O—, $C_{1-6}$-haloalkyl-O—, $C_{1-6}$-alkyl-HN—, ($C_{1-6}$-alkyl)$_2$-HN—, $C_{1-6}$-alkyl-HN—$C_{1-4}$-alkylene- and ($C_{1-6}$-alkyl)$_2$-HN—$C_{1-4}$-alkylene-;

A is a bond or independently selected from —O—, —S—, —N($R^5$)—, —C(O)N($R^5$)—, —N($R^5$)C(O)—, —S(O)$_2$N($R^5$)—, —N($R^5$)S(O)$_2$—, —S(O)(=N$R^5$)—N($R^5$)—, —N($R^5$)(N$R^5$=), S(O)—, —S(=N$R^5$)$_2$—N($R^5$)—, —N($R^5$)(N$R^5$=)$_2$S—, —C($R^5$)=C($R^5$)—, —C≡C—, —C(O)O—, —OC(O)—, —C(O)—, —S(O)—, S(O)$_2$—, —S(=N$R^5$)—, —S(O)(=N$R^5$)—, —S(=N$R^5$)$_2$—, —($R^5$)(O)S=N—, —($R^5$N=)(O)S— and —N=(O)($R^5$)S—;

$R^5$ is independently selected from H, $C_{1-6}$-alkyl- and NC—;

or a salt thereof.

Preferred is a compound of formula 1, wherein $R^1$ is $R^{1.a}$ and $R^{1.a}$ is independently selected from H, $C_{1-4}$-alkyl-, F and HO—, or two $R^1$ are together $C_{1-4}$-alkylene;

$R^2$ is selected of the examples of the Table 1 $R^2$—Embodiments of the invention; preferably examples (E#) 7-51, preferably one of the groups selected from 7, 8, 9, 10, 11, 12, 13, 14, 15, 16, 17, 18 or 19, 20, 21, 22, 23, 24, 25, 26, 27, 28, 29, 30, 31, 32, 33, 34, 35, 36, 37, 38, 39 or 40, 41, 42, 43, 44, 45, 45, 46, 47, 48, 49, 50, 51;

$R^3$ is H or F;

$R^4$ is $R^{4.a}$ and $R^{4.a}$ is F, Cl, phenyl-$H_2C$—O—, HO—, $C_{1-4}$-alkyl-, $C_{1-4}$-haloalkyl-, $C_{3-6}$-cycloalkyl-, $C_{1-4}$-alkyl-O— and $C_{1-4}$-haloalkyl-O—;

A is a bond or independently selected from —O—, —S—, —N($R^5$)—, —C(O)N($R^5$)—, —N($R^5$)C(O)—, —S(O)$_2$N($R^5$)—, —N($R^5$)S(O)$_2$—, —S(O)(=N$R^5$)—N($R^5$)—, —N($R^5$)(N$R^5$=) S(O)—, —S(=N$R^5$)$_2$—N($R^5$)—, —N($R^5$)(N$R^5$=)$_2$S—, —C($R^5$)=C($R^5$)—, —C≡C—, —C(O)O—, —OC(O)—, —C(O)—, —S(O)—, S(O)$_2$—, —S(=N$R^5$)—, —S(O)(=N$R^5$)—, —S(=N$R^5$)$_2$—, —($R^5$)(O)S=N—, —($R^5$N=)(O)S— and —N=(O)($R^5$)S—;

$R^5$ is independently selected from H, $C_{1-6}$-alkyl- and NC—;

or a salt thereof.

Preferred is a compound of formula 1, wherein $R^1$ is $R^{1.a}$ and $R^{1.a}$ is independently selected from H, $C_{1-4}$-alkyl-, F and HO—, or two $R^1$ are together $C_{1-4}$-alkylene;

$R^2$ is selected of the examples of the Table 1 $R^2$—Embodiments of the invention; preferably examples (E#) 7-51, preferably one of the groups selected from 13, 14, 15, 16, 17, 18 or 25, 26, 27, 28, 29, 30, 34, 35, 36, 37, 38, 39 or 43, 44, 45, 46, 47 and 48;

$R^3$ is H or F;

$R^4$ is $R^{4.a}$ and $R^{4.a}$ is selected from F, Cl, phenyl-$H_2C$—O—, HO—, $C_{1-4}$-alkyl-, $C_{1-4}$-haloalkyl-, $C_{3-6}$-cycloalkyl-, $C_{1-4}$-alkyl-O— and $C_{1-4}$-haloalkyl-O—;

A is $A^a$ and $A^a$ is a bond or independently selected from —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, S(O)$_2$—, —($R^5$)(O)S=N—, —($R^5$N=)(O)S— and —N=(O)($R^5$)S—;

$R^5$ is $R^{5.a}$ and $R^{5.a}$ is independently selected from H, $C_{1-4}$-alkyl- and NC—;

or a salt thereof.

Preferred is a compound of formula 1, wherein $R^1$ is $R^{1.b}$ and $R^{1.b}$ is H; or two $R^1$ are together —$CH_2$—;

$R^2$ is selected of the examples of the Table 1 $R^2$—Embodiments of the invention; preferably examples (E#) 7-51, preferably one of the groups selected from 13, 14, 15, 16, 17, 18 or 25, 26, 27, 28, 29, 30, 34, 35, 36, 37, 38, 39 or 43, 44, 45, 46, 47 and 48;

$R^3$ is H or F;

$R^4$ is $R^{4.b}$ and $R^{4.b}$ is F;

A is $A^a$ and $A^a$ is a bond or independently selected from —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, S(O)$_2$—, —($R^5$)(O)S=N—, —($R^5$N=)(O)S— and —N=(O)($R^5$)S—;

$R^5$ is $R^{5.a}$ and $R^{5.a}$ is independently selected from H, $C_{1-4}$-alkyl- and NC—;

or a salt thereof.

Preferred is a compound of formula 1, wherein $R^1$ is $R^{1.b}$ and $R^{1.b}$ is H; or two $R^1$ are together —CH$_2$—;

$R^2$ is selected of the examples of the Table 1 $R^2$—Embodiments of the invention; preferably examples (E#) 7-51, preferably one of the groups selected from 13, 14, 15, 16, 17, 18 or 25, 26, 27, 28, 29, 30, 34, 35, 36, 37, 38, 39 or 43, 44, 45, 46, 47 and 48;

$R^3$ is H or F;

$R^4$ is $R^{4.b}$ and $R^{4.b}$ is F;

A is $A^a$ and $A^a$ is a bond or independently selected from —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, S(O)$_2$—, —($R^5$)(O)S=N—, —($R^5$N=)(O)S— and —N=(O)($R^5$)S—;

$R^5$ is $R^{5.a}$ and $R^{5.a}$ is independently selected from H, $C_{1-4}$-alkyl- and NC—;

or a salt thereof.

Preferred is a compound of formula 1, wherein $R^1$ is $R^{1.b}$ and $R^{1.b}$ is H; or two $R^1$ are together —CH$_2$—;

$R^2$ is selected from $R^{2.1}$;

phenyl-; optionally substituted with one or two residues independently selected from $R^{2.1}$; optionally substituted with one $R^{2.3}$;

$C_5$-heteroaryl-; containing two or three independently selected from S, O and N, wherein carbon atoms of the ring are optionally and independently from each other substituted with one $R^{2.1}$; wherein nitrogen atoms of the ring are optionally and independently from each other substituted with one $R^{2.2}$;

monocyclic $C_6$-heterocyclyl containing one or two nitrogen atoms, wherein the ring is fully or partially saturated, wherein carbon atoms of the ring are optionally and independently from each other substituted with one $R^{2.1}$; wherein nitrogen atoms of the ring are optionally and independently from each other substituted with one $R^{2.2}$; and bicyclic $C_{9 \text{ or } 10}$-heterocyclyl-; containing one, two, three or four heteroatoms independently selected from S(O)$_2$, O and N, wherein the ring is fully or partially saturated, wherein carbon atoms of the ring are optionally and independently from each other substituted with one, two or three $R^{2.1}$; wherein nitrogen atoms of the ring are optionally and independently from each other substituted with one $R^{2.2}$;

$R^{2.1}$ is independently selected from halogen, NC—, O=, H-A-, H-A-$C_{1-4}$-alkylene-, $R^{2.1.1}$-A-, $C_{1-4}$-alkyl-A-, $C_{3-6}$-cycloalkyl-A-, $R^{2.1.1}$—$C_{1-4}$-alkylene-A-, $C_{1-4}$-alkyl-A-$C_{1-4}$-alkylene-, HO—$C_{1-4}$-alkylene-A-$C_{1-4}$-alkylene-; preferably F, NC—, O=, H-A-, H-A-CH$_2$—, $R^{2.1.1}$-A-, H$_3$C-A-, H$_3$C—CH$_2$-A-, Cyclopropyl-A-, $R^{2.1.1}$—CH$_2$—CH$_2$-A-, $R^{2.1.1}$—CH$_2$-A-, H$_3$C-A-CH$_2$—CH$_2$— and HO—$C_4$-alkylene-A-CH$_2$—;

$R^{2.1.1}$ is independently selected from phenyl-; and $C_{5 \text{ or } 6}$-heterocyclyl-; containing one or two heteroatoms independently selected from 0 and N, wherein the ring is fully or partially saturated, wherein nitrogen atoms of the ring are optionally and independently from each other substituted with one $C_{1-4}$-alkyl-; preferably H$_3$C—;

$R^{2.2}$ is independently selected from H-A-$C_{1-4}$-alkylene-, $C_{3-6}$-cycloalkyl-, $C_{1-4}$-alkyl-A-$C_{1-4}$-alkylene-, $R^{2.1.1}$-A-$C_{1-4}$-alkylene-, $R^{2.1.1}$-A-, $C_{1-4}$-alkyl-C(O)—; preferably H-A-CH$_2$—, H-A-CH$_2$—CH$_2$—, cyclopropyl-, H$_3$C-A-CH$_2$—CH$_2$—, $R^{2.1.1}$-A-CH$_2$— and H$_3$C—C(O)—;

$R^{2.3}$ and $R^4$ are together a group selected from —N($R^{2.3.1}$)—, —C(O)N($R^{2.3.2}$)— or —N($R^{2.3.1}$)C(O)—;

$R^{2.3.1}$ is independently selected from H and H$_3$C—;

$R^3$ is H or F;

$R^4$ is $R^{4.b}$ and $R^{4.b}$ is F;

A is a bond or independently selected from —O—, —C(O)N($R^5$)—, —N($R^5$)C(O)—, —S(O)$_2$N($R^5$)—, —N($R^5$)S(O)$_2$—, —C(O)O—, —OC(O)—, —C(O)—, —S(O)$_2$— and —N=(O)($R^5$)S—;

$R^5$ is independently selected from H or $C_{1-4}$-alkyl-;

or a salt thereof.

Preferred are the above compounds of formula 1, wherein $R^3$ is $R^{3.a}$ and $R^{3.a}$ is H, and $R^4$ is $R^{4.b}$ and $R^{4.b}$ is F;

Particularly preferred are the above compounds of formula 1, wherein $R^3$ is H, $R^4$ is F and $R^2$ is $R^{2.q}$ and $R^{2.q}$ is selected from among the substituents (a1) to (q1).

Particularly preferred are the above compounds of formula 1, wherein $R^3$ is F and $R^2$ and $R^4$ together denote a group selected from among (r1) to (t1).

Preferably (a1) to (q1) or (r1) to (t1) are independently substituted by a substituent selected from among =O, Me, MeSO$_2$—, Me-piperazinyl-SO$_2$—, morpholinyl, furanyl, Me$_2$N—CH$_2$—CH$_2$—, F$_2$CH—CH$_2$—, —CN and F.

Preferred are the compounds of formula I, wherein the compounds are selected from the group consisting of examples 2, 3, 6, 16, 43, 155, 193, 249, 250, 254, 283, 284, 322, 323, 324, 325, 326, 328, 329, 330, 331, 333, 342, 343, 351, 352, 353, 354, 355, 356, 357, 358 and 359.

Particularly preferred are the compounds of formula I, wherein the compounds are selected from the group consisting of examples 322, 323, 324, 325 and 326.

Preferred are the above compounds of formula 1, in its enantiomerically pure form of formula 1'

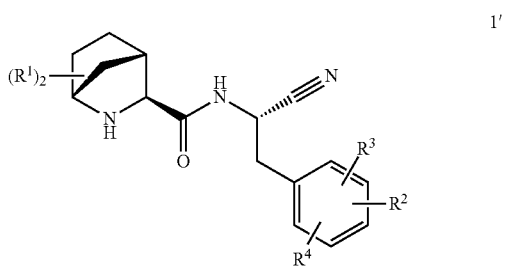

wherein $R^1$, $R^2$, $R^3$ and $R^4$ have the above mentioned meaning.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, S(O), $S(O)_2$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-4}$-alkyl-" means an aryl group which is bound to a $C_{1-4}$-alkyl-group, the latter of which is bound to the core or to the group to which the substituent is attached.

Alternatively "*" indicates within a chemical entity the binding site, i.e. the point of attachment.

In case a compound of the present invention is depicted in form of a chemical name and as a formula in case of any discrepancy the formula shall prevail. An asterisk is may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine(2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine(2, 2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2, 5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (–)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (–)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The term halogen generally denotes fluorine, chlorine, bromine and iodine.

The term "$C_{1-11}$-alkyl", wherein n is an integer selected from 2, 3, 4, 5 or 6, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer selected from 2, 3, 4, 5 or 6, preferably 4 or 6, either alone or in combination with another radical, denotes an acyclic, straight or branched chain divalent alkyl radical containing from 1 to n carbon atoms. For example the term $C_{1-4}$-alkylene includes —$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH(CH_3)$—$CH_2$—$CH_2$—, —$CH_2$—$CH(CH_3)$—$CH_2$—, —$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$— and —$C(CH_3)(CH_2CH_3)$—.

The term "$C_{3-n}$-cycloalkyl", wherein n is an integer selected from 4, 5, 6, 7 or 8, preferably 4, 5 or 6, either alone or in combination with another radical denotes a cyclic, saturated, unbranched hydrocarbon radical with 3 to 8 C atoms. For example the term $C_{3-8}$-cycloalkyl includes cyclopropyl, cyclobutyl, cyclopentyl, cyclohexyl, cycloheptyl, cyclooctyl.

By the term "halo" added to a "alkyl", "alkylene" or "cycloalkyl" group (saturated or unsaturated) is such a alkyl or cycloalkyl group wherein one or more hydrogen atoms are replaced by a halogen atom selected from among fluorine, chlorine or bromine, preferably fluorine and chlorine, particularly preferred is fluorine. Examples include: $H_2FC$—, $HF_2C$—, $F_3C$—.

The term "aryl" as used herein, either alone or in combination with another radical, denotes a carbocyclic aromatic monocyclic group containing 6 carbon atoms which may be further fused to a second five- or six-membered, carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "$C_{5-10}$-heterocyclyl" means a saturated or unsaturated mono- or polycyclic-ring systems including aromatic ring system containing one or more heteroatoms independently selected from N, O or S(O)$_r$, wherein r=0, 1 or 2, consisting of 5 to 10 ring atoms wherein none of the heteroatoms is part of the aromatic ring. The term "heterocyclyl" is intended to include all the possible isomeric forms. Thus, the term "heterocyclyl" includes the following exemplary structures which are not depicted as radicals as each form may be attached through a covalent (single or double) bond to any atom so long as appropriate valences are maintained:

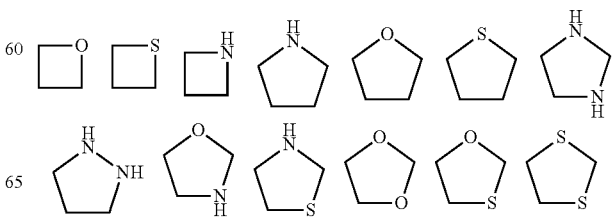

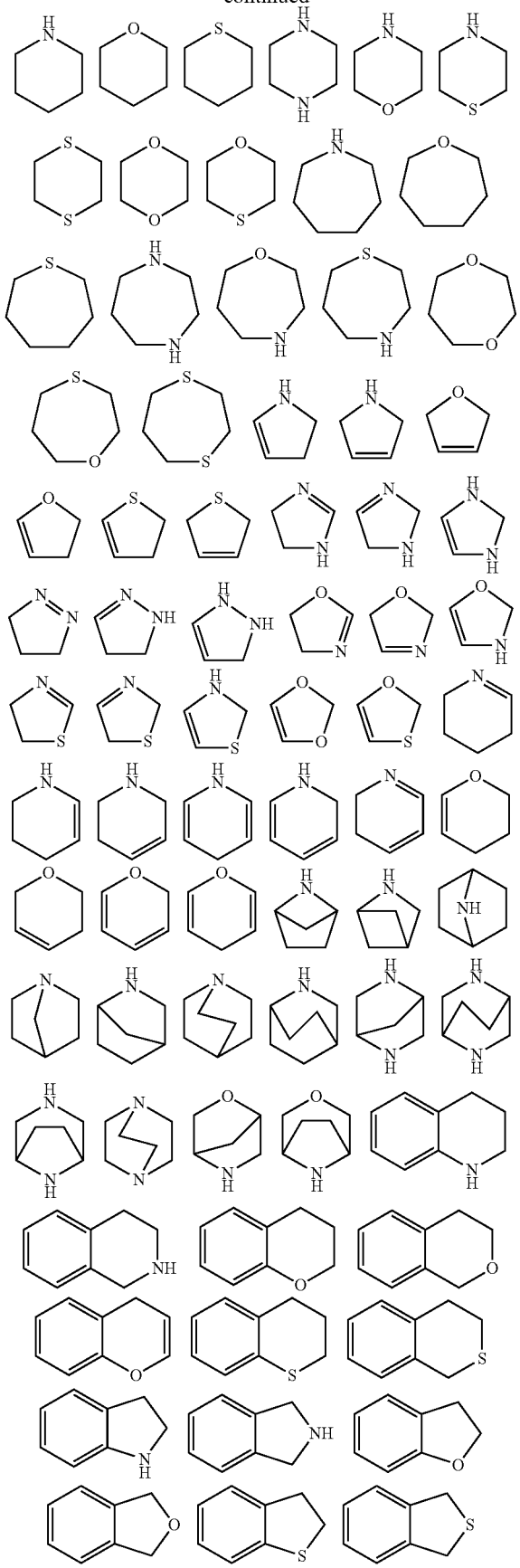

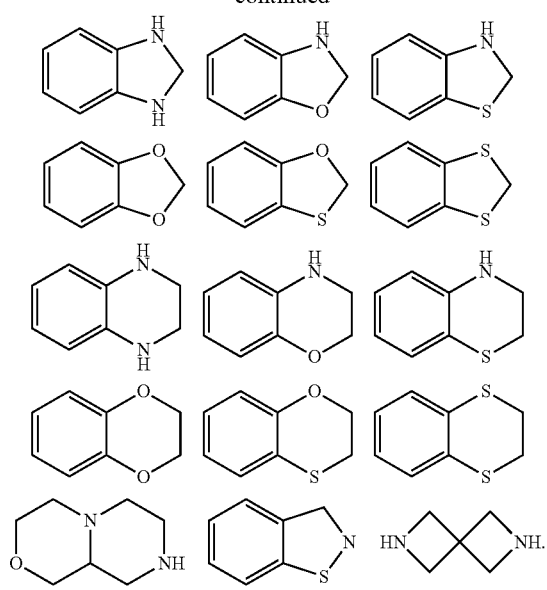

The term "$C_{5-10}$-heteroaryl" means a mono- or polycyclic-ring systems containing one or more heteroatoms independently selected from N, O or $S(O)_r$, wherein r=0, 1 or 2, consisting of 5 to 10 ring atoms wherein at least one of the heteroatoms is part of aromatic ring. The term "heteroaryl" is intended to include all the possible isomeric forms. Thus, the term "heteroaryl" includes the following exemplary structures which are not depicted as radicals as each form may be attached through a covalent bond to any atom so long as appropriate valences are maintained:

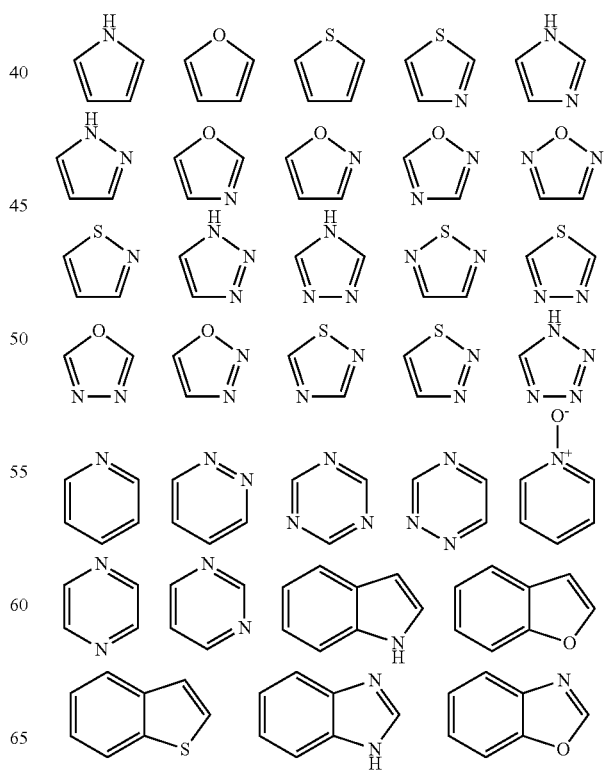

-continued

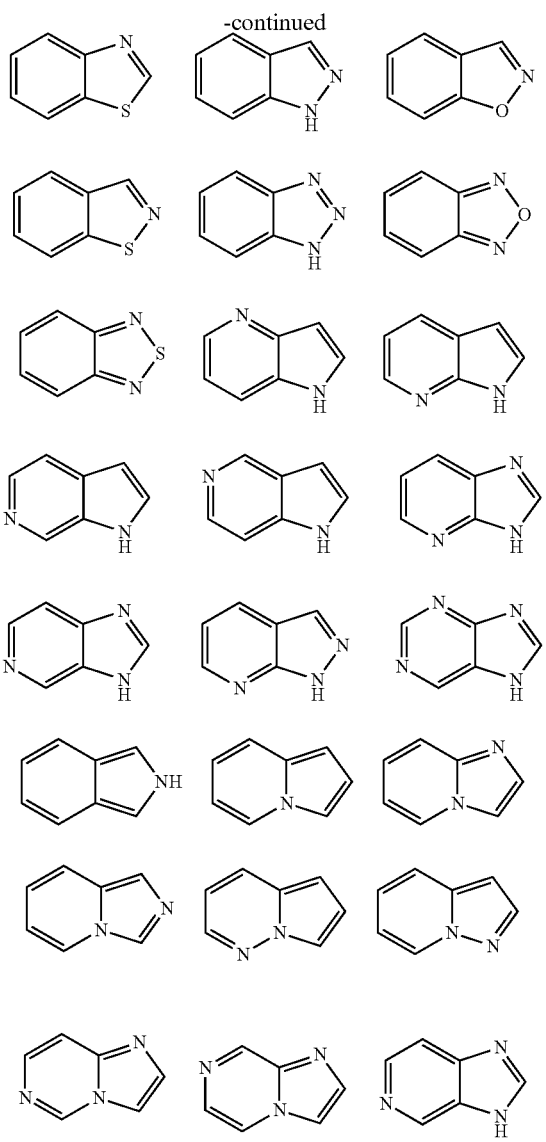

-continued

Preparation

General Synthetic Methods

The invention also provides processes for making a compound of Formula I. In all methods, unless specified otherwise, $R^1$, $R^2$ and n in the formulas below shall have the meaning of $R^1$, $R^2$ and n in Formula I of the invention described herein above.

Optimal reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel, HPLC and/or by recrystallization. The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

A compound of Formula V, VII and IX may be made by the method outlined in Scheme 1:

Scheme 1

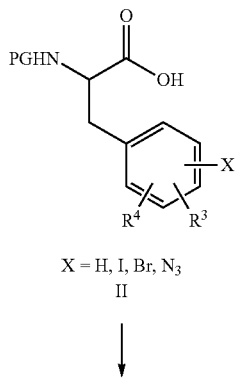

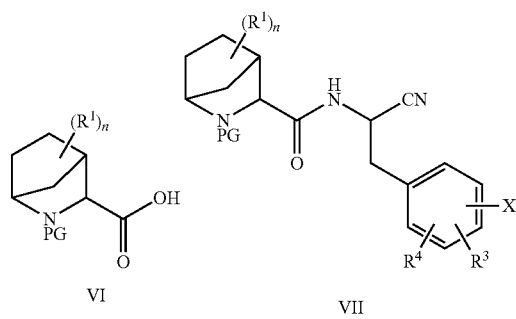

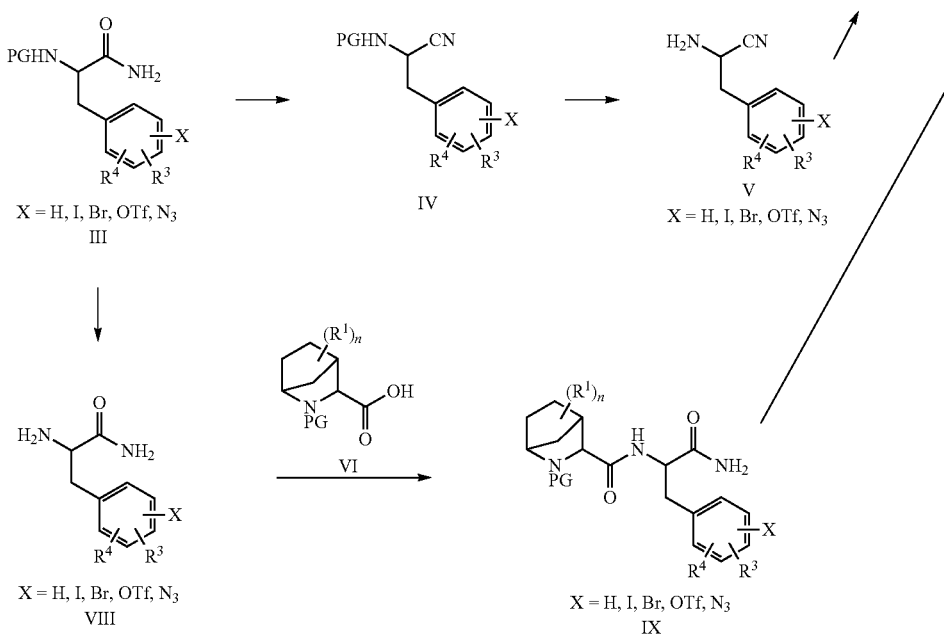

As illustrated in Scheme 1, a compound of Formula II, wherein PG represents a protecting group (e.g. tert-butoxycarbonyl), may be reacted with an aqueous ammonia solution, using standard literature procedures for the formation of an amide. For example, in the presence of a base such as N-methyl-morpholine or N-ethyl-morpholine and an activating agent such as O-(7-Azabenzotriazol-1-yl)-N,N,N',N'-tetramethyluronium hexafluorophosphate (HATU) or O-(Benzotriazol-1-yl)-N,N,N',N'-tetramethyluroniumtetrafluoroborate (TBTU). The reaction is conveniently carried out in a suitable solvent such as N, N-dimethylformamide. Standard peptide coupling reactions known in the art (see for example M. Bodanszky, 1984, The Practice of Peptide Synthesis, Springer-Verlag) may be employed in these syntheses.

Dehydration of an amide such as in a compound of Formula III or Formula IX to the corresponding nitrile of Formula IV or VII may be carried out by use of a dehydration agent such as (methoxycarbonylsulfamoyl)triethyl ammonium hydroxide, in a suitable solvent such as dichloromethane (DCM).

Reacting an acid of Formula VI using standard literature procedures for the formation of an amide, for example in the presence of a base such as N, N-diisopropylethylamine (DIPEA) and an activating agent such as HATU or TBTU, with an amine of Formula V or VIII in a suitable solvent, provides a compound of Formula VII or IX. Standard peptide coupling reactions known in the art (see for example M. Bodanszky, 1984, The Practice of Peptide Synthesis, Springer-Verlag) may be employed in these syntheses.

The protection and deprotection of functional groups is described in 'Protective Groups in Organic Synthesis', T. W. Greene and P. G. M. Wuts, Wiley-Interscience. For example, for the deprotection of tert-butoxycarbonyl, an acid such as formic acid, trifluoroacetic acid, p-toluenesulfonic acid or HCl may be used in a suitable solvent such as water, DCM or dioxane. Another method to deprotect tert-butoxycarbonyl is the reaction with trimethyliodosilane or trimethylchlorosilane in combination with sodium iodide in an appropriate solvent like acetonitrile, DMF or DCM.

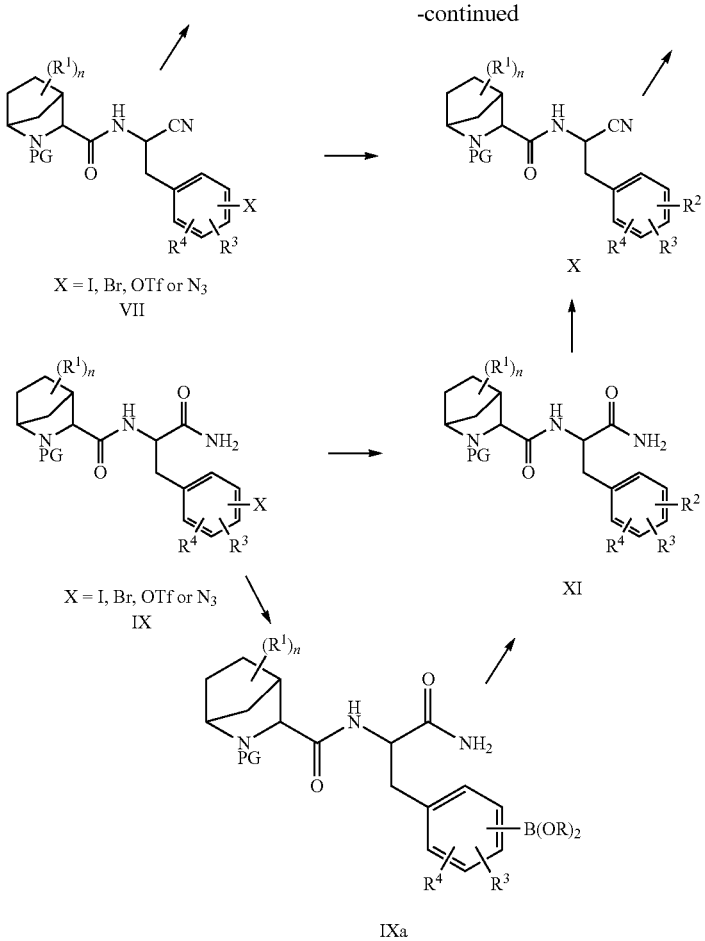

During the reaction sequences depicted in Scheme 1 and Scheme 2 a hydroxy group (X=OH) can be converted to a trifluoromethanesulfonyl group (X=OTf) at any level. Especially, a compound IX with X=OH is transformed to the appropriate triflate (X=OTf) by reaction with N,N-bis-(trifluoromethanesulfonyl) aniline, or trifluoromethanesulfonyl chloride or anhydride, in the presence of an organic base e.g. triethylamine, morpholine, piperidine, DIPEA in an appropriate anhydrous solvent, e.g. DCM.

As illustrated in Scheme 2, (transition) metal catalyzed reaction of a compound of Formula VII or IX wherein X is I, Br, Cl or OTf, provides a compound of Formula X or XI. For example, reaction with a boronic acid or the corresponding boronic acid ester, in a suitable solvent such as acetonitrile, in the presence of a suitable catalyst such as 1,1-bis(di-tert-butylphosphino)ferrocene palladium dichloride and a suitable base such as $K_2CO_3$ provides a compound of Formula X or XI. Alternatively, reaction of a compound of Formula VII or IX, wherein X is I, Br, Cl or OTf with a tributyl(vinyl)tin reagent in the presence of a suitable catalyst such as bis-(triphenylphosphin)-palladiumchloride, in a suitable solvent such as dimethylformamide (DMF) and if desirable in the presence of an additive such as tetraethylammonium chloride provides compounds of Formula X or XI. Further, reaction of a compound of Formula VII or IX, wherein X is I or Br, may be reacted with an amine in the presence of a suitable catalyst such as Cu(I)I and a suitable base such as caesium carbonate and a suitable promotor such as L-proline provides a compound of Formula X or XI.

In an inversed fashion compounds of formula VII or IX (X: I, Br, Cl, OTf) can be converted into the corresponding boronic acid derivatives VIIa or IXa, wherein R can be H or lower alkyl independently and the residues R can form a ring. For example, VII or IX can be reacted with bis-pinacolato-diboron in the presence of a suitable catalyst such as 1,1-bis(di-tert-butylphosphino)ferrocene palladium dichloride and a suitable base such as potassium acetate or sodium, potassium or cesium carbonate or phosphate, in a suitable solvent such as dioxan, dimethylformamide (DMF), or dichloromethane (DCM) to yield the boronic esters VIIa or IXa, respectively. These can be reacted with appropriate aromatic halides in analogy as above to yield the desired coupling products of formula X or XI.

Further, as illustrated in Scheme 2, reaction of a compound of Formula VII or IX, wherein X is $N_3$ with an alkyne in the presence of a suitable catalyst such as copper(II) sulfate pentahydrate and a suitable reducing agent such as L-ascorbic acid in a suitable solvent such as dimethyl sulfoxide (DMSO)/water provides a compound of Formula X or XI.

Further modifications of compounds of Formula X, XI and I by methods known in the art and illustrated in the Examples below, may be used to prepare additional compounds of the invention.

Dehydration of an amide of Formula XI to the corresponding nitrile of Formula X may be carried out by use of a dehydration agent such as (methoxycarbonylsulfamoyl) triethyl ammonium hydroxide, in a suitable solvent such as DCM.

Scheme 3

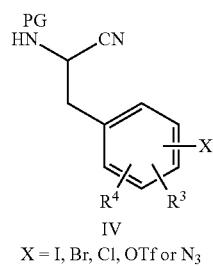

IV
X = I, Br, Cl, OTf or N₃

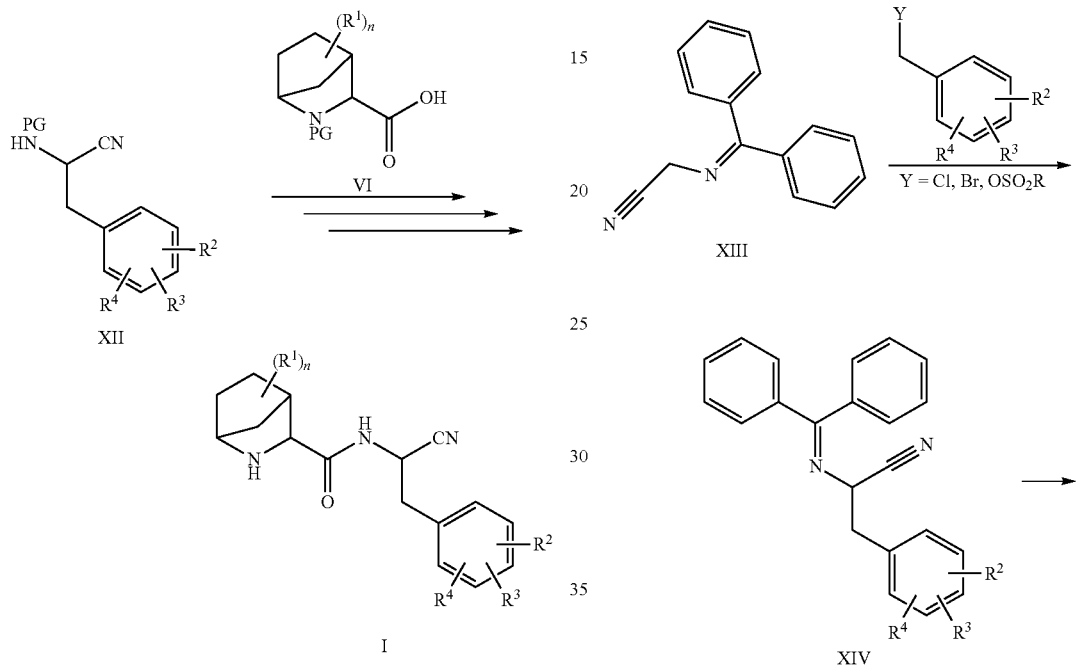

formed on the crude amide coupling product to provide a compound of Formula I. Another method to deprotect tert-butoxycarbonyl is the reaction with trimethyliodosilane or trimethylchlorosilane in combination with sodium iodide in an appropriate solvent like acetonitrile, DMF or DCM.

Scheme 4

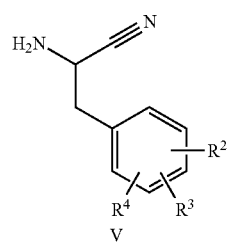

As illustrated in Scheme 3, (transition) metal catalyzed reaction of a compound of Formula IV wherein X is I, Br, Cl or OTf, provides a compound of Formula XII. For example, reaction with a boronic acid or the corresponding boronic acid ester, in a suitable solvent such as acetonitrile, in the presence of a suitable catalyst such as 1,1-bis(di-tert-butylphosphino)ferrocene palladium dichloride and a suitable base such as $K_2CO_3$ provides a compound of Formula XII.

An acid of Formula VI using standard literature procedures for the formation of an amide, for example in the presence of a base such as DIPEA and an activating agent such as HATU or TBTU, can be reacted with an amine of Formula XII in a suitable solvent. Standard peptide coupling reactions known in the art (see for example M. Bodanszky, 1984, The Practice of Peptide Synthesis, Springer-Verlag) may be employed in these syntheses. Deprotection of functional groups is described in 'Protective Groups in Organic Synthesis', T. W. Greene and P. G. M. Wuts, Wiley-Interscience. For example, for the deprotection of tert-butoxycarbonyl, an acid such as formic acid, p-toluenesulfonic acid, trifluoroacetic acid or HCl may be used in a suitable solvent such as water, DCM or dioxane and can be per- As illustrated in Scheme 4, amino nitrile derivatives of Formula XIII can be converted to substituted amino nitriles of Formula V via alkylation to compounds of Formula XIV, followed by deprotection of the amino group. During the alkylation step a suitable base is used in an appropriate solvent, using a benzylation agent XV with an appropriate leaving group like Cl, Br, or sulfonates. Especially useful is the use of sodium hydroxide as base in water and DCM under phase transfer conditions using benzyltrimethylammonium chloride as described for example by Naidu et al, WO2011/46873. The protective group is removed under acidic conditions, e.g. aq. HCl in dioxan. The amino nitrile V is further processed as depicted in Scheme 1.

Scheme 5

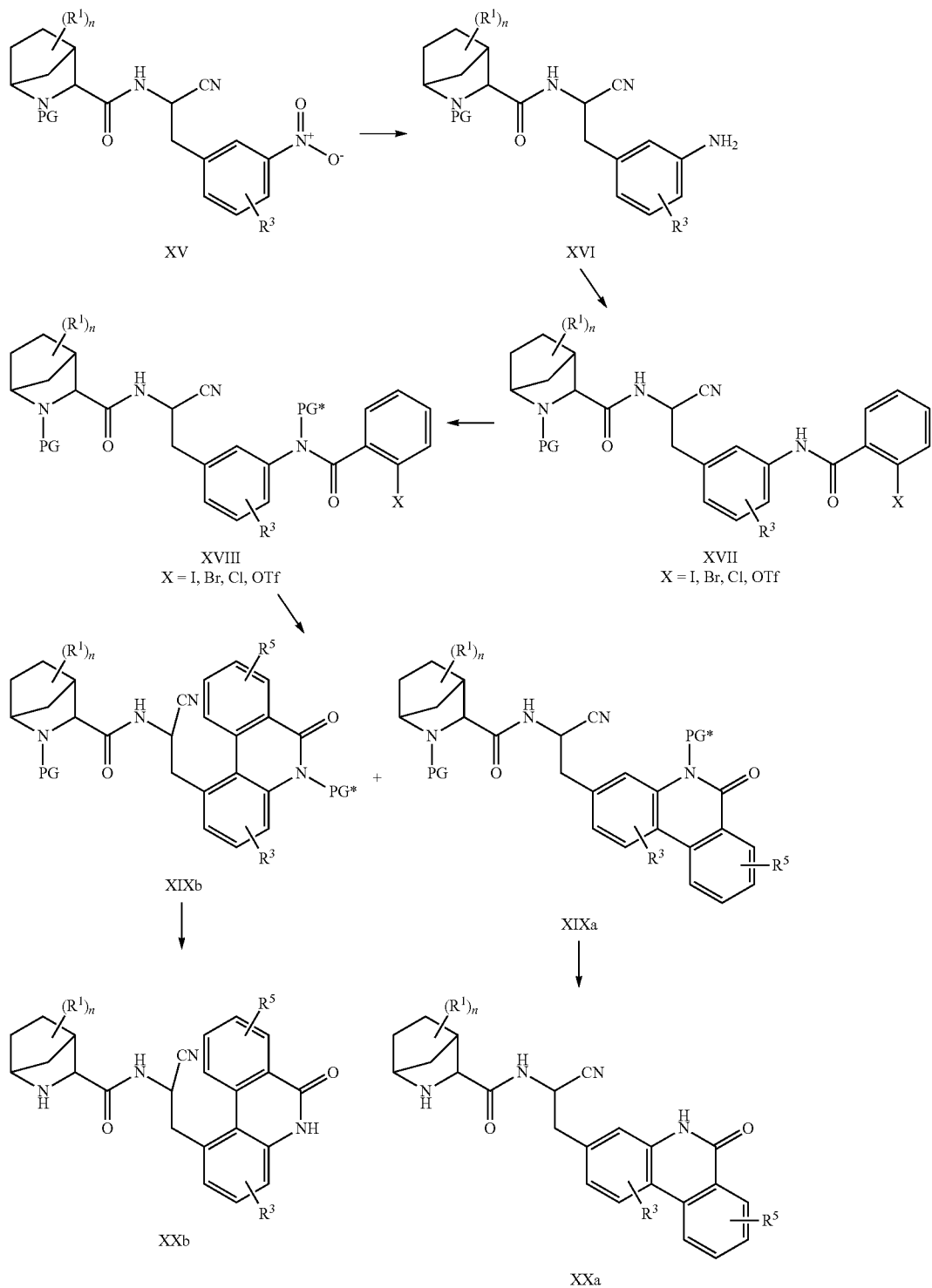

As illustrated in Scheme 5, nitro compounds of formula XV can be reduced to anilines of formula XVI by catalytic hydrogenation under conditions, where the nitrile group is still stable. Better suited are reagents like sodium dithionite, $SnCl_2$ or iron in a suitable solvent like water, methanol, ethanol, acetonitrile or ethyl acetate.

Reacting of 2-halo-benzoic acid, especially 2-iodo-benzoic acid using standard literature procedures for the formation of an amide, for example in the presence of a base such as N, N-diisopropylethylamine (DIPEA) and an activating agent such as HATU or TBTU, with an amine of Formula XVI in a suitable solvent, provides a compound of Formula XVII. Standard peptide coupling reactions known in the art (see for example M. Bodanszky, 1984, The Practice of Peptide Synthesis, Springer-Verlag) may be employed in these syntheses.

The benzoic amide group as in Formula XVII can be protected by an acid labile group, especially by alkoxymethyl or silylalkoxymethyl groups as mentioned for example in 'Protective Groups in Organic Synthesis', T. W. Greene and P. G. M. Wuts, Wiley-Interscience. Especially useful is the use of 2-trimethylsilylethoxymethylchloride as alkylating agent after having removed the amide proton by a strong base such as NaH in an inert solvent like DMF, THF or dioxan. The products are compounds of the formula XVIII.

Cyclisation of compounds like formula XVIII can be performed with the aid of a palladium catalyst like Pd(PPh$_3$)$_4$ (tetrakis(triphenylphosphine)palladium(0) and a base like potassium acetate or sodium, potassium or cesium carbonate or phosphate, especially sodium carbonate in a suitable solvent, e.g. DMF, preferably under elevated temperature. This results in the formation of compound of the formula XIXa and XIXb, which can be separated or processed further as a mixture.

Compounds like XIXa or XIXb or a mixture thereof can be deprotected in acidic medium. Deprotection of functional groups is described in 'Protective Groups in Organic Synthesis', T. W. Greene and P. G. M. Wuts, Wiley-Interscience. For example, an acid such as formic acid, p-toluenesulfonic acid, trifluoroacetic acid or HCl may be used in a suitable solvent such as water, DCM or dioxane and can be performed on the crude amide coupling product to provide a compound of Formula XXa and XXb. Another method to deprotect first the tert-butoxycarbonyl is the reaction with trimethyliodosilane or trimethylchlorosilane in combination with sodium iodide in an appropriate solvent like acetonitrile, DMF or DCM. After that the trimethylsilylmethoxymethyl group can be removed in acidic medium as mentioned above, especially with formic acid again leading to compounds of the formula XXa and XXb.

SYNTHETIC EXAMPLES

The following are representative compounds of the invention which can be made by the general synthetic schemes, the examples, and known methods in the art. Starting materials and intermediates were either commercially available and purchased from catalogues of AATPHARM, ABCR, ACROS, ACTIVATE, ALDRICH, ALFA, ALLICHEM, ANICHEM, ANISYN, ANISYN Inc., APAC, APOLLO, APOLLO-INTER, ARKPHARM, ARKPHARMINC, ASIBA PHARMATECH, ATOMOLE, BACHEM, BEPHARM, BIOFOCUS, BIOGENE, BORON-MOL, BOROPHARM, CHEMBRIDGE, CHEMCOLLECT, CHEMFUTURE, CHEMGENX, CHEMIMPEX, CHESS, COMBI-BLOCKS, COMBIPHOS, DLCHIRAL, EGA, E-MERCK, EMKA-CHEMIE, ENAMINE, EPSILON, FLROCHEM, FLUKA, FOCUS, FRONTIER, ISOCHEM, JW PHARMLAB, KINGSTONCHEM, LANCASTER, MANCHESTER, MANCHESTER ORGANICS, MAYBRIDGE, MAYBR-INT, MERCACHEM, MERCK, MILESTONE, MOLBRIDGE, NETCHEM, OAKWOOD, PHARMABRIDGE, PLATTE, RIEDEL DE HAEN, SMALL-MOL, SPECS, SPECTRA GROUP LIMITED, INC, SYNCHEM OHG, SYNCHEM-INC, SYNCOM, TCI, VIJAYA PHARMA, WAKO, WUXI-APPTEC or were synthesized according to literature or as described below in "Synthesis of starting materials/educts"

"Liquid chromatography-mass spectroscopy" (LCMS) retention time and observed m/z data for the compounds below are obtained by one of the following methods:

LC-MS Method 001_CA07

| | | | | |
|---|---|---|---|---|
| Device-Description Waters Acquity with DAD and MSD | | | | |
| Column Waters Sunfire C18 | | | | |
| Column Dimension 2.1 × 50 mm | | | | |
| Particle Size 2.5 µm | | | | |

| Gradient/Solvent Time [min] | % Sol [H$_2$O 0.1% TFA] | % Sol [Acetonitrile 0.08% TFA] | Flow [ml/min] | Temp [° C.] |
|---|---|---|---|---|
| 0.0 | 95.0 | 5.0 | 1.5 | 60.0 |
| 0.75 | 0.0 | 100.0 | 1.5 | 60.0 |
| 0.85 | 0.0 | 100.0 | 1.5 | 60.0 |

LC-MS Method 002_CA03

| | | | | |
|---|---|---|---|---|
| Device-Description Agilent 1100 with DAD and MSD | | | | |
| Column Waters Sunfire C18 | | | | |
| Column Dimension 3.0 × 30 mm | | | | |
| Particle Size 2.5 µm | | | | |

| Gradient/Solvent Time [min] | % Sol [H$_2$O 0.1% TFA] | % Sol [Acetonitrile] | Flow [ml/min] | Temp [° C.] |
|---|---|---|---|---|
| 0.0 | 99.0 | 1.0 | 2.0 | 60.0 |
| 0.9 | 0.0 | 100.0 | 2.0 | 60.0 |
| 1.1 | 0.0 | 100.0 | 2.0 | 60.0 |

LC-MS Method 002_CA07

| | | | | |
|---|---|---|---|---|
| Device-Description Waters Acquity with 3100 MS | | | | |
| Column Waters XBridge BEH C18 | | | | |
| Column Dimension 3.0 × 30 mm | | | | |
| Particle Size 1.7 µm | | | | |

| Gradient/Solvent Time [min] | % Sol [H$_2$O 0.1% NH4OH] | % Sol [Acetonitrile] | Flow [ml/min] | Temp [° C.] |
|---|---|---|---|---|
| 0.0 | 95.0 | 5.0 | 1.5 | 60.0 |
| 0.7 | 0.1 | 99.9 | 1.5 | 60.0 |
| 0.8 | 0.1 | 99.9 | 1.5 | 60.0 |
| 0.81 | 95.0 | 5.0 | 1.5 | 60.0 |
| 1.1 | 95.0 | 5.0 | 1.5 | 60.0 |

LC-MS Method 003_CA04

| | | | | |
|---|---|---|---|---|
| Device-Description Agilent 1100 with DAD and MSD | | | | |
| Column Waters XBridge C18 | | | | |
| Column Dimension 3.0 × 30 mm | | | | |
| Particle Size 2.5 µm | | | | |

| Gradient/Solvent Time [min] | % Sol [H$_2$O 0.1% NH4OH] | % Sol [Acetonitrile] | Flow [ml/min] | Temp [° C.] |
|---|---|---|---|---|
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

LC-MS Method 004_CA01

| | |
|---|---|
| Device-Description | Agilent 1100 with DAD, Waters Autosampler and MSD |
| Column | Waters Sunfire C18 |
| Column Dimension | 4.6 × 30 mm |
| Particle Size | 3.5 μm |

| Gradient/Solvent Time [min] | % Sol [H$_2$O 0.1% TFA] | % Sol [Acetonitrile] | Flow [ml/min] | Temp [° C.] |
|---|---|---|---|---|
| 0.0 | 98.0 | 2.0 | 2.5 | 60.0 |
| 1.5 | 0.0 | 100.0 | 2.5 | 60.0 |
| 1.8 | 0.0 | 100.0 | 2.5 | 60.0 |

LC-MS Method 004_CA05

| | |
|---|---|
| Device-Description | Waters Acquity with DAD and MSD, CTC Autosampler |
| Column | Waters XBridge C18 |
| Column Dimension | 3.0 × 30 mm |
| Particle Size | 2.5 μm |

| Gradient/Solvent Time [min] | % Sol [H$_2$O 0.1% NH$_4$OH] | % Sol [Acetonitrile] | Flow [ml/min] | Temp [° C.] |
|---|---|---|---|---|
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

LC-MS Method 004_CA07

| | |
|---|---|
| Device-Description | Waters Acquity with with 3100 MS |
| Column | YMC Triart C18 |
| Column Dimension | 2.0 × 30 mm |
| Particle Size | 1.9 μm |

| Gradient/Solvent Time [min] | % Sol [H$_2$O 0.1% NH4OH] | % Sol [Acetonitrile] | Flow [ml/min] | Temp [° C.] |
|---|---|---|---|---|
| 0.0 | 95.0 | 5.0 | 1.5 | 60.0 |
| 0.75 | 0.1 | 99.9 | 1.5 | 60.0 |
| 0.8 | 0.1 | 99.9 | 1.5 | 60.0 |
| 0.81 | 95.0 | 5.0 | 1.5 | 60.0 |
| 1.1 | 95.0 | 5.0 | 1.5 | 60.0 |

LC-MS Method 005_CA01

| | |
|---|---|
| Device-Description | Agilent 1100 with DAD, Waters Autosampler and MS-Detector |
| Column | Waters Sunfire C18 |
| Column Dimension | 3.0 × 30 mm |
| Particle Size | 2.5 μm |

| Gradient/Solvent Time [min] | % Sol [H$_2$O 0.1% TFA] | % Sol [Acetonitrile] | Flow [ml/min] | Temp [° C.] |
|---|---|---|---|---|
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

LC-MS Method V001_003

| | |
|---|---|
| Device-Description | Waters Alliance with DAD and MSD |
| Column | Waters XBridge C18 |
| Column Dimension | 4.6 × 30 mm |
| Particle Size | 3.5 μm |

| Gradient/Solvent Time [min] | % Sol [H2O, 0.1% TFA] | % Sol [Methanol] | Flow [ml/min] | Temp [° C.] |
|---|---|---|---|---|
| 0.0 | 95 | 5 | 4 | 60 |
| 0.20 | 95 | 5 | 4 | 60 |
| 1.5 | 0 | 100 | 4 | 60 |
| 1.75 | 0 | 100 | 4 | 60 |

LC-MS Method V001_007

| | |
|---|---|
| Device-Description | Waters Alliance with DAD and MSD |
| Column | Waters XBridge C18 |
| Column Dimension | 4.6 × 30 mm |
| Particle Size | 3.5 μm |

| Gradient/Solvent Time [min] | % Sol [H2O, 0.1% TFA] | % Sol [Methanol] | Flow [ml/min] | Temp [° C.] |
|---|---|---|---|---|
| 0.0 | 95 | 5 | 4 | 60 |
| 1.6 | 0 | 100 | 4 | 60 |
| 1.85 | 0 | 100 | 4 | 60 |
| 1.9 | 95 | 5 | 4 | 60 |

LC-MS Method V003_003

| | |
|---|---|
| Device-Description | Waters Alliance with DAD and MSD |
| Column | Waters XBridge C18 |
| Column Dimension | 4.6 × 30 mm |
| Particle Size | 3.5 μm |

| Gradient/Solvent Time [min] | % Sol [H$_2$O, 0.1% NH$_3$] | % Sol [Methanol] | Flow [ml/min] | Temp [° C.] |
|---|---|---|---|---|
| 0.0 | 95 | 5 | 4 | 60 |
| 0.2 | 95 | 5 | 4 | 60 |
| 1.5 | 0 | 100 | 4 | 60 |
| 1.75 | 0 | 100 | 4 | 60 |

LC-MS Method V011_S01

| | |
|---|---|
| Device-Description | Waters Alliance with DAD and MSD |
| Column | Waters XBridge C18 |
| Column Dimension | 4.6 × 30 mm |
| Particle Size | 3.5 μm |

| Solvent Gradient time [min] | % Sol [H$_2$O, 0.1% NH$_3$] | % Sol [Acetonitril] | Flow [ml/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

LC-MS Method V012_S01

| | |
|---|---|
| Device-Description | Waters Alliance with DAD and MSD |
| Column | Waters XBridge C18 |
| Column Dimension | 4.6 × 30 mm |
| Particle Size | 3.5 μm |

| Solvent Gradient time [min] | % Sol [H$_2$O, 0.1% TFA] | % Sol [Acetonitril] | Flow [ml/min] | Temp [° C.] |
|---|---|---|---|---|
| 0.0 | 97 | 3 | 5 | 60 |
| 0.2 | 97 | 3 | 5 | 60 |

| Device-Description Waters Alliance with DAD and MSD Column Waters XBridge C18 Column Dimension 4.6 × 30 mm Particle Size 3.5 μm | | | | |
|---|---|---|---|---|
| Solvent Gradient time [min] | % Sol [H$_2$O, 0.1% TFA] | % Sol [Acetonitril] | Flow [ml/min] | Temp [° C.] |
| 1.6 | 0 | 100 | 5 | 60 |
| 1.7 | 0 | 100 | 5 | 60 |

LC-MS Method V018_S01

| Device-Description Waters Alliance with DAD and MSD Column Waters Sunfire C18 Column Dimension 4.6 × 30 mm Particle Size 3.5 μm | | | | |
|---|---|---|---|---|
| Solvent Gradient time [min] | % Sol [H$_2$O, 0.1% TFA] | % Sol [Acetonitril] | Flow [ml/min] | Temp [° C.] |
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

LC-MS Method W018_S01

| Device-Description Waters 1525 with DAD and MSD Column Waters Sunfire C18 Column Dimension 4.6 × 30 mm Particle Size 2.5 μm | | | | |
|---|---|---|---|---|
| Solvent Gradient time [min] | % Sol [H$_2$O, 0.1% TFA] | % Sol [Acetonitril] | Flow [ml/min] | Temp [° C.] |
| 0.0 | 97 | 3 | 4 | 60 |
| 0.15 | 97 | 3 | 3 | 60 |
| 2.15 | 0 | 100 | 3 | 60 |
| 2.20 | 0 | 100 | 4.5 | 60 |
| 2.40 | 0 | 100 | 4.5 | 60 |

LC-MS Method X001_002

| Device-Description Waters Acquity with DAD and MSD Column Waters XBridge BEH C18 Column Dimension 2.1 × 30 mm Particle Size 1.7 μm | | | | |
|---|---|---|---|---|
| Gradient/Solvent Time [min] | % Sol [H$_2$O, 0.10% TFA] | % Sol [Methanol] | Flow [ml/min] | Temp [° C.] |
| 0.0 | 99 | 1 | 1.3 | 60 |
| 0.05 | 99 | 1 | 1.3 | 60 |
| 1.05 | 0 | 100 | 1.3 | 60 |
| 1.2 | 0 | 100 | 1.3 | 60 |

LC-MS Method X001_004

| Device-Description Waters Acquity with DAD and MSD Column Waters XBridge C18 Column Dimension 2.1 × 20 mm Particle Size 2.5 μm | | | | |
|---|---|---|---|---|
| Gradient/Solvent Time [min] | % Sol [H$_2$O, 0.10% TFA] | % Sol [Methanol] | Flow [ml/min] | Temp [° C.] |
| 0.0 | 95 | 5 | 1.4 | 60 |
| 0.05 | 95 | 5 | 1.4 | 60 |
| 1.00 | 0 | 100 | 1.4 | 60 |
| 1.1 | 0 | 100 | 1.4 | 60 |

LC-MS Method X002_002

| Device-Description Waters Acquity with DAD and MSD Column Waters Sunfire C18 Column Dimension 2.1 × 30 mm Particle Size 2.5 μm | | | | |
|---|---|---|---|---|
| Gradient/Solvent Time [min] | % Sol [H2O, 0.10% TFA] | % Sol [Methanol] | Flow [ml/min] | Temp [° C.] |
| 0.00 | 99 | 1 | 1.2 | 60 |
| 0.15 | 99 | 1 | 1.2 | 60 |
| 1.10 | 0 | 100 | 1.2 | 60 |
| 1.25 | 0 | 100 | 1.2 | 60 |

LC-MS Method X011_S02

| Device-Description Waters Acquity with DAD and MSD Column Waters XBridge BEH C18 Column Dimension 2.1 × 30 mm Particle Size 1.7 μm | | | | |
|---|---|---|---|---|
| Solvent Gradient time [min] | % Sol [H2O, 0.1% NH3] | % Sol [Acetonitril] | Flow [ml/min] | Temp [° C.] |
| 0.00 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

LC-MS Method X011_S03

| Device-Description Waters Acquity with DAD and MSD Column Waters XBridge BEH C18 Column Dimension 2.1 × 30 mm Particle Size 1.7 μm | | | | |
|---|---|---|---|---|
| Solvent Gradient time [min] | % Sol [H2O, 0.1% NH3] | % Sol [Acetonitril] | Flow [ml/min] | Temp [° C.] |
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

LC-MS Method X012_S01

| Device-Description Waters Acquity with DAD and MSD Column Waters XBridge BEH C18 Column Dimension 2.1 × 30 mm Particle Size 1.7 μm | | | | |
|---|---|---|---|---|
| Solvent Gradient time [min] | % Sol [H$_2$O, 0.1% TFA] | % Sol [Acetonitril] | Flow [ml/min] | Temp [° C.] |
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

LC-MS Method X012 S02

| | Device-Description Waters Acquity with DAD and MSD Column Waters XBridge BEH C18 Column Dimension 2.1 × 30 mm Particle Size 1.7 µm | | | |
|---|---|---|---|---|
| Solvent Gradient time [min] | % Sol [H2O, 0.1% TFA] | % Sol [Acetonitril] | Flow [ml/min] | Temp [° C.] |
| 0.0 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

LC-MS Method X016_S01

| | Device-Description Waters Acquity with DAD and MSD Column Waters XBridge BEH Phenyl Column Dimension 2.1 × 30 mm Particle Size 1.7 µm | | | |
|---|---|---|---|---|
| Solvent Gradient time [min] | % Sol [H$_2$O, 0.1% TFA] | % Sol [Acetonitril] | Flow [ml/min] | Temp [° C.] |
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

LC-MS Method X018_S01

| | Device-Description Waters Acquity with DAD and MSD Column Waters Sunfire C18 Column Dimension 2.1 × 30 mm Particle Size 2.5 µm | | | |
|---|---|---|---|---|
| Gradient/Solvent Time [min] | % Sol [H$_2$O, 0.1% TFA] | % Sol [Acetonitril] | Flow [ml/min] | Temp [° C.] |
| 0.0 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

LC-MS Method X018 S02

| | Device-Description Waters Acquity with DAD and MSD Column Waters Sunfire C18 Column Dimension 2.1 × 30 mm Particle Size 2.5 µm | | | |
|---|---|---|---|---|
| Gradient/Solvent Time [min] | % Sol [H$_2$O, 0.1% TFA] | % Sol [Acetonitril] | Flow [ml/min] | Temp [° C.] |
| 0.0 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

LC-MS Method Z001_002

| | Device-Description Agilent 1200 with DAD and MSD Column Waters XBridge C18 Column Dimension 3 × 30 mm Particle Size 2.5 µm | | | |
|---|---|---|---|---|
| Gradient/Solvent Time [min] | % Sol [H$_2$O, 0.1% TFA] | % Sol [Methanol] | Flow [ml/min] | Temp [° C.] |
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

LC-MS Method Z011_S03

| | Device-Description Agilent 1200 with DAD and MSD Column Waters XBridge C18 Column Demension 3 × 30 mm Particle Size 2.5 µm | | | |
|---|---|---|---|---|
| Gradient/Solvent Time [min] | % Sol [H$_2$O, 0.1% NH3] | % Sol [Acetonitril] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

LC-MS Method Z011_U03

| | Device-Description Agilent 1200 with DAD and MSD Column Waters XBridge C18 Column Dimension 3 × 30 mm Particle Size 2.5 µm | | | |
|---|---|---|---|---|
| Gradient/Solvent Time [min] | % Sol [H$_2$O, 0.1% NH3] | % Sol [Acetonitril] | Flow [ml/min] | Temp [° C.] |
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

LC-MS Method Z012 S04

| | Device-Description Agilent 1200 with DAD and MSD Column Waters XBridge C18 Column Dimension 3 × 30 mm Particle Size 2.5 µm | | | |
|---|---|---|---|---|
| Gradient/Solvent Time [min] | % Sol [H$_2$O, 0.1% NH3] | % Sol [Acetonitril] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

LC-MS Method Z018 S04

Device-Description Agilent 1200 with DAD and MSD
Column Waters Sunfire C18
Column Dimension 3 × 30 mm
Particle Size 2.5 μm

| Solvent Gradient time [min] | % Sol [H$_2$O, 0.1% TFA] | % Sol [Acetonitril] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

LC-MS Method Z020_S01

Device-Description Agilent 1200 with DAD and MSD
Column Waters Sunfire C18
Column Dimension 3 × 30 mm
Particle Size 2.5 μm

| Solvent Gradient time [min] | % Sol [H$_2$O, 0.1% FA] | % Sol [Acetonitril] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

LC-MS Method V001_007

Device-Description Waters Alliance with DA- and MS-Detector
Column XBridge C18
Column Dimension 4.6 × 30 mm
Particle Size 3.5 μm

| Solvent Gradient time[min] | % Sol [H$_2$O, 0.1% FA] | % Sol [Methanol] | Flow [ml/min] | Temp [° C.] |
|---|---|---|---|---|
| 0.0 | 95 | 5 | 4.0 | 60 |
| 1.6 | 0 | 100 | 4.0 | 60 |
| 1.85 | 0 | 100 | 4.0 | 60 |
| 1.9 | 95 | 5 | 4.0 | 60 |

LC-MS Method I_ADH_15_MEOH_DEA.M

Device-Description Agilent 1260 SFC with DAD
Column Daicel Chiralpak AD-H
Column Dimension 4.6 × 250 mm
Particle Size 5 μm

| Solvent Gradient time [min] | % Sol [scCO$_2$] | % Sol [Methanol, 0.2% Diethylamine] | Flow [ml/min] | Temp [° C.] | Backpressure [bar] |
|---|---|---|---|---|---|
| 0.00 | 85 | 15 | 4 | 40 | 150 |
| 10.00 | 85 | 15 | 4 | 40 | 150 |

LC-MS Method I_OJH_10_IPROP_DEA.M

Device-Description Agilent 1260 SFC with DAD
Column Daicel Chiralcel OJ-H
Column Dimension 4.6 × 250 mm
Particle Size 5 μm

| Solvent Gradient time [min] | % Sol [scCO$_2$] | % Sol [Isopropanal, 0.2% Diethylamine] | Flow [ml/min] | Temp [° C.] | Backpressure [bar] |
|---|---|---|---|---|---|
| 0.00 | 90 | 10 | 4 | 40 | 150 |
| 10.00 | 90 | 10 | 4 | 40 | 150 |

LC-MS Method I_IC_20_MEOH_NH3.M

Device-Description Agilent 1260 SFC with DAD and MSD
Column Daicel Chiralpak IC
Column Dimension 4.6 × 250 mm
Particle Size 5 μm

| Solvent Gradient time [min] | % Sol [scCO$_2$] | % Sol [20 mM NH3 in Methanol] | Flow [ml/min] | Temp [° C.] | Backpressure [bar] |
|---|---|---|---|---|---|
| 0.00 | 80 | 20 | 4 | 40 | 150 |
| 10.00 | 80 | 20 | 4 | 40 | 150 |

LC-MS Method I_ADH_40_MEOH_DEA.M

Device-Description Agilent 1260 SFC with DAD
Column Daicel Chiralpak AD-H
Column Dimension 4.6 × 250 mm
Particle Size 5 μm

| Solvent Gradient time [min] | % Sol [scCO$_2$] | % Sol [Methanol, 0.2% Diethylamine] | Flow [ml/min] | Temp [° C.] | Backpressure [bar] |
|---|---|---|---|---|---|
| 0.00 | 60 | 40 | 4 | 40 | 150 |
| 10.00 | 60 | 40 | 4 | 40 | 150 |

LC-MS Method I_ASH_30_10 MIN_SS4P.M

Device-Description Berger SFC Analytix with DAD
Column Daicel Chiralpak AS-H
Column Dimension 4.6 × 250 mm
Particle Size 5 μm

| Solvent Gradient time [min] | % Sol [scCO$_2$] | % Sol [Ethanol, 0.2% Diethylamine] | Flow [ml/min] | Temp [° C.] | Backpressure [bar] |
|---|---|---|---|---|---|
| 0.00 | 70 | 30 | 4 | 40 | 120 |
| 10.00 | 70 | 30 | 4 | 40 | 120 |

LC-MS Method I_OJH_10_MEOH_DEA.M

| Device-Description Agilent 1260 SFC with DAD Column Daicel Chiralcel OJ-H Column Dimension 4.6 × 250 mm Particle Size 5 μm | | | | | |
|---|---|---|---|---|---|
| Solvent Gradient time [min] | % Sol [scCO$_2$] | % Sol [Methanol, 0.2% Diethylamine] | Flow [ml/min] | Temp [° C.] | Backpressure [bar] |
| 0.00 | 90 | 10 | 4 | 40 | 150 |
| 10.00 | 90 | 10 | 4 | 40 | 150 |

Mixture of stereoisomers can be separated on preparative scale by one of the following chiral SFC methods. 2× describes two columns switched in a row.
Methode: Chiral SFC A
Column: 2× Daicel Chiralpak AD-H 5 μm 20×250 mm
Eluent: 85% scCO$_2$, 15% Methanol 0.2% Diethylamine
Flow: 55 mL/min
Temperature: 40° C.
Backpressure: 120 bar
Wavelength: 254 nm
Concentration: 52 mg/ml in Methanol
Injection volume: 300 μl
Device-Description: Thar MultiGram II
Methode: Chiral SFC B
Column: 2× Chiralcel OJ-H 5 μm, 20×250 mm
Eluent: 90% scCO$_2$, 10% Isopropanol 0.2% Diethylamine
Flow: 60 mL/min
Temperature: 40° C.
Backpressure: 150 bar
Wavelength: 254 nm
Concentration: 50 mg/ml in Methanol
Injection volume: 200 μl
Device-Description: Janco Rockclaw 150
Methode: Chiral SFC C
Column: 2× Daicel Chiralpak AD-H 5 nm, 10×250 mm
Eluent: 85% scCO$_2$, 15% Methanol 0.2% Diethylamine
Flow: 10 mL/min
Temperature: 40° C.
Backpressure: 120 bar
Wavelength: 254 nm
Concentration: 15 mg/ml in Methanol
Injection volume: 100 μl
Device-Description: Thar MiniGram
Methode: Chiral SFC D
Column: 1× Daicel Chiralpak AD-H, 5 μm, 20×250 mm
Eluent: 60% scCO$_2$, 40% Methanol 0.2% Diethylamine
Flow: 60 mL/min
Temperature: 40° C.
Backpressure: 120 bar
Wavelength: 254 nm
Concentration: 50 mg/ml in Methanol
Injection volume: 400 μl
Device-Description: Thar MultiGram II
Methode: Chiral SFC E
Column: 2× Daicel Chiralpak AS-H 5 μm, 20×250 mm
Eluent: 70% CO$_2$, 30% Ethanol 0.2% Diethylamine
Flow: 55 mL/min
Temperature: 40° C.
Backpressure: 120 bar
Wavelength: 254 nm
Concentration: 100 mg/ml in Methanol
Injection volume: 200 μl
Device-Description: Thar MultiGram II Methode: Chiral SFC F
Column: Daicel Chiralpak IC 5 nm, 20×250 mm
Eluent: 85% scCO$_2$, 15% Ethanol
Flow: 60 mL/min
Temperature: 40° C.
Backpressure: 150 bar
Wavelength: 254 nm
Concentration: 35 mg/ml in Methanol
Injection volume: 500 μl
Device-Description: Sepiatec Prep SFC 100
Methode: Chiral SFC G
Column: Chiralpak AY-10 μm, 50×300 mm
Eluent: A for CO$_2$, and B for ethanol: n-heptane=1:1
Gradient: B 10%
Flow: 170 mL/min
Temperature: 38° C.
Backpressure: 100 bar
Wavelength: 220 nm
Concentration: 300 mg/ml in ethanol
Injection volume: 4 mL per injection
Cycle time: 3.5 min
Device-Description: Thar 200 preparative SFC
Synthesis Methods
Method A Synthesis of (1S,2S,4R)-N-[(1S)-1-cyano-2-[2-fluoro-4-(2-methylisoindolin-5-yl)phenyl]ethyl]-3-azabicyclo[2.2.1]heptane-2-carboxamide (Example 1)

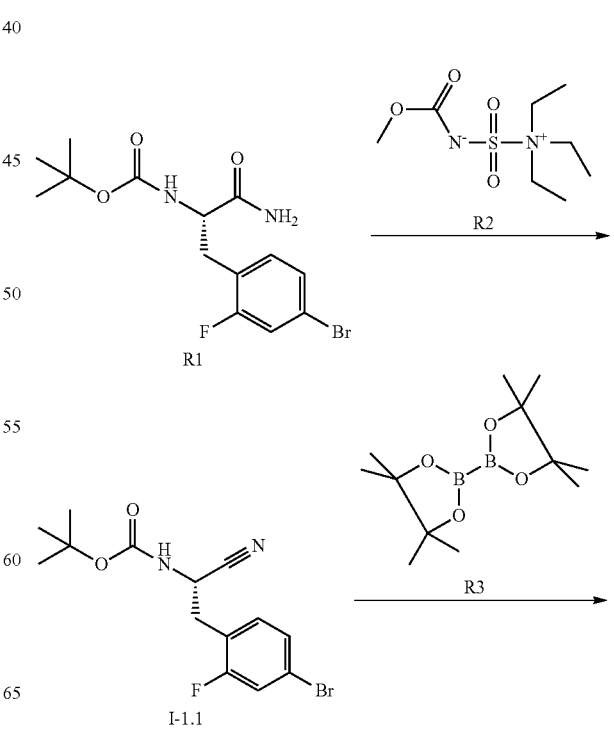

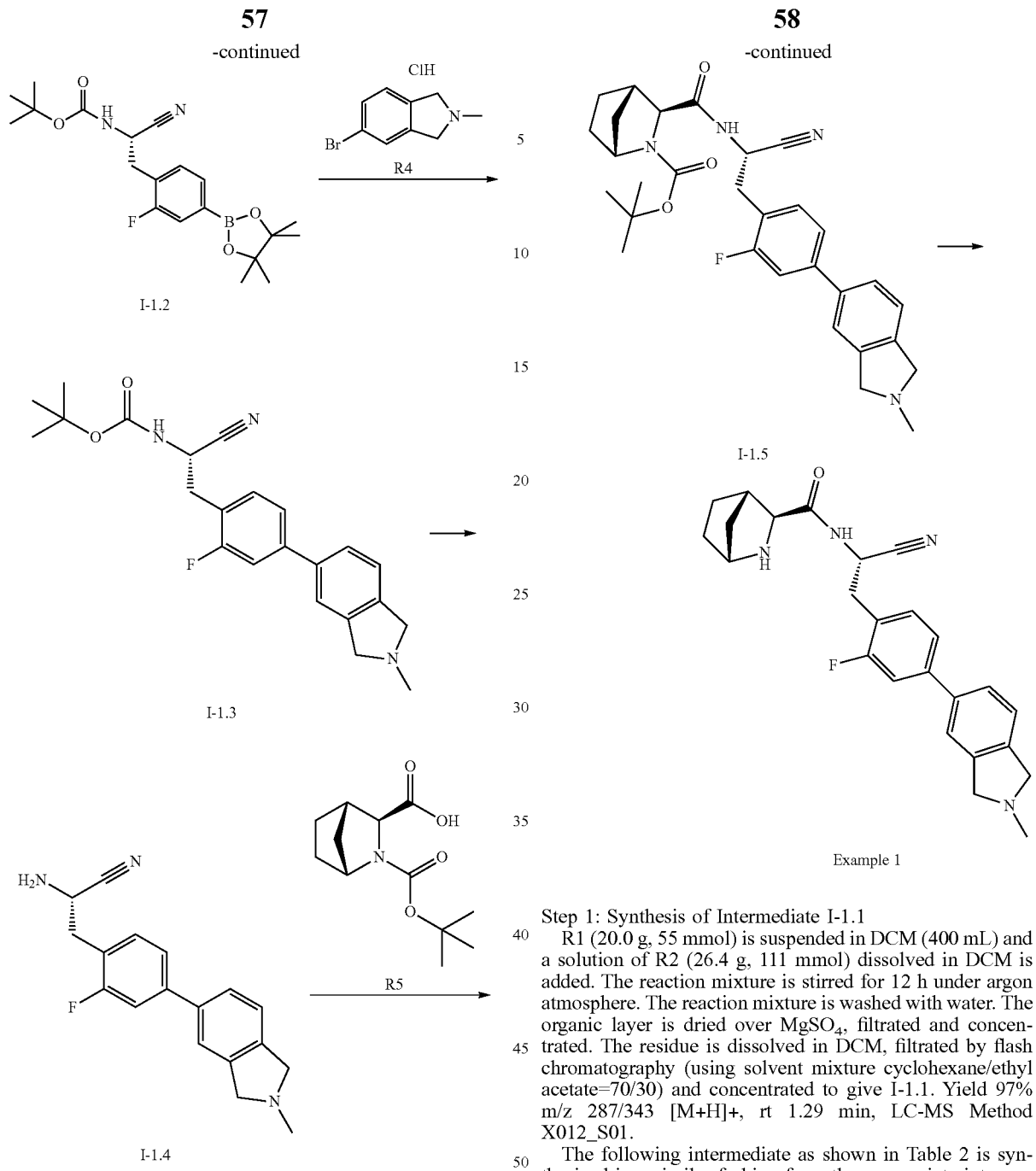

Example 1

Step 1: Synthesis of Intermediate I-1.1

R1 (20.0 g, 55 mmol) is suspended in DCM (400 mL) and a solution of R2 (26.4 g, 111 mmol) dissolved in DCM is added. The reaction mixture is stirred for 12 h under argon atmosphere. The reaction mixture is washed with water. The organic layer is dried over $MgSO_4$, filtrated and concentrated. The residue is dissolved in DCM, filtrated by flash chromatography (using solvent mixture cyclohexane/ethyl acetate=70/30) and concentrated to give I-1.1. Yield 97% m/z 287/343 [M+H]+, rt 1.29 min, LC-MS Method X012_S01.

The following intermediate as shown in Table 2 is synthesized in a similar fashion from the appropriate intermediates:

TABLE 2

| Intermediate | Educt | Structure | m/z [M + H]+ | rt (min) | LC-MS method |
|---|---|---|---|---|---|
| I-1.1.1 | R1.1 | 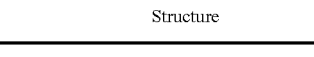 | 391 | 1.29 | V012_S01 |

Step 2: Synthesis of Intermediate I-1.2

To I-1.1 (5.80 g, 17 mmol) in anhydrous dioxane (60 mL) R3 (5.20 g, 20 mmol) and potassium acetate (4.98 g, 51 mmol) are added. The mixture is purged with argon, [1,1'-Bis(diphenylphosphino)ferrocene]dichloropalladium(II) (PdCl$_2$(dppf)) (1.38 g, 1.7 mmol) is added to the mixture and heated to 80° C. for 2 h. DCM is added and the mixture is filtrated. The filtrate is diluted with water and extracted with DCM. The organic layer is dried over MgSO$_4$, filtrated and concentrated. The residue is purified by flash chromatography (cyclohexane/ethyl acetate=8/2) and concentrated. Yield 97% m/z 291/335/391 [M+H]+, rt 1.36 min, LC-MS Method V012_S01.

Step 3: Synthesis of Intermediate I-1.3

I-1.2 (1.22 g, 5 mmol) and R4 (2.30 g, 5.9 mmol) are dissolved in acetonitrile (25 mL). Na$_2$CO$_3$-solution (2 mol/L, 4.9 mL) and 1,1'-Bis(di-tert-butylphosphino)ferrocene-palladium dichloride (319 mg, 0.49 mmol) are added. The reaction mixture is stirred at 80° C. for 1 h. The crude mixture is extracted with ethyl acetate, washed with half saturated brine. The organic layer is dried over MgSO$_4$, filtrated and concentrated and the residue is purified by reversed phase HPLC. Yield 59%, m/z=396 [M+H]+, rt 0.96 min, LC-MS Method V012_S01.

The following intermediates as shown in Table 3 are synthesized in a similar fashion from the appropriate intermediates:

TABLE 3

| Intermediate | Educt | Structure of Intermediate | m/z [M + H]+ | rt (min) | LC-MS method |
|---|---|---|---|---|---|
| I-1.3.1 | I-1.1.1, direct coupling with boronic ester R7.3 | | 444 | 1.21 | V-018_S01 |
| I-1.3.2 | I-1.2 | | 446 | 1.18 | V012_S01 |

TABLE 3-continued

| Intermediate | Educt | Structure of Intermediate | m/z [M + H]+ | rt (min) | LC-MS method |
|---|---|---|---|---|---|
| I-1.3.3 | I-1.1, direct coupling with boronic ester R7.1 | | 444 | 1.14 | V011_S01 |

Step 4: Synthesis of Intermediate I-1.4

I-1.3 (1.15 g, 2.91 mmol) is dissolved in acetonitrile. 1.39 g p-toluenesulfonic acid monohydrate is added and stirred for 48 h. The precipitate is filtered off, dissolved in ethyl acetate and washed with saturated NaHCO₃-solution. The organic layer is dried over MgSO₄, filtrated and concentrated. Yield 78%. m/z 296 [M+H]+, rt 1.03 min, LC-MS Method V011_S01.

The following intermediates as shown in Table 4 are synthesized in a similar fashion from the appropriate intermediates:

TABLE 4

| Intermediate | Educt | Structure of Intermediate | m/z [M + H]+ | rt (min) | LC-MS method |
|---|---|---|---|---|---|
| I-1.4.1 | I-1.3.1 | 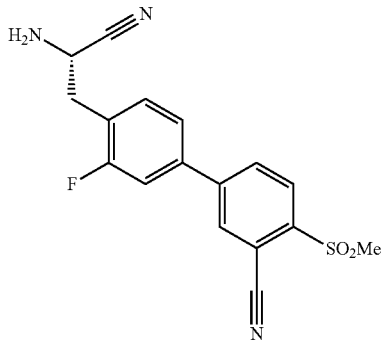 [SMILES: CS(=O)(=O)c1ccc(-c2ccc(C[C@H](N)C#N)c(F)c2)cc1C#N] | 344 | 0.76 | V018_S01 |
| I-1.4.2 | I-1.3.2 | 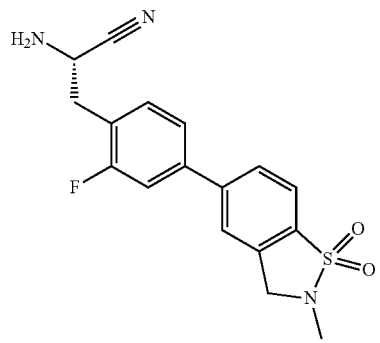 [SMILES: CN1Cc2cc(-c3ccc(C[C@H](N)C#N)c(F)c3)ccc2S1(=O)=O] | 346 | 0.96 | V011_S01 |

TABLE 4-continued

| Intermediate | Educt | Structure of Intermediate | m/z [M + H]+ | rt (min) | LC-MS method |
|---|---|---|---|---|---|
| I-1.4.3 | I-1.3.3 | H2N-CH(CN)-CH2-C6H3(F)-C6H3(SO2Me)-CN | 344 | 0.77 | V018_S01 |

Step 5: Synthesis of Intermediate I-1.5

To R5 (purchased from Aldrich or synthesized in analogy to Tararov et al, Tetrahedron Asymmetry 13 (2002), 25-28) (98 mg, 0.4 mmol) in DMF (1.5 mL) diisopropylethylamine (0.18 mL, 1.0 mmol) and HATU (154 mg, 0.4 mmol) are added and the reaction mixture is stirred for 15 min. Then intermediate I-1.4 (100 mg, 0.3 mmol) is added and the mixture is stirred for 12 h. DCM is added and the mixture is washed with saturated Na2CO3 solution. The organic layer is dried over MgSO$_4$, filtrated, and the residue is concentrated. Then the residue is purified by reversed phase HPLC. Yield 68%, m/z 419/463/518 [M+H]+, rt 1.29 min, LC-MS Method V011_S01.

The following intermediates as shown in Table 5 are synthesized in a similar fashion from the appropriate intermediates:

TABLE 5

| Intermediate | Educt | Structure of Intermediate | m/z [M + H]+ | rt (min) | LC-MS method |
|---|---|---|---|---|---|
| I-1.5.1 | I-1.4.1 | (structure shown) | 567 | 1.24 | V018_S01 |
| I-1.5.2 | I-1.4.2 | (structure shown) | 569 | 1.24 | V011_S01 |

TABLE 5-continued

| Intermediate | Educt | Structure of Intermediate | m/z [M + H]+ | rt (min) | LC-MS method |
|---|---|---|---|---|---|
| I-1.5.3 | I-1.4.3 | | 567 | 1.14 | V011_S01 |

Step 6 : Synthesis of Example 1

To I-1.5 (120 mg, 0.23 mmol) in acetonitrile, p-toluenesulfonic acid monohydrate (110 mg, 0.58 mmol) is added and stirred for 3 d. The reaction solution is purified by reversed phase HPLC. Yield 47%, m/z 419 [M+H]+, rt 1.16 min, LC-MS Method V011_S01.

Method A1

Synthesis of (1S,2S,4R)-N-[(1S)-1-cyano-2-[2-fluoro-4-(1-methyl-2-oxo-indolin-6-yl)phenyl]ethyl]-3-azabicyclo[2.2.1]heptane-2-carboxamide (Example 2)

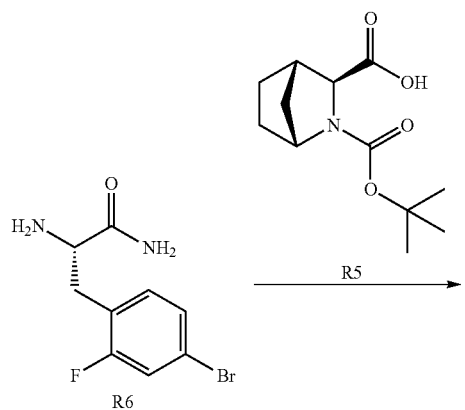

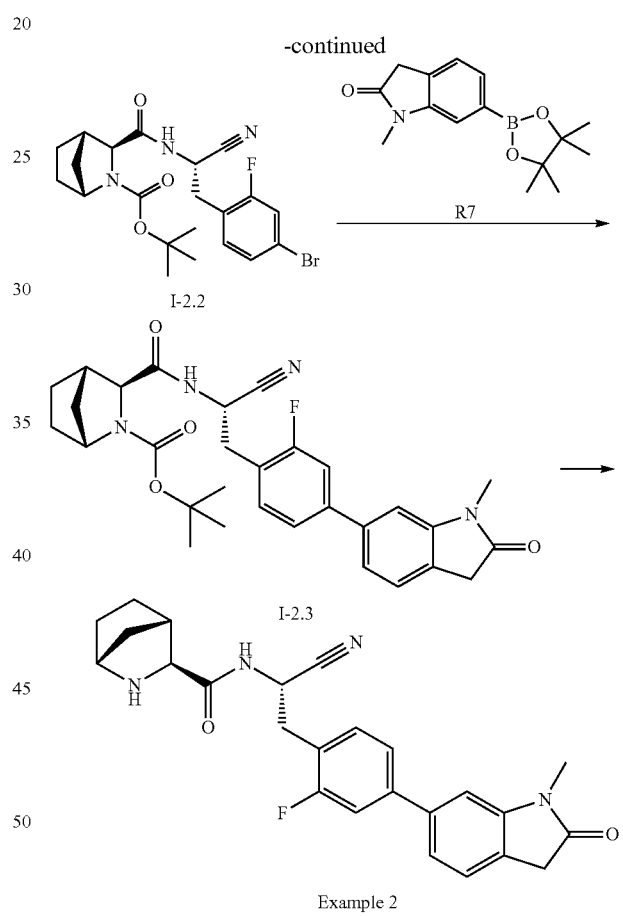

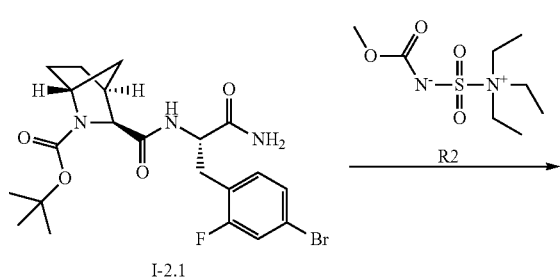

Step 1: Synthesis of Intermediate I-2.1

To R5 (7.59 g, 31 mmol) in DCM (300 mL) diisopropylethylamine (4.8 mL, 28 mmol) and HATU (11.5 g, 30 mmol) are added and stirred for 25 min. Then R6 (10.4 g, 28 mmol) and diisopropylethylamine (7.2 mL, 42 mmol) are added and stirred for 3 h. The solvent is evaporated, dissolved in ethyl acetate and washed with water, 0.5 M HCl and aq. NaHCO3 solution (10%). The organic layer is dried over MgSO$_4$, filtrated and concentrated. The residue is purified by flash chromatography (using solvent mixture DCM/methanol=95/5). Yield >95%, m/z 484 [M+H]+, rt 1.18 min, LC-MS Method V011_S01.

The following intermediates as shown in Table 6 are synthesized in a similar fashion from the appropriate intermediate:

TABLE 6

| Intermediate | Structure | m/z [M + H]+ | rt (min) | LC-MS method |
|---|---|---|---|---|
| I-2.1.1 | 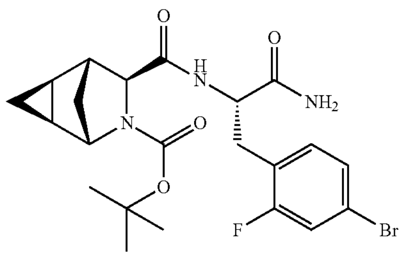 [SMILES: CC(C)(C)OC(=O)N1[C@H](C(=O)N[C@@H](Cc2ccc(Br)cc2F)C(N)=O)[C@@H]2C[C@H]1[C@H]1C[C@@H]21] | 496 | 0.95 | Z018_S04 |
| I-2.1.2 | 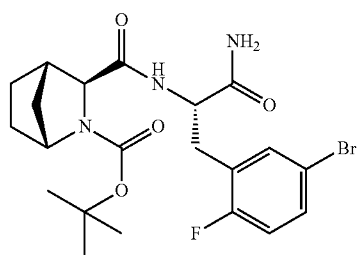 [SMILES: CC(C)(C)OC(=O)N1[C@@H]2CC[C@@H](C2)[C@H]1C(=O)N[C@@H](Cc1cc(Br)ccc1F)C(N)=O] | 484/486 | 0.71 | X018_S02 |
| I-2.1.3 | 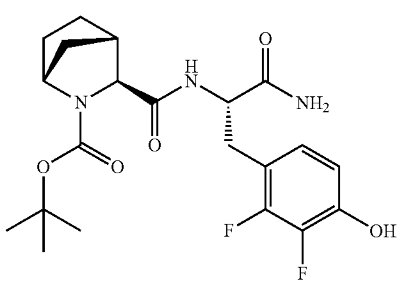 [SMILES: CC(C)(C)OC(=O)N1[C@@H]2CC[C@@H](C2)[C@H]1C(=O)N[C@@H](Cc1ccc(O)c(F)c1F)C(N)=O] | 440 | 0.55 | Z011_S03 |

Step 2: Synthesis of Intermediate I-2.2

To I-2.1 (12.7 g, 26 mmol) in DCM (130 mL) R2 (12.5 g, 52 mmol) is added. The reaction mixture is stirred for 12 h. The solvent is evaporated, dissolved in ethyl acetate and washed with water, 0.1 M HCl and aq. NaHCO3 solution (5%). The organic layer is dried over MgSO$_4$ and concentrated. The residue is recrystallized from DCM and acetonitrile. Yield 64% m/z 466 [M+H]+, rt 1.30 min, LC-MS Method V011_S01.

The following intermediates as shown in Table 7 are synthesized in a similar fashion from the appropriate intermediate:

TABLE 7

| Intermediate | Educt | Structure of Intermediate | m/z [M + H]+ | rt (min) | LC-MS method |
|---|---|---|---|---|---|
| I-2.2.1 | I-2.1.1 | | 478 | 1.03 | Z018_S04 |

TABLE 7-continued

| Intermediate | Educt | Structure of Intermediate | m/z [M + H]+ | rt (min) | LC-MS method |
|---|---|---|---|---|---|
| I-2.2.3 | I-2.1.2 | | 466/468 | 1.27 | V011_S01 |

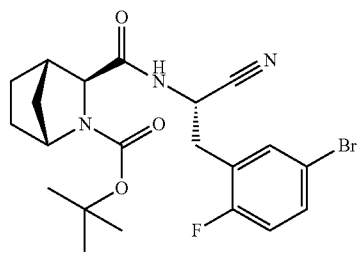 [SMILES: CC(C)(C)OC(=O)N1[C@@H]2CC[C@@H](C2)[C@H]1C(=O)N[C@H](C#N)Cc1cc(Br)ccc1F]

Synthesis of Intermediate I-2.2.2

Synthesis of tert-butyl(1S,2S,4R)-2-[[(1S)-2-amino-1-[[2,3-difluoro-4-trifluoromethylsulfonyl oxy)phenyl]methyl]-2-oxo-ethyl]carbamoyl]-3-azabicyclo[2.2.1]heptane-3-carboxylate

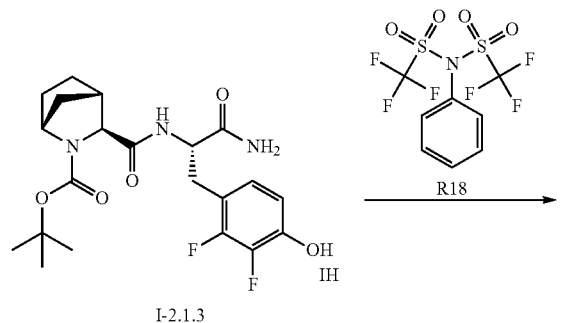

The phenol I-2.1.3 is transformed into the corresponding trifluoromethanesulfonate I-2.2.2:I.2.1.3 (200 mg, 0.46 mmol) is dissolved in anhydrous DCM (1.5 mL). Triethylamine (95 μL, 0.69 mmol) is added and the reaction mixture is cooled to 0° C. R18 (179 mg, 0.50 mmol) is then added and the mixture was stirred at 0° C. for 90 minutes and additional 12 h at room temperature. The mixture is concentrated and the residue is purified by reversed phase HPLC. Yield 85%, m/z 472 [M+H-BOC]+, rt 0.97 min, LC-MS Method Z011_S03.

Step 3: Synthesis of Intermediate I-2.3

To I-2.2 (5.00 g, 10 mmol) in acetonitrile (100 mL) R7 (3.07 g, 11 mmol) is added. The mixture is purged with argon, 1,1-Bis(di-tert-butylphosphino)ferrocene palladium dichloride (0.70 g, 1.1 mmol) and aq. sodium carbonate solution (2 mol/L, 1.07 mL) are added and the mixture is heated to 70° C. for 3.5 h. Ethyl acetate and water are added to the reaction mixture. The organic layer is washed with aq. NaHCO3 solution (5%) and water. The organic layer is dried over MgSO4 and concentrated. The residue is purified by flash chromatography (cyclohexane/ethyl acetate=1/1). Yield 41% m/z 533 [M+H]+, rt 1.25 min, LC-MS Method V011_S01.

The following intermediates as shown in Table 8 are synthesized in a similar fashion from the appropriate intermediates ((R,S)=1:1 mixture of stereoisomers at the carbon adjacent to the nitrile group):

TABLE 8

| Intermediate | Educt | Structure of Intermediate | m/z [M + H]+ | rt (min) | LC-MS method |
|---|---|---|---|---|---|
| I-2.3.1 | I-2.2 | | 560 | 0.76 | X018_S01 |
| I-2.3.2 | I-2.2 | | 528 | 0.88 | 004_CA01 |
| I-2.3.3 | I-2.2 | | 470 | 0.90 | 004_CA05 |
| I-2.3.4 | I-2.2 | | 510 | 0.87 | 004_CA05 |

TABLE 8-continued
| Intermediate | Educt | Structure of Intermediate | m/z [M + H]+ | rt (min) | LC-MS method |
|---|---|---|---|---|---|
| I-2.3.5 | I-2.2 | 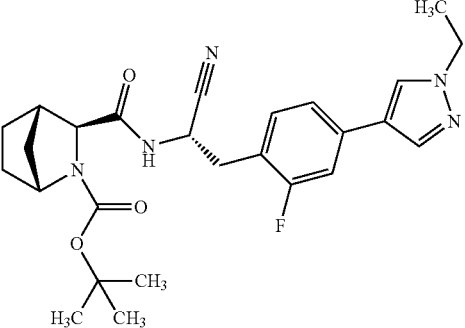 [SMILES: CCn1cc(-c2ccc(C[C@@H](C#N)NC(=O)[C@@H]3[C@H]4CC[C@H](C4)N3C(=O)OC(C)(C)C)c(F)c2)cn1] | 482 | 0.77 | 004_CA05 |
| I-2.3.6 | I-2.2 | 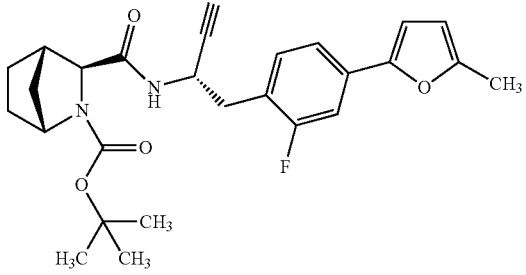 | 468 | 0.92 | 004_CA05 |
| I-2.3.7 | I-2.2 | 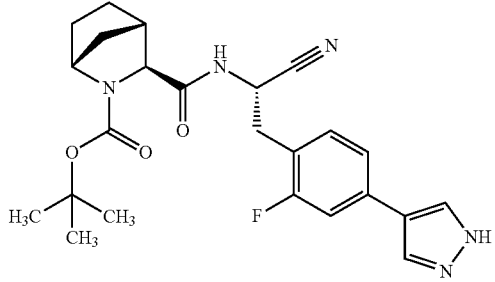 [SMILES: CC(C)(C)OC(=O)N1[C@@H]2CC[C@@H](C2)[C@H]1C(=O)N[C@H](C#N)Cc1ccc(-c2cn[nH]c2)cc1F] | 454 | 0.82 | Z011_S03 |
| I-2.3.8 | I-2.2 | 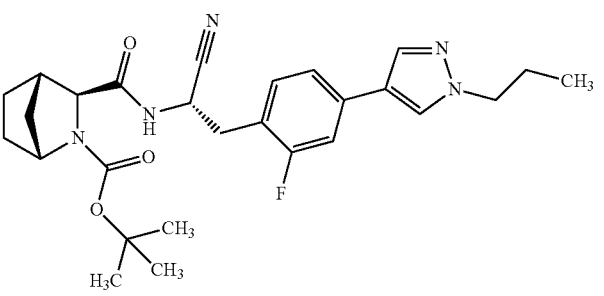 [SMILES: CCCn1cc(-c2ccc(C[C@@H](C#N)NC(=O)[C@@H]3[C@H]4CC[C@H](C4)N3C(=O)OC(C)(C)C)c(F)c2)cn1] | 496 | 0.82 | 004_CA05 |
| I-2.3.9 | I-2.2 | 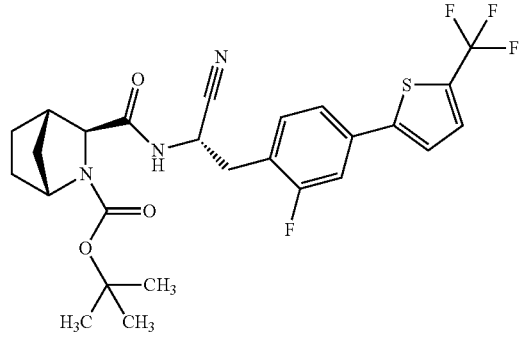 [SMILES: CC(C)(C)OC(=O)N1[C@@H]2CC[C@@H](C2)[C@H]1C(=O)N[C@H](C#N)Cc1ccc(-c2ccc(C(F)(F)F)s2)cc1F] | 538 | 1.00 | 004_CA05 |

TABLE 8-continued
| Intermediate | Educt | Structure of Intermediate | m/z [M + H]+ | rt (min) | LC-MS method |
|---|---|---|---|---|---|
| I-2.3.10 | I-2.2 | 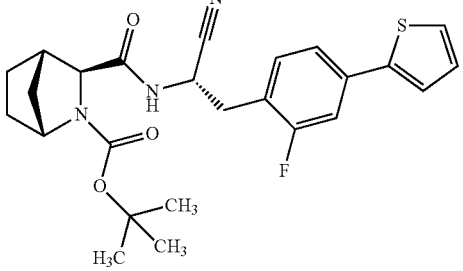 | 470 | 0.91 | 004_CA05 |
| I-2.3.11 | I-2.2 | 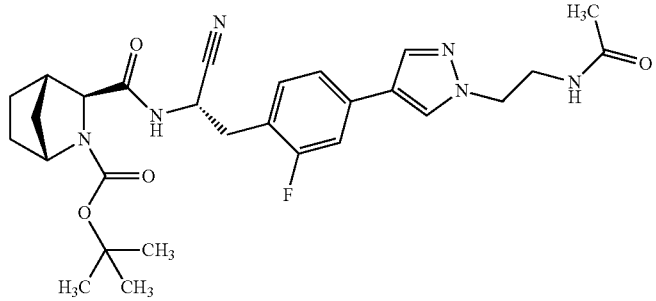 [SMILES: CC(=O)NCCn1cc(-c2ccc(C[C@@H](C#N)NC(=O)[C@@H]3[C@H]4CC[C@H](C4)N3C(=O)OC(C)(C)C)c(F)c2)cn1] | 539 | 0.66 | 004_CA05 |
| I-2.3.12 | I-2.2 | 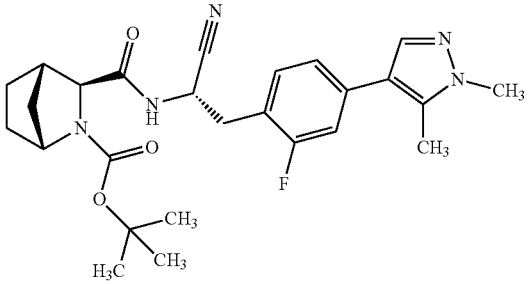 [SMILES: Cc1c(-c2ccc(C[C@@H](C#N)NC(=O)[C@@H]3[C@H]4CC[C@H](C4)N3C(=O)OC(C)(C)C)c(F)c2)cnn1C] | 482 | 0.75 | 004_CA05 |
| I-2.3.13 | I-2.2.1 | 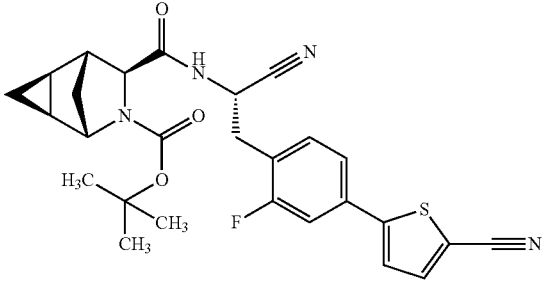 [SMILES: CC(C)(C)OC(=O)N1[C@H](C(=O)N[C@H](C#N)Cc2ccc(-c3ccc(C#N)s3)cc2F)[C@@H]2C[C@H]1[C@H]1C[C@@H]21] | 407 | 1.03 | Z018_S04 |
| I-2.3.14 | I-2.2 | 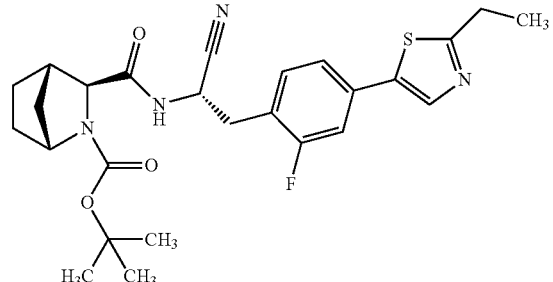 | 499 | 0.86 | 004_CA05 |

TABLE 8-continued
| Intermediate | Educt | Structure of Intermediate | m/z [M + H]+ | rt (min) | LC-MS method |
|---|---|---|---|---|---|
| I-2.3.15 | I-2.2 | 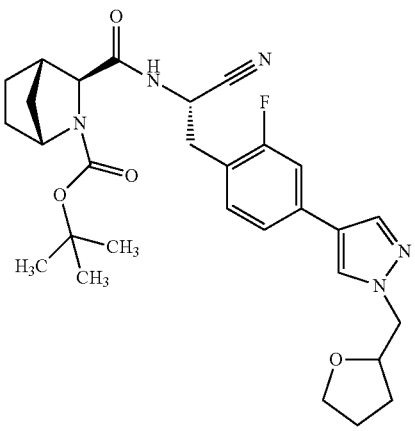 [SMILES: CC(C)(C)OC(=O)N1[C@@H]2CC[C@@H](C2)[C@H]1C(=O)N[C@H](C#N)Cc1ccc(-c2cnn(CC3CCCO3)c2)cc1F] | 438 [M + H − BOC]+ | 0.94 | X018_S04 |
| I-2.3.16 | I-2.2 | 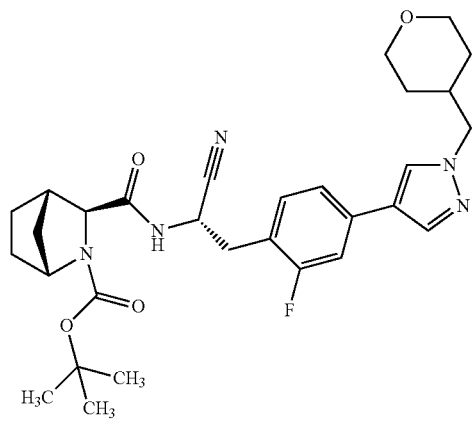 [SMILES: CC(C)(C)OC(=O)N1[C@@H]2CC[C@@H](C2)[C@H]1C(=O)N[C@H](C#N)Cc1ccc(-c2cnn(CC3CCOCC3)c2)cc1F] | 552 | 0.77 | 004_CA05 |
| I-2.3.17 | I-2.2 | 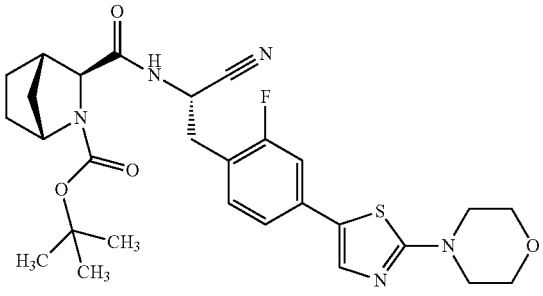 [SMILES: CC(C)(C)OC(=O)N1[C@@H]2CC[C@@H](C2)[C@H]1C(=O)N[C@H](C#N)Cc1ccc(-c2cnc(N3CCOCC3)s2)cc1F] | 556 | 0.91 | X018_S04 |
| I-2.3.18 | I-2.2 | 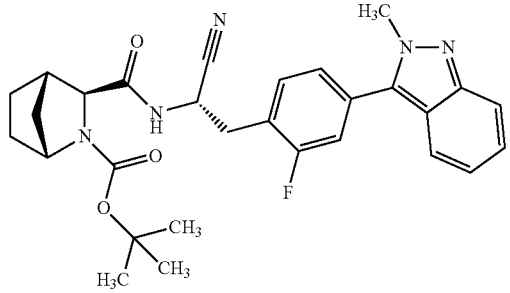 [SMILES: Cn1nc2ccccc2c1-c1ccc(C[C@@H](C#N)NC(=O)[C@@H]2[C@H]3CC[C@H](C3)N2C(=O)OC(C)(C)C)c(F)c1] | 518 | 0.89 | 004_CA05 |

TABLE 8-continued
| Intermediate | Educt | Structure of Intermediate | m/z [M + H]+ | rt (min) | LC-MS method |
|---|---|---|---|---|---|
| I-2.3.19 | I-2.2 | 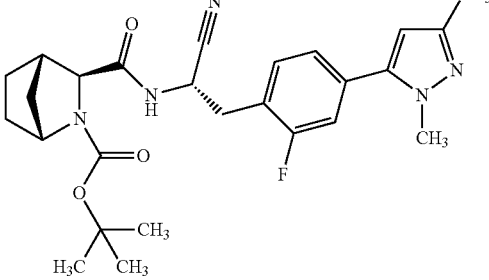 | 482 | 0.77 | 004_CA05 |
| I-2.3.20 | I-2.2 | 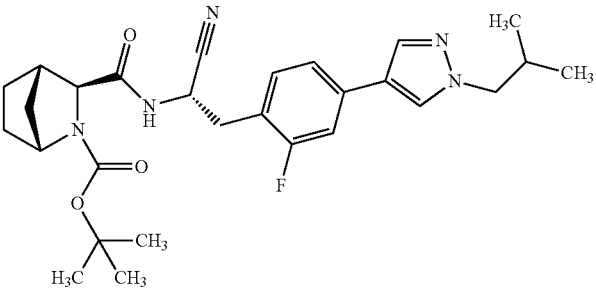 [SMILES: CC(C)Cn1cc(-c2ccc(C[C@@H](C#N)NC(=O)[C@@H]3[C@H]4CC[C@H](C4)N3C(=O)OC(C)(C)C)c(F)c2)cn1] | 510 | 0.86 | 004_CA05 |
| I-2.3.21 | I-2.2 | 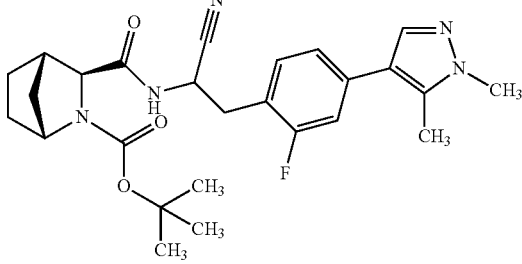 | 482 | 0.75 | 004_CA01 |
| I-2.3.22 | I-2.2 | 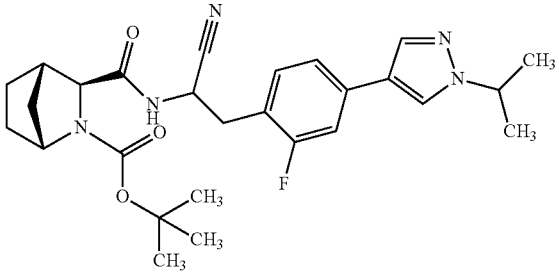 [SMILES: CC(C)n1cc(-c2ccc(CC(C#N)NC(=O)[C@@H]3[C@H]4CC[C@H](C4)N3C(=O)OC(C)(C)C)c(F)c2)cn1] | 496 | 0.82 | 004_CA01 |
| I-2.3.23 | I-2.2 | 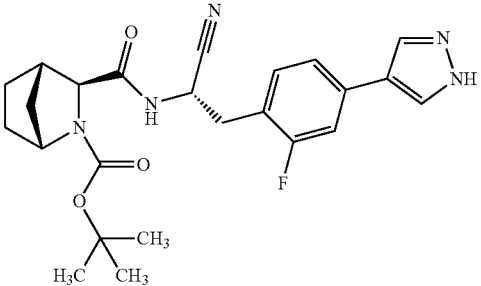 [SMILES: CC(C)(C)OC(=O)N1[C@@H]2CC[C@@H](C2)[C@H]1C(=O)N[C@H](C#N)Cc1ccc(-c2cn[nH]c2)cc1F] | 554 | 0.68 | 004_CA05 |

TABLE 8-continued
| Intermediate | Educt | Structure of Intermediate | m/z [M + H]+ | rt (min) | LC-MS method |
|---|---|---|---|---|---|
| I-2.3.24 | I-2.2.1 | 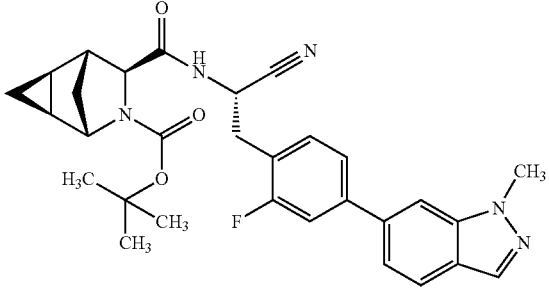 [SMILES: Cn1ncc2ccc(-c3ccc(C[C@@H](C#N)NC(=O)[C@@H]4[C@@H]5C[C@@H]([C@H]6C[C@@H]56)N4C(=O)OC(C)(C)C)c(F)c3)cc21] | 530 | 1.02 | Z018_S04 |
| I-2.3.25 | I-2.2 | 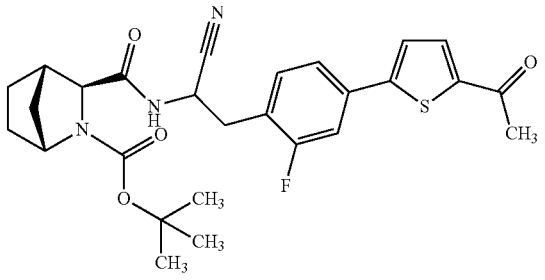 [SMILES: CC(=O)c1ccc(-c2ccc(CC(C#N)NC(=O)[C@@H]3[C@H]4CC[C@H](C4)N3C(=O)OC(C)(C)C)c(F)c2)s1] | 512 | 0.83 | 004_CA01 |
| I-2.3.26 | I-2.2 | 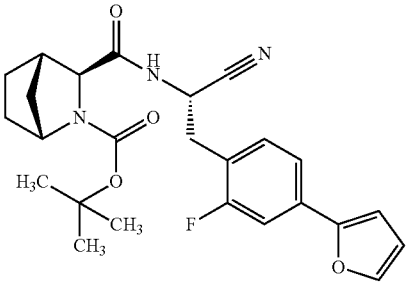 [SMILES: CC(C)(C)OC(=O)N1[C@@H]2CC[C@@H](C2)[C@H]1C(=O)N[C@H](C#N)Cc1ccc(-c2ccco2)cc1F] | 354 | 1.02 | Z018_S04 |
| I-2.3.27 | I-2.2 | 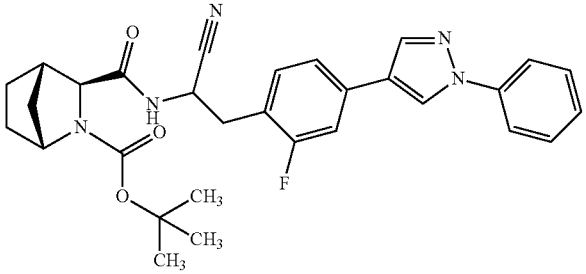 [SMILES: CC(C)(C)OC(=O)N1[C@@H]2CC[C@@H](C2)[C@H]1C(=O)NC(C#N)Cc1ccc(-c2cnn(-c3ccccc3)c2)cc1F] | 530 | 0.91 | 004_CA01 |
| I-2.3.28 | I-2.2 | 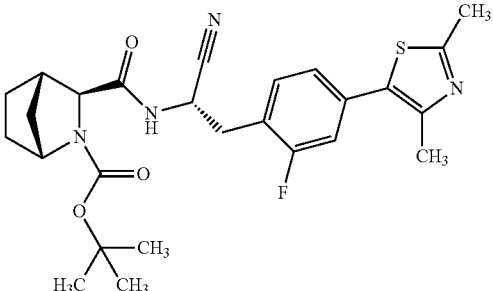 [SMILES: Cc1nc(C)c(-c2ccc(C[C@@H](C#N)NC(=O)[C@@H]3[C@H]4CC[C@H](C4)N3C(=O)OC(C)(C)C)c(F)c2)s1] | 499 | 0.82 | 004_CA05 |

TABLE 8-continued
| Intermediate | Educt | Structure of Intermediate | m/z [M + H]+ | rt (min) | LC-MS method |
|---|---|---|---|---|---|
| I-2.3.29 | I-2.2 | 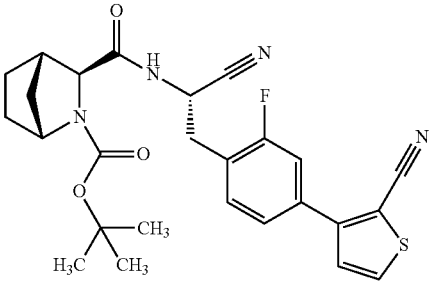 [SMILES: CC(C)(C)OC(=O)N1[C@@H]2CC[C@@H](C2)[C@H]1C(=O)N[C@H](C#N)Cc1ccc(-c2ccsc2C#N)cc1F] | 395 [M + H − BOC]+ | 1.02 | Z018_S04 |
| I-2.3.30 | I-2.2 | 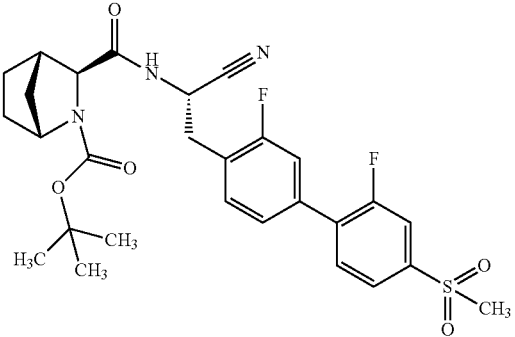 [SMILES: CC(C)(C)OC(=O)N1[C@@H]2CC[C@@H](C2)[C@H]1C(=O)N[C@H](C#N)Cc1ccc(-c2ccc(S(C)(=O)=O)cc2F)cc1F] | 560 | 0.76 | X018_S01 |
| I-2.3.31 | I-2.2 | 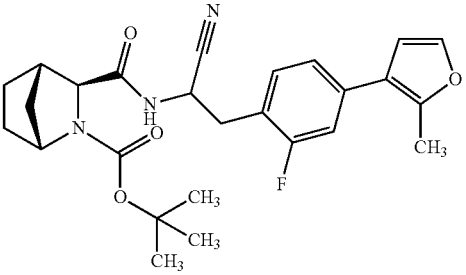 [SMILES: Cc1occc1-c1ccc(CC(C#N)NC(=O)[C@@H]2[C@H]3CC[C@H](C3)N2C(=O)OC(C)(C)C)c(F)c1] | 468 | 0.9 | 004_CA01 |
| I-2.3.32 | I-2.2.1 | 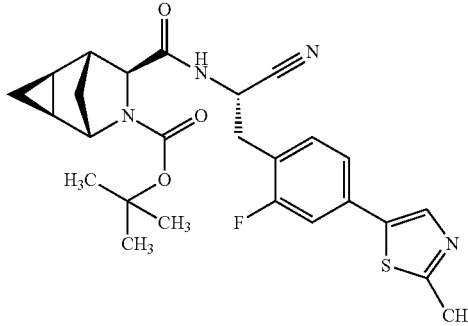 | 397 | 0.97 | Z018_S04 |

TABLE 8-continued
| Intermediate | Educt | Structure of Intermediate | m/z [M + H]+ | rt (min) | LC-MS method |
|---|---|---|---|---|---|
| I-2.3.33 | I-2.2 | 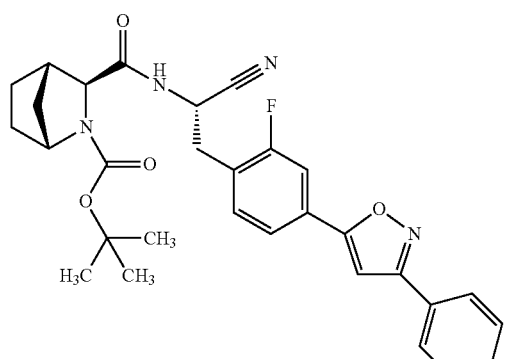 | 431 | 1.07 | Z018_S04 |
| I-2.3.34 | I-2.2 | 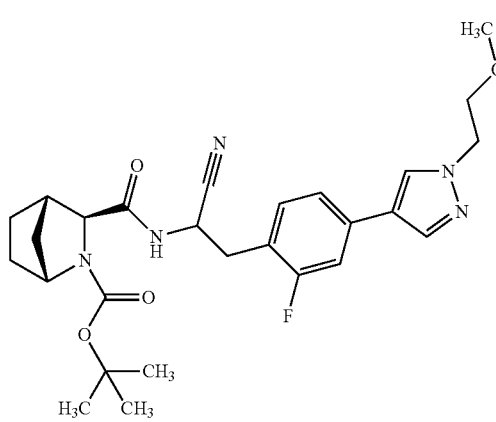 | 512 | 0.75 | 004_CA01 |
| I-2.3.35 | I-2.2 | 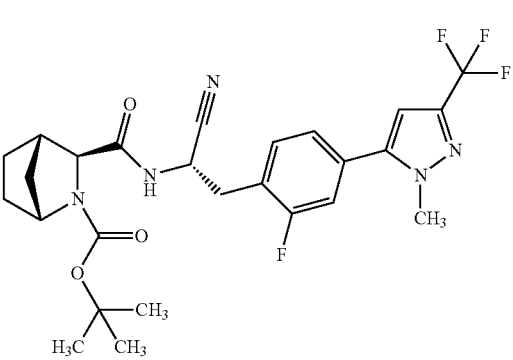 [SMILES: Cn1nc(C(F)(F)F)cc1-c1ccc(C[C@@H](C#N)NC(=O)[C@@H]2[C@H]3CC[C@H](C3)N2C(=O)OC(C)(C)C)c(F)c1] | 536 | 0.89 | 004_CA05 |
| I-2.3.36 | I-2.2 | 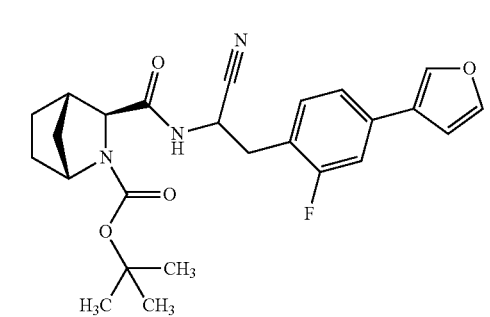 [SMILES: CC(C)(C)OC(=O)N1[C@@H]2CC[C@@H](C2)[C@H]1C(=O)NC(C#N)Cc1ccc(-c2ccoc2)cc1F] | 454 | 0.85 | 004_CA01 |

TABLE 8-continued
| Intermediate | Educt | Structure of Intermediate | m/z [M + H]+ | rt (min) | LC-MS method |
|---|---|---|---|---|---|
| I-2.3.37 | I-2.2 | 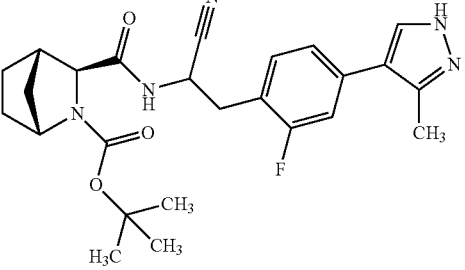 | 468 | 0.69 | 004_CA01 |
| I-2.3.38 | I-2.2 | 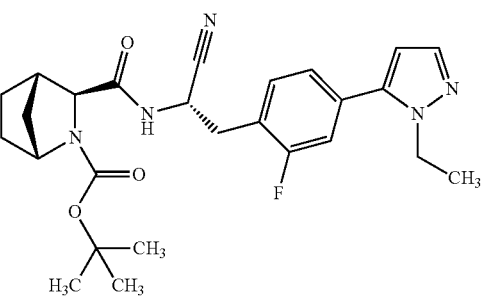 [SMILES: CCn1nccc1-c1ccc(C[C@@H](C#N)NC(=O)[C@@H]2[C@H]3CC[C@H](C3)N2C(=O)OC(C)(C)C)c(F)c1] | 482 | 0.78 | 004_CA01 |
| I-2.3.39 | I-2.2.1 | 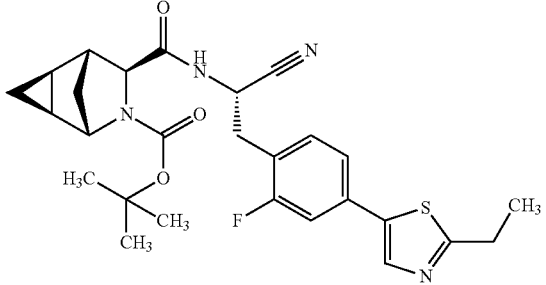 [SMILES: CCc1ncc(-c2ccc(C[C@@H](C#N)NC(=O)[C@@H]3[C@@H]4C[C@@H]([C@H]5C[C@@H]45)N3C(=O)OC(C)(C)C)c(F)c2)s1] | 411 | 1.01 | Z018_S04 |
| I-2.3.40 | I-2.2 | 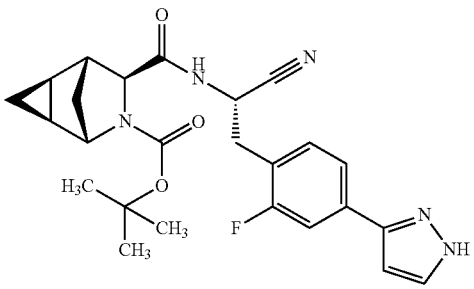 [SMILES: CC(C)(C)OC(=O)N1[C@H](C(=O)N[C@H](C#N)Cc2ccc(-c3cc[nH]n3)cc2F)[C@@H]2C[C@H]1[C@H]1C[C@@H]21] | 354 | 0.87 | Z018_S04 |
| I-2.3.41 | I-2.2 | 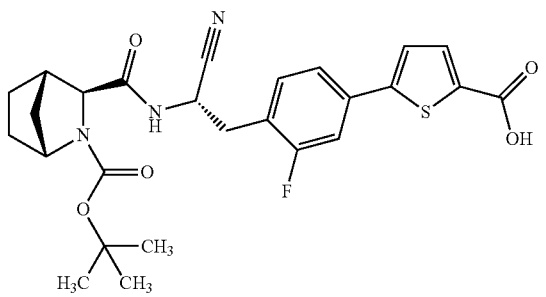 [SMILES: CC(C)(C)OC(=O)N1[C@@H]2CC[C@@H](C2)[C@H]1C(=O)N[C@H](C#N)Cc1ccc(-c2ccc(C(=O)O)s2)cc1F] | 514 | 0.44 | 004_CA05 |

TABLE 8-continued

| Intermediate | Educt | Structure of Intermediate | m/z [M + H]+ | rt (min) | LC-MS method |
|---|---|---|---|---|---|
| I-2.3.42 | I-2.2 | | 538 | 0.76 | 004_CA01 |
| I-2.3.43 | I-2.2 | | 483 | 0.93 | V012_S01 |
| I-2.3.44 | I-2.2 | | 536 | 0.85 | 004_CA05 |
| I-2.3.45 | I-2.2 | | 483 | 0.81 | 004_CA05 |
| I-2.3.46 | I-2.2 | | 482 | 0.77 | 004_CA05 |

TABLE 8-continued
| Intermediate | Educt | Structure of Intermediate | m/z [M + H]+ | rt (min) | LC-MS method |
|---|---|---|---|---|---|
| I-2.3.47 | I-2.2.1 | 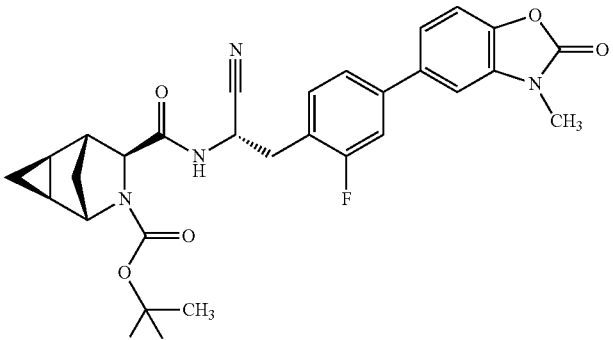 | 547 | 0.83 | 004_CA05 |
| I-2.3.48 | I-2.2.1 | 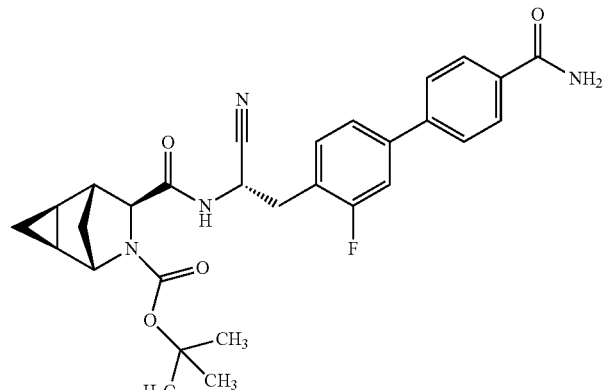 | 519 | 0.71 | 004_CA05 |
| I-2.3.49 | I-2.2.1 | 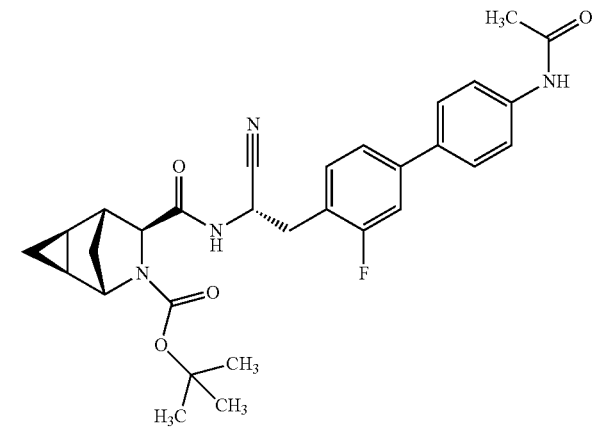 [SMILES: CC(=O)Nc1ccc(-c2ccc(C[C@@H](C#N)NC(=O)[C@@H]3[C@@H]4C[C@@H]([C@H]5C[C@@H]45)N3C(=O)OC(C)(C)C)c(F)c2)cc1] | 533 | 0.77 | 004_CA05 |
| I-2.3.50 | I-2.2.1 | 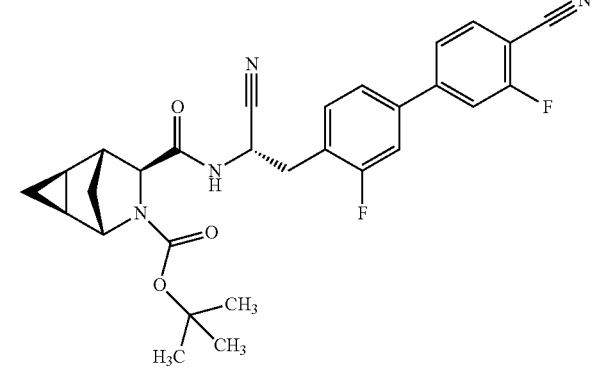 | 519 | 0.89 | 004_CA05 |

TABLE 8-continued
| Intermediate | Educt | Structure of Intermediate | m/z [M + H]+ | rt (min) | LC-MS method |
|---|---|---|---|---|---|
| I-2.3.51 | I-2.2.1 |  | 540 | 0.9 | 004_CA05 |
| I-2.3.52 | I-2.2.1 | 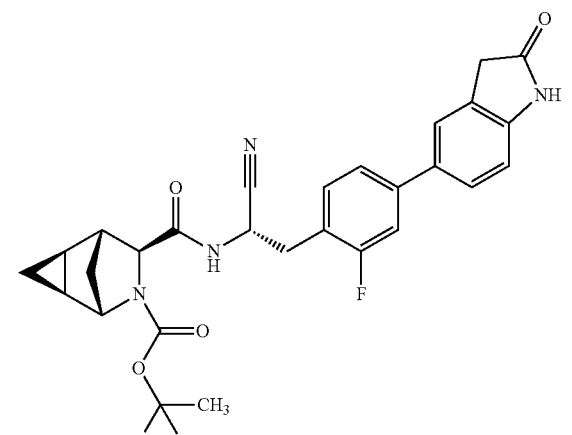 | 531 | 0.74 | 004_CA05 |
| I-2.3.53 | I-2.2.1 | 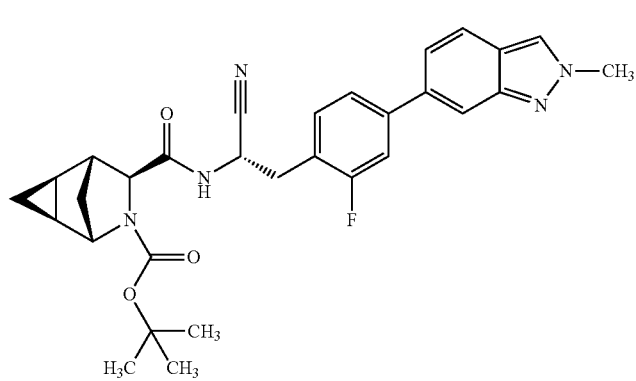 [SMILES: Cn1cc2ccc(-c3ccc(C[C@@H](C#N)NC(=O)[C@@H]4[C@@H]5C[C@@H]([C@H]6C[C@@H]56)N4C(=O)OC(C)(C)C)c(F)c3)cc2n1] | 530 | 0.81 | 004_CA05 |

TABLE 8-continued
| Intermediate | Educt | Structure of Intermediate | m/z [M + H]+ | rt (min) | LC-MS method |
|---|---|---|---|---|---|
| I-2.3.54 | I-2.2.1 | 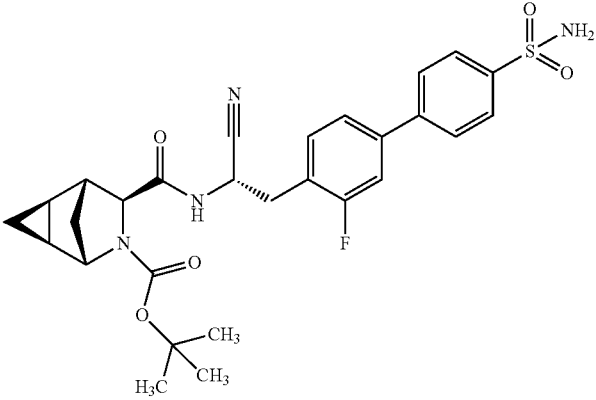 [SMILES: CC(C)(C)OC(=O)N1[C@H](C(=O)N[C@H](C#N)Cc2ccc(-c3ccc(S(N)(=O)=O)cc3)cc2F)[C@@H]2C[C@H]1[C@H]1C[C@@H]21] | 555 | 0.72 | 004_CA05 |
| I-2.3.55 | I-2.2.1 | 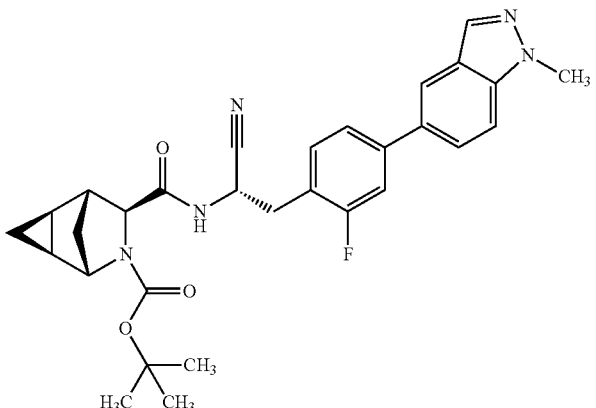 | 530 | 0.85 | 004_CA05 |
| I-2.3.56 | I-2.2.1 | 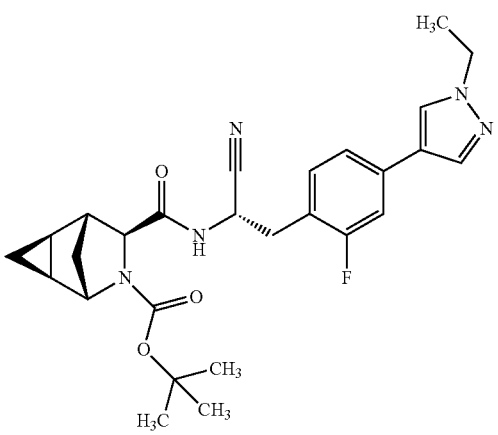 [SMILES: CCn1cc(-c2ccc(C[C@@H](C#N)NC(=O)[C@@H]3[C@@H]4C[C@@H]([C@H]5C[C@@H]45)N3C(=O)OC(C)(C)C)c(F)c2)cn1] | 494 | 0.79 | 004_CA05 |

TABLE 8-continued
| Intermediate | Educt | Structure of Intermediate | m/z [M + H]+ | rt (min) | LC-MS method |
|---|---|---|---|---|---|
| I-2.3.57 | I-2.2.1 | 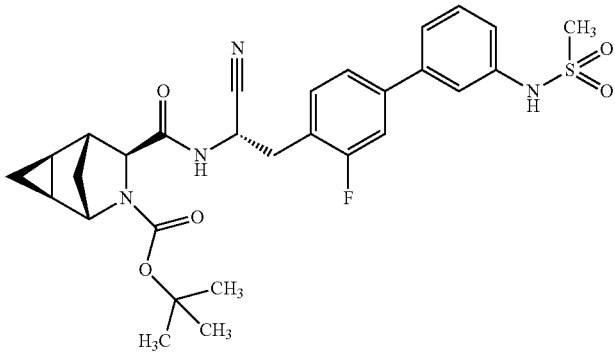 [SMILES: CC(C)(C)OC(=O)N1[C@H](C(=O)N[C@H](C#N)Cc2ccc(-c3cccc(NS(C)(=O)=O)c3)cc2F)[C@@H]2C[C@H]1[C@H]1C[C@@H]21] | 569 | 0.71 | 004_CA05 |
| I-2.3.58 | I-2.2.1 | 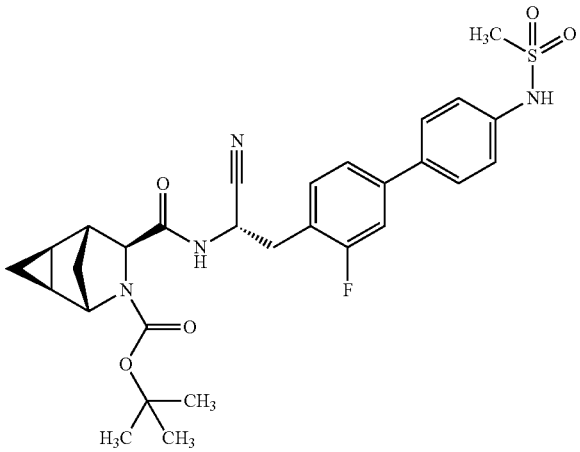 [SMILES: CC(C)(C)OC(=O)N1[C@H](C(=O)N[C@H](C#N)Cc2ccc(-c3ccc(NS(C)(=O)=O)cc3)cc2F)[C@@H]2C[C@H]1[C@H]1C[C@@H]21] | 569 | 0.66 | 004_CA05 |
| I-2.3.59 | I-2.2.1 | 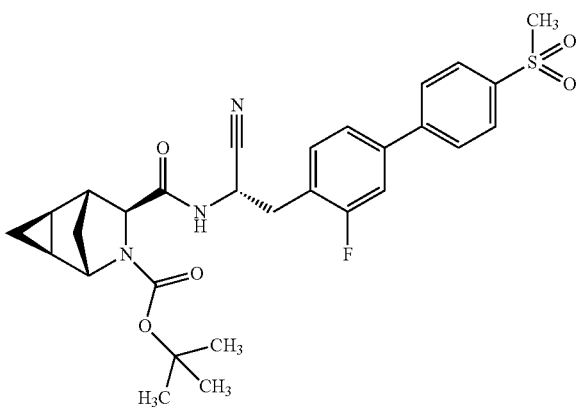 [SMILES: CC(C)(C)OC(=O)N1[C@H](C(=O)N[C@H](C#N)Cc2ccc(-c3ccc(S(C)(=O)=O)cc3)cc2F)[C@@H]2C[C@H]1[C@H]1C[C@@H]21] | 554 | 0.79 | 004_CA05 |

TABLE 8-continued
| Intermediate | Educt | Structure of Intermediate | m/z [M + H]+ | rt (min) | LC-MS method |
|---|---|---|---|---|---|
| I-2.3.60 | I-2.2.1 | 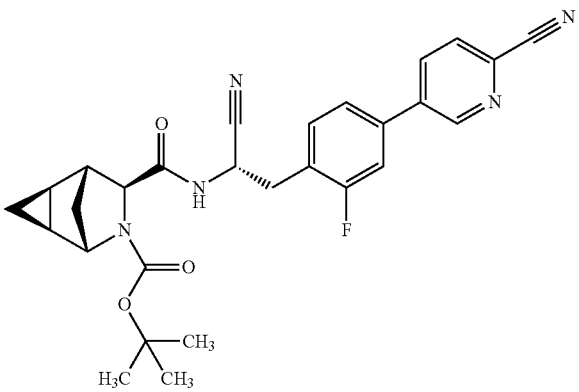 [SMILES: CC(C)(C)OC(=O)N1[C@H](C(=O)N[C@H](C#N)Cc2ccc(-c3ccc(C#N)nc3)cc2F)[C@@H]2C[C@H]1[C@H]1C[C@@H]21] | 502 | 0.81 | 004_CA05 |
| I-2.3.61 | I-2.2.1 |  | 555 | 0.74 | 004_CA05 |
| I-2.3.62 | I-2.2.1 | 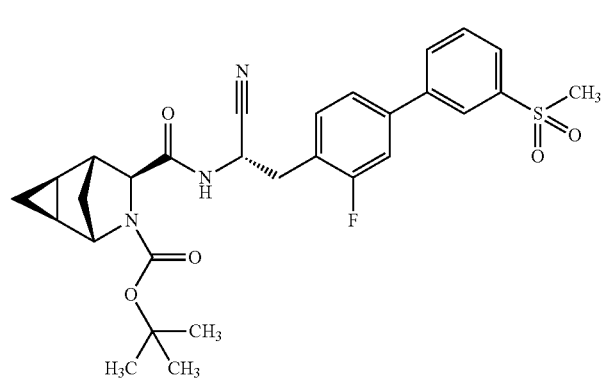 [SMILES: CC(C)(C)OC(=O)N1[C@H](C(=O)N[C@H](C#N)Cc2ccc(-c3cccc(S(C)(=O)=O)c3)cc2F)[C@@H]2C[C@H]1[C@H]1C[C@@H]21] | 554 | 0.79 | 004_CA05 |
| I-2.3.63 | I-2.2.1 | 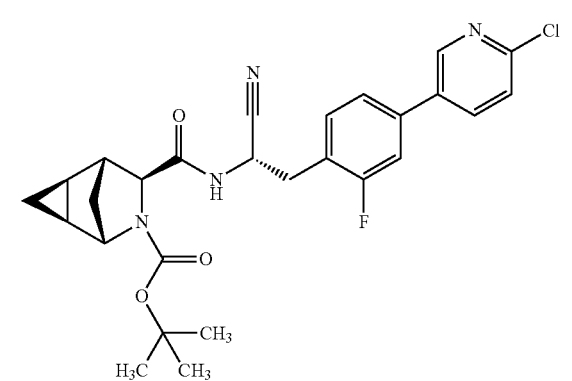 [SMILES: CC(C)(C)OC(=O)N1[C@H](C(=O)N[C@H](C#N)Cc2ccc(-c3ccc(Cl)nc3)cc2F)[C@@H]2C[C@H]1[C@H]1C[C@@H]21] | 511 | 0.87 | 004_CA05 |

TABLE 8-continued

| Intermediate | Educt | Structure of Intermediate | m/z [M + H]+ | rt (min) | LC-MS method |
|---|---|---|---|---|---|
| I-2.3.64 | I-2.2.1 | | 519 | 0.73 | 004_CA05 |
| I-2.3.65 | I-2.2.1 | | 531 | 0.71 | 004_CA05 |
| I-2.3.66 | I-2.2.1 | | 545 | 0.74 | 004_CA05 |

TABLE 8-continued
| Intermediate | Educt | Structure of Intermediate | m/z [M + H]+ | rt (min) | LC-MS method |
|---|---|---|---|---|---|
| I-2.3.67 | I-2.2.1 | 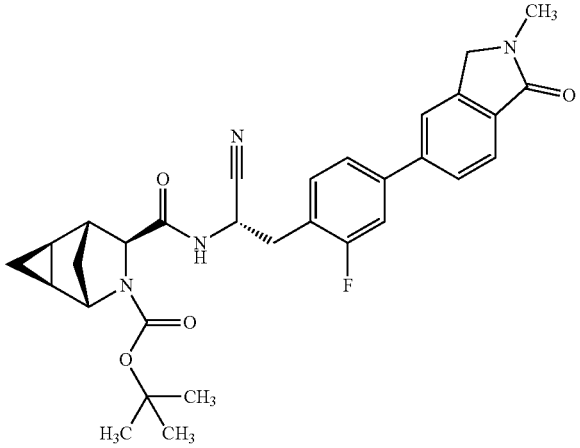 [SMILES: CN1Cc2cc(-c3ccc(C[C@@H](C#N)NC(=O)[C@@H]4[C@@H]5C[C@@H]([C@H]6C[C@@H]56)N4C(=O)OC(C)(C)C)c(F)c3)ccc2C1=O] | 545 | 0.76 | 004_CA05 |
| I-2.3.68 | I-2.2.1 | 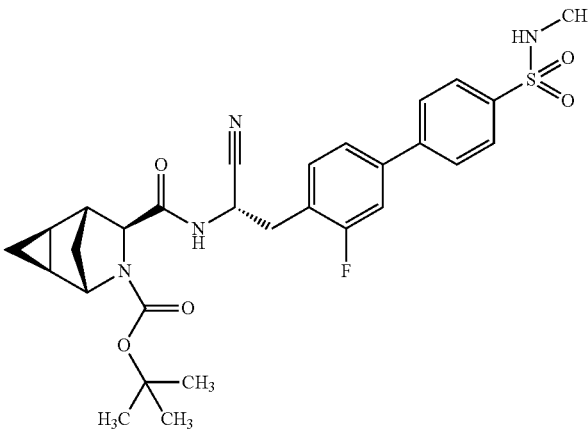 [SMILES: CNS(=O)(=O)c1ccc(-c2ccc(C[C@@H](C#N)NC(=O)[C@@H]3[C@@H]4C[C@@H]([C@H]5C[C@@H]45)N3C(=O)OC(C)(C)C)c(F)c2)cc1] | 569 | 0.79 | 004_CA05 |
| I-2.3.69 | I-2.2.1 | 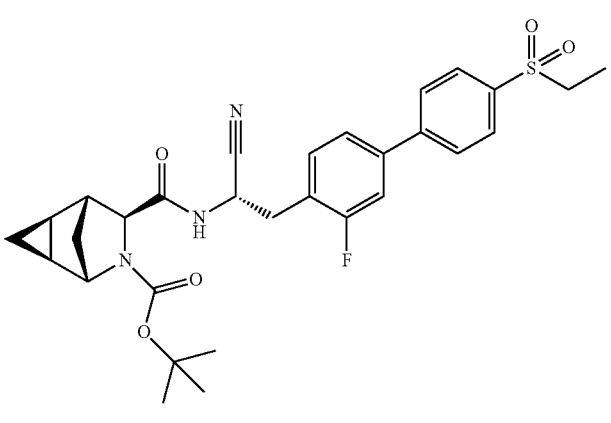 [SMILES: CCS(=O)(=O)c1ccc(-c2ccc(C[C@@H](C#N)NC(=O)[C@@H]3[C@@H]4C[C@@H]([C@H]5C[C@@H]45)N3C(=O)OC(C)(C)C)c(F)c2)cc1] | 568 | 0.82 | 004_CA05 |

TABLE 8-continued
| Intermediate | Educt | Structure of Intermediate | m/z [M + H]+ | rt (min) | LC-MS method |
| --- | --- | --- | --- | --- | --- |
| I-2.3.70 | I-2.2 | 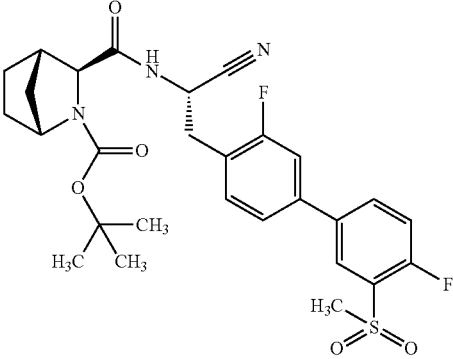 [SMILES: CC(C)(C)OC(=O)N1[C@@H]2CC[C@@H](C2)[C@H]1C(=O)N[C@H](C#N)Cc1ccc(-c2ccc(F)c(S(C)(=O)=O)c2)cc1F] | 460 [M + H − BOC]+ | 0.97 | X018_S04 |
| I-2.3.71 | I-2.2 | 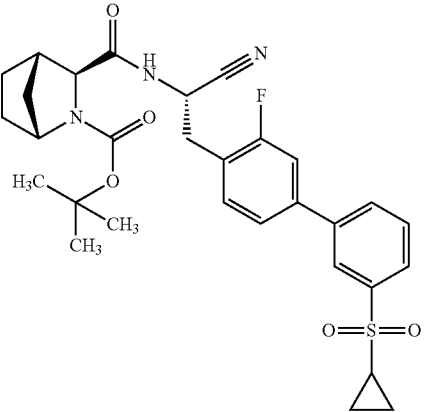 [SMILES: CC(C)(C)OC(=O)N1[C@@H]2CC[C@@H](C2)[C@H]1C(=O)N[C@H](C#N)Cc1ccc(-c2cccc(S(=O)(=O)C3CC3)c2)cc1F] | 468 [M + H − BOC]+ | 1.00 | X018_S04 |
| I-2.3.72 | I-2.2 | 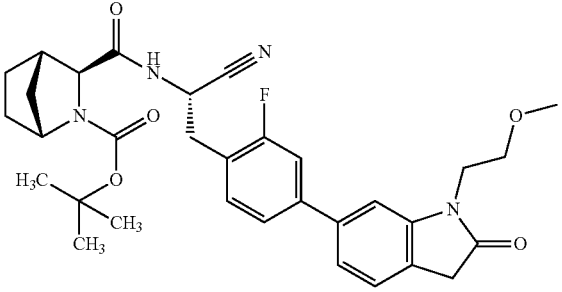 [SMILES: COCCN1C(=O)Cc2ccc(-c3ccc(C[C@@H](C#N)NC(=O)[C@@H]4[C@H]5CC[C@H](C5)N4C(=O)OC(C)(C)C)c(F)c3)cc21] | 577 | n.d. | n.d. |
| I-2.3.73 | I-2.2 | 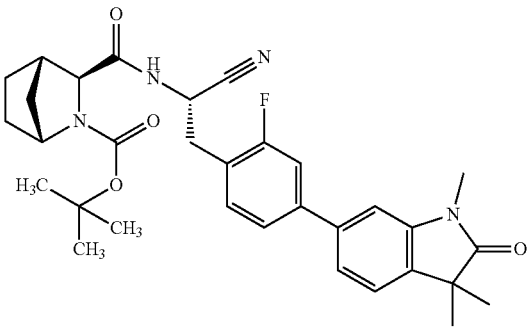 [SMILES: CN1C(=O)C(C)(C)c2ccc(-c3ccc(C[C@@H](C#N)NC(=O)[C@@H]4[C@H]5CC[C@H](C5)N4C(=O)OC(C)(C)C)c(F)c3)cc21] | 561 | n.d. | n.d. |

TABLE 8-continued

| Intermediate | Educt | Structure of Intermediate | m/z [M + H]+ | rt (min) | LC-MS method |
|---|---|---|---|---|---|
| I-2.3.74 | I-2.2.2 | | 469 | 0.89 | Z018_S04 |
| I-2.3.75 | I-2.2.2 | | 578 | 0.88 | Z018_S04 |
| I-2.3.76 | I-2.2.2 | | 455 (M + H − BOC)+ | 0.85 | Z018_S04 |
| I-2.3.77 | I-2.2.2 | | 488 (M + H − BOC) | 0.89 | Z018_S04 |

TABLE 8-continued

| Intermediate | Educt | Structure of Intermediate | m/z [M + H]+ | rt (min) | LC-MS method |
|---|---|---|---|---|---|
| I-2.3.78 | I-2.2.2 | | 503 (M + H − BOC)+ | 0.89 | Z018_S04 |
| I-2.3.79 | I-2.2 | | 626 | 0.54 | X012_S01 |
| I-2.3.80 | I-2.2 | | 398 (M + H − BOC)+ | 0.89 | Z018_S04 |
| I-2.3.81 | I-2.2 | | 398 [M + H − BOC]+ | 0.89 | n.d. |

TABLE 8-continued

| Intermediate | Educt | Structure of Intermediate | m/z [M + H]+ | rt (min) | LC-MS method |
|---|---|---|---|---|---|
| I-2.3.82 | I-2.2 | | 508 | 0.94 | Z018_S04 |
| I-2.3.83 | I-2.2 | | n.d. | n.d. | n.d. |

During the synthesis of intermediates I-2.3.17 and I-2.3.29 the bromide (I-2.2) is transformed into the corresponding dioxaborolane compound. Coupling with aromatic bromides is performed in analogy to the synthesis of intermediate I-1.3 (method A).

Intermediate I-2.3.43 is further processed via hydrogenation before the BOC group is removed (step 4)

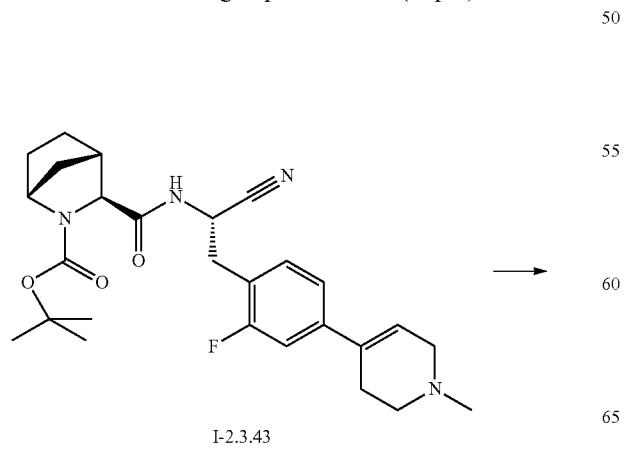

I-2.3.43

-continued

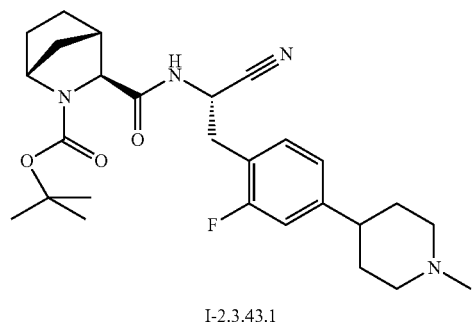

I-2.3.43.1

To I-2.3.43 (90 mg, 0.19 mmol) in methanol (10 mL) Pd/C (10%, 20 mg) is added. The reaction mixture is stirred under hydrogen (50 psi) for 3 h. Then the mixture is filtered and concentrated. The crude product is carried on with step 4. Yield >95%

In analogy the following intermediates as shown in Table 9 are prepared.

TABLE 9
| Intermediate | educt | Structure | m/z [M + H]+ | rt (min) | LC-MS method |
|---|---|---|---|---|---|
| I-2.3.43.2 | I-3.2.78 | 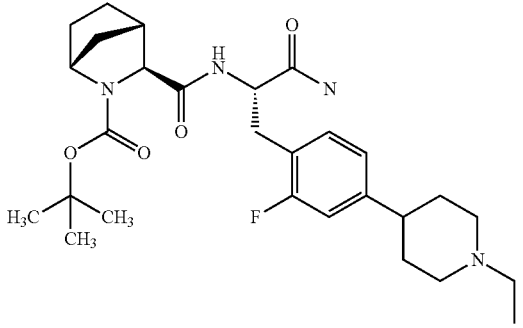 [SMILES: CCN1CCC(c2ccc(C[C@H](NC(=O)[C@@H]3[C@H]4CC[C@H](C4)N3C(=O)OC(C)(C)C)C(N)=O)c(F)c2)CC1] | 517 | 0.47. | X012_S02 |
| I-2.3.43.3 | I-2.3.83 | 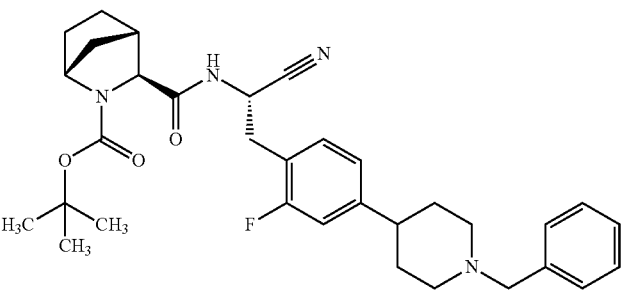 [SMILES: CC(C)(C)OC(=O)N1[C@@H]2CC[C@@H](C2)[C@H]1C(=O)N[C@H](C#N)Cc1ccc(C2CCN(Cc3ccccc3)CC2)cc1F] | 561 | n.d. | n.d. |
Intermediates I-2.3.74-78 and I-2.3.43.2 are converted to the corresponding nitriles in analogy to step 2 of method A1 to yield the compounds in the following Table 10.
TABLE 10
| Intermediate | Educt | Structure of Intermediate | m/z [M + H]+ | rt (min) | LC-MS method |
|---|---|---|---|---|---|
| I-2.3.74.1 | I-2.3.74 | 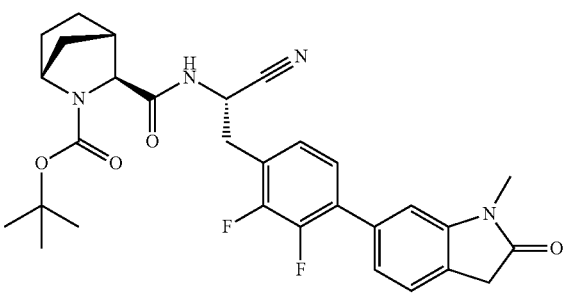 [SMILES: CN1C(=O)Cc2ccc(-c3ccc(C[C@@H](C#N)NC(=O)[C@@H]4[C@H]5CC[C@H](C5)N4C(=O)OC(C)(C)C)c(F)c3F)cc21] | 451 [M + H − BOC]+ | 0.98 | Z018_S01 |
| I-2.3.75.1 | I-2.3.75 | 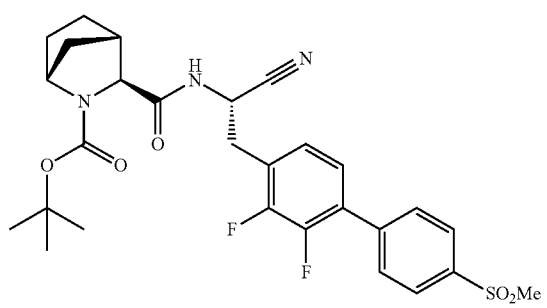 [SMILES: CC(C)(C)OC(=O)N1[C@@H]2CC[C@@H](C2)[C@H]1C(=O)N[C@H](C#N)Cc1ccc(-c2ccc(S(C)(=O)=O)cc2)c(F)c1F] | 460 (M + H+) − BOC | 0.96 | Z018_S04 |

TABLE 10-continued

| Intermediate | Educt | Structure of Intermediate | m/z [M + H]+ | rt (min) | LC-MS method |
|---|---|---|---|---|---|
| I-2.3.76.1 | I-2.3.76 | | 437 (M + H − BOC)+ | 0.93 | Z018_S04 |
| I-2.3.77.1 | I-2.3.77 | | 470 (M + H − BOC)+ | 0.96 | Z018_S04 |
| I-2.3.78.1 | I-2.3.78 | | 485 (M + H − BOC)+ | 0.96 | Z018_S04 |
| I-2.3.43.2.1 | I-2.3.43.2 | | 499 | 0.54 | X012_S02 |

117

The intermediate I-2.3.7 is combined with appropriate halogenides or acid chlorides before (in step 4) the BOC group is removed

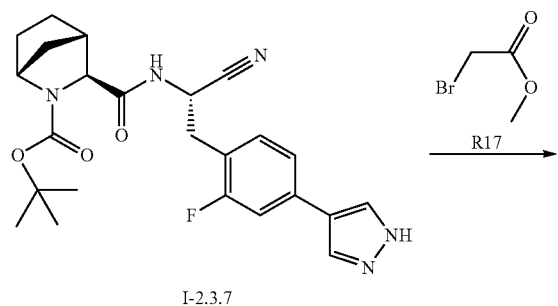

I-2.3.7

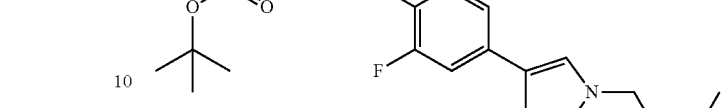

-continued

I-2.3.7.1

To I-2.3.7 (45 mg, 0.10 mmol) and R17 (19 µL, 0.20 mmol) in DMF (1.5 mL) potassium carbonate (42 mg, 0.30 mmol) is added. The reaction mixture is heated to 80° C. for 12 h. The mixture is purified directly by reversed phase HPLC. Yield 65%, m/z 526 [M+H]+, rt 0.71 min, LC-MS Method X018_S01.

The following intermediates as shown in Table 11 are synthesized in a similar fashion from the appropriate intermediates:

TABLE 11

| Intermediate | educt | Structure of Intermediate | m/z [M + H]+ | rt (min) | LC-MS method |
|---|---|---|---|---|---|
| I-2.3.7.3 | I-2.3.7 | 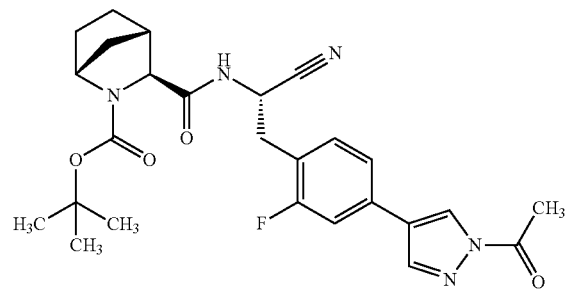 [SMILES: CC(=O)n1cc(-c2ccc(C[C@@H](C#N)NC(=O)[C@@H]3[C@H]4CC[C@H](C4)N3C(=O)OC(C)(C)C)c(F)c2)cn1] | 496 | 0.77 | X018_S01 |
| I-2.3.7.4 | I-2.3.7 | 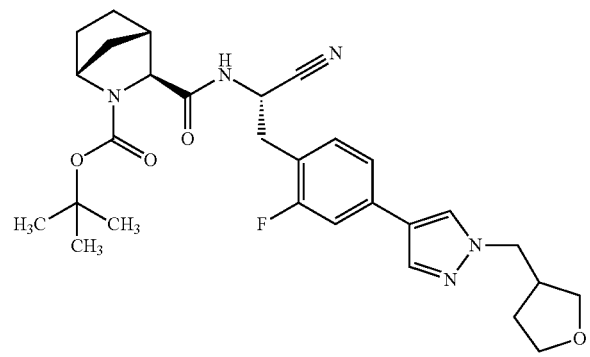 [SMILES: CC(C)(C)OC(=O)N1[C@@H]2CC[C@@H](C2)[C@H]1C(=O)N[C@H](C#N)Cc1ccc(-c2cnn(CC3CCOC3)c2)cc1F] | 538 | 0.72 | X018_S01 |

TABLE 11-continued

| Intermediate | educt | Structure of Intermediate | m/z [M + H]+ | rt (min) | LC-MS method |
|---|---|---|---|---|---|
| I-2.3.7.5 | I-2.3.7 | | 552 | 0.79 | X018_S01 |
| I-2.3.7.6 | I-2.3.7 | | 512 | 0.72 | X018_S01 |
| I-2.3.7.7 | I-2.3.7 | | 438 [M + H − BOC]+ | 1.11 | X018_S01 |
| I-2.3.7.8 | I-2.3.7 | | 593 | 0.69 | X018_S01 |

TABLE 11-continued

| Intermediate | educt | Structure of Intermediate | m/z [M + H]+ | rt (min) | LC-MS method |
|---|---|---|---|---|---|
| I-2.3.7.9 | I-2.3.7 | 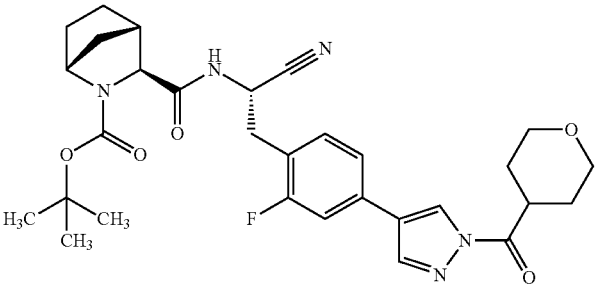 [SMILES: CC(C)(C)OC(=O)N1[C@@H]2CC[C@@H](C2)[C@H]1C(=O)N[C@H](C#N)Cc1ccc(-c2cnn(C(=O)C3CCOCC3)c2)cc1F] | 566 | 0.79 | X018_S01 |
| I-2.3.7.10 | I-2.3.7 | 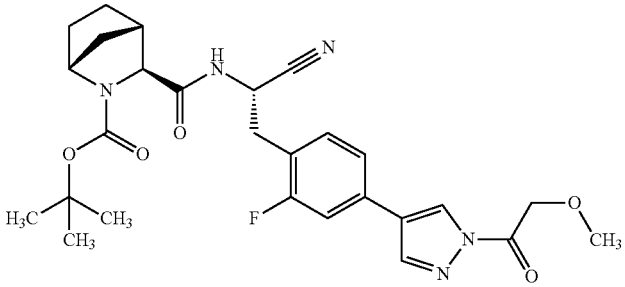 [SMILES: COCC(=O)n1cc(-c2ccc(C[C@@H](C#N)NC(=O)[C@@H]3[C@H]4CC[C@H](C4)N3C(=O)OC(C)(C)C)c(F)c2)cn1] | 526 | 0.75 | X018_S01 |
| I-2.3.7.11 | I-2.3.7 | 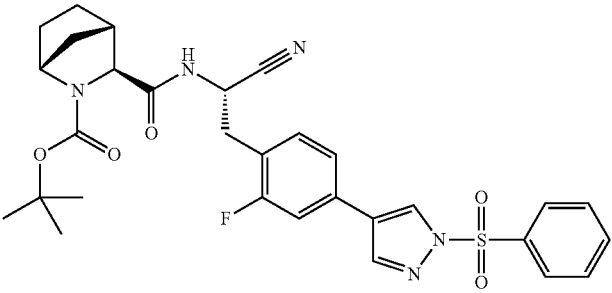 [SMILES: CC(C)(C)OC(=O)N1[C@@H]2CC[C@@H](C2)[C@H]1C(=O)N[C@H](C#N)Cc1ccc(-c2cnn(S(=O)(=O)c3ccccc3)c2)cc1F] | 494(M + H − BOC)+ | 1.03 | Z018_S04 |

The reaction conditions for I-2.3.7.11 differ: Pyridine and dichlormethane instead of potassium carbonate and DMF is used.

Intermediate I-2.3.7.4 is separated according to method chiral SFC B to give the following intermediates as shown in Table 11.1

TABLE 11.1

| Intermediate | Educt | Structure of Intermediate | m/z [M + H]+ | rt (min) | LC-MS method |
|---|---|---|---|---|---|
| I-2.3.7.4.1 | I-2.3.7.4 | 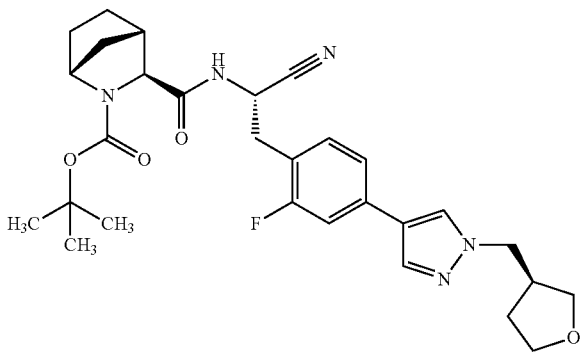 [SMILES: CC(C)(C)OC(=O)N1[C@@H]2CC[C@@H](C2)[C@H]1C(=O)N[C@H](C#N)Cc1ccc(-c2cnn(C[C@@H]3CCOC3)c2)cc1F] | n.d. | 3.90 | I_OJH_10_IPROP_DEA.M |

TABLE 11.1-continued

| Intermediate | Educt | Structure of Intermediate | m/z [M + H]+ | rt (min) | LC-MS method |
|---|---|---|---|---|---|
| I-2.3.7.4.2 | I-2.3.7.4 | | n.d. | 3.4 | I_OJH_10_IPROP_DEA.M |

Step 4: Synthesis of Example 2

To I-2.3 (2.35 g, 4.4 mmol) in acetonitrile (50 mL) sodium iodide (1.98 g, 13 mmol) and chlorotrimethylsilane (1.44 g, 13 mmol) are added. The mixture is stirred for 1 h, then methanol is added, stirred for additional 30 min and then concentrated. The residue is purified by reversed phase HPLC. Yield 47%, m/z 433 [M+H]+, rt 0.59 min, LC-MS Method X011_S01.

Method A2.1 le;2qSynthesis of (1S,2S,4R)-N-[(1S)-1-cyano-2-[2-fluoro-4-(1-oxo-3H-isobenzofuran-5-yl)phenyl]ethyl]-3-azabicyclo[2.2.1]heptane-2-carboxamide (Example 3)

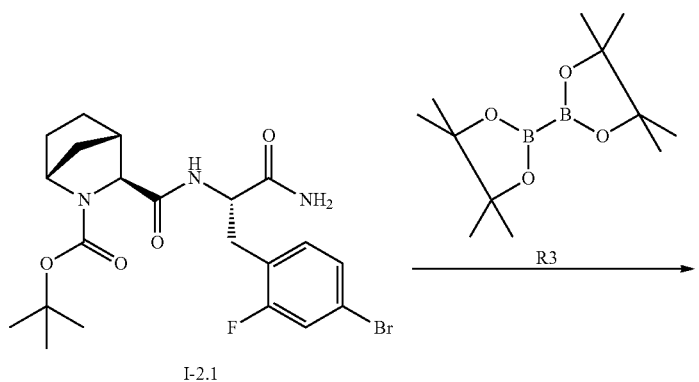

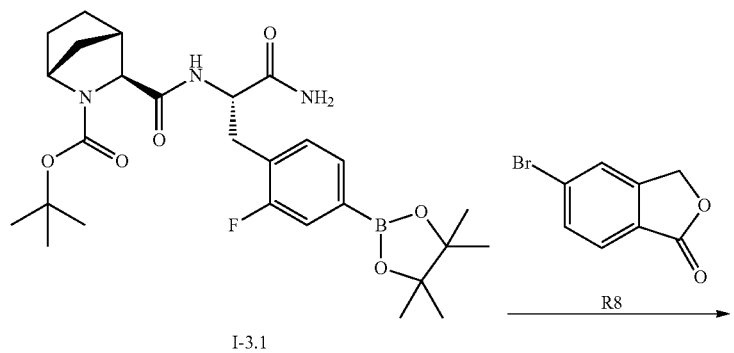

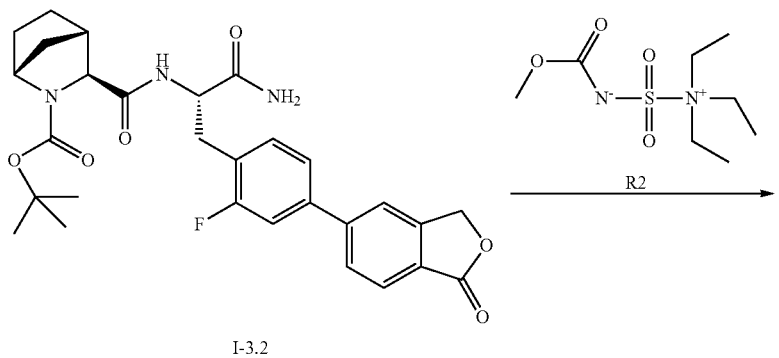

I-3.2

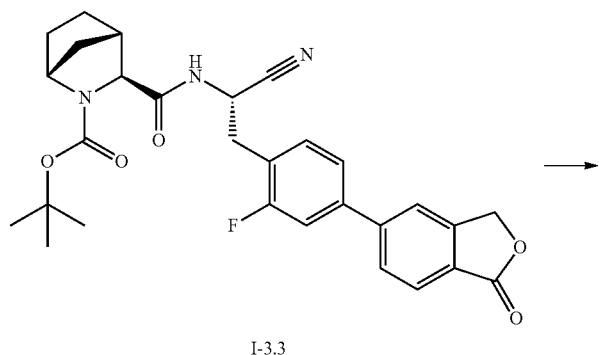

I-3.3

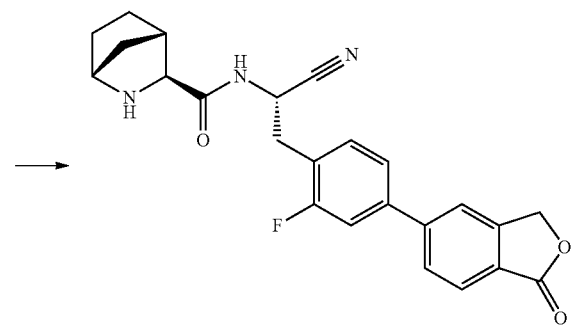

Example 3

Step 1: Synthesis of Intermediate I-3.1

To I-2.1 (1.00 g, 2.1 mmol) in dioxane (5 mL) R3 (0.58 g, 2.3 mmol) is added. The mixture is purged with argon. [1,1'-Bis(diphenylphosphino)ferrocene]dichloropalladium (II) as a complex with dichloromethane (34 mg, 0.04 mmol) and potassium acetate (0.39 g, 3.9 mmol) are added. The mixture is heated to 100° C. for 12 h. Water is added to the reaction mixture, which is extracted with diethyl ether. The organic layer is washed with brine, dried over MgSO$_4$, filtrated and concentrated. Yield 74% m/z 532 [M+H]+

The following intermediates as shown in Table 12a are synthesized in a similar fashion from the appropriate intermediate:

TABLE 12a

| Intermediate | Educt | Structure of Intermediate | m/z [M + H]+ | rt (min) | LC-MS method |
|---|---|---|---|---|---|
| I-3.1.1 | (1RS)-I-2.2 | 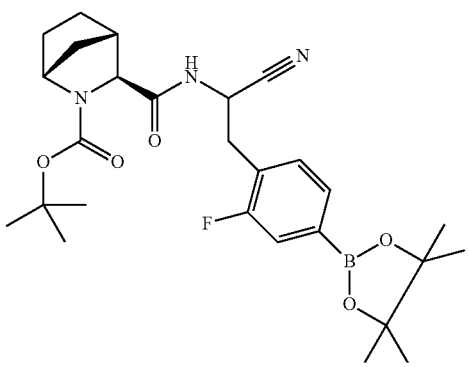 [SMILES: CC(C)(C)OC(=O)N1[C@@H]2CC[C@@H](C2)[C@H]1C(=O)NC(C#N)Cc1ccc(B2OC(C)(C)C(C)(C)O2)cc1F] | 514 | 0.90 | V011_S01 |

TABLE 12a-continued

| Intermediate | Educt | Structure of Intermediate | m/z [M + H]+ | rt (min) | LC-MS method |
|---|---|---|---|---|---|
| I-3.1.2 | I-2.2 | | 432 | 1.05 | V018_S01 |
| I-3.1.3 | I-2.2 | | 514 | 0.95 | Z011_S03 |
| I-3.1.5 | I.2.1 | | 450 (Boron acid) | 0.67 | V011_S01 |

During the synthesis of intermediate I-3.1.2, I-3.1.4 and I-3.1.5 instead of R3 5,5,5',5'-Tetramethyl-[2,2']bi[[1,3,2] dioxaborinanyl] is used.

During the synthesis of intermediate I-3.1 I-3.1.2 and I-3.1.4 also the corresponding boronic acid is isolated as shown in Table 12b. Either the boronic ester or boronic acid is used for the next steps.

TABLE 12b

| Intermediate | Educt | Structure of Intermediate | m/z [M + H]+ | rt (min) | LC-MS method |
|---|---|---|---|---|---|
| I-3.1.4 | I-2.2.3 | | 432 | 0.88 | V011_S01 |

TABLE 12b-continued

| Intermediate | Educt | Structure of Intermediate | m/z [M + H]+ | rt (min) | LC-MS method |
|---|---|---|---|---|---|
| I-3.1.6 | I-2.1 | 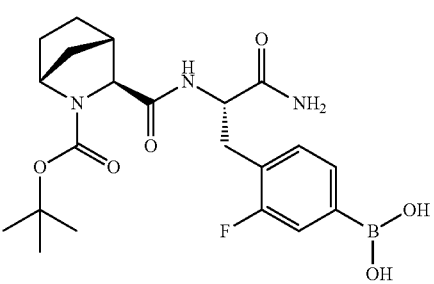 [SMILES: CC(C)(C)OC(=O)N1[C@@H]2CC[C@@H](C2)[C@H]1C(=O)N[C@@H](Cc1ccc(B(O)O)cc1F)C(N)=O] | 449 | 0.42 | X016_S01 |
| I-3.1.7 | I.2.2 | 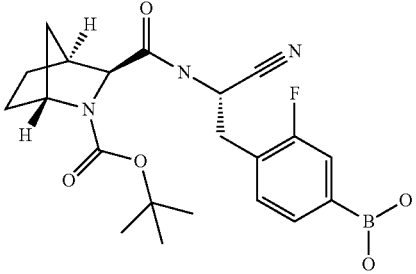 [SMILES: CC(C)(C)OC(=O)N1[C@@H]2CC[C@@H](C2)[C@H]1C(=O)N[C@H](C#N)Cc1ccc(B(O)O)cc1F] | 432 | 0.56 | X018_S01 |

Step 2: Synthesis of Intermediate I-3.2

To I-3.1 (295 mg, 0.66 mmol, as boronic acid (I-3.1.6)) in acetonitrile (4 mL) aq. Na$_2$CO$_3$-solution (2 M, 663 µL) is added. The mixture is purged with argon, R8 (154 mg, 0.72 mmol) and [1,1'-Bis(diphenylphosphino)ferrocene]dichloropalladium(II) as a complex with dichloromethane (80 mg, 0.10 mmol) are added. The reaction is stirred at 70° C. for 4 h. Ethyl acetate is added and the mixture is filtrated. The filtrate is washed with water and aq. Na$_2$CO$_3$ solution (10%). The organic layer is dried over MgSO$_4$ and concentrated. The residue is purified by flash chromatography (DCM/methanol=97/3). Yield 53%.

The following intermediates as shown in Table 13 are synthesized in a similar fashion from the appropriate intermediate ((R,S)=1:1 mixture of stereoisomers at the carbon adjacent to the nitrile group):

TABLE 13

| Intermediate | Educt | Structure of Intermediate | m/z [M + H]+ | rt (min) | LC-MS method |
|---|---|---|---|---|---|
| I-3.2.1 | I-3.1 | 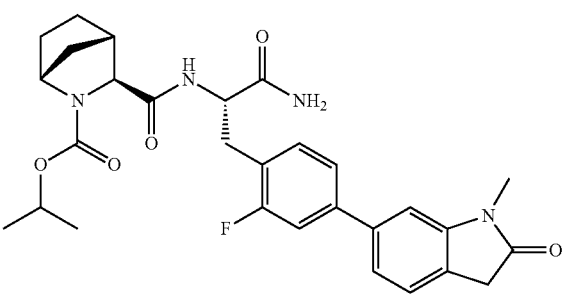 [SMILES: CC(C)OC(=O)N1[C@@H]2CC[C@@H](C2)[C@H]1C(=O)N[C@@H](Cc1ccc(-c2ccc3c(c2)N(C)C(=O)C3)cc1F)C(N)=O] | 551 | 1.08 | V011_S01 |

TABLE 13-continued

| Intermediate | Educt | Structure of Intermediate | m/z [M + H]+ | rt (min) | LC-MS method |
|---|---|---|---|---|---|
| I-3.2.2 | I-3.1.1 | | 520 | 1.21 | V011_S01 |
| I-3.2.5 | I-3.1 | | n.d. | n.d. | n.d. |
| I-3.2.6 | (1S)-I-3.1.1 | | 447/491/547 | 1.18 | V011_S01 |
| I-3.2.8 | I-3.1 | | n.d. | n.d. | n.d. |

TABLE 13-continued

| Intermediate | Educt | Structure of Intermediate | m/z [M + H]+ | rt (min) | LC-MS method |
|---|---|---|---|---|---|
| I-3.2.10 | (1S)-I-3.1.1 | | 519 | 1.11 | V011_S01 |
| I-3.2.11 | I-3.1.1 | | n.d. | n.d. | n.d. |
| I-3.2.12 | I-3.1.1 | | n.d. | n.d. | n.d. |
| I-3.2.13 | I-3.1.1 | | n.d. | n.d. | n.d. |

TABLE 13-continued

| Intermediate | Educt | Structure of Intermediate | m/z [M + H]+ | rt (min) | LC-MS method |
|---|---|---|---|---|---|
| I-3.2.15 | I-3.1 | | n.d. | n.d. | n.d. |
| I-3.2.16 | I-3.1 | | n.d. | n.d. | n.d. |
| I-3.2.17 | I-3.1 | | n.d. | n.d. | n.d. |
| I-3.2.36 | I-3.1.3 | | 368 (M + H − BOC)+ | 0.73 | 004_CA05 |

TABLE 13-continued
| Intermediate | Educt | Structure of Intermediate | m/z [M + H]+ | rt (min) | LC-MS method |
|---|---|---|---|---|---|
| I-3.2.37 | I-3.1.3 | 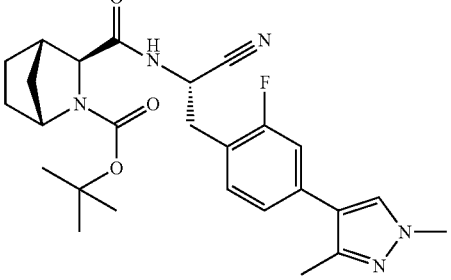 | 382 (M + H − BOC)+ | 0.75 | 004_CA05 |
| I-3.2.38 | I-3.1.3 | 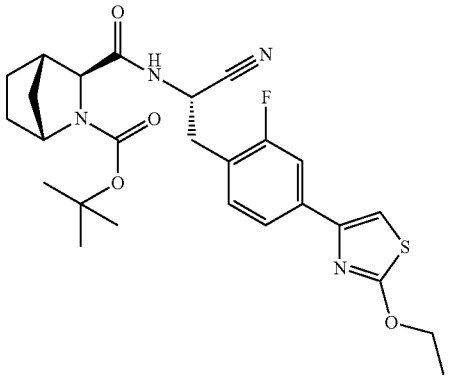 [SMILES: CCOc1nc(-c2ccc(C[C@@H](C#N)NC(=O)[C@@H]3[C@H]4CC[C@H](C4)N3C(=O)OC(C)(C)C)c(F)c2)cs1] | 415 (M+ H − BOC)+ | 0.95 | 004_CA05 |
| I-3.2.39 | I-3.1.3 | 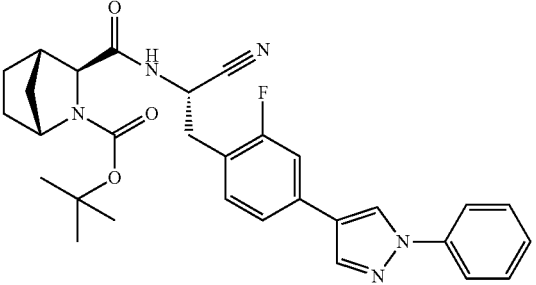 [SMILES: CC(C)(C)OC(=O)N1[C@@H]2CC[C@@H](C2)[C@H]1C(=O)N[C@H](C#N)Cc1ccc(-c2cnn(-c3ccccc3)c2)cc1F] | 430 (M + H − BOC)+ | 0.91 | 004_CA05 |
| I-3.2.40 | I-3.1.3 | 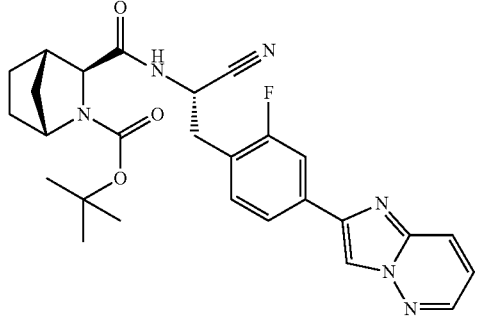 [SMILES: CC(C)(C)OC(=O)N1[C@@H]2CC[C@@H](C2)[C@H]1C(=O)N[C@H](C#N)Cc1ccc(-c2cn3ncccc3n2)cc1F] | 405 (M + H − BOC)+ | 0.74 | 004_CA05 |

TABLE 13-continued

| Intermediate | Educt | Structure of Intermediate | m/z [M + H]+ | rt (min) | LC-MS method |
|---|---|---|---|---|---|
| I-3.2.41 | I-3.1.3 | | 405 (M + H − BOC)+ | 0.67 | 004_CA05 |
| I-3.2.42 | I-3.1.3 | | 405 (M + H − BOC)+ | 0.77 | 004_CA05 |
| I-3.2.43 | I-3.1.3 | | 382 (M + H − BOC)+ | 0.72 | 004_CA05 |
| I-3.2.44 | I-3.1.3 | | 394 (M + H − BOC)+ | 0.70 | 004_CA05 |

TABLE 13-continued

| Intermediate | Educt | Structure of Intermediate | m/z [M + H]+ | rt (min) | LC-MS method |
|---|---|---|---|---|---|
| I-3.2.45 | I-3.1.3 | | 411 (M + H − BOC)+ | 0.88 | 004_CA05 |
| I-3.2.46 | I-3.1.3 | | 397 (M + H − BOC)+ | 0.68 | 004_CA05 |
| I-3.2.47 | I-3.1.3 | | 379 (M + H − BOC)+ | 0.85 | 004_CA05 |
| I-3.2.48 | I-3.1.3 | | 442 (M + H − BOC)+ | 0.92 | 004_CA05 |

TABLE 13-continued

| Intermediate | Educt | Structure of Intermediate | m/z [M + H]+ | rt (min) | LC-MS method |
|---|---|---|---|---|---|
| I-3.2.49 | I-3.1.3 | | 442 (M + H − BOC)+ | 0.94 | 004_CA05 |
| I-3.2.50 | I-3.1.3 | | 412 (M + H − BOC)+ | 0.84 | 004_CA05 |
| I-3.2.51 | I-3.1.3 | | 611 | n.d. | n.d. |
| I-3.2.52 | I-3.1.3 | | 613 | 1.24 | V012_S01 |

TABLE 13-continued

| Intermediate | Educt | Structure of Intermediate | m/z [M + H]+ | rt (min) | LC-MS method |
|---|---|---|---|---|---|
| I-3.2.53 | I-3.1.3 | | 466 (M + H − BOC)+ | 0.91 | Z018_S04 |
| I-3.2.54 | I-3.1.3 | | 647 | n.d. | n.d. |
| I-3.2.55 | I-3.1.2 | | 568 | 1.23 | V-11_S01 |
| I-3.2.56 | I-3.1.2 | | 622 | 1.24 | V011_S01 |

TABLE 13-continued

| Intermediate | Educt | Structure of Intermediate | m/z [M + H]+ | rt (min) | LC-MS method |
|---|---|---|---|---|---|
| I-3.2.57 | I-3.1.2 | | 547 | 0.76 | X011_S03 |
| I-3.2.58 | I-3.1.2 | | 494 | 0.57 | X011_S03 |
| I-3.2.59 | I-3.1.2 | | 494 | 0.56 | X011_S03 |
| I-3.2.60 | I-3.1.2 | | 552 | 0.58 | X011_S03 |

TABLE 13-continued
| Intermediate | Educt | Structure of Intermediate | m/z [M + H]+ | rt (min) | LC-MS method |
|---|---|---|---|---|---|
| I-3.2.61 | I-3.1.2 | 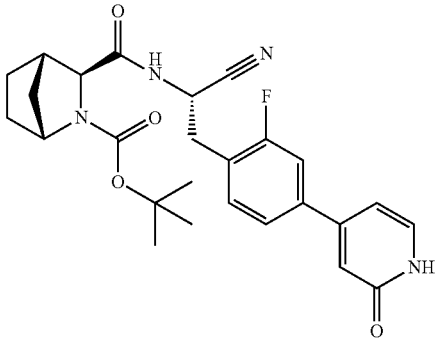 | 380 (M + H − BOC)+ | 0.52 | X011_S03 |
| I-3.2.62 | I-3.1.2 | 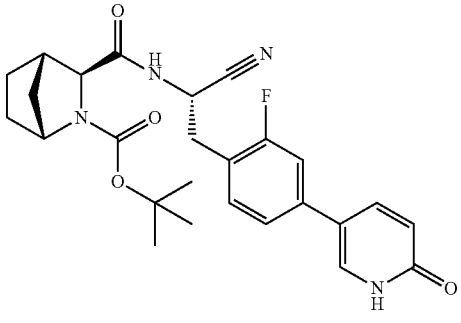 | 380 (M + H − BOC)+ | 0.52 | X011_S03 |
| I-3.2.63 | I-3.1.3 | 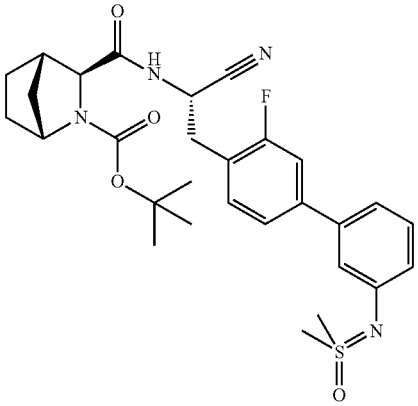 [SMILES: CC(C)(C)OC(=O)N1[C@@H]2CC[C@@H](C2)[C@H]1C(=O)N[C@H](C#N)Cc1ccc(-c2cccc(N=S(C)(C)=O)c2)cc1F] | 455 (M + H − BOC)+ | 0.93 | Z018_S04 |
| I-3.2.64 | I-3.1.3 | 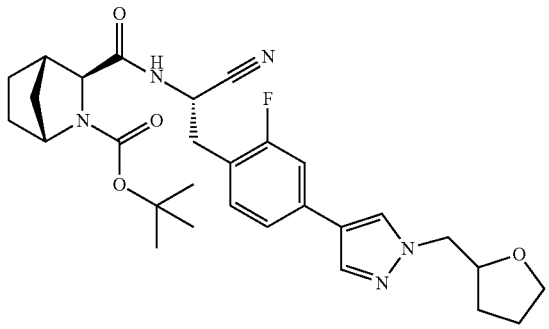 [SMILES: CC(C)(C)OC(=O)N1[C@@H]2CC[C@@H](C2)[C@H]1C(=O)N[C@H](C#N)Cc1ccc(-c2cnn(CC3CCCO3)c2)cc1F] | 538 | 0.94 | Z018_S04 |

TABLE 13-continued

| Intermediate | Educt | Structure of Intermediate | m/z [M + H]+ | rt (min) | LC-MS method |
|---|---|---|---|---|---|
| I-3.2.65 | I-3.1.3 | | 466 (M + H − BOC)+ | 0.91 | Z018_S04 |
| I-3.2.66 | I-3.1.3 | | 525 (M + H − BOC)+ | 0.93 | Z011_S03 |
| I-3.2.67 | I-3.1.7 | | 538 | 0.83 | X018_S01 |
| I-3.2.68 | I-3.1.7 | | 526 | 1.11 | V011_S01 |

TABLE 13-continued
| Intermediate | Educt | Structure of Intermediate | m/z [M + H]+ | rt (min) | LC-MS method |
|---|---|---|---|---|---|
| I-3.2.69 | I-3.1.7 | 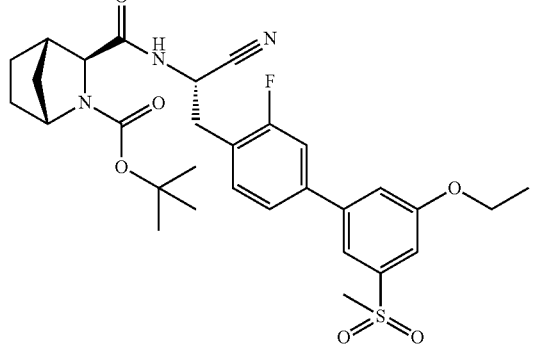 | 586 | 1.29 | V011_S01 |
| I-3.2.70 | I-3.1.7 | 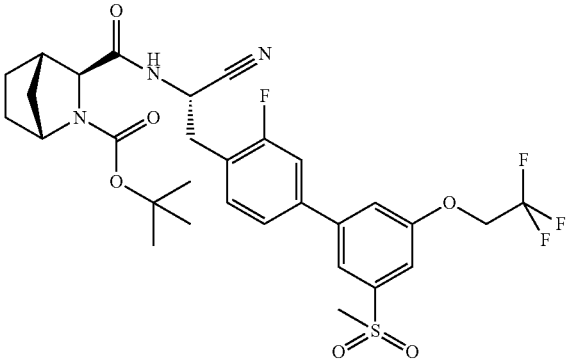 [SMILES: CC(C)(C)OC(=O)N1[C@@H]2CC[C@@H](C2)[C@H]1C(=O)N[C@H](C#N)Cc1ccc(-c2cc(OCC(F)(F)F)cc(S(C)(=O)=O)c2)cc1F] | 640 | 1.31 | V011_S01 |
| I-3.2.71 | I-3.1.7 | 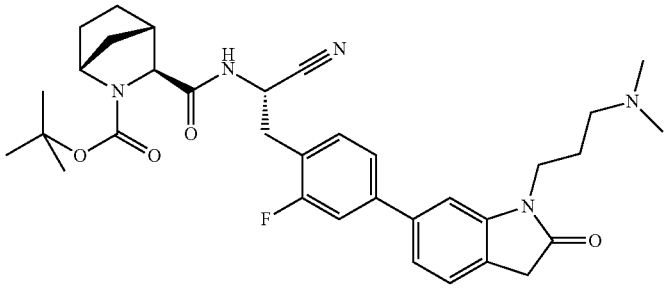 [SMILES: CN(C)CCCN1C(=O)Cc2ccc(-c3ccc(C[C@@H](C#N)NC(=O)[C@@H]4[C@H]5CC[C@H](C5)N4C(=O)OC(C)(C)C)c(F)c3)cc21] | 604 | n.d. | n.d. |
| I-3.2.72 | I-3.1.7 | 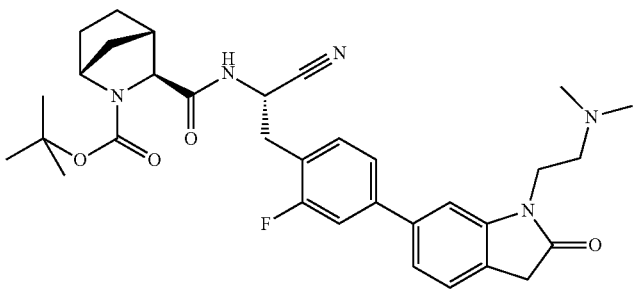 [SMILES: CN(C)CCN1C(=O)Cc2ccc(-c3ccc(C[C@@H](C#N)NC(=O)[C@@H]4[C@H]5CC[C@H](C5)N4C(=O)OC(C)(C)C)c(F)c3)cc21] | n.d. | n.d. | n.d. |

TABLE 13-continued
| Intermediate | Educt | Structure of Intermediate | m/z [M + H]+ | rt (min) | LC-MS method |
|---|---|---|---|---|---|
| I-3.2.73 | I-3.1.7 | 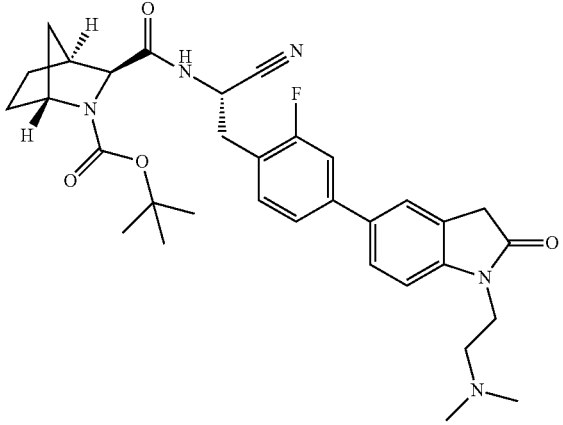 [SMILES: CN(C)CCN1C(=O)Cc2cc(-c3ccc(C[C@@H](C#N)NC(=O)[C@@H]4[C@H]5CC[C@H](C5)N4C(=O)OC(C)(C)C)c(F)c3)ccc21] | 590 | 1.03 | Z011_S03 |
| I-3.2.74 | I-3.1 | 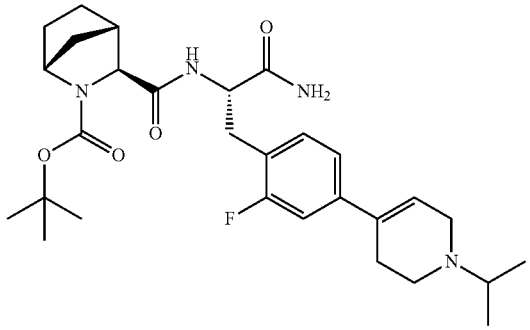 [SMILES: CC(C)N1CC=C(c2ccc(C[C@H](NC(=O)[C@@H]3[C@H]4CC[C@H](C4)N3C(=O)OC(C)(C)C)C(N)=O)c(F)c2)CC1] | 529 | 0.48 | X012_S02 |
| I-3.2.75 | I-3.1 | 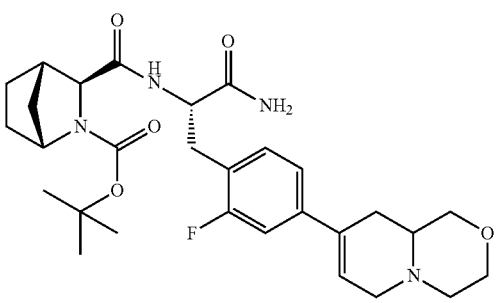 [SMILES: CC(C)(C)OC(=O)N1[C@@H]2CC[C@@H](C2)[C@H]1C(=O)N[C@@H](Cc1ccc(C2=CCN3CCOCC3C2)cc1F)C(N)=O] | 543 | 1.04 | V011_S01 |
| I-3.2.76 | I-3.1 | 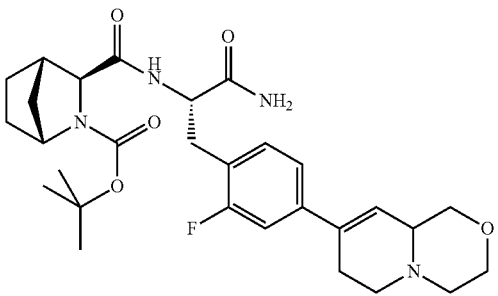 [SMILES: CC(C)(C)OC(=O)N1[C@@H]2CC[C@@H](C2)[C@H]1C(=O)N[C@@H](Cc1ccc(C2=CC3COCCN3CC2)cc1F)C(N)=O] | 543 | 1.02 | V011_S01 |

TABLE 13-continued
| Intermediate | Educt | Structure of Intermediate | m/z [M + H]+ | rt (min) | LC-MS method |
|---|---|---|---|---|---|
| I-3.2.77 | I-3.1.4 | 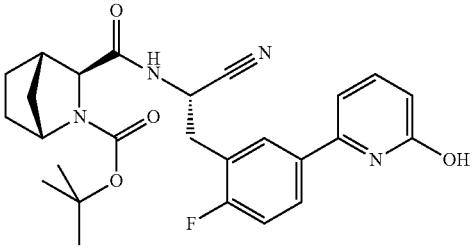 [SMILES: CC(C)(C)OC(=O)N1[C@@H]2CC[C@@H](C2)[C@H]1C(=O)N[C@H](C#N)Cc1cc(-c2cccc(O)n2)ccc1F] | n.d. | n.d. | n.d. |
| I-3.2.78 | I-3.1 | 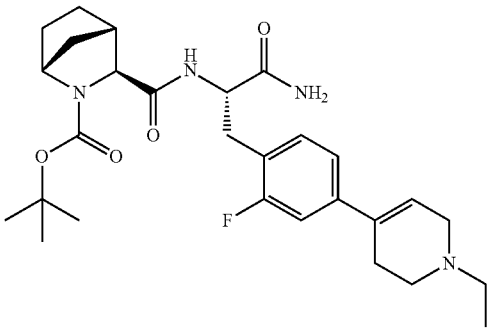 [SMILES: CCN1CC=C(c2ccc(C[C@H](NC(=O)[C@@H]3[C@H]4CC[C@H](C4)N3C(=O)OC(C)(C)C)C(N)=O)c(F)c2)CC1] | n.d. | n.d. | n.d. |
| I-3.2.79 | I-3.1.7 | 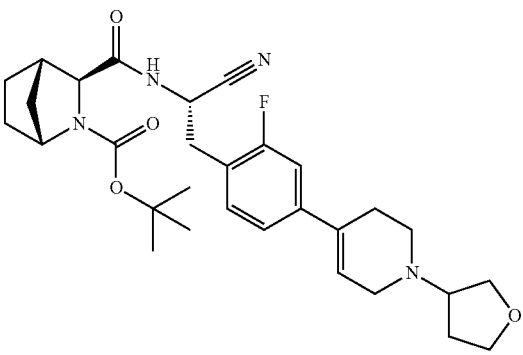 [SMILES: CC(C)(C)OC(=O)N1[C@@H]2CC[C@@H](C2)[C@H]1C(=O)N[C@H](C#N)Cc1ccc(C2=CCN(C3CCOC3)CC2)cc1F] | 539 | 1.18 | V011_S01 |
| I-3.2.80 | I-3.1.7 | 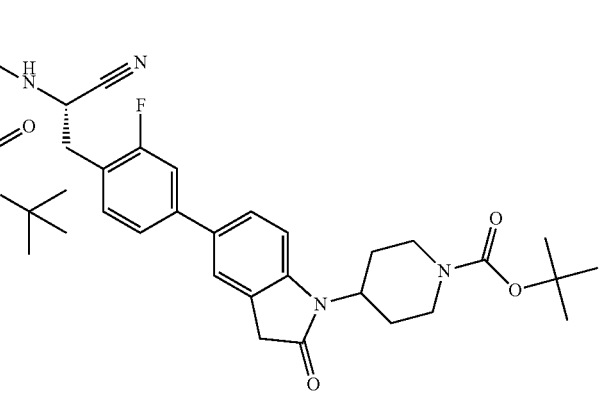 | 546 (M + H − Boc-t-Bu) | 1.106 | Z020_S01 |

TABLE 13-continued
| Intermediate | Educt | Structure of Intermediate | m/z [M + H]+ | rt (min) | LC-MS method |
|---|---|---|---|---|---|
| I-3.2.81 | I-3.1.6 | 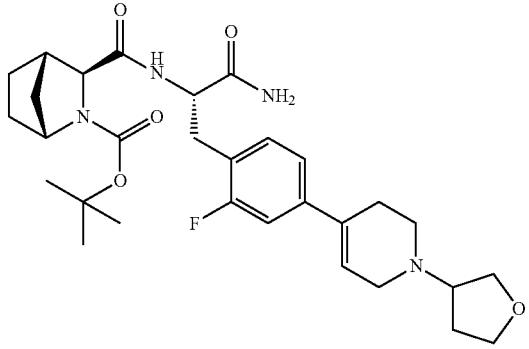 [SMILES: CC(C)(C)OC(=O)N1[C@@H]2CC[C@@H](C2)[C@H]1C(=O)N[C@@H](Cc1ccc(C2=CCN(C3CCOC3)CC2)cc1F)C(N)=O] | 557 | 1.05 | V011_S01 |
| I-3.2.82 | I-3.1.6 | 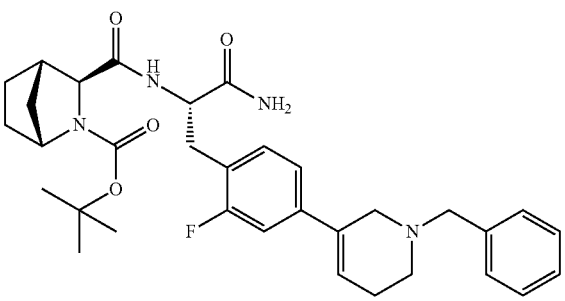 [SMILES: CC(C)(C)OC(=O)N1[C@@H]2CC[C@@H](C2)[C@H]1C(=O)N[C@@H](Cc1ccc(C2=CCCN(Cc3ccccc3)C2)cc1F)C(N)=O] | 577 | 0.50 | X018_S02 |
| I-3.2.83 | I-3.1.1 | 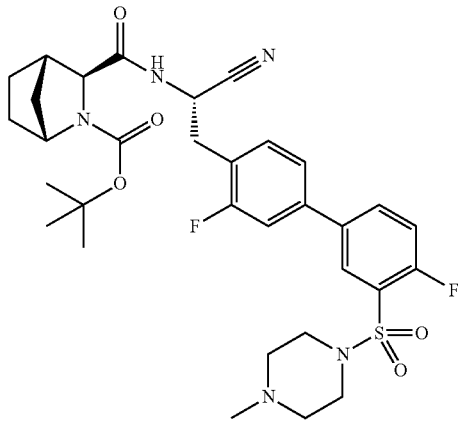 [SMILES: CN1CCN(S(=O)(=O)c2cc(-c3ccc(C[C@@H](C#N)NC(=O)[C@@H]4[C@H]5CC[C@H](C5)N4C(=O)OC(C)(C)C)c(F)c3)ccc2F)CC1] | 644 | 0.53 | X012_S01 |
| I-3.2.84 | I-3.1.7 | 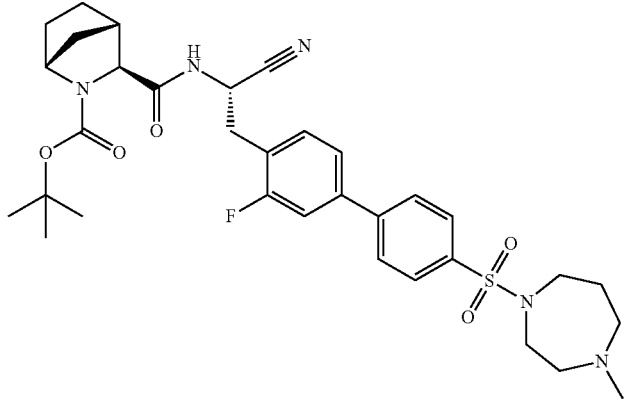 [SMILES: CN1CCCN(S(=O)(=O)c2ccc(-c3ccc(C[C@@H](C#N)NC(=O)[C@@H]4[C@H]5CC[C@H](C5)N4C(=O)OC(C)(C)C)c(F)c3)cc2)CC1] | 640 | 0.53 | X12_S01 |

TABLE 13-continued
| Intermediate | Educt | Structure of Intermediate | m/z [M + H]+ | rt (min) | LC-MS method |
|---|---|---|---|---|---|
| I-3.2.85 | I-3.1.7 | 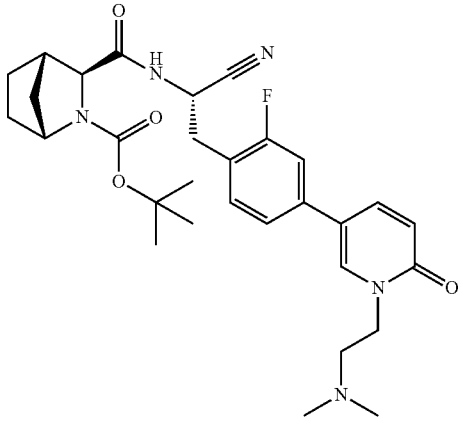 [SMILES: CN(C)CCn1cc(-c2ccc(C[C@@H](C#N)NC(=O)[C@@H]3[C@H]4CC[C@H](C4)N3C(=O)OC(C)(C)C)c(F)c2)ccc1=O] | 551 | 0.59 | X011_S03 |
| I-3.2.86 | I-3.1.7 | 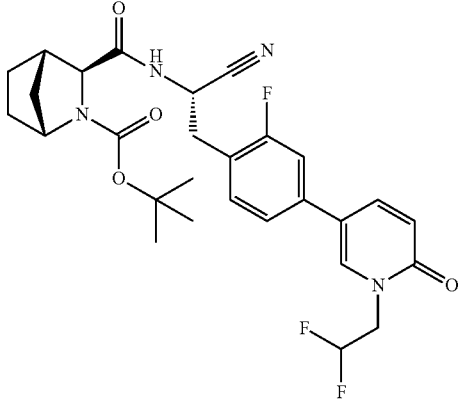 [SMILES: CC(C)(C)OC(=O)N1[C@@H]2CC[C@@H](C2)[C@H]1C(=O)N[C@H](C#N)Cc1ccc(-c2ccc(=O)n(CC(F)F)c2)cc1F] | 544 | 0.60 | X012_S02 |
| I-3.2.87 | I-3.1.7 | 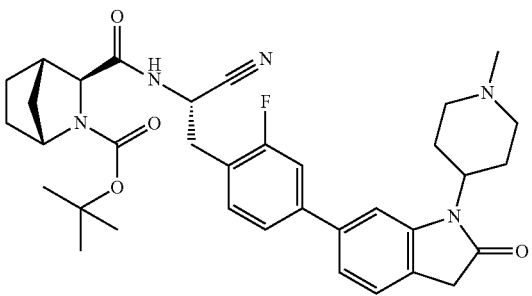 [SMILES: CN1CCC(N2C(=O)Cc3ccc(-c4ccc(C[C@@H](C#N)NC(=O)[C@@H]5[C@H]6CC[C@H](C6)N5C(=O)OC(C)(C)C)c(F)c4)cc32)CC1] | n.d. | n.d. | n.d. |
| I-3.2.88 | I-3.1.2 | 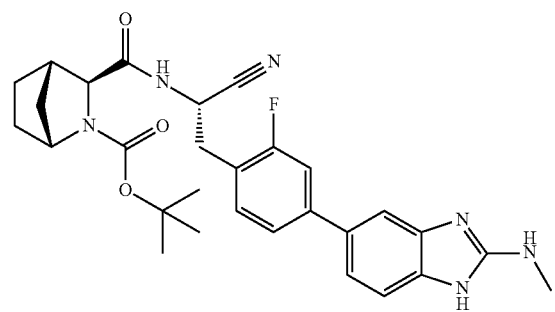 [SMILES: CNc1nc2cc(-c3ccc(C[C@@H](C#N)NC(=O)[C@@H]4[C@H]5CC[C@H](C5)N4C(=O)OC(C)(C)C)c(F)c3)ccc2[nH]1] | 533 | 1.08 | V011_S01 |

TABLE 13-continued

| Intermediate | Educt | Structure of Intermediate | m/z [M + H]+ | rt (min) | LC-MS method |
|---|---|---|---|---|---|
| I-3.2.90 | I-3.1.6 | | 563 | 1.29 | V011_S01 |
| I-3.2.91 | I-3.1.7 | | n.d. | n.d. | n.d. |

Intermediate I-3.2.64 is separated according to method chiral SFC A to give the following intermediates as shown in Table 13.1

TABLE 13.1

| Intermediate | Educt | Structure | m/z [M + H]+ | rt (min) | LC-MS method |
|---|---|---|---|---|---|
| I-3.2.64.1 | I-3.2.64 | 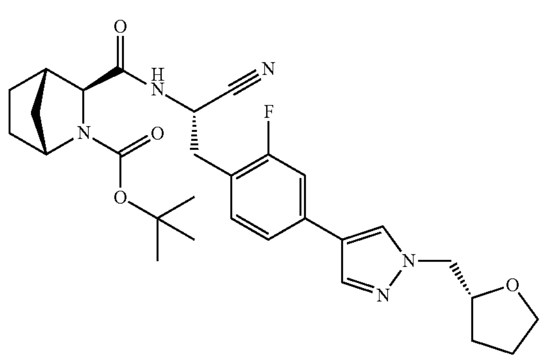 [SMILES: CC(C)(C)OC(=O)N1[C@@H]2CC[C@@H](C2)[C@H]1C(=O)N[C@H](C#N)Cc1ccc(-c2cnn(C[C@H]3CCCO3)c2)cc1F] | n.d. | 3.828 | I_ADH_15_MEOH_DEA.M |

TABLE 13.1-continued

| Intermediate | Educt | Structure | m/z [M + H]+ | rt (min) | LC-MS method |
|---|---|---|---|---|---|
| I-3.2.64.2 | I-3.2.64 | 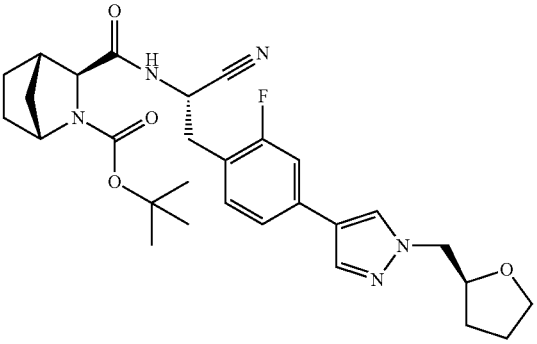 [SMILES: CC(C)(C)OC(=O)N1[C@@H]2CC[C@@H](C2)[C@H]1C(=O)N[C@H](C#N)Cc1ccc(-c2cnn(C[C@@H]3CCCO3)c2)cc1F] | n.d. | 4.631 | I_ADH_15_MEOH_DEA.M |

Intermediate I-3.2.74, I-3.2.75, I-3.2.81, I-3.2.82, I-3.2.89, I-3.2.90, I-3.2.113, is further processed via hydrogenation before the BOC group is removed (step 4)

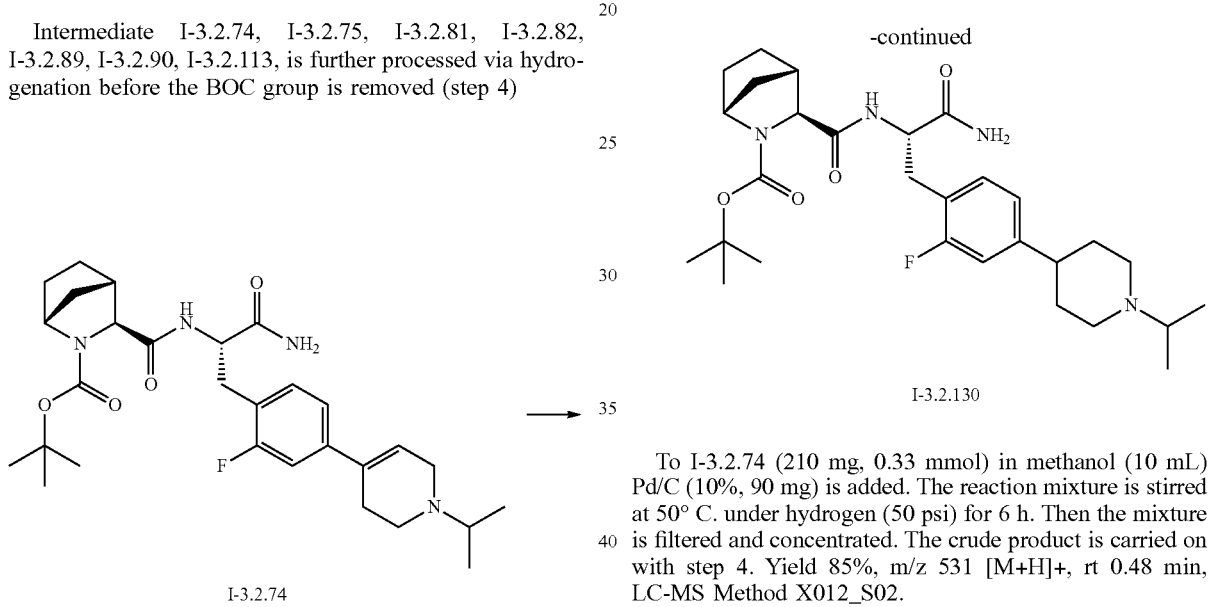

To I-3.2.74 (210 mg, 0.33 mmol) in methanol (10 mL) Pd/C (10%, 90 mg) is added. The reaction mixture is stirred at 50° C. under hydrogen (50 psi) for 6 h. Then the mixture is filtered and concentrated. The crude product is carried on with step 4. Yield 85%, m/z 531 [M+H]+, rt 0.48 min, LC-MS Method X012_S02.

In analogy the following intermediates as shown in Table 17 are prepared.

TABLE 17

| Intermediate | Educt | Structure of Intermediate | m/z [M + H]+ | rt (min) | LC-MS method |
|---|---|---|---|---|---|
| I-3.2.122 | I-3.2.75 | 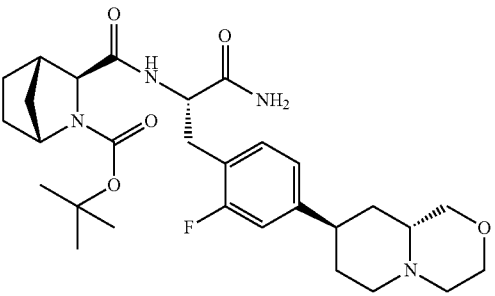 [SMILES: CC(C)(C)OC(=O)N1[C@@H]2CC[C@@H](C2)[C@H]1C(=O)N[C@@H](Cc1ccc([C@@H]2CCN3CCOC[C@H]3C2)cc1F)C(N)=O] | 545 | 0.98 | V011_S01 |

TABLE 17-continued

| Intermediate | Educt | Structure of Intermediate | m/z [M + H]+ | rt (min) | LC-MS method |
|---|---|---|---|---|---|
| I-3.2.123 | I-3.2.75 | | 545 | 1.03 | V011_S01 |
| I-3.2.124 | I-3.2.81 | | 559 | 0.62 | X011_S03 |
| I-3.2.125 | I-3.2.82 | | 489 | 0.44 | X018_S02 |
| I-3.2.126 | I-3.2.89 | | 516 | 1.02 | V011_S01 |

TABLE 17-continued
| Intermediate | Educt | Structure of Intermediate | m/z [M + H]+ | rt (min) | LC-MS method |
|---|---|---|---|---|---|
| I-3.2.127 | I-3.2.90 | | 475 | 0.41 | X018_S02 |
| I-3.2.128 | I-3.2.113 | | 530 | 1.12 | V011_S01 |
| I-3.2.129 | I-3.2.113 | | 530 | 1.00 | V011_S01 |
Intermediate I-3.2.91 is further processed in the following way:
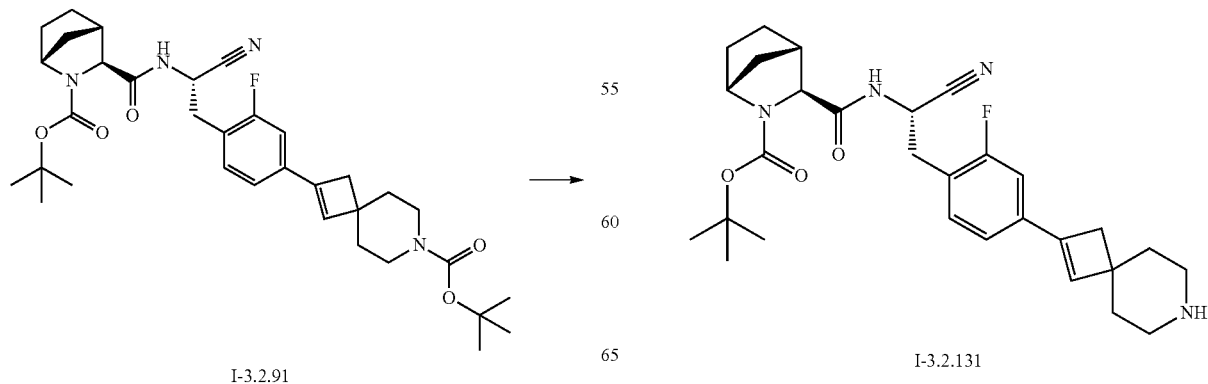
I-3.2.91 → I-3.2.131

To I-3.2.91 (200 mg, 0.28 mmol) in ACN (3 mL) is added p-toluene sulfonic acid monohydrate (79.67 mg, 0.42 mmol) and stirred at r.t. for 2.5 h. The reaction mixture is diluted with TEA, filtered and purified by reversed phase HPLC.

Yield 68%

Intermediate I-3.2.125, I-3.2.126, I-3.2.129 and I-3.2.131 is further processed via reductive amination before the BOC group is removed (step 4)

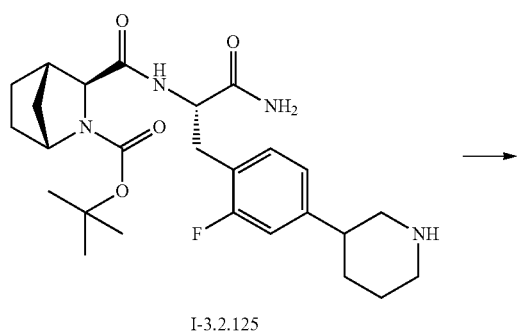

I-3.2.125

→

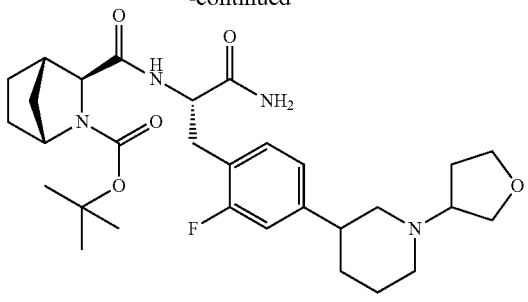

I-3.2.132

To I-3.2.125 (130 mg, 0.266 mmol) in dichlormethane is added 3-oxotetrahydrofuran (27.49 mg, 0.319 mmol) and glacial acetic acid (15.22 µL, 0.266 mmol) and stirred for 45 min at r.t. Sodium triacetoxyborohydride (83.1 mg, 0.372 mmol) is added and the reaction mixture is stirred at r.t. overnight.

The reaction mixture is diluted with dichlormethane and sat. NaHCO$_3$. The organic layer is separated, dried and concentrated. The crude product is used for the next step without further purification.

Yield 99%, m/z 559 [M+H]+, rt 0.44 min, LC-MS Method X018_502.

In analogy the following intermediates as shown in Table 18 are prepared.

TABLE 18

| Intermediate | Educt | Structure of Intermediate | m/z [M + H]+ | rt (min) | LC-MS method |
|---|---|---|---|---|---|
| I-3.2.133, | I-3.2.126, | | 586 | 0.50 | X012_S02 |
| I-3.2.134 | I-3.2.126 | | 530 | 1.14 | V011_S01 |

TABLE 18-continued

| Intermediate | Educt | Structure of Intermediate | m/z [M + H]+ | rt (min) | LC-MS method |
|---|---|---|---|---|---|
| I-3.2.135 | I-3.2.129 | | 586 | 1.09 | V011_S01 |
| I-3.2.136 | I-3.2.131 | | n.d. | n.d. | n.d. |

The reaction time for I-3.2.133 and I-3.2.135 is 30 min at r.t. and for I-3.2.134 2 h at r.t. and for I-3.2.136 1 h at r.t.

Intermediate I-3.2.136 is deprotected (see example 359) and further processes via hydrogenation to give example 358:

To example 359 (20 mg, 0.047 mmol) in methanol (3 mL) Pd/C (10%, 5 mg) is added. The reaction mixture is stirred at r.t. under hydrogen (50 psi) for 10 min. Then the mixture is filtered and concentrated. The crude product is purified by reversed phase HPLC to give example 358. Yield 35%, m/z 425 rt 0.715 min, LC-MS Method Z012_S04.

Intermediate I-3.2.127 is further processed via alkylation before the BOC group is removed (step 4)

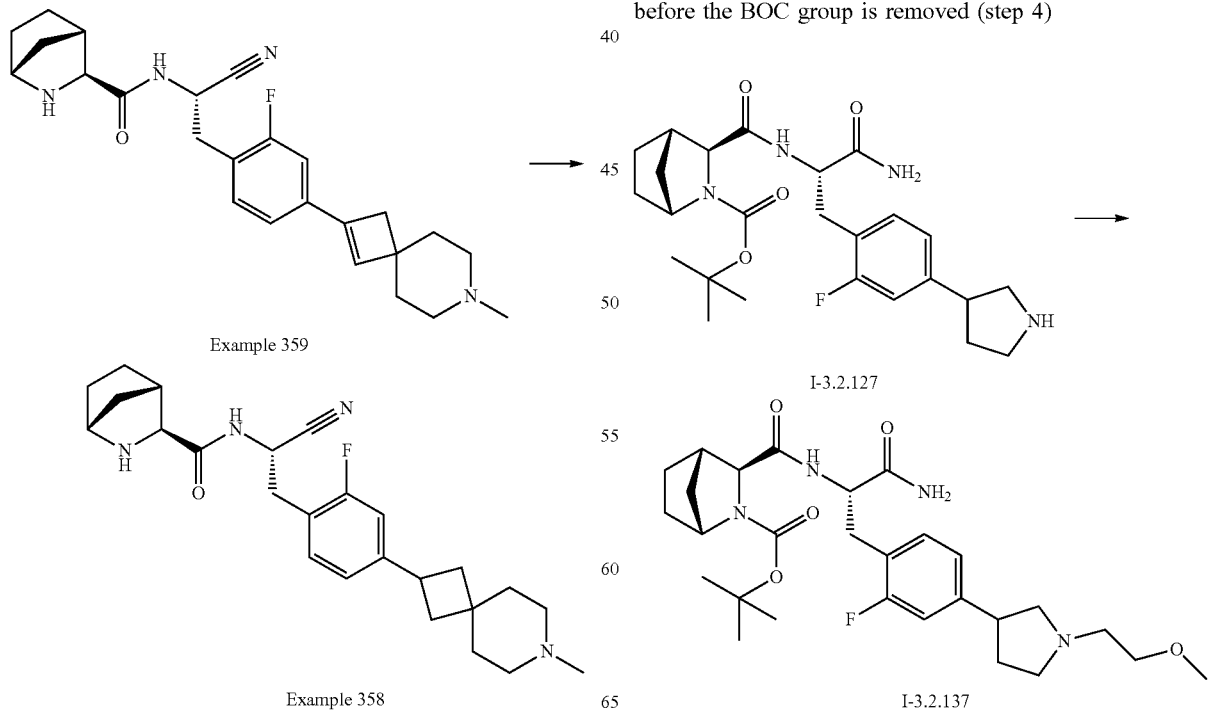

Example 359

Example 358

I-3.2.127

I-3.2.137

To I-3.2.127 (71 mg, 0.15 mmol) in DMF (2 mL) is added 2-bromoethyl methyl ether (29.53 μL, 0.31 mmol) and potassium carbonate (41.36, 0.266 mmol) and stirred overnight at r.t. The reaction mixture is diluted with dichlormethane and water. The organic layer is separated, dried and concentrated. The crude product is purified by reversed phase HPLC. Yield 40%, m/z 533 [M+H]+, rt 1.05 min, LC-MS Method V011_S01.

Step 3: Synthesis of Intermediate I-3.3

To I-3.2 (187 mg, 0.35 mmol) in DCM (12 mL) R2 (182 mg, 0.77 mmol) is added. The reaction mixture is stirred for 12 h, concentrated, dissolved in ethyl acetate and extracted with 0.1M HCl and water. The organic layer is dried over $MgSO_4$ and concentrated. Yield 86%.

The following intermediates as shown in Table 19 are synthesized in a similar fashion from the appropriate intermediate:

TABLE 19

| Intermediate | Educt | Structure of Intermediate | m/z [M + H]+ | rt (min) | LC-MS method |
|---|---|---|---|---|---|
| I-3.3.1 | I-3.2.1 | | 533 | 1.21 | V011_S01 |
| I-3.3.3 | I-3.2.5 | | n.d. | n.d. | n.d. |
| I-3.3.4 | I-3.2.8 | | n.d. | n.d. | n.d. |

TABLE 19-continued
| Intermediate | Educt | Structure of Intermediate | m/z [M + H]+ | rt (min) | LC-MS method |
|---|---|---|---|---|---|
| I-3.3.5 | I-3.2.15 | 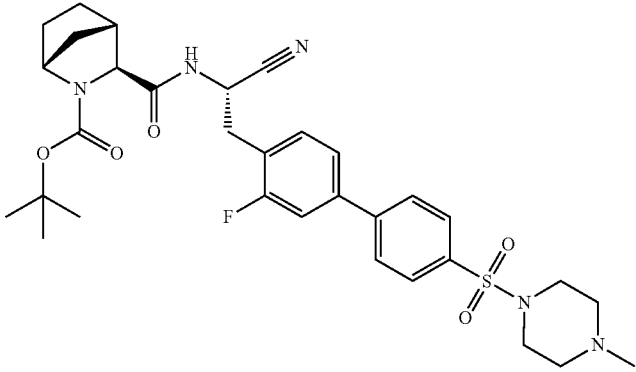 [SMILES: CN1CCN(S(=O)(=O)c2ccc(-c3ccc(C[C@@H](C#N)NC(=O)[C@@H]4[C@H]5CC[C@H](C5)N4C(=O)OC(C)(C)C)c(F)c3)cc2)CC1] | 626 | n.d. | n.d. |
| I-3.3.6 | I-3.2.16 | 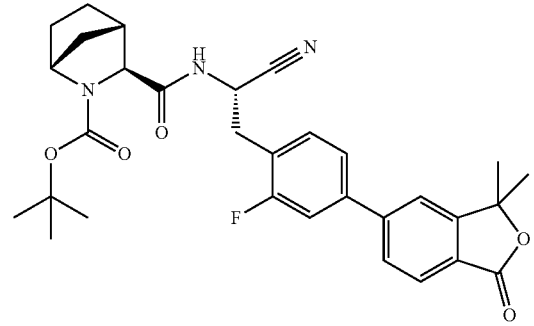 [SMILES: CC(C)(C)OC(=O)N1[C@@H]2CC[C@@H](C2)[C@H]1C(=O)N[C@H](C#N)Cc1ccc(-c2ccc3c(c2)C(C)(C)OC3=O)cc1F] | n.d. | n.d. | n.d. |
| I-3.3.7 | I-3.2.17 | 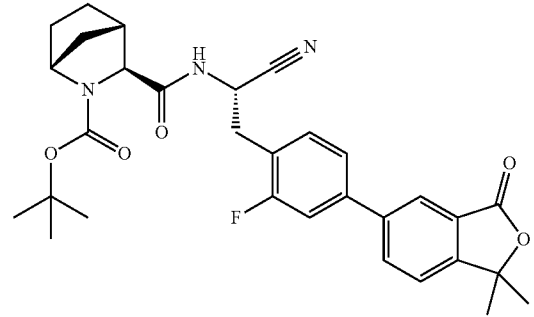 [SMILES: CC(C)(C)OC(=O)N1[C@@H]2CC[C@@H](C2)[C@H]1C(=O)N[C@H](C#N)Cc1ccc(-c2ccc3c(c2)C(=O)OC3(C)C)cc1F] | n.d. | n.d. | n.d. |
| I-3.3.8 | I-3.2.130 | 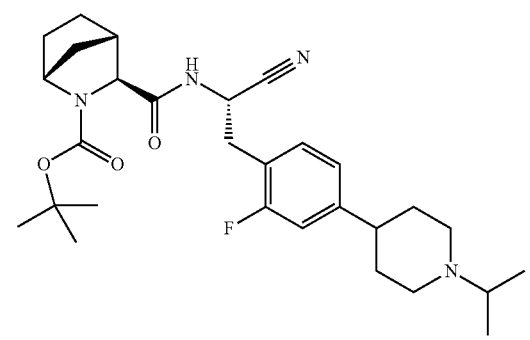 [SMILES: CC(C)N1CCC(c2ccc(C[C@@H](C#N)NC(=O)[C@@H]3[C@H]4CC[C@H](C4)N3C(=O)OC(C)(C)C)c(F)c2)CC1] | 513 | 0.55 | X012_S02 |

TABLE 19-continued

| Intermediate | Educt | Structure of Intermediate | m/z [M + H]+ | rt (min) | LC-MS method |
|---|---|---|---|---|---|
| I-3.3.9 | I-3.2.75 | | 525 | 1.17 | V011_S01 |
| I-3.3.10 | I-3.2.76 | | 525 | 1.15 | V011_S01 |
| I-3.3.11 | I-3.2.122 | | 527 | 1.15 | V011_S01 |
| I-3.3.12 | I-3.2.123 | | 527 | 1.12 | V011_S01 |
| I-3.3.13 | I-3.2.78 | | 496 | 0.54 | X012_S02 |

TABLE 19-continued
| Intermediate | Educt | Structure of Intermediate | m/z [M + H]+ | rt (min) | LC-MS method |
|---|---|---|---|---|---|
| I-3.3.14 | I-3.2.124 | 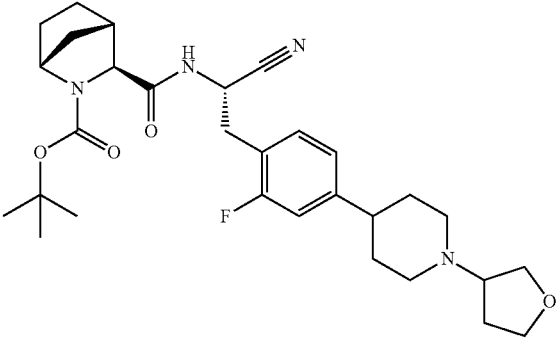 [SMILES: CC(C)(C)OC(=O)N1[C@@H]2CC[C@@H](C2)[C@H]1C(=O)N[C@H](C#N)Cc1ccc(C2CCN(C3CCOC3)CC2)cc1F] | 541 | 0.71 | X011_S03 |
| I-3.3.15; | I-3.2.132 | 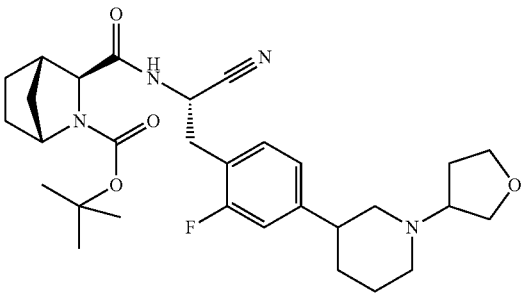 [SMILES: CC(C)(C)OC(=O)N1[C@@H]2CC[C@@H](C2)[C@H]1C(=O)N[C@H](C#N)Cc1ccc(C2CCCN(C3CCOC3)C2)cc1F] | 541 | 0.49 | X018_S02 |
| I-3.3.16 | I-3.2.133 | 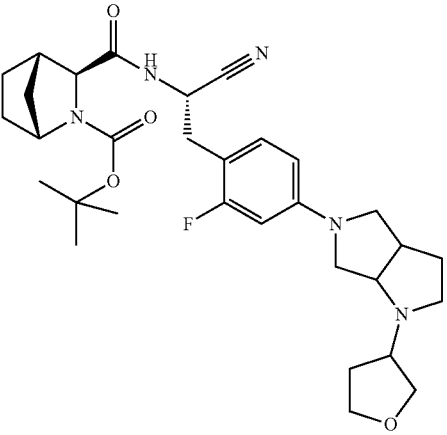 [SMILES: CC(C)(C)OC(=O)N1[C@@H]2CC[C@@H](C2)[C@H]1C(=O)N[C@H](C#N)Cc1ccc(N2CC3CCN(C4CCOC4)C3C2)cc1F] | 568 | 1.22 | V011_S01 |
| I-3.3.17 | I-3.2.134 | 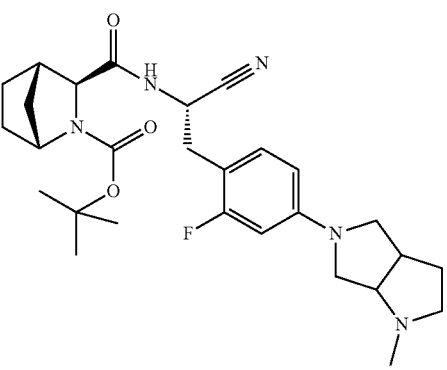 [SMILES: CN1CCC2CN(c3ccc(C[C@@H](C#N)NC(=O)[C@@H]4[C@H]5CC[C@H](C5)N4C(=O)OC(C)(C)C)c(F)c3)CC21] | 512 | 1.26 | V011_S01 |

US 9,713,606 B2

183                                                                184

TABLE 19-continued

| Intermediate | Educt | Structure of Intermediate | m/z [M + H]+ | rt (min) | LC-MS method |
|---|---|---|---|---|---|
| I-3.3.18 | I-3.2.137 | | 515 | 1.17 | V011_S01 |
| I-3.3.19 | I-3.2.128 | | 512 | 1.25 | V011_S01 |
| I-3.3.20 | I-3.2.135 | | 568 | 1.23 | V011_S01 |

Step 4: Synthesis of Example 3

To I-3.3 (155 mg, 0.30 mmol) in acetonitrile, sodium iodide (134 mg, 0.89 mmol) and chlorotrimethylsilane (114 µl, 0.89 mmol) are added. The mixture is stirred for 2 h, then methanol is added, stirred for additional 30 min and then concentrated. The residue is purified by reversed phase HPLC. Yield 62%, m/z 420 [M+H]+, rt 0.41 min, LC-MS Method X016_S01.

Method A2.2

Synthesis of (1S,2S,4R)-N-[(1S)-1-cyano-2-[2-fluoro-4-(4-phenylpiperazin-1-yl)phenyl]ethyl]-3-azabicyclo[2.2.1]heptane-2-carboxamide (Example 32)

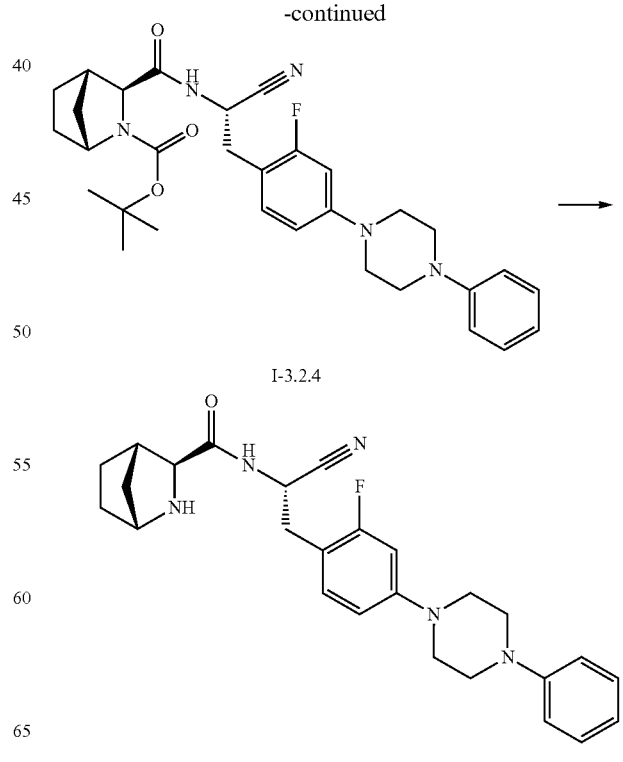

Example 32

Step 1: Synthesis of Intermediate I-3.2.4

To I-3.1.2 (150 mg, 0.30 mmol) in DCM (6 mL), triethylamine (85 µL, 0.61 mmol), R112 (55.22 mg, 0.34 mmol) and copper(II)acetate (85 mg, 0.47 mmol) are added. The mixture is stirred for 72 h at r.t. 7M ammonium solution in methanol is added, the mixture is concentrated. The residue dissolved in acetonitrile and filtrated. The product is purified by reversed phase HPLC. Yield 54%, m/z 548 [M+H]+, rt 1.37 min, LC-MS Method V011_S01.

The following intermediates as shown in Table 14 are synthesized in a similar fashion from the appropriate intermediate

TABLE 14

| Intermediate | Educt | Structure of Intermediates | m/z [M + H]+ | LC-MS rt (min) | method |
|---|---|---|---|---|---|
| I-3.2.7 | I-3.1.2 | 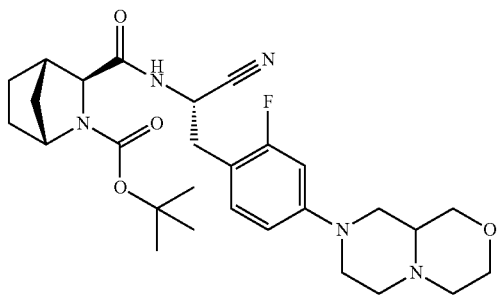 [SMILES: CC(C)(C)OC(=O)N1[C@@H]2CC[C@@H](C2)[C@H]1C(=O)N[C@H](C#N)Cc1ccc(N2CCN3CCOCC3C2)cc1F] | 528 | 1.10 | V011_S01 |
| I-3.2.9 | I-3.1.2 | 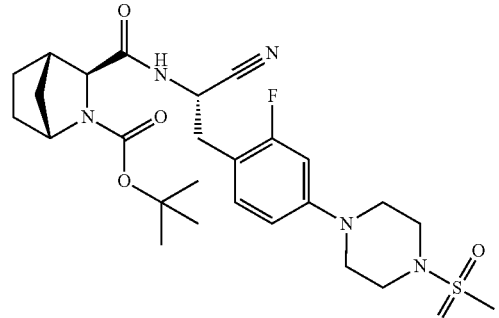 | 550 | 1.11 | V011_S01 |
| I-3.2.14 | I-3.1.2 | 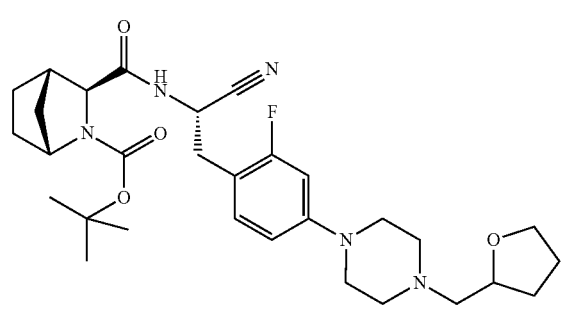 [SMILES: CC(C)(C)OC(=O)N1[C@@H]2CC[C@@H](C2)[C@H]1C(=O)N[C@H](C#N)Cc1ccc(N2CCN(CC3CCCO3)CC2)cc1F] | 556 | 1.20 | V011_S01 |
| I-3.2.19 | I-3.1.2 | 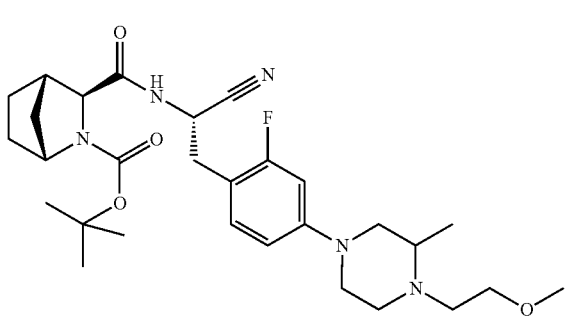 [SMILES: COCCN1CCN(c2ccc(C[C@@H](C#N)NC(=O)[C@@H]3[C@H]4CC[C@H](C4)N3C(=O)OC(C)(C)C)c(F)c2)CC1C] | 544 | 1.22 | V011_S01 |

TABLE 14-continued

| Intermediate | Educt | Structure of Intermediates | m/z [M + H]+ | rt (min) | LC-MS method |
| --- | --- | --- | --- | --- | --- |
| I-3.2.20 | I-3.1.2 | | 354 (M + H − BOC)+ | 1.20 | V011_S01 |
| I-3.2.22 | I-3.1.2 | | 530 | 1.13 | V011_S01 |
| I-3.2.24 | I-3.1.2 | | 512 | 1.28 | V011_S01 |
| I-3.2.25 | I-3.1.2 | | 500 | 1.21 | V011_S01 |
| I-3.2.26 (forms together with I-3.2.27) | I-3.1.2 | | 516 | 1.02 | V011_S01 |

TABLE 14-continued
| Intermediate | Educt | Structure of Intermediates | m/z [M + H]+ | rt (min) | LC-MS method |
|---|---|---|---|---|---|
| I-3.2.27 (forms together with I-3.2.26) | I-3.1.2 | 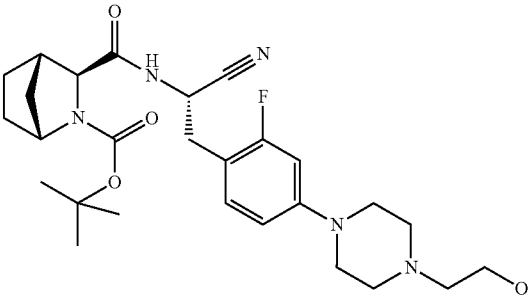 [SMILES: CC(C)(C)OC(=O)N1[C@@H]2CC[C@@H](C2)[C@H]1C(=O)N[C@H](C#N)Cc1ccc(N2CCN(CCO)CC2)cc1F] | 516 | 1.02 | V011_S01 |
| I-3.2.28; | I-3.1.2 | 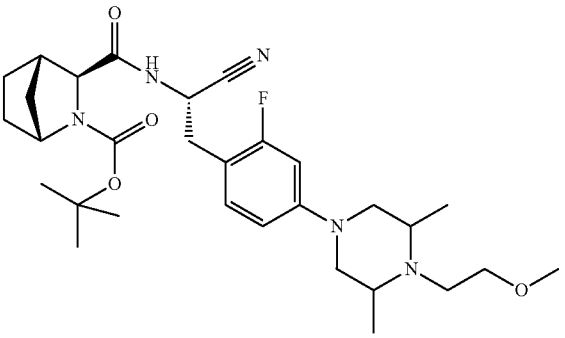 [SMILES: COCCN1C(C)CN(c2ccc(C[C@@H](C#N)NC(=O)[C@@H]3[C@H]4CC[C@H](C4)N3C(=O)OC(C)(C)C)c(F)c2)CC1C] | 558 | 1.25 | V011_S01 |
| I-3.2.29 | I-3.1.2 | 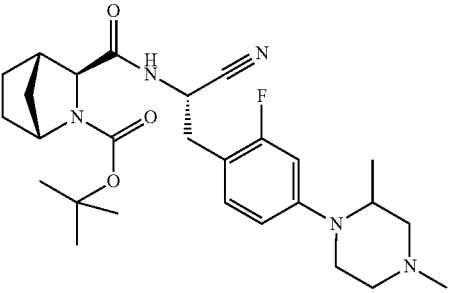 [SMILES: CC1CN(C)CCN1c1ccc(C[C@@H](C#N)NC(=O)[C@@H]2[C@H]3CC[C@H](C3)N2C(=O)OC(C)(C)C)c(F)c1] | 500 | 1.21 | V011_S01 |
| I-3.2.30 | I-3.1.2 | 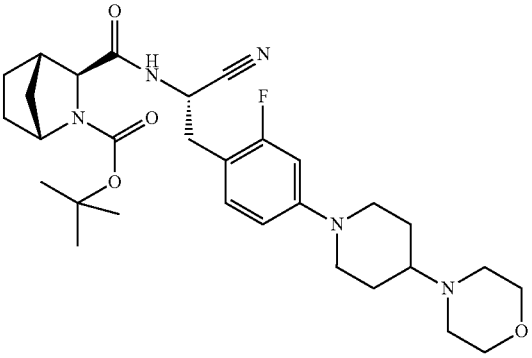 [SMILES: CC(C)(C)OC(=O)N1[C@@H]2CC[C@@H](C2)[C@H]1C(=O)N[C@H](C#N)Cc1ccc(N2CCC(N3CCOCC3)CC2)cc1F] | 556 | 1.13 | V011_S01 |

TABLE 14-continued
| Intermediate | Educt | Structure of Intermediates | m/z [M + H]+ | rt (min) | LC-MS method |
|---|---|---|---|---|---|
| I-3.2.31 | I-3.1.2 | 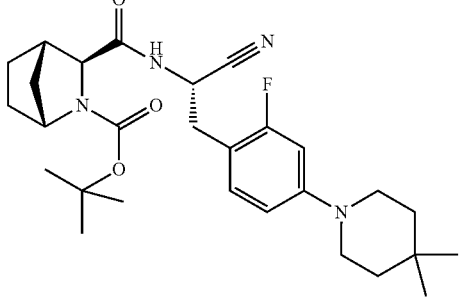 | 499 | 1.49 | V011_S01 |
| I-3.2.32; | I-3.1.2 | 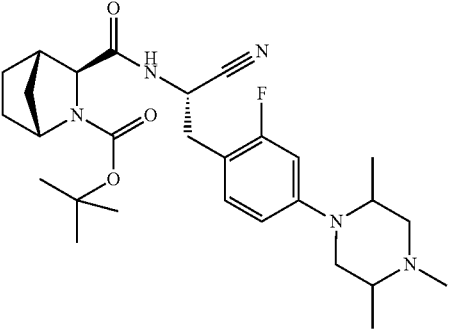 [SMILES: CC1CN(c2ccc(C[C@@H](C#N)NC(=O)[C@@H]3[C@H]4CC[C@H](C4)N3C(=O)OC(C)(C)C)c(F)c2)C(C)CN1C] | 514 | 1.21 | V011_S01 |
| I-3.2.33 | I-3.1.2 | 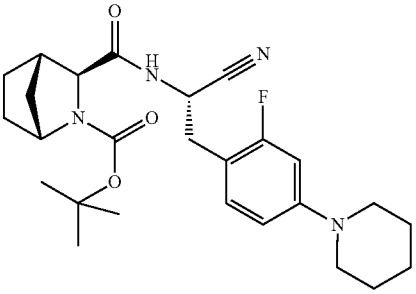 [SMILES: CC(C)(C)OC(=O)N1[C@@H]2CC[C@@H](C2)[C@H]1C(=O)N[C@H](C#N)Cc1ccc(N2CCCCC2)cc1F] | 471 | 1.39 | V011_S01 |
| I-3.2.34 | I-3.1.2 | 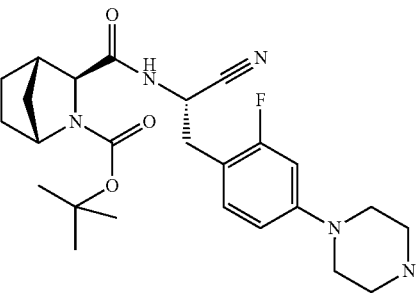 [SMILES: CC(C)(C)OC(=O)N1[C@@H]2CC[C@@H](C2)[C@H]1C(=O)N[C@H](C#N)Cc1ccc(N2CCNCC2)cc1F] | 472 | 1.36 | V011_S01 |
| I-3.2.35 | I-3.1.2 | 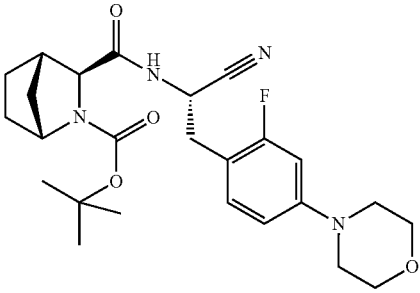 [SMILES: CC(C)(C)OC(=O)N1[C@@H]2CC[C@@H](C2)[C@H]1C(=O)N[C@H](C#N)Cc1ccc(N2CCOCC2)cc1F] | 473 | 1.17 | V011_S011 |

TABLE 14-continued

| Intermediate | Educt | Structure of Intermediates | m/z [M + H]+ | rt (min) | LC-MS method |
|---|---|---|---|---|---|
| I-3.2.92 | I-3.1.2 | | n.d. | 0.67 | X011_S03 |
| I-3.2.93; | I-3.1.2 | | 540 | 1.09 | V011_S01 |
| I-3.2.94 | I-3.1.2 | | 561 | 1.07 | V011_S01 |
| I-3.2.95 | I-3.1.2 | | 559 | 1.08 | V011_S01 |

TABLE 14-continued
| Intermediate | Educt | Structure of Intermediates | m/z [M + H]+ | rt (min) | LC-MS method |
|---|---|---|---|---|---|
| I-3.2.96 | I-3.1.2 | 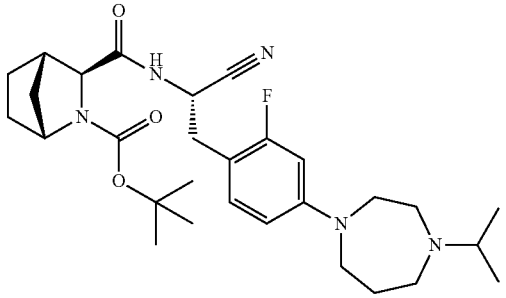 [SMILES: CC(C)N1CCCN(c2ccc(C[C@@H](C#N)NC(=O)[C@@H]3[C@H]4CC[C@H](C4)N3C(=O)OC(C)(C)C)c(F)c2)CC1] | 528 | 0.78 | X011_S03 |
| I-3.2.97 | I-3.1.2 | 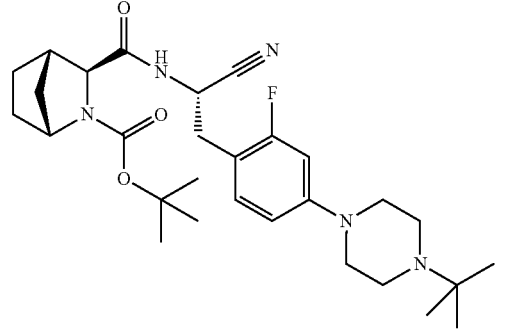 [SMILES: CC(C)(C)OC(=O)N1[C@@H]2CC[C@@H](C2)[C@H]1C(=O)N[C@H](C#N)Cc1ccc(N2CCN(C(C)(C)C)CC2)cc1F] | 528 | 0.77 | X011_S03 |
| I-3.2.98 | I-3.1.7 | 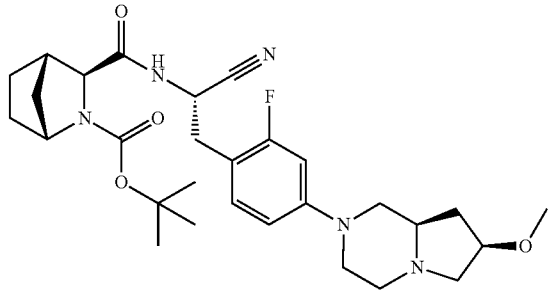 [SMILES: CO[C@@H]1C[C@@H]2CN(c3ccc(C[C@@H](C#N)NC(=O)[C@@H]4[C@H]5CC[C@H](C5)N4C(=O)OC(C)(C)C)c(F)c3)CCN2C1] | 542 | 1.26 | V011_S01 |
| I-3.2.99 | I-3.1.7 | 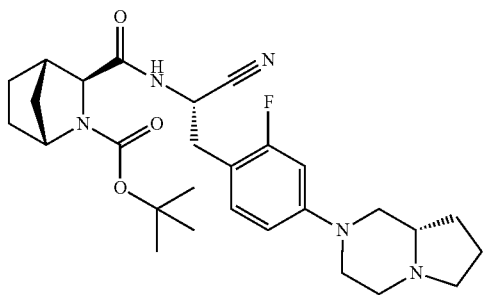 [SMILES: CC(C)(C)OC(=O)N1[C@@H]2CC[C@@H](C2)[C@H]1C(=O)N[C@H](C#N)Cc1ccc(N2CCN3CCC[C@H]3C2)cc1F] | 512 | 1.26 | V011_S01 |
| I-3.2.100 | I-3.1.7 | 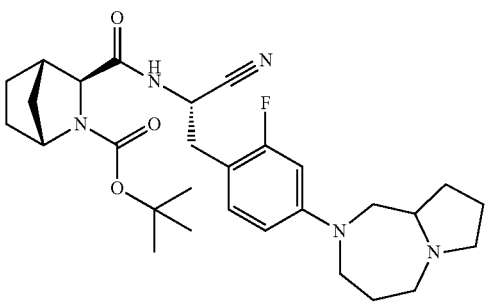 [SMILES: CC(C)(C)OC(=O)N1[C@@H]2CC[C@@H](C2)[C@H]1C(=O)N[C@H](C#N)Cc1ccc(N2CCCN3CCCC3C2)cc1F] | 526 | 0.72 | X011_S03 |

TABLE 14-continued

| Intermediate | Educt | Structure of Intermediates | m/z [M + H]+ | rt (min) | LC-MS method |
|---|---|---|---|---|---|
| I-3.2.101 | I-3.1.7 | | 500 | 1.24 | V011_S01 |
| I-3.2.102 | I-3.1.4 | | 486 | 1.13 | V011_S01 |
| I-3.2.103 | I-3.1.2 | | 584 | 1.36 | V011_S01 |
| I-3.2.104 | I-3.1.7 | | 512 | 1.31 | V011_S01 |

TABLE 14-continued
| Intermediate | Educt | Structure of Intermediates | m/z [M + H]+ | rt (min) | LC-MS method |
|---|---|---|---|---|---|
| I-3.2.105 | I-3.1.7 | 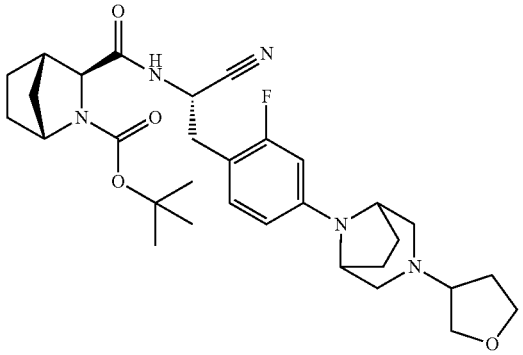 [SMILES: CC(C)(C)OC(=O)N1[C@@H]2CC[C@@H](C2)[C@H]1C(=O)N[C@H](C#N)Cc1ccc(N2C3CCC2CN(C2CCOC2)C3)cc1F] | 568 | 0.75 | X011_S03 |
| I-3.2.106 | I-3.1.7 | 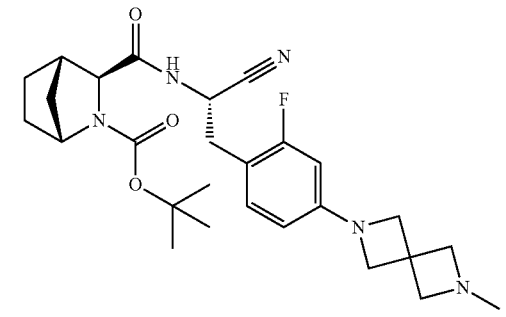 [SMILES: CN1CC2(C1)CN(c1ccc(C[C@@H](C#N)NC(=O)[C@@H]3[C@H]4CC[C@H](C4)N3C(=O)OC(C)(C)C)c(F)c1)C2] | 498 | 1.20 | V011_S01 |
| I-3.2.107 | I-3.1.7 | 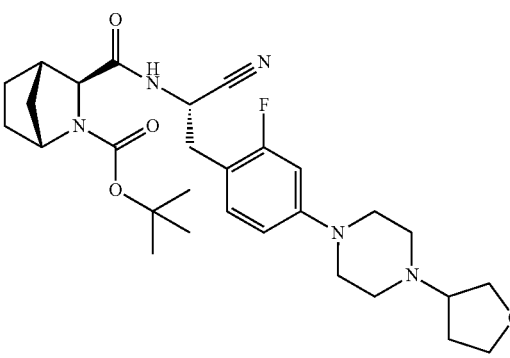 | 542 | 1.13 | V011_S01 |
| I-3.2.108 | I-3.1.7 | 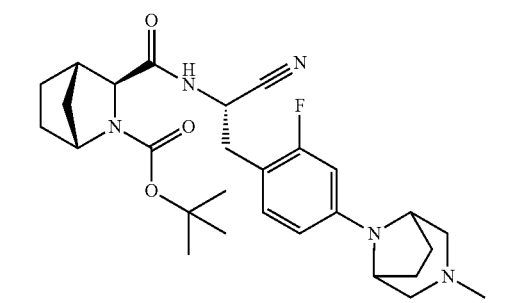 [SMILES: CN1CC2CCC(C1)N2c1ccc(C[C@@H](C#N)NC(=O)[C@@H]2[C@H]3CC[C@H](C3)N2C(=O)OC(C)(C)C)c(F)c1] | 512 | 1.29 | V011_S01 |

TABLE 14-continued

| Intermediate | Educt | Structure of Intermediates | m/z [M + H]+ | rt (min) | LC-MS method |
|---|---|---|---|---|---|
| I-3.2.109 | I-3.1.2 | | 572 | 1.36 | V011_S01 |
| I-3.2.110 | I-3.1.2 | | 556 | 0.65 | X011_S03 |
| I-3.2.111 | I-3.1.1 | | 528 | 0.79 | X011_S03 |
| I-3.2.112 | I-3.1.7 | | 513 | 0.69 | X011_S03 |

TABLE 14-continued
| Intermediate | Educt | Structure of Intermediates | m/z [M + H]+ | rt (min) | LC-MS method |
|---|---|---|---|---|---|
| I-3.2.114 | I-3.1.7 | 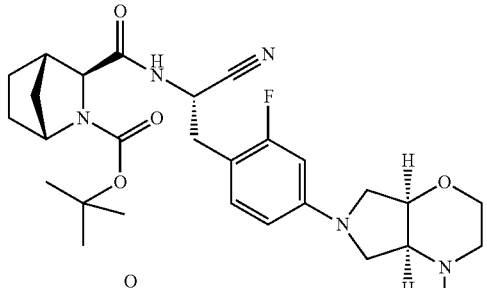 | n.d. | n.d. | n.d. |
| I-3.2.115 | I-3.1.7 | 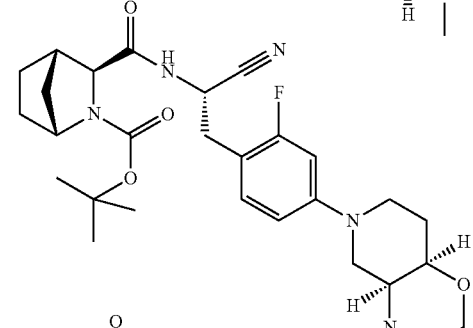 | 542 | 0.99 | Z011_S03 |
| I-3.2.116 | I-3.1.7 | 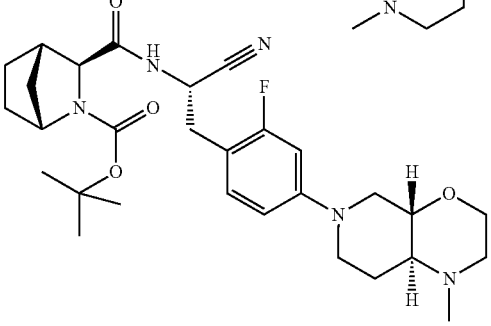 | 542 | 1.017 | Z011_S03 |
For the synthesis of the intermediates I-3.2.117 and I-3.2.118 to the educt I-3.1.2 with the appropriate amine in MeOH 0.14 eq copper(I)oxide is added (as shown in Table 15).
TABLE 15
| Intermediate | Educt | Structure of Intermediate | m/z [M + H]+ | rt (min) | LC-MS method |
|---|---|---|---|---|---|
| I-3.2.117 | I-3.1.2 | 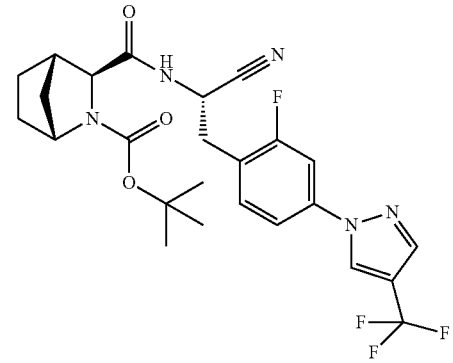 [SMILES: CC(C)(C)OC(=O)N1[C@@H]2CC[C@@H](C2)[C@H]1C(=O)N[C@H](C#N)Cc1ccc(-n2cc(C(F)(F)F)cn2)cc1F] | 422 (M + H − BOC)+ | 1.32 | V011_S01 |

TABLE 15-continued

| Intermediate | Educt | Structure of Intermediate | m/z [M + H]+ | rt (min) | LC-MS method |
|---|---|---|---|---|---|
| I-3.2.118 | I-3.1.2 | 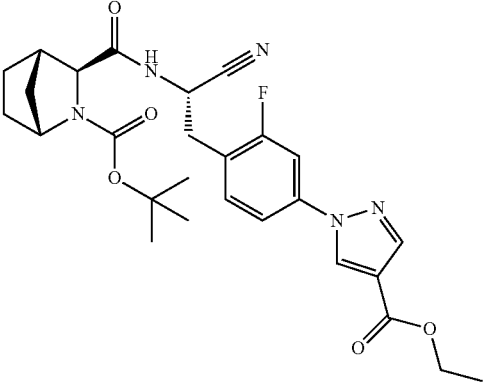 [SMILES: CCOC(=O)c1cnn(-c2ccc(C[C@@H](C#N)NC(=O)[C@@H]3[C@H]4CC[C@H](C4)N3C(=O)OC(C)(C)C)c(F)c2)c1] | 526 | 1.28 | V011_S01 |
| I-3.2.119 | I-3.2.118 | 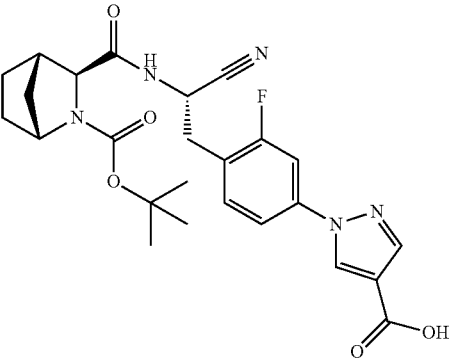 [SMILES: CC(C)(C)OC(=O)N1[C@@H]2CC[C@@H](C2)[C@H]1C(=O)N[C@H](C#N)Cc1ccc(-n2cc(C(=O)O)cn2)cc1F] | 498 | 1.84 | I_OJH_10_MEOH_DEA.M |
| I-3.2.120 | I-3.2.119 | 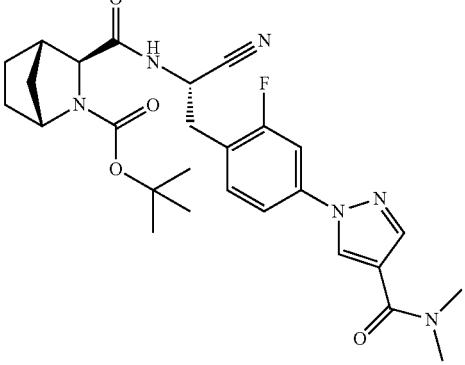 | 525 | 1.10. | V011_S01 |

The synthesis of I-3.2.119 proceeds in the following way: I-3.2.118 (785 mg, 1.49 mmol) is dissolved in THF. LiOH (1.5 eq.) as aq. solution is added and stirred at r.t. for 9 h. The product mixture is acidified with 1 M HCl to pH 5 and purified by HPLC-MS. Yield: 61%.

The amide coupling for synthesis of intermediate I-3.2.120 proceeds in the following way: I-3.2.119 (40 mg, 0.08 mmol) HATU (33.6 mg, 0.088 mmol) and DIPEA (55.3 µL, 0.322 mmol) are dissolved in DMF. The mixture is stirred at r.t. for 15 min. Dimethylamine (120.6 µL, 0.241 mmol) is added, and the reaction mixture is stirred at r.t. for 1.5 h. The product mixture is separated by HPLC-MS. The fractions are combined and freeze-dried. Yield: 85%.

The following intermediate as shown in Table 16 is synthesized in a similar fashion from the appropriate intermediate

TABLE 16

| Intermediate | Educt | Structure of Intermediate | m/z [M + H]+ | rt (min) | LC-MS method |
|---|---|---|---|---|---|
| I-3.2.121 | I-3.2.119 | 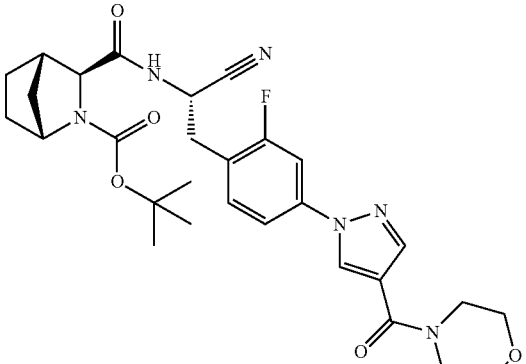 | 567 | 1.10 | V011_S01 |

The reaction conditions for I-3.2.94 and I-3.2.95 differ: Pyridine instead of TEA is used. The reaction conditions are 80° C. overnight.

The reaction conditions for I-3.2.111 differ: 2 eq of N-Methylmorpholine N-Oxide is added to the reaction.

Step 2: Synthesis of Example 32

To I-3.2.4 (82 mg, 0.15 mmol) in acetonitrile, p-toluenesulfonic acid monohydrate (95 mg, 0.50 mmol) is added and stirred overnight at r.t. The reaction mixture is basified with ammonium solution. 0.5 mL water and 1 mL ACN are added. The precipitate is filtered off, washed with ACN and dried. The crude product is triturated with aq. sodium hydrogencarbonate solution, filtered by suction and dried. Yield 31%, m/z 448 [M+H]+, rt 1.28 min, LC-MS Method V011_S01.

Method A3

Synthesis of (1S,2S,4R)-N-[(1S)-1-cyano-2-[2-fluoro-4-(3-methylsulfonylphenyl)phenyl]ethyl]-3-azabicyclo[2.2.1]heptane-2-carboxamide (Example 4)

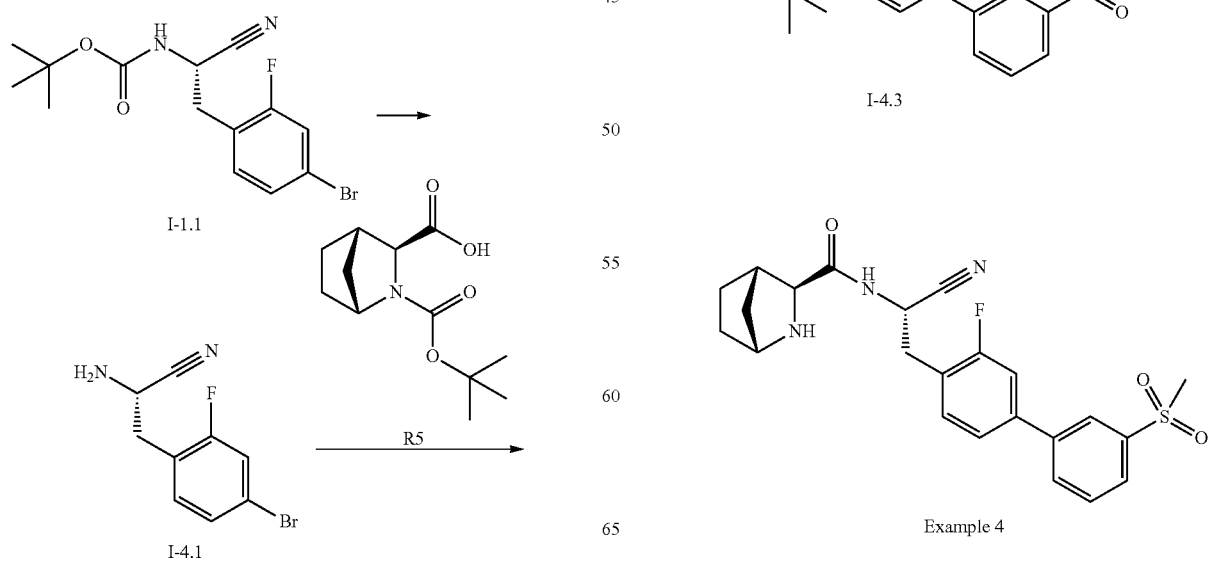

Example 4

Step 1: Synthesis of Intermediate I-4.1

To I-1.1 (5.00 g, 14 mmol) in acetonitrile (250 mL) p-toluenesulfonic acid monohydrate (3.05 g, 16 mmol) is added and the mixture is stirred for 3 d. The precipitate is filtered off and the solution is washed with acetonitrile. The residue is stirred with aq. NaHCO3 solution (2%), and extracted with ethyl acetate. The organic layer is dried over MgSO$_4$ and concentrated. Yield 78%, m/z 243/245 [M+H]+, rt 0.76 min, LC-MS Method V018_S01.

The further intermediates belong to the following description

Synthesis of
2-amino-3-(4-bromo-2-fluoro-phenyl)propanenitrile

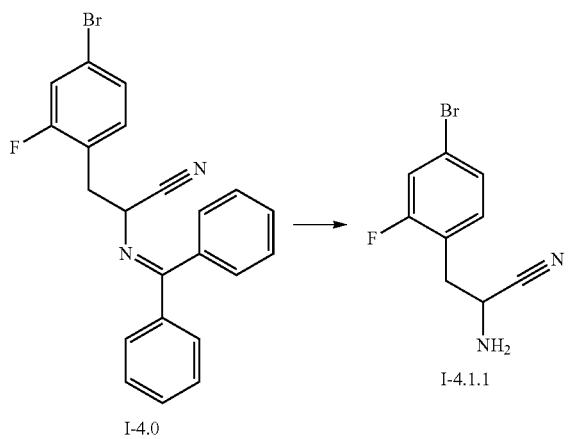

Step 1.1: Synthesis of Intermediate I-4.0 (Compare with Synthesis of Intermediate I-7.1)

To R19 (28.1 g, 104 mmol) and R20 (21.0 g, 95 mmol) in DCM (130 mL) benzyltrimethylammonium chloride (1.77 g, 9.5 mmol) is added. Under strong stirring water (8 mL) and aq. NaOH solution (19 mol/L, 9 mL) are added (exothermic reaction). The reaction mixture is stirred for 12 h. Water is added and the product is extracted with DCM. The organic layer is dried over MgSO$_4$ and concentrated. The crude product is used in step 2. Yield >95%, rt 1.56 min, LC-MS Method V003_003.

The following intermediates as shown in Table 20 are synthesized in a similar fashion from the appropriate intermediate ((R,S)=1:1 mixture of stereoisomers at the carbon adjacent to the nitrile group):

TABLE 20

| Intermediate | Structure | m/z [M + H]+ | LC-MS rt (min) | method |
|---|---|---|---|---|
| I-4.0.1 | 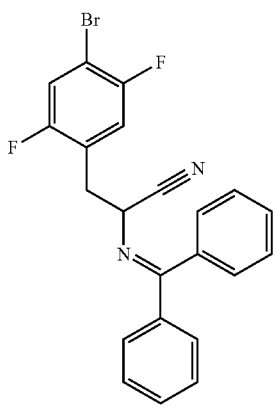 [SMILES: N#CC(Cc1cc(F)c(Br)cc1F)N=C(c1ccccc1)c1ccccc1] | n.d. | n.d. | n.d. |

TABLE 20-continued

| Intermediate | Structure | m/z [M + H]+ | rt (min) | LC-MS method |
|---|---|---|---|---|
| I-4.0.2 | 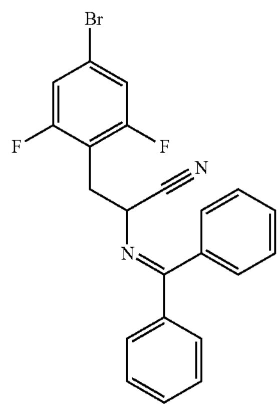 [SMILES: N#CC(Cc1c(F)cc(Br)cc1F)N=C(c1ccccc1)c1ccccc1] | 425/427 | 1.51 | V011_S01 |
| I-4.0.3 | 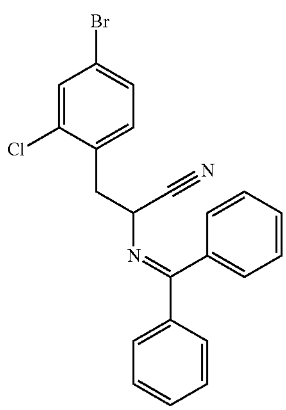 [SMILES: N#CC(Cc1ccc(Br)cc1Cl)N=C(c1ccccc1)c1ccccc1] | n.d. | n.d. | n.d. |
| I-4.0.4 | 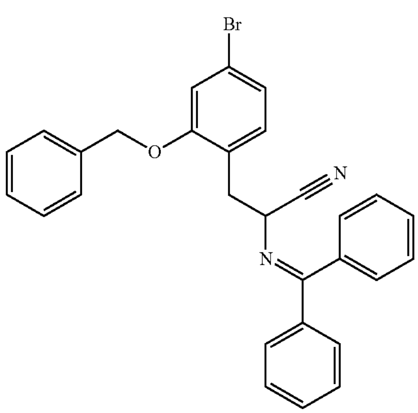 [SMILES: N#CC(Cc1ccc(Br)cc1OCc1ccccc1)N=C(c1ccccc1)c1ccccc1] | 495/497 | 0.96 | X018_S01 |

Step 1.2: Synthesis of Intermediate I-4.1.1 (Compare with Synthesis of Intermediate I-7.2)

To I-4.0 (40.8 g, 100 mmol) in dioxane (400 mL) hydrogen chloride solution in dioxane (4 mol/L, 27.5 mL, 9.5 mmol) is added. The reaction mixture is stirred for 12 h. Aq. hydrochloric acid (1 mol/L, 100 mL) is added and the mixture is stirred for additional 2 h. The reaction is concentrated, the residue is stirred with acetonitrile and the precipitate is filtered off. Yield 49%, m/z 243 rt 0.42 min, LC-MS Method X001_004.

The following intermediates as shown in Table 21 are synthesized in a similar fashion from the appropriate intermediate ((R,S)=1:1 mixture of stereoisomers at the carbon adjacent to the nitrile group):

TABLE 21

| Intermediate | educt | Structure | m/z [M + H]+ | rt (min) | LC-MS method |
|---|---|---|---|---|---|
| I-4.1.1.1 | I-4.0.1 | (4-bromo-2,5-difluorophenyl, CH2-CH(NH2)-CN) | 261 | 0.35 | Z001_002 |
| I-4.1.1.2 | I-4.0.2 | (4-bromo-2,6-difluorophenyl, CH2-CH(NH2)-CN) | 261/263 | 0.34 | V012_S01 |
| I-4.1.1.3 | I-4.0.3 | (4-bromo-2-chlorophenyl, CH2-CH(NH2)-CN) | 259 | 0.39 | X001_004 |
| I-4.1.1.4 | I-4.0.4 | (4-bromo-2-benzyloxyphenyl, CH2-CH(NH2)-CN) | 331/333 | 0.48 | V018_S01 |

Step 2: Synthesis of Intermediate I-2.2

To R5 (2.82 g, 11 mmol) in dry DCM (150 mL) diisopropylethylamine (5.8 mL, 33 mmol) and HATU (5.1 g, 13 mmol) are added and the mixture is stirred for 30 min. Then a solution of I-4.1 (2.75 g, 11 mmol) in DCM (50 mL) is added and stirred for 12 h. The mixture is washed with water, aq. K2CO3 solution (5%) and 1 M HCl. The organic layer is dried over MgSO$_4$ and concentrated. Yield 68%, m/z 466/468 [M+H]+, rt 1.25 min, LC-MS Method V011_S01.

The following intermediates as shown in Table 22 are synthesized in a similar fashion from the appropriate intermediate: ((R,S)=1:1 mixture of stereoisomers at the carbon adjacent to the nitrile group)

TABLE 22

| Intermediate | educt | Structure | m/z [M + H]+ | rt (min) | LC-MS method |
|---|---|---|---|---|---|
| I-4.2.1 | I-4.1.1 | (Boc-azabicyclic-C(O)NH-CH(CN)-CH2-(2-fluoro-4-bromophenyl)) | 466 | 0.78 | X001_004 |

TABLE 22-continued

| Intermediate | educt | Structure | m/z [M + H]+ | rt (min) | LC-MS method |
|---|---|---|---|---|---|
| I-4.2.2 | I-4.1.1.1 | 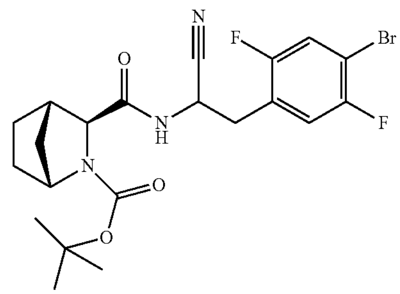 [SMILES: CC(C)(C)OC(=O)N1[C@@H]2CC[C@@H](C2)[C@H]1C(=O)NC(C#N)Cc1cc(F)c(Br)cc1F] | 484 | 1.29 | V011_S01 |
| I-4.2.3 | I-4.1.1.2 | 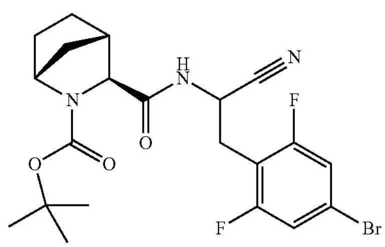 [SMILES: CC(C)(C)OC(=O)N1[C@@H]2CC[C@@H](C2)[C@H]1C(=O)NC(C#N)Cc1c(F)cc(Br)cc1F] | 484/486 | 1.29 | V011_S01 |
| I-4.2.4 | I-4.1.1.3 | 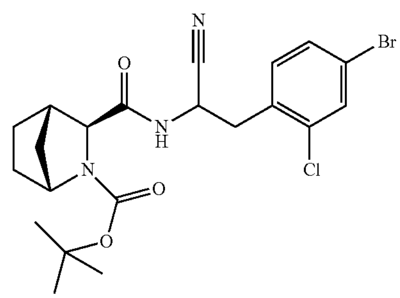 [SMILES: CC(C)(C)OC(=O)N1[C@@H]2CC[C@@H](C2)[C@H]1C(=O)NC(C#N)Cc1ccc(Br)cc1Cl] | n.d. | n.d. | n.d. |
| I-4.2.5 | I-4.1.1.4 | 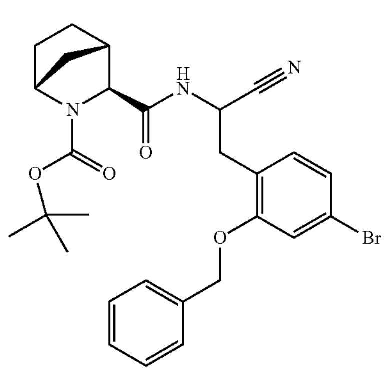 [SMILES: CC(C)(C)OC(=O)N1[C@@H]2CC[C@@H](C2)[C@H]1C(=O)NC(C#N)Cc1ccc(Br)cc1OCc1ccccc1] | 554 | 1.42 | V011_S01 |

Step 3: Synthesis of Intermediate I-4.3

To I-2.2 (300 mg, 0.64 mmol) in acetonitrile (7.5 mL) R9 (142 mg, 0.71 mmol) is added. The mixture is purged with argon 1,1-Bis(di-tert-butylphosphino)ferrocene palladium dichloride (42 mg, 0.10 mmol) and aq. sodium carbonate solution (2 mol/L, 0.64 mL) are added and heated to 70° C. for 2.5 h. Ethyl acetate and water are added to the reaction mixture. The organic layer is washed with aq. NaHCO3 solution (5%) and water. The organic layer is dried over MgSO4 and concentrated. Yield raw product >95% m/z 442 [M+H]+, rt 0.93 min, LC-MS Method Z018_S04.

The following intermediates as shown in Table 23 are synthesized in a similar fashion from the appropriate intermediate ((R,S)=1:1 mixture of stereoisomers at the carbon adjacent to the nitrile group):

TABLE 23
| Intermediate | Educt | Structure of Intermediate | m/z [M + H]+ | rt (min) | LC-MS method |
|---|---|---|---|---|---|
| I-4.3.1 | I-4.2.1 | 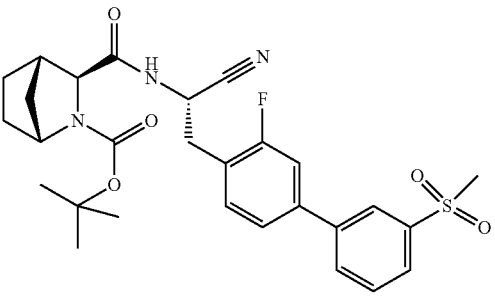 | 567 | 1.19 | V011_S01 |
| I-4.3.2 | I-4.2.1 | 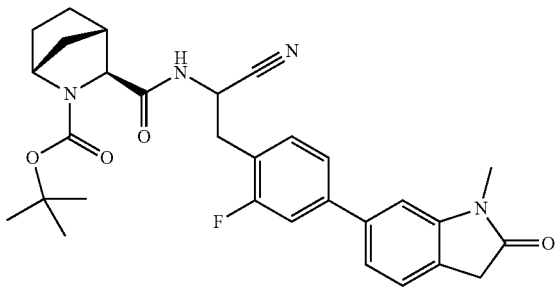 [SMILES: CN1C(=O)Cc2ccc(-c3ccc(CC(C#N)NC(=O)[C@@H]4[C@H]5CC[C@H](C5)N4C(=O)OC(C)(C)C)c(F)c3)cc21] | 533 | 0.75 | X001_004 |
| I-4.3.3 | I-2.2 | 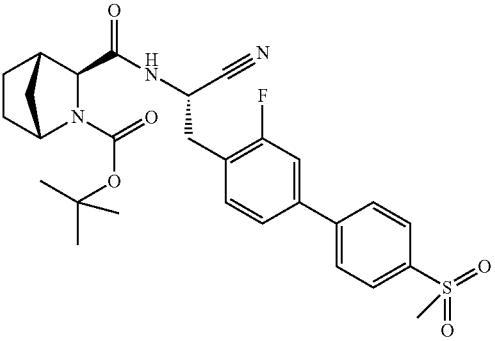 [SMILES: CC(C)(C)OC(=O)N1[C@@H]2CC[C@@H](C2)[C@H]1C(=O)N[C@H](C#N)Cc1ccc(-c2ccc(S(C)(=O)=O)cc2)cc1F] | 442 | 0.92 | Z018_S04 |
| I-4.3.4 | I-4.2.3 | 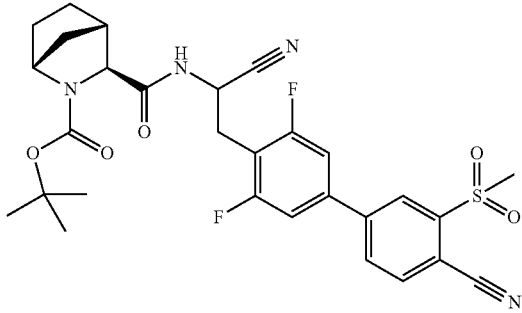 [SMILES: CC(C)(C)OC(=O)N1[C@@H]2CC[C@@H](C2)[C@H]1C(=O)NC(C#N)Cc1c(F)cc(-c2ccc(C#N)c(S(C)(=O)=O)c2)cc1F] | 585 | 1.20 | V011_S01 |
| I-4.3.5 | I-4.2.1 | 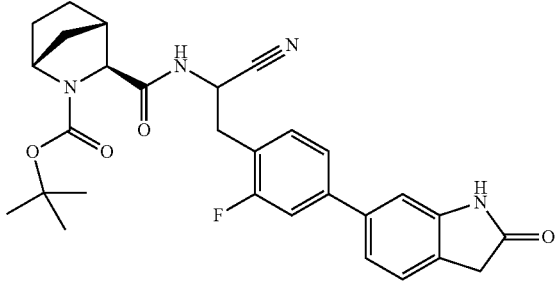 [SMILES: CC(C)(C)OC(=O)N1[C@@H]2CC[C@@H](C2)[C@H]1C(=O)NC(C#N)Cc1ccc(-c2ccc3c(c2)NC(=O)C3)cc1F] | 519 | 0.62 | Z001_002 |

TABLE 23-continued
| Intermediate | Educt | Structure of Intermediate | m/z [M + H]+ | rt (min) | LC-MS method |
|---|---|---|---|---|---|
| I-4.3.6 | I-2.2 | 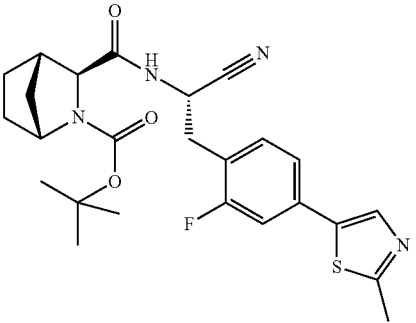 [SMILES: Cc1ncc(-c2ccc(C[C@@H](C#N)NC(=O)[C@@H]3[C@H]4CC[C@H](C4)N3C(=O)OC(C)(C)C)c(F)c2)s1] | 429 | 0.95 | Z018_S04 |
| I-4.3.8 | I-4.2.2 | 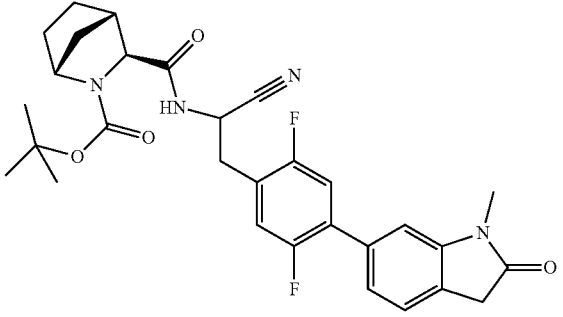 [SMILES: CN1C(=O)Cc2ccc(-c3cc(F)c(CC(C#N)NC(=O)[C@@H]4[C@H]5CC[C@H](C5)N4C(=O)OC(C)(C)C)cc3F)cc21] | 551 | 1.22 | V011_S01 |
| I-4.3.9 | I-4.2.1 | 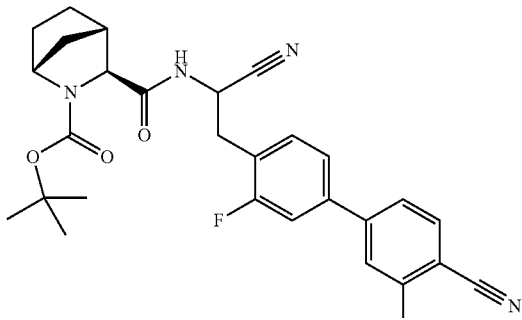 | n.d. | 1.39 | V003_003 |
| I-4.3.10 | I-4.2.1 | 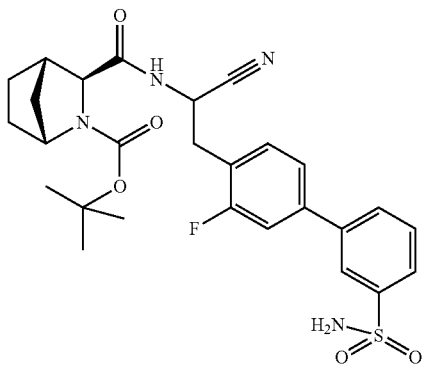 [SMILES: CC(C)(C)OC(=O)N1[C@@H]2CC[C@@H](C2)[C@H]1C(=O)NC(C#N)Cc1ccc(-c2cccc(S(N)(=O)=O)c2)cc1F] | 543 | 0.57 | 001_CA07 |

TABLE 23-continued

| Intermediate | Educt | Structure of Intermediate | m/z [M + H]+ | rt (min) | LC-MS method |
|---|---|---|---|---|---|
| I-4.3.11 | I-4.2.1 | | 518 | 0.55 | 001_CA07 |
| I-4.3.12 | I-4.2.1 | | n.d. | n.d. | n.d. |
| I-4.3.13 | I-4.2.1 | | 532 | 0.57 | 001_CA07 |
| I-4.3.14 | I-4.2.1 | | 556 | 0.60 | 001_CA07 |

TABLE 23-continued
| Intermediate | Educt | Structure of Intermediate | m/z [M + H]+ | rt (min) | LC-MS method |
|---|---|---|---|---|---|
| I-4.3.15 | I-4.2.3 | 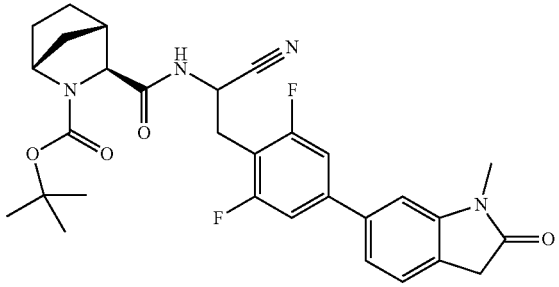 | 551 | 1.21 | V011_S01 |
| I-4.3.16 | I-4.2.1 | 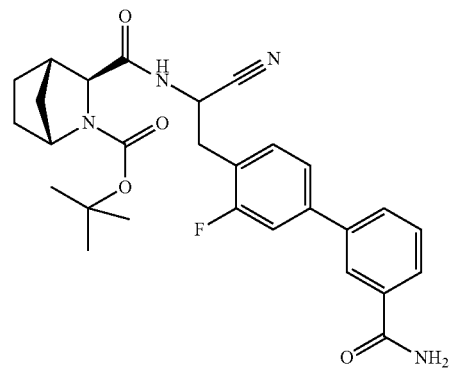 [SMILES: CC(C)(C)OC(=O)N1[C@@H]2CC[C@@H](C2)[C@H]1C(=O)NC(C#N)Cc1ccc(-c2cccc(C(N)=O)c2)cc1F] | 506 | 0.56 | 001_CA07 |
| I-4.3.17 | I-4.2.1 | 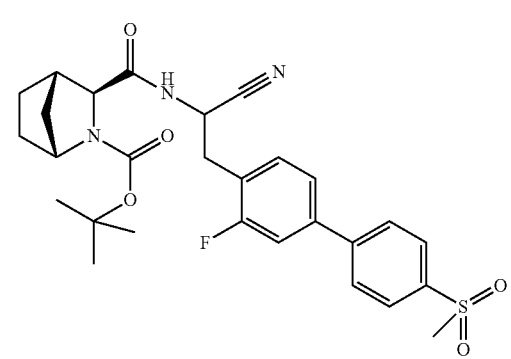 [SMILES: CC(C)(C)OC(=O)N1[C@@H]2CC[C@@H](C2)[C@H]1C(=O)NC(C#N)Cc1ccc(-c2ccc(S(C)(=O)=O)cc2)cc1F] | 541 | 0.60 | 001_CA07 |
| I-4.3.18 | I-4.2.1 | 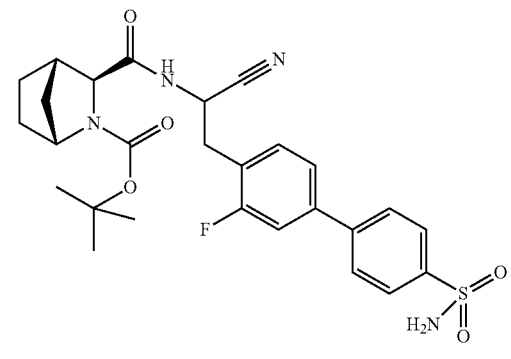 [SMILES: CC(C)(C)OC(=O)N1[C@@H]2CC[C@@H](C2)[C@H]1C(=O)NC(C#N)Cc1ccc(-c2ccc(S(N)(=O)=O)cc2)cc1F] | 542 | 0.56 | 001_CA07 |

TABLE 23-continued
| Intermediate | Educt | Structure of Intermediate | m/z [M + H]+ | rt (min) | LC-MS method |
|---|---|---|---|---|---|
| I-4.3.19 | I-4.2.5 | 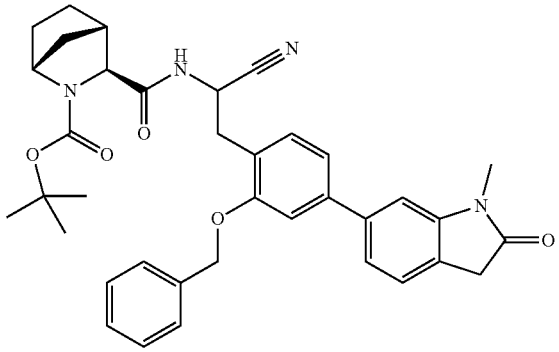 [SMILES: CN1C(=O)Cc2ccc(-c3ccc(CC(C#N)NC(=O)[C@@H]4[C@H]5CC[C@H](C5)N4C(=O)OC(C)(C)C)c(OCc4ccccc4)c3)cc21] | 621 | 1.33 | V011_S01 |
| I-4.3.20 | I-4.2.1 | 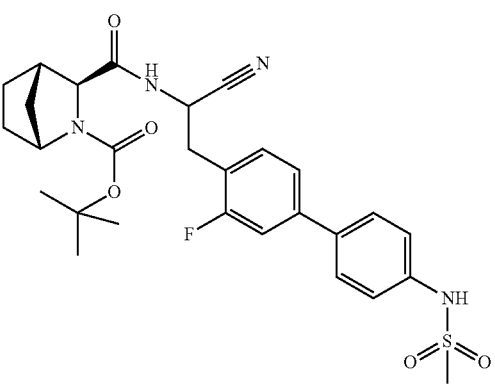 [SMILES: CC(C)(C)OC(=O)N1[C@@H]2CC[C@@H](C2)[C@H]1C(=O)NC(C#N)Cc1ccc(-c2ccc(NS(C)(=O)=O)cc2)cc1F] | 556 | 0.60 | 001_CA07 |
| I-4.3.21 | I-4.2.1 | 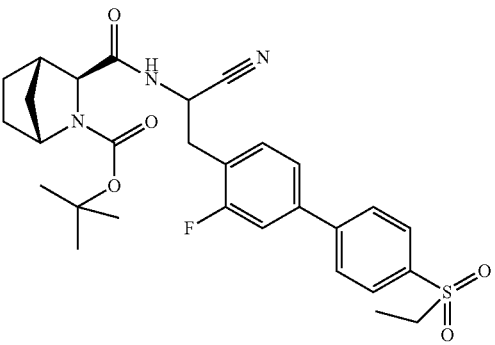 [SMILES: CCS(=O)(=O)c1ccc(-c2ccc(CC(C#N)NC(=O)[C@@H]3[C@H]4CC[C@H](C4)N3C(=O)OC(C)(C)C)c(F)c2)cc1] | 556 | 0.62 | 001_CA07 |
| I-4.3.22 | I-4.2.1 | 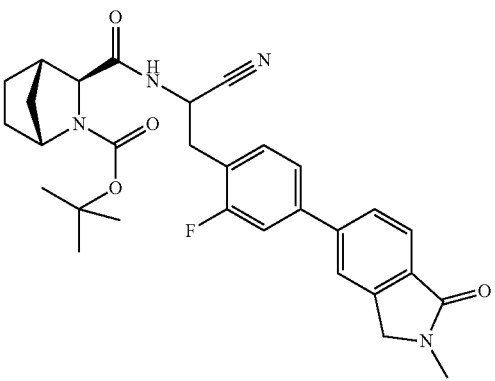 [SMILES: CN1Cc2cc(-c3ccc(CC(C#N)NC(=O)[C@@H]4[C@H]5CC[C@H](C5)N4C(=O)OC(C)(C)C)c(F)c3)ccc2C1=O] | 532 | 0.58 | 001_CA07 |

US 9,713,606 B2

227                                                                 228

TABLE 23-continued

| Intermediate | Educt | Structure of Intermediate | m/z [M + H]+ | rt (min) | LC-MS method |
|---|---|---|---|---|---|
| I-4.3.23 | I-4.2.1 | | n.d. | 1.22 | Z018_S04 |
| I-4.3.24 | I-4.2.4 | | n.d. | n.d. | n.d. |
| I-4.3.25 | I-4.2.1 | | 506 | 0.55 | 001_CA07 |
| I-4.3.26 | I-4.2.1 | | n.d. | n.d. | n.d. |

TABLE 23-continued

| Intermediate | Educt | Structure of Intermediate | m/z [M + H]+ | rt (min) | LC-MS method |
|---|---|---|---|---|---|
| I-4.3.27 | I-4.2.1 | | 534 | 0.63 | 001_CA07 |
| I-4.3.28 | I-2.2 | | 500 | 0.98 | V011_S01 |
| I-4.3.29 | I-2.2 | | 442 (M + H − BOC)+ | 1.09 | Z018_S04 |
| I-4.3.30 | I-4.3.29 | | 414 (M + H − BOC)+ | 0.60 | Z011_S03 |

TABLE 23-continued

| Intermediate | Educt | Structure of Intermediate | m/z [M + H]+ | rt (min) | LC-MS method |
|---|---|---|---|---|---|
| I-4.3.31 | I-2.2 | | 408 (M + H − BOC)+ | 0.93 | Z018_S04 |

The reaction conditions for I-4.3.28 differ: Under argon atmosphere I-2.2 (250 mg, 0.54 mmol), potassium carbonate (150 mg, 1.07 mmol), copper (I) iodide (10 mg, 0.05 mmol), N,N'-dimethylethylenediamine (25 μL, 0.23 mmol) and 4-methyl-piperazin-2-one (75 mg, 0.66 mmol) in dioxane (10 mL) are heated to 80° C. for 8 d. The reaction mixture is filtered and the solution is concentrated. The residue is purified by reversed phase HPLC. Yield 30%, m/z 500 [M+H]+, rt 0.98 min, LC-MS Method V011_S01.

The synthesis of I-4.3.30 proceeds in the following way: I-4.3.29 (509 mg, 0.94 mmol) is dissolved in dioxane. LiOH (1.5 eq.) as aq. solution is added dropwise to the solution and stirred at r.t. for 8 h. The product mixture is extracted 2× with DCM. The organic layer is extracted twice with water. The water phase is acidified with 1 M HCl to pH 4, the solvent removed in vacuo to yield the crude product, which is purified by HPLC-MS (Gilson, mass flow 120 mL/min, 10 μM, 200 g Xbridge RP18, ACN/water/NH₃). Yield: 44%.

Intermediate I-4.3.19 is additionally treated with BBr₃ to give example 120:

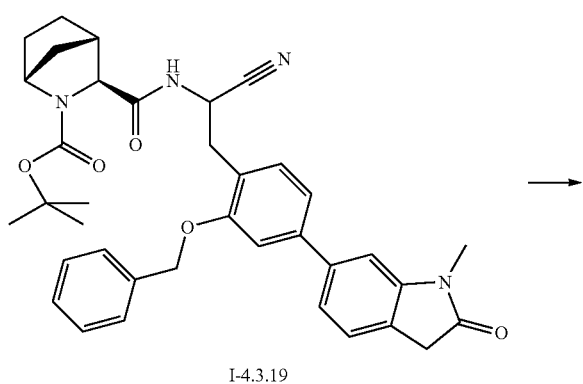

I-4.3.19

-continued

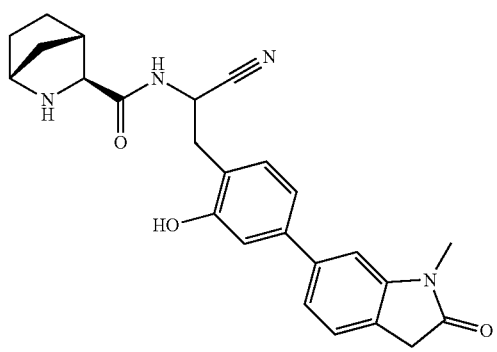

example 120

I-4.3.19 (600 mg, 0.97 mmol) in DCM (50 mL) is stirred at −5° C. Then boron tribromide solution (1 mol/L in DCM, 2.90 mL) is added dropwise. The reaction mixture is stirred at 0° C. for 90 min and then stirred at room temperature for additional 12 h. The mixture is cooled down again to −5° C. and is quenched with conc ammonia solution. The mixture is concentrated and purified by reversed phase HPLC. Yield 5%, m/z 429 [M+H]+, rt 0.81 min, LC-MS Method V018_S04.

Additional Step: Amide Coupling to Afford I-4.3.32

The amide coupling for synthesis of intermediate I-4.3.32 proceeds in the following way: I-4.3.30 (35 mg, 0.068 mmol) TBTU (45 mg, 0.14 mmol) and N-methylmorpholine (75 μL, 0.68 mmol) are dissolved in DMF. The mixture is stirred at r.t. for 5 min 0.5 M ammonia in dioxane (2 mL, 1 mmol) is added, and the reaction mixture is stirred at r.t. for 12 h. The product mixture is separated by HPLC-MS (Waters, 30×100 mm, 10 μM, sunfire RP18, ACN/water/TFA). The fractions are combined and freeze-dried. Yield: 59%.

The following amide intermediates as shown in Table 24.1 are synthesized in a similar fashion from the appropriate intermediates:

TABLE 24.1
| Intermediate | Educt | Structure of Intermediate | m/z [M + H]+ | rt (min) | LC-MS method |
|---|---|---|---|---|---|
| I-4.3.32 | I-4.3.30 | 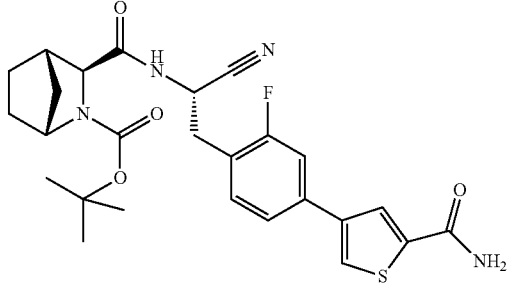 [SMILES: CC(C)(C)OC(=O)N1[C@@H]2CC[C@@H](C2)[C@H]1C(=O)N[C@H](C#N)Cc1ccc(-c2csc(C(N)=O)c2)cc1F] | 413 (M + H − BOC)+ | 0.89 | Z018_S04 |
| I-4.3.33 | I-4.3.30 | 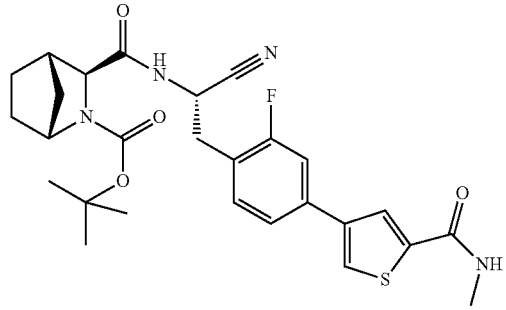 [SMILES: CNC(=O)c1cc(-c2ccc(C[C@@H](C#N)NC(=O)[C@@H]3[C@H]4CC[C@H](C4)N3C(=O)OC(C)(C)C)c(F)c2)cs1] | 427 (M + H − BOC)+ | 0.92 | Z018_S04 |
| I-4.3.34 | I-4.3.30 | 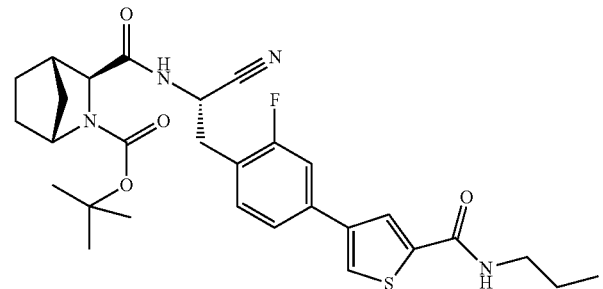 [SMILES: CCCNC(=O)c1cc(-c2ccc(C[C@@H](C#N)NC(=O)[C@@H]3[C@H]4CC[C@H](C4)N3C(=O)OC(C)(C)C)c(F)c2)cs1] | 455 (M + H − BOC)+ | 1.00 | Z018_S04 |
| I-4.3.35 | I-4.3.30 | 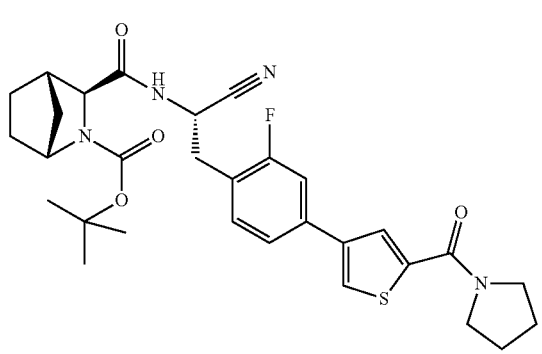 [SMILES: CC(C)(C)OC(=O)N1[C@@H]2CC[C@@H](C2)[C@H]1C(=O)N[C@H](C#N)Cc1ccc(-c2csc(C(=O)N3CCCC3)c2)cc1F] | 467 (M + H − BOC)+ | 0.99 | Z018_S04 |
| I-4.3.36 | I-4.3.30 | 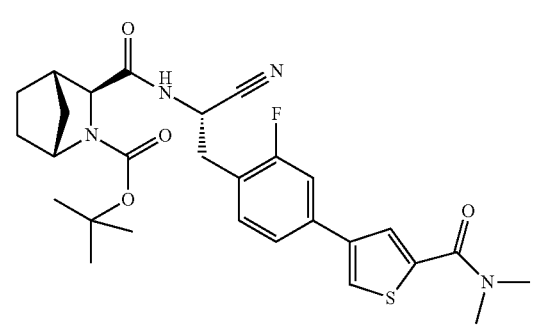 [SMILES: CN(C)C(=O)c1cc(-c2ccc(C[C@@H](C#N)NC(=O)[C@@H]3[C@H]4CC[C@H](C4)N3C(=O)OC(C)(C)C)c(F)c2)cs1] | 441 (M + H − BOC)+ | 0.95 | Z018_S04 |

TABLE 24.1-continued

| Intermediate | Educt | Structure of Intermediate | m/z [M + H]+ | rt (min) | LC-MS method |
|---|---|---|---|---|---|
| I-4.3.37 | I-4.3.31 | | 435 (M + H − BOC)+ | 0.95 | Z018_S04 |
| I-4.3.38 | I-4.3.31 | | 490 (M + H − BOC)+ | 0.75 | Z018_S04 |
| I-4.3.39 | I-4.3.31 | | 421 (M + H − BOC)+ | 0.91 | Z018_S04 |
| I-4.3.40 | I-4.3.31 | | 491 (M + H − BOC)+ | 0.94 | Z018_S04 |

TABLE 24.1-continued
| Intermediate | Educt | Structure of Intermediate | m/z [M + H]+ | rt (min) | LC-MS method |
|---|---|---|---|---|---|
| I-4.3.41 | I-4.3.31 | 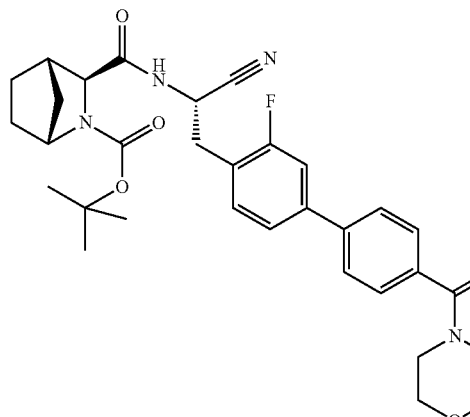 | 477 (M + H − BOC)+ | 0.93 | Z018_S04 |
| I-4.3.42 | I-4.3.31 | 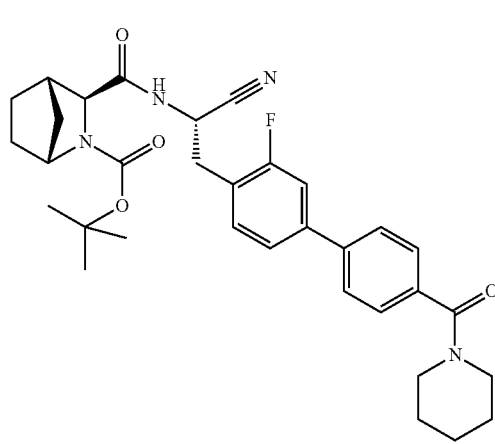 [SMILES: CC(C)(C)OC(=O)N1[C@@H]2CC[C@@H](C2)[C@H]1C(=O)N[C@H](C#N)Cc1ccc(-c2ccc(C(=O)N3CCCCC3)cc2)cc1F] | 475 (M + H − BOC)+ | 1.02 | Z018_S04 |
| I-4.3.43 | I-4.3.31 | 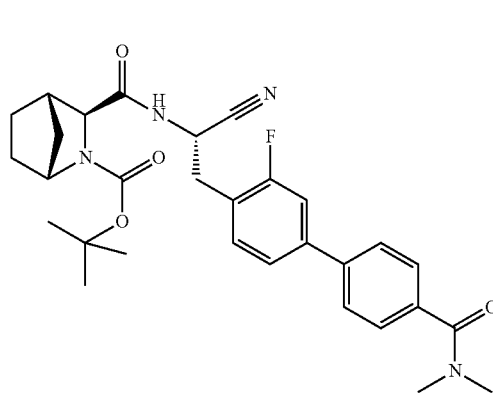 [SMILES: CN(C)C(=O)c1ccc(-c2ccc(C[C@@H](C#N)NC(=O)[C@@H]3[C@H]4CC[C@H](C4)N3C(=O)OC(C)(C)C)c(F)c2)cc1] | 435 (M + H − BOC)+ | 0.94 | Z018_S04 |

TABLE 24.1-continued

| Intermediate | Educt | Structure of Intermediate | m/z [M + H]+ | rt (min) | LC-MS method |
|---|---|---|---|---|---|
| I-4.3.44 | I-4.3.31 | | 461 (M + H − BOC)+ | 0.97 | Z018_S04 |
| I-4.3.45 | I-4.3.30 | | 496 (M + H − BOC)+ | 0.89 | Z011_S03 |
| I-4.3.46 | I-4.3.30 | | 519 (M + H − BOC)+ | 0.90 | Z018_S04 |
| I-4.3.47 | I-4.3.30 | | 524 (M + H − BOC)+ | 0.97 | Z011_S03 |

TABLE 24.1-continued
| Intermediate | Educt | Structure of Intermediate | m/z [M + H]+ | rt (min) | LC-MS method |
|---|---|---|---|---|---|
| I-4.3.48 | I-4.3.30 | 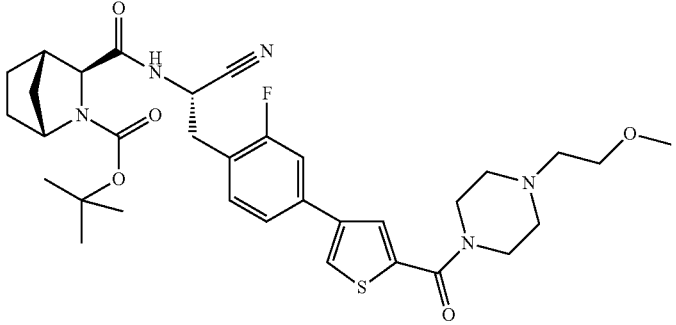 [SMILES: COCCN1CCN(C(=O)c2cc(-c3ccc(C[C@@H](C#N)NC(=O)[C@@H]4[C@H]5CC[C@H](C5)N4C(=O)OC(C)(C)C)c(F)c3)cs2)CC1] | 540 (M + H − BOC)+ | 0.91 | Z011_S03 |
| I-4.3.49 | I-4.3.30 | 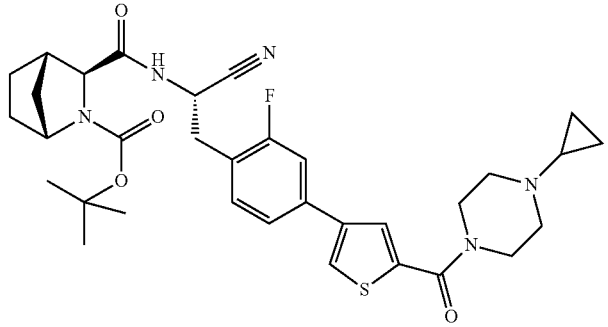 | 422 (M + H − BOC)+ | 0.98 | Z011_S03 |
| I-4.3.50 | I-4.3.30 | 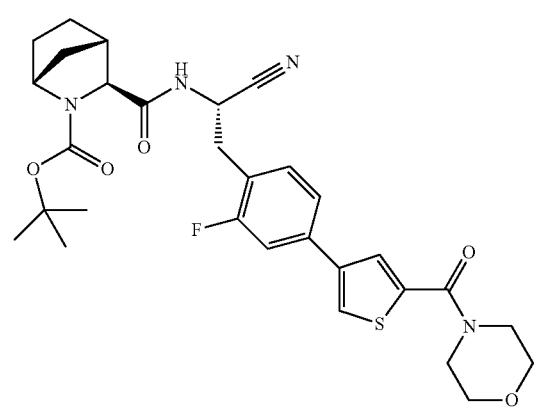 [SMILES: CC(C)(C)OC(=O)N1[C@@H]2CC[C@@H](C2)[C@H]1C(=O)N[C@H](C#N)Cc1ccc(-c2csc(C(=O)N3CCOCC3)c2)cc1F] | 483 (M + H − BOC)+ | 0.90 | Z011_S03 |
| I-4.3.51 | I-4.3.30 | 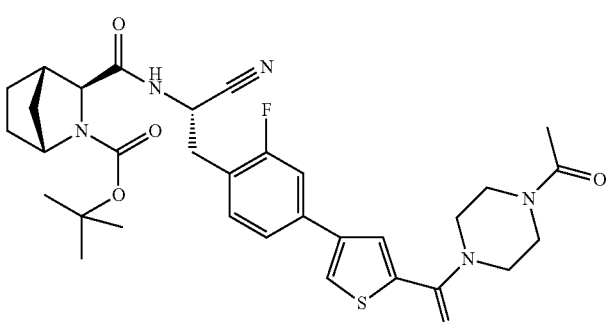 | 424 (M + H − BOC)+ | 0.86 | Z011_S03 |

TABLE 24.1-continued
| Intermediate | Educt | Structure of Intermediate | m/z [M + H]+ | rt (min) | LC-MS method |
|---|---|---|---|---|---|
| I-4.3.52 | I-4.3.30 | 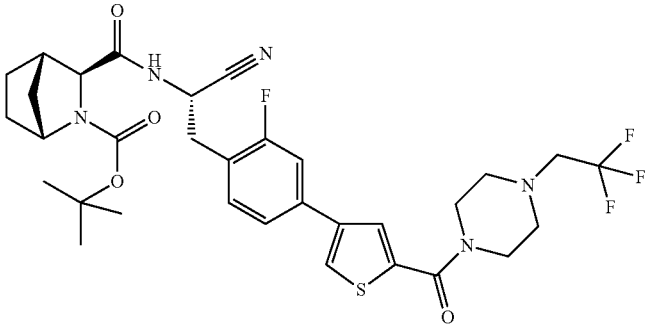 [SMILES: CC(C)(C)OC(=O)N1[C@@H]2CC[C@@H](C2)[C@H]1C(=O)N[C@H](C#N)Cc1ccc(-c2csc(C(=O)N3CCN(CC(F)(F)F)CC3)c2)cc1F] | 564 (M + H − BOC)+ | 0.98 | Z018_S04 |
| I-4.3.53 | I-4.3.30 | 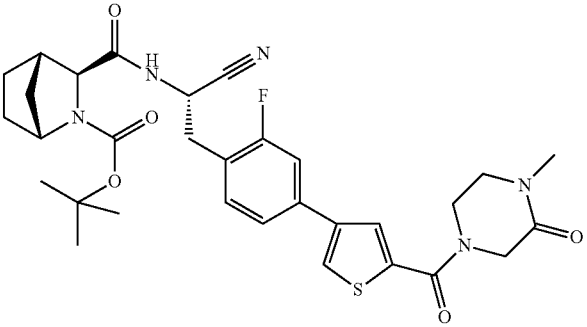 [SMILES: CN1CCN(C(=O)c2cc(-c3ccc(C[C@@H](C#N)NC(=O)[C@@H]4[C@H]5CC[C@H](C5)N4C(=O)OC(C)(C)C)c(F)c3)cs2)CC1=O] | 510 (M + H − BOC)+ | 0.85 | Z011_S03 |
| I-4.3.54 | I-4.3.30 | 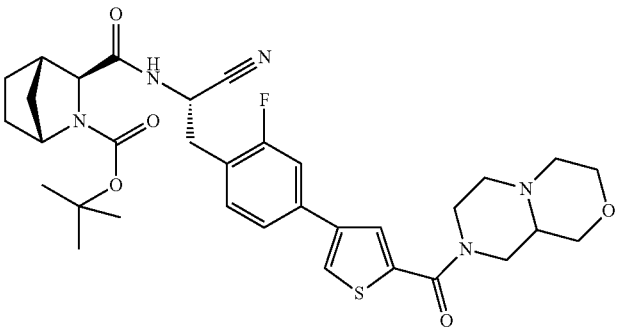 | 583 (M + H − BOC)+ | 0.89 | Z011_S03 |
| I-4.3.55 | I-4.3.30 | 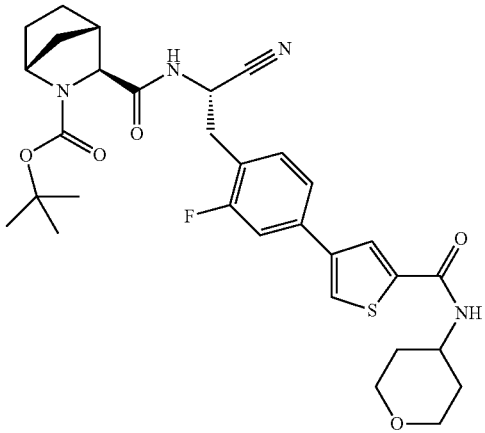 [SMILES: CC(C)(C)OC(=O)N1[C@@H]2CC[C@@H](C2)[C@H]1C(=O)N[C@H](C#N)Cc1ccc(-c2csc(C(=O)NC3CCOCC3)c2)cc1F] | 497 (M + H − BOC)+ | 0.91 | Z011_S03 |

TABLE 24.1-continued
| Intermediate | Educt | Structure of Intermediate | m/z [M + H]+ | rt (min) | LC-MS method |
|---|---|---|---|---|---|
| I-4.3.56 | I-2.3.41 | 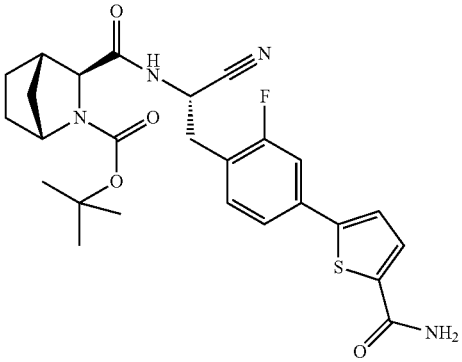 [SMILES: CC(C)(C)OC(=O)N1[C@@H]2CC[C@@H](C2)[C@H]1C(=O)N[C@H](C#N)Cc1ccc(-c2ccc(C(N)=O)s2)cc1F] | 413 (M + H − BOC)+ | 0.84 | Z011_S03 |
| I-4.3.57 | I-2.3.41 | 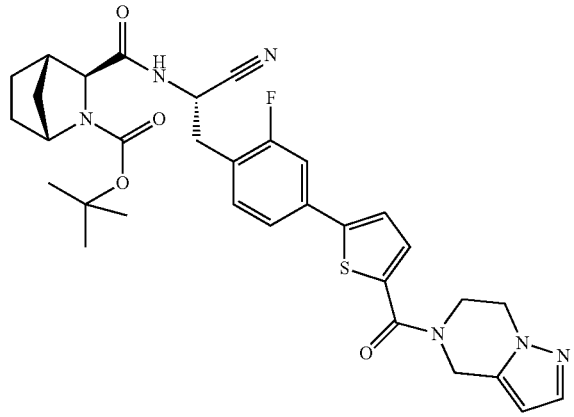 [SMILES: CC(C)(C)OC(=O)N1[C@@H]2CC[C@@H](C2)[C@H]1C(=O)N[C@H](C#N)Cc1ccc(-c2ccc(C(=O)N3CCn4nccc4C3)s2)cc1F] | 519 (M + H − BOC)+ | 0.94 | Z018_S04 |
| I-4.3.58 | I-2.3.80 | 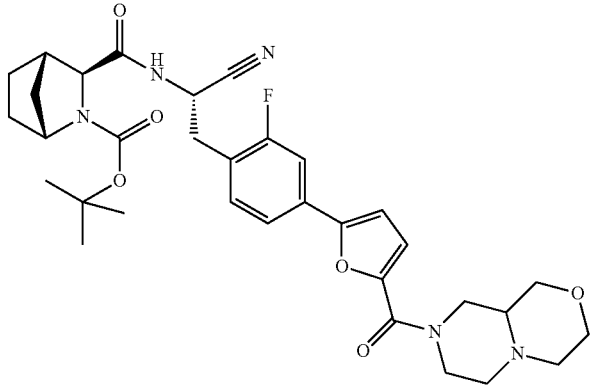 [SMILES: CC(C)(C)OC(=O)N1[C@@H]2CC[C@@H](C2)[C@H]1C(=O)N[C@H](C#N)Cc1ccc(-c2ccc(C(=O)N3CCN4CCOCC4C3)o2)cc1F] | 522 (M + H − BOC)+ | 0.87 | Z018_S04 |
| I-4.3.59 | I-2.3.81 | 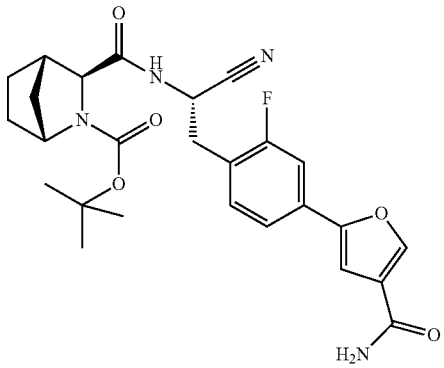 [SMILES: CC(C)(C)OC(=O)N1[C@@H]2CC[C@@H](C2)[C@H]1C(=O)N[C@H](C#N)Cc1ccc(-c2cc(C(N)=O)co2)cc1F] | 397 (M + H − BOC)+ | 0.86 | Z018_S04 |

TABLE 24.1-continued
| Intermediate | Educt | Structure of Intermediate | m/z [M + H]+ | rt (min) | LC-MS method |
|---|---|---|---|---|---|
| I-4.3.60 | I-2.3.81 | 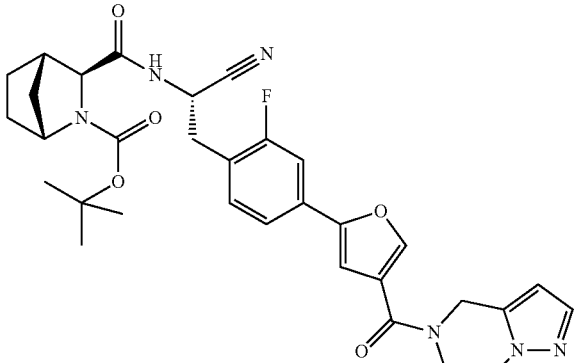 | 503 (M + H − BOC)+ | 0.88 | Z011_S03 |
| I-4.3.61 | I-2.3.81 | 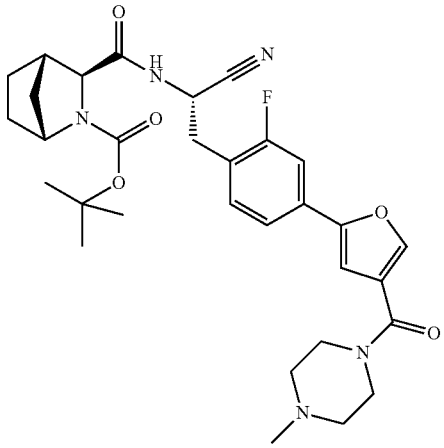 [SMILES: CN1CCN(C(=O)c2coc(-c3ccc(C[C@@H](C#N)NC(=O)[C@@H]4[C@H]5CC[C@H](C5)N4C(=O)OC(C)(C)C)c(F)c3)c2)CC1] | 480 (M + H − BOC)+ | 0.74 | Z018_S04 |
| I-4.3.62 | I-2.3.81 | 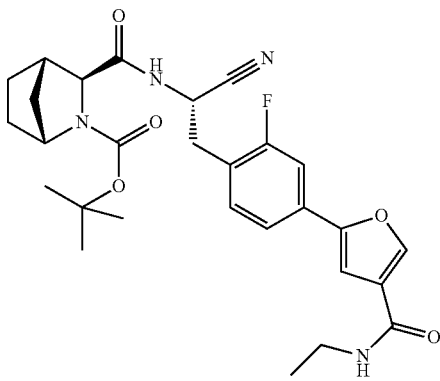 [SMILES: CCNC(=O)c1coc(-c2ccc(C[C@@H](C#N)NC(=O)[C@@H]3[C@H]4CC[C@H](C4)N3C(=O)OC(C)(C)C)c(F)c2)c1] | 425 (M + H − BOC)+ | 0.91 | Z018_S04 |
| I-4.3.63 | I-2.3.82 | 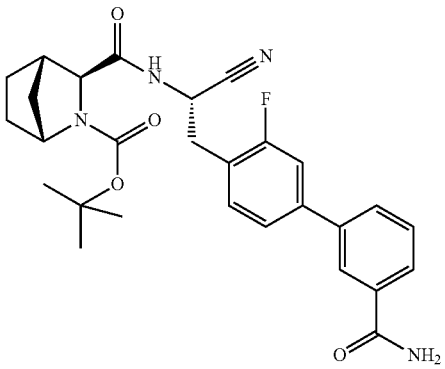 [SMILES: CC(C)(C)OC(=O)N1[C@@H]2CC[C@@H](C2)[C@H]1C(=O)N[C@H](C#N)Cc1ccc(-c2cccc(C(N)=O)c2)cc1F] | 407 (M + H − BOC)+ | 1.02 | Z018_S04 |

TABLE 24.1-continued

| Intermediate | Educt | Structure of Intermediate | m/z [M + H]+ | rt (min) | LC-MS method |
|---|---|---|---|---|---|
| I-4.3.64 | I-2.3.82 | | 490 (M + H − BOC)+ | 0.76 | Z018_S04 |
| I-4.3.65 | I-2.3.80 | | 467 (M + H − BOC)+ | 0.91 | Z018_S04 |
| I-4.3.66 | I-2.3.80 | | 480 (M + H − BOC)+ | 0.73 | Z018_S04 |

The reaction conditions for I-4.3.63 differ: I-2.3.82 (100 mg, 0.197 mmol), HATU (82.4 mg, 0.217 mmol) and DIPEA (68 μL, 2 eq) are dissolved in DMF. The mixture is stirred at r.t. for 30 min Ammonium chloride (63.2 mg, 1.182 mmol) and DIPEA (204 μL, 6 eq) are added, and the reaction mixture is stirred at r.t. for 3 h. The product mixture is separated by HPLC-MS (Waters, 30×100 mm, 10 μM, xBridge RP18, ACN/water/TFA). The fractions are combined and freeze-dried. Yield: 27%.

The reaction conditions for I-4.3.65 and I-4.3.66 differ: DCM is used as solvent instead of DMF.

Step 4: Synthesis of Example 4

I-4.3 (348 mg, 0.64 mmol) in formic acid is stirred for 10 min at 40° C. The reaction solution is diluted with DMF and directly purified by reversed phase HPLC. Yield 86%, m/z 442 [M+H]+, rt 0.65 min, LC-MS Method Z018_S04.

Method A4

Synthesis of (1S,2S,4R)-N-[(1S)-1-cyano-2-[2-fluoro-4-[4-(1H-indol-5-yl)triazol-1-yl]phenyl]ethyl]-3-azabicyclo[2.2.1]heptane-2-carboxamide (Example 5)

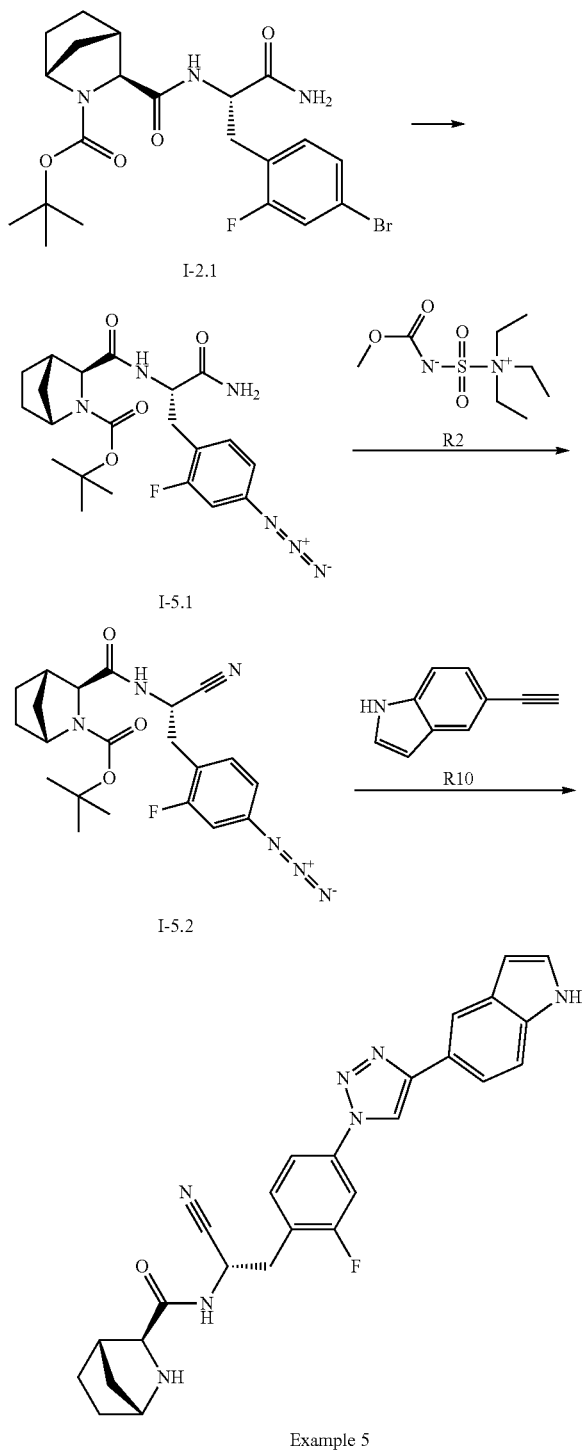

Step 1: Synthesis of Intermediate I-5.1

I-2.1 (2.26 g, 4.7 mmol), sodium azide (0.61 g, 9.3 mmol), trans-(1R,2R)-N,N'-bismethyl-1,2-cylcohexane diamine (147 µl, 0.93 mmol), copper(I)iodide (89 mg, 0.47 mmol) and L-ascorbic acid sodium salt (92 mg, 0.47 mmol) are dissolved in ethanol/water=7/3 (60 mL). The mixture is heated to 100° C. for 1.5 h. Water and DCM are added to the reaction mixture. The organic layer is washed with water and brine, dried over MgSO₄ and concentrated. The residue is purified by reversed phase HPLC. Yield 85% m/z 447 [M+H]+, rt 0.91 min, LC-MS Method Z018_S04.

Step 2: Synthesis of Intermediate I-5.2

To I-5.1 (1.76 g, 3.9 mmol) in anhydrous DCM (30 mL) R2 (2.35 g, 9.9 mmol) is added. The reaction mixture is stirred for 11 h. The reaction mixture is extracted with 0.5M HCl and water. The organic layer is extracted with half saturated Na2CO3 solution, water and brine. The residue is purified by reversed phase HPLC. Yield 54% m/z 329 [M+H]+, rt 0.96 min, LC-MS Method Z018_S04.

Step 3: Synthesis of Example 5

To R10 (28 mg, 0.20 mmol) in DMSO (1.3 mL) I-5.2 (43 mg, 0.10 mmol) is added. Then copper(II) sulfate pentahydrate (2.2 mg, 0.01 mmol), L-ascorbic acid sodium salt (11 mg, 0.05 mmol) and 100 µL water are added. The reaction mixture is stirred for 12 h. The reaction mixture is diluted with DMF and directly purified by reversed phase HPLC. The achieved substance is dissolved in formic acid, stirred at 40° C. for 10 min and the reaction mixture is purified again by reversed phase HPLC. Yield 34% m/z 470 [M+H]+, rt 0.70 min, LC-MS Method Z018_S04.

Method A5

Synthesis of (1S,2S,4R)-N-[(1S)-1-cyano-2-[2-fluoro-4-(4-methylpiperazin-1-yl)phenyl]ethyl]-3-azabicyclo[2.2.1]heptane-2-carboxamide (Example 6)

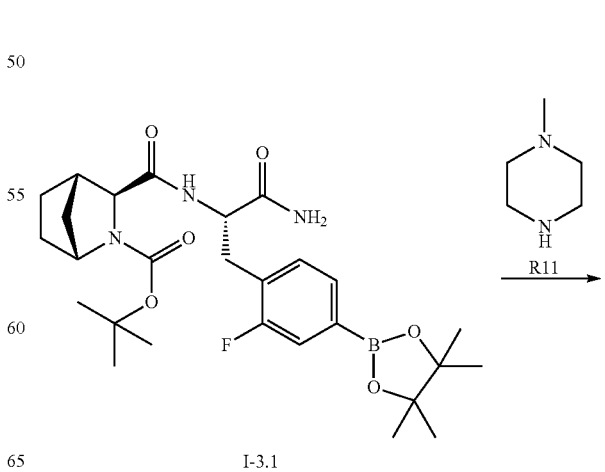

253
-continued

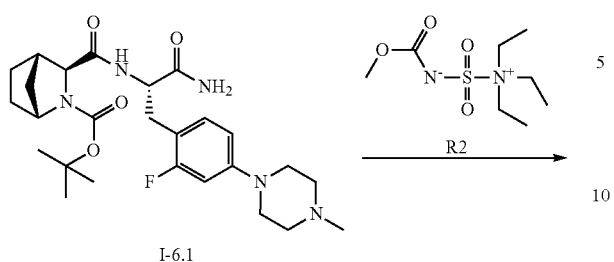

I-6.1

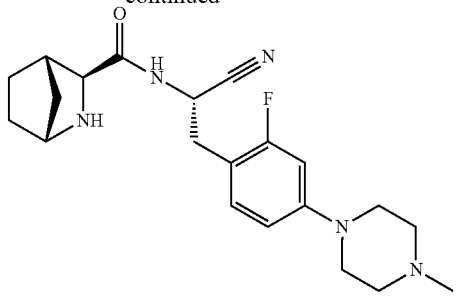

Example 6

Step 1: Synthesis of Intermediate I-6.1

To I-3.1 (90 mg, 0.20 mmol) in DCM (4 mL), triethylamine (60 µL, 0.43 mmol), R11 (23 µL, 0.21 mmol) and copper(II)acetate (55 mg, 0.30 mmol) are added. The mixture is stirred for 12 h. 7M ammonium solution in methanol is added, the mixture is concentrated. The residue dissolved in acetonitrile and filtrated. The product is purified by reversed phase HPLC. Yield 32%, m/z 504 [M+H]+, rt 1.00 min, LC-MS Method V011_S01.

The following intermediates as shown in Table 24.2 are synthesized in a similar fashion from the appropriate intermediates:

TABLE 24.2

| Intermediate | Educt | Structure of Intermediate | m/z [M + H]+ | rt (min) | LC-MS method |
|---|---|---|---|---|---|
| I-3.2.89 | I-3.1.5 | | 606 | 1.40 | V011_S01 |
| I-3.2.113 | I-3.1.5 | | 606 | 1.37 | V011_S01 |

Step 2: Synthesis of Intermediate I-6.2

To I-6.1 (40 mg, 0.08 mmol) in DCM (1 mL) R2 (35 mg, 0.15 mmol) is added. The reaction mixture is stirred for 12 h. The reaction mixture is concentrated and the residue is purified by reversed phase HPLC. Yield 67%, m/z 486 [M+H]+, rt 1.12 min, LC-MS Method V011_S01.

Step 3: Synthesis of Example 6

To I-6.2 (25 mg, 0.05 mmol) in acetonitrile, p-toluenesulfonic acid monohydrate (35 mg, 0.18 mmol) is added and stirred for 12 h. The product is purified by reversed phase HPLC. Yield 86%, m/z 386 [M+H]+, rt 0.98 min, LC-MS Method V011_S01.

Method B

Synthesis of (1S,2S,4R)-N-[2-[4-(1-acetyl-5-methyl-pyrazol-3-yl)-2-fluoro-phenyl]-1-cyano-ethyl]-3-azabicyclo[2.2.1]heptane-2-carboxamide (Example 7)

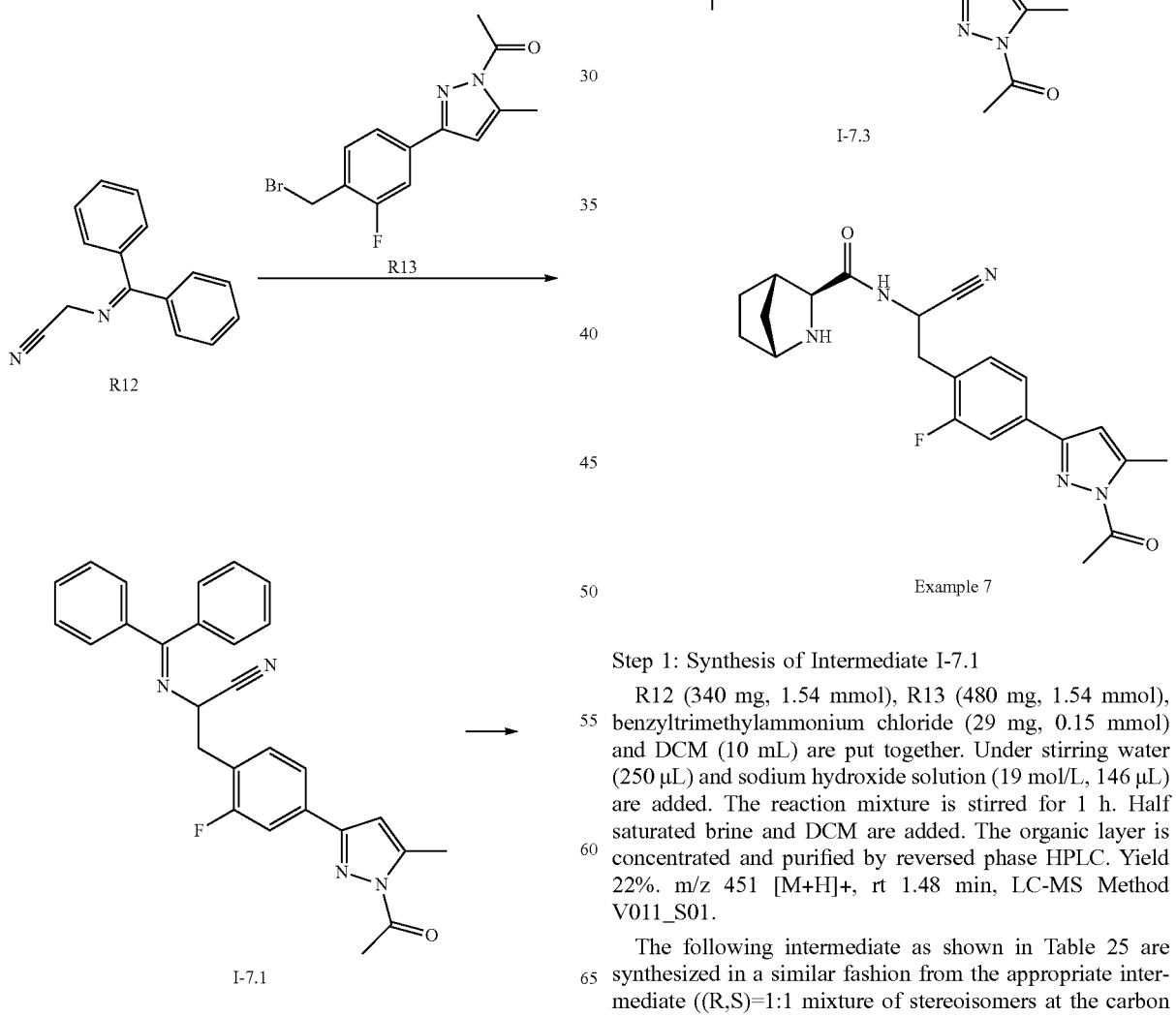

Step 1: Synthesis of Intermediate I-7.1

R12 (340 mg, 1.54 mmol), R13 (480 mg, 1.54 mmol), benzyltrimethylammonium chloride (29 mg, 0.15 mmol) and DCM (10 mL) are put together. Under stirring water (250 µL) and sodium hydroxide solution (19 mol/L, 146 µL) are added. The reaction mixture is stirred for 1 h. Half saturated brine and DCM are added. The organic layer is concentrated and purified by reversed phase HPLC. Yield 22%. m/z 451 [M+H]+, rt 1.48 min, LC-MS Method V011_S01.

The following intermediate as shown in Table 25 are synthesized in a similar fashion from the appropriate intermediate ((R,S)=1:1 mixture of stereoisomers at the carbon adjacent to the nitrile group):

TABLE 25

| Intermediate | Structure | m/z [M + H]+ | rt (min) | LC-MS method |
|---|---|---|---|---|
| I-7.1.1 | 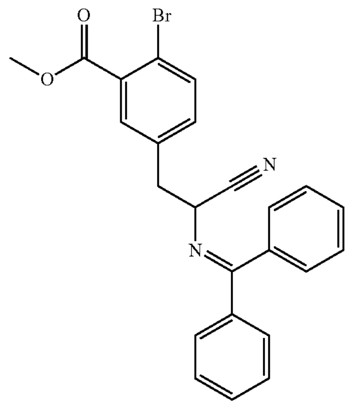 [SMILES: COC(=O)c1cc(CC(C#N)N=C(c2ccccc2)c2ccccc2)ccc1Br] | 447/449 | 0.78 | X012_S01 |
| I-7.1.2 | 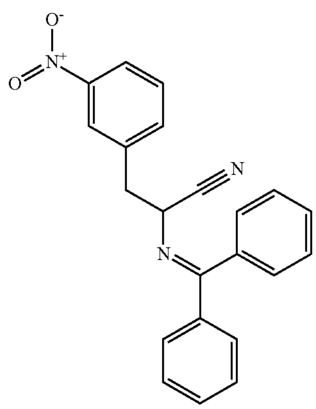 [SMILES: N#CC(Cc1cccc([N+](=O)[O-])c1)N=C(c1ccccc1)c1ccccc1] | 356 | 0.75 | X012_S01 |
| I-7.1.3 | 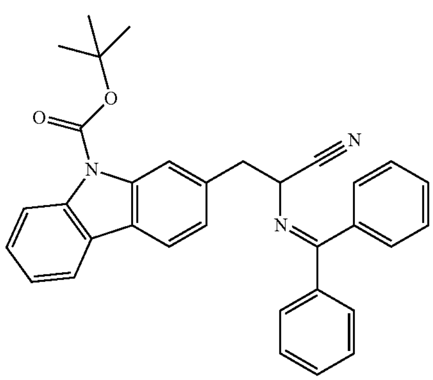 [SMILES: CC(C)(C)OC(=O)n1c2ccccc2c2ccc(CC(C#N)N=C(c3ccccc3)c3ccccc3)cc21] | 500 | 0.95 | X012_S01 |
| I-7.1.4 | 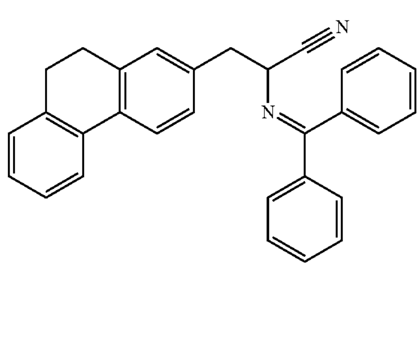 [SMILES: N#CC(Cc1ccc2c(c1)CCc1ccccc1-2)N=C(c1ccccc1)c1ccccc1] | 413 | 0.90 | X012_S01 |

TABLE 25-continued

| Intermediate | Structure | m/z [M + H]+ | rt (min) | LC-MS method |
|---|---|---|---|---|
| I-7.1.5 | 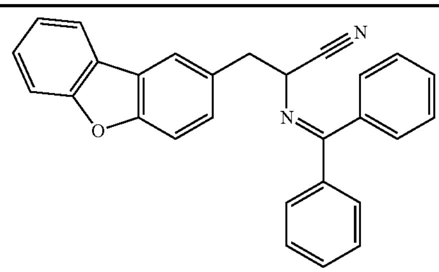 | 401 | 0.86 | X012_S01 |
| I-7.1.6 | 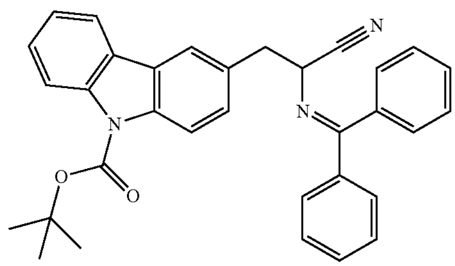 [SMILES: CC(C)(C)OC(=O)n1c2ccccc2c2cc(CC(C#N)N=C(c3ccccc3)c3ccccc3)ccc21] | 500 | 0.95 | X012_S01 |
| I-7.1.7 | 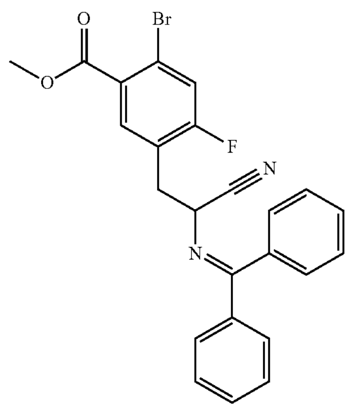 [SMILES: COC(=O)c1cc(CC(C#N)N=C(c2ccccc2)c2ccccc2)c(F)cc1Br] | 466 | 0.82 | X011_S02 |

Step 2: Synthesis of Intermediate I-7.2

To I-7.1 (155 mg, 0.34 mmol) in dioxane (6 mL) aq. HCl (1 mol/L, 361 µL) is added. The reaction mixture is stirred for 1 h. 135 µL aq. HCl (1 M) is added and stirred for additional 30 min. The product is purified by reversed phase HPLC. Yield >95%. m/z 287 [M+H]+, rt 1.01 min, LC-MS Method V011_S01.

The following intermediates as shown in Table 26 are synthesized in a similar fashion from the appropriate intermediate ((R,S)=1:1 mixture of stereoisomers at the carbon adjacent to the nitrile group):

TABLE 26

| Intermediate | Educt | Structure of Intermediate | m/z [M + H]+ | rt (min) | LC-MS method |
|---|---|---|---|---|---|
| I-7.2.1 | I-7.1.1 | | 284/286 | 0.48 | X012_S01 |

TABLE 26-continued

| Intermediate | Educt | Structure of Intermediate | m/z [M + H]+ | rt (min) | LC-MS method |
|---|---|---|---|---|---|
| I-7.2.2 | I-7.1.2 | (3-nitrobenzyl aminonitrile structure) | n.d. | n.d. | n.d. |
| I-7.2.3 | I-7.1.3 | (N-Boc-carbazole aminonitrile structure) | 336 | 0.56 | X012_S01 |
| I-7.2.4 | I-7.1.4 | (dihydrophenanthrene aminonitrile structure) | 249 | 0.47 | X012_S01 |
| I-7.2.5 | I-7.1.5 | (dibenzofuran aminonitrile structure) | 227 | 0.43 | X012_S01 |
| I-7.2.6 | I-7.1.6 | (N-Boc-carbazole aminonitrile structure) | 336 | 0.55 | X012_S01 |
| I-7.2.7 | I-7.1.7 | (methyl 2-bromo-4-fluoro-5-(2-amino-2-cyanoethyl)benzoate) | 318/320 (M + H2O) | 0.48 | X011_S02 |

Step 3: Synthesis of Intermediate I-7.3

To R5 (50 mg, 0.21 mmol) in DMF (1.5 mL) HATU (87 mg, 0.23 mmol) and diisopropylethylamine (143 µL, 0.83 mmol) are added and the reaction mixture is stirred for 15 min. Then intermediate I-7.2 (87 mg, 0.22 mmol) is added and the mixture stirred for 12 h. The reaction solution is purified by reversed phase HPLC. Yield 81%, m/z 510/454/410 rt 1.28 min, LC-MS Method V011_S01.

The following intermediates as shown in Table 27 are synthesized in a similar fashion from the appropriate intermediate ((R,S)=1:1 mixture of stereoisomers at the carbon adjacent to the nitrile group):

TABLE 27

| Intermediate | Educt | Structure of Intermediate | m/z [M + H]+ | rt (min) | LC-MS method |
|---|---|---|---|---|---|
| I-7.3.1 | I-7.2.1 | | 506/508 | 0.66 | X012_S01 |
| I-7.3.2 | I-7.2.2 | | 415 | 0.61 | X012_S01 |
| I-7.3.3 | I-7.2.3 | | 559 | 0.84 | X012_S01 |
| I-7.3.4 | I-7.2.4 | | 472 | 0.78 | X012_S01 |
| I-7.3.5 | I-7.2.5 | | 460 | 0.74 | X012_S01 |

TABLE 27-continued

| Intermediate | Educt | Structure of Intermediate | m/z [M + H]+ | rt (min) | LC-MS method |
|---|---|---|---|---|---|
| I-7.3.6 | I-7.2.6 | | 559 | 0.84 | X012_S01 |
| I-7.3.7 | I-7.2.7 | | 524/526 | 0.71 | X011_S02 |

Intermediate I-7.3.7 is separated according to method "Chiral SFC F" to give the following compounds of Table 28

TABLE 28

| Intermediate | Educt | Structure | m/z [M + H]+ | rt (min) | SFC method |
|---|---|---|---|---|---|
| I-7.3.8 | I-7.3.7 | 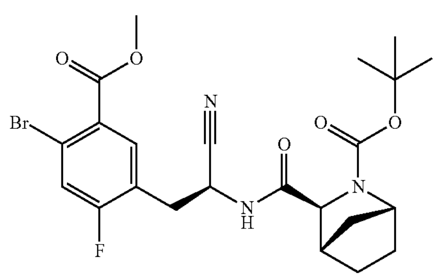 [SMILES: COC(=O)c1cc(C[C@@H](C#N)NC(=O)[C@@H]2[C@H]3CC[C@H](C3)N2C(=O)OC(C)(C)C)c(F)cc1Br] | n.d. | 2.432 | I_IC-20_MEOH_NH3.M |
| I-7.3.9 | I-7.3.7 | 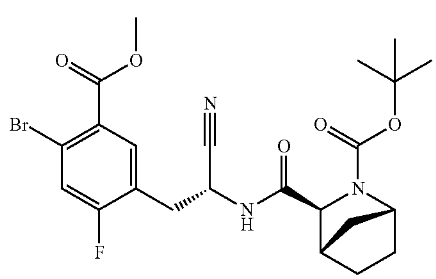 [SMILES: COC(=O)c1cc(C[C@H](C#N)NC(=O)[C@@H]2[C@H]3CC[C@H](C3)N2C(=O)OC(C)(C)C)c(F)cc1Br] | n.d. | 1.946 | I_IC_20_MEOH_NH3.M |

Step 4: Synthesis of Example 7

To I-7.3 (40 mg, 0.08 mmol) in acetonitrile (1 mL) sodium iodide (14 mg, 0.09 mmol) and chlorotrimethylsilane (12 µL, 0.09 mmol) are added. The mixture is stirred for 20 min. The product is purified by reversed phase HPLC. Yield 39%, m/z 410 [M+H]+, rt 0.96 min, LC-MS Method V018_S01

For example 58 I-7.3 is stirred in formic acid at 50° C. for 10 min in a pressure vessel.

Method C

Synthesis of (1S,2S,4R)-N-[1-cyano-2-(1H-indazol-5-yl)ethyl]-3-azabicyclo[2.2.1]heptane-2-carboxamide (Example 8)

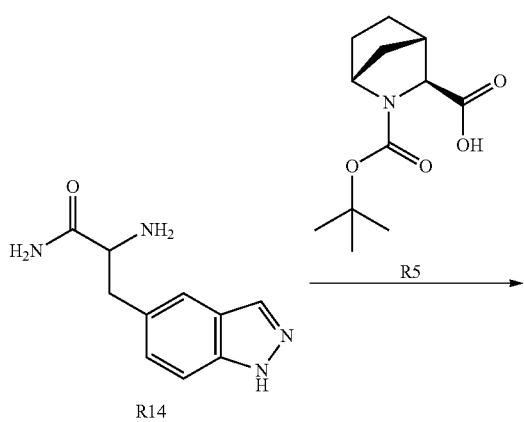

Step 1: Synthesis of Intermediate I-8.1

To R5 (102 mg, 0.42 mmol) in DMF (3 mL) diisopropylethylamine (296 μL, 1.70 mmol) and TBTU (136 mg, 0.23 mmol) are added and the reaction mixture is stirred for 15 min. Then R14 (135 mg, 0.42 mmol) is added and the mixture is stirred for additional 1 h. Water is added to the reaction mixture and extracted with ethyl acetate. The organic layer is washed with brine, dried over Na2SO4 and concentrated. Yield 70%.

The following intermediate as shown in Table 29 is synthesized in a similar fashion from the appropriate intermediate ((R,S)=1:1 mixture of stereoisomers at the carbon adjacent to the amide group):

TABLE 29

| Intermediate | educt | Structure | m/z [M + H]+ | rt (min) | LC-MS method |
|---|---|---|---|---|---|
| I-8.1.1 | R14.1 | 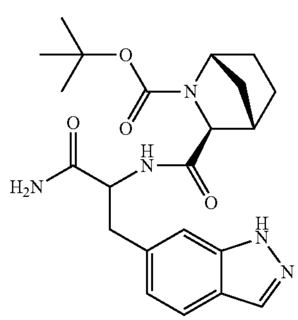 [SMILES: CC(C)(C)OC(=O)N1[C@@H]2CC[C@@H](C2)[C@H]1C(=O)NC(Cc1ccc2cn[nH]c2c1)C(N)=O] | 428 | 0.91 | V011_S01 |

TABLE 29-continued

| Intermediate | educt | Structure | m/z [M + H]+ | rt (min) | LC-MS method |
|---|---|---|---|---|---|
| I-8.1.2 | R14.2 | 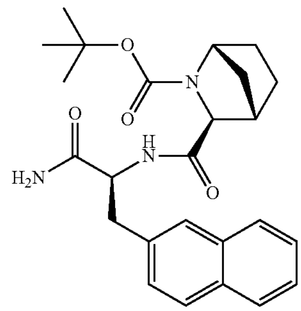 [SMILES: CC(C)(C)OC(=O)N1[C@@H]2CC[C@@H](C2)[C@H]1C(=O)N[C@@H](Cc1ccc2ccccc2c1)C(N)=O] | 437 | 0.64 | X012_S01 |
| I-8.1.3 | R47 | 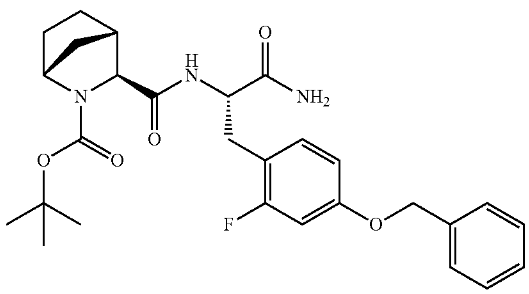 [SMILES: CC(C)(C)OC(=O)N1[C@@H]2CC[C@@H](C2)[C@H]1C(=O)N[C@@H](Cc1ccc(OCc2ccccc2)cc1F)C(N)=O] | 512 | 1.26 | V011_S01 |
| I-8.1.4 | R49 | 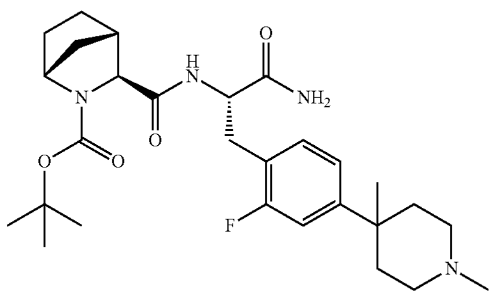 [SMILES: CN1CCC(C)(c2ccc(C[C@H](NC(=O)[C@@H]3[C@H]4CC[C@H](C4)N3C(=O)OC(C)(C)C)C(N)=O)c(F)c2)CC1] | 517 | 1.09 | V011_S01 |

The reaction conditions for I-8.1.3 and I-8.1.4 differ: HATU is used instead of TBTU.

Step 2: Synthesis of Intermediate I-8.2

To I-8.1 (126 mg, 0.29 mmol) in DCM (1 mL) R2 (155 mg, 0.65 mmol) is added. The reaction mixture is stirred for 12 h and then concentrated. Yield 100% m/z 310/354/410 [M+H]+, rt 1.02 min, LC-MS Method V012_S01.

The following intermediates as shown in Table 30 are synthesized in a similar fashion from the appropriate intermediate ((R,S)=1:1 mixture of stereoisomers at the carbon adjacent to the nitrile group):

TABLE 30

| Intermediate | educt | Structure | m/z [M + H]+ | rt (min) | LC-MS method |
|---|---|---|---|---|---|
| I-8.2.1 | I-8.1.1 | 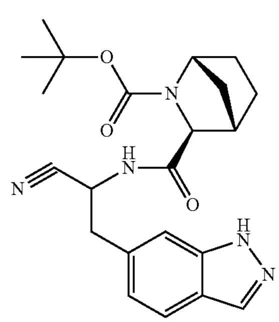 [SMILES: CC(C)(C)OC(=O)N1[C@@H]2CC[C@@H](C2)[C@H]1C(=O)NC(C#N)Cc1ccc2cn[nH]c2c1] | n.d. | n.d. | n.d. |

TABLE 30-continued

| Intermediate | educt | Structure | m/z [M + H]+ | rt (min) | LC-MS method |
|---|---|---|---|---|---|
| I-8.2.2 | I-8.1.2 | 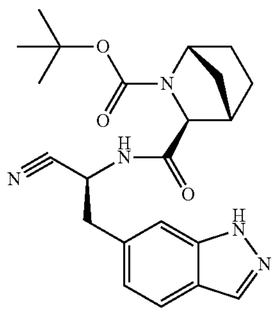 [SMILES: CC(C)(C)OC(=O)N1[C@@H]2CC[C@@H](C2)[C@H]1C(=O)N[C@H](C#N)Cc1ccc2cn[nH]c2c1] | 420 | 0.70 | X012_S01 |
| I-8.2.3 | I-8.1.3 | 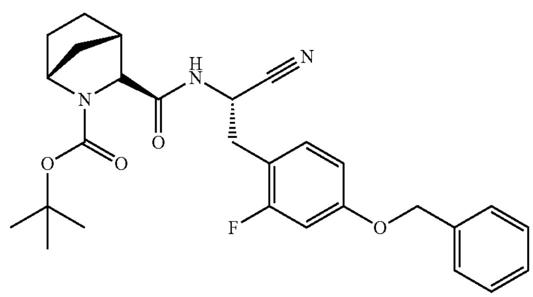 | 494 | 1.37 | V011_S01 |
| I-8.2.4 | I-8.1.4 | 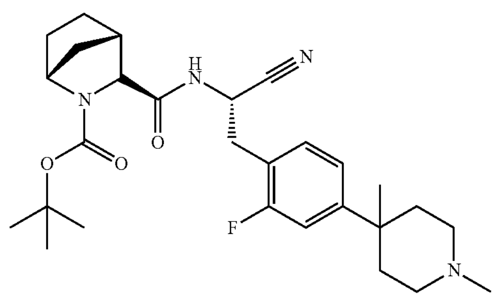 | 499 | 1.22 | V011_S01 |
| I-8.2.5 | I-24.3.2 | 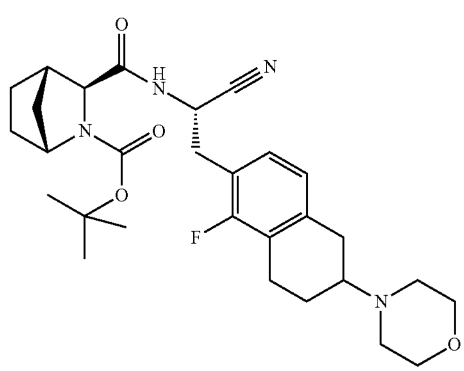 [SMILES: CC(C)(C)OC(=O)N1[C@@H]2CC[C@@H](C2)[C@H]1C(=O)N[C@H](C#N)Cc1ccc2c(c1F)CCC(N1CCOCC1)C2] | 527 | 0.66 | X011_S03 |

Step 3: Synthesis of Example 8

To I-8.1 (120 mg, 0.29 mmol) in acetonitrile (7 mL) sodium iodide (132 mg, 0.88 mmol) and chlorotrimethylsilane (106 µl, 0.88 mmol) are added. The mixture is stirred for 12 h, then methanol (7 mL) is added, stirred for 1 h and then concentrated. The residue is dissolved in ethyl acetate, washed with water and brine, dried over $Na_2SO_4$ and concentrated. The product is purified by reversed phase HPLC. Yield 19%, m/z 310 [M+H]+, rt 0.86 min, LC-MS Method V011_S01.

Method D

Synthesis of (1S,2S,4R)-N-[1-cyano-2-(6-oxo-5H-phenanthridin-8-yl)ethyl]-3-azabicyclo[2.2.1]heptane-2-carboxamide (Example 9)

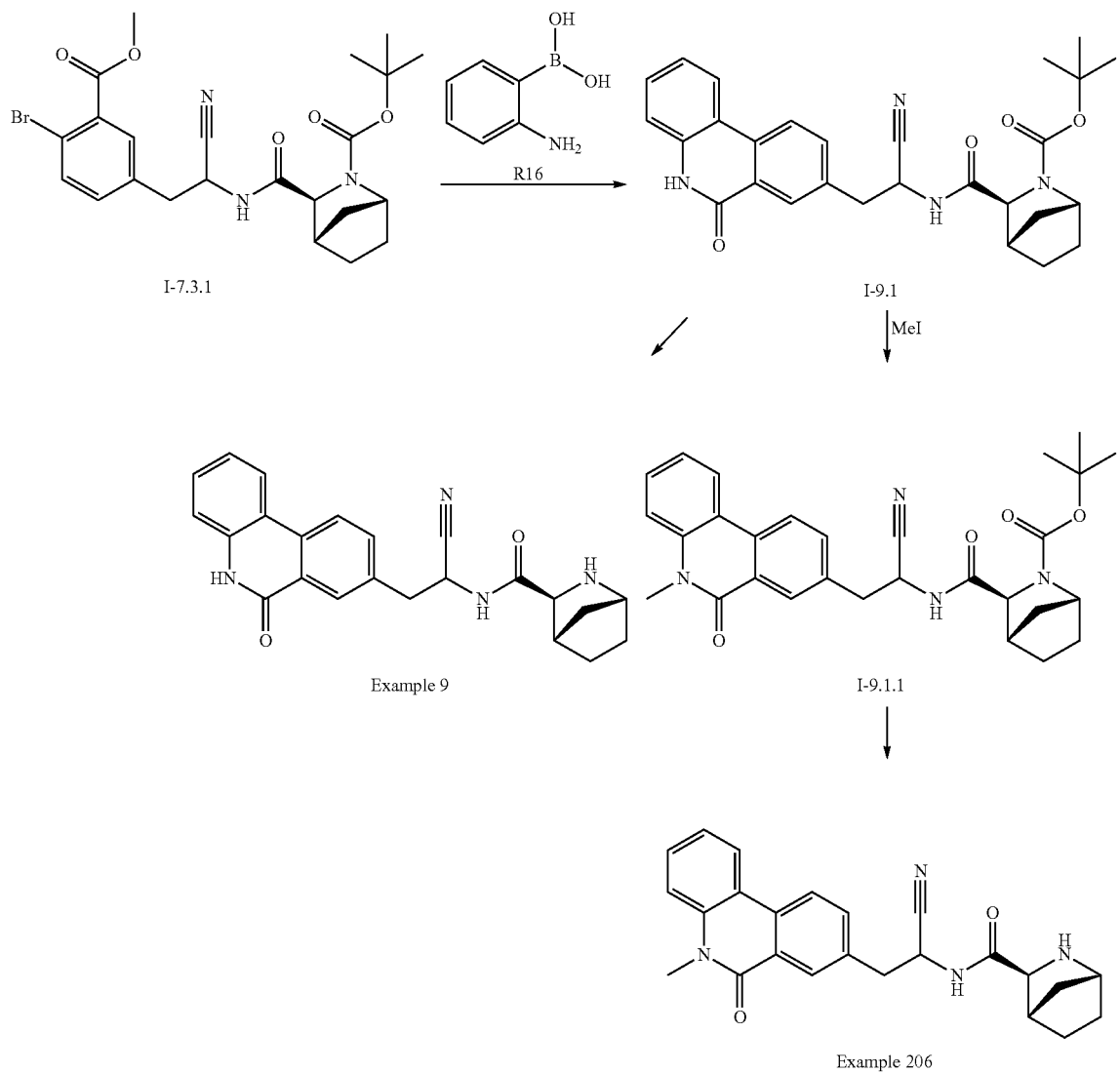

Step 1: Synthesis of Intermediate I-9.1

I-7.3.1 (200 mg, 0.39 mmol) and R16 (65 mg, 0.47 mmol) in acetonitrile (5 mL) is purged with argon. 1,1-Bis(di-tert-butylphosphino)ferrocene palladium dichloride (26 mg, 0.04 mmol) and aq. sodium carbonate solution (2 mol/L, 395 µL) are added and heated to 70° C. for 3 h. DCM and water are added to the reaction mixture. The organic layer is dried over $MgSO_4$ and concentrated. The product is purified by reversed phase HPLC. Yield 50% m/z 487 [M+H]+, rt 0.60 min, LC-MS Method X012_S01.

Step 2: Synthesis of Example 9

To I-9.4 (115 mg, 0.24 mmol) in acetonitrile (5 mL) sodium iodide (106 mg, 0.71 mmol) and chlorotrimethylsilane (90 µL, 0.71 mmol) are added. The mixture is stirred for 90 min. The product is purified by reversed phase HPLC. Yield 32%, m/z 387 [M+H]+, rt 0.39 min, LC-MS Method X012_S01.

Synthesis of Intermediate I-9.1.1

I-9.1 (100 mg, 0.2 mmol) and MeI (14.2 µL, 0.23 mmol) are dissolved in 2 mL DMF, and NaH (9.04 mg, 0.23 mmol, as 60% suspension in paraffin oil) is added. After stirring for 12 h at r.t., the mixture is diluted with methanol, filtered and purified by HPLC. The product fractions are freeze-dried to yield 42 mg (41%) I-9.1.1. m/z 501 [M+H]+, rt 0.65 min, LC-MS Method X012_S01.

Boc deprotection to Example 206 is performed in analogy to the synthesis of Example 9.

Method D1

Synthesis of (1S,2S,4R)-N-[2-(3-chloro-5-methyl-6-oxo-phenanthridin-8-yl)-1-cyano-ethyl]-3-azabicyclo[2.2.1]heptane-2-carboxamide (Example 305)

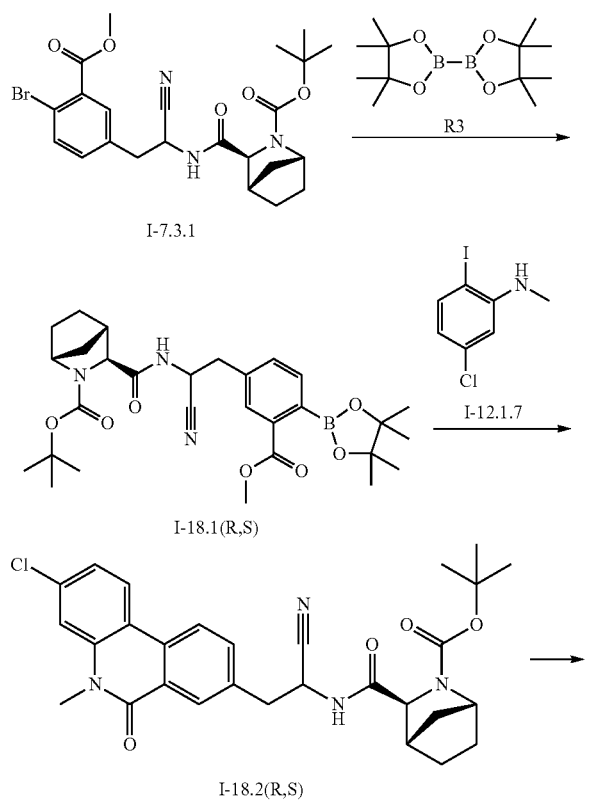

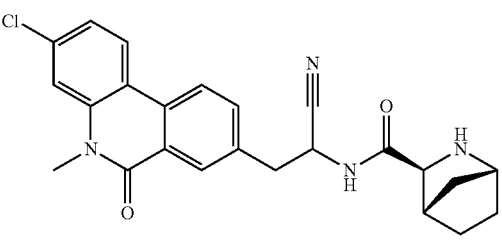

Example 305

Step 1: Synthesis of Intermediate I-18.1

To I-7.3.1 (4.0 g, 7.9 mmol) in anhydrous dioxane (50 mL) R3 (2.93 g, 11.5 mmol) and potassium acetate (2.27 g, 23.2 mmol) are added. The mixture is purged with argon, [1,1'-Bis(diphenylphosphino)ferrocene]dichloropalladium (II) dichlormethan complex (PdCl₂(dppf)) (0.66 g, 0.81 mmol) is added to the mixture and heated to 70° C. overnight. The reaction mixture is diluted with DCM and water. The organic layer is separated, dried and concentrated. The residue is purified by reversed phase HPLC. Yield 71% m/z 554 [M+H]+, rt 0.74 min, LC-MS Method X011_S03.

The following intermediates as shown in Table 31 are synthesized in a similar fashion from the appropriate intermediate ((R,S)=1:1 mixture of stereoisomers at the carbon adjacent to the nitrile group):

TABLE 31

| Intermediate | educt | Structure | m/z [M + H]+ | rt (min) | LC-MS method |
|---|---|---|---|---|---|
| I-18.1.1 | I-7.3.7 | 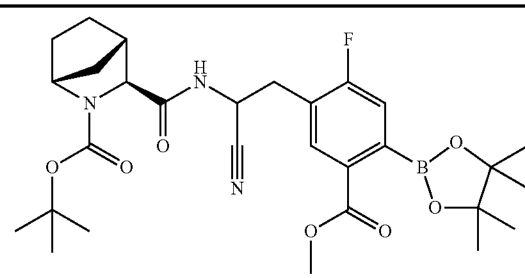 | 572 | 0.72 | X011_S02 |
| I-18.1.2 | I-7.3.8 | 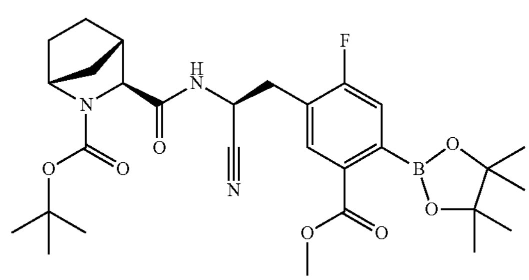 [SMILES: COC(=O)c1cc(C[C@@H](C#N)NC(=O)[C@@H]2[C@H]3CC[C@H](C3)N2C(=O)OC(C)(C)C)c(F)cc1B1OC(C)(C)C(C)(C)O1] | 572 | 0.74 | X012_S01 |

Step 2: Synthesis of Intermediate I-18.2

To I-18.1 (150 m g, 0.27 mmol) in anhydrous ACN (5 mL) (5-chloro-2-iodophenyl)methanamine (72.498 m g, 0.27 mmol) is added and purged with argon. 1,1 bis(di-tert.butylphosphino)ferrocene palladium dichloride (17.66 mg, 0.027 mmol) and a solution of sodium carbonate in water 2 mol/L (0.271 mL, 0.54 mmol) are added, purged again with argon and heated to 70° C. for 6 h. The reaction mixture is diluted with DCM and water. The organic layer is separated, dried and concentrated. The crude residue is used for the next step without further purification. Yield 93% m/z 536 [M+H]+, rt 0.71 min, LC-MS Method X012_S01.

The following intermediates as shown in Table 32 are synthesized in a similar fashion from the appropriate intermediate ((R,S)=1:1 mixture of stereoisomers at the carbon adjacent to the nitrile group):

TABLE 32

| Intermediate | Educt | Structure | m/z [M + H]+ | rt (min) | LC-MS method |
|---|---|---|---|---|---|
| I-18.2.1 | I-18.1.1 | 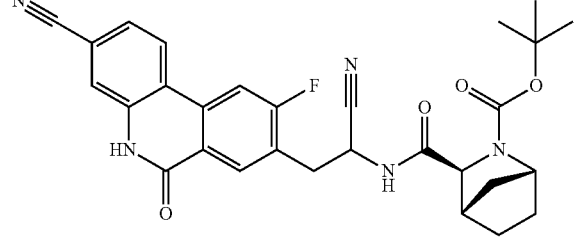 | 530 | 0.62 | X011_S03 |
| I-18.2.2 | I-18.1.1 | 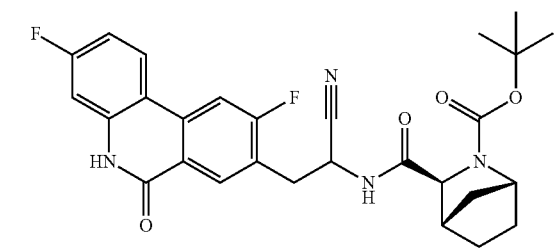 [SMILES: CC(C)(C)OC(=O)N1[C@@H]2CC[C@@H](C2)[C@H]1C(=O)NC(C#N)Cc1cc2c(=O)[nH]c3cc(F)ccc3c2cc1F] | 523 | 0.66 | X011_S02 |
| I-18.2.3 | I-18.1 | 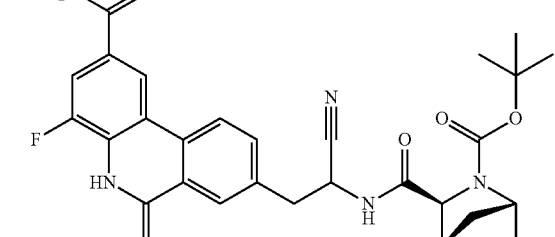 | 548 | 0.48 | X011_S03 |
| I-18.2.4 | I-18.1.1 | 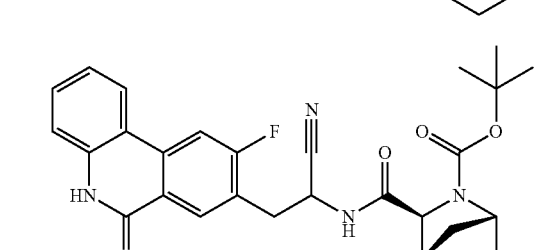 | 505 | 0.65 | X011_S02 |
| I-18.2.5 | I-18.1.1 | 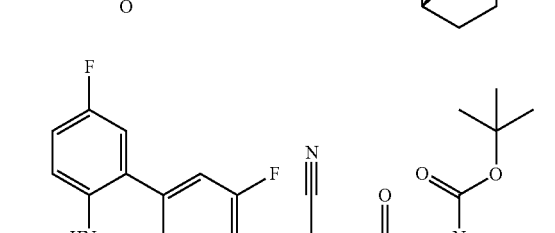 | 523 | 0.66 | X011_S02 |

TABLE 32-continued
| Intermediate | Educt | Structure | m/z [M + H]+ | rt (min) | LC-MS method |
|---|---|---|---|---|---|
| I-18.2.6 | I-18.1 | 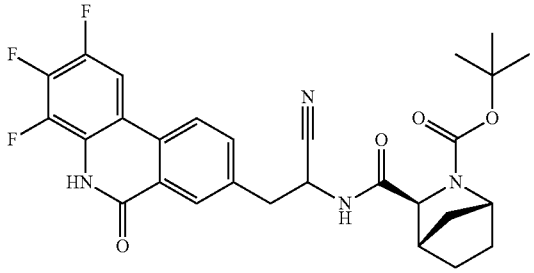 [SMILES: CC(C)(C)OC(=O)N1[C@@H]2CC[C@@H](C2)[C@H]1C(=O)NC(C#N)Cc1ccc2c(c1)c(=O)[nH]c1c(F)c(F)c(F)cc12] | 541 | 0.69 | X012_S02 |
| I-18.2.7 | I-18.1 | 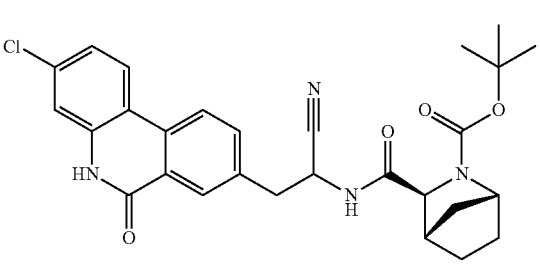 [SMILES: CC(C)(C)OC(=O)N1[C@@H]2CC[C@@H](C2)[C@H]1C(=O)NC(C#N)Cc1ccc2c(c1)c(=O)[nH]c1cc(Cl)ccc12] | 522 | 0.65 | X012_S01 |
| I-18.2.8 | I-18.1 | 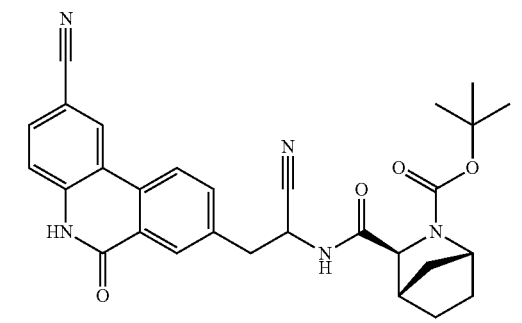 [SMILES: CC(C)(C)OC(=O)N1[C@@H]2CC[C@@H](C2)[C@H]1C(=O)NC(C#N)Cc1ccc2c(c1)c(=O)[nH]c1ccc(C#N)cc12] | 512 | 0.57 | X012_S01 |
| I-18.2.9 | I-18.1 | 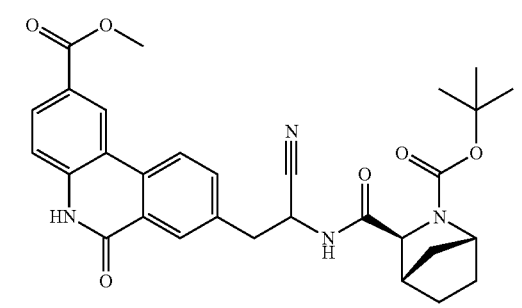 [SMILES: COC(=O)c1ccc2[nH]c(=O)c3cc(CC(C#N)NC(=O)[C@@H]4[C@H]5CC[C@H](C5)N4C(=O)OC(C)(C)C)ccc3c2c1] | 545 | 0.61 | X011_S03 |
| I-18.2.10 | I-18.1 | 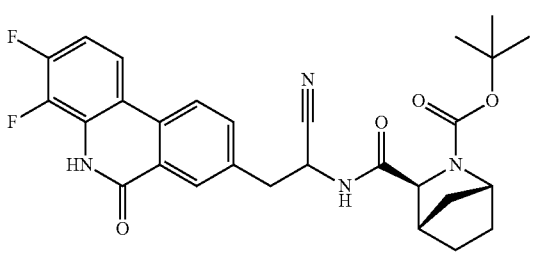 [SMILES: CC(C)(C)OC(=O)N1[C@@H]2CC[C@@H](C2)[C@H]1C(=O)NC(C#N)Cc1ccc2c(c1)c(=O)[nH]c1c(F)c(F)ccc12] | 523 | 0.68 | X012_S02 |

TABLE 32-continued

| Intermediate | Educt | Structure | m/z [M + H]+ | rt (min) | LC-MS method |
|---|---|---|---|---|---|
| I-18.2.11 | I-18.1 | 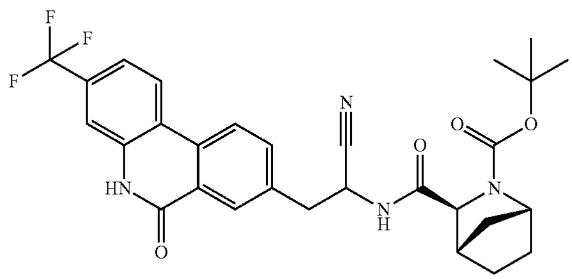 [SMILES: CC(C)(C)OC(=O)N1[C@@H]2CC[C@@H](C2)[C@H]1C(=O)NC(C#N)Cc1ccc2c(c1)c(=O)[nH]c1cc(C(F)(F)F)ccc12] | 555 | 0.69 | X011_S03 |
| I-18.2.12 | I-18.1 | 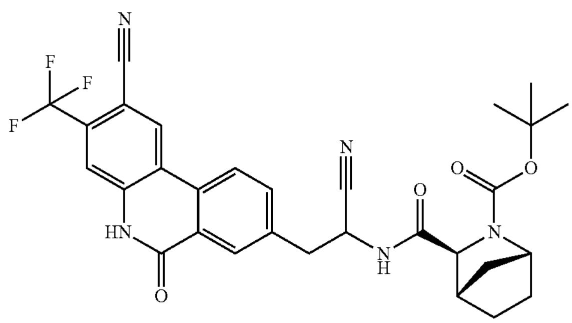 [SMILES: CC(C)(C)OC(=O)N1[C@@H]2CC[C@@H](C2)[C@H]1C(=O)NC(C#N)Cc1ccc2c(c1)c(=O)[nH]c1cc(C(F)(F)F)c(C#N)cc12] | 580 | 0.60 | X011_S03 |
| I-18.2.13 | I-18.1 | 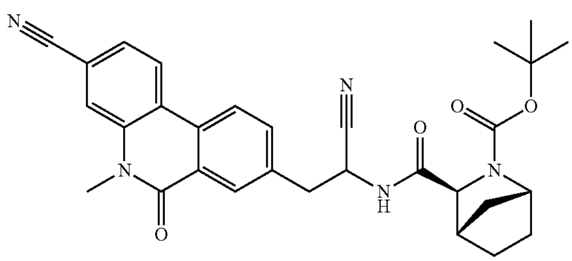 [SMILES: Cn1c(=O)c2cc(CC(C#N)NC(=O)[C@@H]3[C@H]4CC[C@H](C4)N3C(=O)OC(C)(C)C)ccc2c2ccc(C#N)cc21] | 526 | 0.64 | X012_S01 |
| I-18.2.14 | I-18.1 | 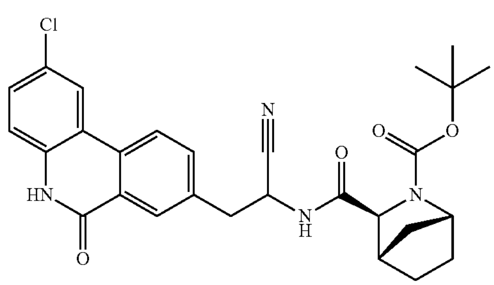 [SMILES: CC(C)(C)OC(=O)N1[C@@H]2CC[C@@H](C2)[C@H]1C(=O)NC(C#N)Cc1ccc2c(c1)c(=O)[nH]c1ccc(Cl)cc12] | 521 | 0.67 | X011_S03 |
| I-18.2.15 | I-18.1 | 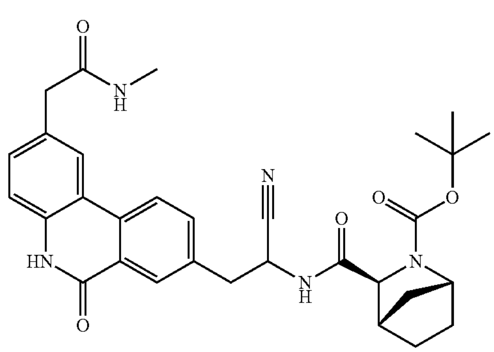 [SMILES: CNC(=O)Cc1ccc2[nH]c(=O)c3cc(CC(C#N)NC(=O)[C@@H]4[C@H]5CC[C@H](C5)N4C(=O)OC(C)(C)C)ccc3c2c1] | 558 | 0.50 | X012_S01 |

TABLE 32-continued
| Intermediate | Educt | Structure | m/z [M + H]+ | rt (min) | LC-MS method |
|---|---|---|---|---|---|
| I-18.2.16 | I-18.1 | 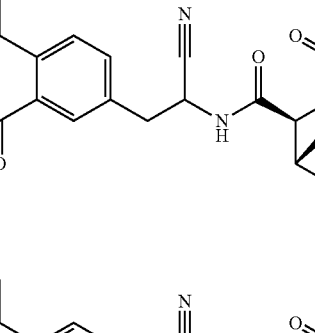 | 530 | 0.54 | X011_S03 |
| I-18.2.17 | I-18.1 | 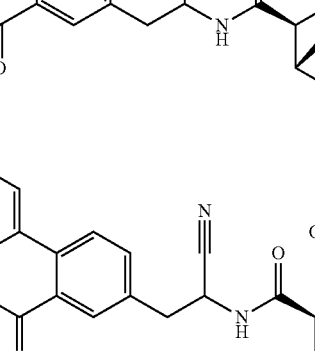 | 505 | 0.61 | X012_S01 |
| I-18.2.18 | I-18.1 | 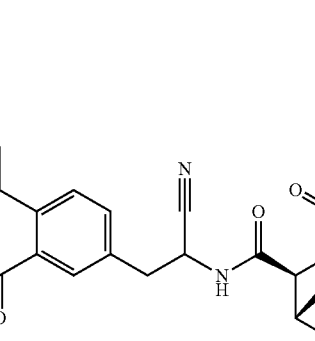 | 512 | 0.45 | X012_S01 |
| I-18.2.19 | I-18.1 | 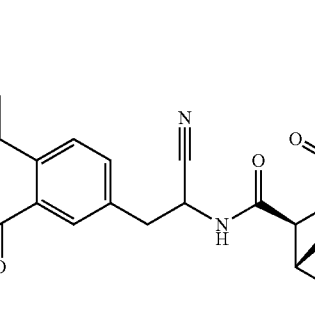 | 523 | 0.62 | X012_S01 |
| I-18.2.20 | I-18.1 | 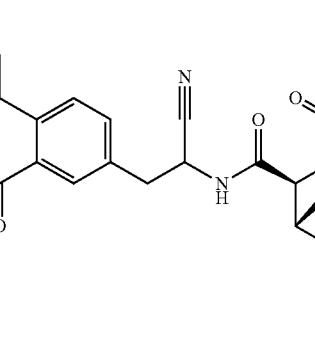 | 545 | 0.61 | X011_S03 |

TABLE 32-continued

| Intermediate | Educt | Structure | m/z [M + H]+ | rt (min) | LC-MS method |
|---|---|---|---|---|---|
| I-18.2.21 | I-18.1 | 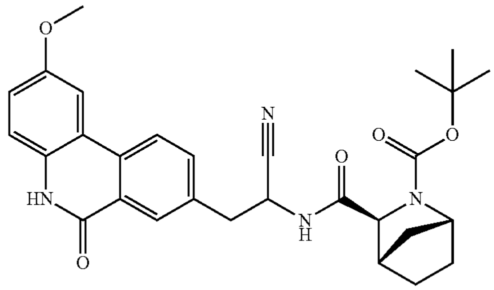 [SMILES: COc1ccc2[nH]c(=O)c3cc(CC(C#N)NC(=O)[C@@H]4[C@H]5CC[C@H](C5)N4C(=O)OC(C)(C)C)ccc3c2c1] | 517 | 0.61 | X011_S03 |
| I-18.2.22 | I-18.1 | 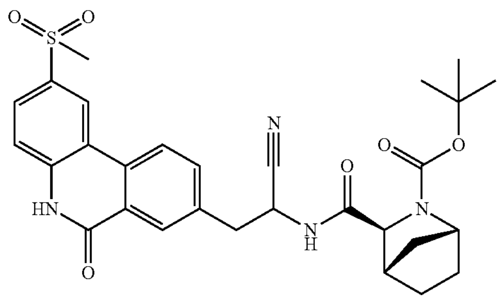 [SMILES: CC(C)(C)OC(=O)N1[C@@H]2CC[C@@H](C2)[C@H]1C(=O)NC(C#N)Cc1ccc2c(c1)c(=O)[nH]c1ccc(S(C)(=O)=O)cc12] | 565 | 0.53 | X012_S01 |
| I-18.2.23 | I-18.1 | 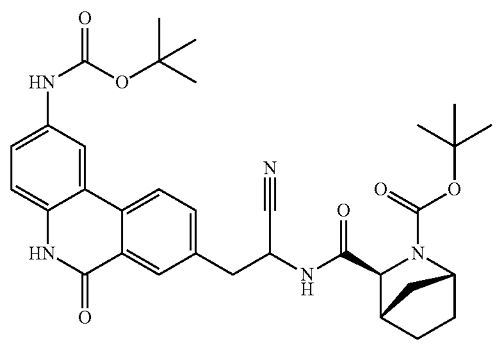 [SMILES: CC(C)(C)OC(=O)Nc1ccc2[nH]c(=O)c3cc(CC(C#N)NC(=O)[C@@H]4[C@H]5CC[C@H](C5)N4C(=O)OC(C)(C)C)ccc3c2c1] | 602 | 0.66 | X012_S01 |
| I-18.2.24 | I-18.1.2 | 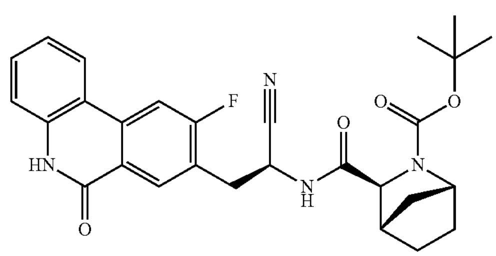 [SMILES: CC(C)(C)OC(=O)N1[C@@H]2CC[C@@H](C2)[C@H]1C(=O)N[C@H](C#N)Cc1cc2c(=O)[nH]c3ccccc3c2cc1F] | 505 | 0.61 | X012_S01 |
| I-18.2.25 | I-18.1.2 | 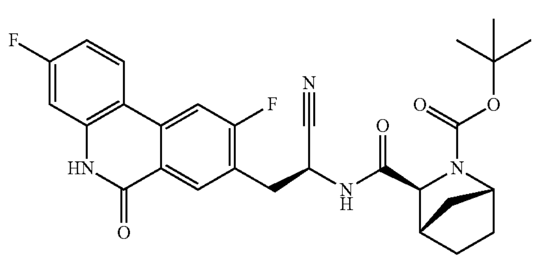 [SMILES: CC(C)(C)OC(=O)N1[C@@H]2CC[C@@H](C2)[C@H]1C(=O)N[C@H](C#N)Cc1cc2c(=O)[nH]c3cc(F)ccc3c2cc1F] | 523 | 0.63 | X012_S01 |

TABLE 32-continued
| Intermediate | Educt | Structure | m/z [M + H]+ | rt (min) | LC-MS method |
|---|---|---|---|---|---|
| I-18.2.26 | I-18.1.2 | 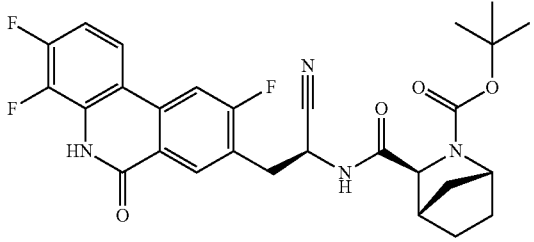 [SMILES: CC(C)(C)OC(=O)N1[C@@H]2CC[C@@H](C2)[C@H]1C(=O)N[C@H](C#N)Cc1cc2c(=O)[nH]c3c(F)c(F)ccc3c2cc1F] | 541 | 0.64 | X012_S01 |
| I-18.2.27 | I-18.1.2 | 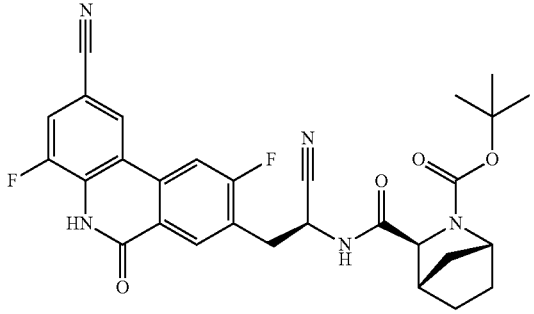 [SMILES: CC(C)(C)OC(=O)N1[C@@H]2CC[C@@H](C2)[C@H]1C(=O)N[C@H](C#N)Cc1cc2c(=O)[nH]c3c(F)cc(C#N)cc3c2cc1F] | 548 | 0.60 | X012_S01 |
| I-18.2.28 | I-18.1.2 | 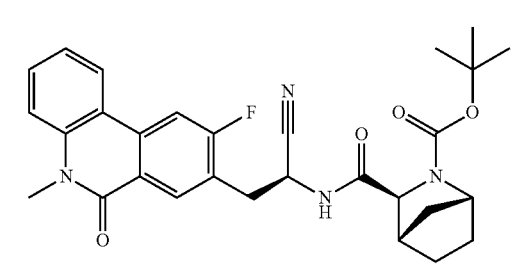 [SMILES: Cn1c(=O)c2cc(C[C@@H](C#N)NC(=O)[C@@H]3[C@H]4CC[C@H](C4)N3C(=O)OC(C)(C)C)c(F)cc2c2ccccc21] | 519 | 0.67 | X012_S01 |
| I-18.2.29 | I-18.1 | 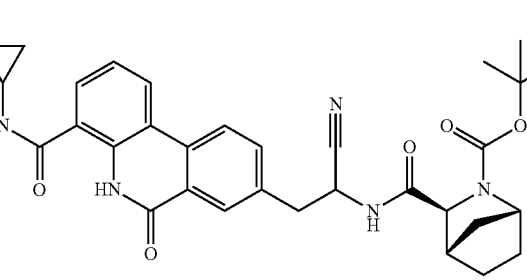 | 570 | 0.59 | X012_S01 |
Step 3: Synthesis of Example 305
To I-18.2 (270 mg, 0.25 mmol) in THF (3 mL) methanesulfonic acid (81.87 μL, 1.26 mmol) is added and the reaction mixture is stirred at r.t. overnight. The reaction mixture is concentrated and the residue is purified by reversed phase HPLC. Yield 14% m/z 435 [M+H]+, rt 0.48 min, LC-MS Method X012_S01.

Method E

Synthesis of (1S,2S,4R)-N-[1-cyano-2-(6-oxo-5H-phenanthridin-3-yl)ethyl]-3-azabicyclo[2.2.1]heptane-2-carboxamide and (1S,2S,4R)-N-[1-cyano-2-(6-oxo-5H-phenanthridin-1-yl)ethyl]-3-azabicyclo[2.2.1]heptane-2-carboxamide (Example 123 and 128)

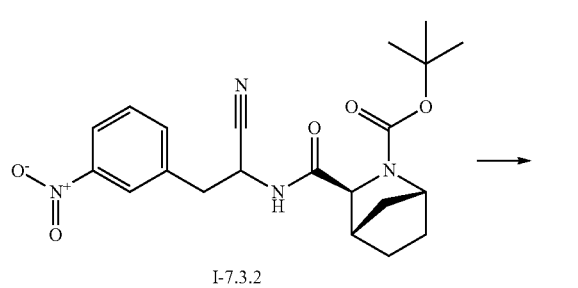

I-7.3.2

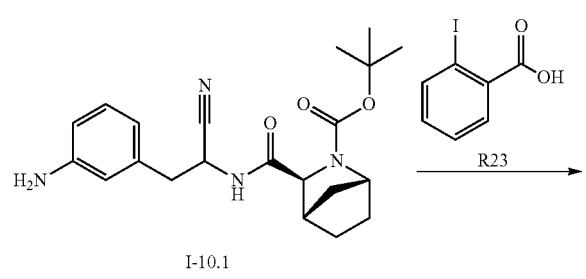

I-10.1

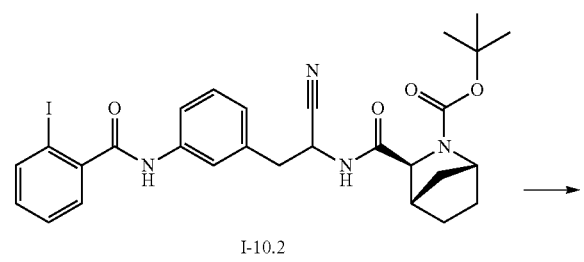

I-10.2

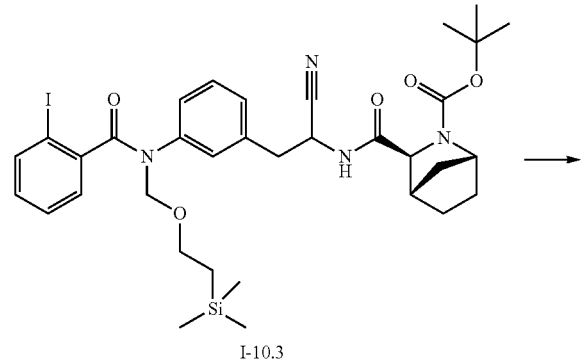

I-10.3

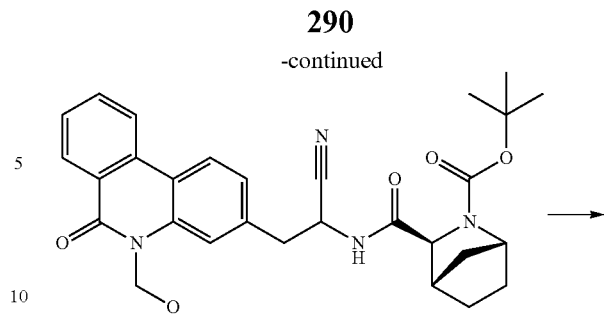

I-10.4

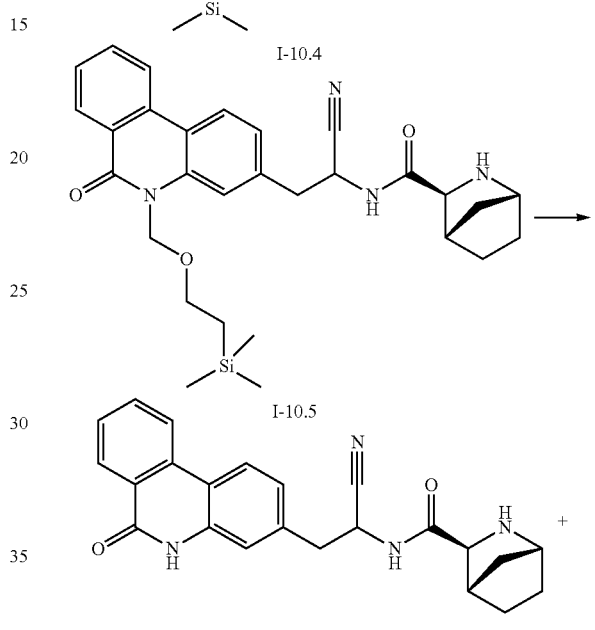

I-10.5

Example 123

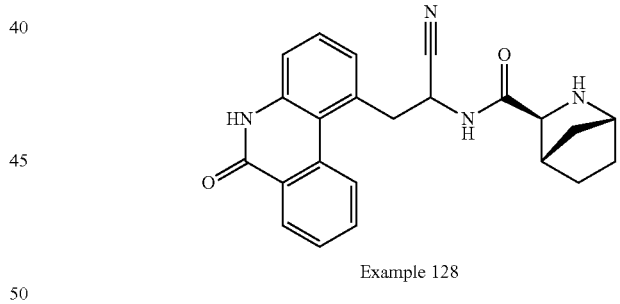

Example 128

Step 1: Synthesis of Intermediate I-10.1

To I-7.3.2 (6.0 g, 14.5 mmol) in ethyl acetate (100 mL) tin(II)chloride dihydrate (16.3 g, 72.4 mmol) is added. The reaction mixture is stirred for 12 h. The mixture is set basic with potassium carbonate and aq. sodium hydroxide solution. The organic layer is separated, is dried over $MgSO_4$ and is concentrated. The residue is purified by reversed phase HPLC. Yield 32% m/z 385 [M+H]+, rt 0.42 min, LC-MS Method X012_S01.

Step 2: Synthesis of Intermediate I-10.2

To R23 (0.70 g, 2.81 mmol) in DCM (20 mL) diisopropylethylamine (1.20 mL, 7.02 mmol) and HATU (1.09 g, 2.81 mmol) are added and the reaction mixture is stirred for 7 min. Then intermediate I-10.1 (0.90 g, 2.34 mmol) is added and the mixture is stirred for additional 12 h. The mixture is concentrated and the residue is purified by flash chromatography (cyclohexane/ethyl acetate=70/30). Yield 90% m/z 615 [M+H]+, rt 0.66 min, LC-MS Method X012_S01.

The following intermediate as shown in Table 33 is synthesized in a similar fashion from the appropriate intermediate ((R,S)=1:1 mixture of stereoisomers at the carbon adjacent to the nitrile group):

TABLE 33

| Intermediate | educt | Structure | m/z [M + H]+ | rt (min) | LC-MS method |
|---|---|---|---|---|---|
| I-10.2.1 | I-10.1 | 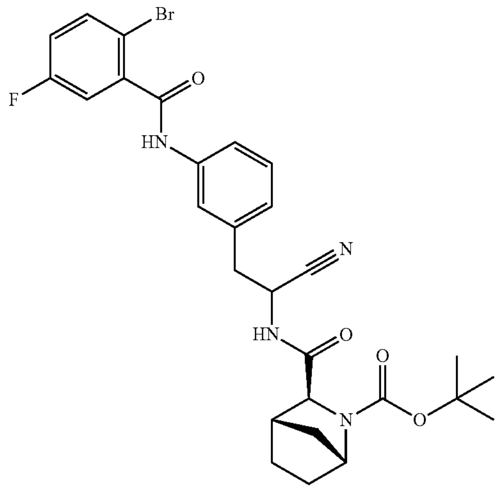 [SMILES: CC(C)(C)OC(=O)N1[C@@H]2CC[C@@H](C2)[C@H]1C(=O)NC(C#N)Cc1cccc(NC(=O)c2cc(F)ccc2Br)c1] | 585/587 | 0.67 | X012_S01 |

Step 3: Synthesis of Intermediate I-10.3

To I-10.2 (800 mg, 1.30 mmol) in DMF (20 mL) sodium hydride (58 mg, 1.43 mmol) is added and the reaction mixture is stirred for 10 min. Then 2-(trimethylsilyl)ethoxymethylchloride (0.25 mL, 1.43 mmol) is added and the mixture is stirred for additional 2 h. Water and DCM is added to the mixture and the organic layer is concentrated. The residue is purified by reversed phase HPLC. Yield 26% m/z 745 [M+H]+, rt 0.85 min, LC-MS Method X012_S01.

The following intermediate as shown in Table 34 is synthesized in a similar fashion from the appropriate intermediate:

Step 4: Synthesis of Intermediate I-10.4

To I-10.3 (200 mg, 0.27 mmol) in anhydrous DMF (10 mL) tetrakis(triphenylphosphine)palladium (16 mg, 0.01 mmol) and sodium carbonate (58 mg, 0.55 mmol) is added. The reaction mixture is heated to 150° C. for 5 h. Water and ethyl acetate is added to the mixture. The organic layer is dried over $MgSO_4$ and is concentrated. The residue is purified by reversed phase HPLC. Yield 34% m/z 617 [M+H]+, rt 0.84 min, LC-MS Method X012_S01.

During this ring cyclization both isomers are obtained; but it is first possible to separated them by reversed phase HPLC on the last step (see step 6).

The following intermediate as shown in Table 35 is synthesized in a similar fashion from the appropriate intermediate:

TABLE 34

| Intermediate | Educt | Structure | m/z [M + H]+ | rt (min) | LC-MS method |
|---|---|---|---|---|---|
| I-10.3.1 | I-10.2.1 | 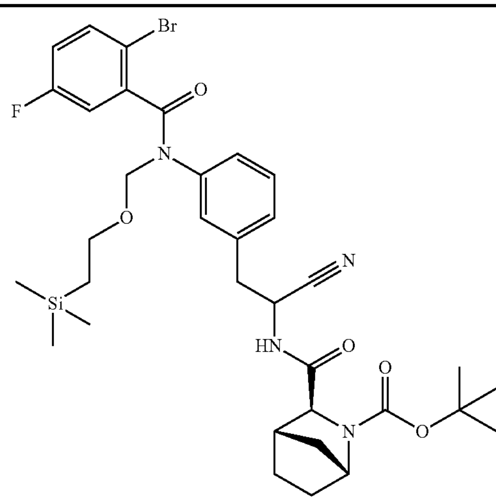 | 715/717 | 0.84 | X012_S01 |

TABLE 35

| Intermediate | Educt | Structure | m/z [M + H]+ | rt (min) | LC-MS method |
|---|---|---|---|---|---|
| I-10.4.1 | I-10.3.1 | 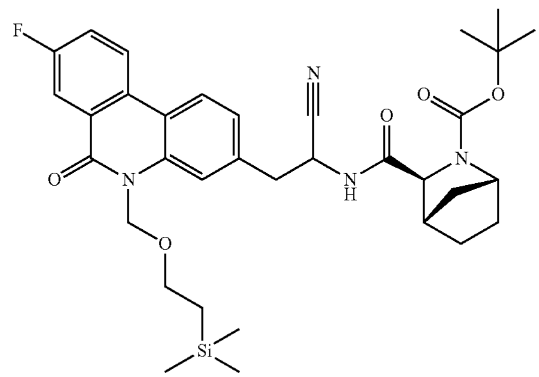 [SMILES: CC(C)(C)OC(=O)N1[C@@H]2CC[C@@H](C2)[C@H]1C(=O)NC(C#N)Cc1ccc2c3ccc(F)cc3c(=O)n(COCC[Si](C)(C)C)c2c1] | 635 | 0.86 | X012_S01 |

Step 5: Synthesis of Intermediate I-10.5

To I-10.4 (57 mg, 0.09 mmol) in acetonitrile (5 mL) sodium iodide (42 mg, 0.28 mmol) and chlorotrimethylsilane (35 µL, 0.28 mmol) are added. The mixture is stirred for 90 min. Then methanol (5 mL) is added and the mixture is stirred for additional 15 min. The mixture is concentrated and DCM and water is added to the residue. The organic layer is separated, is dried over MgSO₄ and concentrated again. The crude product is carried on with step 6. Yield >95%, m/z 517 [M+H]+, rt 0.62 min, LC-MS Method X012_S01.

Step 6: Synthesis of Example 123 and 128

I-10.5 (48 mg, 0.09 mmol) is stirred in formic acid for 48 h. The mixture is purified by reversed phase HPLC. It is possible to separate the both isomers:

Isomer 1=example 123: yield 3%, m/z 387 [M+H]+, rt 0.38 min, LC-MS Method X012_S01, Isomer 2=example 128: yield 6%, m/z 387 [M+H]+, rt 0.35 min, LC-MS Method X012_S01.

Method W

Synthesis of (1S,2S,4R)-N-[(1S)-1-cyano-2-[2-fluoro-4-[(1-methyl-4-piperidyl)oxy]phenyl]ethyl]-3-azabicyclo[2.2.1]heptane-2-carboxamide (Example 319)

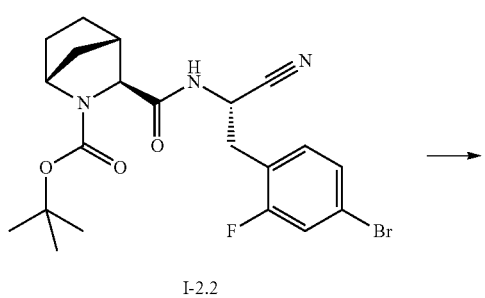

I-2.2

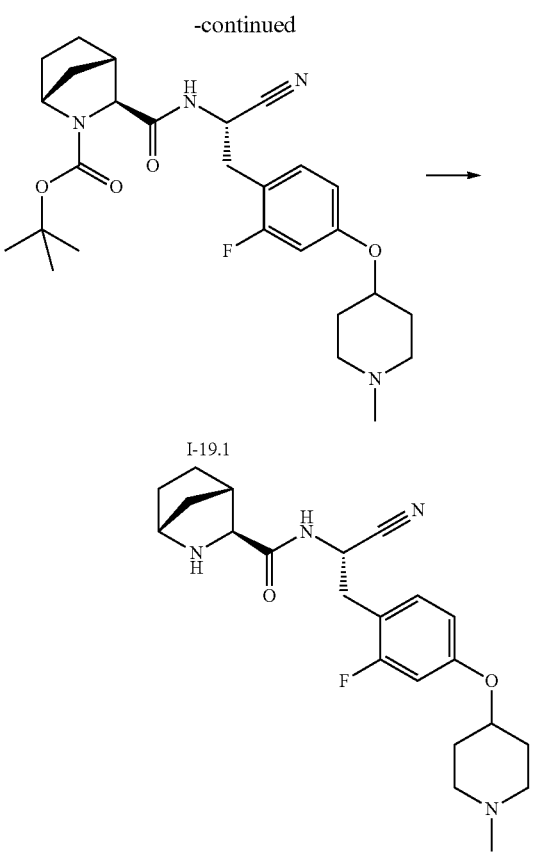

I-19.1

Example 319

Step 1: Synthesis of Intermediate I-19.1

I-2.2 (300 mg, 0.64 mmol) in anhydrous toluene is purged with argon. 4-hydroxy-1-methylpiperidine (148.18 mg, 1.29 mmol), allylpalladium chloride dimer (5.88 mg, 0.016 mmol), 2-(di-t-butylphosphino)-3-methoxy-6-methyl-2'-4'-6'-tri-i-propyl-1,1'-biphenyl (18.09 mg, 0.039 mmol), cesium carbonate (314.4 mg, 0.965 mmol) and molecular sieve (4 A) are added and purged with argon again. The reaction mixture is stirred at 90° C. for 21 h. Afterwards filtered through a pad of celite, washed with ethyl acetate and concentrated. The crude residue is purified by reversed phase HPLC and freeze dried. Yield 16%.

Step 2: Synthesis of Example 319
see method A2, Step 4

To I-19.1 (50 m g, 0.1 mmol) in acetonitrile (6 mL) sodium iodide (45 mg, 0.3 mmol) and chlorotrimethylsilane (38.1 μL, 0.3 mmol) are added. The mixture is stirred for 2 h, then methanol is added, stirred for additional 30 min and then concentrated. The residue is purified by reversed phase HPLC. Yield 34%, m/z 401 [M+H]+, rt 0.31 min, LC-MS Method X012_S02.

Method W1

Synthesis of (1S,2S,4R)-N-[(1S)-1-cyano-2-[4-[3-(dimethylamino)-1-piperidyl]-2-fluoro-phenyl]ethyl]-3-azabicyclo[2.2.1]heptane-2-carboxamide (Example 344)

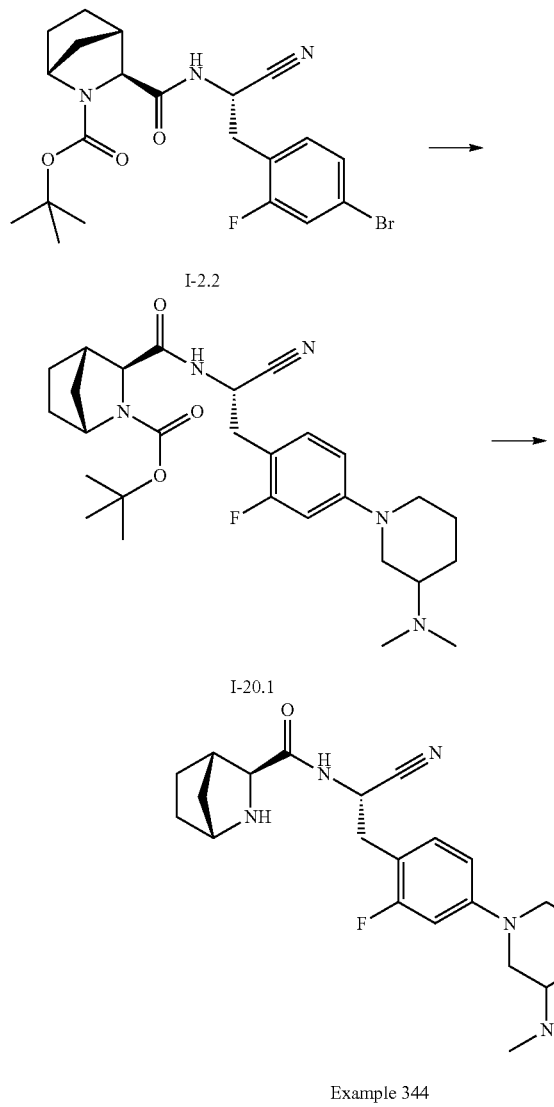

Step 1: Synthesis of Intermediate I-20.1

To I-2.2 (300 mg, 0.64 mmol) in anhydrous dioxane (8 mL) are added 3-dimethylamino-piperidine (164.96 mg, 1.29 mmol) and cesium carbonate (846.87 mg, 2.57 mmol). The mixture is purged with argon and chloro(2-dicyclohex-ylphosphino-2',4',6'-tri-i-propyl-1,1'-biphenyl)[2-(2-aminoethyl)phenyl]palladium(II) (95.05 mg, 0.13 mmol) is added and stirred at 90° C. for 2 h. The reaction mixture is filtered and concentrated. The residue is diluted with dichlormethane and water. The organic layer is separated, dried and concentrated. The crude product is purified by reversed phase HPLC. Yield 12%.

Step 2: Synthesis of Example 344
See Method A5, Step 3

To I-20.1 (53 mg, 0.1 mmol) in acetonitrile (8 mL) p-toluenesulfonic acid monohydrate (68.70 mg, 0.36 mmol) is added and stirred at r.t. for 6 h. The mixture is concentrated, diluted with methanol and purified by reversed phase HPLC. Yield 28%, m/z 414 [M+H]+, rt 0.74 min, LC-MS Method 004_CA05.

Method Z

Synthesis of (1S,2S,4R)-N-[1-cyano-2-(3-fluoro-phenanthridin-8-yl)ethyl]-3-azabicyclo[2.2.1]heptane-2-carboxamide (Example 315)

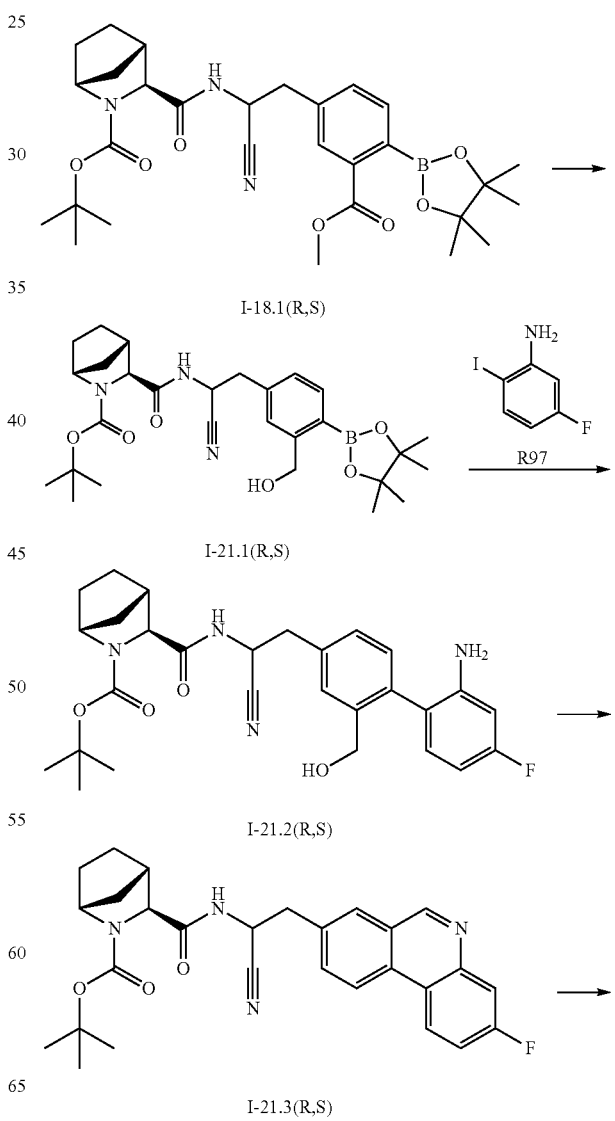

37%.

Step 2: Synthesis of Intermediate I-21.2

To I-21.1 (260 m g, 0.495 mmol) in anhydrous ACN (5 mL) 5-fluoro-2-iodo-aniline (117.28 m g, 0.495 mmol), 1,1 bis(diphenylphosphino)ferrocene palladium dichloride (36.21 mg, 0.049 mmol) and a solution of sodium carbonate in water 2 mol/L (0.742 mL, 1.48 mmol) are added and purged with argon and heated to 80° C. for 1 h. The reaction mixture is diluted with DCM and water. The organic layer is separated, dried and concentrated. The crude residue is purified by reversed phase HPLC. Yield 41%, m/z 509[M+H]+, rt 0.66 min, LC-MS Method X011_S03.

The following intermediate as shown in Table 36 is synthesized in a similar fashion from the appropriate intermediate ((R,S)=1:1 mixture of stereoisomers at the carbon adjacent to the nitrile group):

TABLE 36

| Intermediate | Educt | Structure of Intermediate | m/z [M + H]+ | rt (min) | LC-MS method |
|---|---|---|---|---|---|
| I-21.2.1 | I-21.1 | | 491 | 0.63 | X011_S03 |

Step 3: Synthesis of Intermediate I-21.3

To I-21.2 (103 mg, 0.2 mmol) in DCM manganese(IV) oxide (153.65 mg, 8.73 mmol) is added under cooling. The reaction mixture is stirred at r.t. overnight and 1 h at 50° C. Another manganese(IV)oxide (50 mg, 2.84 mmol) is added and stirred for further 2 h at 50° C. The reaction mixture is filtered through a pad of cellulose and concentrated in vacuo. The residue is purified by reversed phase HPLC.

Yield 27%.

The following intermediate as shown in Table 37 is synthesized in a similar fashion from the appropriate intermediate ((R,S)=1:1 mixture of stereoisomers at the carbon adjacent to the nitrile group):

TABLE 37

| Intermediate | Educt | Structure of Intermediate | m/z [M + H]+ | rt (min) | LC-MS method |
|---|---|---|---|---|---|
| I-21.3.1 | I-21.2.1 | | n.d. | n.d. | n.d. |

Step 4: Synthesis of Example 315

To I-21.3 (26.4 mg, 0.054 mmol) in acetonitrile, p-toluenesulfonic acid monohydrate (35.98 mg, 0.189 mmol) is added and stirred for 5 h. The reaction solution is purified by reversed phase HPLC. Yield 60%, m/z 389 [M+H]+, rt 0.37 min, LC-MS Method X12_S01.

Synthesis of Starting Materials/Educts

Synthesis of tert-butyl N-[(1S)-2-amino-1-[(4-bromo-2-fluoro-phenyl)methyl]-2-oxo-ethyl]carbamate (R1)

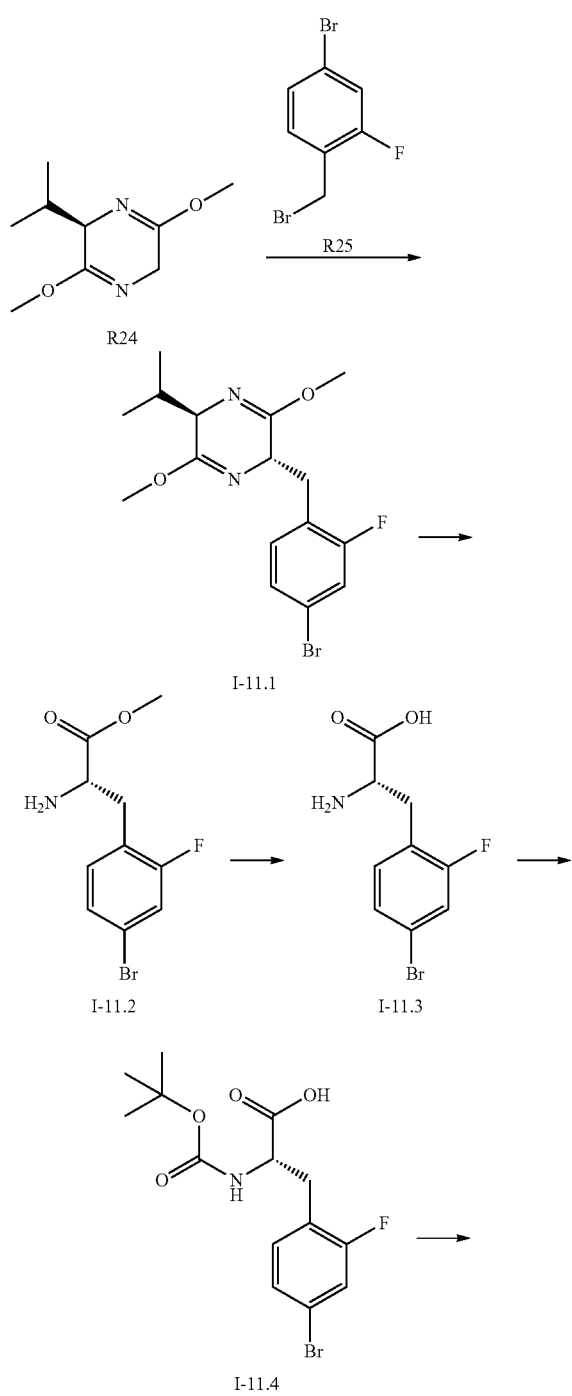

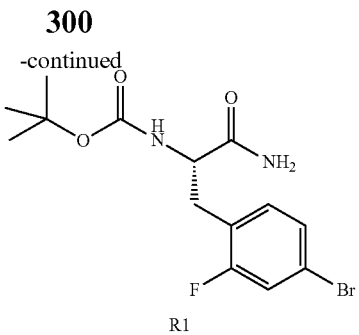

Step 1: Synthesis of Intermediate I-11.1

R2.4 (212 g, 1151 mmol) in tetrahydrofuran (dry) (600 mL) is cooled to −78° C. Then n-butyllithium (2.5 M in hexanes, 552 mL, 1381 mmol) is added dropwise, keeping the temperature below −78° C. After 30 min R25 (324 g, 1209 mmol) in tertahydrofuran (dry) (120 mL) is added dropwise. The reaction mixture is stirred at −78° C. for 1 h. The mixture is quenched with saturated NH$_4$Cl solution and extracted three times with ethyl acetate. The organic layer is washed with brine, dried over Na$_2$SO$_4$ and evaporated in vacuo. The residue is purified by flash chromatography (heptane/ethyl acetate=80/20). Yield 60%.

Step 2: Synthesis of Intermediate I-11.2

To I-11.1 (104 g, 265 mmol) in acetonitrile (600 mL) aq. 0.2 M HCl (2788 mL, 558 mmol) is added.

The mixture is stirred at RT for 12 h. The mixture is extracted with diethylether and the pH of the aq. layer is adjusted to ~8 with sat. NaHCO$_3$-solution. Then it is extracted three times with ethyl acetate. The organic layer is washed with brine, dried over Na$_2$SO$_4$ and concentrated. Yield 80%.

Step 3: Synthesis of Intermediate I-11.3

I-11.2 (62.4 g, 211 mmol) is stirred in aq. 3 M HCl (3 mol/L, 1000 mL) at 60° C. for 16 h. The mixture is cooled down and the pH is adjusted to ~7 with aq. 6 M NaOH. Then the reaction mixture is filtered, washed three times with water and dried in a vacuum oven at 40° C. for 12 h. Yield 74%.

Step 4: Synthesis of Intermediate I-11.4

To I-11.3 (151 g, 546 mmol) in 1,4-dioxane (2.2 L) is added aq. 2 M sodium carbonate (301 mL) and di-tertbutyl dicarbonate (138 g, 147 mL). The mixture is stirred for 4 h. Then water is added and the pH is adjusted to ~4-5 with citric acid. The mixture is extracted three times with ethyl acetate. The organic layer is washed with brine, dried over Na$_2$SO$_4$ and concentrated. The residue is stirred in heptane for 15 min and the product is filtered off. Yield 87%.

Step 5: Synthesis of R1

To I-11.4 (181 g, 476 mmol) in dry DMF (1200 mL) N-methylmorpholine (72 g, 713 mmol) and TBTU (153 g, 476 mmol) are added and the reaction mixture is stirred for 30 min. Then the reaction mixture is cooled to 0° C. and aq. 35% ammonium chloride solution (47 mL, 856 mmol) is added and the mixture is stirred at room temperature for 12 h. Water is added and the formed product is filtered off and washed three times with water. The product is dried in a vacuum oven at 40° C. for 72 h. Yield 64%.

The following intermediate as shown in Table 38 is synthesized in a similar fashion from the appropriate intermediates:

TABLE 38
| Intermediate | Structure | m/z [M + H]+ | rt (min) | LC-MS method |
|---|---|---|---|---|
| R1.1 | 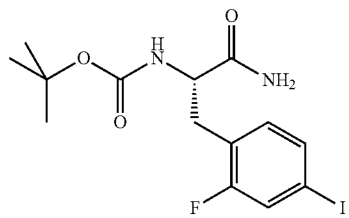 | 409 | 1.05 | V011_S01 |
| R1.2 | 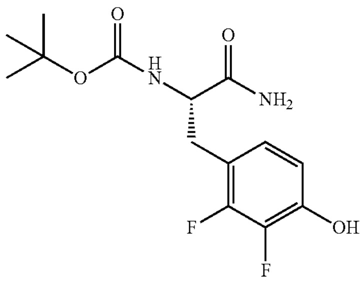 | 217 [M + H − BOC]+ | 0.69 | Z018_S04 |
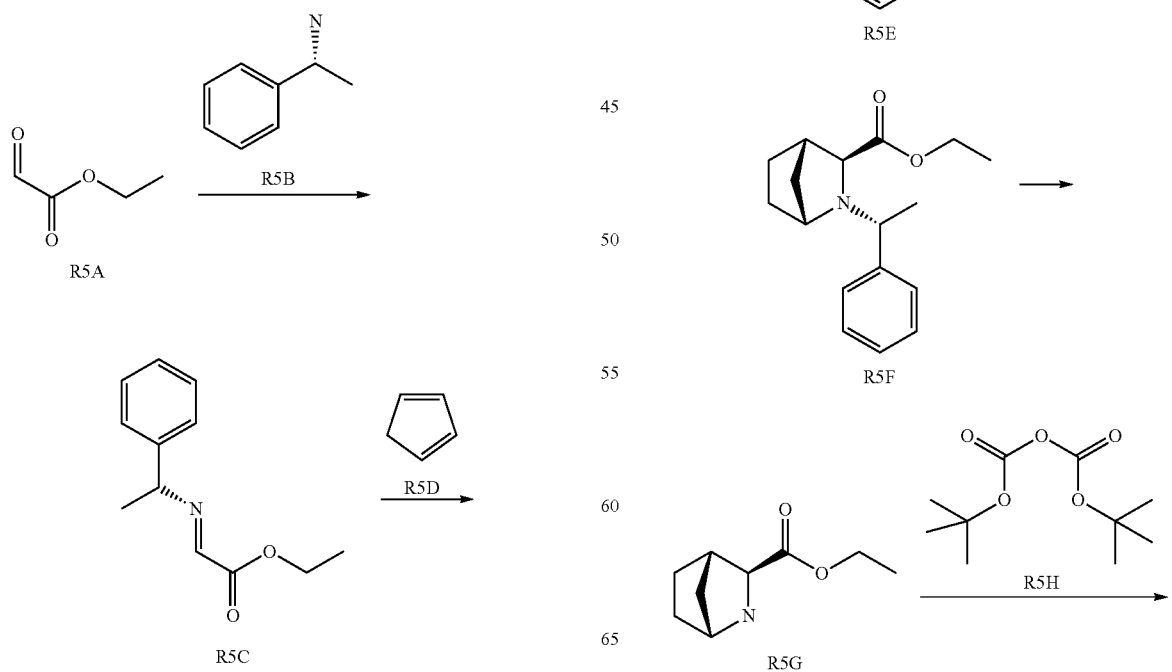
Synthesis of (1S,2S,4R)-3-[(tert.-butoxy)carbonyl]-3-azabicyclo[2.2.1]heptane-2-carboxylate (R5)
The compound is commercially available or can be synthesized in analogy to Tararov et al, Tetrahedron Asymmetry 13 (2002), 25-28.

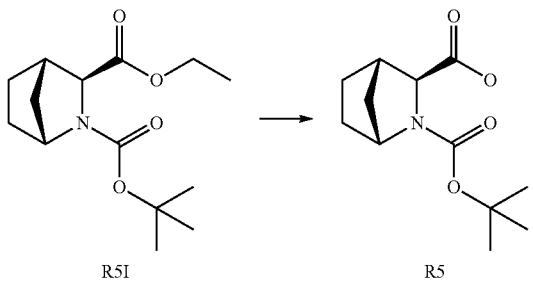

Step 1: Synthesis of R5C

A solution of R5A (44.9 g, 0.44 mol), freshly distilled from a commercially available solution in toluene (at 50 mbar, 55° C.) in diethylether (300 ml) is cooled at −10° C., followed by dropwise addition of R5B (53 g, 440 mmol), keeping the temperature below 0° C. After complete addition, MgSO4*H2O(91 g, 660 mmol) is added, and the resulting mixture stirred at room temperature overnight. The mixture is filtrated, the solution phase concentrated in vacuo and the residue distilled under reduced pressure to yield R5C (47 g, m/z 206 [M+H]+, rt 1.29 min, LC-MS Method V003_003). The product is used without further purification.

Step 2: A solution of R5C (47 g; 229 mmol) and R5D (30 g; 458 mmol) (freshly distilled from dicyclopentadiene) in DMF (150 ml) and 120 μl water is cooled to 0° C., before TFA (18 ml; 234 mmol) is added dropwise. The mixture is stirred overnight at room temperature, then added to a solution of 40 g NaHCO3 in 1200 ml water and extracted with diethylether. The organic layer is separated, washed subsequently with aqueous NaHCO3 and water, dried over MgSO4, and concentrated in vacuo. The residue is worked up by column chromatography on silica (cyclohexane/ethyl acetate=9:1) to yield R5E (Yield 52% m/z 272 [M+H]+, rt 0.42 min, LC-MS Method X001_004)

Step 3: To a solution of R5E (24.8 g, 91 mmol) in ethanol (250 ml), Raney-nickel is added (2.5 g) and reacted at 50 psi under a hydrogen atmosphere at room temperature. The catalyst is filtered of, the solution concentrated in vacuo and the residue worked up by chromatography on silica (cyclohexane/ethyl acetate 9:1). After evaporation of the organic solvent, the obtained product is redissolved in diethylether and triturated with solution of HCl in dioxane, concentrated in vacuo, redissolved in 200 ml ethanol and concentrated in vacuo to yield R5F: (Yield 78% m/z 274 [M+H]+, rt 0.42 min, LC-MS Method X001_004).

Step 4: To a solution of R5F (22 g, 71 mmol) in ethanol (250 ml), 10% Pd/C is added (2.5 g) and reacted at 15 bar under a hydrogen atmosphere at room temperature. The catalyst is filtered of, the solution concentrated in vacuo. The residue is washed with diisopropylether to yield R5G. (Yield 98% m/z 170 [M+H]+, rt 0.48 min, LC-MS Method V001_007).

Step 5: To R5G in a solution of triethylamine (24.6 ml), THF (150 ml) and water (2 ml), R5I (15.9 g; 73 mmol) is added and the resulting mixture stirred for 40 hours at room temperature, then concentrated in vacuo. Ethyl acetate is added to the residue, subsequently extracted with water, 1 N acidic acid and water, before the organic layer is dried over MgSO4 and concentrated in vacuo to yield R5I. (Yield 95% m/z 270 [M+H]+, rt 1.33 min, LC-MS Method V003_003).

Step 6: A mixture of R5I (16.9 g; 63 mmol) in acetone (152 ml), water (50 ml) and lithium hydroxide (3 g, 126 mmol) is stirred overnight at room temperature. Water (100 ml) was added, the volume reduced in vacuo before cooling to 0° C. followed by the addition of 1N aqueous HCl to acidify to a pH of 2-3, immediately followed by extraction with ethyl acetate. The organic layer was washed with water, dried (MgSO4) and concentrated. To the residue, dichloromethane (100 ml) and cyclohexane (100 ml) was added, the volume reduced in vacuo by half and the mixture temperated at 15° C. The precipitate was filtered of, washed with cyclohexane to yield R5 (Yield 66%, m/z 242 [M+H]+).

Synthesis of (2S)-2-amino-3-(4-bromo-2-fluorophenyl)propanamide (R6)

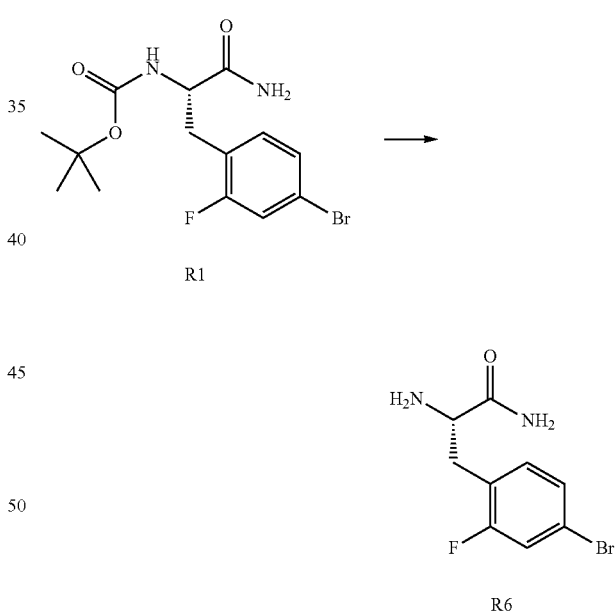

To R1 (10.0 g, 27.7 mmol) in DCM (70 mL) TFA (25 mL, 162.0 mmol) is added and the reaction mixture is stirred for 12 h. Then the reaction mixture is concentrated, the residue is dissolved in DCM and diisopropylether is added. The product precipitates and is filtered by suction and washed with diisopropylether. Yield >95% m/z 261 [M+H]+, rt 0.67 min, LC-MS Method V018_S01.

The following intermediate as shown in Table 38.1 is synthesized in a similar fashion from the appropriate intermediates:

TABLE 38.1

| Intermediate | Structure | m/z [M + H]+ | rt (min) | LC-MS method |
|---|---|---|---|---|
| R6.1 | 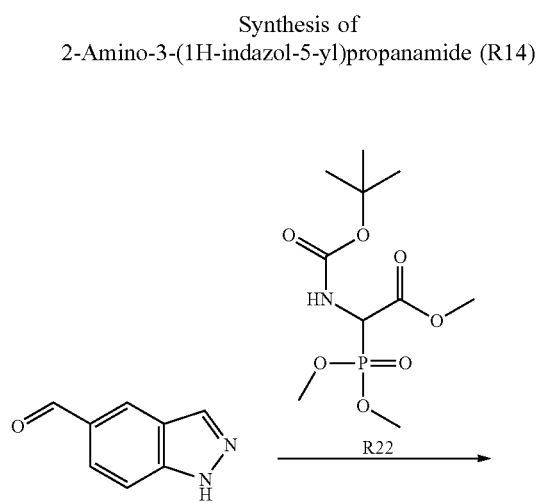 | 217 | 0.08 | Z011_S03 |

For R6.1 the reaction time is 2 h. After the reaction mixture is concentrated, the crude residue is freeze-dried and used without further purification for the next step.

Synthesis of 2-Amino-3-(1H-indazol-5-yl)propanamide (R14)

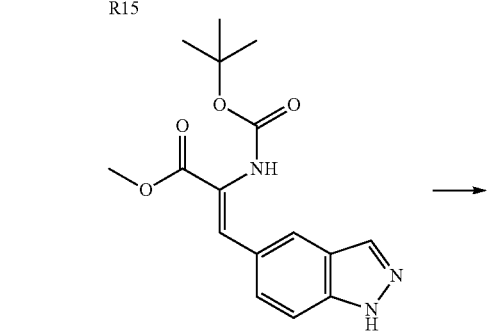

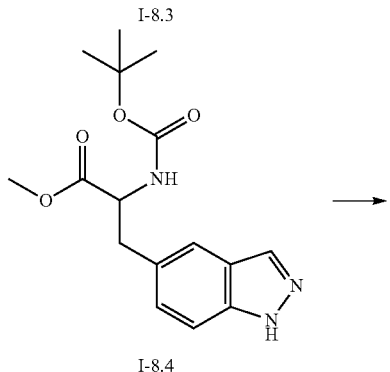

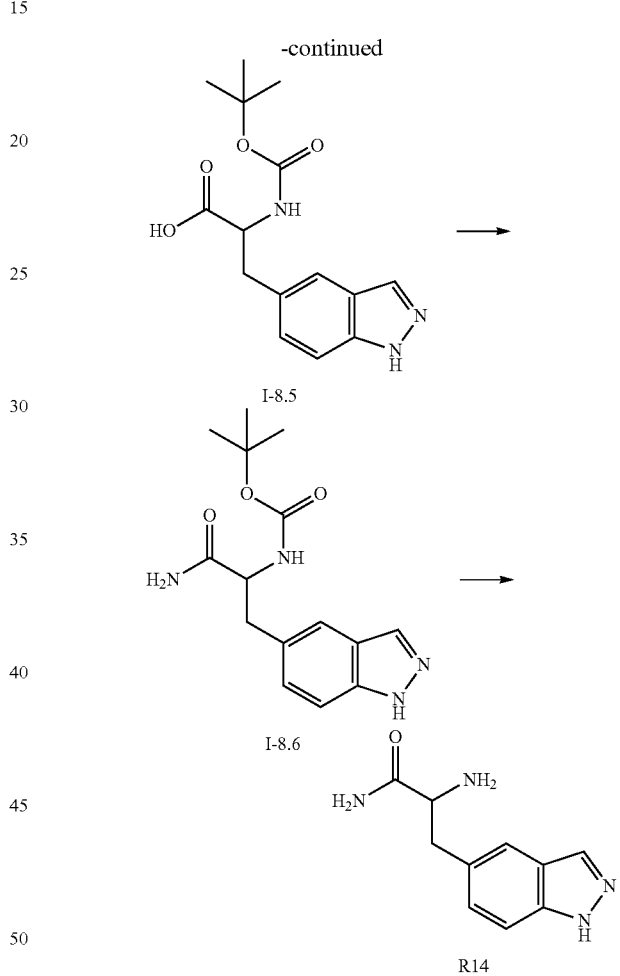

Step 1: Synthesis of Intermediate I-8.3

1,1,3,3,-Tetramethylguanidin (0.44 mL, 3.51 mmol) in THF (5 mL) is cooled down to −70° C. Educt R22 (1.00 g, 3.36 mmol) is dissolved in 5 mL THF and is added. The mixture is stirred for 5 min before R15 (0.49 g, 3.36 mmol)—also dissolved in 5 mL THF—is added dropwise. The cooling is removed and the mixture warms up to room temperature. The reaction mixture is heated to 80° C. for 12 h. Because of remaining educt Tetramethylguanidin and R22 are added twice and the mixture is stirred at 80° C. for additional 4 h. The reaction mixture is concentrated. Ethyl acetate and water are added to the residue. 1 M sulfuric acid is added and the organic layer is separated, is dried over MgSO₄ and concentrated. Yield 87%, m/z 318 [M+H]+, rt 0.97 min, LC-MS Method V011_S01.

The following intermediate as shown in Table 39 is synthesized in a similar fashion from the appropriate intermediate:

TABLE 39

| Intermediate | Structure | m/z [M + H]+ | rt (min) | LC-MS method |
|---|---|---|---|---|
| I-8.3.1 | 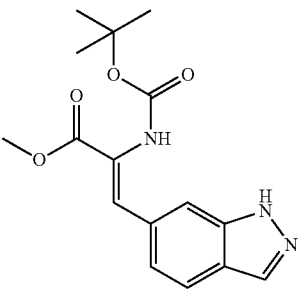 [SMILES: COC(=O)/C(=C/c1ccc2cn[nH]c2c1)NC(=O)OC(C)(C)C] | 318 | 1.00 | V012_S01 |

Step 2: Synthesis of Intermediate I-8.4

To I-8.3 (925 mg, 2.91 mmol) in methanol (30 mL) Pd/C (10%, 130 mg) is added. The reaction mixture is stirred under hydrogen (3 bar) for 16 h. Then the mixture is filtered and the filtrate is concentrated. The residue is triturated with diethyl ether and the product is filtered by suction. Yield 88%, m/z 320 [M+H]+, rt 0.99 min, LC-MS Method V011_S01.

The following intermediate as shown in Table 40 is synthesized in a similar fashion from the appropriate intermediate:

TABLE 40

| Intermediate | Educt | Structure of Intermediate | m/z [M + H]+ | rt (min) | LC-MS method |
|---|---|---|---|---|---|
| I-8.4.1 | I-8.3.1 | 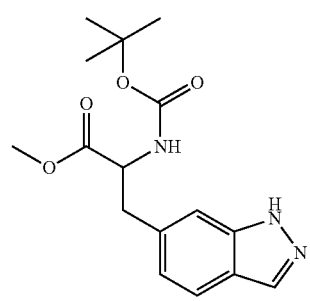 [SMILES: COC(=O)C(Cc1ccc2cn[nH]c2c1)NC(=O)OC(C)(C)C] | 320 | 0.96 | V011_S01 |

Step 3: Synthesis of Intermediate I-8.5

To I-8.4 (820 mg, 2.57 mmol) in methanol (15 mL) sodium hydroxide solution (2.5 mL, 1 mol/L) is added. The reaction mixture is heated to 40° C. for 2 h. The mixture is concentrated partially and 1 M HCl is added to neutralization. The precipitation is filtered with suction, is dissolved in methanol and concentrated quickly. Yield 65%, m/z 306 [M+H]+, rt 0.57 min, LC-MS Method V011_S01.

The following intermediate as shown in Table 41 is synthesized in a similar fashion from the appropriate intermediate:

TABLE 41

| Intermediate | educt | Structure | m/z [M + H]+ | rt (min) | LC-MS method |
|---|---|---|---|---|---|
| I-8.5.1 | I-8.4.1 | 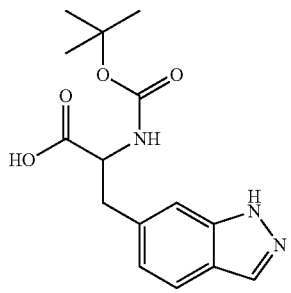 [SMILES: CC(C)(C)OC(=O)NC(Cc1ccc2cn[nH]c2c1)C(=O)O] | 306 | 0.55 | V011_S01 |

Step 4: Synthesis of Intermediate I-8.6

To I-8.5 (400 mg, 1.31 mmol) in DMF (5 mL) diisopropylethylamine (502 µL, 2.88 mmol) and TBTU (421 mg, 1.31 mmol) are added and the reaction mixture is stirred for 15 min. Then aq. 30% ammonia solution (545 µL, 9.61 mmol) is added and the mixture is stirred for additional 12 h. Water is added to the reaction mixture and extracted with ethyl acetate. The organic layer is washed with brine and saturated NaHCO$_3$ solution, is dried over MgSO$_4$ and concentrated. Yield 55%, m/z 305 [M+H]+, rt 0.75 min, LC-MS Method V011_S01.

The following intermediate as shown in Table 42 is synthesized in a similar fashion from the appropriate intermediate:

For I-8.6.2 N-methylmorpholine is used instead of diisopropylethylamine (in analogy to synthesis of R1)

Step 5: Synthesis of R14

To I-8.6 (130 mg, 0.43 mmol) in DCM (3 mL) TFA (358 µL, 0.47 mmol) is added and the reaction mixture is heated to 30° C. for 12 h. Then the reaction mixture is concentrated. Yield >95%.

The following intermediate as shown in Table 43 is synthesized in a similar fashion from the appropriate intermediate:

TABLE 42

| Intermediate | Educt | Structure of Intermediate | m/z [M + H]+ | rt (min) | LC-MS method |
|---|---|---|---|---|---|
| I-8.6.1 | I-8.5.1 | 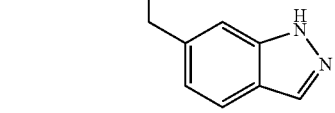 | 327 [M + Na]+ | 0.77 | V011_S01 |
| I-8.6.2 | commercially available | 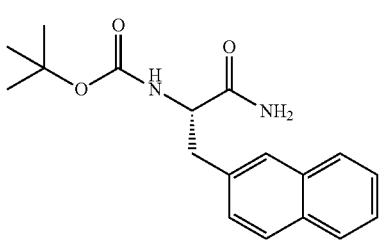 [SMILES: CC(C)(C)OC(=O)N[C@@H](Cc1ccc2ccccc2c1)C(N)=O] | 315 | n.d. | n.d. |

TABLE 43

| Intermediate | Educt | Structure of Intermediate | m/z [M + H]+ | rt (min) | LC-MS method |
|---|---|---|---|---|---|
| R14.1 | I-8.6.1 | (structure: indazole with CH2-CH(NH2)-C(O)NH2) | 227 [M + Na]+ | 0.53 | V011_S01 |
| R14.2 | I-8.6.2 | (structure: naphthalene with CH2-CH(NH2)-C(O)NH2) | 214 | 0.31 | X012_S01 |

Synthesis of 5-bromo-2-methyl-isoindoline (R4)

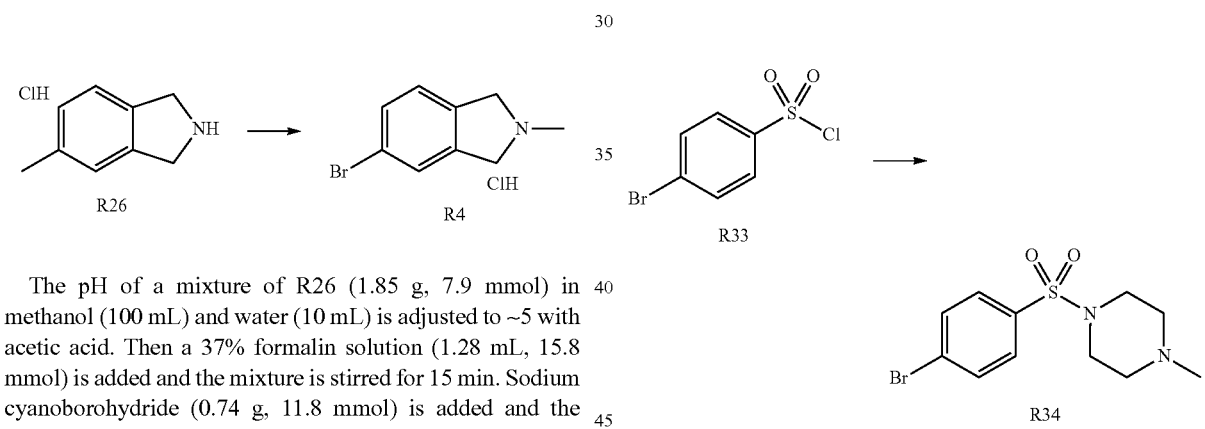

The pH of a mixture of R26 (1.85 g, 7.9 mmol) in methanol (100 mL) and water (10 mL) is adjusted to ~5 with acetic acid. Then a 37% formalin solution (1.28 mL, 15.8 mmol) is added and the mixture is stirred for 15 min. Sodium cyanoborohydride (0.74 g, 11.8 mmol) is added and the reaction mixture is stirred for additional 12 h. The mixture is concentrated and ethyl acetate and aq. 1 M NaOH solution are added to the residue. The organic layer is washed with NaCl solution, dried over MgSO$_4$ and concentrated. The residue is dissolved in diethyl ether and ethereal HCl is added dropwise. The resulting precipitate is filtered off. Yield 62% m/z 212/214 [M+H]+, rt 0.65 min, LC-MS Method V012_S01.

Synthesis of 1-(4-bromo-benzenesulfonyl)-4-methyl-piperazine (R34)

R33 (800 mg, 3.1 mmol) is dissolved in DCM, N-methyl-piperazine (313 mg, 3.1 mmol) is added and stirred for 12 h. After addition of 2 mL 1N HCl under stirring the phases are separated. The organic phase is dried over MgSO$_4$ and after filtration evaporated in vacuo. Yield: 84% m/z 319 (M+H)+.

The following intermediates as shown in Table 44 are synthesized in a similar fashion from the appropriate intermediate:

TABLE 44

| Intermediate | Educt | Structure of Intermediate | m/z [M + H]+ | rt (min) | LC-MS method |
|---|---|---|---|---|---|
| R34.1 | R33 | (structure: 4-bromophenylsulfonyl-piperidine) | 304 | n.d. | n.d. |

TABLE 44-continued

| Intermediate | Educt | Structure of Intermediate | m/z [M + H]+ | rt (min) | LC-MS method |
|---|---|---|---|---|---|
| R34.2 | R33 | ![structure] | 306 | n.d. | n.d. |
| R34.3 | R33 | ![structure] | 340 | 0.64 | X012_S01 |
| R34.4 | | ![structure] | 337/339 | 0.36 | X012_S01 |
| R34.5 | R33 | ![structure] | 333/335 | 0.36 | X012_S01 |

For R34.4 and R34.5 additional 2 eq. of DIPEA are added to the reaction mixture.

Synthesis of Reagent R37

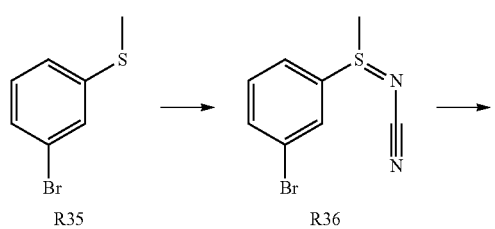

Step 1: Synthesis of R36

R35 (200 µL, 1.448 mmol) is dissolved in 10 mL methanol. Cyanamide (79.112 mg, 1.882 mmol), potassium tert-butoxide (194.9 mg, 1.737 mmol) and N-bromosuccinimide (386.282 mg, 2.171 mmol) are added and stirred for 1 h at room temperature. The product is purified by preparative HPLC (Waters 30×100 mm, 10 µm, sunfire RP18, acetonitrile/water/TFA). The fractions containing the product are combined and lyophilized. Yield 87%, m/z 244 [M+H]+, rt 0.62 min, LC-MS Method Z018_S04.

In analogy the following reagent as shown in Table 45 is prepared:

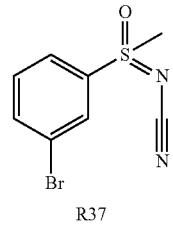

R37

TABLE 45

| Intermediate | Educt | Structure | m/z [M + H]+ | rt (min) | LC-MS method |
|---|---|---|---|---|---|
| R36.1 | commercially available | ![structure] | 243 | 0.64 | Z018_S04 |

Step 2: Synthesis of R37

R36 (335 mg, 1.378 mmol) is dissolved in 3 mL ethanol. Potassium carbonate (571.315 mg, 4.134 mmol) and 3-chloroperbenzoic acid (356.696 mg, 2.067 mmol) are added at 0° C., and the mixture is stirred for 2 h at room temperature. The solvent is evaporated in vacuo and the residue is dissolved in DMF. The product is purified by preparative HPLC (Waters 30×100 mm, 10 μm, sunfire RP18, acetonitrile/water/TFA). The fractions containing the product are combined and lyophilized Yield 71%, m/z 260 [M+H]+, rt 0.68 min, LC-MS Method Z018_S04.

In analogy the following reagent as shown in Table 46 is prepared:

TABLE 46

| Intermediate | Educt | Structure of Intermediate | m/z [M + H]+ | rt (min) | LC-MS method |
|---|---|---|---|---|---|
| R37.1 | R36.1 | 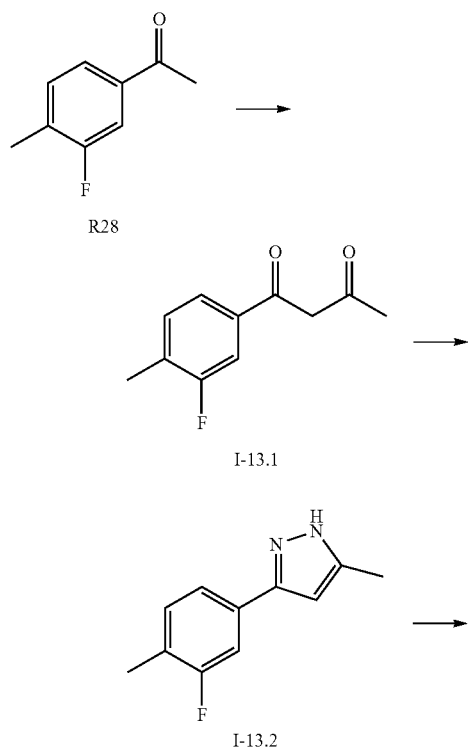 | 259 | 0.67 | Z011_S03 |

Synthesis of 1-[13-[4-(bromomethyl)-3-fluoro-phenyl]-5-methyl-pyrazol-1-yl]ethanone (R13)

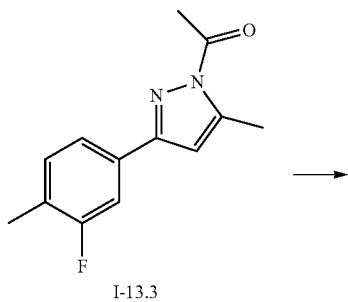

I-13.3

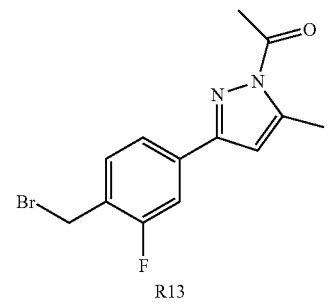

R13

Step 1: Synthesis of Intermediate I-13.1

To potassium tert.-butylate (7.4 g, 65.6 mmol) in anhydrous THF (300 mL) is added crown ether 18-6 (12.2 g, 46.0 mmol). The mixture is cooled down to 0° C. and R28 (5.0 g, 32.9 mmol) is added and stirred for 15 min at room temperature. Then acetic acid methyl ester (5.2 mL 65.7 mmol) is added and the reaction mixture is stirred for additional 1 h. The mixture is concentrated and the residue is purified via flash chromatography (cyclohexane/ethyl acetate=95:5). Yield 79%, m/z 195 [M+H]+, rt 0.66 min, LC-MS Method V011_S01.

Step 2: Synthesis of Intermediate I-13.2

To I-13.1 (5.1 g, 26.1 mmol) 1 M hydrazine solution in THF (78.2 mL, 78.2 mmol) is added and the reaction mixture is heated to 80° C. for 12 h. The reaction mixture is concentrated and the residue is purified via flash chromatography (cyclohexane/ethyl acetate=70:30). Yield 90%, m/z 191 [M+H]+, rt 1.01 min, LC-MS Method V011_S01.

Step 3: Synthesis of Intermediate I-13.3

I-13.2 (1.00 g, 5.3 mmol) and acetic acid anhydride (5.00 mL, 53.0 mmol) are stirred for 12 h. Water and methanol are added to the reaction mixture, the precipitate is filtered by suction and dried in vacuo. Yield 87%, m/z 233 [M+H]+, rt 1.31 min, LC-MS Method V011_S01.

Step 4: Synthesis of R13

To I-13.3 (0.95 g, 4.1 mmol) in DCM (25 mL) is added N-bromo succinimide (0.80 g, 4.5 mmol) and 2,2'-azobis(isobutyronitrile) (50 mg). The reaction mixture is refluxed for 12 h under radiation with an Hg lamp. The mixture is concentrated and the residue is purified via flash chromatography (cyclohexane/DCM=75:25). Yield 39%, m/z 311 [M+H]+, rt 1.43 min, LC-MS Method V018_S01.

Synthesis of 6-bromo-2-methyl-3,4-dihydroisoquinolin-1-one (R32)

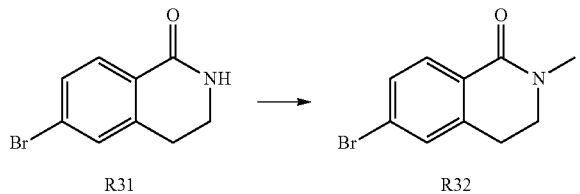

R31 (500 mg, 2.2 mmol) in DMF (3 mL) is cooled down to 0° C. Under argon atmosphere NaH (60%, 121 mg, 3.0 mmol) is added and stirred for 20 min. Then methyl iodide (0.275 mL, 4.4 mmol) is added and the mixture is stirred for additional 1 h at 0° C. Ice water is added to the reaction mixture and the precipitate is filtered by suction and dried at 50° C. in the vacuum oven for 12 h. Yield 73%, m/z 240/242 [M+H]+, rt 0.89 min, LC-MS Method V012_S01.

Synthesis of tert-butyl 2-(bromomethyl)-9H-carbazole-9-carboxylate (R13.1 for Synthesis of I-7.1.3)

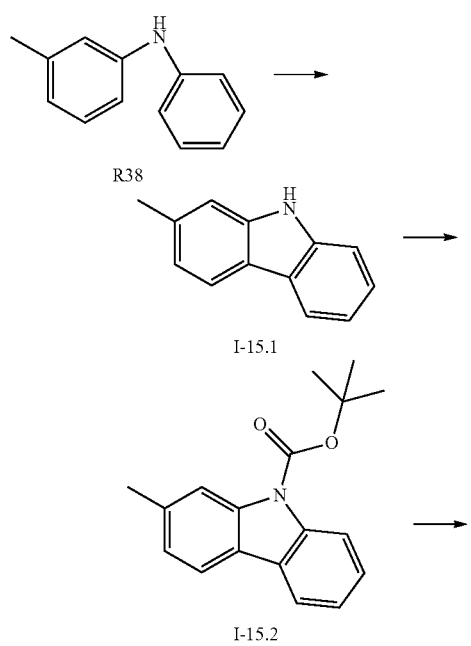

Step 1: Synthesis of Intermediate I-15.1

3-Methyl-diphenylamine R38 (1.0 g, 5.5 mmol), K$_2$CO$_3$ (75 mg, 0.55 mmol) and palladium acetate (37 mg, 0.16 mmol) in 2,2-dimethyl-1-propanol (5 mL) is stirred at 110° C. for 14 h. Water is added to the reaction mixture and extracted with dichloromethane. The combined organic layer is concentrated in vacuo, residue triturated with methanol/dichloromethane and dried in vacuo and directly taken to the next step. Yield 29%, m/z 182 [M+H]+, rt 0.67 min, LC-MS Method X012_S01.

Step 2: Synthesis of Intermediate I-15.2

I-15.1 (285 mg, 1.6 mmol), di-tert.-butyl dicarbonate (412 mg, 1.9 mmol) and DMAP (50 mg, 0.41 mmol) in dichloromethane (10 ml) are stirred at room temperature for 16 hours. The reaction mixture extracted with water, the organic layer is separated and concentrated in vacuo and directly taken to the next step. Yield 86%, m/z 282 [M+H]+, rt 0.89 min, LC-MS Method X012_S01.

Step 3: Synthesis of Intermediate R13.1

I-15.2 (380 mg, 1.4 mmol), N-bromosuccinimide (289 mg, 1.6 mmol), AIBN (20 mg, 0.12 mmol) in tetrachloromethane (5 mL) is heated to reflux over 16 h. Water and dichloromethane are added to the reaction mixture, the organic layer separated and concentrated. The residue is triturated with methanol and used directly in the next step. Yield 41%, m/z 360 [M+H]+, rt 0.67 min, LC-MS Method V011_S01.

Synthesis of tert-butyl 3-(chloromethyl)-9H-carbazole-9-carboxylate (R13.2 for Synthesis of I-7.1.6)

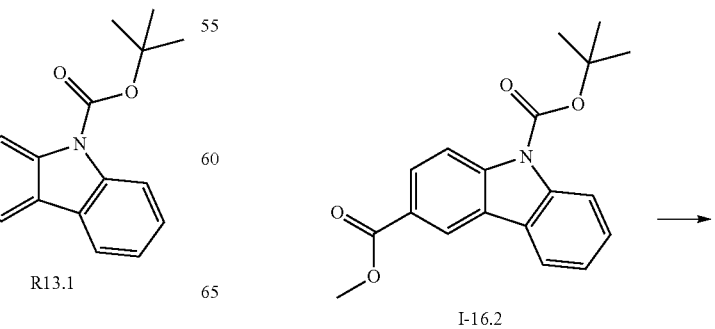

319
-continued

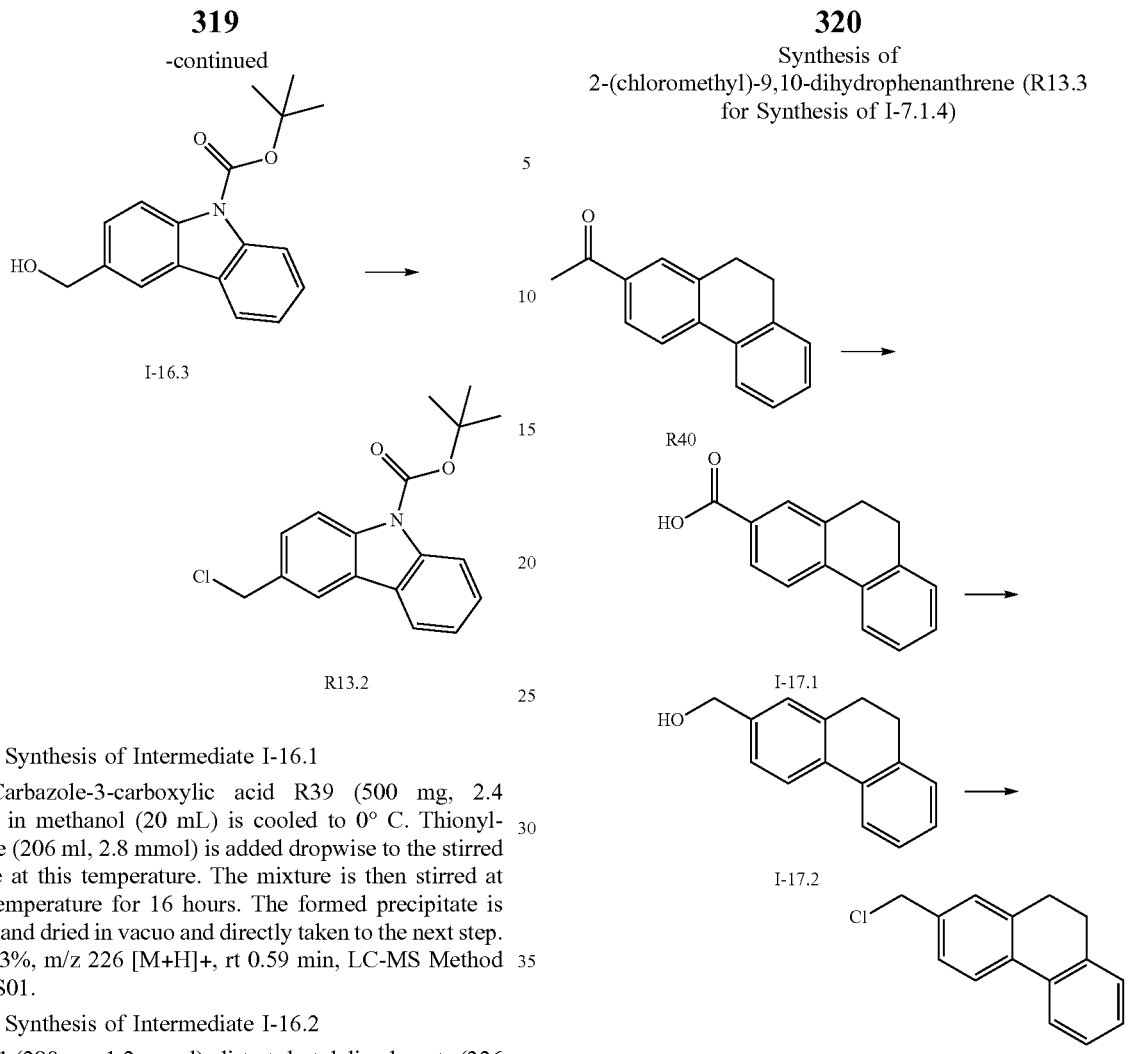

Step 1: Synthesis of Intermediate I-16.1

9H-Carbazole-3-carboxylic acid R39 (500 mg, 2.4 mmol), in methanol (20 mL) is cooled to 0° C. Thionyl-chloride (206 ml, 2.8 mmol) is added dropwise to the stirred mixture at this temperature. The mixture is then stirred at room temperature for 16 hours. The formed precipitate is filtered and dried in vacuo and directly taken to the next step. Yield 53%, m/z 226 [M+H]+, rt 0.59 min, LC-MS Method X012_S01.

Step 2: Synthesis of Intermediate I-16.2

I-16.1 (280 mg, 1.2 mmol), di-tert.-butyl dicarbonate (326 mg, 1.5 mmol) and DMAP (50 mg, 0.41 mmol) in dichloromethane (10 ml) are stirred at room temperature for 16 hours. The reaction mixture extracted with water, the organic layer is separated and concentrated in vacuo and directly taken to the next step. Yield 99%, m/z 326 [M+H]+, rt 0.84 min, LC-MS Method X012_S01.

Step 3: Synthesis of Intermediate I-16.3

I-16.2 (400 mg, 1.2 mmol) and boronhydride-tetrahydrofuran adduct (1,2 ml 1M in THF, 1.2 mmol) are dissolved in THF (5 ml). LiBH4 is repeatedly added in small portions at 50° C., until HPLC shows completion of reaction. Water and dichloromethane are added to the reaction mixture, the organic layer separated, concentrated and purified via HPLC. Yield 40%, m/z 280 [M−H2O+H]+, rt 0.70 min, LC-MS Method X012_S01.

Step 4: Synthesis of Intermediate R13.2

I-16.3 (145 mg, 0.5 mmol) and DIPEA (171 µl, 1.0 mmol) are dissolved in dichloromethane (10 ml) and cooled to −10° C. Methanesulfonylchloride (46 µl, 0.6 mmol) in dichloromethane (1 ml) is added dropwise. After complete addition, the mixture is stirred for 16 h at room temperature. Water is added to the reaction mixture, the organic layer separated, concentrated in vacuo to yield R13.2, which is directly taken to the next step. Yield 73%, rt 0.87 min, LC-MS Method X012_S01.

320
Synthesis of 2-(chloromethyl)-9,10-dihydrophenanthrene (R13.3 for Synthesis of I-7.1.4)

Step 1: Synthesis of Intermediate I-17.1

2-Acetyl-9,10-dihydro-phenanthrene R40 (1.0 g, 4.5 mmol) is added to solution of bromine (924.7 µl, 18 mmol) and KOH (3.3 g, 58.5 mmol) in water (20 ml) at 0° C. After addition is completed, the reaction mixture is heated to 55° C. for 16 hours. The mixture is cooled to r.t., extracted with dichloromethane. The aqueous phase is separated, acidified with 1 M HCl aq and the precipitating product is filtered off and dried in vacuo at 50° C. Yield 92%, m/z 225 [M+H]+, rt 0.62 min, LC-MS Method X012_S01.

Step 2: Synthesis of Intermediate I-17.2

I-17.1 (930 mg, 4.2 mmol) is dissolved in THF (10 ml), CDI (874 mg, 5.4 mmol) is added in small portions and the mixture is stirred for 1 h at 50° C. The mixture is added slowly to sodium borohydride (470 mg, 12.4 mmol) in ice water, so that the temperature remains below 10° C. The mixture is stirred for 16 hours at r.t. and extracted with dichloromethane/water. The organic layer is separated and concentrated in vacuo, the remaining crude product purified via HPLC. Yield 53%, m/z 210 [M]+, 193 [M−H2O]+, rt 0.61 min, LC-MS Method X012_S01.

Step 3: Synthesis of Intermediate R13.3

I-17.2 (460 mg, 2.2 mmol), DIPEA (766 µl, 4.4 mmol) are dissolved in dichloromethane (10 ml) and cooled to −10° C. Methanesulfonylchloride (207 µl, 2.6 mmol) in dichloromethane (1 ml) is added dropwise. After complete addition, the mixture is stirred for 16 h at room temperature. Water is added to the reaction mixture, the organic layer separated, concentrated in vacuo and the remaining crude product purified via HPLC. Yield 67%, m/z 228 [M]+, rt 0.79 min, LC-MS Method X012_S01.

Synthesis of 6-Aza-tricyclo[3.2.1.0*2,4*]octane-6,7-dicarboxylic acid 6-tert-butylester (R6.2)

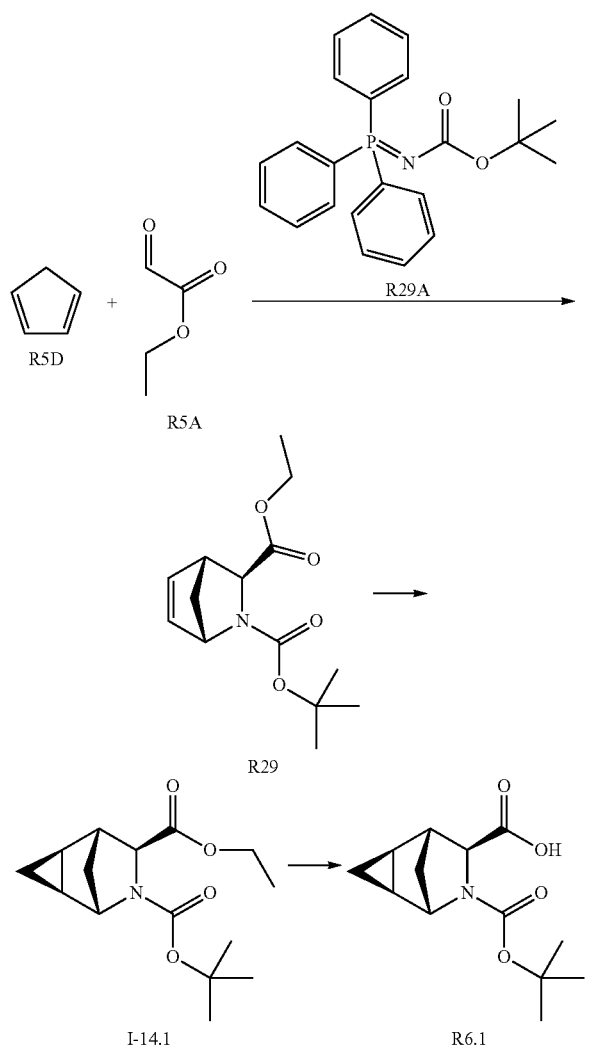

TABLE 46.1

| Intermediate | Structure of Intermediate |
| --- | --- |
| R29.1 | |
| R29.2 | |

Step 2: Synthesis of Intermediate I-14.1

To R29.2 (5.00 g, 18.7 mmol) in diethylether (100 mL) is added palladium(II) acetate (0.42 g, 1.87 mmol). Under stirring diazomethane solution in diethylether (62 mmol) is added. The reaction mixture is stirred for 12 h. To destroy remaining diazomethane, silica gel and 3 mL acetic acid are added. Then the mixture is stirred for additional 1 h and filtrated. The solution is concentrated and extracted with DCM, water and brine. Yield 98%, m/z 226 [M+H-tButyl]+, rt 0.64 min, LC-MS Method X012_S01.

Step 3: Synthesis of R6.2

To I-14.1 (5.40 g, 19.2 mmol) in dioxane (60 mL) is added aq. 4 M NaOH (20 mL, 80 mmol). The reaction mixture is heated to 50° C. for 3 h. The mixture is extracted two times with DCM, then the water layer neutralized with 2 M HCl and extracted three times with DCM. The combined organic layers are dried over MgSO$_4$ and concentrated. The residue is dissolved in diethylether and evaporated, the product crystallizes. Yield 88%, m/z 198 [M+H-tButyl]+, rt 0.48 min, LC-MS Method X012_S01.

Synthesis of 1-Methyl-6-(4,4,5,5-tetramethyl-[1,3,2]dioxaborolan-2-yl)-1,3-dihydro-indol-2-one (R7)

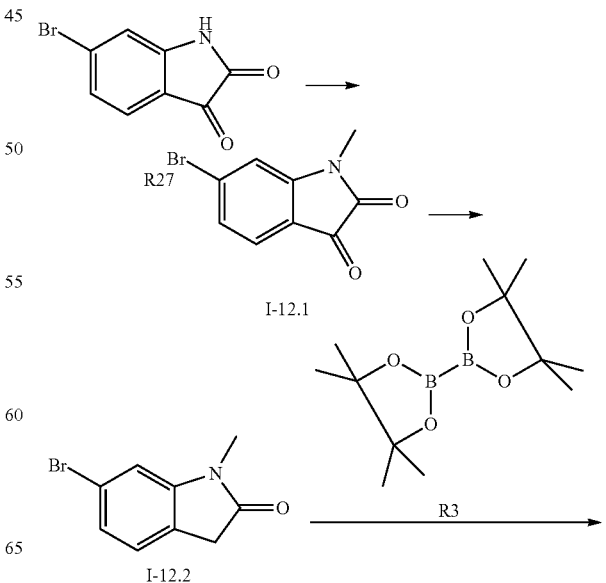

Step 1: Synthesis of Intermediate R29.2

Dicyclopenta-1,3-diene is cracked and distilled at 42° C. and 1013 mbar to give cyclopenta-1,3-diene.

Ethyl 2-oxoacetate is also freshly distilled from a commercially available solution in toluene.

Assumed concentration is 50%.

To N-boc-imino-(triphenyl)phosphorane (11.32 g, 30.00 mmol) in toluene (100 mL) is added ethyl 2-oxoacetate (15 mL, 60.00 mmol) and cyclopenta-1,3-diene (5 mL, 60.00 mmol) and stirred overnight at r.t. The reaction mixture is concentrated and the crude residue is purified over silica gel (cyclohexane/ethyl acetate 7:3). Yield 16%

R29.2 can be obtained through preparative chiral chromatography from this mixture of R29.1 and R29.2 (table 46.1) using method Chiral SFC G.

-continued

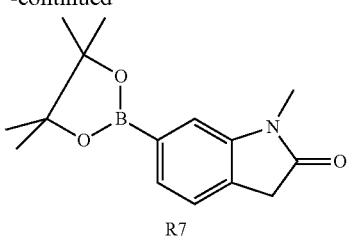

Step 1: Synthesis of Intermediate I-12.1

To R27 (25.0 g, 111 mmol) in acetonitrile (750 mL) is added Met (15 mL, 241 mmol) and $K_2CO_3$ (60.0 g, 434 mmol) and the reaction mixture is stirred at 60° C. for 2 h. The reaction mixture is filtered and concentrated. Water and ethyl acetate are added to the residue. The organic layer is extracted twice with water, dried over $MgSO_4$ and concentrated. Yield 56%, m/z 240/242 [M+H]+, rt 0.48 min, LC-MS Method X001_004.

The following intermediates as shown in Table 47 are synthesized in a similar fashion from the appropriate intermediates:

TABLE 47

| Intermediate | Structure | m/z [M + H]+ | rt (min) | LC-MS method |
|---|---|---|---|---|
| I-12.1.1 | 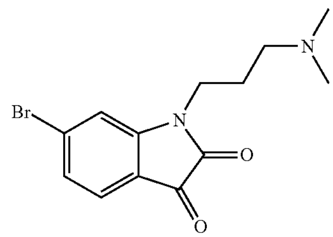 [SMILES: CN(C)CCCN1C(=O)C(=O)c2ccc(Br)cc21] | 311/313 | 0.362 | Z020_S01 |
| I-12.1.2 | 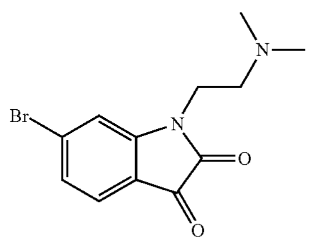 [SMILES: CN(C)CCN1C(=O)C(=O)c2ccc(Br)cc21] | n.d. | n.d. | n.d. |
| I-12.1.3 | 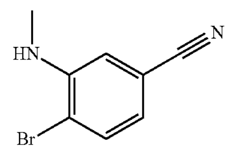 | 211/213 | 0.55 | X012_S01 |
| I-12.1.4 | 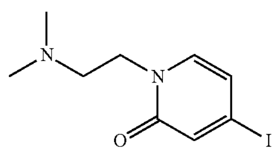 | n.d. | n.d. | n.d. |
| I-12.1.5 | 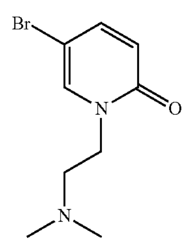 | 245 | 0.21 | X012_S01 |
| I-12.1.6 | 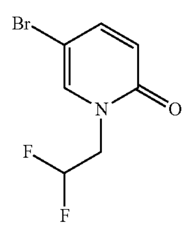 | n.d. | n.d. | n.d. |

TABLE 47-continued

| Intermediate | Structure | m/z [M + H]+ | rt (min) | LC-MS method |
|---|---|---|---|---|
| I-12.1.7 | 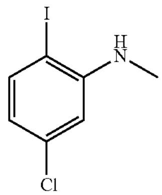 | 268 | 0.71 | X012_S01 |
| I-12.1.8 | 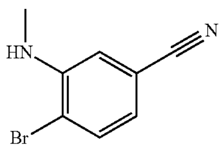 | 211/213 | 0.55 | X012_S01 |

For I-12.1.1, I-12.1.2, I-12.1.3, I-12.1.5, I-12.1.7 and I-12.1.8 sodium hydride and DMF is used instead of potassium carbonate and ACN.

For I-12.1.3, I-12.1.7 and I-12.1.8 the reaction temperature is r.t.

For I-12.1.4 DMF is used.

For I-12.1.6 the reaction conditions differ: 1,1-Difluoro-2-trifluoromethanesulfonyl-ethane is used as alkylation reagent in triethylamine as solvent at r.t.

Step 2: Synthesis of Intermediate I-12.2

I-12.1 (15.0 g, 63 mmol) and hydrazine hydrate (30 mL, 618 mmol) are heated to 125° C. for 72 h. To the cool reaction mixture DCM is added and extracted with water and 1 M HCl. The organic layer is dried over $MgSO_4$ and concentrated. The crystallized residue is dissolved in DCM, methanol is added and the DCM is removed in vacuo. The crystallized product is filtered by suction and washed with cold methanol. Yield 63%, m/z 226/228 [M+H]+, rt 1.16 min, LC-MS Method V001_003.

The following intermediates as shown in Table 48 are synthesized in a similar fashion from the appropriate intermediates:

TABLE 48

| Intermediate | Structure | m/z [M + H]+ | rt (min) | LC-MS method |
|---|---|---|---|---|
| I-12.2.1 | 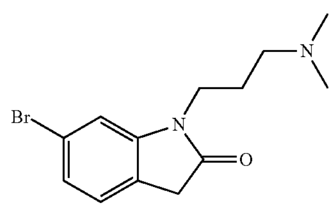 [SMILES: CN(C)CCCN1C(=O)Cc2ccc(Br)cc21] | n.d. | n.d. | n.d. |
| I-12.2.2 | 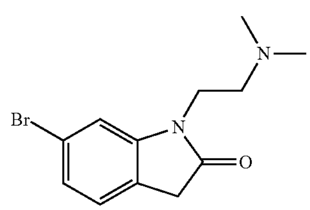 [SMILES: CN(C)CCN1C(=O)Cc2ccc(Br)cc21] | 283/285 | 0.832 | n.d. |
| I-12.2.3 | 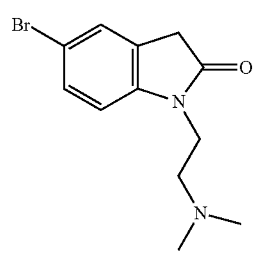 [SMILES: CN(C)CCN1C(=O)Cc2cc(Br)ccc21] | n.d. | n.d. | n.d. |

Step 3: Synthesis of Intermediate R7

To I-12.2 (32.0 g, 142 mmol) in anhydrous dioxane (400 mL) is added R3 (54.4 g, 241 mmol) and potassium acetate (41.6 g, 424 mmol). The mixture is purged with Argon, [1,1'-Bis(diphenylphosphino)ferrocene]dichloropalladium (II) as a complex with dichloromethane (11.2 g, 14 mmol) is added and the mixture is heated to 90° C. for 2 h. The reaction mixture is diluted with ethyl acetate and water, the organic layer is washed with water, dried over MgSO$_4$ and concentrated. The residue is purified via flash chromatography (cyclohexane/EA=70:30). Yield 72%, m/z 274 [M+H]+, rt 0.67 min, LC-MS Method V011_S01.

The following intermediates as shown in Table 49 are synthesized in a similar fashion from the appropriate intermediates:

TABLE 49

| Intermediate | Structure | m/z [M + H]+ | rt (min) | LC-MS method |
|---|---|---|---|---|
| R7.1 | 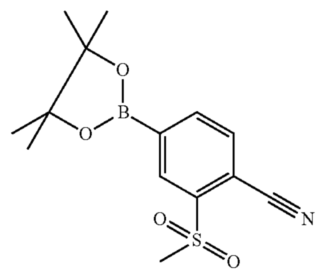 | 325 [M + NH$_4$]+ | 0.30 | X018_S01 |
| R7.2 | 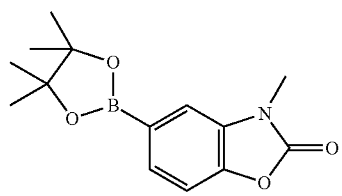 | 276 [M + H]+ | 0.94 | X002_002 |
| R7.3 | 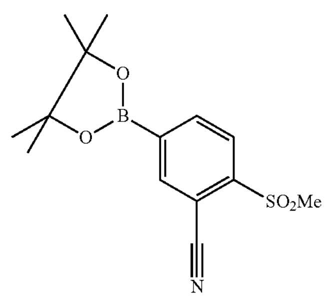 | n.d. | n.d. | n.d. |
| R7.4 | 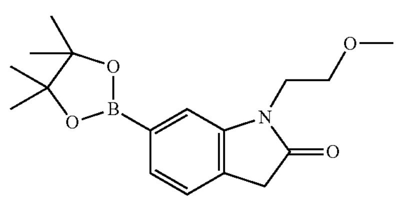 | 318 | 0.92 | Z018_S04 |
| R7.5 | 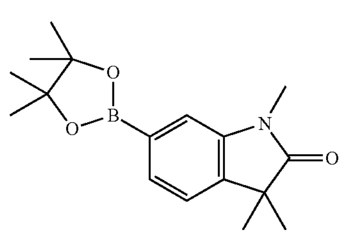 | 302 | n.d. | n.d. |

TABLE 49-continued

| Intermediate | Structure | m/z [M + H]+ | rt (min) | LC-MS method |
|---|---|---|---|---|
| R7.6 | 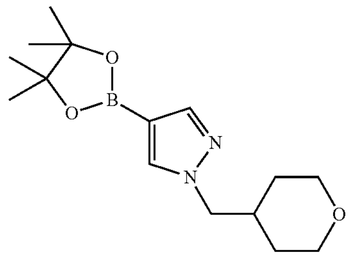 | 294 | 0.85 | Z018_S04 |
| R7.7 | 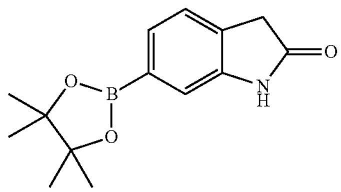 | 260 | 0.65 | X001_004 |
| R7.8 | 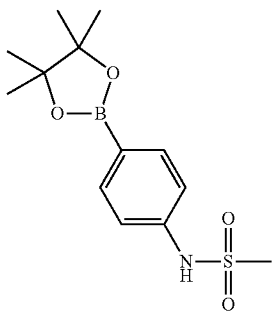 | n.d. | n.d. | n.d. |
| R7.9 | 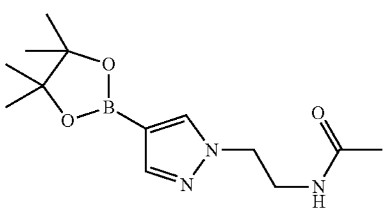 | 280 | 0.63 | X001_002 |

Synthesis of Boronic Ester R7.6

2 g (10.3 mmol) 4-(4,4,5,5-Tetramethyl-1,3,2-dioxaborolan-2-yl)-1H-pyrazole and 2.9 mL (20.6 mmol) 4-(iodomethyl)-tetrahydro-2H-pyran are dissolved in 200 mL DMF and 4.274 g (30.9 mmol) $K_2CO_3$ are added. The mixture is shaken at 80° C. for 5 h. After cooling to r.t. the mixture is filtered, the filtrate is concentrated in vacuo to approximately 60 mL. The product is separated using HPLC-MS (Gilson, mass flow 120 mL/min, 10 μm, 200 g Sunfire RP18, ACN/water/TFA). The product fractions are combined and freeze-dried to yield 115 mg product (3.8%) R7.6.

Synthesis of Boronic Ester R7.8

4-(4,4,5,5-tetramethyl-1,3,2-dioxaborolan-2-yl)aniline (1 g, 4.56 mmol) and pyridine (10 mL) are cooled down with an ice bath. Methanesulfonyl chloride (0.933 mL, 12.01 mmol) is dissolved in dichlormethane (10 mL) and added slowly dropwise. The reaction mixture is allowed to come to room temperature and concentrated. The residue is diluted with dichlormethane and water. The organic layer is separated, dried and concentrated. The crude product is used without further purification. Yield: >95%

Synthesis of Boronic Ester R7.9

Under nitrogen atmosphere to sodium hydride (50%) (0.218 g, 4.54 mmol) and DMF (3 mL) is added 4-(4,4,5, 5-Tetramethyl-1,3,2-dioxaborolan-2-yl)-1H-pyrazole (0.5 g, 2.5 mmol) and stirred for 30 min at r.t. N-(2-chloroethyl) acetamide (0.775 mL, 7.52 mmol) is added and stirred at 90° C. overnight. Due to no reaction N-(2-chloroethyl)acetamide (0.26 mL) and copper(I)iodide (25 mg, 0.13 mmol) are added and stirred at 90° C. for 24 h. The reaction mixture is diluted with methanol, filtered through a thiol cartridge and concentrated. The crude product is used without further purification. Yield: 100%

All other boronic acid derivatives R9 and R16 and alkynes R10 are purchased or prepared by literature known procedures.

331
Synthesis of tert-butyl(1S,2S,4R)-2-(1-methoxycarbonylvinylcarbamoyl)-3-azabicyclo[2.2.1]heptane-3-carboxylate R41

332
Synthesis of methyl(E)-2-(benzyloxycarbonylamino)-3-[4-(1,4-dimethyl-4-piperidyl)-2-fluorophenyl]prop-2-enoate (R42)

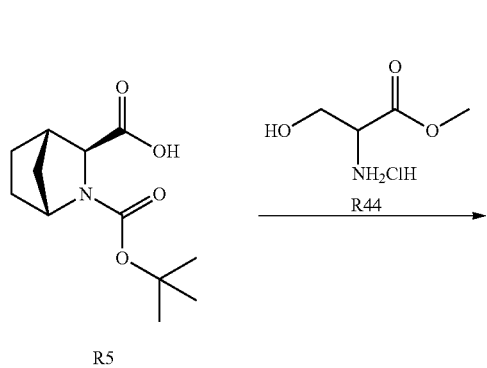

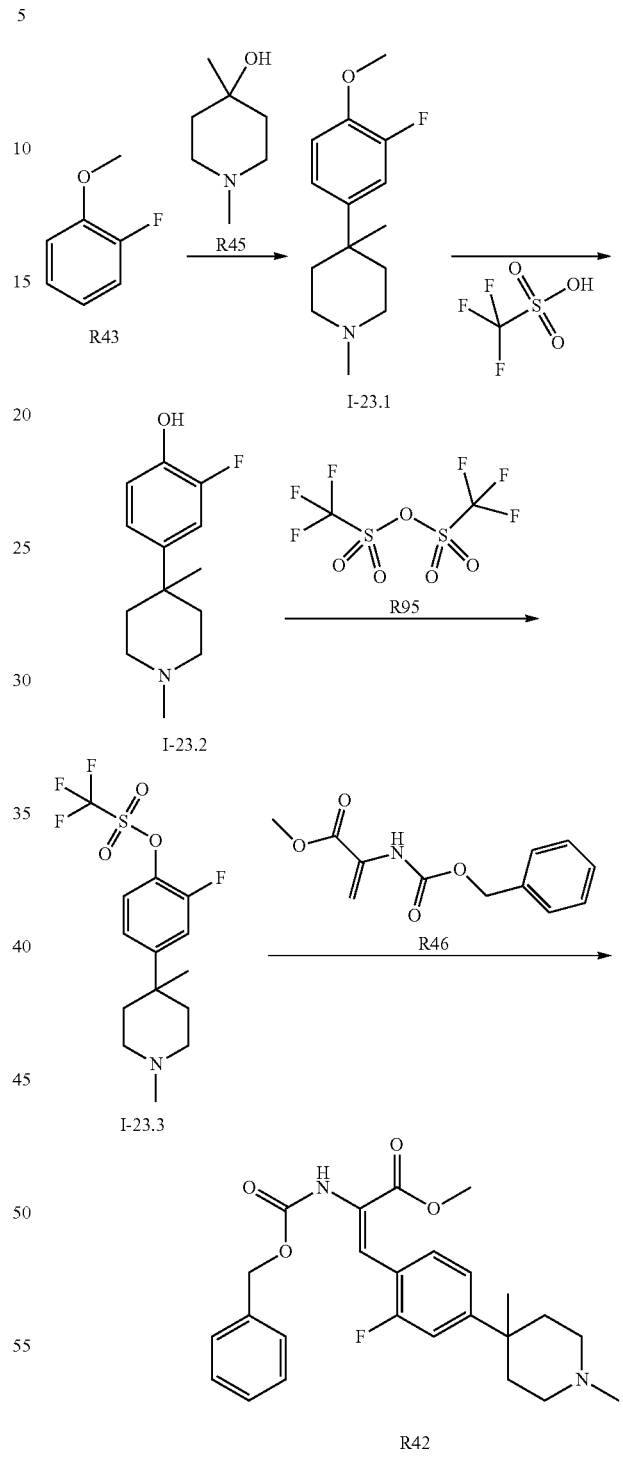

Step 1: Synthesis of Intermediate I-22.1

To R5 (500 mg, 2.07 mmol) in DMF (5 mL) are added HATU (866.72 mg, 2.28 mmol) and DIPEA (1.43 mL, 8.29 mmol) and stirred at r.t. for 15 min To the reaction mixture is added methyl 2-amino-3-hydroxy-propanoate hydrochloride (354.64 mg, 2.28 mmol) and stirred at r.t. for 4 h. The reaction mixture is diluted with ACN and water and purified by reversed phase HPLC. Yield 79%, m/z 343 [M+H]+, rt 0.44 min, LC-MS Method X011_S03.

Step 2: Synthesis of R41

I-22.1 (100 mg, 0.29 mmol) is dissolved in dichlormethane (2 mL) and cooled down to 0° C. 4-dimethylamino pyridine (1.78 mg, 0.015 mmol), TEA (65.13 µL, 0.47 mmol) and methansulfonyl chloride (29.59 µL, 0.38 mmol) are added and stirred at r.t. for 3 h. The reaction mixture is diluted with sodium carbonate solution. The organic layer is separated, dried and concentrated. The crude residue is purified by reversed phase HPLC.

Yield 27%, m/z 324 [M+H]+, rt 0.63 min, LC-MS Method X011_S03.

Step 1: Synthesis of Intermediate I-23.1

To 1-fluoro-2-methoxy-benzene (25 mL, 222.79 mmol) and 1,4-dimethylpiperidin-4-ol (7 g, 54.18 mmol) is added trifluoromethanesulfonic acid (50 mL, 565.04 mmol) under ice bath cooling. The reaction mixture is stirred at r.t. overnight, poured into iced water and extracted with PE. To the aqueous phase is added solid sodium carbonate and extracted with ethyl acetate. The organic layer is dried and concentrated. The crude product is triturated with diisopropylether and the precipitate is filtered off. Yield 82%, m/z 238 [M+H]+, rt 0.39 min, LC-MS Method X018_S02.

Step 2: Synthesis of Intermediate I-23.2

To I-23.1 (16.9 g, 43.63 mmol) in dichlormethane (150 mL) is added boron tribromide 1M in dichlormethane (44 mL, 44 mmol) and stirred at r.t. overnight. The reaction mixture is diluted with dichlormethane and 10% $K_2CO_3$-solution. The resulting precipitate is filtered off. The aq. layer is repeatedly extracted with dichlormethane, the precipitate formed upon standing at rt is filtered off and washed with dichlormethane. The dichloromethane phase is concentrated and purified by reversed HPLC and freeze dried. The isolated precipitates and the corresponding HPLC fractions are combined to yield the desired product.

Yield 18%, m/z 224 [M+H]+, rt 0.61 min, LC-MS Method V011_S01.

Step 3: Synthesis of Intermediate I-23.3

To I-23.2 (1.4 g, 6.27 mmol) in anhydrous dichlormethane (40 mL) triethylamine (1.8 mL, 12.985 mmol) is added and cooled down to −20° C. Trifluoromethanesulfonic acid anhydride (1.1 mL, 6.538 mmol) is added dropwise and stirred at −10° C. for 30 min. The reaction mixture is diluted with dichlormethane, washed with $K_2CO_3$-solution and brine. The organic layer is dried and concentrated. The crude product is used for the next step without further purification. Yield 98%, m/z 356 [M+H]+, rt 1.30 min, LC-MS Method V011_S01.

Step 4: Synthesis of R42

2-benzyloxycarbonylamino-acrylicacidmethylester (2.274 g, 9.67 mmol), bis(dibenzylideneacetone) palladium (0) (295 mg, 0.32 mmol), (2-biphenylyl)di-tert-butylphosphine (345 mg, 1.156 mmol) and lithium chloride (710 mg, 16.73 mmol) are purged with argon. I-23.3 (2.29 g, 6.44 mmol) is dissolved in DMF (15 mL) and triethylamine are added and stirred at 80° C. overnight.

The reaction mixture is concentrated, then diluted with dichlormethane and washed with 5% $K_2CO_3$-solution. The organic layer is dried and concentrated. The crude product is purified by reversed phase HPLC.

Yield 33%, m/z 441 [M+H]+, rt 1.23 min, LC-MS Method V011_S01.

The following intermediate as shown in Table 50 is synthesized in an analogous manner from the appropriate intermediate R41 and R91:

Synthesis of (2S)-2-amino-3-(4-benzyloxy-2-fluorophenyl)propanamide hydrochloride (R47)

TABLE 50

| Intermediate | Structure | m/z [M + H]+ | rt (min) | LC-MS method |
|---|---|---|---|---|
| R42.1 | 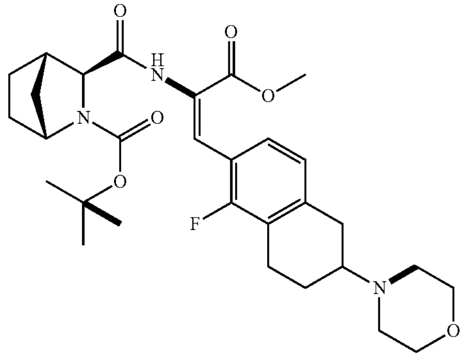 | 558 | 0.47 | X018_S01 |

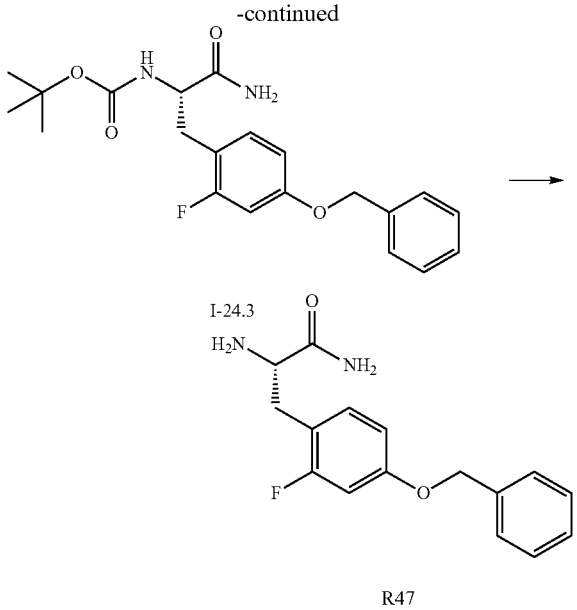

R47

Step 1: Synthesis of Intermediate I-24.1

R22 (22.58 g, 75.97 mmol) in Me-THF (50 mL) is cooled down to −10° C., 1,1,3,3-tetramethylguanidine (9.55 mL, 75.97 mmol) is added and stirred for 30 min. 4-benzyloxy-2-fluoro-benzaldehyde (15.9 g, 69.06 mmol) dissolved in 100 mL Me-THF is added dropwise and stirred for 3 h at −10° C. to 0° C. The cooling is removed and the mixture warms up to room temperature.

The reaction mixture is diluted with 300 mL Me-THF and extracted with water. The organic layer is treated with activated carbon, dried over $MgSO_4$ and concentrated.

The crude product is recristallized with cyclohexane and filtered off.

Yield 97%, m/z 402 [M+H]+, rt 0.80 min, LC-MS Method X018_S01.

The following intermediate as shown in Table 50.1 is synthesized in an analogous manner from the appropriate intermediates:

TABLE 50.1

| Intermediate | Structure | m/z [M + H]+ | rt (min) | LC-MS method |
|---|---|---|---|---|
| I-24.1.1 | 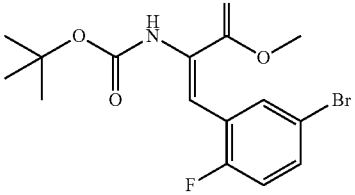 | 374/376 | 0.77 | X018_S02 |

Step 2: Synthesis of Intermediate I-24.2

I-24.1 (2.8 g, 6.98 mmol) and (+)-1,2-bis((2S,5S)-2,5-diethylphospholano)benzene(cyclooctadiene)rhodium(I) trifluoromethanesulfonate (250 mg, 0.346 mmol) in methanol (60 mL) are stirred under hydrogen (50 psi) at r.t. for 2 h. Then the mixture is filtered and the filtrate is concentrated. Yield 100%, m/z 404 [M+H]+, rt 1.40 min, LC-MS Method V001_S01.

The following intermediates as shown in Table 51 are synthesized in an analogous manner from the appropriate intermediates:

TABLE 51

| Intermediate | Structure | m/z [M + H]+ | rt (min) | LC-MS method |
|---|---|---|---|---|
| I-24.2.1 | 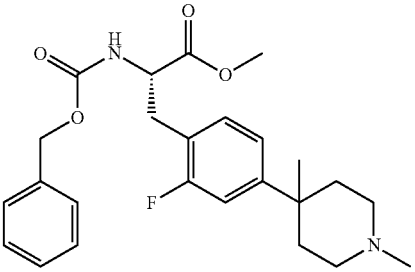 [SMILES: COC(=O)[C@H](Cc1ccc(C2(C)CCN(C)CC2)cc1F)NC(=O)OCc1ccccc1] | 443 | 1.24 | V011_S01 |

TABLE 51-continued

| Intermediate | Structure | m/z [M + H]+ | rt (min) | LC-MS method |
|---|---|---|---|---|
| I-24.2.2 | 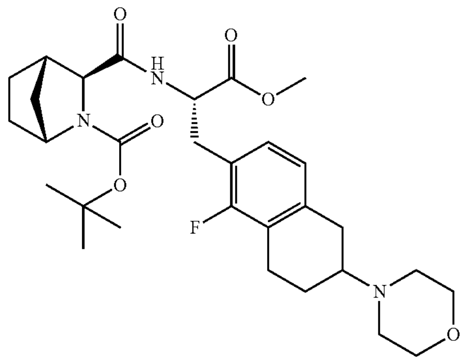 [SMILES: COC(=O)[C@H](Cc1ccc2c(c1F)CCC(N1CCOCC1)C2)NC(=O)[C@@H]1[C@H]2CC[C@H](C2)N1C(=O)OC(C)(C)C] | 560 | 0.68 | X011_S03 |
| I-24.2.3 | 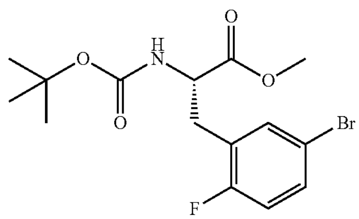 [SMILES: COC(=O)[C@H](Cc1cc(Br)ccc1F)NC(=O)OC(C)(C)C] | 376 | n.d. | n.d. |

Step 3: Synthesis of Intermediate I-24.3

I-24.2 (2.95 g, 6.95 mmol) is dissolved in anhydrous methanol (15 mL). Calcium chloride (812 mg, 7.32 mmol) and ammonia in methanol 7N (15 mL, 10.5 mmol) is added and stirred at r.t. overnight. The reaction mixture is diluted with water (45 mL) and the precipitate is filtered off and washed with water.

Yield 90%, m/z 389 [M+H]+, rt 0.65 min, LC-MS Method X011_S03.

The following intermediate as shown in Table 52 is synthesized an analogous manner from the appropriate intermediates:

TABLE 52

| Intermediate | Structure | m/z [M + H]+ | rt (min) | LC-MS method |
|---|---|---|---|---|
| I-24.3.1 | 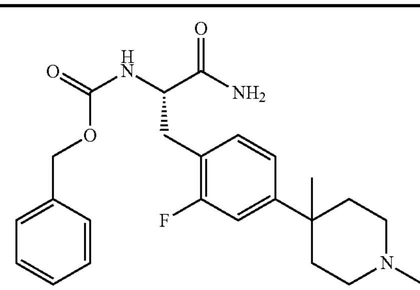 | 428 | 1.05 | V011_S01 |
| I-24.3.2 | 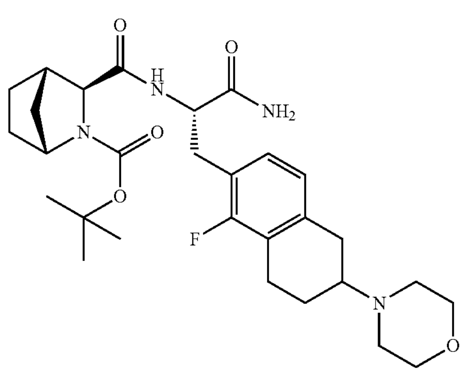 [SMILES: CC(C)(C)OC(=O)N1[C@@H]2CC[C@@H](C2)[C@H]1C(=O)N[C@@H](Cc1ccc2c(c1F)CCC(N1CCOCC1)C2)C(N)=O] | 545 | 0.57 | X011_S03 |

TABLE 52-continued

| Intermediate | Structure | m/z [M + H]+ | rt (min) | LC-MS method |
|---|---|---|---|---|
| I-24.3.3 | (Boc-NH-CH(CH2-Ar(F,Br))-C(O)NH2) | 361/363 | 0.64 | X018_S02 |

Intermediate I-24.3.1 is purified by reversed phase HPLC.

Step 4: Synthesis of R47

To I-24.3 (2.42 g, 6.23 mmol) in dichlormethane (20 mL) is added HCl in dioxane 4 mol/L (7.79 mL, 31.15 mmol) and stirred at r.t. for 3 h. The reaction mixture is diluted with TBME and the precipitate is filtered off and washed with TBME.

Yield 95%, m/z 289 [M+H]+, rt 0.50 min, LC-MS Method X011_S03.

The following intermediate as shown in Table 52.1 is synthesized in an analogous manner from the appropriate intermediates:

TABLE 52.1

| Intermediate | Structure | m/z [M + H]+ | rt (min) | LC-MS method |
|---|---|---|---|---|
| R47.1 | (H2N-CH(CH2-Ar(F,Br))-C(O)OMe · ClH) | 261/263 | 0.31 | X018_S02 |

Synthesis of (2S)-2-amino-3-[4-(1,4-dimethyl-4-piperidyl)-2-fluoro-phenyl]propanamide R49

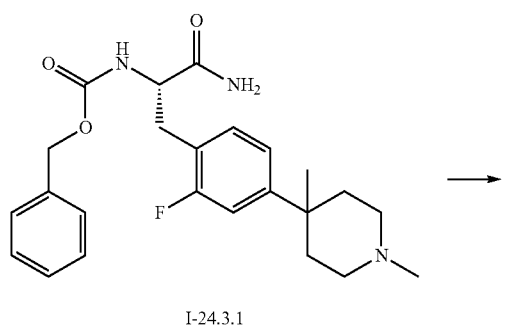

I-24.3.1

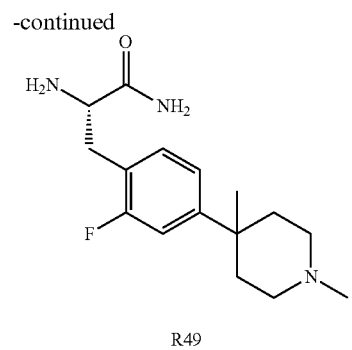

R49

I-24.3.1 (625 mg, 1.46 mmol) and Pd/C 10% (150 mg) in methanol (60 mL) is stirred under hydrogen (50 psi) at r.t. for 3.5 h. The reaction mixture is filtered and concentrated. Yield 99%, m/z 294 [M+H]+, rt 0.80 min, LC-MS Method V011_S01.

Synthesis of (1-ethyl-3,6-dihydro-2H-pyridin-4-yl) trifluoromethanesulfonate (R51)

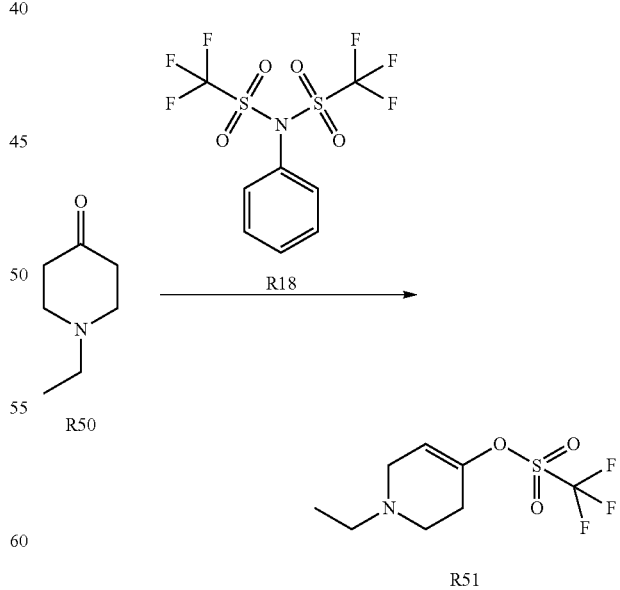

The reaction is carried out under argon atmosphere.

Diisopropylamine (5.289 mL, 38 mmol) in anhydrous THF (25 mL) is cooled down to −50° C. N-butyllithium in hexane 2.5M (13.786 mL, 34.47 mmol) is added dropwise and stirred for 45 min, then the solution is allowed to warm up to 0° C. and cooled down to −50° C. again. 1-Ethyl-4-piperidone (4 g, 31.45 mmol) dissolved in 30 mL THF is added dropwise and stirred for 30 min R18 (11.797 g, 33.02 mmol) dissolved in 30 mL THF is added dropwise. The cooling is removed and the reaction mixture stirred for 2 h.

The reaction mixture is diluted with 50 mL toluene. The organic layer is washed with 1N sodium hydroxide, half saturated brine, dried and concentrated. The residue is purified over silica gel.

Yield 15%, m/z 260 [M+H]+, rt 0.30 min, LC-MS Method X012_S01.

The following intermediates as shown in Table 53 are synthesized in an analogous manner from the appropriate intermediates:

TABLE 53

| Intermediate | Structure | m/z [M + H]+ | rt (min) | LC-MS method |
|---|---|---|---|---|
| R51.1 | 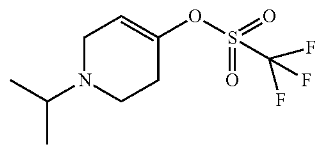 | 274 | n.d. | n.d. |
| R51.2 | 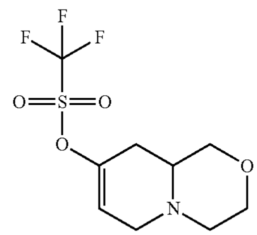 | n.d. | n.d. | n.d. |
| R51.3 | 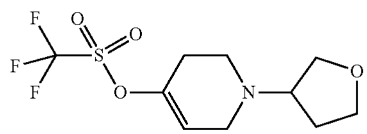 | n.d. | n.d. | n.d. |
| R51.4 | 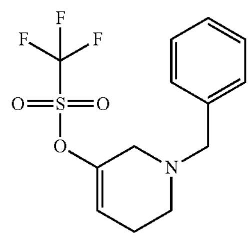 | 322 | 1.41 | V011-S01 |
| R51.5 | 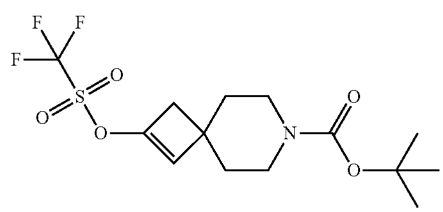 | 316 | 1.23 | Z012_S04 |
| R51.6 | 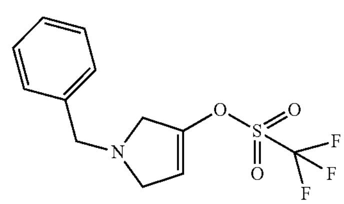 | 308 | 1.38 | V11_S01 |

For Intermediate R51.2, R51.3, R51.4 and R51.6 the reaction conditions differ: lithium bis(trimethylsilyl)amide is used and the reaction is carried out at −78° C. The crude product is used for the next step without further purification.

Intermediate R51.4 is purified over silica gel.

For Intermediate R51.5 the reaction conditions differ: lithium bis(trimethylsilyl)amide is used and the reaction is carried out at −50° C. The crude product is purified over silica gel.

343

Synthesis of (5-ethyl-1-isobutyl-pyrazol-3-yl) trifluoromethanesulfonate (R54)

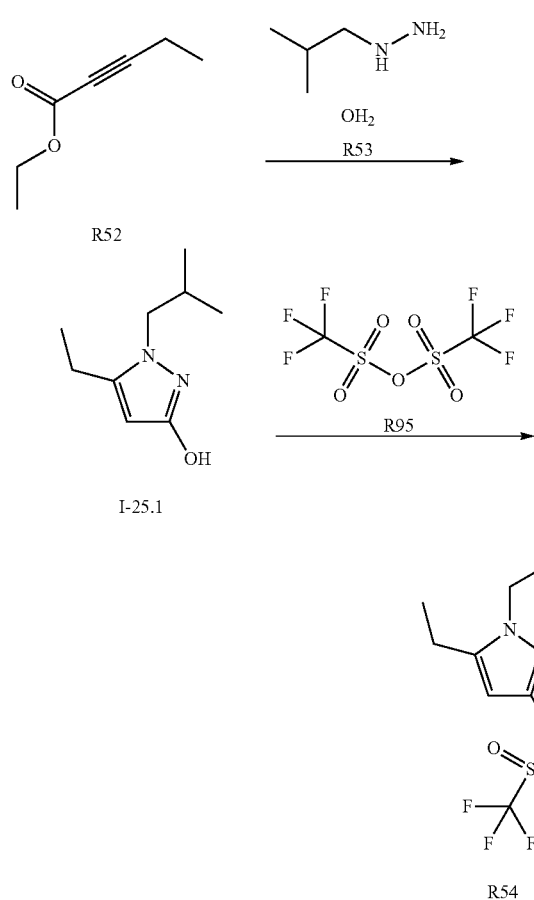

Step 1: Synthesis of Intermediate I-25.1

Ethyl pent-2-ynoate (300 μL, 2 mmol), isobutylhydrazine hydrate (240 μL, 2 mmol), methanol (1 mL) and water (1 mL) are stirred together in the microwave at 140° C. for 15 min.

The crude product is used for the next step without further purification.

Step 2: Synthesis R54

Intermediate I-25.1 (380 mg, 2 mmol) is dissolved in anhydrous dichlormethane (10 mL), DIPEA (1.2 mL, 6.94 mmol) is added and cooled down to 0° C. Trifluoromethylsulfonyl trifluoromethanesulfonate (375 μL, 2.26 mmol) dissolved in dichlormethane is added dropwise and stirred for 45 min Another trifluoromethylsulfonyl trifluoromethanesulfonate (188 μL, 1.13 mmol) is added and stirred for 30 min. The reaction mixture is extracted with NaHCO$_3$-solution (5%). The organic layer is separated, dried and concentrated. The residue is purified over silica gel.

Yield 21%, m/z 301 [M+H]+, rt 0.86 min, LC-MS Method X018_S02.

344

Synthesis of 1-bromo-3-methylsulfonyl-5-(2,2,2-trifluoroethoxy)benzene(R57)

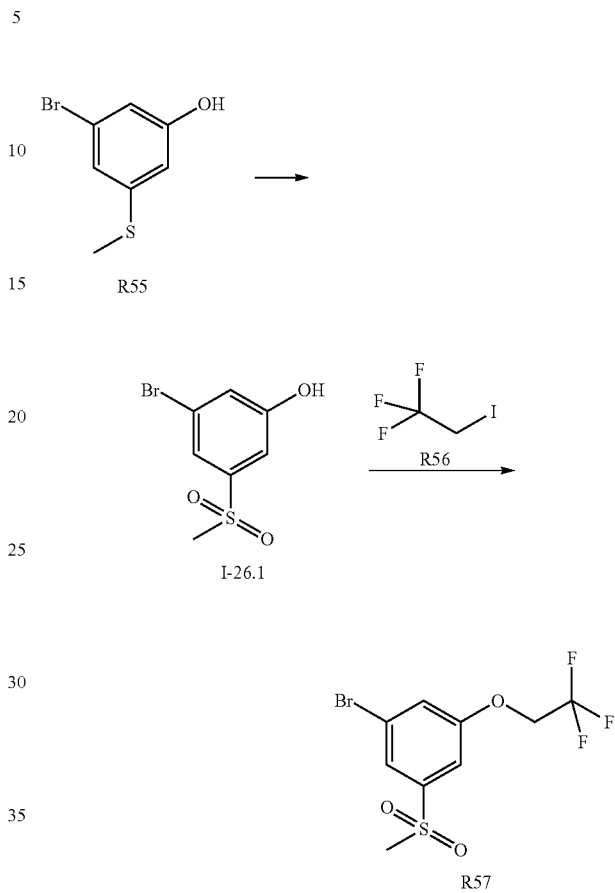

Step 1: Synthesis of Intermediate I-26.1

3-bromo-5-methylsulfanyl-phenol (5 g, 22.82 mmol) is dissolved in dichlormethane (100 mL) and cooled down to 0° C. 3-chloroperbenzoic acid (10.23 g, 45.64 mmol) is added and stirred at r.t. overnight. The reaction mixture is diluted with dichlormethane and water. The organic layer is separated, dried and concentrated. The crude product is purified by reversed phase HPLC and freeze dried.

Yield 55%, m/z 251/253 [M+H]+, rt 0.47 min, LC-MS Method X018_S01.

Step 2: Synthesis R57

To I-26.1 (150 mg, 0.597 mmol) and potassium carbonate (206.41 mg, 1.49 mmol) in DMF is added 1,1,1-trifluoro-2-iodo-ethane (147.196 μL, 1.493 mmol) and stirred over 3 days at 85° C.

The reaction mixture is diluted with water, the precipitate is filtered off, washed with water and dried. Yield 52%, m/z 350/352 [M+H]+, rt 1.16 min, LC-MS Method V011_S01.

The following intermediates as shown in Table 54 are synthesized in a similar fashion from the appropriate intermediates:

TABLE 54

| Intermediate | Structure | m/z [M + H]+ | rt (min) | LC-MS method | elab |
|---|---|---|---|---|---|
| R57.1 | 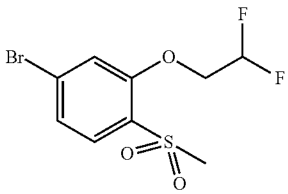 | 332/334 [M + NH₄]+ | 1.01 | V011_S01 | LG1SLA00459 |
| R57.2 | 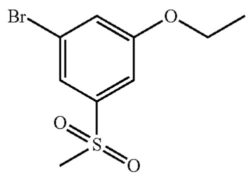 | 296/298 [M + NH₄]+ | 1.11 | V011_S01 | LG1SLA00495 |

The two intermediates in the table above are purified by reversed phase HPLC.

Synthesis of 4-bromo-N1-methyl-benzene-1,2-diamine (R58)

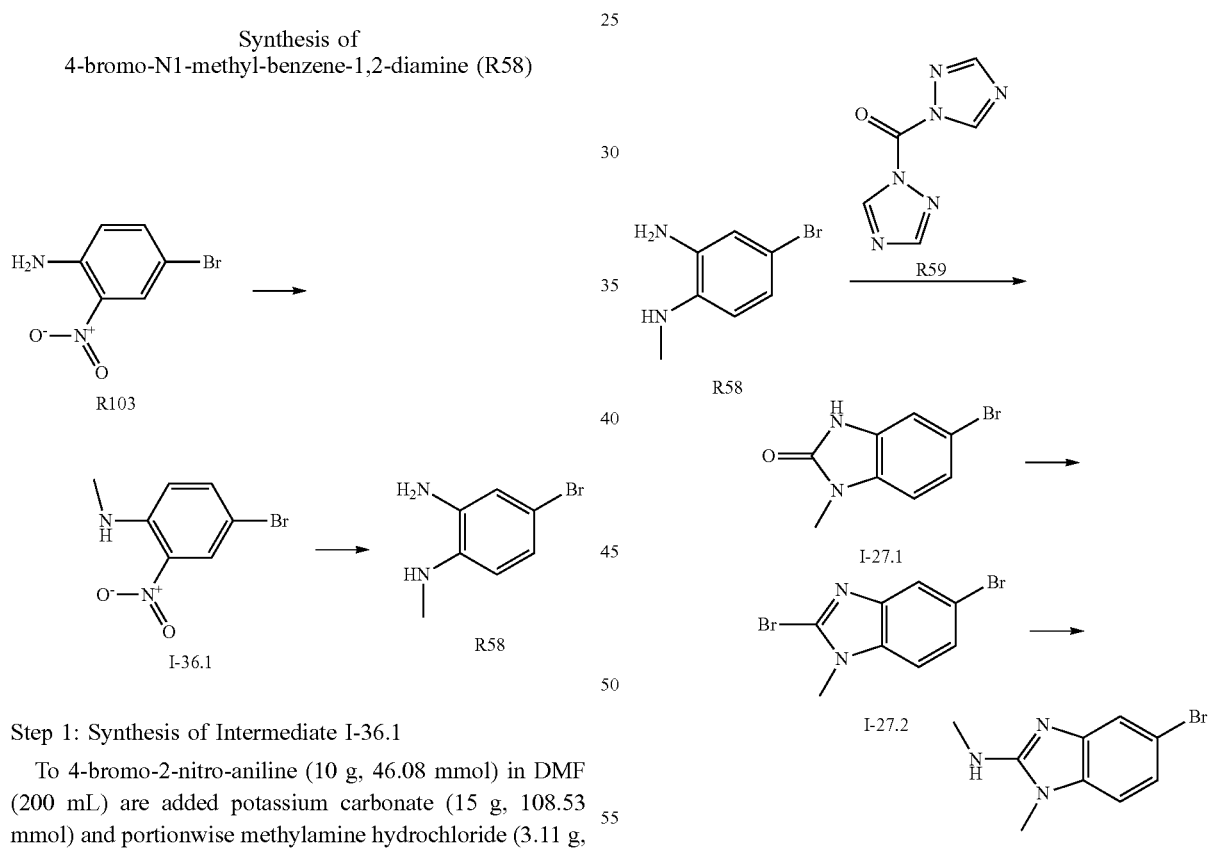

Synthesis of 5-bromo-N,1-dimethyl-benzimidazol-2-amine (R60)

Step 1: Synthesis of Intermediate I-36.1

To 4-bromo-2-nitro-aniline (10 g, 46.08 mmol) in DMF (200 mL) are added potassium carbonate (15 g, 108.53 mmol) and portionwise methylamine hydrochloride (3.11 g, 46.08 mmol) and stirred overnight at r.t. The reaction mixture is filtered and concentrated. The crude product is triturated with DIPE, filtered off and dried. Yield 86%

Step 2: Synthesis of R58

To I-36.1 (5.27 g, 22.81 mmol) in ethyl acetate is added platinum on carbon (550 mg) and stirred under hydrogen (5 bar) at r.t. for 4 h. The reaction mixture is filtered through a pad of celite and concentrated. The crude product is used without further purification for the next step Yield 96%

Step 1: Synthesis of Intermediate I-27.1

4-bromo-1-n-methylbenzene-1,2-diamine (4.42 g, 21.98 mmol), N,N'-carbonyl-di-(1,2,3-triazole (4.178 g, 24.18 mmol), and TEA (9.184 mL, 65.95 mmol) in THF (70 mL) are stirred at r.t. for 30 min, then heated under reflux overnight. The reaction mixture is concentrated, triturated with water, filtered off and dried. The residue is triturated again with DIPE and filtered off.

Yield 88%

Step 2: Synthesis of Intermediate I-27.2

I-27.1 (4.41 g, 19.42 mmol) and phosphoroxybromide (27.84 g, 97.11 mmol) are stirred at 100° C. for 3 h. The reaction mixture is diluted with iced water. The precipitate is filtered off and triturated with DIPE.

Yield 89%

Step 3: Synthesis of R60

I-27.2 (200 mg, 0.69 mmol) and methylamine in methanol 2 mol/L (2 mL, 4 mmol) are stirred at 80° C. for 16 h. The reaction mixture is purified by reversed phase HPLC.

Yield 63%, m/z 240/242 [M+H]+, rt 0.48 min, LC-MS Method X011_S03.

Synthesis of (7R,8aR)-7-methoxy-1,2,3,4,6,7,8,8a-octahydropyrrolo[1,2-a]pyrazine (R63)

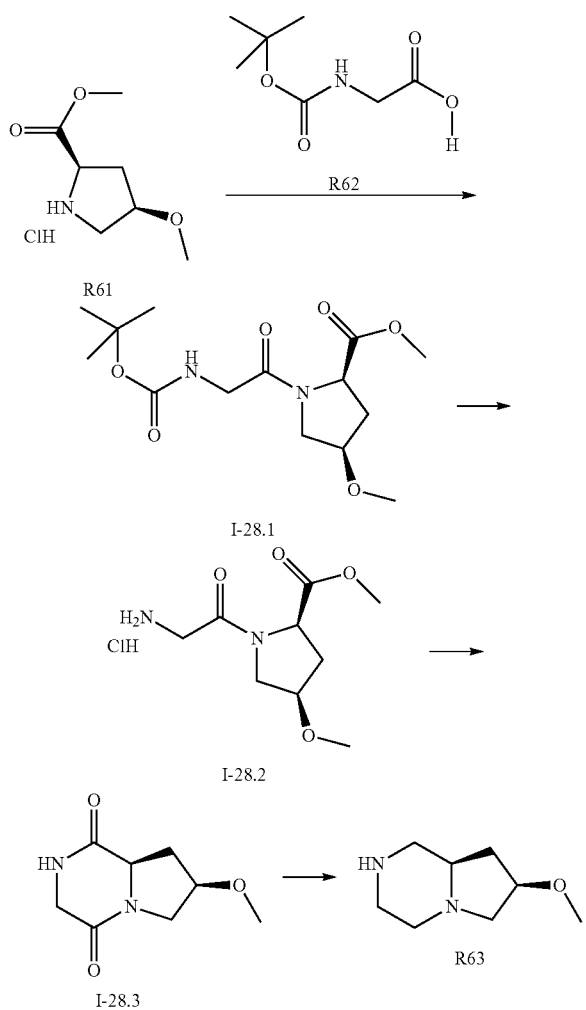

Step 1: Synthesis of Intermediate I-28.1

To 2-(tert-butoxycarbonylamino)acetic acid (1.5 g, 8.56 mmol) and HATU (3.58 g, 9.42 mmol) in DMF (15 mL) is added DIPEA (5.89 mL, 34.25 mmol) and stirred for 15 min Methyl(2R,4R)-4-methoxypyrrolidine-2-carboxylate hydrochloride (1.675 g, 8.56 mmol) is added and stirred at r.t. overnight. The reaction mixture is diluted with dichlormethan and NaHCO₃-solution. The organic layer is separated and washed with brine, dried and concentrated. The crude residue is purified by reversed phase HPLC.

Yield 74%, m/z 317 [M+H]+, rt 0.47 min, LC-MS Method X018_S01.

Step 2: Synthesis of Intermediate I-28.2

I-28.1 (2 g, 6.32 mmol), hydrochloric acid in dioxane 4 mol/L (10 mL, 40 mmol) and dioxane (30 mL) are stirred at r.t. overnight. The reaction mixture is directly used for the next step.

Step 3: Synthesis of Intermediate I-28.3

To the reaction mixture from the previous step is added TEA till a pH value of 8 is reached. The precipitate is filtered off and the mother liquor is concentrated to isolate the desired product. Yield 97%, m/z 185 rt 0.18 min, LC-MS Method V011_S01.

Step 4: Synthesis of R63

To lithiumaluminium hydride 1 mol/L in THF (12.215 mL, 12.215 mmol) in THF (8 mL) is added a solution of I-28.3 (900 mg, 4.886 mmol) in THF (4 mL) dropwise and stirred at r.t. for 1.5 h. Under cooling the reaction mixture is poured into aq. sodium hydroxide (1 mol/L) and diluted with THF (30 ml). The precipitate is filtered off and the mother liquor is concentrated. The residue is diluted with methanol and stirred a few minutes at 50° C. The precipitate is filtered off and the mother liquor is concentrated to give the crude product which is purified over amino phase silica gel. Yield 36%

Synthesis of 3,4,4a,5,6,7,8,8a-octahydro-2H-2,6-naphthyridin-1-one (R65)

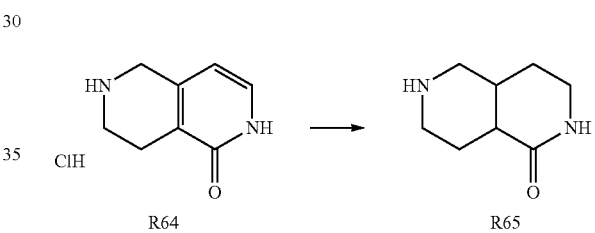

5,6,7,8-tetrahydro-2H-2,6-naphthyridin-1-one hydrochloride (250 mg, 1.339 mmol), platinum oxide (100 mg) and glacial acetic acid (10 mL) are stirred under hydrogen (5 bar) at r.t. for 24 h.

The reaction mixture is filtered off and concentrated. The crude product is purified over amino phase silica gel.

Yield 71%.

Synthesis of 4-bromo-2-isopropyl-1-methylsulfinyl-benzene (R67)

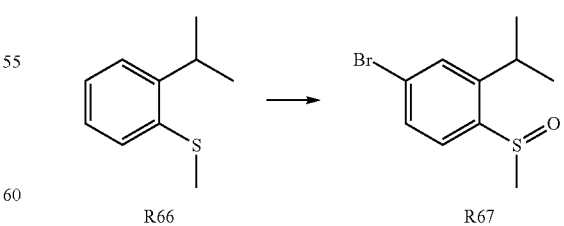

1-isopropyl-2-methylsulfanyl-benzene (400 mg, 2.41 mmol) is dissolved in dichlormethane (4 mL) and cooled down to 0° C. Bromine (123.21 μL, 2.41 mmol) is added and stirred at r.t. for 3 days. The reaction mixture is concentrated and purified by reversed phase HPLC.

Yield 53%, m/z 261/263 [M+H]+, rt 1.06 min, LC-MS Method V011_S01.

Synthesis of (3-bromophenyl)imino-dimethyl-oxo-sulfane (R70)

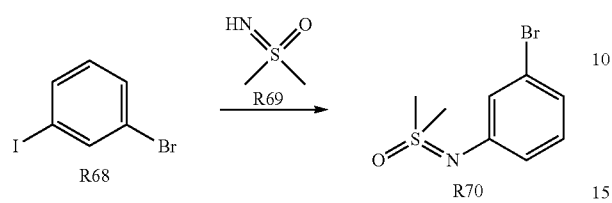

1-Bromo-3-iodo-benzene (250 μL, 1.96 mmol), (methylsulfonimidoyl) methane (219.188 mg, 2.353 mmol), cesium carbonate (894.466 mg, 2.745 mmol) and dioxane (12 mL) are purged with argon. (5-diphenylphosphanyl-9,9-dimethyl-xanthen-4-yl)-diphenyl-phosphane (85.098, 0.147 mmol) and tris(dibenzylideneacetone)dipalladium(0) (44.89 mg, 0.049 mmol) are added, purged again with argon and stirred at 105° C. for 3 h.

The reaction mixture is filtered through a pad of celite. The filtrate is concentrated and purified by reversed phase HPLC.

Yield 94%, m/z 249 [M+H]+, rt 0.74 min, LC-MS Method Z018_S04.

The following intermediate as shown in Table 55 is synthesized in a similar fashion from the appropriate intermediates:

TABLE 55

| Intermediate | Structure | m/z [M + H]+ | rt (min) | LC-MS method | elab |
| --- | --- | --- | --- | --- | --- |
| R70.1 | 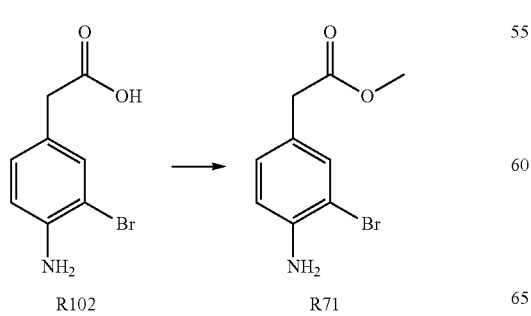 | 318 | 0.83 | Z018_S04 | CCCYUJ00250 |

Synthesis of 2-(4-amino-3-bromo-phenyl)-N-methyl-acetamide (R71)

To 2-(4-amino-3-bromo-phenyl)acetic acid (5 g, 21.73 mmol) in methanol (50 mL) and dichlormethane (100 mL) is added at −5° C. trimethylsilyldiazomethane in diethylether 2 mol/L (31.51 mL, 63.03 mmol) dropwise over a period of 30 min. The reaction mixture is allowed to warm up to r.t. and concentrated. The crude product is used without further purification. Yield 95%, m/z 244/246 [M+H]+, rt 0.48 min, LC-MS Method X011_S03.

Synthesis of 2-(4-amino-3-bromo-phenyl)-N-methyl-acetamide; 2,2,2-trifluoroacetic acid (R72)

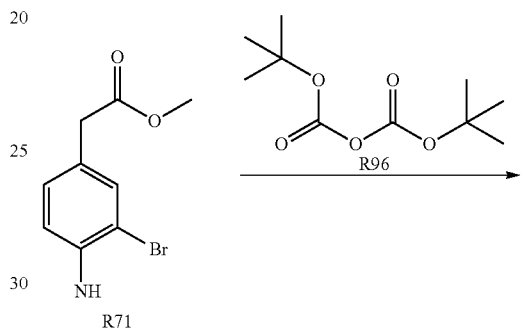

-continued

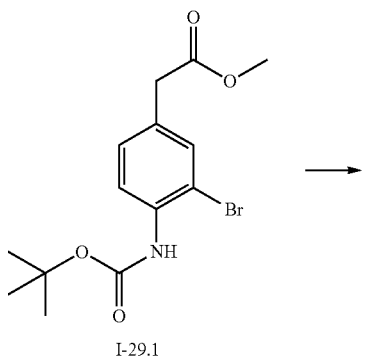

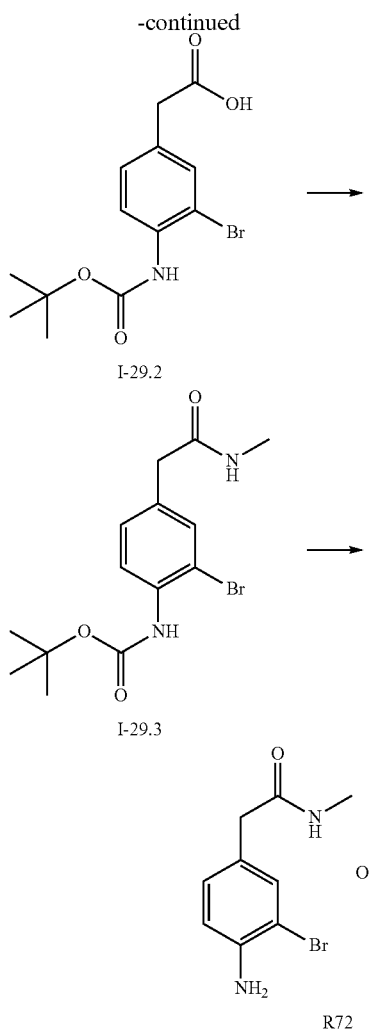

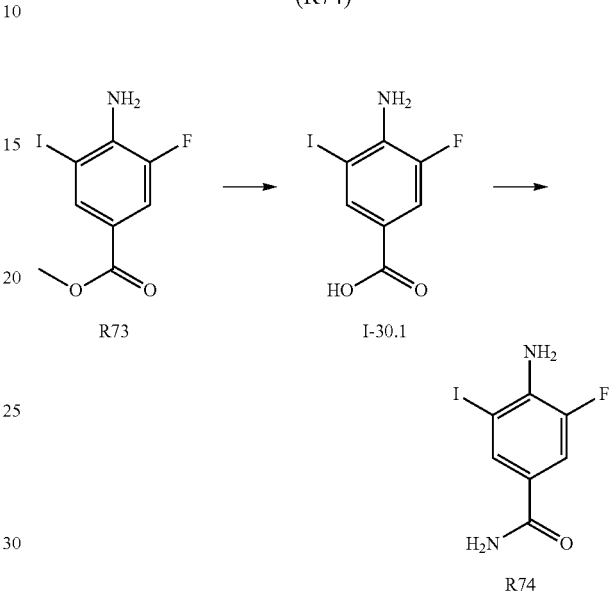

Step 4: Synthesis of R72

To I-29.3 (97 mg, 0.28 mmol) in dichlormethane (2 mL) is added trifluoracetic acid (0.5 mL) and stirred at r.t. for 1 h. The reaction mixture is concentrated.

Yield 99%, m/z 243/245 [M+H]+, rt 0.26 min, LC-MS Method X012_S01.

Synthesis of 4-amino-3-fluoro-5-iodo-benzamide (R74)

Step 1: Synthesis of Intermediate I-30.1

2-fluoro-6-iodo-4-(methoxycarbonyl)aniline (30 g, 0.1 mol), ethanol (300 mL) and NaOH 20% (30 mL) are stirred together under reflux for 2 h. The reaction mixture is diluted with water and acidified with $KHSO_4$-solution (1 mol/L). The precipitate is filtered off and recristallized with ethanol.

Yield 86%

Step 2: Synthesis of R74

To I-30.1 (26 g, 0.092 mol) in DMF (200 mL) is added 1,1'-carbonyldiimidazole (17.8 g, 0.11 mol) and ammonium carbonate (48 g, 0.5 mol) and stirred at 50° C. for 30 min. The reaction mixture is concentrated and the residue is diluted with water. The precipitate is filtered off and recristallized with ethanol.

Yield 83%

Synthesis of 4-amino-3-fluoro-5-iodo-benzonitrile (R74.1)

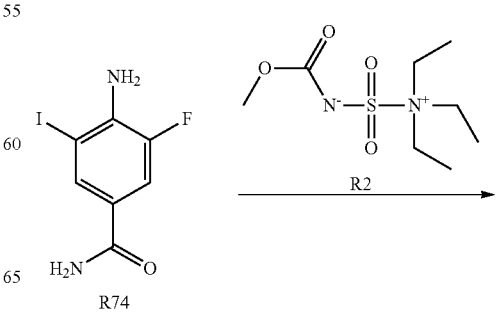

Step 1: Synthesis of Intermediate I-29.1

4-amino-3-bromophenylacetic acid methyl ester (22 g, 81.12 mmol), di-t-butyl-dicarbonate (20.13 g, 92.22 mmol), 4-dimethylaminopyridine (991.02 mg, 8.11 mmol) and dichlormethane (300 mL) are stirred together at r.t. overnight. The reaction mixture is extracted with $KHSO_4$-solution (10%), $NaHCO_3$-solution and brine. The organic layer is separated, dried and concentrated. The residue is purified over silica gel.

Yield 8%, m/z 344/346 [M+H]+, rt 1.34 min, LC-MS Method V011_S01.

Step 2: Synthesis of Intermediate I-29.2

To I-29.1 (4 g, 11.62 mmol) in dioxane (50 mL) is added a solution of lithium hydroxide (400 mg, 13.95 mmol) in water (5 mL) and stirred at r.t. overnight. The precipitate is filtered by suction and dried.

Yield 91%, m/z 274/276 [M+H-isobutene]+, rt 0.29 min, LC-MS Method X011_S03.

Step 3: Synthesis of Intermediate I-29.3

To I-29.2 (150 mg, 0.45 mmol) in DMF (2 mL) is added TBTU (175.04 mg, 0.55 mmol) and after 7 min methylamine 2 mol/L in THF (0.9 ml, 1.82 mmol) is added. The reaction mixture is stirred at r.t. overnight and purified by reversed phase HPLC.

Yield 35%, m/z n.d. [M+H]+, rt 0.55 min, LC-MS Method X011_S03.

-continued

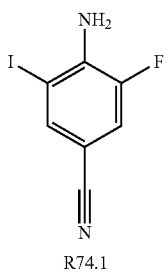

R74.1

To R74 (2 g, 7.14 mmol) in dichlormethane (50 mL) is added R2 (3.4 g, 14.28 mmol) and stirred at r.t. overnight. The reaction mixture is extracted with water. The organic layer is separated, dried and concentrated. The crude residue is filtered through a pad of silica gel (eluent (ethyl acetate/cyclohexane 3:7).

Yield 53%, m/z 263 [M+H]+, rt 0.47 min, LC-MS Method X012_S01.

Synthesis of 3-tetrahydrofuran-3-yl-3,8-diazabicyclo[3.2.1]octane (R77)

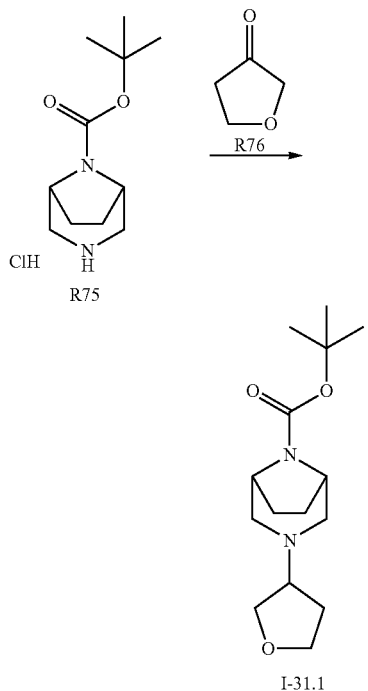

Step 1: Synthesis of Intermediate I-31.1

To tert-butyl 3,8-diazabicyclo[3.2.1]octane-8-carboxylate hydrochloride (300 mg, 1.21 mmol) in THF (5 mL) is added tetrahydrofuran-3-one (114.21 mg, 1.33 mmol) and sodium triacetoxyborhydride (349.78 mg, 1.57 mmol) and stirred at r.t. for 0.5 h.

Sodium acetate (148.40 mg, 1.81 mmol) is added and stirred at r.t. overnight.

The reaction mixture is diluted with aq. sodiumhydrogen carbonate solution and extracted with ethyl acetate. The organic layer is separated, dried and concentrated. The crude residue is purified by reversed phase HPLC.

Yield 61%, m/z 283 [M+H]+, rt 0.61 min, LC-MS Method V011_S01.

The following intermediates as shown in Table 56 are synthesized in an analogous manner from the appropriate intermediates:

TABLE 56

| Intermediate | Structure | m/z [M + H]+ | rt (min) | LC-MS method |
|---|---|---|---|---|
| I-31.1.1 | 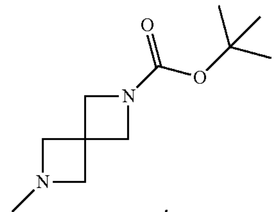 | 213 | n.d. | n.d. |
| I-31.1.2 | 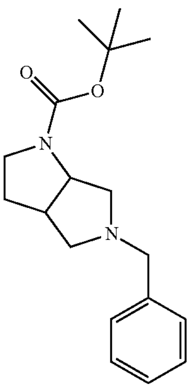 [SMILES: CC(C)(C)OC(=O)N1CCC2CN(Cc3ccccc3)CC21] | 303 | 1.34 | V11_S01 |

For I-31.1.1 sodium cyanoborhydride and methanol is used instead of sodium triacetoxyborhydride and THF.

Step 2: Synthesis of R77

I-31.1 (206 mg, 0.73 mmol) and hydrochloric acid in ether 1 mol/L (5 mL) is stirred at r.t. for 3 h. The reaction mixture is concentrated, diluted in dichlormethan/methanol 7/3 and filtered over amino phase silica gel.

Yield 99%, m/z 183 [M+H]+, rt 0.28 min, LC-MS Method V011_S01.

The following intermediates as shown in Table 56.1 are synthesized in an analogous manner from the appropriate intermediates:

TABLE 56.1

| Intermediate | Structure | m/z [M + H]+ | rt (min) | LC-MS method |
|---|---|---|---|---|
| R77.1 | 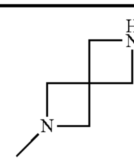 | n.d. | n.d. | n.d. |
| R77.2 | 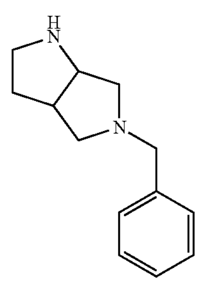 | 203 | 0.91 | V11_S01 |

For R77.1 p-toluenesulfonic acid monohydrate is used for the deprotection.

Synthesis of tert-butyl 4-(5-bromo-2-oxo-indolin-1-yl)piperidine-1-carboxylate (R79)

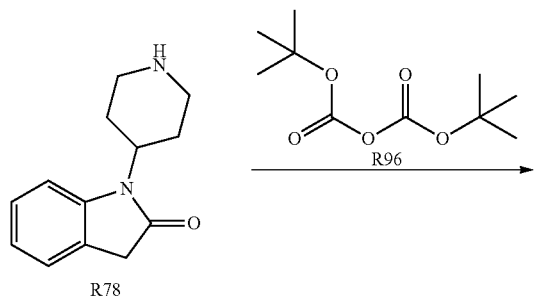

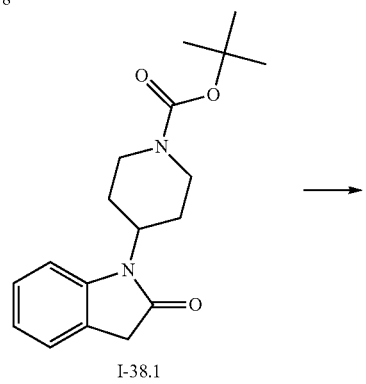

I-38.1

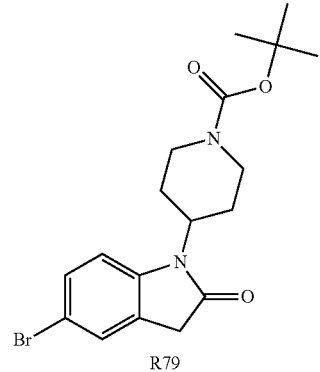

R79

Step 1: Synthesis of Intermediate I-38.1

To 1,3-dihydro-1-(piperidin-4-yl)-(2H)-indol-2-one (200 mg, 0.93 mmol) in dichlormethane (5 mL) are added TEA (0.129 mL, 0.93 mmol) and di-t-butyl-dicarbonate (201.82 mg, 0.93 mmol). The reaction mixture is stirred for 10 min, diluted with water and sodium hydrogencarbonate solution and extracted with dichlormethane. The organic layer is dried and concentrated.

Yield>95%, m/z 261 [M+H-tert.butyl]+, rt 1.055 min, LC-MS Method Z020_S01.

Step 2: Synthesis of R79

Tert-butyl 4-(2-oxoindolin-1-yl)piperidine-1-carboxylate (100 mg, 0.32 mmol) in ACN is cooled down to −10° C., N-bromosuccinimide (56.47 mg, 0.32 mmol) is added and stirred at −10° C. for 2 h. The reaction mixture is diluted with dichlormethane and water. The organic layer is separated, dried and concentrated. The crude product is used for the next step without further purification. Yield 99%, m/z 395 [M+H]+, rt 1.126 min, LC-MS Method Z020_S01.

Synthesis of 2-amino-N-cyclopropyl-3-iodo-benzamide (R82)

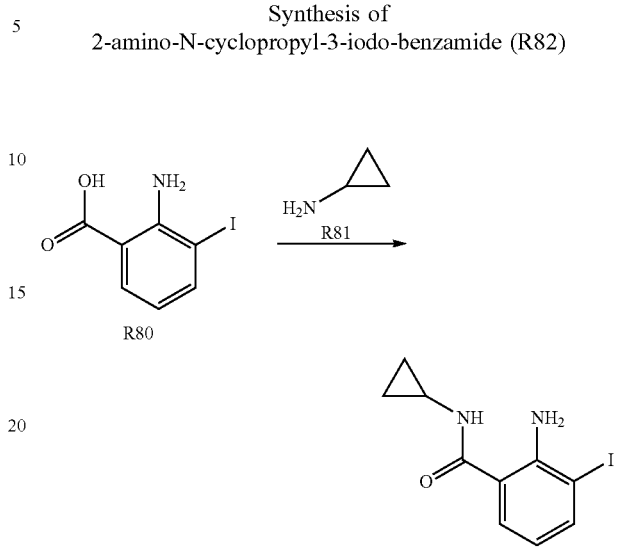

Synthesis of R82

To 2-amino-3-iodo-benzoic acid (200 mg, 0.76 mmol) in DMF (1 mL) TBTU (244.15 mg, 0.76 mmol) and DIPEA (245.69 µL, 1.52 mmol) are added and stirred at r.t. for 7 min Cyclopropylamine (52.69 µL, 0.76 mmol) is added and stirred at r.t. overnight. The reaction mixture is diluted with water and the precipitate is filtered off and dried.

Yield 89%, m/z 303 [M+H]+, rt 0.49 min, LC-MS Method X012_S01.

Synthesis of 6-bromo-1-(1-methyl-4-piperidyl)indolin-2-one (R85)

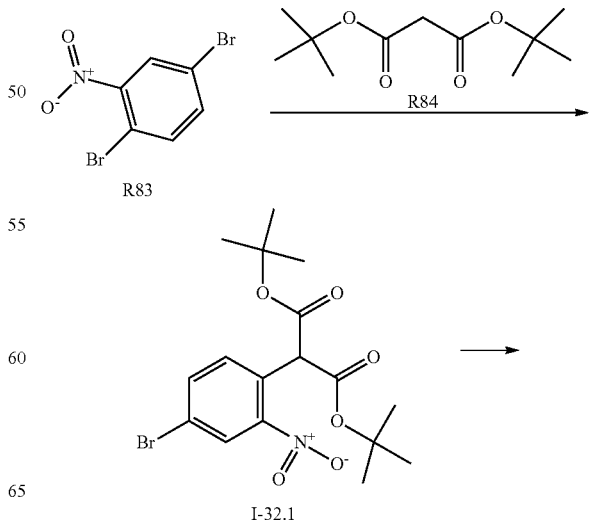

I-32.1

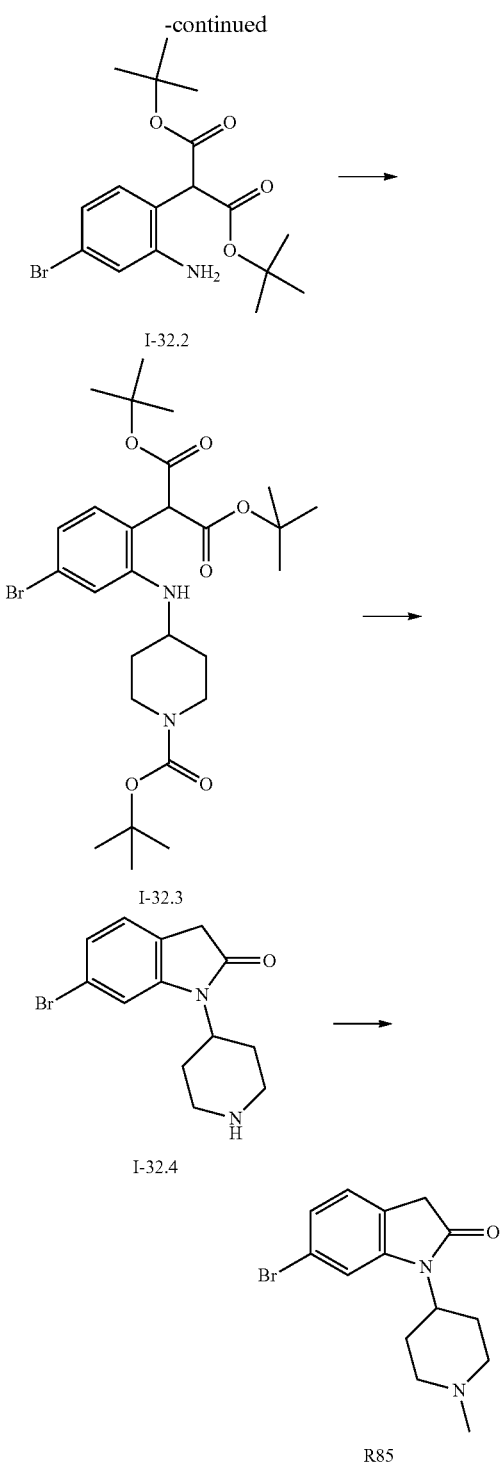

Step 1: Synthesis of Intermediate I-32.1

To sodium hydride 60% (1.536 g, 38.4 mmol) in DMSO (30 mL) under nitrogen atmosphere is added di-tert.butyl-malonate (8.61 mL, 38.4 mmol) dropwise. The reaction mixture is stirred at 100° C. for 1 h, cooled down to 10° C. and a solution of 2,5-dibromonitrobenzene (4.93 g, 17.55 mmol) in DMSO (25 mL) is added dropwise. After the addition the reaction mixture is stirred at 100° C. for 1 h again.

The reaction mixture is poured into ammoniumchloride solution and the pH is adjusted with sodium hydrogensulfate to pH 7. Water and a mixture of ethylycetate/cyclohexane 1/1 is added. The aq. layer is extracted with this mixture. The organic layer is separated, washed with brine, dried and concentrated. The crude product is used for the next step without further purification.

Yield 45%, m/z 414/416 [M+H]+, rt 1.215 min, LC-MS Method Z011_S03.

Step 2: Synthesis of Intermediate I-32.2

To I-32.1 (1 g, 2.4 mmol) in ethanol is added platinum on carbon (50 mg) and stirred under hydrogen (50 psi) at r.t. for 67 h. The reaction mixture is filtered and concentrated. The crude residue is purified by reversed phase HPLC.

Yield 34%, m/z 274/276 [M+H]+, rt 1.156 min, LC-MS Method Z011_S03.

Step 3: Synthesis of Intermediate I-32.3

To I-32.2 (316.66 mg, 0.81 mmol) in dichlormethane (2 mL) and glacial acetic acid (73.88 mL, 1.22 mmol) are added Boc-4-piperidone (210.41 mg, 1.06 mmol), titanium (IV)isopropoxide (346.17 mg, 1.22 mmol) and sodium triacetoxyborhydride (258.14 mg, 1.22 mmol) and stirred at 50° C. for 3 h and at r.t. over 3 days. The reaction mixture is diluted with dichlormethane and water. The organic layer is separated and concentrated. The crude product is purified by reversed phase HPLC.

Yield 27%, m/z 569/571 [M+H]+, rt 1.049 min, LC-MS Method Z011_U03.

Step 4: Synthesis of Intermediate I-32.4

To I-32.3 (125.3 mg, 0.2 mmol) in toluene (1 mL) is added 4-ethyl-benzenesulfonic acid (163.9 mg, 0.9 mmol) and stirred at 140° C. by microwave irridation. The reaction mixture is concentrated and diluted with sodium hydroxide 1 mol/L and dichlormethane and concentrated again. The crude product is used without further purification for the next step.

Yield 92%, m/z 295/7 [M+H]+, rt 0.867 min, LC-MS Method Z011_S03.

Step 5: Synthesis of R85

To I-32.4 (60 mg, 0.20 mmol) in methanol (1 mL) are added formaldehyde in water (37%) (75.67 μL, 1.02 mmol) and glacial acetic acid (17.44 μL, 0.31 mmol), stirred at r.t. for 75 min, afterwards sodium triacetoxyborhydride (107.70 mg, 0.51 mmol) is added. The reaction mixture is stirred at r.t. overnight.

The reaction mixture is diluted with sodium hydroxide 1 mol/L and dichlormethane. The organic layer is separated, washed with brine, dried and concentrated. The crude product is used for the next step without further purification.

Yield 52%, m/z 309/311 [M+H]+, rt 0.912 min, LC-MS Method Z011_S03.

Synthesis of
6-bromo-N-methyl-1H-benzimidazol-2-amine (R88)

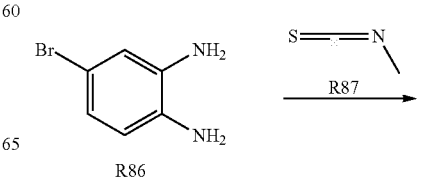

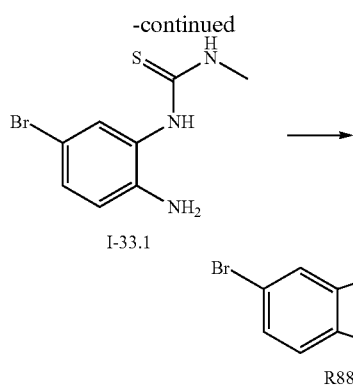

I-33.1

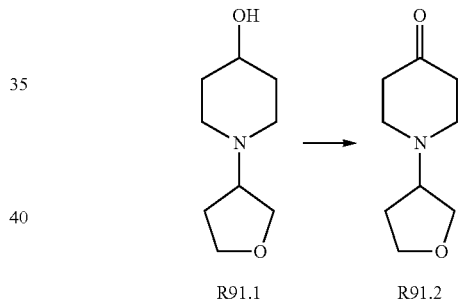

R88

Step 1: Synthesis of Intermediate I-33.1

To 4-bromobenzene-1,2-diamine (0.5 g, 3 mmol) in dichlormethane (10 mL) and DIPEA (0.55 mL, 3 mmol) is added methylimino(thioxo)methane (0.2 g, 3 mmol) and stirred at 50° C. for 4 h and at r.t. overnight. The reaction mixture is extracted with, aq. acetic acid (1%), aq. sodium carbonate (10%) and brine. The organic layer is separated, dried and concentrated. The residue is purified over silica gel.

Yield 69%, m/z 260/262 [M+H]+, rt 0.45 min, LC-MS Method X018_S02.

Step 2: Synthesis of R88

To I-33.1 (130 mg, 0.50 mmol) in ACN (2.5 mL) are added benzotriazol-1-yl-oxy-tris(dimethylamino)phosphonium hexafluorophosphate (BOP reagent) (330 mg, 0.50 mmol) and DBU (150 μL, 1.00 mmol) and stirred at r.t. for 0.5 h. The reaction mixture is purified by reversed phase HPLC.

Yield 51%

Synthesis of 4-(6-bromo-5-fluoro-tetralin-2-yl)morpholine (R91)

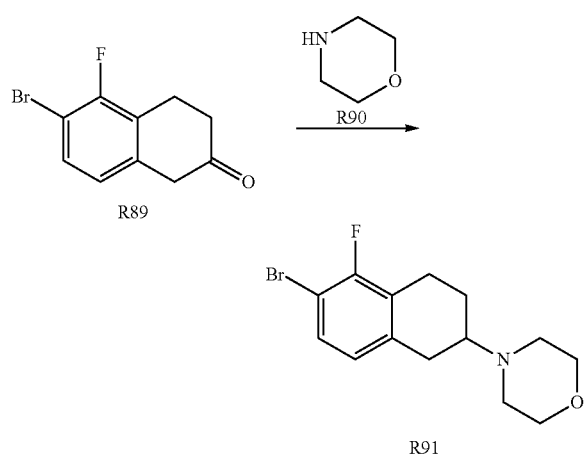

To 6-bromo-5-fluoro-tetralin-2-one (1 g, 4.11 mmol) and morpholine (0.36 mL, 4.11 mmol) in dichlormethane is added glacial acetic acid (0.52 mL, 9.05 mmol). The reaction mixture is cooled with an ice bath and sodium triacetoxyborhydride (1.74 g, 8.23 mmol) is added. The reaction mixture is stirred at r.t. overnight. Morpholine (0.2 mL) is added and stirred again at r.t. overnight. The reaction mixture is basified with potassium carbonate solution (20%) and stirred for 15 min. The organic layer is separated and the aq. layer is washed two times with dichlormethane. The organic layers are dried and concentrated. The crude product is purified by reversed phase HPLC Yield 57%, m/z 314/316 [M+H]+, rt 0.68 min, LC-MS Method X011_S03.

The following intermediate as shown in Table 57 is synthesized in a similar fashion from the appropriate intermediates:

TABLE 57

| Intermediate | Structure | m/z [M + H]+ | rt (min) | LC-MS method |
|---|---|---|---|---|
| R91.1 | 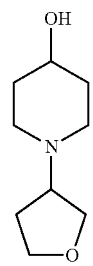 | 172 | n.d. | n.d. |

Synthesis of 1-tetrahydrofuran-3-ylpiperidin-4-one (R91.2)

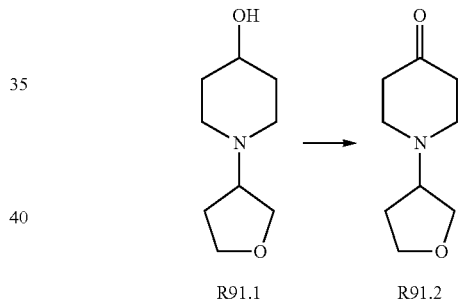

R91.1 R91.2

To R91.1 1-tetrahydrofuran-3-ylpiperidin-4-ol (200 mg, 1.17 mmol) in dichlormethane (5 mL) is added Dess-Martin periodine (595 mg, 1.40 mmol) and stirred at r.t. for 5 h. The reaction mixture is filtered through ALOX/N and washed with cyclohexane/ethyl acetate 1:3. The filtrate is concentrated.

Yield 51%

Synthesis of (4aS,7aR)-2,3,4,4a,5,6,7,7a-octahydropyrrolo[3,4-b][1,4]oxazine (R93)

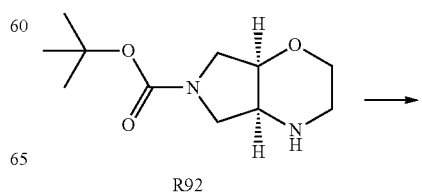

R92

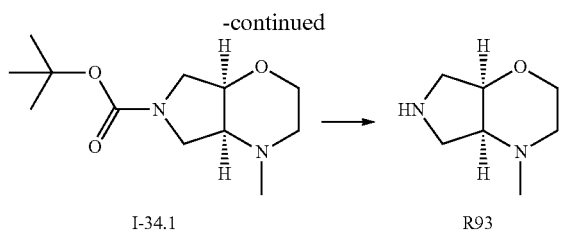

I-34.1 → R93

Step 1: Synthesis of Intermediate I-34.1

To tert-butyl(4aS,7aR)-3,4,4a,5,7,7a-hexahydro-2H-pyrrolo[3,4-b][1,4]oxazine-6-carboxylate (200 mg, 0.88 mmol) in methanol (3 mL) are added formaldehyde in water (37%) (26.44 mg, 0.33 mmol) and glacial acetic acid (79.71 mg, 1.31 mmol), stirred at r.t. for 75 min, afterwards sodium triacetoxyborhydride (464.19 mg, 2.19 mmol) is added. The reaction mixture is stirred at r.t. for 2 h Additional formaldehyde in water (37%) (26.44 mg, 0.33 mmol) is added and stirred in a 50° C. warm water bath for 10 min, sodium triacetoxyborhydride (464.19 mg, 2.19 mmol) is added and stirred at r.t. for 1.5 h. The reaction mixture is diluted with aq. sodium hydrogencarbonate solution and water and extracted with ethyl acetate. The organic layer is washed with aq. sodium hydrogencarbonate solution and brine, dried and concentrated. Yield 79

The following intermediates as shown in Table 58 are synthesized in a similar fashion from the appropriate intermediates:

TABLE 58

| Intermediate | Structure | m/z [M + H]+ | rt (min) | LC-MS method |
|---|---|---|---|---|
| I-34.1.1 | (structure) | n.d. | n.d. | n.d. |
| I-34.1.2 | (structure) | n.d. | n.d. | n.d. |

Step 2: Synthesis of R93

To I-34.1 (167 mg, 0.69 mmol) in dichlormethan (3 mL) p-toluenesulfonic acid monohydrate (655.48 mg, 3.45 mmol) is added and stirred at r.t. overnight. The reaction mixture is extracted with sodium hydroxide 1 mol/L. The organic layer is separated dried and concentrated. Due to less yield the aq. layer is saturated with sodium chloride and extracted with dichlormethane.

The aq layer is concentrated and extracted again with dichlormethane. All organic layers are combine, dried and concentrated. Yield 76%

The following intermediates as shown in Table 59 are synthesized in a similar fashion from the appropriate intermediates:

TABLE 59

| Intermediate | Structure | m/z [M + H]+ | rt (min) | LC-MS method |
|---|---|---|---|---|
| R93.1 | (structure) | n.d. | n.d. | n.d. |
| R93.2 | (structure) | n.d. | n.d. | n.d. |

Synthesis of 1-bromo-4-(bromomethyl)-2,5-difluoro-benzene (R99)

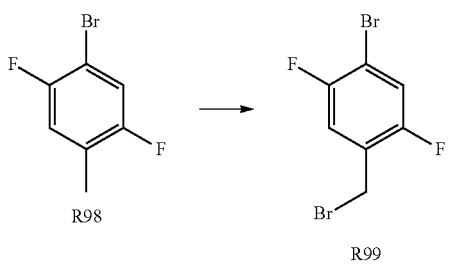

R98 → R99

R98 (31.4 g, 15.17 mmol), N-bromosuccinimide (32.4 g, 1.6 mmol), AIBN (4.98 g, 30.34 mmol) in tetrachloromethane is heated at 90° C. overnight. The reaction mixture is cooled down to r.t. and concentrated. The residue is dissolved in ethyl acetate and extracted with water. The organic layer is dried over $MgSO_4$, filtered and concentrated. The crude product is purified by high vacuum distillation (boiling point 95° C.-98° C. by oil bath temperature of 140° C.) Yield 67%

The following intermediate as shown in Table 60 is synthesized in an analogous manner from the appropriate intermediates:

TABLE 60

| Intermediate | Structure | m/z [M + H]+ | rt (min) | LC-MS method |
|---|---|---|---|---|
| R99.1 | (structure) | n.d. | 0.65 | X012_S01 |

For R99.1 the reaction temperature is 80° C. For the work up the reaction mixture is cooled to r.t. and the precipitate filtered off. The mother liquor is extracted with aq. hydrochloric acid (1 mol/L) and aq. sodium hydroxide (1 mol/L), dried and concentrated. The crude product is used without further purification.

Synthesis of 2-benzyloxy-4-bromo-1-(chloromethyl)benzene (R100)

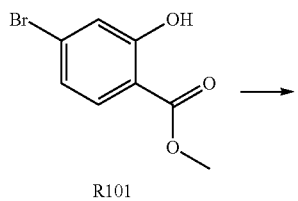

R101

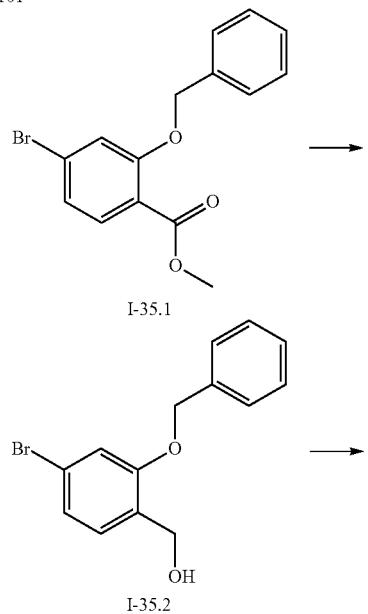

Step 1: Synthesis of Intermediate I-35.1

To methyl 4-bromo-2-hydroxy-benzoate (4.3 g, 18.61 mmol) in acetonitrile (50 mL) are added bromomethylbenzene (2.23 mL, 19.54 mmol) and potassium carbonate (3.86 g, 27.92 mmol) and stirred for 4 h at reflux. The reaction mixture is cooled down to r.t., diluted with water and extracted with ethyl acetate. The organic layer is separated, dried over MgSO$_4$ and concentrated. The crude residue is purified over silica gel (eluent: cyclohexane/ethyl acetate 95:5). Yield 75%

Step 2: Synthesis of Intermediate I-35.2

I-35.1 (4.5 g, 14.01 mmol) is dissolved in THF (50 mL) and a solution of lithium aluminium hydride in THF (8.41 mL, 8.41 mmol) is added dropwise between 5° C.-10° C. The reaction mixture is stirred 1 h under cooling and 1.5 h at r.t. Afterwards the mixture is cooled down and hydrolysed with 30 mL aq. hydrodchloric acid (1 mol/L), diluted with water and extracted with ethyl acetate. The organic layer is washed with water, dried over MgSO$_4$ and concentrated. The crude residue is used for the next step without further purification. Yield 94%

Step 3: Synthesis of R100

To I-35.2 (3.85 g, 13.13 mmol) in dichlormethane (40 mL) is added triethylamine (2.21 mL, 15.76 mmol) and cooled down to 0° C.--2° C. Methanesulfonyl chloride (1.12 mL, 14.45 mmol) dissolved in dichlormethane (3 mL) is added dropwise. The reaction mixture is stirred for 1 h at 2° C.-5° C. and overnight at r.t. The reaction mixture is concentrated, diluted with dichlormethane and water. The organic layer is washed with 1 mol/L hydrochloric acid, water, dried over MgSO$_4$ and concentrated. The crude residue is used for the next step without further purification. Yield 74%

Synthesis of tert-butyl N-(4-amino-3-bromo-phenyl)carbamate (R104)

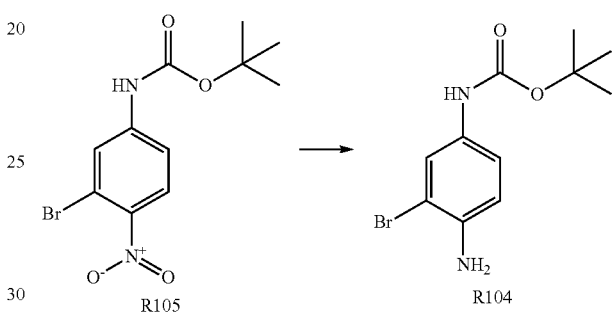

R105 → R104

To tert-butyl N-(3-bromo-4-nitro-phenyl)carbamate (1 g, 3.15 mmol) in ethyl acetate (20 mL) is added tin (II) chloride dihydrate (3.56 g, 15.77 mmol) and stirred overnight at r.t. The reaction mixture is basified with potassium carbonate/sodium hydroxide. The organic layer is separated, dried and concentrated. The crude product is used without further purification for the next step. Yield 83%, m/z 287/289[M+H]+, rt 0.58 min, LC-MS Method X011_S03.

The following intermediate as shown in Table 61 is synthesized in an analogous manner from the appropriate intermediates:

TABLE 61

| Intermediate | Structure | m/z [M + H]+ | rt (min) | LC-MS method |
|---|---|---|---|---|
| R104.1 | 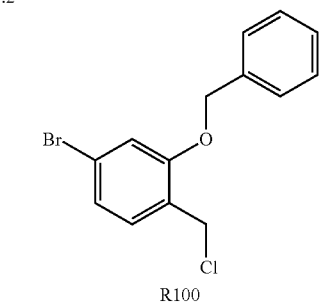 | 197/199 | 0.45 | X012_S01 |

Synthesis of 3,4,6,7,9,9a-hexahydro-1H-pyrido[2,1-c][1,4]oxazin-8-one (R106)

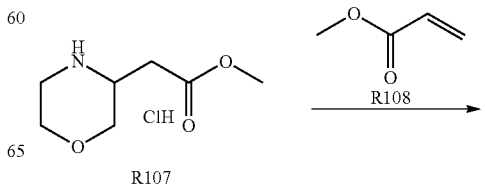

R107 → R108

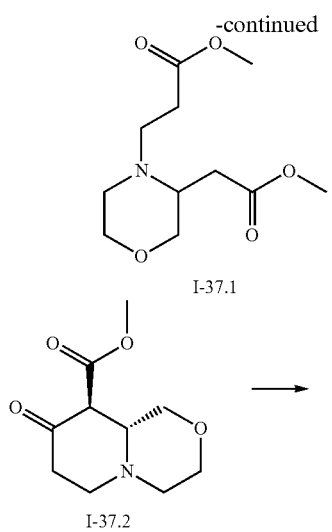

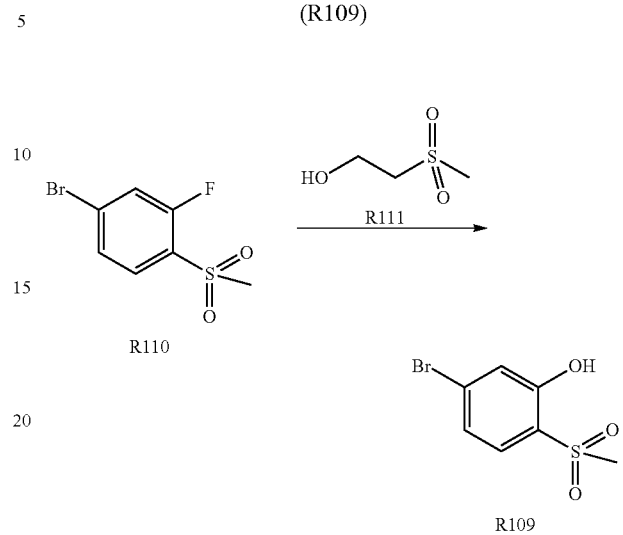

Step 1: Synthesis of Intermediate I-37.1

To methyl 2-morpholin-3-ylacetate hydrochloride (1 g, 5.11 mmol) in methanol (25 mL) are added TEA (0.785 mL, 5.63 mmol) and acrylic acid methyl ester (0.465 mL, 5.16 mmol) and stirred overnight at r.t. Again acrylic acid methyl ester (0.465 mL, 5.16 mmol) is added and stirred 3 days at r.t. The reaction mixture is concentrated and the crude product is purified over silica gel (eluent: ethyl acetate).

Yield 93%, m/z 246[M+H]+, rt 0.77 min, LC-MS Method V011_S01.

Step 2: Synthesis of Intermediate I-37.2

Under argon atmosphere I-37.1 (1.09 g, 4.44 mmol) is dissolved in THF (40 mL) and cooled down to −70° C. Lithium bis(trimethylsilyl)amide 1 mol/L (9 mL, 9 mmol) is added dropwise and stirred for 4 h at −70° C. The reaction mixture is quenched with hydrochloric acid 1 mol/L (15 mL). Afterwards solid sodium carbonate (1 g) is added. The aq. layer is extracted with ethyl acetate. The organic layers are combined, dried and concentrated. The crude product is purified over silica gel (eluent: ethyl acetate). Yield 68%

Step 3: Synthesis of R106

I-37.2 (0.63 g, 2.96 mmol) and hydrochloric acid 4 mol/L (15 mL) are stirred at 100° C. overnight. The reaction mixture is diluted with water and freeze-dried. The crude product is filtered over amino phase silica gel (eluent: dichlormethane/methanol). Yield 82%

Synthesis of 5-bromo-2-methylsulfonyl-phenol (R109)

To 4-bromo-2-fluoro-1-methylsulfonyl-benzene (2 g, 7.9 mmol) in DMF (15 mL) is added 2-methanesulfonyl-ethanol (1.47 g, 11.85 mmol). Sodium hydride (948.16 mg, 23.71 mmol) is added in portions at 0° C. The reaction mixture is allowed to come to r.t. and is added dropwise into cooled aq. hydrochloric acid. The aq. layer is extracted with ethyl acetate. The organic layer is dried over MgSO$_4$, filtered and concentrated. The crude residue is purified by reversed phase HPLC. Yield 86%, m/z 251/253[M+H]+, rt 0.42 min, LC-MS Method X018_501.

EXAMPLES (rt=retention time) Deprotection Methods: TSA (toluene sulfonic acid cf. Example 1), SI (trimethylsilyl iodide cf. example 2 or 3), FA (formic acid cf. example 4 or 7), TFA (trifluoroacetic acid). Stereochemistry at the carbon atom adjacent to the nitrile group is assigned: Stereo bond means S-isomer, non-stereo bond means 1:1 mixture of stereoisomers.

TABLE 62

| Example | Structure | Educt | Syn./Deprot. Method | Yield [%] |
|---|---|---|---|---|
| 1 | 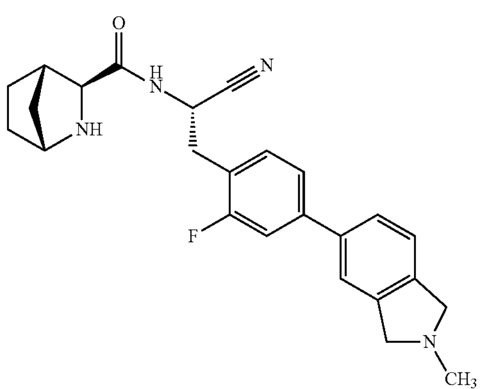 [SMILES: CN1Cc2ccc(-c3ccc(C[C@@H](C#N)NC(=O)[C@H]4N[C@@H]5CC[C@H]4C5)c(F)c3)cc2C1] | I-1.5 | A/TSA | 47 |

TABLE 62-continued

| Example | Structure | Educt | Syn./ Deprot. Method | Yield [%] |
|---|---|---|---|---|
| 2 | 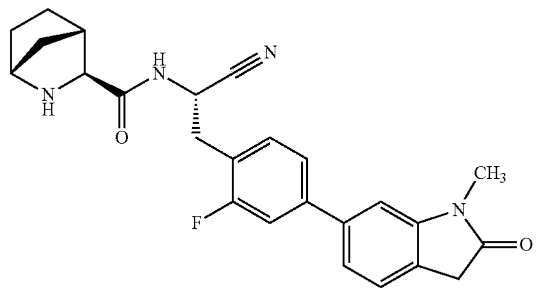 [SMILES: CN1C(=O)Cc2ccc(-c3ccc(C[C@@H](C#N)NC(=O)[C@H]4N[C@@H]5CC[C@H]4C5)c(F)c3)cc21] | I-2.3 | A1/SI | 44 |
| 3 | 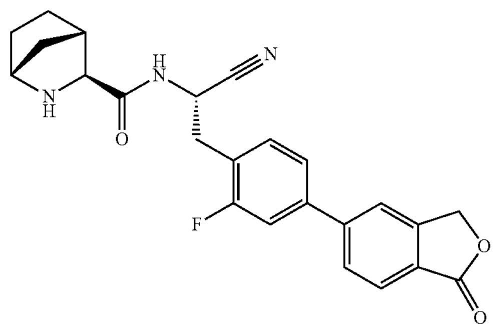 [SMILES: N#C[C@H](Cc1ccc(-c2ccc3c(c2)COC3=O)cc1F)NC(=O)[C@H]1N[C@@H]2CC[C@H]1C2] | I-3.3 | A2.1/SI | 62 |
| 4 | 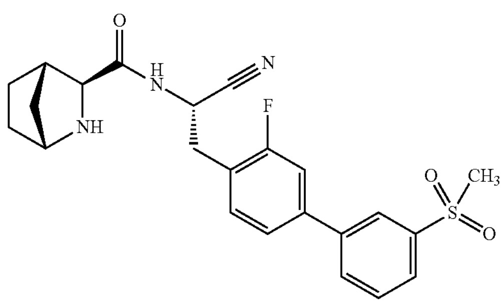 [SMILES: CS(=O)(=O)c1cccc(-c2ccc(C[C@@H](C#N)NC(=O)[C@H]3N[C@@H]4CC[C@H]3C4)c(F)c2)c1] | I-4.3 | A3/FA | 86 |
| 5 | 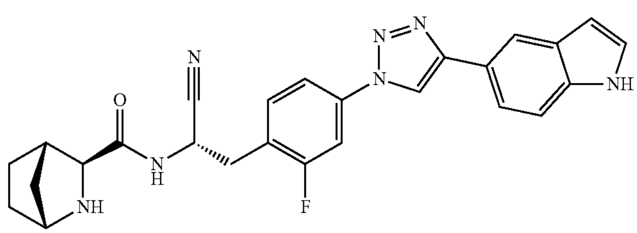 [SMILES: N#C[C@H](Cc1ccc(-n2cc(-c3ccc4[nH]ccc4c3)nn2)cc1F)NC(=O)[C@H]1N[C@@H]2CC[C@H]1C2] | I-5.2 | A4/FA | 34 |
| 6 | 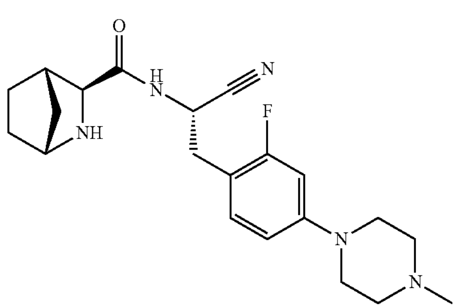 [SMILES: CN1CCN(c2ccc(C[C@@H](C#N)NC(=O)[C@H]3N[C@@H]4CC[C@H]3C4)c(F)c2)CC1] | I-6.2 | A5/TSA | 86 |

TABLE 62-continued

| Example | Structure | Educt | Syn./Deprot. Method | Yield [%] |
|---|---|---|---|---|
| 7 | 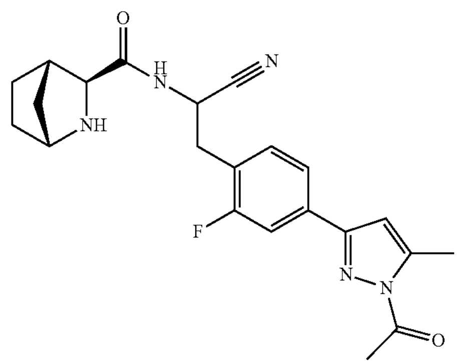 [SMILES: CC(=O)n1nc(-c2ccc(CC(C#N)NC(=O)[C@H]3N[C@@H]4CC[C@H]3C4)c(F)c2)cc1C] | I-7.3 | B/FA | 39 |
| 8 | 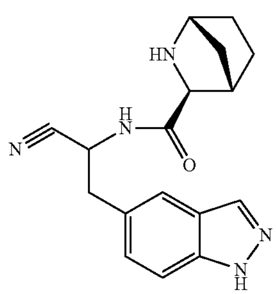 [SMILES: N#CC(Cc1ccc2[nH]ncc2c1)NC(=O)[C@H]1N[C@@H]2CC[C@H]1C2] | I-8.2 | C/SI | 19 |
| 9 | 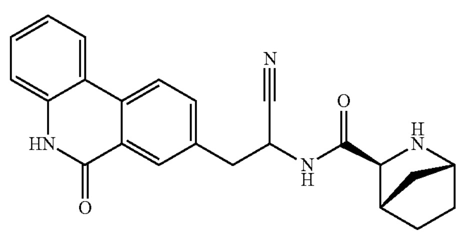 [SMILES: N#CC(Cc1ccc2c(c1)c(=O)[nH]c1ccccc12)NC(=O)[C@H]1N[C@@H]2CC[C@H]1C2] | I-9.1 | D/SI | 32 |
| 10 | 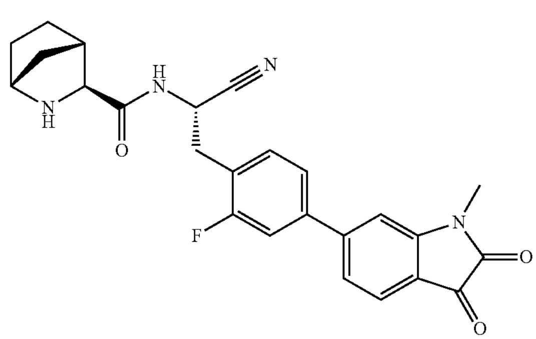 [SMILES: CN1C(=O)C(=O)c2ccc(-c3ccc(C[C@@H](C#N)NC(=O)[C@H]4N[C@@H]5CC[C@H]4C5)c(F)c3)cc21] | I-3.3.1 | A2.1/SI | 25 |

TABLE 62-continued

| Example | Structure | Educt | Syn./Deprot. Method | Yield [%] |
|---|---|---|---|---|
| 11 | 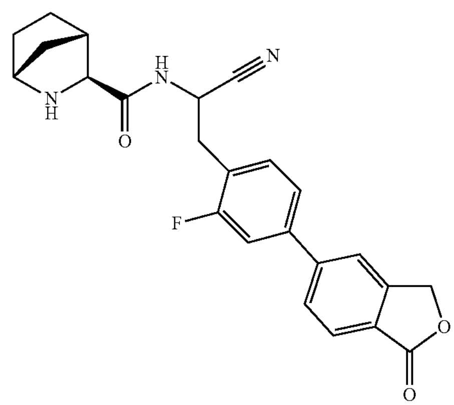 [SMILES: N#CC(Cc1ccc(-c2ccc3c(c2)COC3=O)cc1F)NC(=O)[C@H]1N[C@@H]2CC[C@H]1C2] | I-3.2.2 | A2.1/SI | 17 |
| 12 | 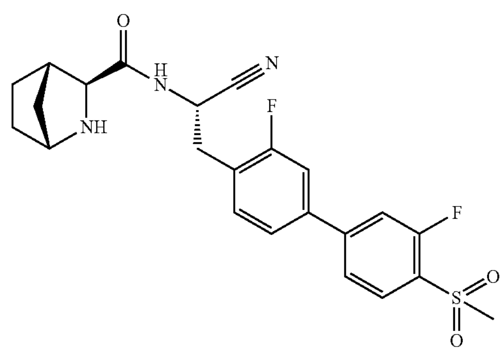 [SMILES: CS(=O)(=O)c1ccc(-c2ccc(C[C@@H](C#N)NC(=O)[C@H]3N[C@@H]4CC[C@H]3C4)c(F)c2)cc1F] | I-2.3.1 | A1/FA | 36 |
| 13 | 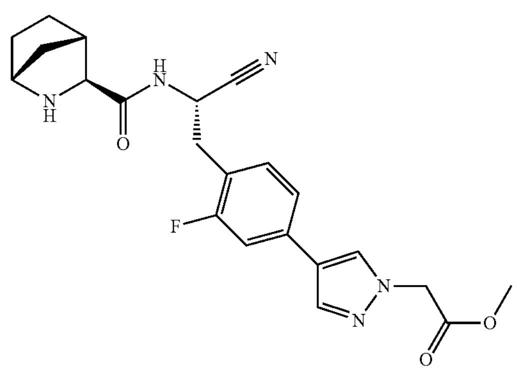 [SMILES: COC(=O)Cn1cc(-c2ccc(C[C@@H](C#N)NC(=O)[C@H]3N[C@@H]4CC[C@H]3C4)c(F)c2)cn1] | I-2.3.7.1 | A1/FA | 56 |
| 14 | 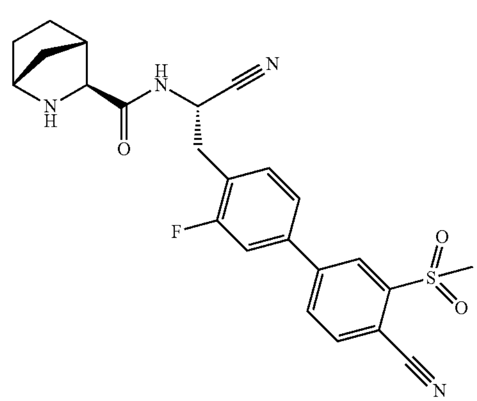 [SMILES: CS(=O)(=O)c1cc(-c2ccc(C[C@@H](C#N)NC(=O)[C@H]3N[C@@H]4CC[C@H]3C4)c(F)c2)ccc1C#N] | I-4.3.1 | A3/SI | 43 |

TABLE 62-continued

| Example | Structure | Educt | Syn./Deprot. Method | Yield [%] |
|---|---|---|---|---|
| 15 | 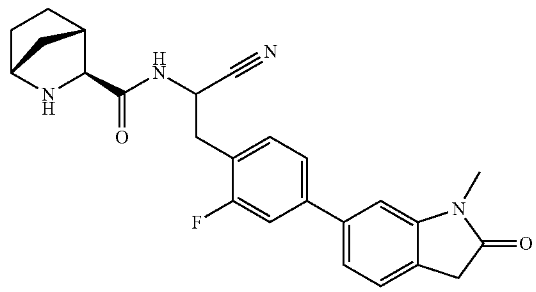 [SMILES: CN1C(=O)Cc2ccc(-c3ccc(CC(C#N)NC(=O)[C@H]4N[C@@H]5CC[C@H]4C5)c(F)c3)cc21] | I-4.3.2 | A3/SI | 21 |
| 16 | 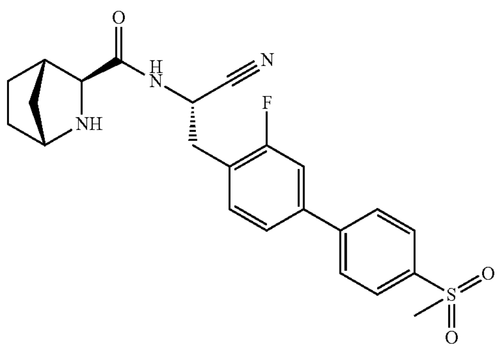 [SMILES: CS(=O)(=O)c1ccc(-c2ccc(C[C@@H](C#N)NC(=O)[C@H]3N[C@@H]4CC[C@H]3C4)c(F)c2)cc1] | I-4.3.3 | A3/TSA | 93 |
| 17 | 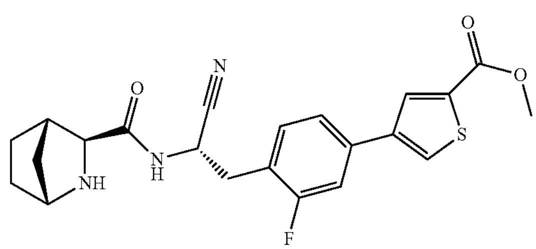 [SMILES: COC(=O)c1cc(-c2ccc(C[C@@H](C#N)NC(=O)[C@H]3N[C@@H]4CC[C@H]3C4)c(F)c2)cs1] | I-2.3.2 | A1/TSA | 16 |
| 18 | 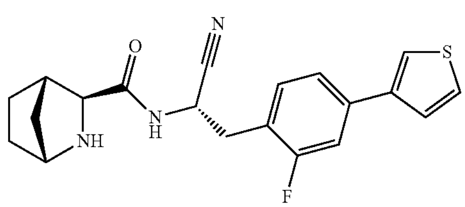 [SMILES: N#C[C@H](Cc1ccc(-c2ccsc2)cc1F)NC(=O)[C@H]1N[C@@H]2CC[C@H]1C2] | I-2.3.3 | A1/TSA | 36 |
| 19 | 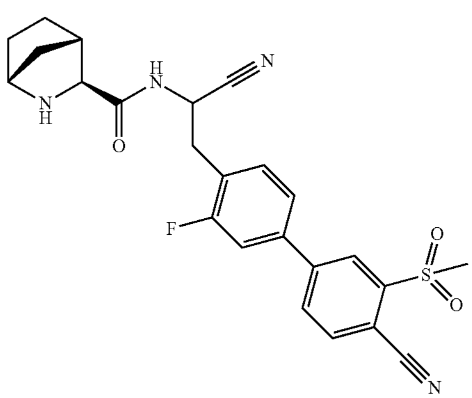 [SMILES: CS(=O)(=O)c1cc(-c2ccc(CC(C#N)NC(=O)[C@H]3N[C@@H]4CC[C@H]3C4)c(F)c2)ccc1C#N] | I-4.3.1 | A3/SI | 59 |

TABLE 62-continued

| Example | Structure | Educt | Syn./Deprot. Method | Yield [%] |
|---|---|---|---|---|
| 20 | 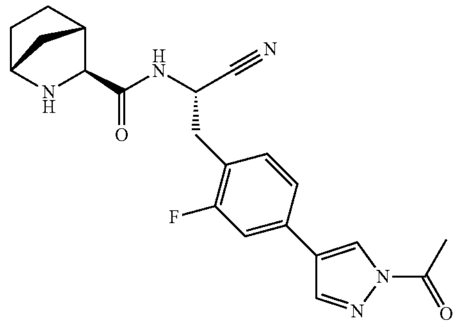 [SMILES: CC(=O)n1cc(-c2ccc(C[C@@H](C#N)NC(=O)[C@H]3N[C@@H]4CC[C@H]3C4)c(F)c2)cn1] | I-2.3.7.3 | A1/TSA | 22 |
| 21 | 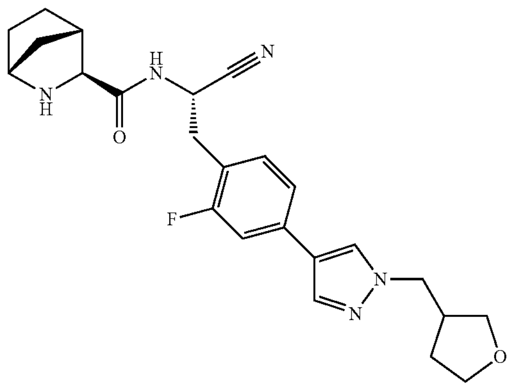 [SMILES: N#C[C@H](Cc1ccc(-c2cnn(CC3CCOC3)c2)cc1F)NC(=O)[C@H]1N[C@@H]2CC[C@H]1C2] | I-2.3.7.4 | A1/FA | 49 |
| 22 | 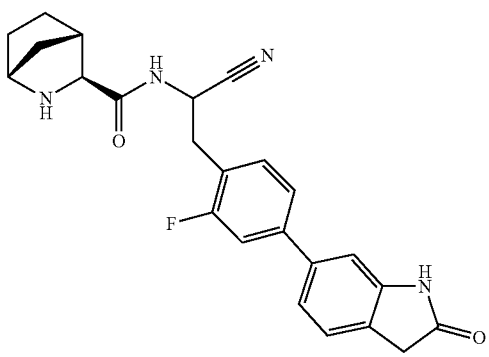 [SMILES: N#CC(Cc1ccc(-c2ccc3c(c2)NC(=O)C3)cc1F)NC(=O)[C@H]1N[C@@H]2CC[C@H]1C2] | I-4.3.5 | A3/SI | 70 |
| 23 | 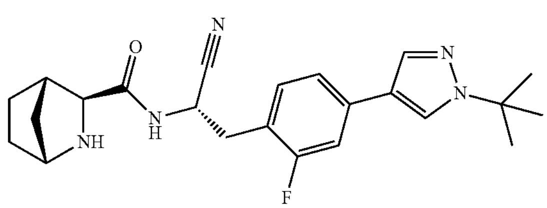 [SMILES: CC(C)(C)n1cc(-c2ccc(C[C@@H](C#N)NC(=O)[C@H]3N[C@@H]4CC[C@H]3C4)c(F)c2)cn1] | I-2.3.4 | A1/TSA | 37 |
| 24 | 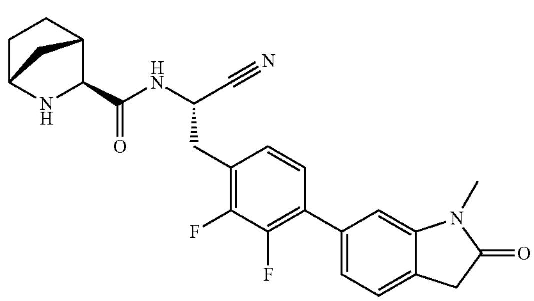 [SMILES: CN1C(=O)Cc2ccc(-c3ccc(C[C@@H](C#N)NC(=O)[C@H]4N[C@@H]5CC[C@H]4C5)c(F)c3F)cc21] | I-2.3.74.1 | A1/TFA | 45 |

TABLE 62-continued

| Example | Structure | Educt | Syn./Deprot. Method | Yield [%] |
|---|---|---|---|---|
| 25 | 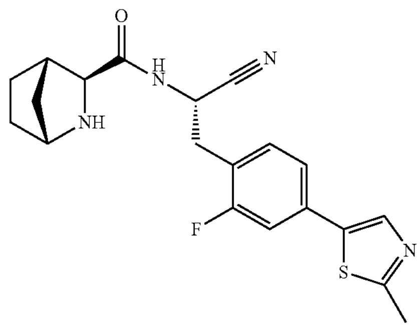 [SMILES: Cc1ncc(-c2ccc(C[C@@H](C#N)NC(=O)[C@H]3N[C@@H]4CC[C@H]3C4)c(F)c2)s1] | I-4.3.6 | A3/TSA | 45 |
| 26 | 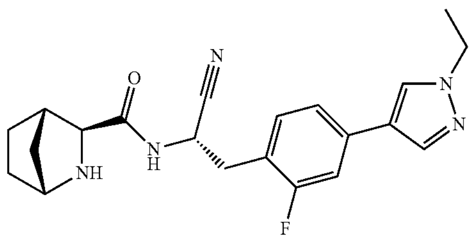 [SMILES: CCn1cc(-c2ccc(C[C@@H](C#N)NC(=O)[C@H]3N[C@@H]4CC[C@H]3C4)c(F)c2)cn1] | I-2.3.5 | A1/TSA | 49 |
| 27 | 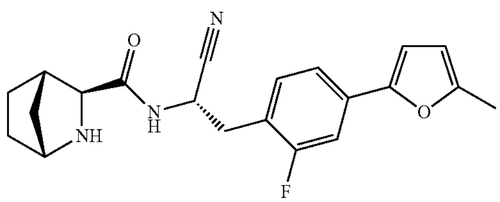 [SMILES: Cc1ccc(-c2ccc(C[C@@H](C#N)NC(=O)[C@H]3N[C@@H]4CC[C@H]3C4)c(F)c2)o1] | I-2.3.6 | A1/TSA | 38 |
| 28 | 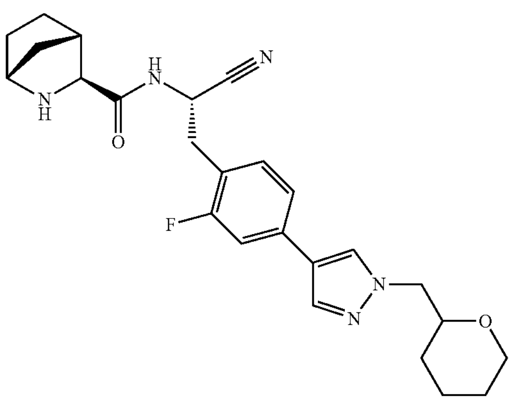 [SMILES: N#C[C@H](Cc1ccc(-c2cnn(CC3CCCCO3)c2)cc1F)NC(=O)[C@H]1N[C@@H]2CC[C@H]1C2] | I-2.3.7.5 | A1/FA | 75 |
| 29 | 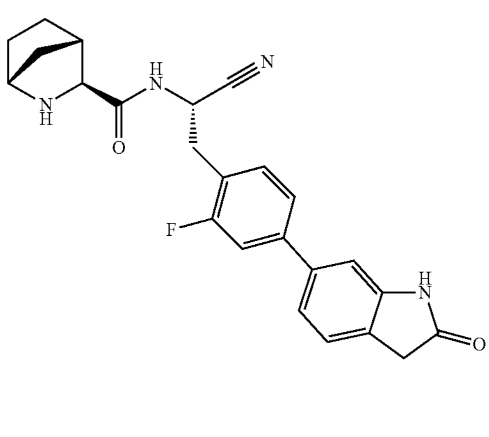 [SMILES: N#C[C@H](Cc1ccc(-c2ccc3c(c2)NC(=O)C3)cc1F)NC(=O)[C@H]1N[C@@H]2CC[C@H]1C2] | I-4.3.7 | A3/SI | 40 |

TABLE 62-continued

| Example | Structure | Educt | Syn./Deprot. Method | Yield [%] |
|---|---|---|---|---|
| 30 | 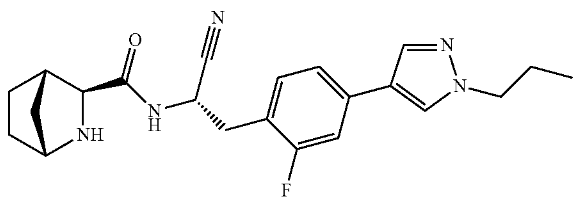 [SMILES: CCCn1cc(-c2ccc(C[C@@H](C#N)NC(=O)[C@H]3N[C@@H]4CC[C@H]3C4)c(F)c2)cn1] | I-2.3.8 | A1/TSA | 46 |
| 31 | 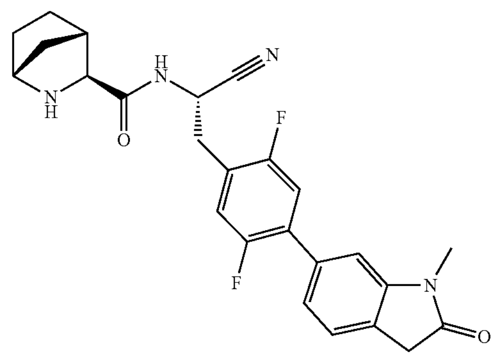 [SMILES: CN1C(=O)Cc2ccc(-c3cc(F)c(C[C@@H](C#N)NC(=O)[C@H]4N[C@@H]5CC[C@H]4C5)cc3F)cc21] | I-4.3.8 | A3/SI | 39 |
| 32 | 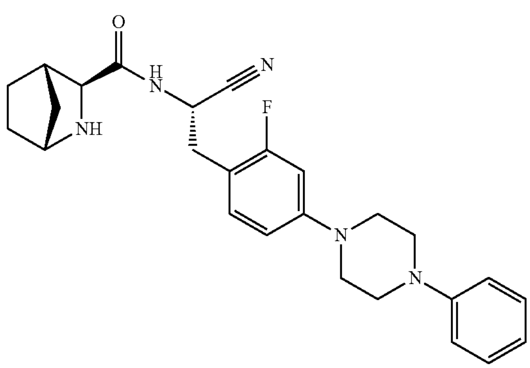 [SMILES: N#C[C@H](Cc1ccc(N2CCN(c3ccccc3)CC2)cc1F)NC(=O)[C@H]1N[C@@H]2CC[C@H]1C2] | I-3.2.4 | A2.2/TSA | 31 |
| 33 | 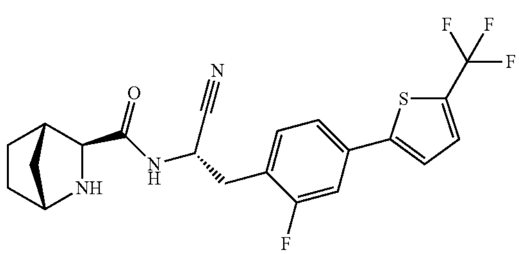 [SMILES: N#C[C@H](Cc1ccc(-c2ccc(C(F)(F)F)s2)cc1F)NC(=O)[C@H]1N[C@@H]2CC[C@H]1C2] | I-2.3.9 | A1/TSA | 16 |
| 34 | 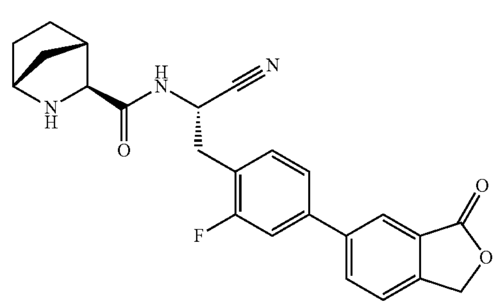 [SMILES: N#C[C@H](Cc1ccc(-c2ccc3c(c2)C(=O)OC3)cc1F)NC(=O)[C@H]1N[C@@H]2CC[C@H]1C2] | I-3.3.3 | A2.1/SI | 32 |

TABLE 62-continued

| Example | Structure | Educt | Syn./Deprot. Method | Yield [%] |
|---|---|---|---|---|
| 35 | 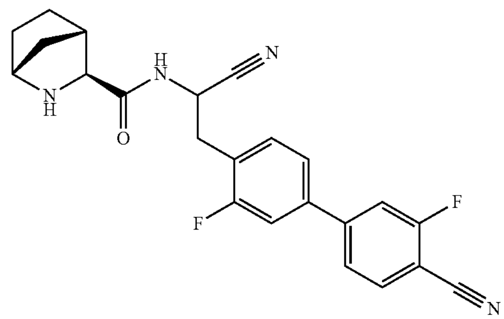 [SMILES: N#Cc1ccc(-c2ccc(CC(C#N)NC(=O)[C@H]3N[C@@H]4CC[C@H]3C4)c(F)c2)cc1F] | I-4.3.9 | A3/SI | 77 |
| 36 | 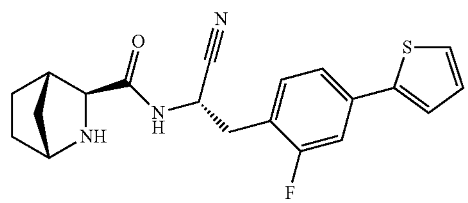 [SMILES: N#C[C@H](Cc1ccc(-c2cccs2)cc1F)NC(=O)[C@H]1N[C@@H]2CC[C@H]1C2] | I-2.3.10 | A1/TSA | 39 |
| 37 | 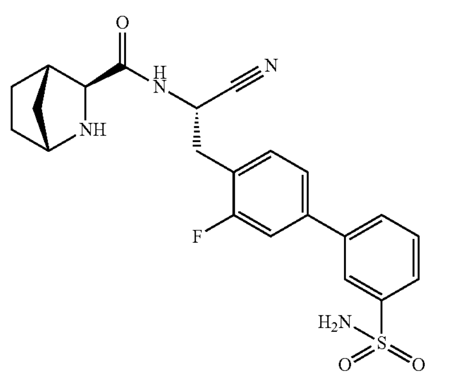 [SMILES: N#C[C@H](Cc1ccc(-c2cccc(S(N)(=O)=O)c2)cc1F)NC(=O)[C@H]1N[C@@H]2CC[C@H]1C2] | I-4.3.10 | A3/FA | 98 |
| 38 | 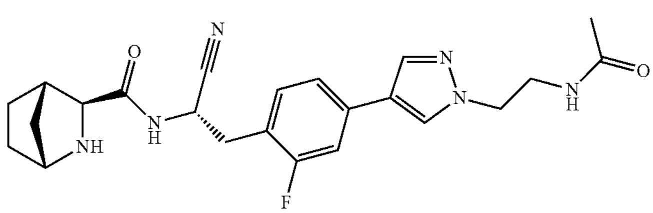 [SMILES: CC(=O)NCCn1cc(-c2ccc(C[C@@H](C#N)NC(=O)[C@H]3N[C@@H]4CC[C@H]3C4)c(F)c2)cn1] | I-2.3.11 | A1/TSA | 6 |
| 39 | 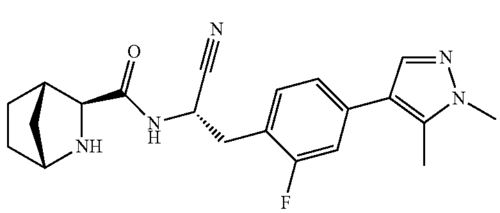 [SMILES: Cc1c(-c2ccc(C[C@@H](C#N)NC(=O)[C@H]3N[C@@H]4CC[C@H]3C4)c(F)c2)cnn1C] | I-2.3.12 | A1/TSA | 30 |

TABLE 62-continued

| Example | Structure | Educt | Syn./Deprot. Method | Yield [%] |
|---|---|---|---|---|
| 40 | 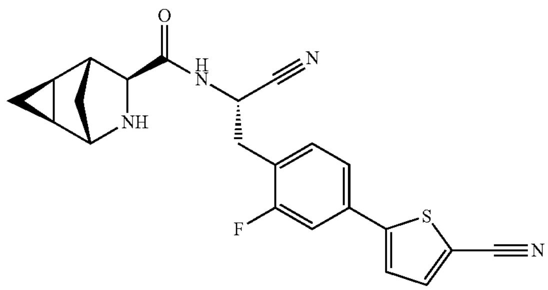 [SMILES: N#Cc1ccc(-c2ccc(C[C@@H](C#N)NC(=O)[C@H]3N[C@H]4C[C@@H]3[C@@H]3C[C@@H]34)c(F)c2)s1] | I-2.3.13 | A1/TSA | 49 |
| 41 | 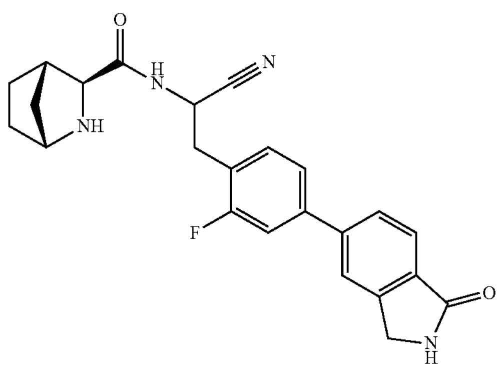 [SMILES: N#CC(Cc1ccc(-c2ccc3c(c2)CNC3=O)cc1F)NC(=O)[C@H]1N[C@@H]2CC[C@H]1C2] | I-4.3.11 | A3/FA | >95 |
| 42 | 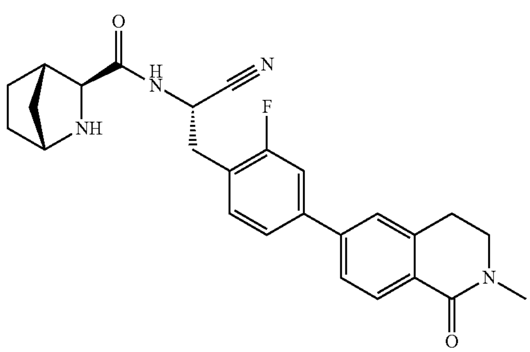 [SMILES: CN1CCc2cc(-c3ccc(C[C@@H](C#N)NC(=O)[C@H]4N[C@@H]5CC[C@H]4C5)c(F)c3)ccc2C1=O] | I-3.2.6 | A2.1/TSA | 75 |
| 43 | 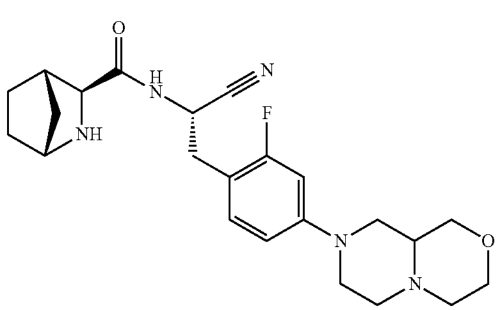 | I-3.2.7 | A2.2/TSA | 84 |

TABLE 62-continued

| Example | Structure | Educt | Syn./ Deprot. Method | Yield [%] |
|---|---|---|---|---|
| 44 | 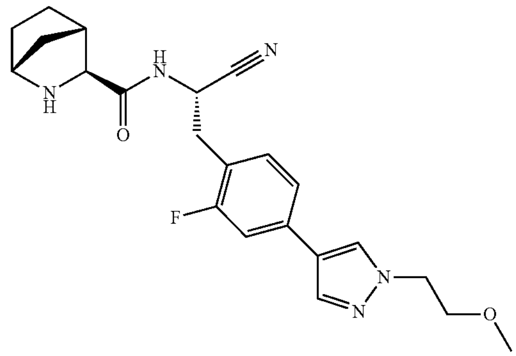 [SMILES: COCCn1cc(-c2ccc(C[C@@H](C#N)NC(=O)[C@H]3N[C@@H]4CC[C@H]3C4)c(F)c2)cn1] | I-2.3.7.6 | A1/FA | 64 |
| 45 | 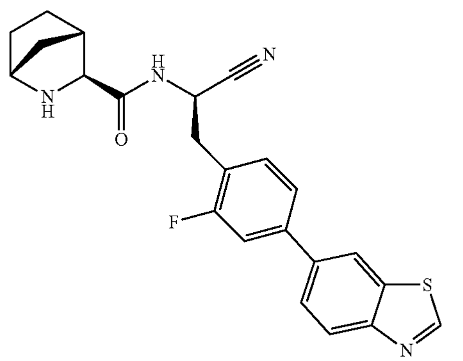 [SMILES: N#C[C@@H](Cc1ccc(-c2ccc3ncsc3c2)cc1F)NC(=O)[C@H]1N[C@@H]2CC[C@H]1C2] | I-4.3.12 | A3/SI | 58 |
| 46 | 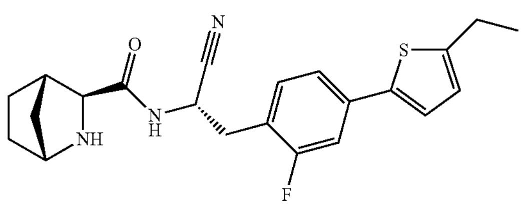 [SMILES: CCc1ccc(-c2ccc(C[C@@H](C#N)NC(=O)[C@H]3N[C@@H]4CC[C@H]3C4)c(F)c2)s1] | I-2.3.14 | A1/TSA | 12 |
| 47 | 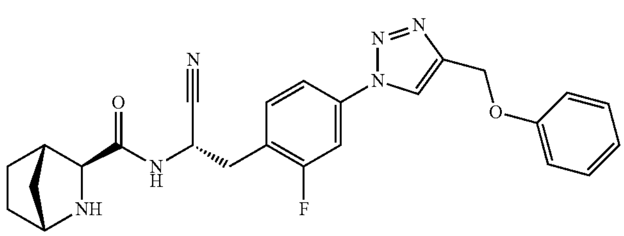 [SMILES: N#C[C@H](Cc1ccc(-n2cc(COc3ccccc3)nn2)cc1F)NC(=O)[C@H]1N[C@@H]2CC[C@H]1C2] | I-5.2 | A4/TSA | 57 |
| 48 | 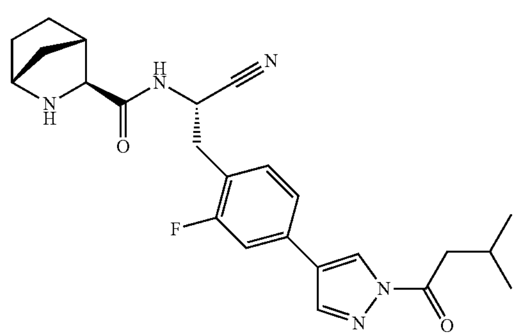 [SMILES: CC(C)CC(=O)n1cc(-c2ccc(C[C@@H](C#N)NC(=O)[C@H]3N[C@@H]4CC[C@H]3C4)c(F)c2)cn1] | I-2.3.7.7 | A1/FA | 20 |

TABLE 62-continued

| Example | Structure | Educt | Syn./Deprot. Method | Yield [%] |
|---|---|---|---|---|
| 49 | 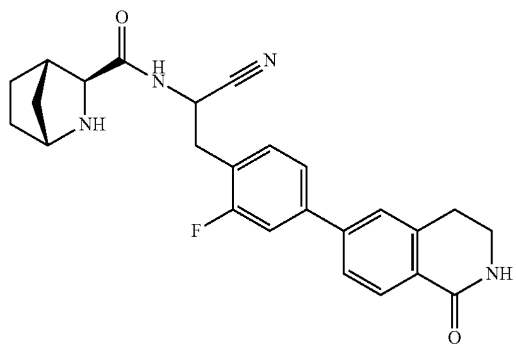 [SMILES: N#CC(Cc1ccc(-c2ccc3c(c2)CCNC3=O)cc1F)NC(=O)[C@H]1N[C@@H]2CC[C@H]1C2] | I-4.3.13 | A3/FA | 93 |
| 50 | 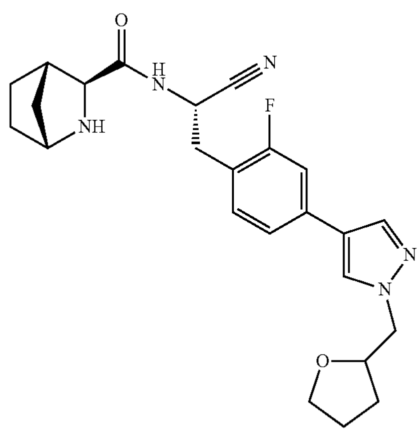 [SMILES: N#C[C@H](Cc1ccc(-c2cnn(CC3CCCO3)c2)cc1F)NC(=O)[C@H]1N[C@@H]2CC[C@H]1C2] | I-2.3.15 | A1/TSA | 31 |
| 51 | 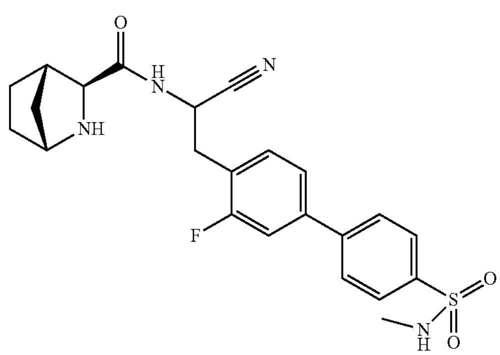 [SMILES: CNS(=O)(=O)c1ccc(-c2ccc(CC(C#N)NC(=O)[C@H]3N[C@@H]4CC[C@H]3C4)c(F)c2)cc1] | I-4.3.14 | A3/FA | 76 |
| 52 | 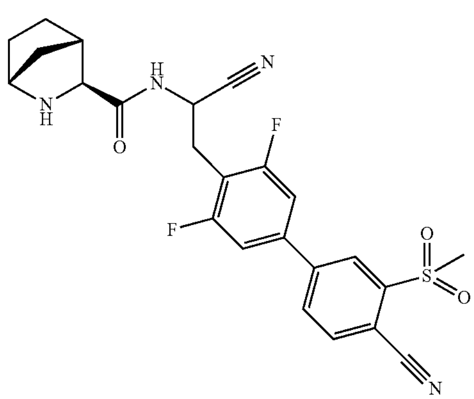 [SMILES: CS(=O)(=O)c1cc(-c2cc(F)c(CC(C#N)NC(=O)[C@H]3N[C@@H]4CC[C@H]3C4)c(F)c2)ccc1C#N] | I-4.3.4 | A3/SI | 33 |

TABLE 62-continued

| Example | Structure | Educt | Syn./Deprot. Method | Yield [%] |
|---|---|---|---|---|
| 53 | 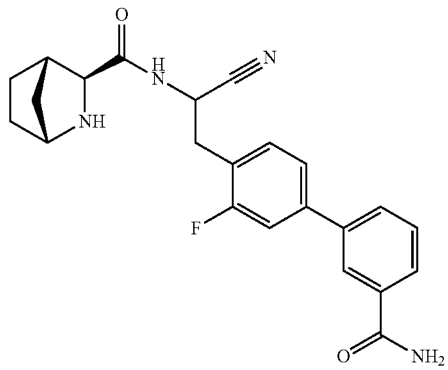 [SMILES: N#CC(Cc1ccc(-c2cccc(C(N)=O)c2)cc1F)NC(=O)[C@H]1N[C@@H]2CC[C@H]1C2] | I-4.3.16 | A3/FA | 85 |
| 54 | 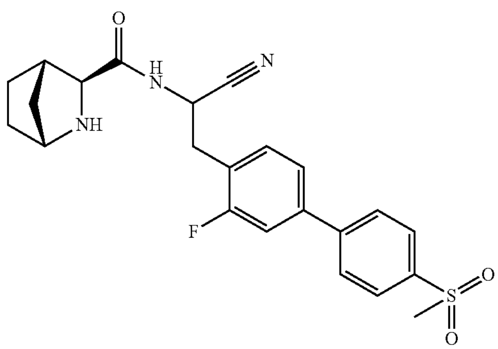 [SMILES: CS(=O)(=O)c1ccc(-c2ccc(CC(C#N)NC(=O)[C@H]3N[C@@H]4CC[C@H]3C4)c(F)c2)cc1] | I-4.3.17 | A3/FA | 96 |
| 55 | 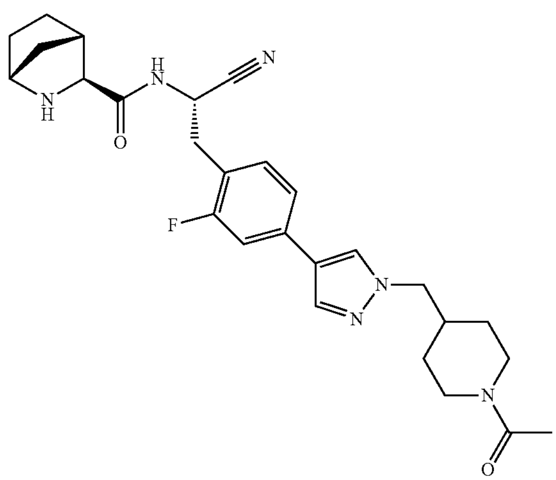 [SMILES: CC(=O)N1CCC(Cn2cc(-c3ccc(C[C@@H](C#N)NC(=O)[C@H]4N[C@@H]5CC[C@H]4C5)c(F)c3)cn2)CC1] | I-2.3.7.8 | A1/FA | 71 |
| 56 | 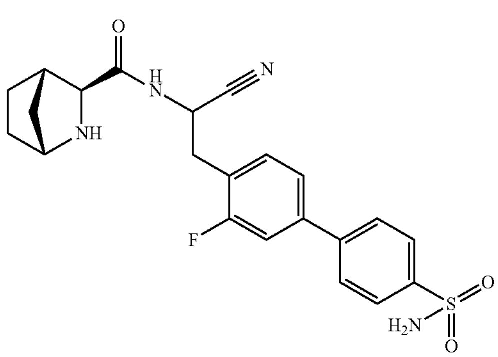 [SMILES: N#CC(Cc1ccc(-c2ccc(S(N)(=O)=O)cc2)cc1F)NC(=O)[C@H]1N[C@@H]2CC[C@H]1C2] | I-4.3.18 | A3/FA | 67 |

TABLE 62-continued

| Example | Structure | Educt | Syn./Deprot. Method | Yield [%] |
|---|---|---|---|---|
| 57 | 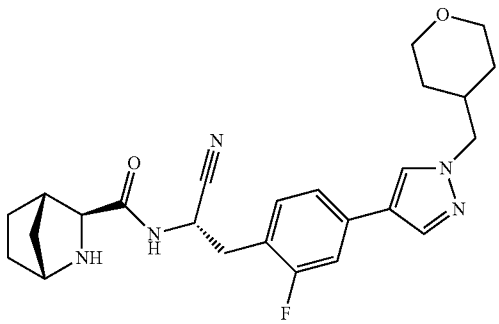 [SMILES: N#C[C@H](Cc1ccc(-c2cnn(CC3CCOCC3)c2)cc1F)NC(=O)[C@H]1N[C@@H]2CC[C@H]1C2] | I-2.3.16 | A1/TSA | 38 |
| 58 | 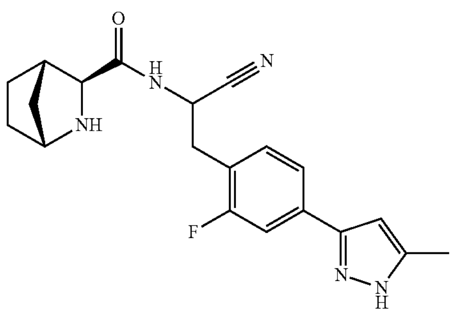 [SMILES: Cc1cc(-c2ccc(CC(C#N)NC(=O)[C@H]3N[C@@H]4CC[C@H]3C4)c(F)c2)n[nH]1] | I-7.3 | B/FA | 90 |
| 59 | 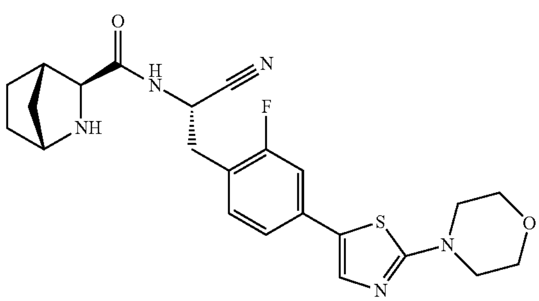 [SMILES: N#C[C@H](Cc1ccc(-c2cnc(N3CCOCC3)s2)cc1F)NC(=O)[C@H]1N[C@@H]2CC[C@H]1C2] | I-2.3.17 | A1/FA | 37 |
| 60 | 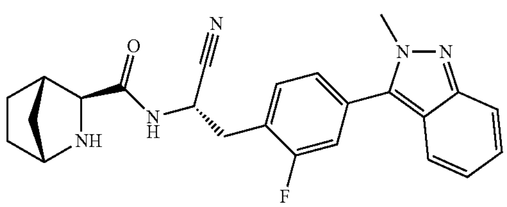 [SMILES: Cn1nc2ccccc2c1-c1ccc(C[C@@H](C#N)NC(=O)[C@H]2N[C@@H]3CC[C@H]2C3)c(F)c1] | I-2.3.18 | A1/TSA | 33 |
| 61 | 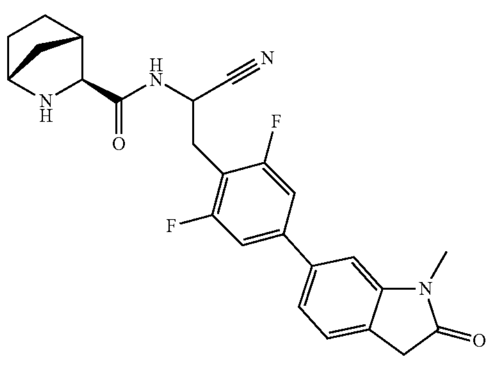 [SMILES: CN1C(=O)Cc2ccc(-c3cc(F)c(CC(C#N)NC(=O)[C@H]4N[C@@H]5CC[C@H]4C5)c(F)c3)cc21] | I-4.3.15 | A3/SI | 47 |

TABLE 62-continued

| Example | Structure | Educt | Syn./Deprot. Method | Yield [%] |
|---|---|---|---|---|
| 62 | 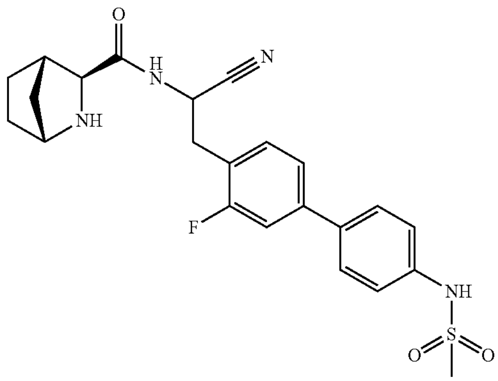 [SMILES: CS(=O)(=O)Nc1ccc(-c2ccc(CC(C#N)NC(=O)[C@H]3N[C@@H]4CC[C@H]3C4)c(F)c2)cc1] | I-4.3.20 | A3/FA | 91 |
| 63 | 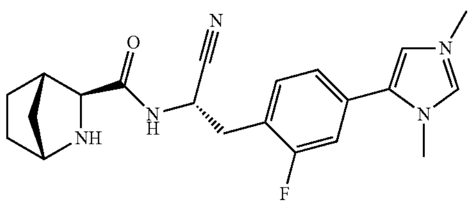 | I-2.3.19 | A1/TSA | 19 |
| 64 | 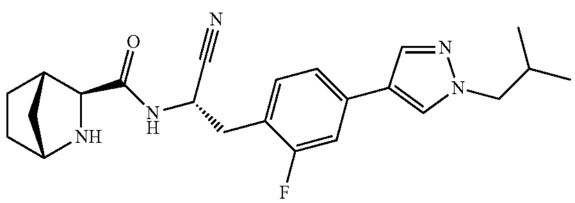 [SMILES: CC(C)Cn1cc(-c2ccc(C[C@@H](C#N)NC(=O)[C@H]3N[C@@H]4CC[C@H]3C4)c(F)c2)cn1] | I-2.3.20 | A1/TSA | 48 |
| 65 | 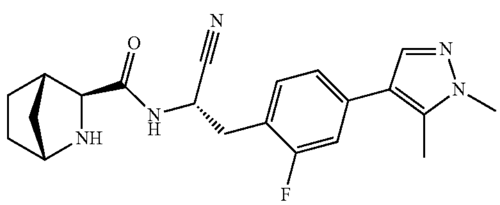 [SMILES: Cc1c(-c2ccc(C[C@@H](C#N)NC(=O)[C@H]3N[C@@H]4CC[C@H]3C4)c(F)c2)cnn1C] | I-2.3.21 | A1/TSA | 6 |
| 66 | 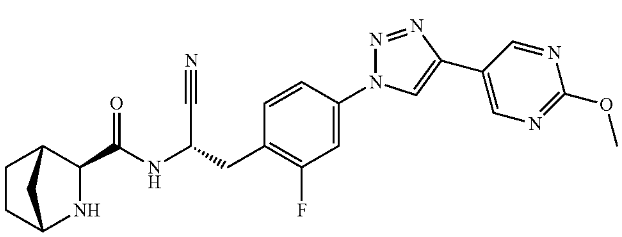 [SMILES: COc1ncc(-c2cn(-c3ccc(C[C@@H](C#N)NC(=O)[C@H]4N[C@@H]5CC[C@H]4C5)c(F)c3)nn2)cn1] | I-5.2 | A4/TSA | 23 |
| 67 | 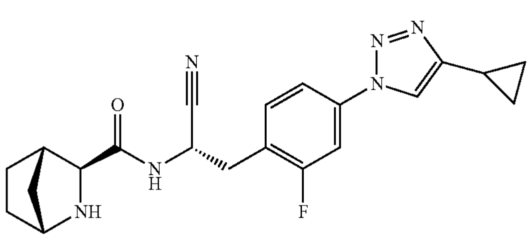 [SMILES: N#C[C@H](Cc1ccc(-n2cc(C3CC3)nn2)cc1F)NC(=O)[C@H]1N[C@@H]2CC[C@H]1C2] | I-5.2 | A4/TSA | 53 |

TABLE 62-continued

| Example | Structure | Educt | Syn./Deprot. Method | Yield [%] |
|---|---|---|---|---|
| 68 | 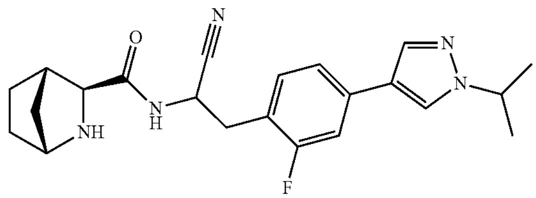 [SMILES: CC(C)n1cc(-c2ccc(CC(C#N)NC(=O)[C@H]3N[C@@H]4CC[C@H]3C4)c(F)c2)cn1] | I-2.3.22 | A1/TSA | 17 |
| 69 | 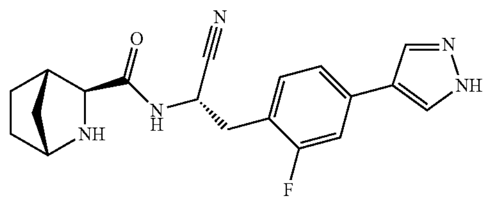 [SMILES: N#C[C@H](Cc1ccc(-c2cn[nH]c2)cc1F)NC(=O)[C@H]1N[C@@H]2CC[C@H]1C2] | I-2.3.23 | A1/TSA | 19 |
| 70 | 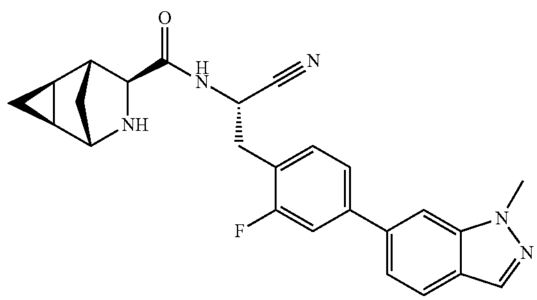 [SMILES: Cn1ncc2ccc(-c3ccc(C[C@@H](C#N)NC(=O)[C@H]4N[C@H]5C[C@@H]4[C@@H]4C[C@@H]45)c(F)c3)cc21] | I-2.3.24 | A1/TSA | 58 |
| 71 | 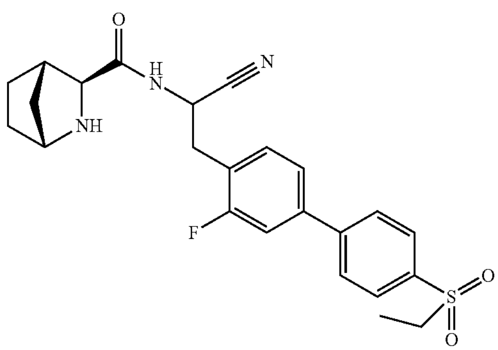 [SMILES: CCS(=O)(=O)c1ccc(-c2ccc(CC(C#N)NC(=O)[C@H]3N[C@@H]4CC[C@H]3C4)c(F)c2)cc1] | I-4.3.21 | A3/FA | >95 |
| 72 | 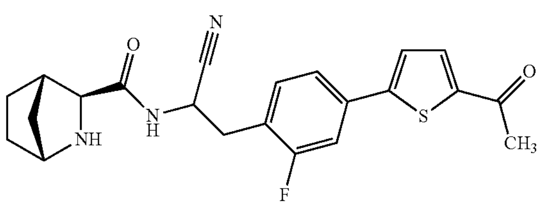 [SMILES: CC(=O)c1ccc(-c2ccc(CC(C#N)NC(=O)[C@H]3N[C@@H]4CC[C@H]3C4)c(F)c2)s1] | I-2.3.25 | A1/TSA | 13 |
| 73 | 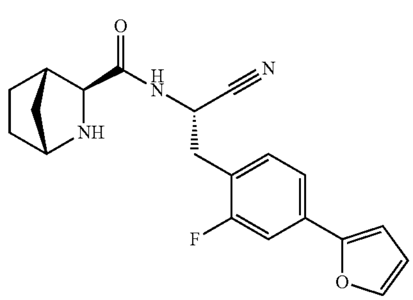 [SMILES: N#C[C@H](Cc1ccc(-c2ccco2)cc1F)NC(=O)[C@H]1N[C@@H]2CC[C@H]1C2] | I-2.3.26 | A1/TSA | 53 |

TABLE 62-continued

| Example | Structure | Educt | Syn./Deprot. Method | Yield [%] |
|---|---|---|---|---|
| 74 | 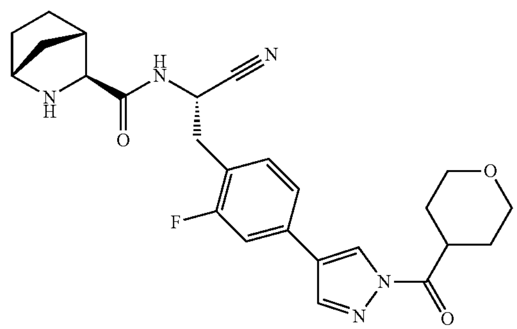 [SMILES: N#C[C@H](Cc1ccc(-c2cnn(C(=O)C3CCOCC3)c2)cc1F)NC(=O)[C@H]1N[C@@H]2CC[C@H]1C2] | I-2.3.7.9 | A1/TSA | 41 |
| 75 | 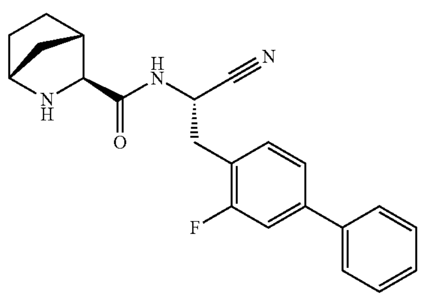 [SMILES: N#C[C@H](Cc1ccc(-c2ccccc2)cc1F)NC(=O)[C@H]1N[C@@H]2CC[C@H]1C2] | I-3.3.4 | A2.1/SI | 4 |
| 76 | 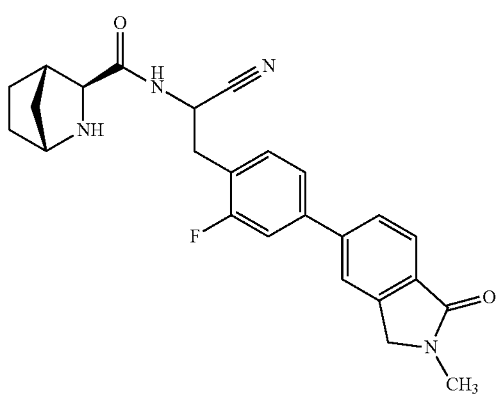 [SMILES: CN1Cc2cc(-c3ccc(CC(C#N)NC(=O)[C@H]4N[C@@H]5CC[C@H]4C5)c(F)c3)ccc2C1=O] | I-4.3.22 | A3/FA | 89 |
| 77 | 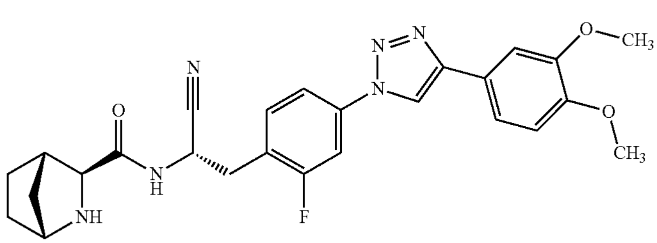 [SMILES: COc1ccc(-c2cn(-c3ccc(C[C@@H](C#N)NC(=O)[C@H]4N[C@@H]5CC[C@H]4C5)c(F)c3)nn2)cc1OC] | I-5.2 | A4/TSA | 40 |
| 78 | 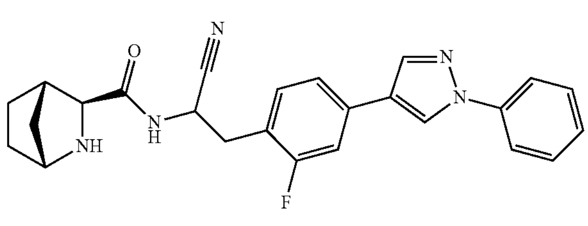 [SMILES: N#CC(Cc1ccc(-c2cnn(-c3ccccc3)c2)cc1F)NC(=O)[C@H]1N[C@@H]2CC[C@H]1C2] | I-2.3.27 | A1/TSA | 7 |

TABLE 62-continued
| Example | Structure | Educt | Syn./Deprot. Method | Yield [%] |
|---|---|---|---|---|
| 79 | 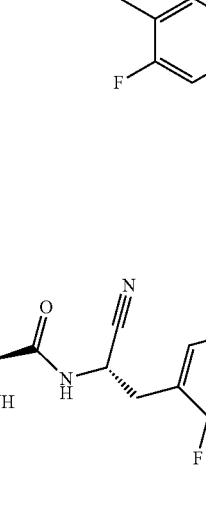 | I-4.3.23 | A3/FA | 80 |
| 80 | 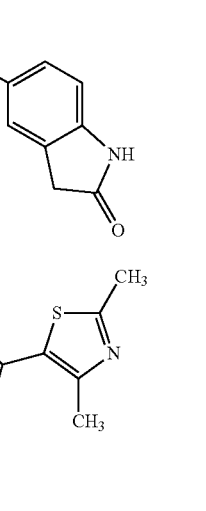 | I-2.3.28 | A1/TSA | 24 |
| 81 | 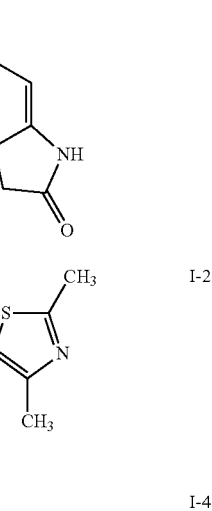 | I-4.3.24 | A3/SI | 31 |
| 82 | 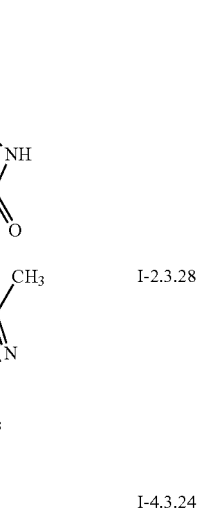 | I-5.2 | A4/TSA | 44 |
| 83 | 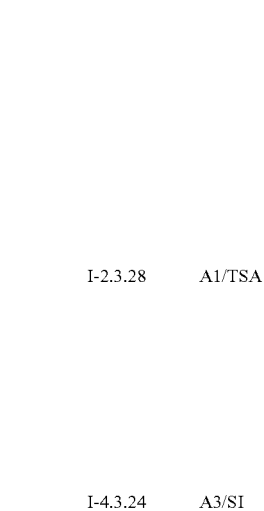 | I-4.3.25 | A3/FA | >95 |

TABLE 62-continued

| Example | Structure | Educt | Syn./Deprot. Method | Yield [%] |
|---|---|---|---|---|
| 84 | 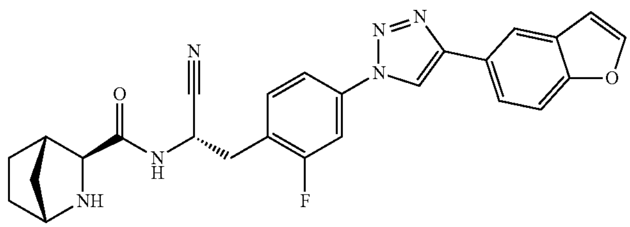 [SMILES: N#C[C@H](Cc1ccc(-n2cc(-c3ccc4occc4c3)nn2)cc1F)NC(=O)[C@H]1N[C@@H]2CC[C@H]1C2] | I-5.2 | A4/TSA | 46 |
| 85 | 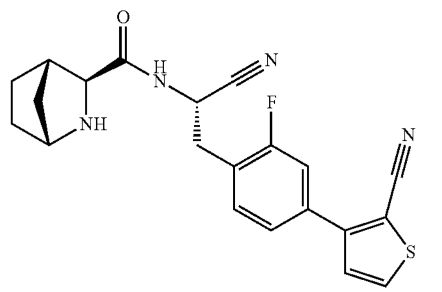 [SMILES: N#Cc1sccc1-c1ccc(C[C@@H](C#N)NC(=O)[C@H]2N[C@@H]3CC[C@H]2C3)c(F)c1] | I-2.3.29 | A1/FA | 60 |
| 86 | 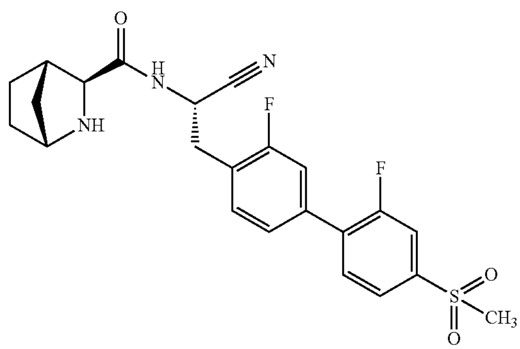 [SMILES: CS(=O)(=O)c1ccc(-c2ccc(C[C@@H](C#N)NC(=O)[C@H]3N[C@@H]4CC[C@H]3C4)c(F)c2)c(F)c1] | I-2.3.30 | A1/FA | 63 |
| 87 | 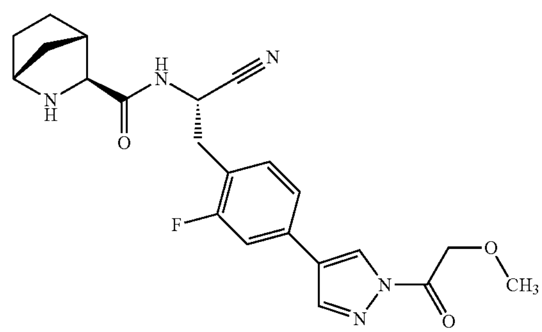 [SMILES: COCC(=O)n1cc(-c2ccc(C[C@@H](C#N)NC(=O)[C@H]3N[C@@H]4CC[C@H]3C4)c(F)c2)cn1] | I-2.3.7.10 | A1/TSA | 8 |
| 88 | 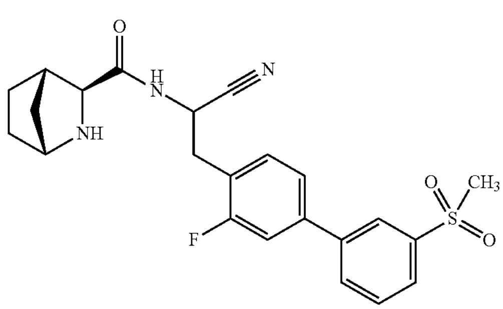 [SMILES: CS(=O)(=O)c1cccc(-c2ccc(CC(C#N)NC(=O)[C@H]3N[C@@H]4CC[C@H]3C4)c(F)c2)c1] | I-4.3.26 | A3/FA | 52 |

TABLE 62-continued

| Example | Structure | Educt | Syn./Deprot. Method | Yield [%] |
|---|---|---|---|---|
| 89 | 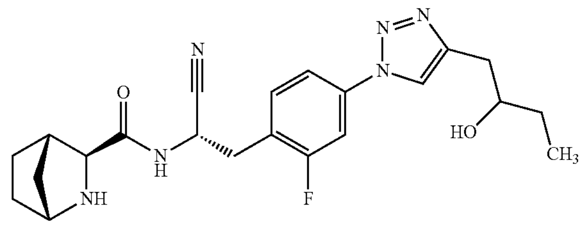 [SMILES: CCC(O)Cc1cn(-c2ccc(C[C@@H](C#N)NC(=O)[C@H]3N[C@@H]4CC[C@H]3C4)c(F)c2)nn1] | I-5.2 | A4/TSA | 48 |
| 90 | 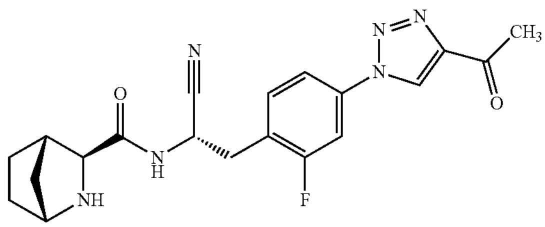 [SMILES: CC(=O)c1cn(-c2ccc(C[C@@H](C#N)NC(=O)[C@H]3N[C@@H]4CC[C@H]3C4)c(F)c2)nn1] | I-5.2 | A4/TSA | 77 |
| 91 | 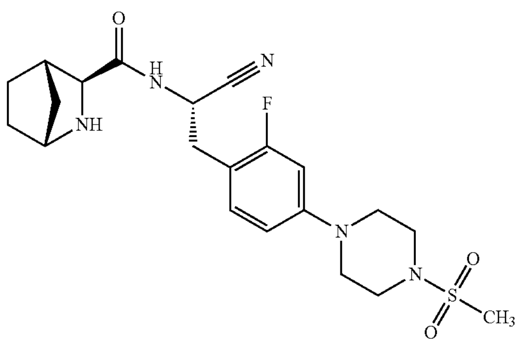 [SMILES: CS(=O)(=O)N1CCN(c2ccc(C[C@@H](C#N)NC(=O)[C@H]3N[C@@H]4CC[C@H]3C4)c(F)c2)CC1] | I-3.2.9 | A2.2/TSA | 92 |
| 92 | 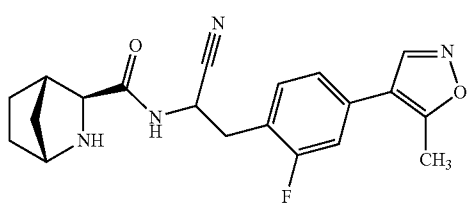 [SMILES: Cc1oncc1-c1ccc(CC(C#N)NC(=O)[C@H]2N[C@@H]3CC[C@H]2C3)c(F)c1] | I-2.3.31 | A1/TSA | 14 |
| 93 | 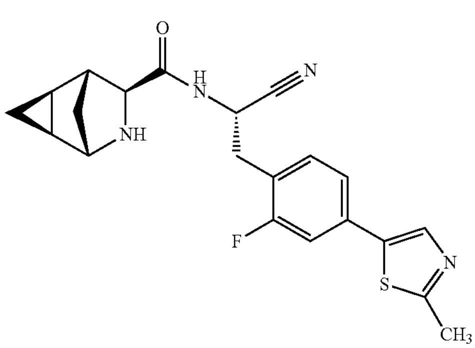 [SMILES: Cc1ncc(-c2ccc(C[C@@H](C#N)NC(=O)[C@H]3N[C@H]4C[C@@H]3[C@@H]3C[C@@H]34)c(F)c2)s1] | I-2.3.32 | A1/TSA | 54 |

TABLE 62-continued

| Example | Structure | Educt | Syn./Deprot. Method | Yield [%] |
|---|---|---|---|---|
| 94 | 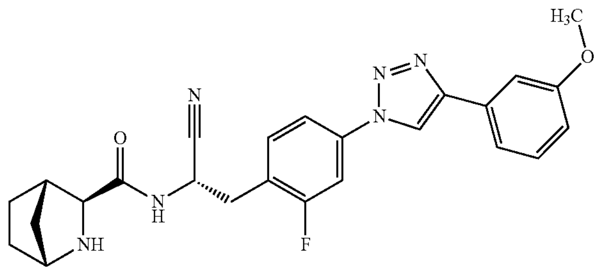 [SMILES: COc1cccc(-c2cn(-c3ccc(C[C@@H](C#N)NC(=O)[C@H]4N[C@@H]5CC[C@H]4C5)c(F)c3)nn2)c1] | I-5.2 | A4/TSA | 80 |
| 95 | 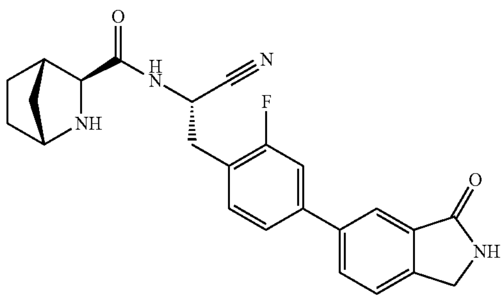 [SMILES: N#C[C@H](Cc1ccc(-c2ccc3c(c2)C(=O)NC3)cc1F)NC(=O)[C@H]1N[C@@H]2CC[C@H]1C2] | I-3.2.10 | A2.1/TSA | 53 |
| 96 | 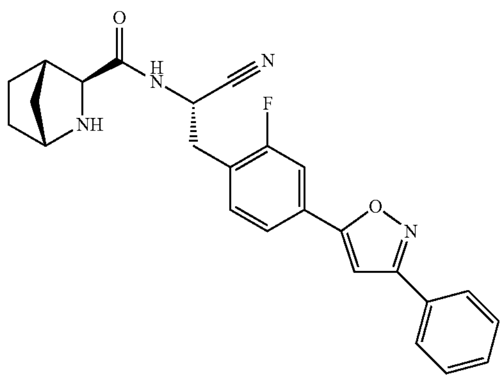 [SMILES: N#C[C@H](Cc1ccc(-c2cc(-c3ccccc3)no2)cc1F)NC(=O)[C@H]1N[C@@H]2CC[C@H]1C2] | I-2.3.33 | A1/FA | 87 |
| 97 | 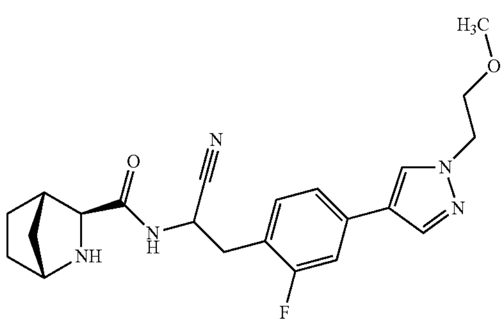 [SMILES: COCCn1cc(-c2ccc(CC(C#N)NC(=O)[C@H]3N[C@@H]4CC[C@H]3C4)c(F)c2)cn1] | I-2.3.34 | A1/TSA | 22 |
| 98 | 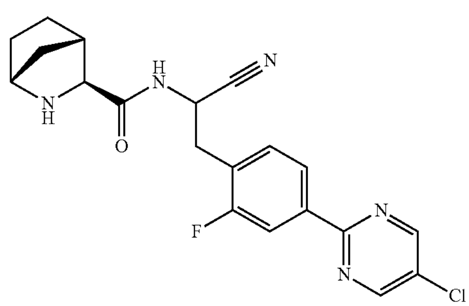 [SMILES: N#CC(Cc1ccc(-c2ncc(Cl)cn2)cc1F)NC(=O)[C@H]1N[C@@H]2CC[C@H]1C2] | I-3.2.11 | A2.1/SI | 83 |

TABLE 62-continued

| Example | Structure | Educt | Syn./Deprot. Method | Yield [%] |
|---|---|---|---|---|
| 99 | 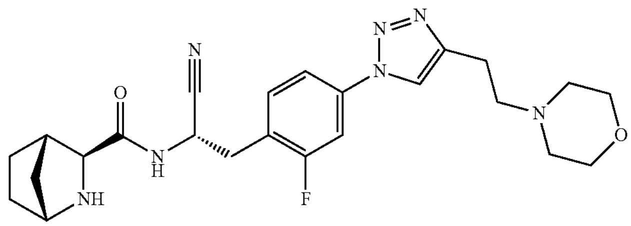 [SMILES: N#C[C@H](Cc1ccc(-n2cc(CCN3CCOCC3)nn2)cc1F)NC(=O)[C@H]1N[C@@H]2CC[C@H]1C2] | I-5.2 | A4/TSA | 34 |
| 100 | 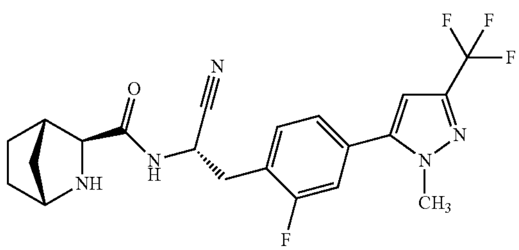 [SMILES: Cn1nc(C(F)(F)F)cc1-c1ccc(C[C@@H](C#N)NC(=O)[C@H]2N[C@@H]3CC[C@H]2C3)c(F)c1] | I-2.3.35 | A1/TSA | 16 |
| 101 | 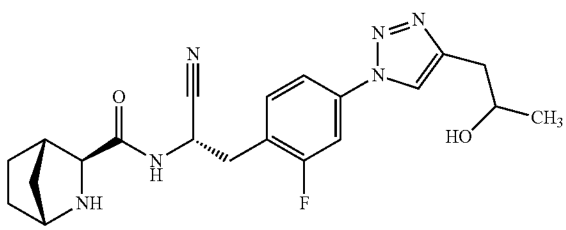 [SMILES: CC(O)Cc1cn(-c2ccc(C[C@@H](C#N)NC(=O)[C@H]3N[C@@H]4CC[C@H]3C4)c(F)c2)nn1] | I-5.2 | A4/TSA | 48 |
| 102 | 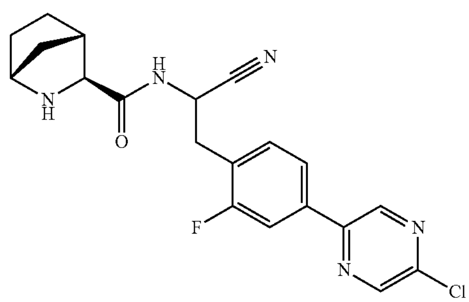 [SMILES: N#CC(Cc1ccc(-c2cnc(Cl)cn2)cc1F)NC(=O)[C@H]1N[C@@H]2CC[C@H]1C2] | I-3.2.12 | A2.1/SI | 29 |
| 103 | 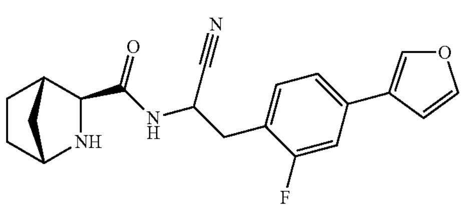 | I-2.3.36 | A1/TSA | 17 |
| 104 | 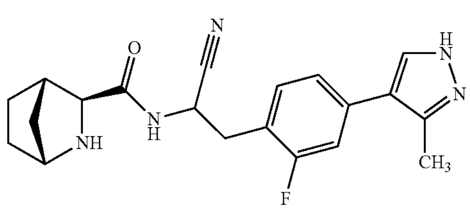 [SMILES: Cc1n[nH]cc1-c1ccc(CC(C#N)NC(=O)[C@H]2N[C@@H]3CC[C@H]2C3)c(F)c1] | I-2.3.37 | A1/TSA | 8 |

TABLE 62-continued

| Example | Structure | Educt | Syn./Deprot. Method | Yield [%] |
|---|---|---|---|---|
| 105 | 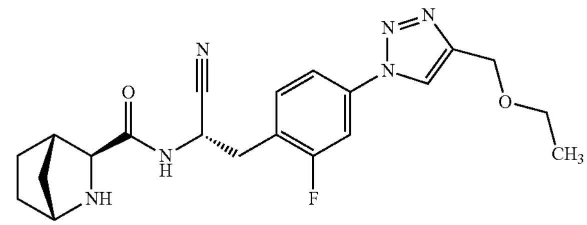 [SMILES: CCOCc1cn(-c2ccc(C[C@@H](C#N)NC(=O)[C@H]3N[C@@H]4CC[C@H]3C4)c(F)c2)nn1] | I-5.2 | A4/TSA/TSA | 26 |
| 106 | 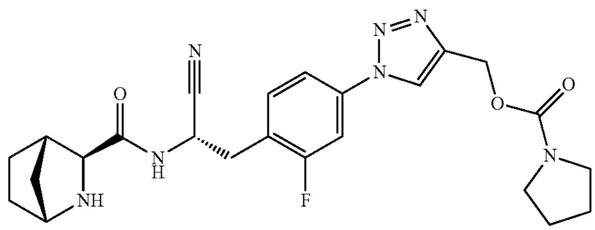 [SMILES: N#C[C@H](Cc1ccc(-n2cc(COC(=O)N3CCCC3)nn2)cc1F)NC(=O)[C@H]1N[C@@H]2CC[C@H]1C2] | I-5.2 | A4/TSA | 30 |
| 107 | 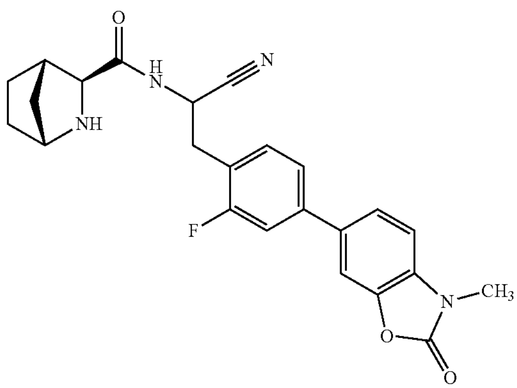 [SMILES: Cn1c(=O)oc2cc(-c3ccc(CC(C#N)NC(=O)[C@H]4N[C@@H]5CC[C@H]4C5)c(F)c3)ccc21] | I-4.3.27 | A3/FA | 80 |
| 108 | 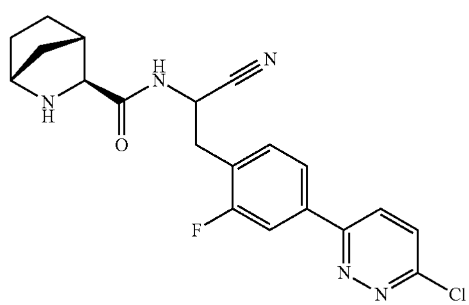 [SMILES: N#CC(Cc1ccc(-c2ccc(Cl)nn2)cc1F)NC(=O)[C@H]1N[C@@H]2CC[C@H]1C2] | I-3.2.13 | A2.1/SI | 42 |
| 109 | 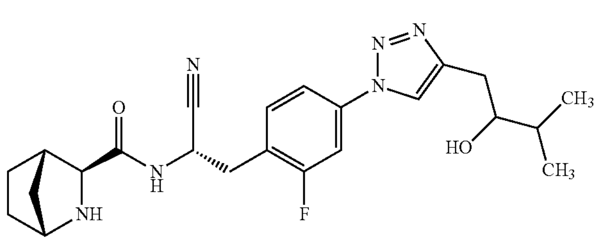 [SMILES: CC(C)C(O)Cc1cn(-c2ccc(C[C@@H](C#N)NC(=O)[C@H]3N[C@@H]4CC[C@H]3C4)c(F)c2)nn1] | I-5.2 | A4/TSA | 41 |

TABLE 62-continued

| Example | Structure | Educt | Syn./Deprot. Method | Yield [%] |
|---|---|---|---|---|
| 110 | 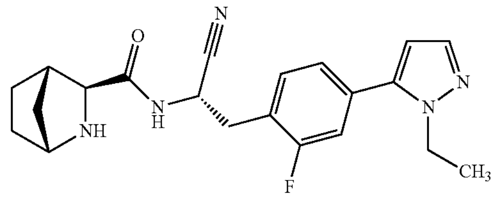 [SMILES: CCn1nccc1-c1ccc(C[C@@H](C#N)NC(=O)[C@H]2N[C@@H]3CC[C@H]2C3)c(F)c1] | I-2.3.38 | A1/TSA | 21 |
| 111 | 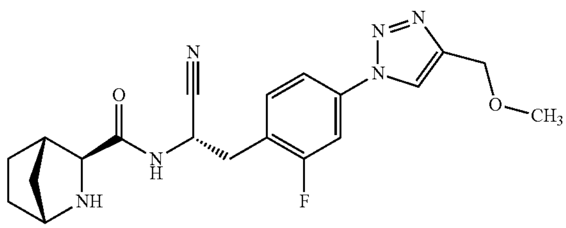 [SMILES: COCc1cn(-c2ccc(C[C@@H](C#N)NC(=O)[C@H]3N[C@@H]4CC[C@H]3C4)c(F)c2)nn1] | I-5.2 | A4/TSA | 84 |
| 112 | 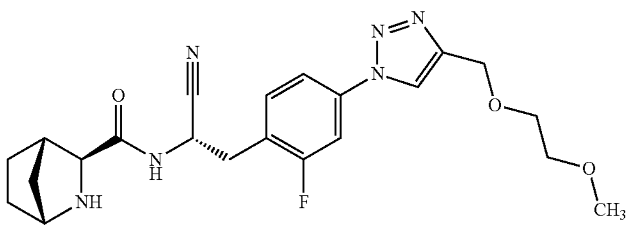 [SMILES: COCCOCc1cn(-c2ccc(C[C@@H](C#N)NC(=O)[C@H]3N[C@@H]4CC[C@H]3C4)c(F)c2)nn1] | I-5.2 | A4/TSA | 22 |
| 113 | 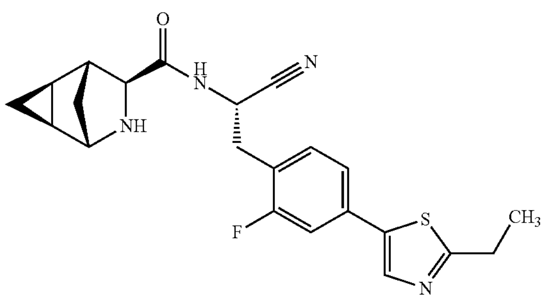 [SMILES: CCc1ncc(-c2ccc(C[C@@H](C#N)NC(=O)[C@H]3N[C@H]4C[C@@H]3[C@@H]3C[C@@H]34)c(F)c2)s1] | I-2.3.39 | A1/TSA | 45 |
| 114 | 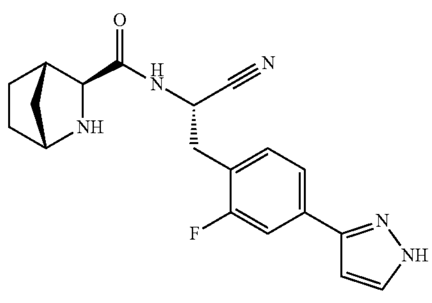 [SMILES: N#C[C@H](Cc1ccc(-c2cc[nH]n2)cc1F)NC(=O)[C@H]1N[C@@H]2CC[C@H]1C2] | I-2.3.40 | A1/TSA | 53 |
| 115 | 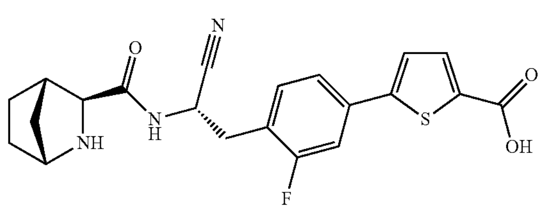 [SMILES: N#C[C@H](Cc1ccc(-c2ccc(C(=O)O)s2)cc1F)NC(=O)[C@H]1N[C@@H]2CC[C@H]1C2] | I-2.3.41 | A1/TSA | 30 |

TABLE 62-continued

| Example | Structure | Educt | Syn./Deprot. Method | Yield [%] |
|---|---|---|---|---|
| 116 | 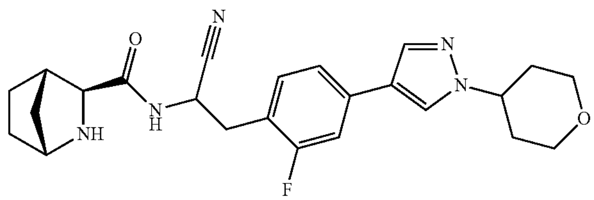 [SMILES: N#CC(Cc1ccc(-c2cnn(C3CCOCC3)c2)cc1F)NC(=O)[C@H]1N[C@@H]2CC[C@H]1C2] | I-2.3.42 | A1/TSA | 8 |
| 117 | 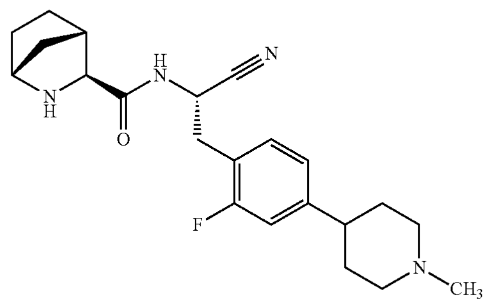 [SMILES: CN1CCC(c2ccc(C[C@@H](C#N)NC(=O)[C@H]3N[C@@H]4CC[C@H]3C4)c(F)c2)CC1] | I-2.3.43.1 | A1/SI | 57 |
| 118 | 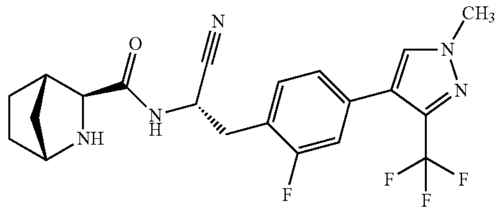 [SMILES: Cn1cc(-c2ccc(C[C@@H](C#N)NC(=O)[C@H]3N[C@@H]4CC[C@H]3C4)c(F)c2)c(C(F)(F)F)n1] | I-2.3.44 | A1/TSA | 40 |
| 119 | 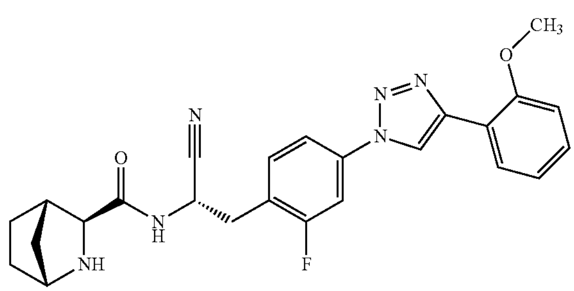 [SMILES: COc1ccccc1-c1cn(-c2ccc(C[C@@H](C#N)NC(=O)[C@H]3N[C@@H]4CC[C@H]3C4)c(F)c2)nn1] | I-5.2 | A4/TSA | 37 |
| 120 | 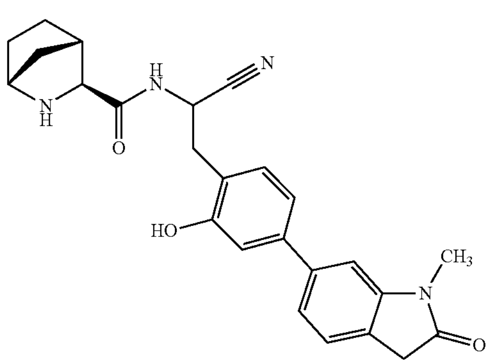 [SMILES: CN1C(=O)Cc2ccc(-c3ccc(CC(C#N)NC(=O)[C@H]4N[C@@H]5CC[C@H]4C5)c(O)c3)cc21] | I-4.3.19 | A3/SI | 5 |

TABLE 62-continued

| Example | Structure | Educt | Syn./Deprot. Method | Yield [%] |
|---|---|---|---|---|
| 121 | 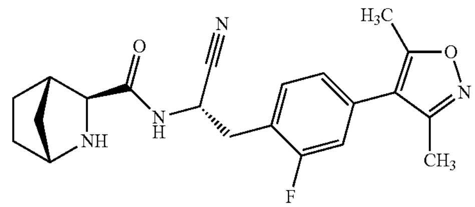 [SMILES: Cc1noc(C)c1-c1ccc(C[C@@H](C#N)NC(=O)[C@H]2N[C@@H]3CC[C@H]2C3)c(F)c1] | I-2.3.45 | A1/TSA | 41 |
| 122 | 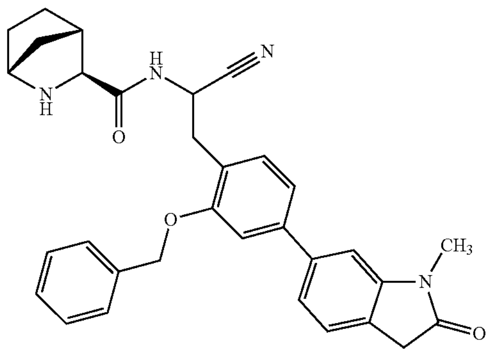 [SMILES: CN1C(=O)Cc2ccc(-c3ccc(CC(C#N)NC(=O)[C@H]4N[C@@H]5CC[C@H]4C5)c(OCc4ccccc4)c3)cc21] | I-4.3.19 | A3/SI | 27 |
| 123 | 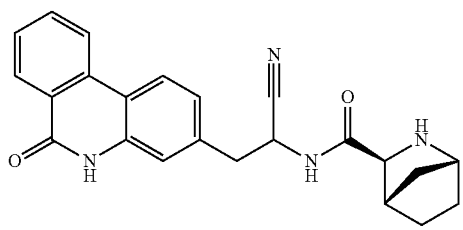 [SMILES: N#CC(Cc1ccc2c(c1)[nH]c(=O)c1ccccc12)NC(=O)[C@H]1N[C@@H]2CC[C@H]1C2] | I-10.5 | E/FA | 10 |
| 124 | 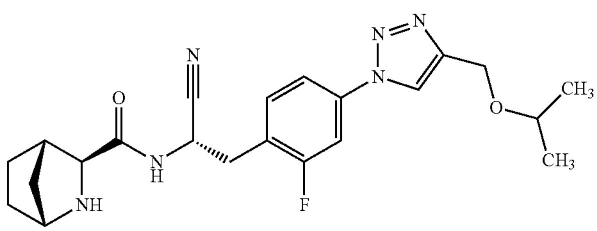 [SMILES: CC(C)OCc1cn(-c2ccc(C[C@@H](C#N)NC(=O)[C@H]3N[C@@H]4CC[C@H]3C4)c(F)c2)nn1] | I-5.2 | A4/TSA | 36 |
| 125 | 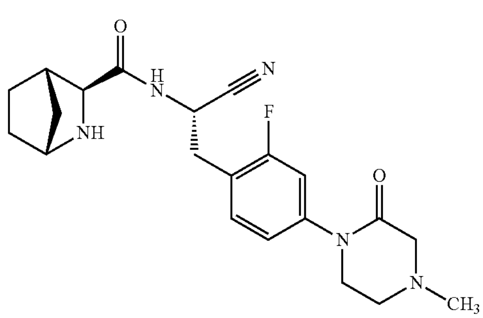 [SMILES: CN1CCN(c2ccc(C[C@@H](C#N)NC(=O)[C@H]3N[C@@H]4CC[C@H]3C4)c(F)c2)C(=O)C1] | I-4.3.28 | A3/TSA | 79 |
| 126 | 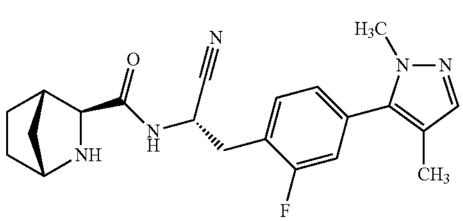 [SMILES: Cc1cnn(C)c1-c1ccc(C[C@@H](C#N)NC(=O)[C@H]2N[C@@H]3CC[C@H]2C3)c(F)c1] | I-2.3.46 | A1/TSA | 7 |

TABLE 62-continued

| Example | Structure | Educt | Syn./Deprot. Method | Yield [%] |
|---|---|---|---|---|
| 127 | 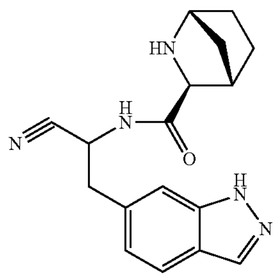 [SMILES: N#CC(Cc1ccc2cn[nH]c2c1)NC(=O)[C@H]1N[C@@H]2CC[C@H]1C2] | I-8.2.1 | C/SI | 36 |
| 128 | 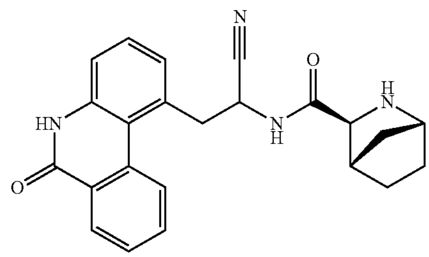 [SMILES: N#CC(Cc1cccc2[nH]c(=O)c3ccccc3c12)NC(=O)[C@H]1N[C@@H]2CC[C@H]1C2] | I-10.5 | E/FA | 5 |
| 129 | 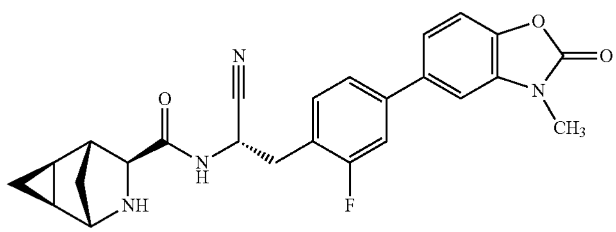 [SMILES: Cn1c(=O)oc2ccc(-c3ccc(C[C@@H](C#N)NC(=O)[C@H]4N[C@H]5C[C@@H]4[C@@H]4C[C@@H]45)c(F)c3)cc21] | I-2.3.47 | A1/TSA | 21 |
| 130 | 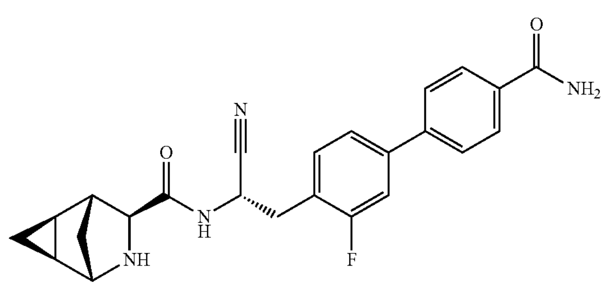 [SMILES: N#C[C@H](Cc1ccc(-c2ccc(C(N)=O)cc2)cc1F)NC(=O)[C@H]1N[C@H]2C[C@@H]1[C@@H]1C[C@@H]12] | I-2.3.48 | A1/TSA | 33 |
| 131 | 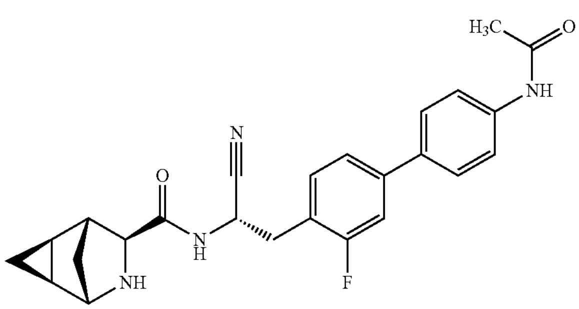 [SMILES: CC(=O)Nc1ccc(-c2ccc(C[C@@H](C#N)NC(=O)[C@H]3N[C@H]4C[C@@H]3[C@@H]3C[C@@H]34)c(F)c2)cc1] | I-2.3.49 | A1/TSA | 28 |

TABLE 62-continued

| Example | Structure | Educt | Syn./Deprot. Method | Yield [%] |
|---|---|---|---|---|
| 132 | 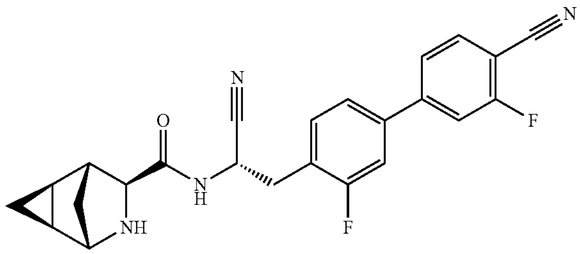 [SMILES: N#Cc1ccc(-c2ccc(C[C@@H](C#N)NC(=O)[C@H]3N[C@H]4C[C@@H]3[C@@H]3C[C@@H]34)c(F)c2)cc1F] | I-2.3.50 | A1/TSA | 36 |
| 133 | 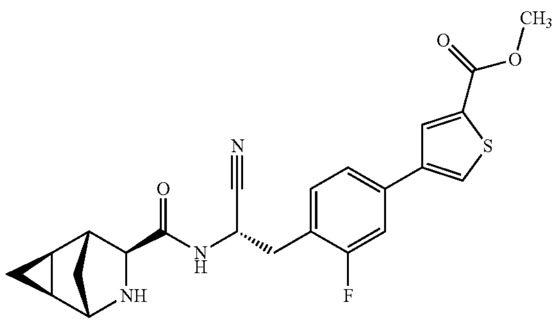 [SMILES: COC(=O)c1cc(-c2ccc(C[C@@H](C#N)NC(=O)[C@H]3N[C@H]4C[C@@H]3[C@@H]3C[C@@H]34)c(F)c2)cs1] | I-2.3.51 | A1/TSA | 28 |
| 134 | 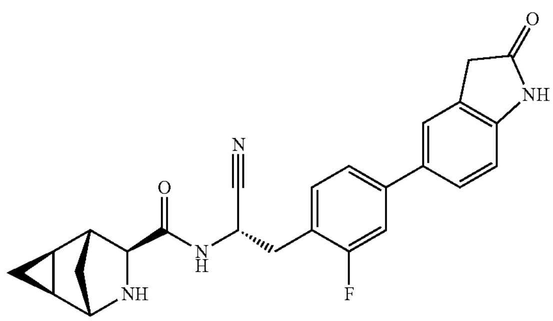 [SMILES: N#C[C@H](Cc1ccc(-c2ccc3c(c2)CC(=O)N3)cc1F)NC(=O)[C@H]1N[C@H]2C[C@@H]1[C@@H]1C[C@@H]12] | I-2.3.52 | A1/TSA | 8 |
| 135 | 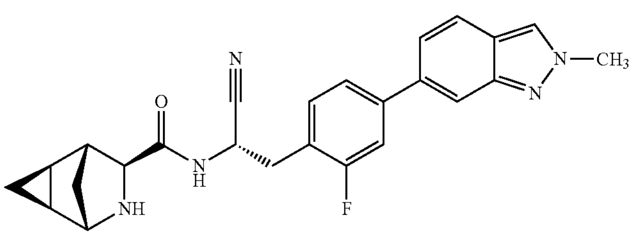 [SMILES: Cn1cc2ccc(-c3ccc(C[C@@H](C#N)NC(=O)[C@H]4N[C@H]5C[C@@H]4[C@@H]4C[C@@H]45)c(F)c3)cc2n1] | I-2.3.53 | A1/TSA | 25 |
| 136 | 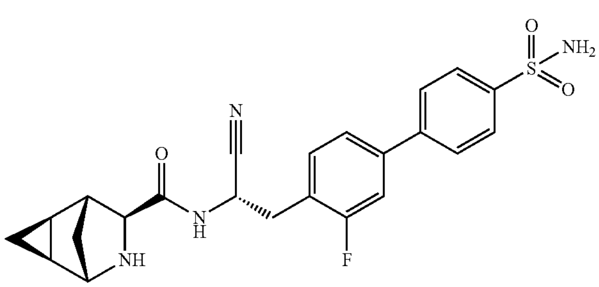 [SMILES: N#C[C@H](Cc1ccc(-c2ccc(S(N)(=O)=O)cc2)cc1F)NC(=O)[C@H]1N[C@H]2C[C@@H]1[C@@H]1C[C@@H]12] | I-2.3.54 | A1/TSA | 33 |

TABLE 62-continued

| Example | Structure | Educt | Syn./Deprot. Method | Yield [%] |
|---|---|---|---|---|
| 137 | 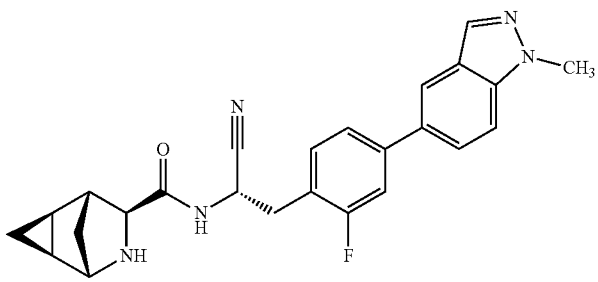 [SMILES: Cn1ncc2cc(-c3ccc(C[C@@H](C#N)NC(=O)[C@H]4N[C@H]5C[C@@H]4[C@@H]4C[C@@H]45)c(F)c3)ccc21] | I-2.3.55 | A1/TSA | 25 |
| 138 | 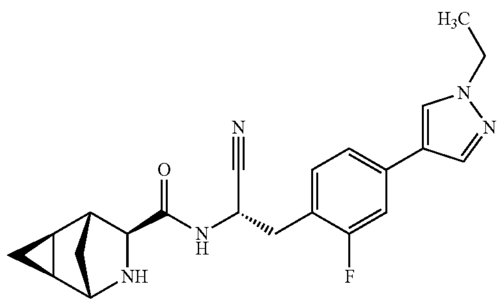 [SMILES: CCn1cc(-c2ccc(C[C@@H](C#N)NC(=O)[C@H]3N[C@H]4C[C@@H]3[C@@H]3C[C@@H]34)c(F)c2)cn1] | I-2.3.56 | A1/TSA | 41 |
| 139 | 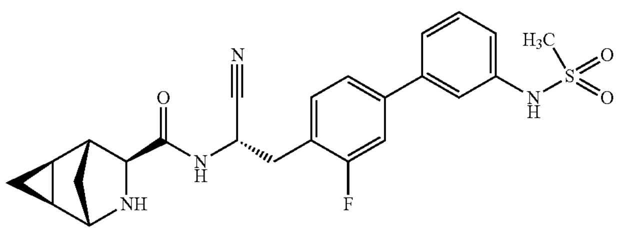 [SMILES: CS(=O)(=O)Nc1cccc(-c2ccc(C[C@@H](C#N)NC(=O)[C@H]3N[C@H]4C[C@@H]3[C@@H]3C[C@@H]34)c(F)c2)c1] | I-2.3.57 | A1/TSA | 26 |
| 140 | 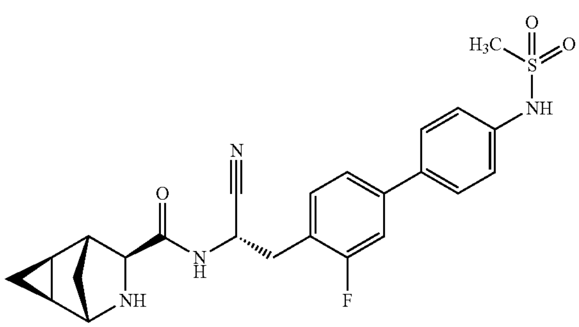 [SMILES: CS(=O)(=O)Nc1ccc(-c2ccc(C[C@@H](C#N)NC(=O)[C@H]3N[C@H]4C[C@@H]3[C@@H]3C[C@@H]34)c(F)c2)cc1] | I-2.3.58 | A1/TSA | 16 |
| 141 | 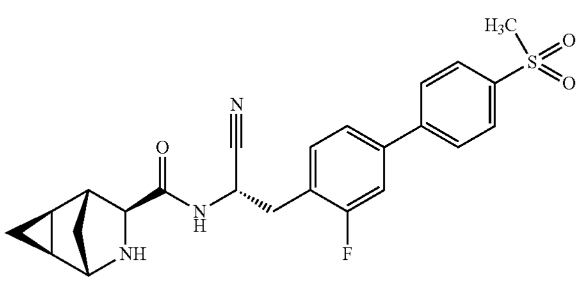 [SMILES: CS(=O)(=O)c1ccc(-c2ccc(C[C@@H](C#N)NC(=O)[C@H]3N[C@H]4C[C@@H]3[C@@H]3C[C@@H]34)c(F)c2)cc1] | I-2.3.59 | A1/TSA | 28 |

TABLE 62-continued

| Example | Structure | Educt | Syn./Deprot. Method | Yield [%] |
|---|---|---|---|---|
| 142 | 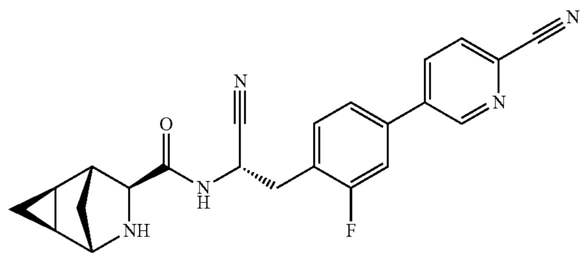 [SMILES: N#Cc1ccc(-c2ccc(C[C@@H](C#N)NC(=O)[C@H]3N[C@H]4C[C@@H]3[C@@H]3C[C@@H]34)c(F)c2)cn1] | I-2.3.60 | A1/TSA | 24 |
| 143 | 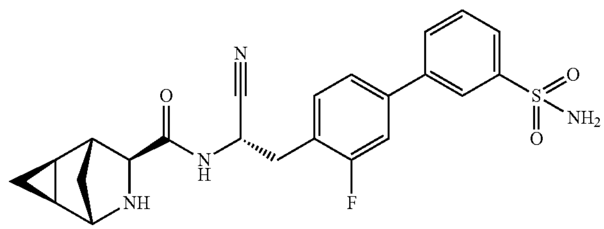 [SMILES: N#C[C@H](Cc1ccc(-c2cccc(S(N)(=O)=O)c2)cc1F)NC(=O)[C@H]1N[C@H]2C[C@@H]1[C@@H]1C[C@@H]12] | I-2.3.61 | A1/TSA | 33 |
| 144 | 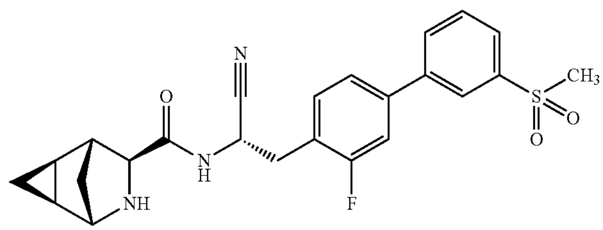 [SMILES: CS(=O)(=O)c1cccc(-c2ccc(C[C@@H](C#N)NC(=O)[C@H]3N[C@H]4C[C@@H]3[C@@H]3C[C@@H]34)c(F)c2)c1] | I-2.3.62 | A1/TSA | 34 |
| 145 | 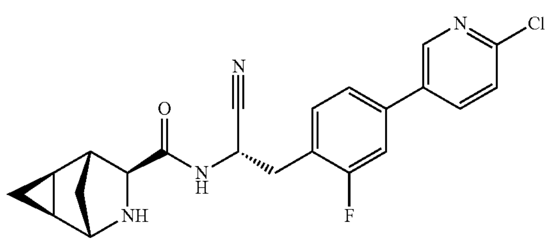 [SMILES: N#C[C@H](Cc1ccc(-c2ccc(Cl)nc2)cc1F)NC(=O)[C@H]1N[C@H]2C[C@@H]1[C@@H]1C[C@@H]12] | I-2.3.63 | A1/TSA | 21 |
| 146 | 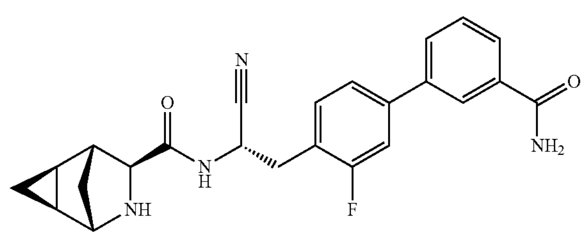 [SMILES: N#C[C@H](Cc1ccc(-c2cccc(C(N)=O)c2)cc1F)NC(=O)[C@H]1N[C@H]2C[C@@H]1[C@@H]1C[C@@H]12] | I-2.3.64 | A1/TSA | 32 |
| 147 | 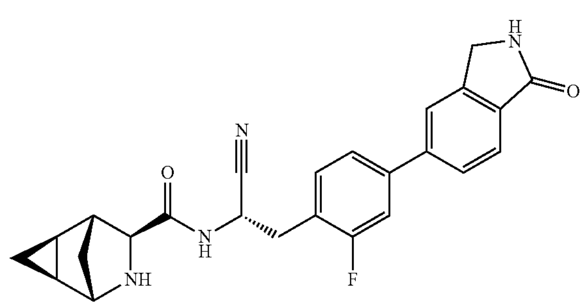 [SMILES: N#C[C@H](Cc1ccc(-c2ccc3c(c2)CNC3=O)cc1F)NC(=O)[C@H]1N[C@H]2C[C@@H]1[C@@H]1C[C@@H]12] | I-2.3.65 | A1/TSA | 34 |

TABLE 62-continued

| Example | Structure | Educt | Syn./ Deprot. Method | Yield [%] |
|---|---|---|---|---|
| 148 | 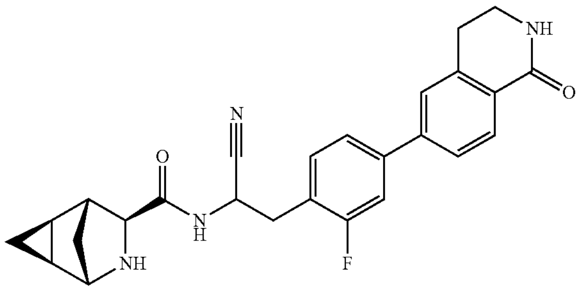 [SMILES: N#CC(Cc1ccc(-c2ccc3c(c2)CCNC3=O)cc1F)NC(=O)[C@H]1N[C@H]2C[C@@H]1[C@@H]1C[C@@H]12] | I-2.3.66 | A1/TSA | 10 |
| 149 | 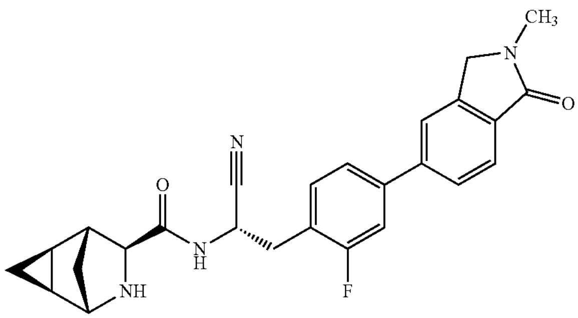 [SMILES: CN1Cc2cc(-c3ccc(C[C@@H](C#N)NC(=O)[C@H]4N[C@H]5C[C@@H]4[C@@H]4C[C@@H]45)c(F)c3)ccc2C1=O] | I-2.3.67 | A1/TSA | 23 |
| 150 | 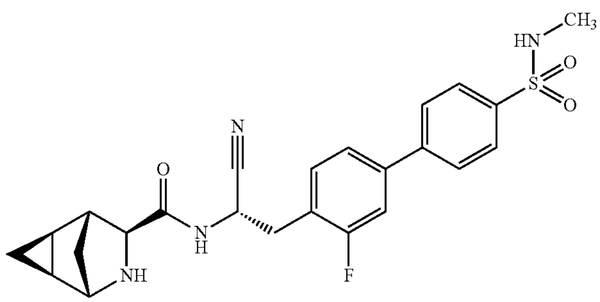 [SMILES: CNS(=O)(=O)c1ccc(-c2ccc(C[C@@H](C#N)NC(=O)[C@H]3N[C@H]4C[C@@H]3[C@@H]3C[C@@H]34)c(F)c2)cc1] | I-2.3.68 | A1/TSA | 33 |
| 151 | 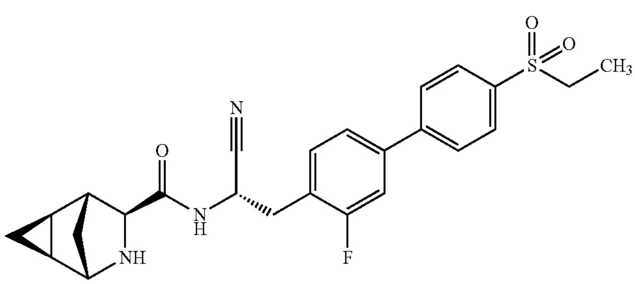 [SMILES: CCS(=O)(=O)c1ccc(-c2ccc(C[C@@H](C#N)NC(=O)[C@H]3N[C@H]4C[C@@H]3[C@@H]3C[C@@H]34)c(F)c2)cc1] | I-2.3.69 | A1/TSA | 25 |
| 152 | 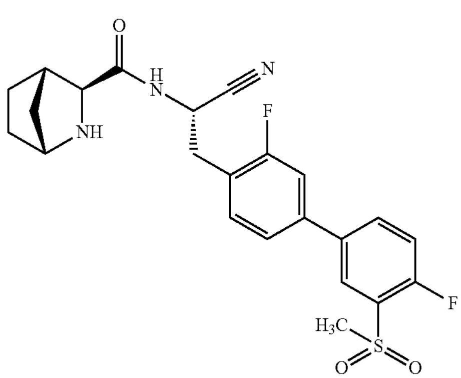 [SMILES: CS(=O)(=O)c1cc(-c2ccc(C[C@@H](C#N)NC(=O)[C@H]3N[C@@H]4CC[C@H]3C4)c(F)c2)ccc1F] | I-2.3.70 | A1/FA | 68 |

TABLE 62-continued

| Example | Structure | Educt | Syn./Deprot. Method | Yield [%] |
|---|---|---|---|---|
| 153 | 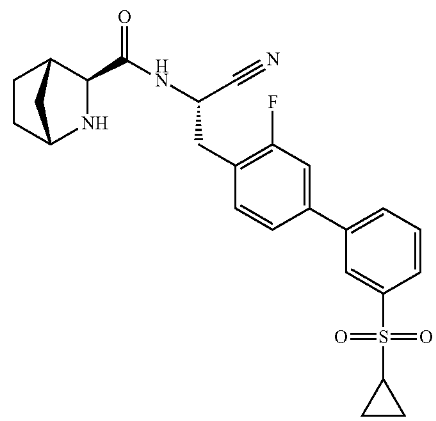 [SMILES: N#C[C@H](Cc1ccc(-c2cccc(S(=O)(=O)C3CC3)c2)cc1F)NC(=O)[C@H]1N[C@@H]2CC[C@H]1C2] | I-2.3.71 | A1/FA | 73 |
| 154 | 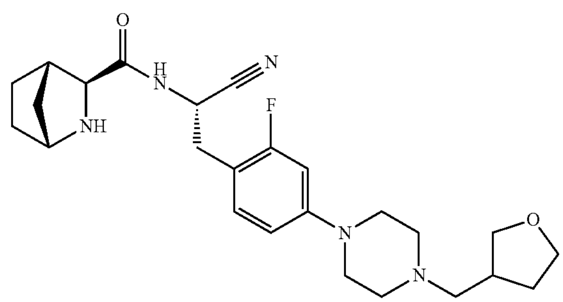 [SMILES: N#C[C@H](Cc1ccc(N2CCN(CC3CCOC3)CC2)cc1F)NC(=O)[C@H]1N[C@@H]2CC[C@H]1C2] | I-3.2.14 | A2.2/TSA | 59 |
| 155 | 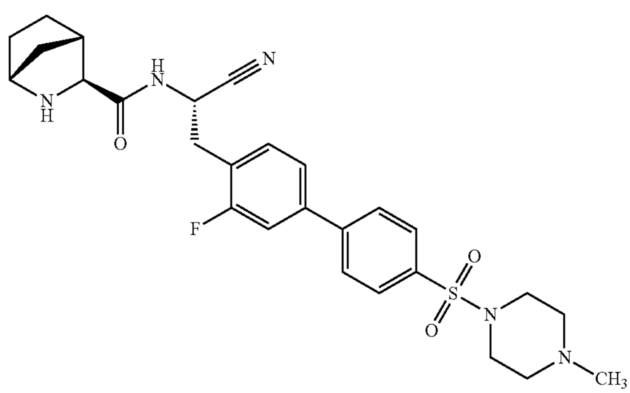 [SMILES: CN1CCN(S(=O)(=O)c2ccc(-c3ccc(C[C@@H](C#N)NC(=O)[C@H]4N[C@@H]5CC[C@H]4C5)c(F)c3)cc2)CC1] | I-3.3.5 | A2.1/SI | 62 |
| 156 | 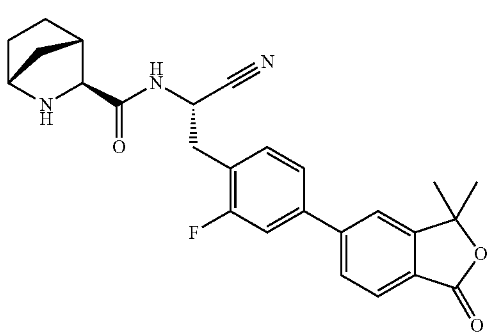 [SMILES: CC1(C)OC(=O)c2ccc(-c3ccc(C[C@@H](C#N)NC(=O)[C@H]4N[C@@H]5CC[C@H]4C5)c(F)c3)cc21] | I-3.3.6 | A2.1/SI | 25 |

TABLE 62-continued

| Example | Structure | Educt | Syn./Deprot. Method | Yield [%] |
|---|---|---|---|---|
| 157 | 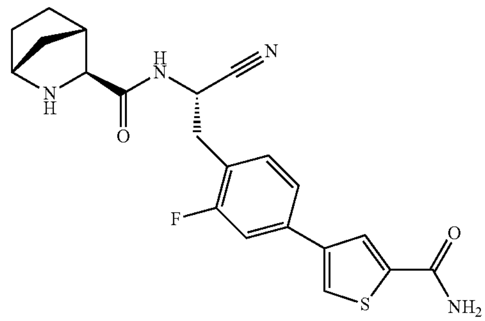 [SMILES: N#C[C@H](Cc1ccc(-c2csc(C(N)=O)c2)cc1F)NC(=O)[C@H]1N[C@@H]2CC[C@H]1C2] | I-4.3.32 | A3/FA | 36 |
| 158 | 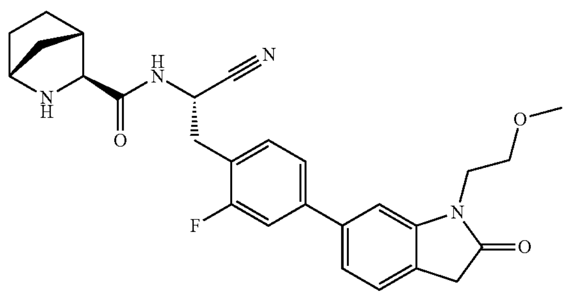 [SMILES: COCCN1C(=O)Cc2ccc(-c3ccc(C[C@@H](C#N)NC(=O)[C@H]4N[C@@H]5CC[C@H]4C5)c(F)c3)cc21] | I-2.3.72 | A1/SI | 57 |
| 159 | 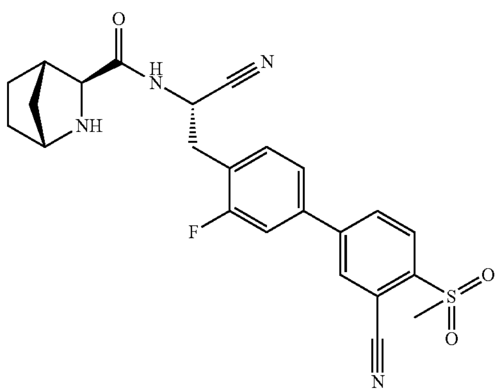 [SMILES: CS(=O)(=O)c1ccc(-c2ccc(C[C@@H](C#N)NC(=O)[C@H]3N[C@@H]4CC[C@H]3C4)c(F)c2)cc1C#N] | I-1.5.1 | A/TSA | 65 |
| 160 | 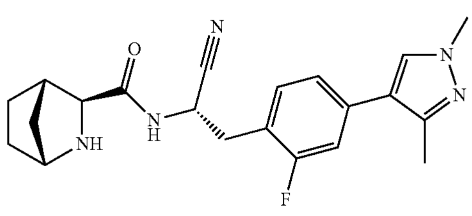 [SMILES: Cc1nn(C)cc1-c1ccc(C[C@@H](C#N)NC(=O)[C@H]2N[C@@H]3CC[C@H]2C3)c(F)c1] | I-3.2.37 | A2.1/TSA | 34 |
| 161 | 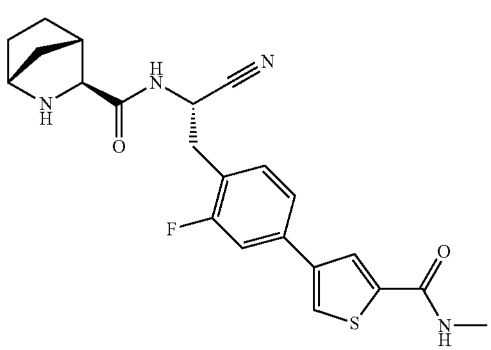 [SMILES: CNC(=O)c1cc(-c2ccc(C[C@@H](C#N)NC(=O)[C@H]3N[C@@H]4CC[C@H]3C4)c(F)c2)cs1] | I-4.3.33 | A3/FA | 75 |

TABLE 62-continued

| Example | Structure | Educt | Syn./Deprot. Method | Yield [%] |
|---|---|---|---|---|
| 162 | 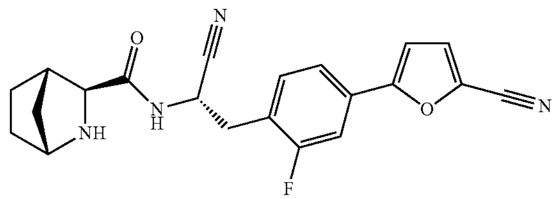 [SMILES: N#Cc1ccc(-c2ccc(C[C@@H](C#N)NC(=O)[C@H]3N[C@@H]4CC[C@H]3C4)c(F)c2)o1] | I-3.2.47 | A2.1/TSA | 52 |
| 163 | 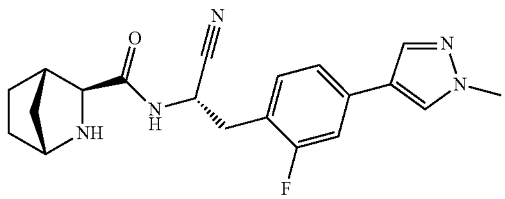 [SMILES: Cn1cc(-c2ccc(C[C@@H](C#N)NC(=O)[C@H]3N[C@@H]4CC[C@H]3C4)c(F)c2)cn1] | I-3.2.36 | A2.1/TSA | 40 |
| 164 | 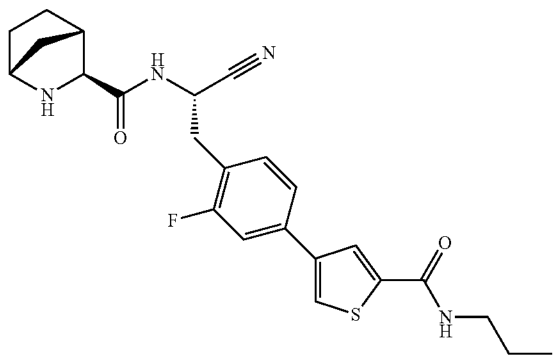 [SMILES: CCCNC(=O)c1cc(-c2ccc(C[C@@H](C#N)NC(=O)[C@H]3N[C@@H]4CC[C@H]3C4)c(F)c2)cs1] | I-4.3.34 | A3/FA | 78 |
| 165 | 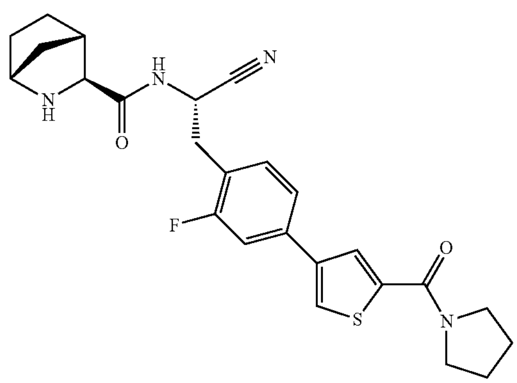 [SMILES: N#C[C@H](Cc1ccc(-c2csc(C(=O)N3CCCC3)c2)cc1F)NC(=O)[C@H]1N[C@@H]2CC[C@H]1C2] | I-4.3.35 | A3/FA | 90 |
| 166 | 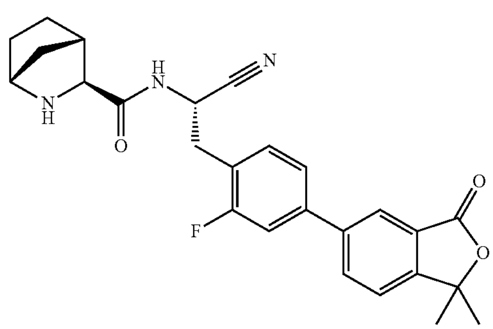 [SMILES: CC1(C)OC(=O)c2cc(-c3ccc(C[C@@H](C#N)NC(=O)[C@H]4N[C@@H]5CC[C@H]4C5)c(F)c3)ccc21] | I-3.3.7 | A2.1/SI | 33 |

TABLE 62-continued

| Example | Structure | Educt | Syn./Deprot. Method | Yield [%] |
|---|---|---|---|---|
| 167 | 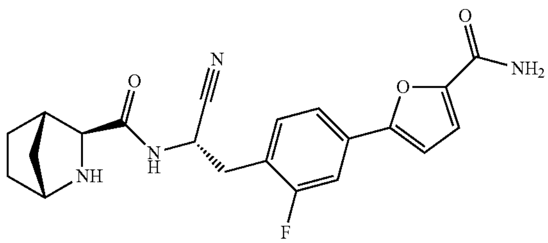 [SMILES: N#C[C@H](Cc1ccc(-c2ccc(C(N)=O)o2)cc1F)NC(=O)[C@H]1N[C@@H]2CC[C@H]1C2] | I-3.2.46 | A2.1/TSA | 49 |
| 168 | 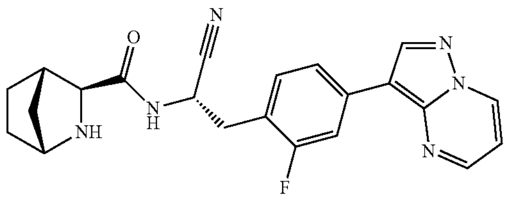 [SMILES: N#C[C@H](Cc1ccc(-c2cnn3cccnc23)cc1F)NC(=O)[C@H]1N[C@@H]2CC[C@H]1C2] | I-3.2.42 | A2.1/TSA | 37 |
| 169 | 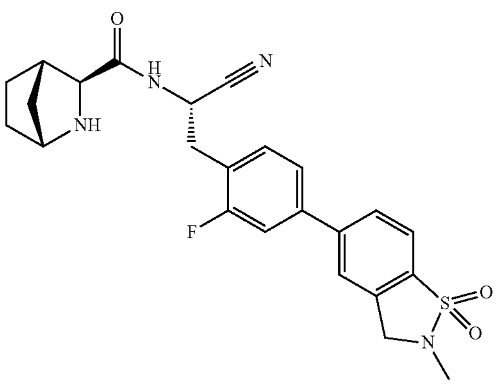 [SMILES: CN1Cc2cc(-c3ccc(C[C@@H](C#N)NC(=O)[C@H]4N[C@@H]5CC[C@H]4C5)c(F)c3)ccc2S1(=O)=O] | I-1.5.2 | A/TSA | 79 |
| 170 | 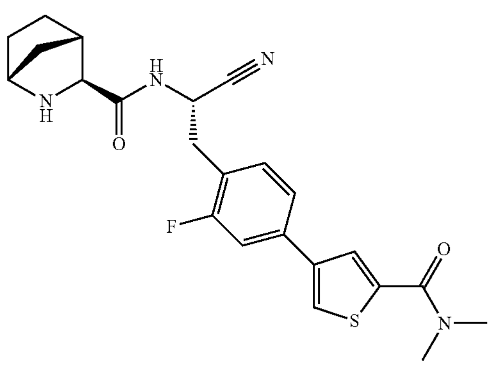 [SMILES: CN(C)C(=O)c1cc(-c2ccc(C[C@@H](C#N)NC(=O)[C@H]3N[C@@H]4CC[C@H]3C4)c(F)c2)cs1] | I-4.3.36 | A3/FA | 77 |
| 171 | 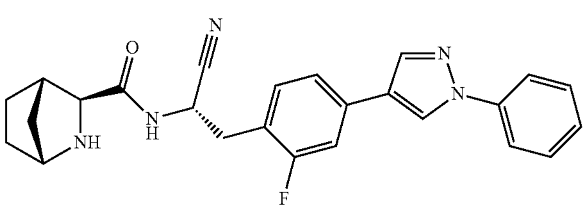 [SMILES: N#C[C@H](Cc1ccc(-c2cnn(-c3ccccc3)c2)cc1F)NC(=O)[C@H]1N[C@@H]2CC[C@H]1C2] | I-3.2.39 | A2.1/TSA | 37 |

TABLE 62-continued

| Example | Structure | Educt | Syn./Deprot. Method | Yield [%] |
|---|---|---|---|---|
| 172 | 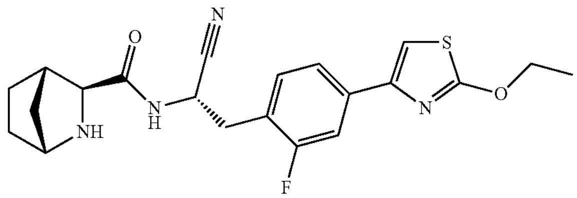 [SMILES: CCOc1nc(-c2ccc(C[C@@H](C#N)NC(=O)[C@H]3N[C@@H]4CC[C@H]3C4)c(F)c2)cs1] | I-3.2.38 | A2.1/TSA | 36 |
| 173 | 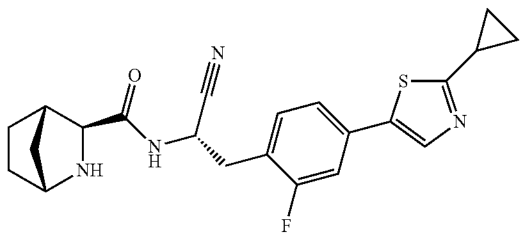 [SMILES: N#C[C@H](Cc1ccc(-c2cnc(C3CC3)s2)cc1F)NC(=O)[C@H]1N[C@@H]2CC[C@H]1C2] | I-3.2.45 | A2.1/TSA | 34 |
| 174 | 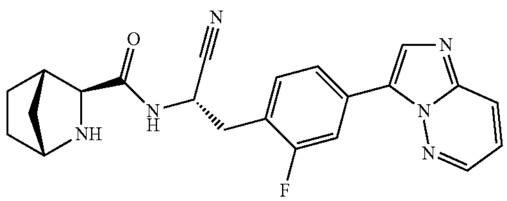 [SMILES: N#C[C@H](Cc1ccc(-c2cnc3cccnn23)cc1F)NC(=O)[C@H]1N[C@@H]2CC[C@H]1C2] | I-3.2.40 | A2.1/TSA | 33 |
| 175 | 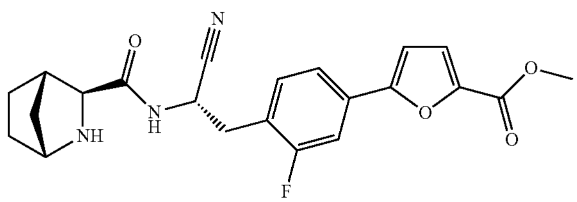 [SMILES: COC(=O)c1ccc(-c2ccc(C[C@@H](C#N)NC(=O)[C@H]3N[C@@H]4CC[C@H]3C4)c(F)c2)o1] | I-3.2.50 | A2.1/TSA | 44 |
| 176 | 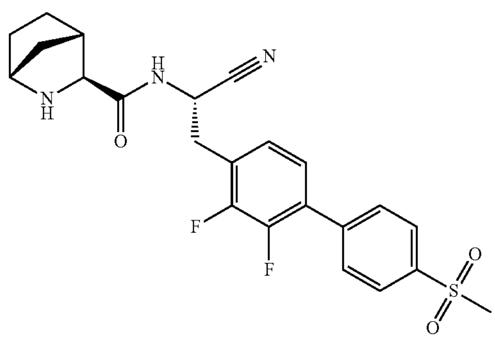 [SMILES: CS(=O)(=O)c1ccc(-c2ccc(C[C@@H](C#N)NC(=O)[C@H]3N[C@@H]4CC[C@H]3C4)c(F)c2F)cc1] | I-2.3.75.1 | A1/FA | 53 |
| 177 | 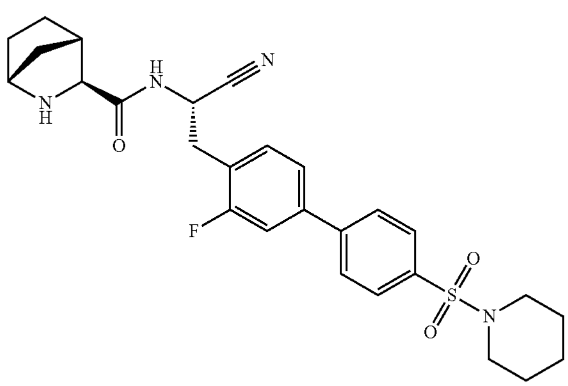 [SMILES: N#C[C@H](Cc1ccc(-c2ccc(S(=O)(=O)N3CCCCC3)cc2)cc1F)NC(=O)[C@H]1N[C@@H]2CC[C@H]1C2] | I-3.2.51 | A2.1/SI | 59 |

TABLE 62-continued

| Example | Structure | Educt | Syn./Deprot. Method | Yield [%] |
|---|---|---|---|---|
| 178 | 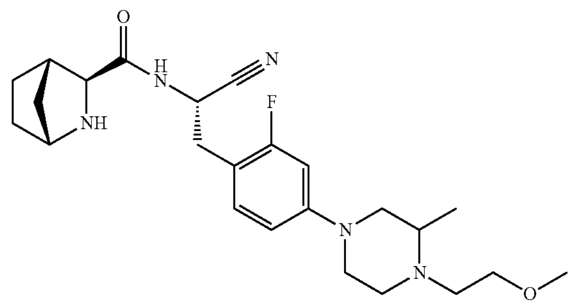 [SMILES: COCCN1CCN(c2ccc(C[C@@H](C#N)NC(=O)[C@H]3N[C@@H]4CC[C@H]3C4)c(F)c2)CC1C] | I-3.2.19 | A2.2/TSA | 81 |
| 179 | 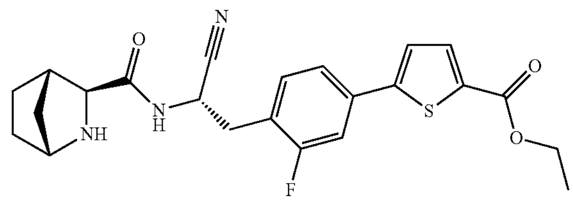 [SMILES: CCOC(=O)c1ccc(-c2ccc(C[C@@H](C#N)NC(=O)[C@H]3N[C@@H]4CC[C@H]3C4)c(F)c2)s1] | I-3.2.49 | A2.1/TSA | 35 |
| 180 | 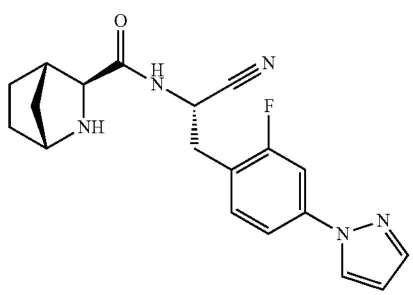 [SMILES: N#C[C@H](Cc1ccc(-n2cccn2)cc1F)NC(=O)[C@H]1N[C@@H]2CC[C@H]1C2] | I-3.2.20 | A2.2/TSA | 56 |
| 181 | 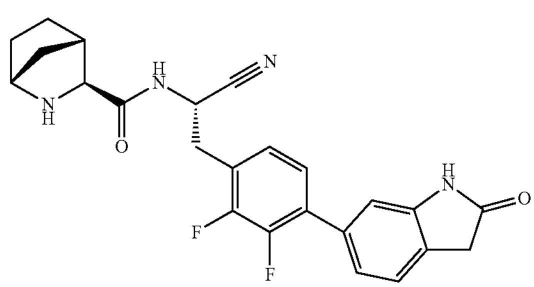 [SMILES: N#C[C@H](Cc1ccc(-c2ccc3c(c2)NC(=O)C3)c(F)c1F)NC(=O)[C@H]1N[C@@H]2CC[C@H]1C2] | I-2.3.76.1 | A1/FA | 31 |
| 182 | 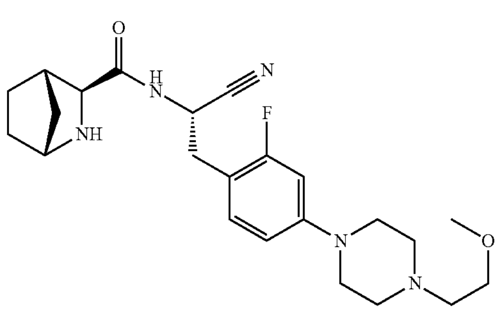 | I-3.2.22 | A2.2/TSA | 31 |

TABLE 62-continued

| Example | Structure | Educt | Syn./Deprot. Method | Yield [%] |
|---------|-----------|-------|---------------------|-----------|
| 183 | 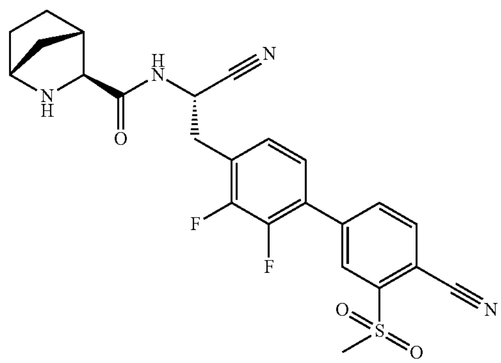 [SMILES: CS(=O)(=O)c1cc(-c2ccc(C[C@@H](C#N)NC(=O)[C@H]3N[C@@H]4CC[C@H]3C4)c(F)c2F)ccc1C#N] | I-2.3.78.1 | A1/FA | 36 |
| 184 | 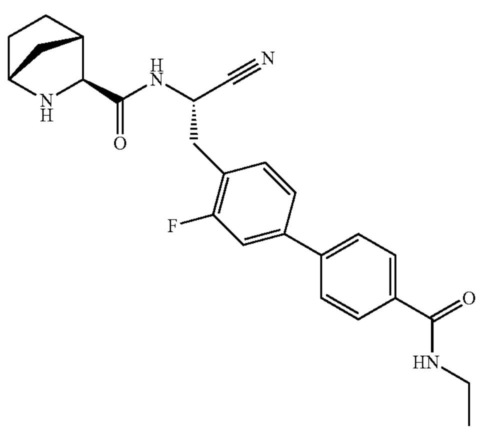 [SMILES: CCNC(=O)c1ccc(-c2ccc(C[C@@H](C#N)NC(=O)[C@H]3N[C@@H]4CC[C@H]3C4)c(F)c2)cc1] | I-4.3.37 | A3/TFA | 51 |
| 185 | 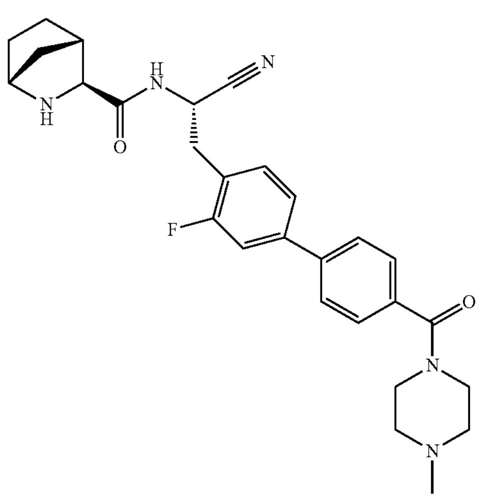 [SMILES: CN1CCN(C(=O)c2ccc(-c3ccc(C[C@@H](C#N)NC(=O)[C@H]4N[C@@H]5CC[C@H]4C5)c(F)c3)cc2)CC1] | I-4.3.38 | A3/TFA | 28 |

TABLE 62-continued

| Example | Structure | Educt | Syn./Deprot. Method | Yield [%] |
|---|---|---|---|---|
| 186 | 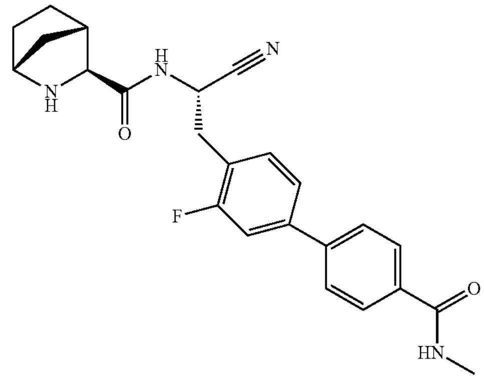 [SMILES: CNC(=O)c1ccc(-c2ccc(C[C@@H](C#N)NC(=O)[C@H]3N[C@@H]4CC[C@H]3C4)c(F)c2)cc1] | I-4.3.39 | A3/TFA | 40 |
| 187 | 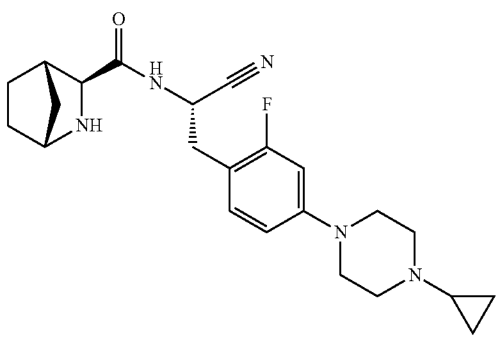 [SMILES: N#C[C@H](Cc1ccc(N2CCN(C3CC3)CC2)cc1F)NC(=O)[C@H]1N[C@@H]2CC[C@H]1C2] | I-3.2.24 | A2.2/SI | 17 |
| 188 | 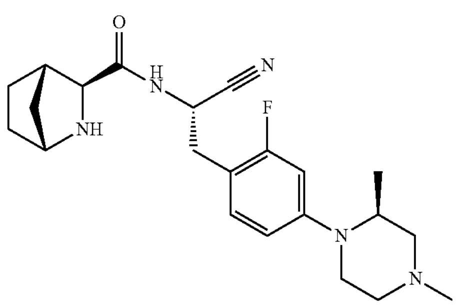 [SMILES: C[C@H]1CN(C)CCN1c1ccc(C[C@@H](C#N)NC(=O)[C@H]2N[C@@H]3CC[C@H]2C3)c(F)c1] | I-3.2.25 | A2.2/TSA | 85 |
| 189 | 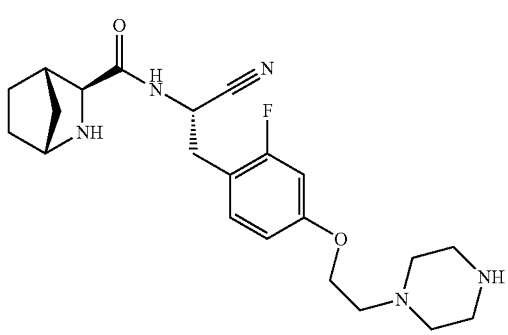 [SMILES: N#C[C@H](Cc1ccc(OCCN2CCNCC2)cc1F)NC(=O)[C@H]1N[C@@H]2CC[C@H]1C2] | I-3.2.26 | A2.2/TSA | 13 |

TABLE 62-continued

| Example | Structure | Educt | Syn./Deprot. Method | Yield [%] |
|---|---|---|---|---|
| 190 | 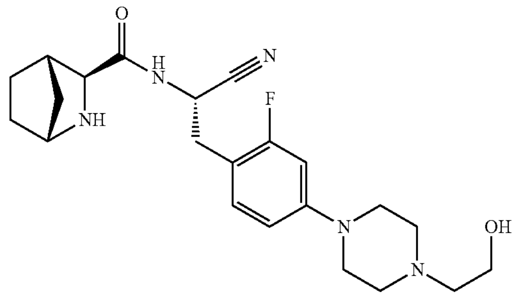 [SMILES: N#C[C@H](Cc1ccc(N2CCN(CCO)CC2)cc1F)NC(=O)[C@H]1N[C@@H]2CC[C@H]1C2] | I-3.2.27 | A2.2/TSA | 19 |
| 191 | 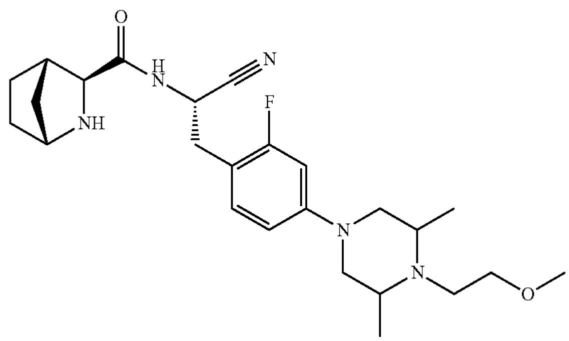 [SMILES: COCCN1C(C)CN(c2ccc(C[C@@H](C#N)NC(=O)[C@H]3N[C@@H]4CC[C@H]3C4)c(F)c2)CC1C] | I-3.2.28 | A2.2/TSA | 84 |
| 192 | 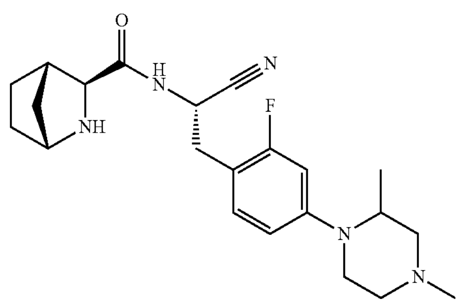 [SMILES: CC1CN(C)CCN1c1ccc(C[C@@H](C#N)NC(=O)[C@H]2N[C@@H]3CC[C@H]2C3)c(F)c1] | I-3.2.29 | A2.2/TSA | 75 |
| 193 | 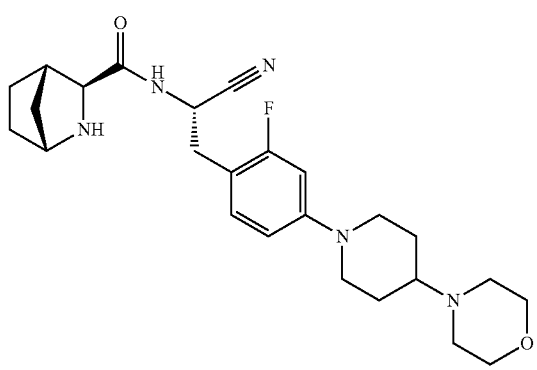 [SMILES: N#C[C@H](Cc1ccc(N2CCC(N3CCOCC3)CC2)cc1F)NC(=O)[C@H]1N[C@@H]2CC[C@H]1C2] | I-3.2.30 | A2.2/TSA | 42 |
| 194 | 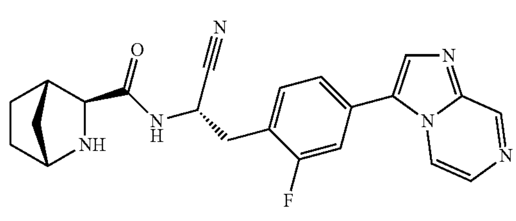 [SMILES: N#C[C@H](Cc1ccc(-c2cnc3cnccn23)cc1F)NC(=O)[C@H]1N[C@@H]2CC[C@H]1C2] | I-3.2.41 | A2.1/TSA | 33 |

TABLE 62-continued

| Example | Structure | Educt | Syn./Deprot. Method | Yield [%] |
|---|---|---|---|---|
| 195 | 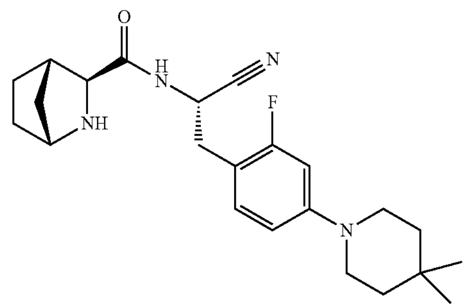 [SMILES: CC1(C)CCN(c2ccc(C[C@@H](C#N)NC(=O)[C@H]3N[C@@H]4CC[C@H]3C4)c(F)c2)CC1] | I-3.2.31 | A2.2/TSA | 86 |
| 196 | 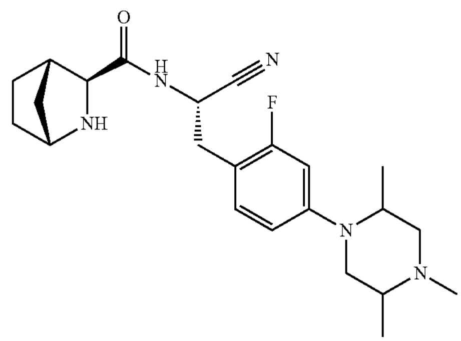 [SMILES: CC1CN(c2ccc(C[C@@H](C#N)NC(=O)[C@H]3N[C@@H]4CC[C@H]3C4)c(F)c2)C(C)CN1C] | I-3.2.32 | A2.2/TSA | 18 |
| 197 | 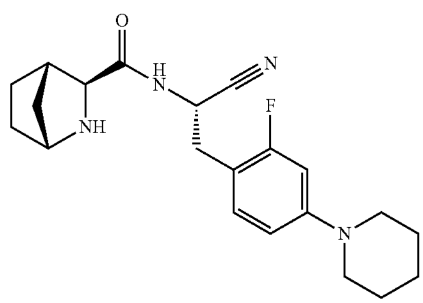 [SMILES: N#C[C@H](Cc1ccc(N2CCCCC2)cc1F)NC(=O)[C@H]1N[C@@H]2CC[C@H]1C2] | I-3.2.33 | A2.2/TSA | 68 |
| 198 | 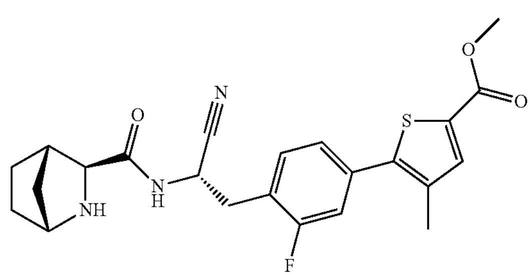 [SMILES: COC(=O)c1cc(C)c(-c2ccc(C[C@@H](C#N)NC(=O)[C@H]3N[C@@H]4CC[C@H]3C4)c(F)c2)s1] | I-3.2.48 | A2.1/TSA | 32 |
| 199 | 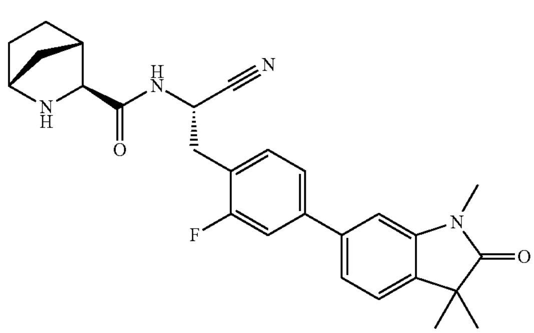 [SMILES: CN1C(=O)C(C)(C)c2ccc(-c3ccc(C[C@@H](C#N)NC(=O)[C@H]4N[C@@H]5CC[C@H]4C5)c(F)c3)cc21] | I-2.3.73 | A1/SI | 56 |

TABLE 62-continued

| Example | Structure | Educt | Syn./Deprot. Method | Yield [%] |
|---|---|---|---|---|
| 200 | 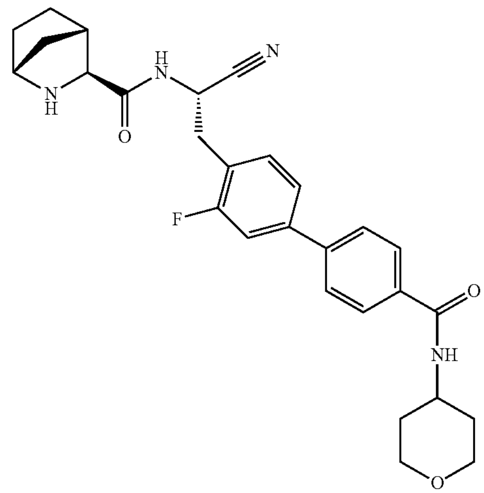 [SMILES: N#C[C@H](Cc1ccc(-c2ccc(C(=O)NC3CCOCC3)cc2)cc1F)NC(=O)[C@H]1N[C@@H]2CC[C@H]1C2] | I-4.3.40 | A3/TFA | 51 |
| 201 | 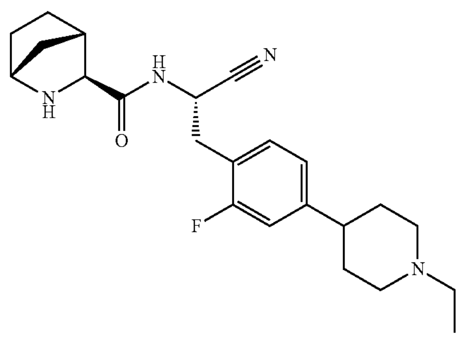 [SMILES: CCN1CCC(c2ccc(C[C@@H](C#N)NC(=O)[C@H]3N[C@@H]4CC[C@H]3C4)c(F)c2)CC1] | I-2.3.43.2.1 | A2/SI | 65 |
| 202 | 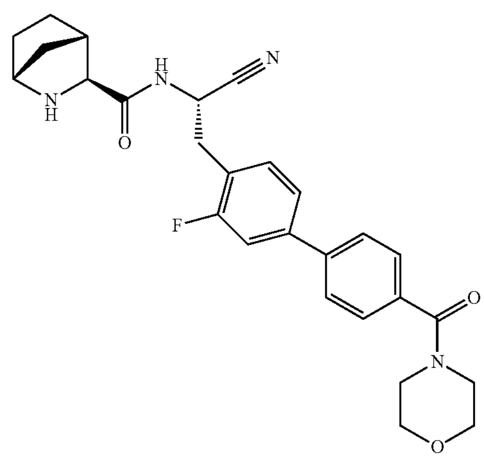 [SMILES: N#C[C@H](Cc1ccc(-c2ccc(C(=O)N3CCOCC3)cc2)cc1F)NC(=O)[C@H]1N[C@@H]2CC[C@H]1C2] | I-4.3.41 | A3/TFA | 52 |
| 203 | 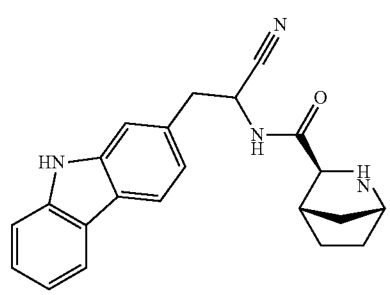 [SMILES: N#CC(Cc1ccc2c(c1)[nH]c1ccccc12)NC(=O)[C@H]1N[C@@H]2CC[C@H]1C2] | I-7.3.3 | B/SI | 56 |

TABLE 62-continued

| Example | Structure | Educt | Syn./Deprot. Method | Yield [%] |
|---|---|---|---|---|
| 204 | 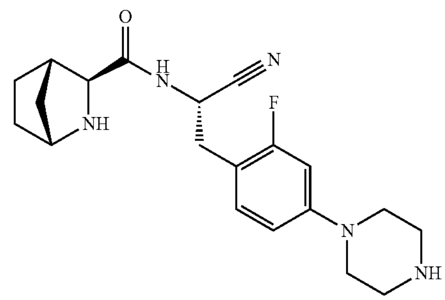 [SMILES: N#C[C@H](Cc1ccc(N2CCNCC2)cc1F)NC(=O)[C@H]1N[C@@H]2CC[C@H]1C2] | I-3.2.34 | A2.2/TSA | 90 |
| 205 | 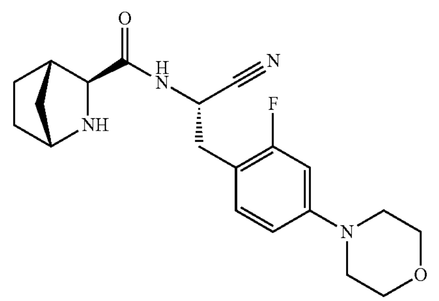 [SMILES: N#C[C@H](Cc1ccc(N2CCOCC2)cc1F)NC(=O)[C@H]1N[C@@H]2CC[C@H]1C2] | I-3.2.35 | A2.2/TSA | 76 |
| 206 | 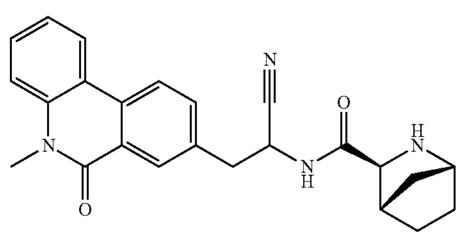 [SMILES: Cn1c(=O)c2cc(CC(C#N)NC(=O)[C@H]3N[C@@H]4CC[C@H]3C4)ccc2c2ccccc21] | I-9.1.1 | D/SI | 39 |
| 207 | 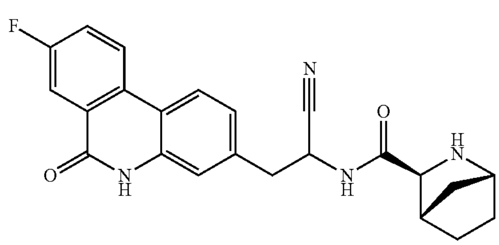 [SMILES: N#CC(Cc1ccc2c(c1)[nH]c(=O)c1cc(F)ccc12)NC(=O)[C@H]1N[C@@H]2CC[C@H]1C2] | I-10.4.1 | E/TFA | 28 |
| 208 | 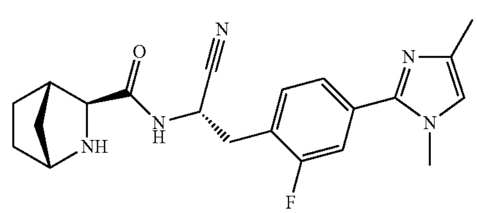 [SMILES: Cc1cn(C)c(-c2ccc(C[C@@H](C#N)NC(=O)[C@H]3N[C@@H]4CC[C@H]3C4)c(F)c2)n1] | I-3.2.43 | A2.1/TSA | 22 |

TABLE 62-continued

| Example | Structure | Educt | Syn./Deprot. Method | Yield [%] |
|---|---|---|---|---|
| 209 | 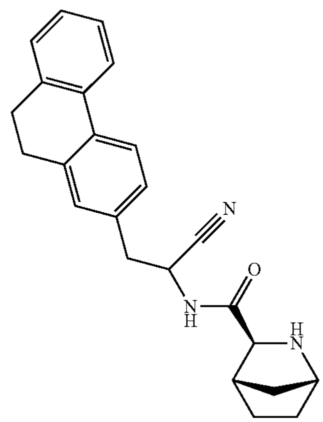 [SMILES: N#CC(Cc1ccc2c(c1)CCc1ccccc1-2)NC(=O)[C@H]1N[C@@H]2CC[C@H]1C2] | I-7.3.4 | B/SI | 55 |
| 210 | 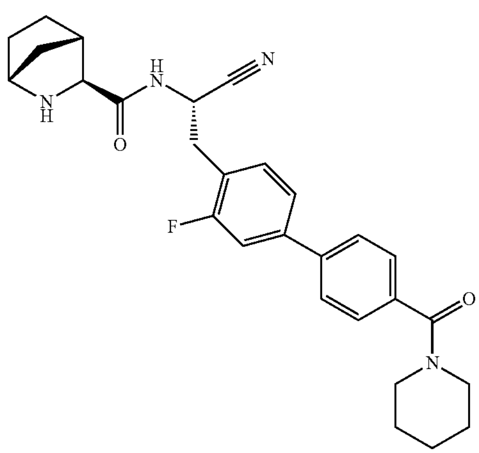 [SMILES: N#C[C@H](Cc1ccc(-c2ccc(C(=O)N3CCCCC3)cc2)cc1F)NC(=O)[C@H]1N[C@@H]2CC[C@H]1C2] | I-4.3.42 | A3/TFA | 46 |
| 211 | 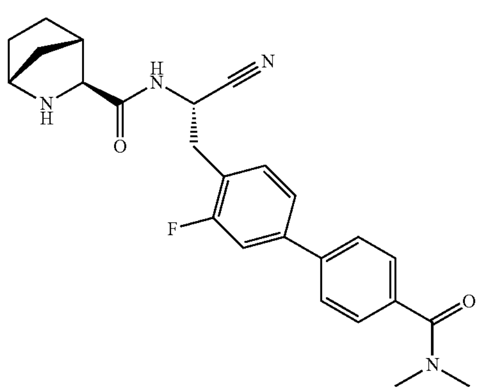 [SMILES: CN(C)C(=O)c1ccc(-c2ccc(C[C@@H](C#N)NC(=O)[C@H]3N[C@@H]4CC[C@H]3C4)c(F)c2)cc1] | I-4.3.43 | A3/TFA | 48 |

TABLE 62-continued

| Example | Structure | Educt | Syn./Deprot. Method | Yield [%] |
|---|---|---|---|---|
| 212 | 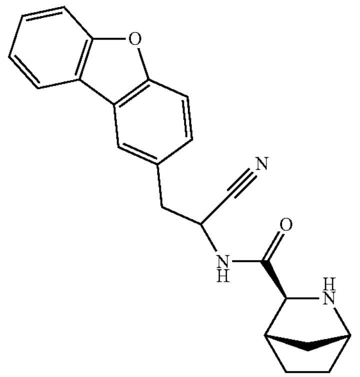 [SMILES: N#CC(Cc1ccc2oc3ccccc3c2c1)NC(=O)[C@H]1N[C@@H]2CC[C@H]1C2] | I-7.3.5 | B/SI | 54 |
| 213 | 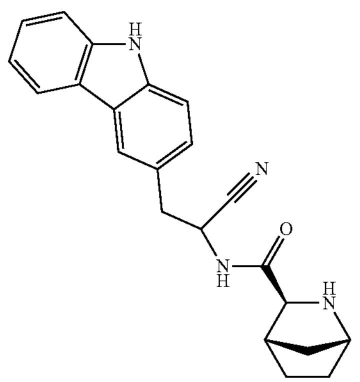 [SMILES: N#CC(Cc1ccc2[nH]c3ccccc3c2c1)NC(=O)[C@H]1N[C@@H]2CC[C@H]1C2] | I-7.3.6 | B/SI | 65 |
| 214 | 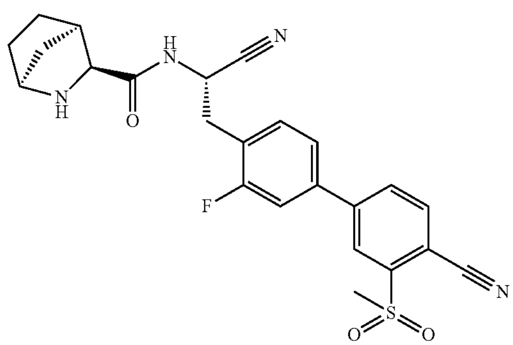 [SMILES: CS(=O)(=O)c1cc(-c2ccc(C[C@@H](C#N)NC(=O)[C@H]3N[C@H]4CC[C@@H]3C4)c(F)c2)ccc1C#N] | I-1.5.3 | A/TSA | 72 |
| 215 | 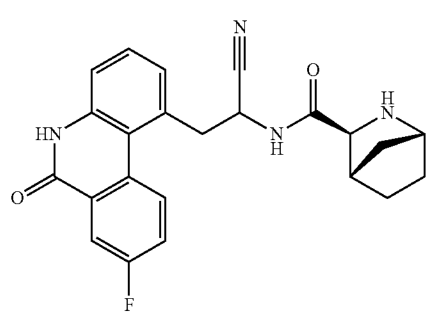 [SMILES: N#CC(Cc1cccc2[nH]c(=O)c3cc(F)ccc3c12)NC(=O)[C@H]1N[C@@H]2CC[C@H]1C2] | I-10.4.1 | E/TFA | 23 |

TABLE 62-continued
| Example | Structure | Educt | Syn./Deprot. Method | Yield [%] |
|---|---|---|---|---|
| 216 | 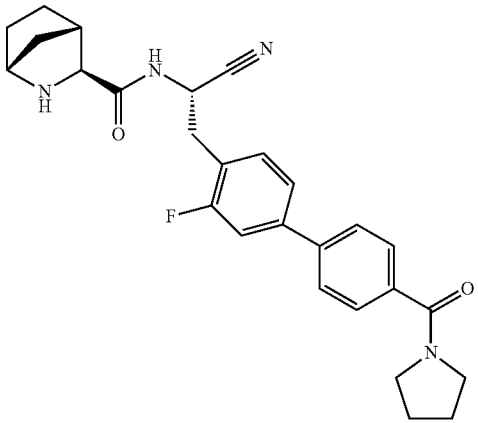 [SMILES: N#C[C@H](Cc1ccc(-c2ccc(C(=O)N3CCCC3)cc2)cc1F)NC(=O)[C@H]1N[C@@H]2CC[C@H]1C2] | I-4.3.44 | A3/TFA | 38 |
| 217 | 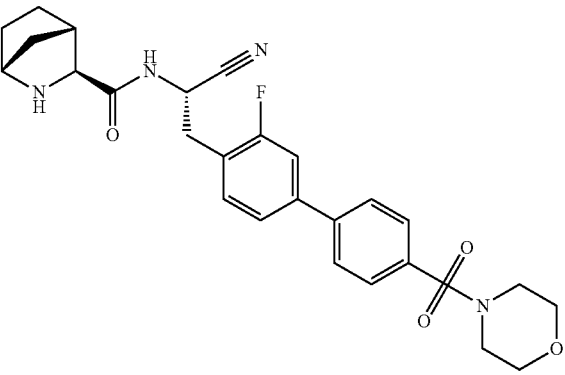 | I-3.2.52 | A2.1/SI | 64 |
| 218 | 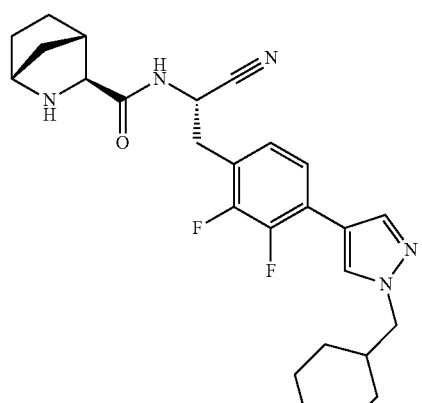 | I-2.3.77.1 | A1/FA | 24 |

TABLE 62-continued

| Example | Structure | Educt | Syn./Deprot. Method | Yield [%] |
|---|---|---|---|---|
| 219 | 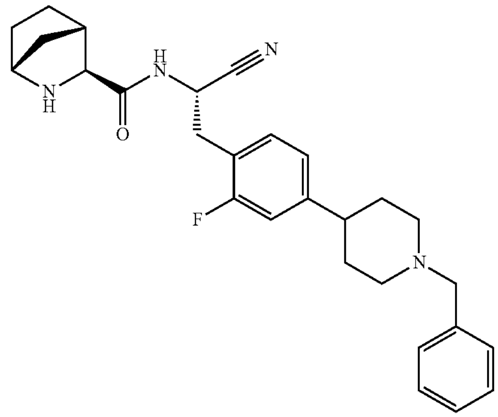 [SMILES: N#C[C@H](Cc1ccc(C2CCN(Cc3ccccc3)CC2)cc1F)NC(=O)[C@H]1N[C@@H]2CC[C@H]1C2] | I-2.3.43.3 | A1/FA | 41 |
| 220 | 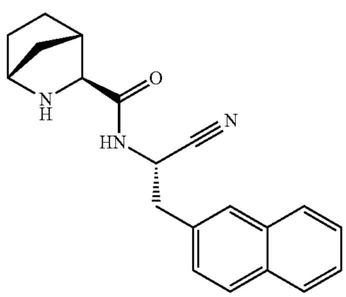 [SMILES: N#C[C@H](Cc1ccc2ccccc2c1)NC(=O)[C@H]1N[C@@H]2CC[C@H]1C2] | I-8.2.2 | C/SI | 69 |
| 221 | 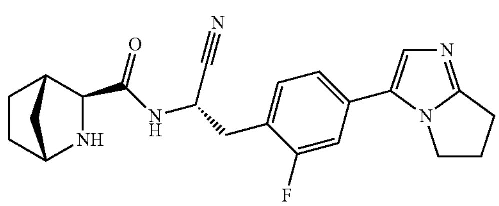 [SMILES: N#C[C@H](Cc1ccc(-c2cnc3n2CCC3)cc1F)NC(=O)[C@H]1N[C@@H]2CC[C@H]1C2] | I-3.2.44 | A2.1/TSA | 17 |
| 222 | 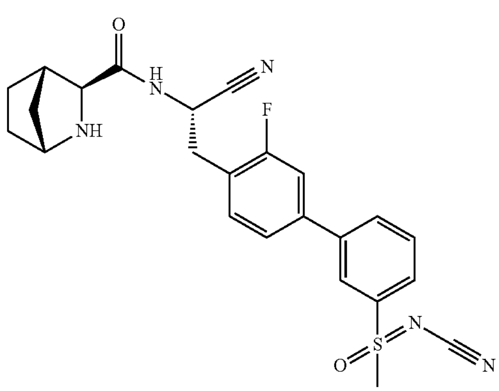 [SMILES: CS(=O)(=NC#N)c1cccc(-c2ccc(C[C@@H](C#N)NC(=O)[C@H]3N[C@@H]4CC[C@H]3C4)c(F)c2)c1] | I-3.2.53 | A2.1/FA | 59 |

TABLE 62-continued

| Example | Structure | Educt | Syn./Deprot. Method | Yield [%] |
|---|---|---|---|---|
| 223 | 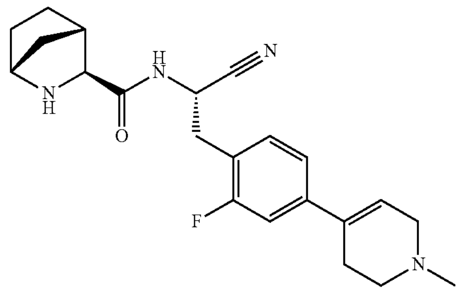 [SMILES: CN1CC=C(c2ccc(C[C@@H](C#N)NC(=O)[C@H]3N[C@@H]4CC[C@H]3C4)c(F)c2)CC1] | I-2.3.43 | A1/SI | 60 |
| 224 | 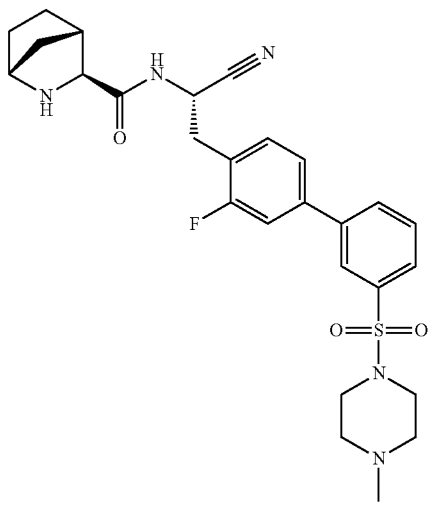 [SMILES: CN1CCN(S(=O)(=O)c2cccc(-c3ccc(C[C@@H](C#N)NC(=O)[C@H]4N[C@@H]5CC[C@H]4C5)c(F)c3)c2)CC1] | I-2.3.79 | A1/SI | 47 |
| 225 | 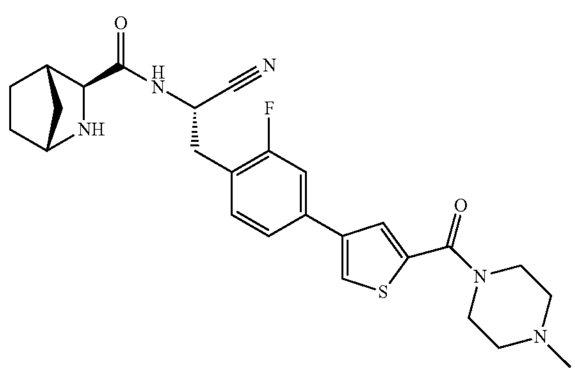 [SMILES: CN1CCN(C(=O)c2cc(-c3ccc(C[C@@H](C#N)NC(=O)[C@H]4N[C@@H]5CC[C@H]4C5)c(F)c3)cs2)CC1] | I-4.3.45 | A3/FA | 15 |
| 226 | 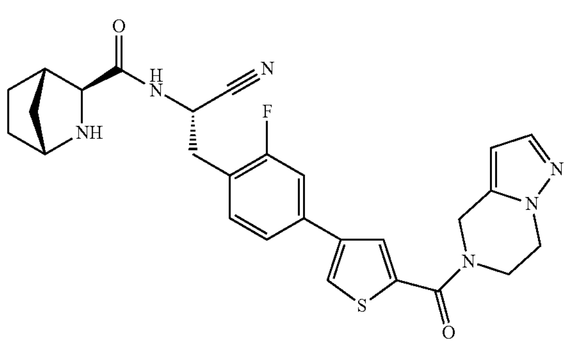 [SMILES: N#C[C@H](Cc1ccc(-c2csc(C(=O)N3CCn4nccc4C3)c2)cc1F)NC(=O)[C@H]1N[C@@H]2CC[C@H]1C2] | I-4.3.46 | A3/FA | 53 |

TABLE 62-continued

| Example | Structure | Educt | Syn./Deprot. Method | Yield [%] |
|---|---|---|---|---|
| 227 | 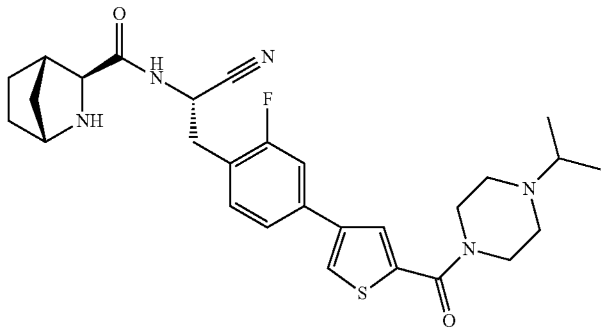 [SMILES: CC(C)N1CCN(C(=O)c2cc(-c3ccc(C[C@@H](C#N)NC(=O)[C@H]4N[C@@H]5CC[C@H]4C5)c(F)c3)cs2)CC1] | I-4.3.47 | A3/FA | 28 |
| 228 | 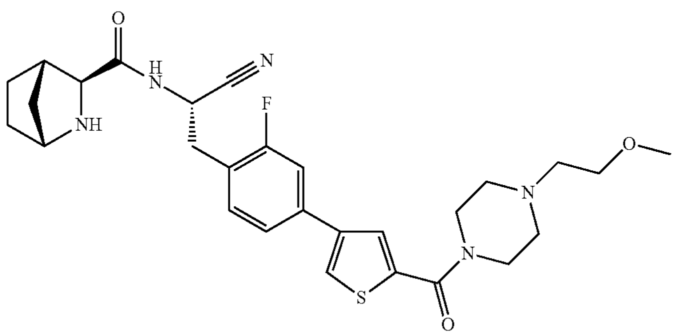 [SMILES: COCCN1CCN(C(=O)c2cc(-c3ccc(C[C@@H](C#N)NC(=O)[C@H]4N[C@@H]5CC[C@H]4C5)c(F)c3)cs2)CC1] | I-4.3.48 | A3/FA | 37 |
| 229 | 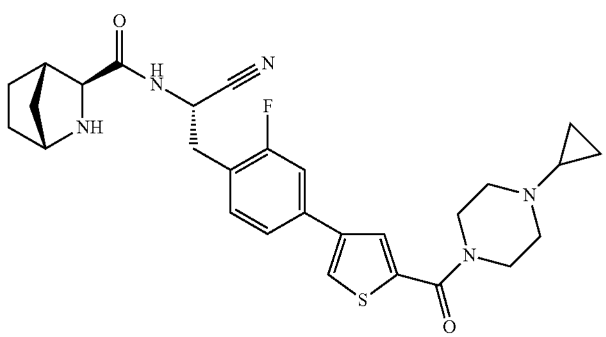 [SMILES: N#C[C@H](Cc1ccc(-c2csc(C(=O)N3CCN(C4CC4)CC3)c2)cc1F)NC(=O)[C@H]1N[C@@H]2CC[C@H]1C2] | I-4.3.49 | A3/FA | 14 |
| 230 | 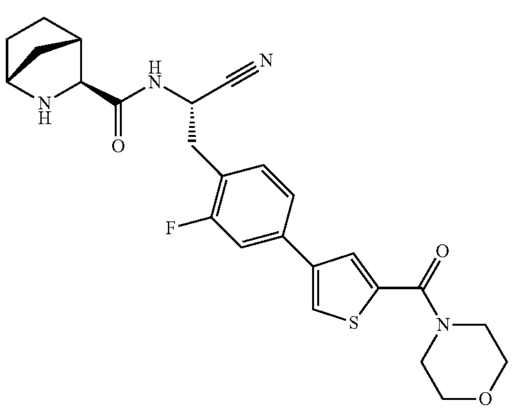 [SMILES: N#C[C@H](Cc1ccc(-c2csc(C(=O)N3CCOCC3)c2)cc1F)NC(=O)[C@H]1N[C@@H]2CC[C@H]1C2] | I-4.3.50 | A3/FA | 47 |

TABLE 62-continued

| Example | Structure | Educt | Syn./Deprot. Method | Yield [%] |
|---|---|---|---|---|
| 231 | 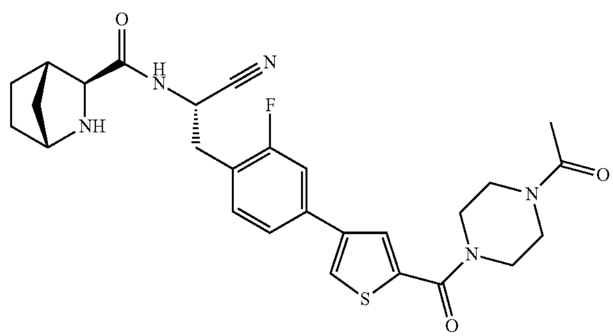 [SMILES: CC(=O)N1CCN(C(=O)c2cc(-c3ccc(C[C@@H](C#N)NC(=O)[C@H]4N[C@@H]5CC[C@H]4C5)c(F)c3)cs2)CC1] | I-4.3.51 | A3/FA | 30 |
| 232 | 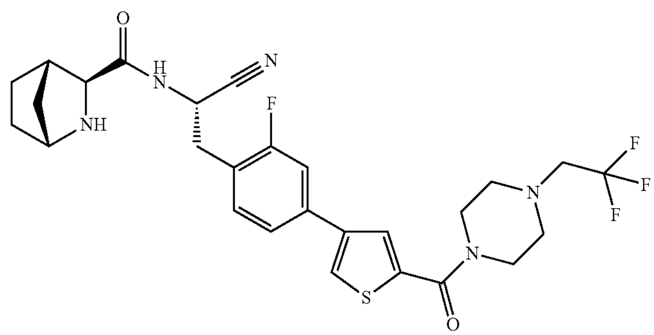 [SMILES: N#C[C@H](Cc1ccc(-c2csc(C(=O)N3CCN(CC(F)(F)F)CC3)c2)cc1F)NC(=O)[C@H]1N[C@@H]2CC[C@H]1C2] | I-4.3.52 | A3/FA | 60 |
| 233 | 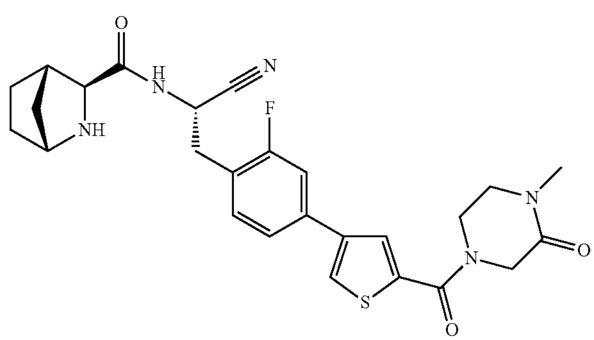 [SMILES: CN1CCN(C(=O)c2cc(-c3ccc(C[C@@H](C#N)NC(=O)[C@H]4N[C@@H]5CC[C@H]4C5)c(F)c3)cs2)CC1=O] | I-4.3.53 | A3/FA | 37 |
| 234 | 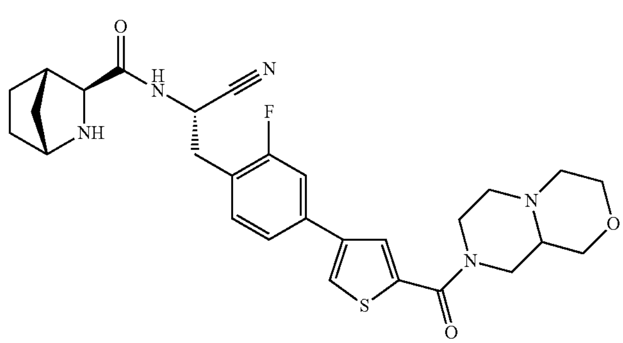 [SMILES: N#C[C@H](Cc1ccc(-c2csc(C(=O)N3CCN4CCOCC4C3)c2)cc1F)NC(=O)[C@H]1N[C@@H]2CC[C@H]1C2] | I-4.3.54 | A3/FA | 71 |

TABLE 62-continued

| Example | Structure | Educt | Syn./Deprot. Method | Yield [%] |
|---|---|---|---|---|
| 235 | 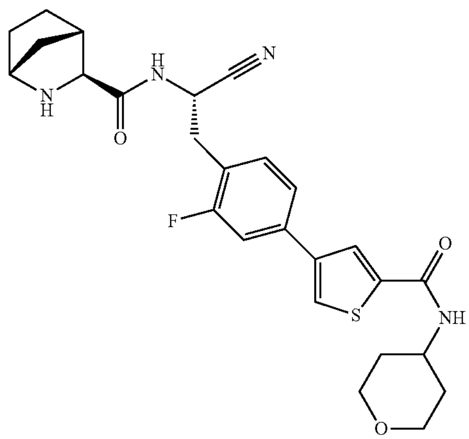 [SMILES: N#C[C@H](Cc1ccc(-c2csc(C(=O)NC3CCOCC3)c2)cc1F)NC(=O)[C@H]1N[C@@H]2CC[C@H]1C2] | I-4.3.55 | A3/FA | 38 |
| 236 | 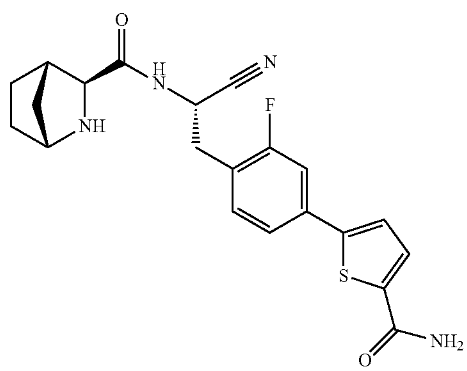 [SMILES: N#C[C@H](Cc1ccc(-c2ccc(C(N)=O)s2)cc1F)NC(=O)[C@H]1N[C@@H]2CC[C@H]1C2] | I-4.3.56 | A1/FA | 41 |
| 237 | 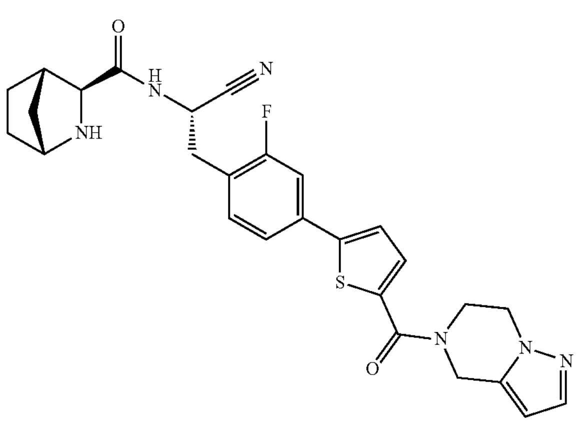 [SMILES: N#C[C@H](Cc1ccc(-c2ccc(C(=O)N3CCn4nccc4C3)s2)cc1F)NC(=O)[C@H]1N[C@@H]2CC[C@H]1C2] | I-4.3.57 | A1/TSA | 67 |

TABLE 62-continued

| Example | Structure | Educt | Syn./Deprot. Method | Yield [%] |
|---|---|---|---|---|
| 238 | 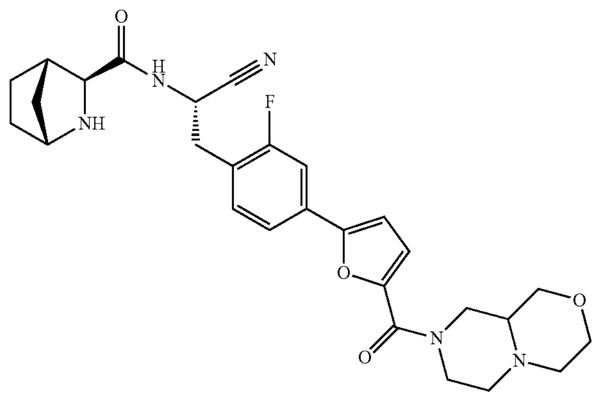 [SMILES: N#C[C@H](Cc1ccc(-c2ccc(C(=O)N3CCN4CCOCC4C3)o2)cc1F)NC(=O)[C@H]1N[C@@H]2CC[C@H]1C2] | I-4.3.58 | A1/FA | 42 |
| 239 | 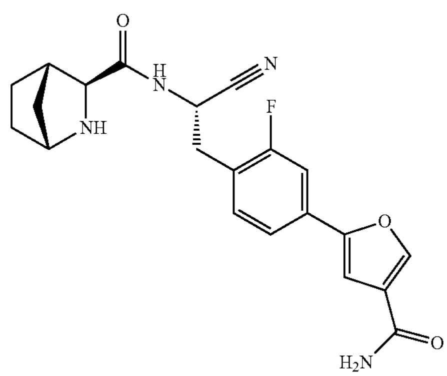 [SMILES: N#C[C@H](Cc1ccc(-c2cc(C(N)=O)co2)cc1F)NC(=O)[C@H]1N[C@@H]2CC[C@H]1C2] | I-4.3.59 | A1/FA | 53 |
| 240 | 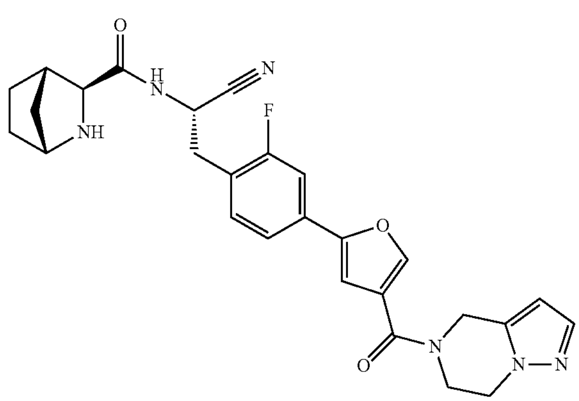 [SMILES: N#C[C@H](Cc1ccc(-c2cc(C(=O)N3CCn4nccc4C3)co2)cc1F)NC(=O)[C@H]1N[C@@H]2CC[C@H]1C2] | I-4.3.60 | A1/FA | 33 |

TABLE 62-continued

| Example | Structure | Educt | Syn./Deprot. Method | Yield [%] |
|---|---|---|---|---|
| 241 | 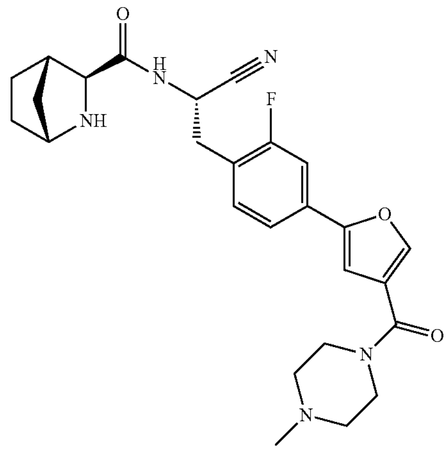 [SMILES: CN1CCN(C(=O)c2coc(-c3ccc(C[C@@H](C#N)NC(=O)[C@H]4N[C@@H]5CC[C@H]4C5)c(F)c3)c2)CC1] | I-4.3.61 | A1/FA | 41 |
| 242 | 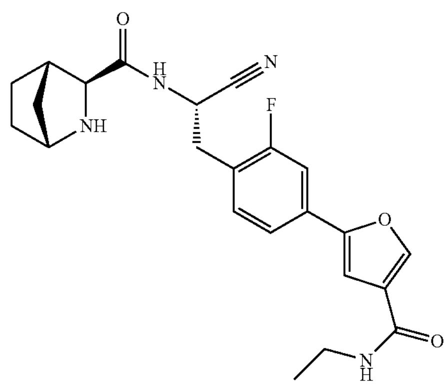 [SMILES: CCNC(=O)c1coc(-c2ccc(C[C@@H](C#N)NC(=O)[C@H]3N[C@@H]4CC[C@H]3C4)c(F)c2)c1] | I-4.3.62 | A1/FA | 52 |
| 243 | 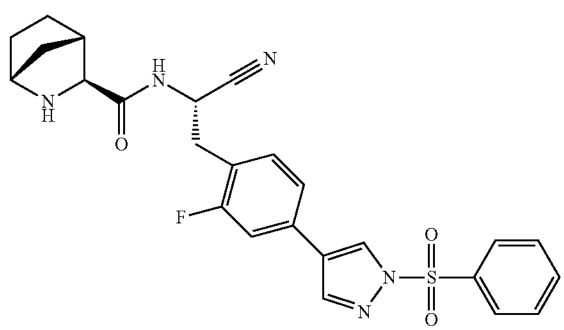 [SMILES: N#C[C@H](Cc1ccc(-c2cnn(S(=O)(=O)c3ccccc3)c2)cc1F)NC(=O)[C@H]1N[C@@H]2CC[C@H]1C2] | I-2.3.7.11 | A1/FA | 62 |
| 244 | 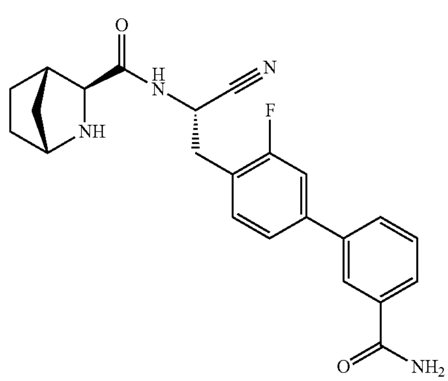 [SMILES: N#C[C@H](Cc1ccc(-c2cccc(C(N)=O)c2)cc1F)NC(=O)[C@H]1N[C@@H]2CC[C@H]1C2] | I-4.3.63 | A1/FA | 43 |

TABLE 62-continued

| Example | Structure | Educt | Syn./Deprot. Method | Yield [%] |
|---|---|---|---|---|
| 245 | 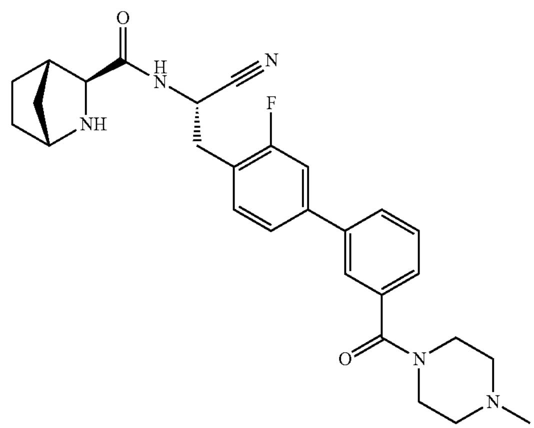 [SMILES: CN1CCN(C(=O)c2cccc(-c3ccc(C[C@@H](C#N)NC(=O)[C@H]4N[C@@H]5CC[C@H]4C5)c(F)c3)c2)CC1] | I-4.3.64 | A1/FA | 42 |
| 246 | 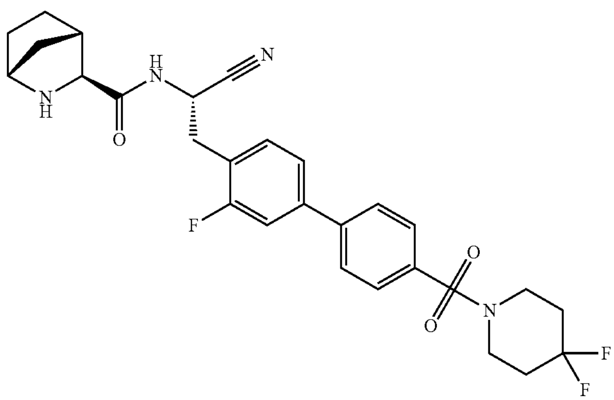 | I-3.2.54 | A2.1/SI | 63 |
| 247 | 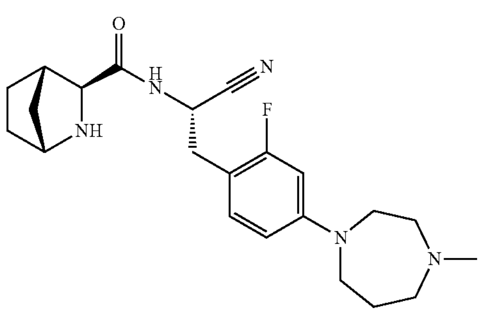 [SMILES: CN1CCCN(c2ccc(C[C@@H](C#N)NC(=O)[C@H]3N[C@@H]4CC[C@H]3C4)c(F)c2)CC1] | I-3.2.92 | A2.2/TSA | 20 |
| 248 | 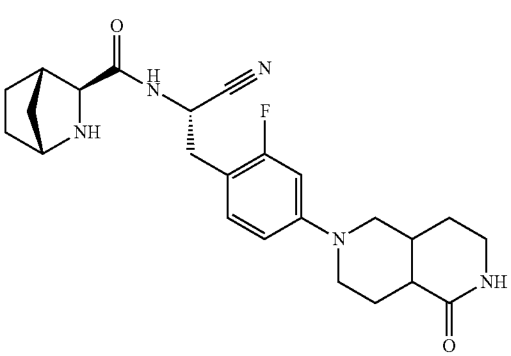 [SMILES: N#C[C@H](Cc1ccc(N2CCC3C(=O)NCCC3C2)cc1F)NC(=O)[C@H]1N[C@@H]2CC[C@H]1C2] | I-3.2.93 | A2.2/TSA | 78 |

TABLE 62-continued

| Example | Structure | Educt | Syn./Deprot. Method | Yield [%] |
|---|---|---|---|---|
| 249 | 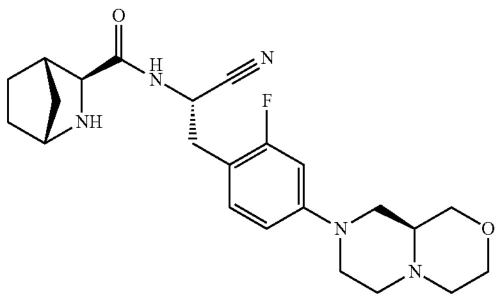 [SMILES: N#C[C@H](Cc1ccc(N2CCN3CCOC[C@@H]3C2)cc1F)NC(=O)[C@H]1N[C@@H]2CC[C@H]1C2] | I-3.2.7 | A2.2/TSA | 6 |
| 250 | 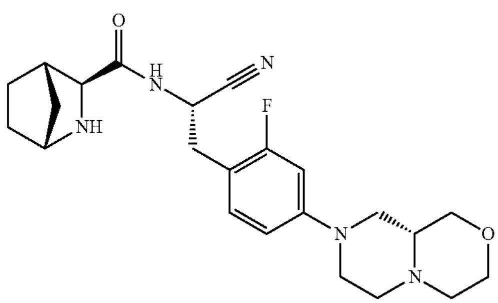 [SMILES: N#C[C@H](Cc1ccc(N2CCN3CCOC[C@H]3C2)cc1F)NC(=O)[C@H]1N[C@@H]2CC[C@H]1C2] | I-3.2.7 | A2.2/TSA | 7 |
| 251 | 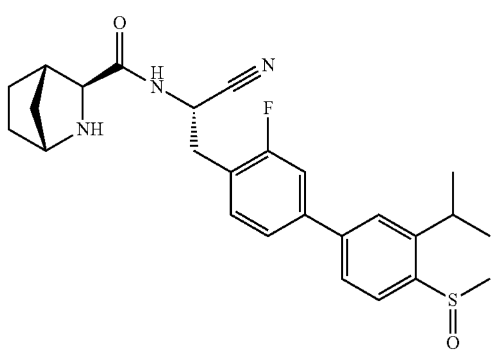 [SMILES: CC(C)c1cc(-c2ccc(C[C@@H](C#N)NC(=O)[C@H]3N[C@@H]4CC[C@H]3C4)c(F)c2)ccc1S(C)=O] | I-3.2.55 | A2.1/TSA | 65 |
| 252 | 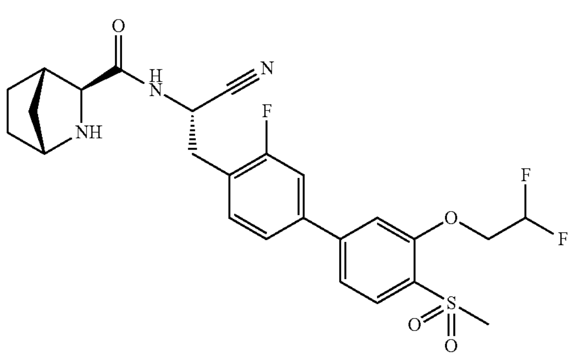 [SMILES: CS(=O)(=O)c1ccc(-c2ccc(C[C@@H](C#N)NC(=O)[C@H]3N[C@@H]4CC[C@H]3C4)c(F)c2)cc1OCC(F)F] | I-3.2.56 | A2.1/TSA | 82 |

TABLE 62-continued

| Example | Structure | Educt | Syn./Deprot. Method | Yield [%] |
|---------|-----------|-------|---------------------|-----------|
| 253 | 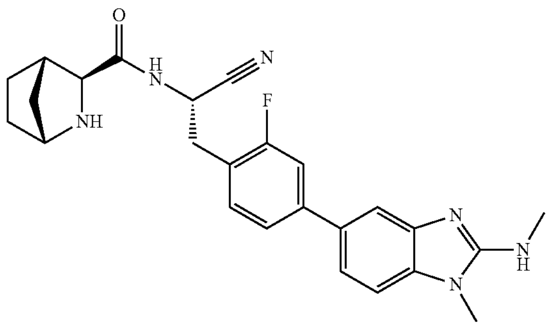 [SMILES: CNc1nc2cc(-c3ccc(C[C@@H](C#N)NC(=O)[C@H]4N[C@@H]5CC[C@H]4C5)c(F)c3)ccc2n1C] | I-3.2.57 | A2.1/TSA | 73 |
| 254 | 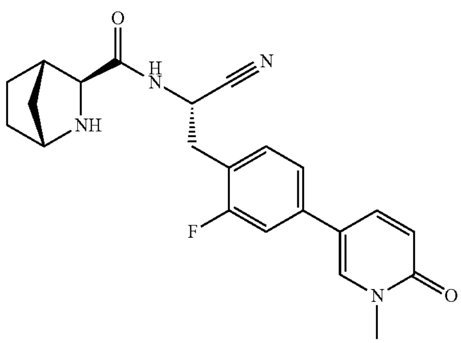 [SMILES: Cn1cc(-c2ccc(C[C@@H](C#N)NC(=O)[C@H]3N[C@@H]4CC[C@H]3C4)c(F)c2)ccc1=O] | I-3.2.58 | A2.1/TSA | 53 |
| 255 | 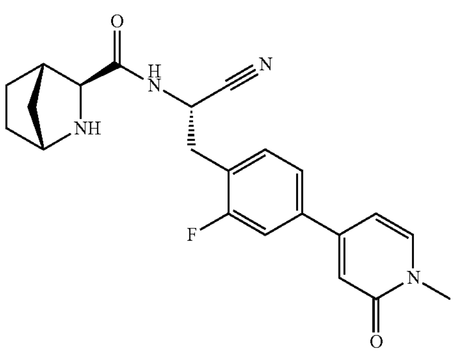 [SMILES: Cn1ccc(-c2ccc(C[C@@H](C#N)NC(=O)[C@H]3N[C@@H]4CC[C@H]3C4)c(F)c2)cc1=O] | I-3.2.59 | A2.1/TSA | 58 |
| 256 | 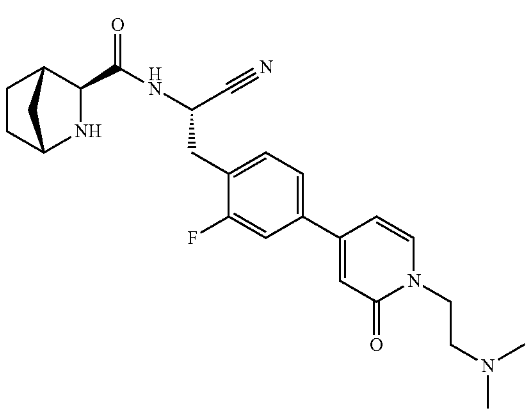 [SMILES: CN(C)CCn1ccc(-c2ccc(C[C@@H](C#N)NC(=O)[C@H]3N[C@@H]4CC[C@H]3C4)c(F)c2)cc1=O] | I-3.2.60 | A2.1/TSA | 52 |

TABLE 62-continued

| Example | Structure | Educt | Syn./Deprot. Method | Yield [%] |
|---|---|---|---|---|
| 257 | 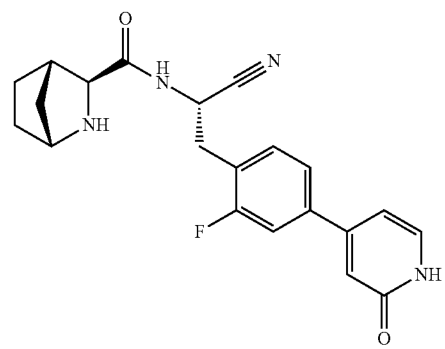 [SMILES: N#C[C@H](Cc1ccc(-c2cc[nH]c(=O)c2)cc1F)NC(=O)[C@H]1N[C@@H]2CC[C@H]1C2] | I-3.2.61 | A2.1/TSA | 41 |
| 258 | 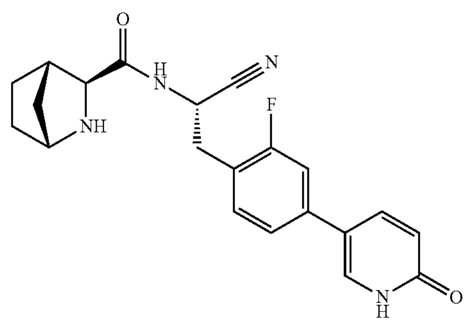 [SMILES: N#C[C@H](Cc1ccc(-c2ccc(=O)[nH]c2)cc1F)NC(=O)[C@H]1N[C@@H]2CC[C@H]1C2] | I-3.2.62 | A2.1/TSA | 19 |
| 259 | 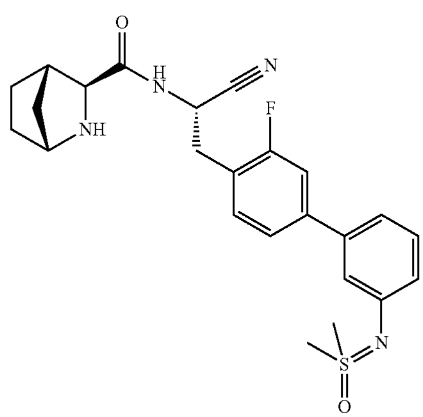 [SMILES: CS(C)(=O)=Nc1cccc(-c2ccc(C[C@@H](C#N)NC(=O)[C@H]3N[C@@H]4CC[C@H]3C4)c(F)c2)c1] | I-3.2.63 | A2.1/FA | 19 |
| 260 | 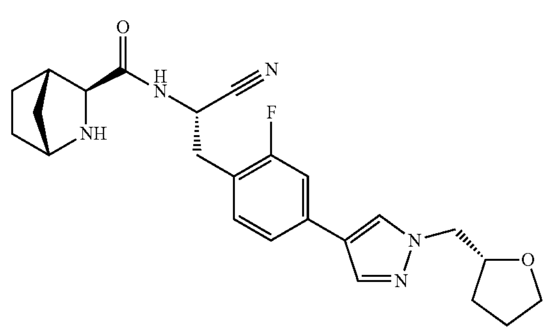 [SMILES: N#C[C@H](Cc1ccc(-c2cnn(C[C@H]3CCCO3)c2)cc1F)NC(=O)[C@H]1N[C@@H]2CC[C@H]1C2] | I-3.2.64.1 | A2.1/FA | 91 |

TABLE 62-continued

| Example | Structure | Educt | Syn./Deprot. Method | Yield [%] |
|---|---|---|---|---|
| 261 | 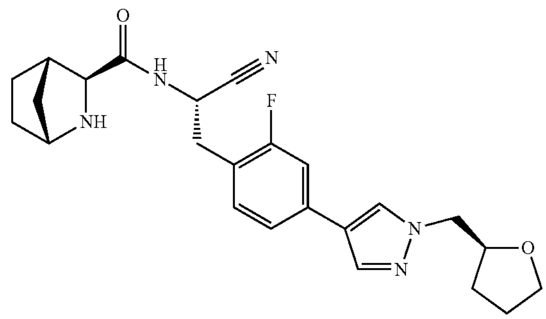 [SMILES: N#C[C@H](Cc1ccc(-c2cnn(C[C@@H]3CCCO3)c2)cc1F)NC(=O)[C@H]1N[C@@H]2CC[C@H]1C2] | I-3.2.64.2 | A2.1/FA | 79 |
| 262 | 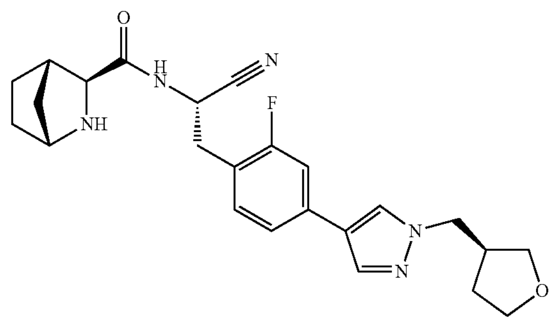 [SMILES: N#C[C@H](Cc1ccc(-c2cnn(C[C@@H]3CCOC3)c2)cc1F)NC(=O)[C@H]1N[C@@H]2CC[C@H]1C2] | I-2.3.7.4.1 | A1/FA | 53 |
| 263 | 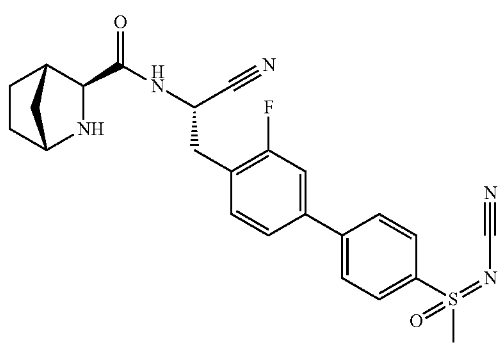 [SMILES: CS(=O)(=NC#N)c1ccc(-c2ccc(C[C@@H](C#N)NC(=O)[C@H]3N[C@@H]4CC[C@H]3C4)c(F)c2)cc1] | I-3.2.65 | A2.1/FA | 52 |
| 264 | 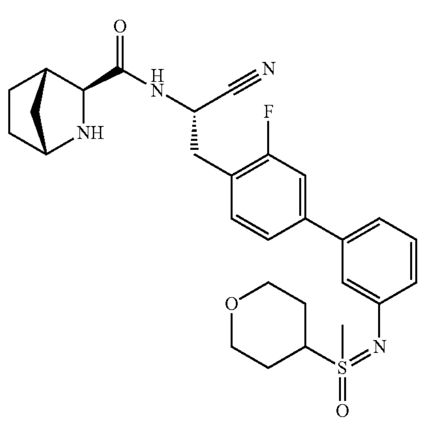 [SMILES: CS(=O)(=Nc1cccc(-c2ccc(C[C@@H](C#N)NC(=O)[C@H]3N[C@@H]4CC[C@H]3C4)c(F)c2)c1)C1CCOCC1] | I-3.2.66 | A2.1/FA | 23 |

TABLE 62-continued

| Example | Structure | Educt | Syn./Deprot. Method | Yield [%] |
|---|---|---|---|---|
| 265 | 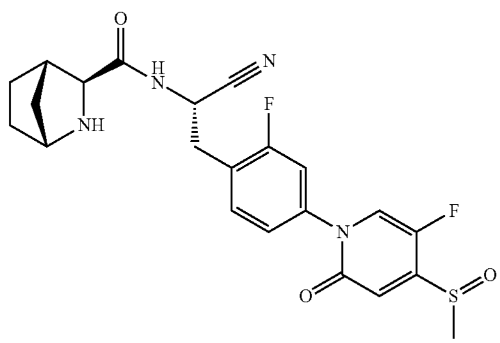 [SMILES: CS(=O)c1cc(=O)n(-c2ccc(C[C@@H](C#N)NC(=O)[C@H]3N[C@@H]4CC[C@H]3C4)c(F)c2)cc1F] | I-3.2.94 | A2.2/TSA | 14 |
| 266 | 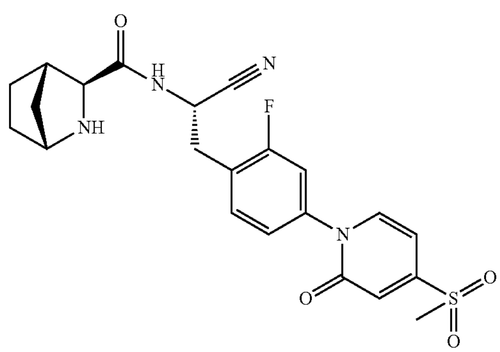 [SMILES: CS(=O)(=O)c1ccn(-c2ccc(C[C@@H](C#N)NC(=O)[C@H]3N[C@@H]4CC[C@H]3C4)c(F)c2)c(=O)c1] | I-3.2.95 | A2.2/TSA | 8 |
| 267 | 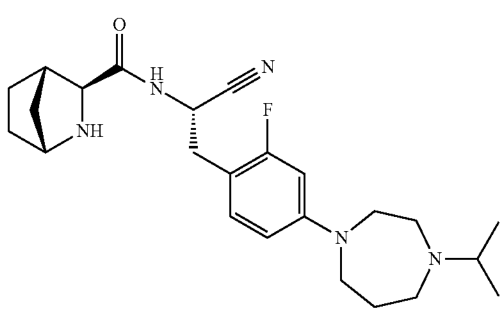 [SMILES: CC(C)N1CCCN(c2ccc(C[C@@H](C#N)NC(=O)[C@H]3N[C@@H]4CC[C@H]3C4)c(F)c2)CC1] | I-3.2.96 | A2.2/TSA | 41 |
| 268 | 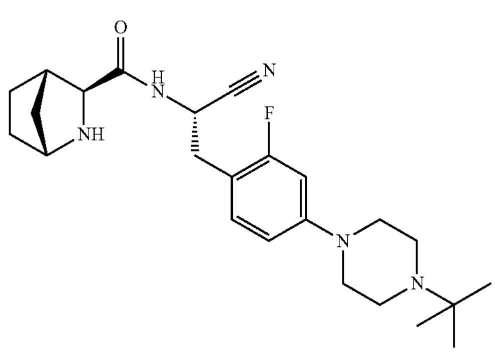 [SMILES: CC(C)(C)N1CCN(c2ccc(C[C@@H](C#N)NC(=O)[C@H]3N[C@@H]4CC[C@H]3C4)c(F)c2)CC1] | I-3.2.97 | A2.2/TSA | 80 |

TABLE 62-continued

| Example | Structure | Educt | Syn./Deprot. Method | Yield [%] |
|---------|-----------|-------|---------------------|-----------|
| 269 | 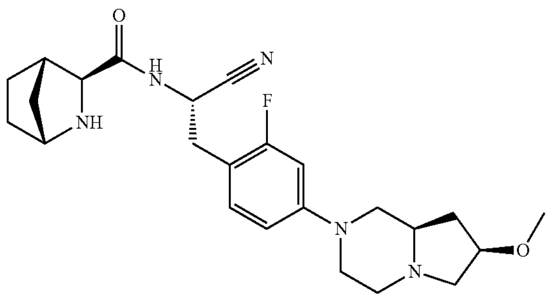 [SMILES: CO[C@@H]1C[C@@H]2CN(c3ccc(C[C@@H](C#N)NC(=O)[C@H]4N[C@@H]5CC[C@H]4C5)c(F)c3)CCN2C1] | I-3.2.98 | A2.2/TSA | 27 |
| 270 | 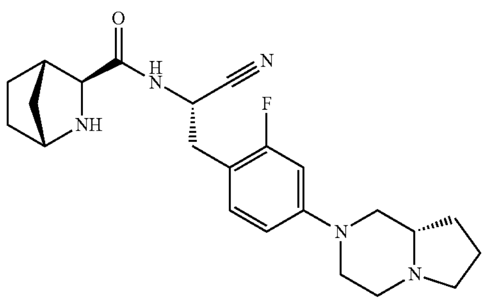 [SMILES: N#C[C@H](Cc1ccc(N2CCN3CCC[C@H]3C2)cc1F)NC(=O)[C@H]1N[C@@H]2CC[C@H]1C2] | I-3.2.99 | A2.2/TSA | 81 |
| 271 | 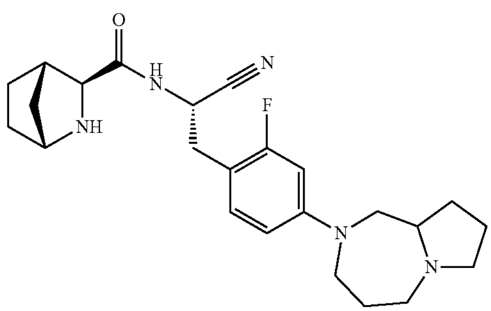 [SMILES: N#C[C@H](Cc1ccc(N2CCCN3CCCC3C2)cc1F)NC(=O)[C@H]1N[C@@H]2CC[C@H]1C2] | I-3.2.100 | A2.2/TSA | 17 |
| 272 | 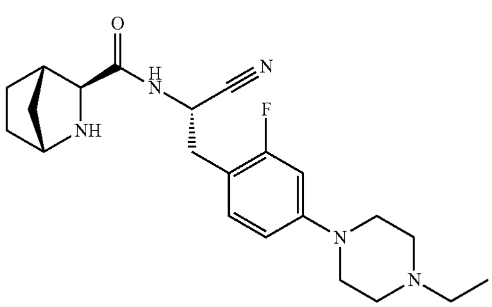 [SMILES: CCN1CCN(c2ccc(C[C@@H](C#N)NC(=O)[C@H]3N[C@@H]4CC[C@H]3C4)c(F)c2)CC1] | I-3.2.101 | A2.2/TSA | 27 |
| 273 | 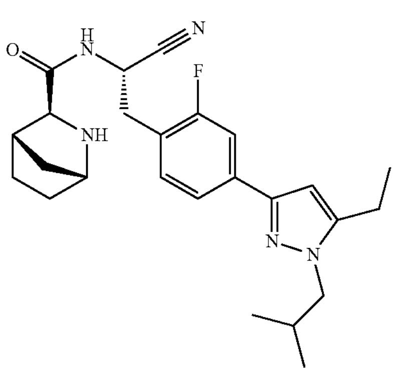 [SMILES: CCc1cc(-c2ccc(C[C@@H](C#N)NC(=O)[C@H]3N[C@@H]4CC[C@H]3C4)c(F)c2)nn1CC(C)C] | I-3.2.67 | A2.1/TSA | 7 |

TABLE 62-continued

| Example | Structure | Educt | Syn./Deprot. Method | Yield [%] |
|---|---|---|---|---|
| 274 | 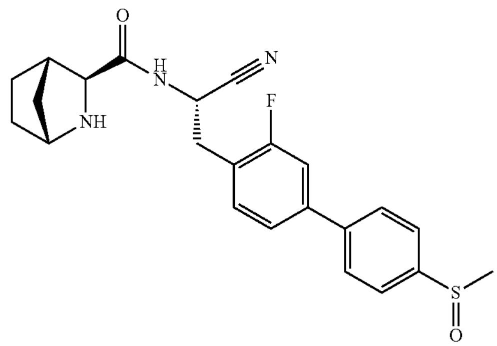 [SMILES: CS(=O)c1ccc(-c2ccc(C[C@@H](C#N)NC(=O)[C@H]3N[C@@H]4CC[C@H]3C4)c(F)c2)cc1] | I-3.2.68 | A2.1/TSA | 73 |
| 275 | 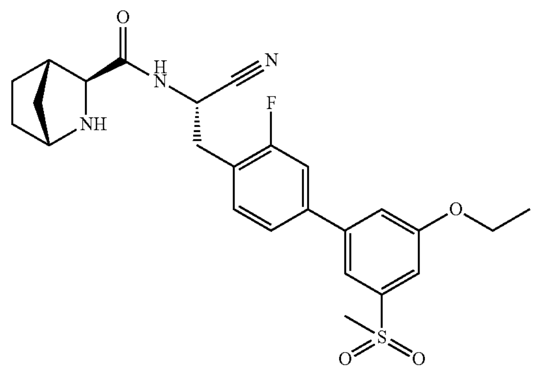 [SMILES: CCOc1cc(-c2ccc(C[C@@H](C#N)NC(=O)[C@H]3N[C@@H]4CC[C@H]3C4)c(F)c2)cc(S(C)(=O)=O)c1] | I-3.2.69 | A2.1/TSA | 71 |
| 276 | 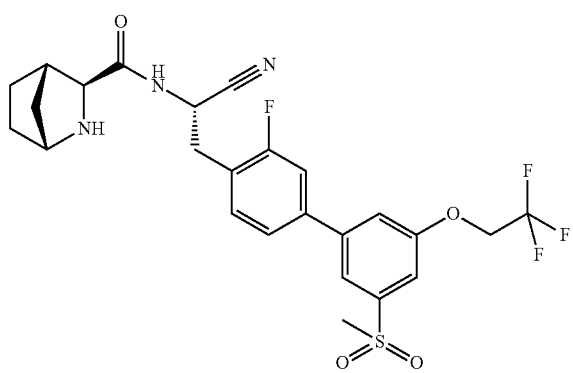 [SMILES: CS(=O)(=O)c1cc(OCC(F)(F)F)cc(-c2ccc(C[C@@H](C#N)NC(=O)[C@H]3N[C@@H]4CC[C@H]3C4)c(F)c2)c1] | I-3.2.70 | A2.1/TSA | 72 |
| 277 | 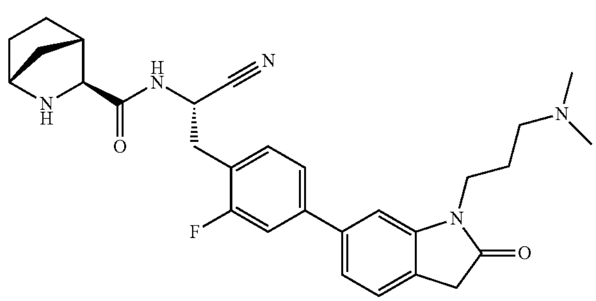 [SMILES: CN(C)CCCN1C(=O)Cc2ccc(-c3ccc(C[C@@H](C#N)NC(=O)[C@H]4N[C@@H]5CC[C@H]4C5)c(F)c3)cc21] | I-3.2.71 | A2.1/TSA | 2 |

TABLE 62-continued

| Example | Structure | Educt | Syn./Deprot. Method | Yield [%] |
|---|---|---|---|---|
| 278 | 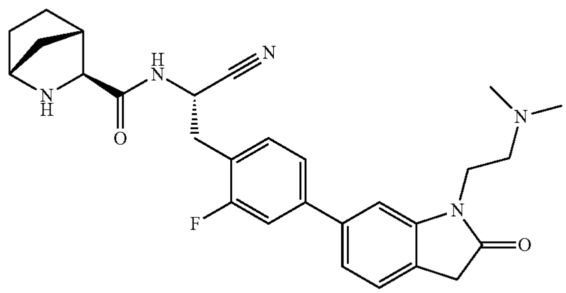 [SMILES: CN(C)CCN1C(=O)Cc2ccc(-c3ccc(C[C@@H](C#N)NC(=O)[C@H]4N[C@@H]5CC[C@H]4C5)c(F)c3)cc21] | I-3.2.72 | A2.1/TSA | 13 |
| 279 | 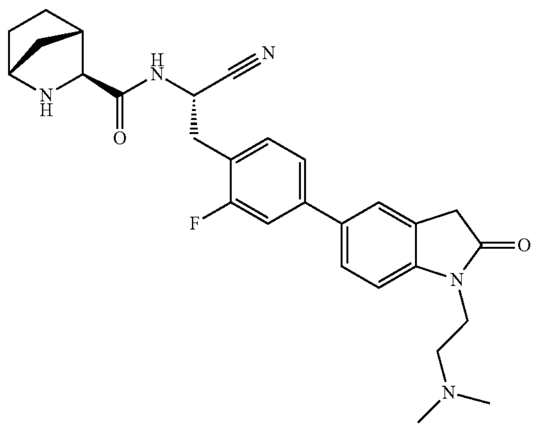 [SMILES: CN(C)CCN1C(=O)Cc2cc(-c3ccc(C[C@@H](C#N)NC(=O)[C@H]4N[C@@H]5CC[C@H]4C5)c(F)c3)ccc21] | I-3.2.73 | A2.1/TSA | 28 |
| 280 | 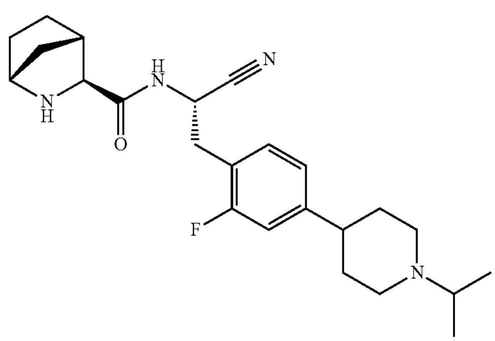 [SMILES: CC(C)N1CCC(c2ccc(C[C@@H](C#N)NC(=O)[C@H]3N[C@@H]4CC[C@H]3C4)c(F)c2)CC1] | I-3.3.8 | A2.1/SI | 90 |
| 281 | 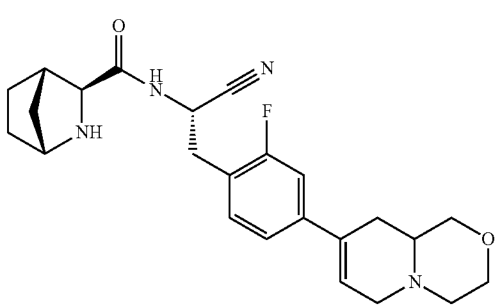 [SMILES: N#C[C@H](Cc1ccc(C2=CCN3CCOCC3C2)cc1F)NC(=O)[C@H]1N[C@@H]2CC[C@H]1C2] | I-3.3.9 | A2.1/TSA | 83 |

TABLE 62-continued

| Example | Structure | Educt | Syn./Deprot. Method | Yield [%] |
|---------|-----------|-------|---------------------|-----------|
| 282 | 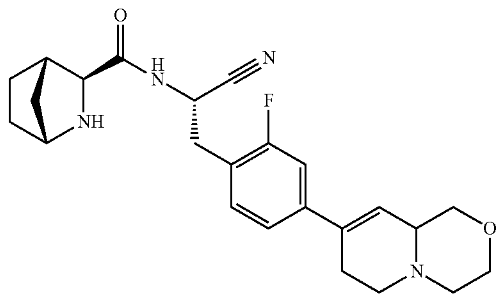 [SMILES: N#C[C@H](Cc1ccc(C2=CC3COCCN3CC2)cc1F)NC(=O)[C@H]1N[C@@H]2CC[C@H]1C2] | I-3.3.10 | A2.1/TSA | 42 |
| 283 | 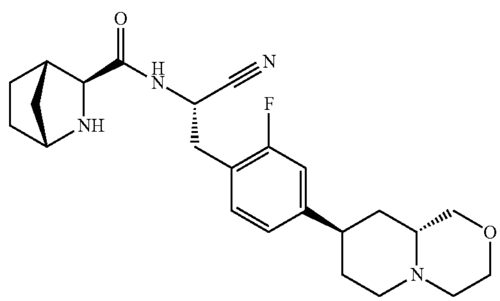 [SMILES: N#C[C@H](Cc1ccc([C@@H]2CCN3CCOC[C@H]3C2)cc1F)NC(=O)[C@H]1N[C@@H]2CC[C@H]1C2] | I-3.3.11 | A2.1/TSA | 91 |
| 284 | 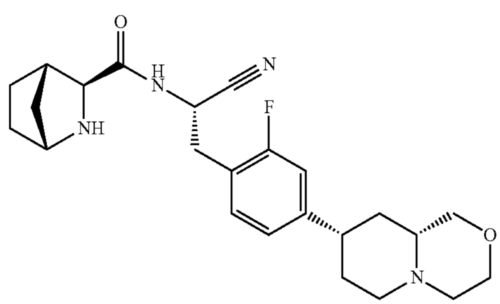 [SMILES: N#C[C@H](Cc1ccc([C@H]2CCN3CCOC[C@H]3C2)cc1F)NC(=O)[C@H]1N[C@@H]2CC[C@H]1C2] | I-3.3.12 | A2.1/TSA | 80 |
| 285 | 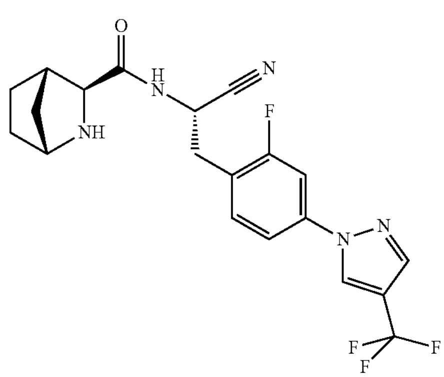 [SMILES: N#C[C@H](Cc1ccc(-n2cc(C(F)(F)F)cn2)cc1F)NC(=O)[C@H]1N[C@@H]2CC[C@H]1C2] | I-3.2.117 | A2.2/TSA | 81 |

TABLE 62-continued

| Example | Structure | Educt | Syn./Deprot. Method | Yield [%] |
|---|---|---|---|---|
| 286 | 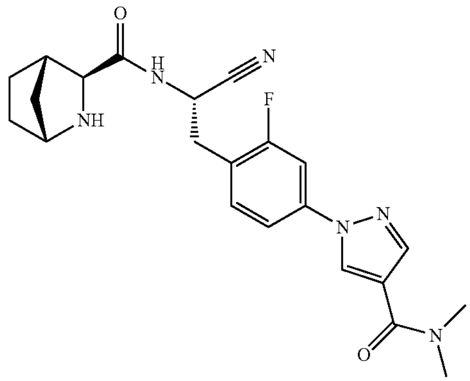 [SMILES: CN(C)C(=O)c1cnn(-c2ccc(C[C@@H](C#N)NC(=O)[C@H]3N[C@@H]4CC[C@H]3C4)c(F)c2)c1] | I-3.2.120 | A2.2/TSA | 80 |
| 287 | 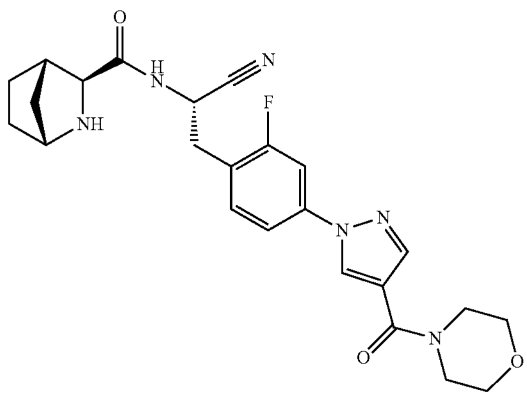 [SMILES: N#C[C@H](Cc1ccc(-n2cc(C(=O)N3CCOCC3)cn2)cc1F)NC(=O)[C@H]1N[C@@H]2CC[C@H]1C2] | I-3.2.121 | A2.2/TSA | 77 |
| 288 | 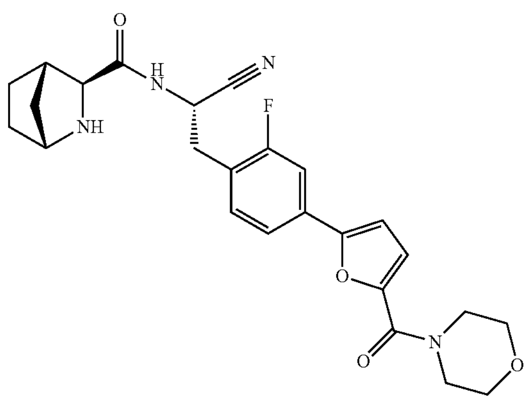 [SMILES: N#C[C@H](Cc1ccc(-c2ccc(C(=O)N3CCOCC3)o2)cc1F)NC(=O)[C@H]1N[C@@H]2CC[C@H]1C2] | I-4.3.65 | A3/FA | 68 |
| 289 | 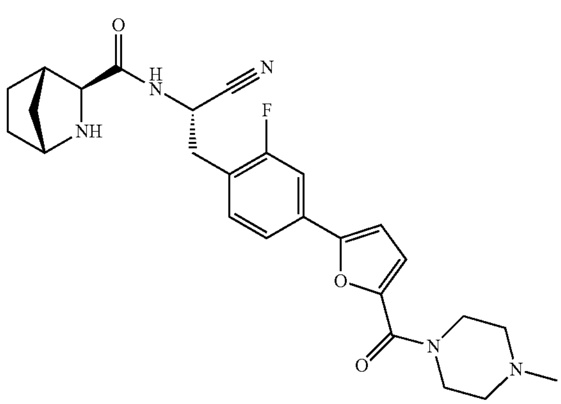 [SMILES: CN1CCN(C(=O)c2ccc(-c3ccc(C[C@@H](C#N)NC(=O)[C@H]4N[C@@H]5CC[C@H]4C5)c(F)c3)o2)CC1] | I-4.3.66 | A3/FA | 66 |

TABLE 62-continued

| Example | Structure | Educt | Syn./Deprot. Method | Yield [%] |
|---|---|---|---|---|
| 290 | 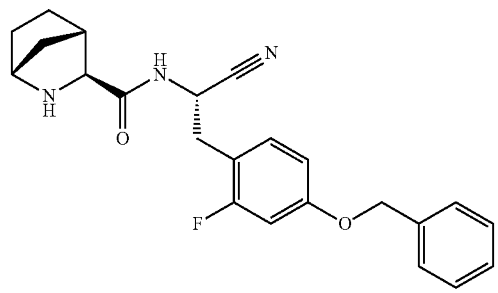 [SMILES: N#C[C@H](Cc1ccc(OCc2ccccc2)cc1F)NC(=O)[C@H]1N[C@@H]2CC[C@H]1C2] | I-8.2.3 | C/TSA | 93 |
| 291 | 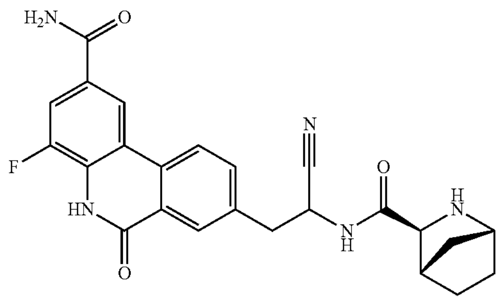 [SMILES: N#CC(Cc1ccc2c(c1)c(=O)[nH]c1c(F)cc(C(N)=O)cc12)NC(=O)[C@H]1N[C@@H]2CC[C@H]1C2] | I-18.2.3 | D1/MSA | 18 |
| 292 | 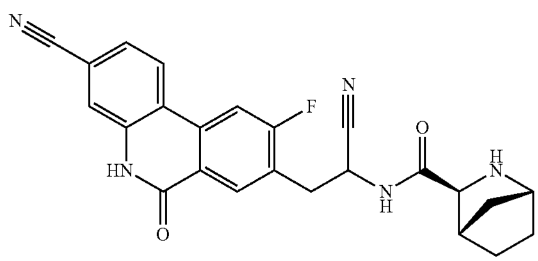 [SMILES: N#Cc1ccc2c(c1)[nH]c(=O)c1cc(CC(C#N)NC(=O)[C@H]3N[C@@H]4CC[C@H]3C4)c(F)cc12] | I-18.2.1 | D1/SI | 11 |
| 293 | 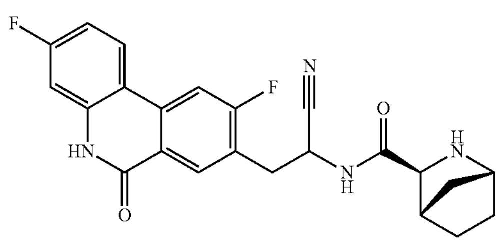 [SMILES: N#CC(Cc1cc2c(=O)[nH]c3cc(F)ccc3c2cc1F)NC(=O)[C@H]1N[C@@H]2CC[C@H]1C2] | I-18.2.2 | D1/SI | 24 |
| 294 | 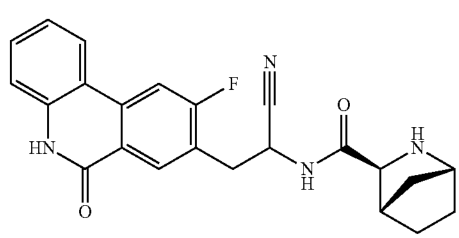 [SMILES: N#CC(Cc1cc2c(=O)[nH]c3ccccc3c2cc1F)NC(=O)[C@H]1N[C@@H]2CC[C@H]1C2] | I-18.2.4 | D1/SI | 20 |

TABLE 62-continued

| Example | Structure | Educt | Syn./Deprot. Method | Yield [%] |
|---|---|---|---|---|
| 295 | 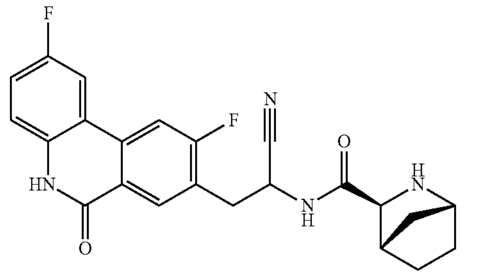 [SMILES: N#CC(Cc1cc2c(=O)[nH]c3ccc(F)cc3c2cc1F)NC(=O)[C@H]1N[C@@H]2CC[C@H]1C2] | I-18.2.5 | D1/SI | 13 |
| 296 | 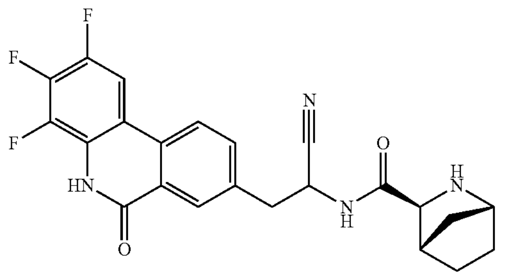 [SMILES: N#CC(Cc1ccc2c(c1)c(=O)[nH]c1c(F)c(F)c(F)cc12)NC(=O)[C@H]1N[C@@H]2CC[C@H]1C2] | I-18.2.6 | D1/TSA | 7 |
| 297 | 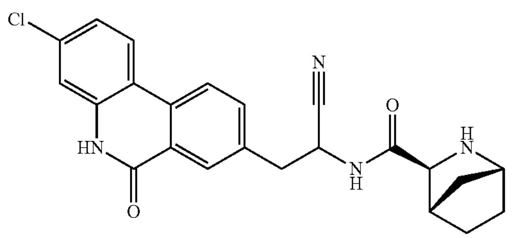 [SMILES: N#CC(Cc1ccc2c(c1)c(=O)[nH]c1cc(Cl)ccc12)NC(=O)[C@H]1N[C@@H]2CC[C@H]1C2] | I-18.2.7 | D1/SI | 43 |
| 298 | 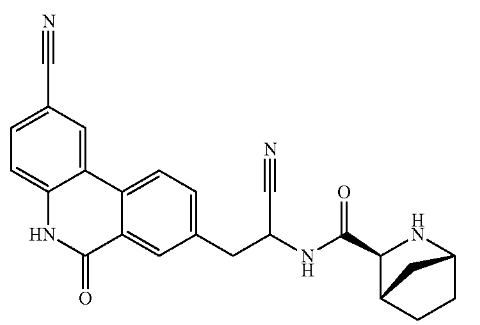 [SMILES: N#Cc1ccc2[nH]c(=O)c3cc(CC(C#N)NC(=O)[C@H]4N[C@@H]5CC[C@H]4C5)ccc3c2c1] | I-18.2.8 | D1/SI | 71 |
| 299 | 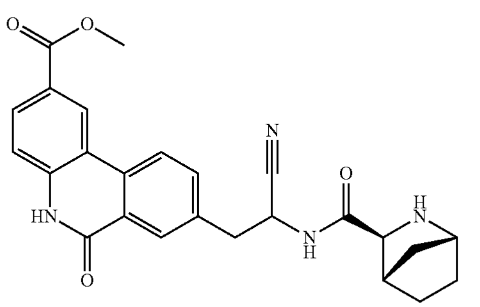 [SMILES: COC(=O)c1ccc2[nH]c(=O)c3cc(CC(C#N)NC(=O)[C@H]4N[C@@H]5CC[C@H]4C5)ccc3c2c1] | I-18.2.9 | D1/SI | 55 |

TABLE 62-continued

| Example | Structure | Educt | Syn./Deprot. Method | Yield [%] |
|---------|-----------|-------|---------------------|-----------|
| 300 | 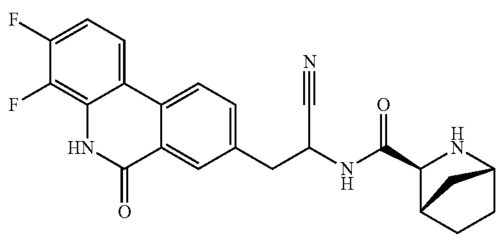 [SMILES: N#CC(Cc1ccc2c(c1)c(=O)[nH]c1c(F)c(F)ccc12)NC(=O)[C@H]1N[C@@H]2CC[C@H]1C2] | I-18.2.10 | D1/TSA | 24 |
| 301 | 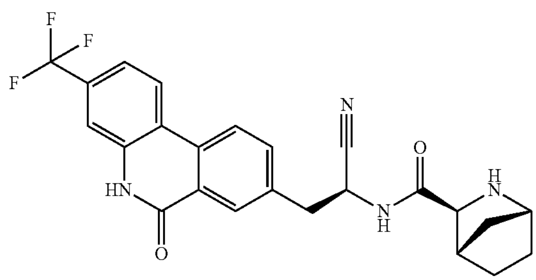 [SMILES: N#C[C@H](Cc1ccc2c(c1)c(=O)[nH]c1cc(C(F)(F)F)ccc12)NC(=O)[C@H]1N[C@@H]2CC[C@H]1C2] | I-18.2.11 | D1/SI | 27 |
| 302 | 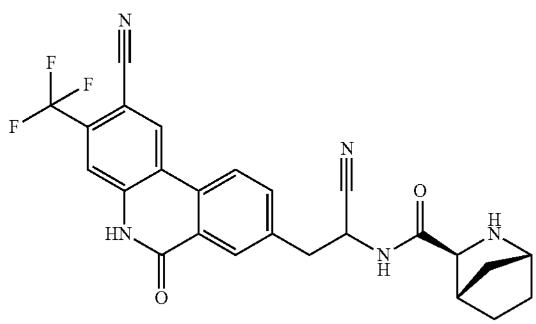 [SMILES: N#Cc1cc2c(cc1C(F)(F)F)[nH]c(=O)c1cc(CC(C#N)NC(=O)[C@H]3N[C@@H]4CC[C@H]3C4)ccc12] | I-18.2.12 | D1/SI | 58 |
| 303 | 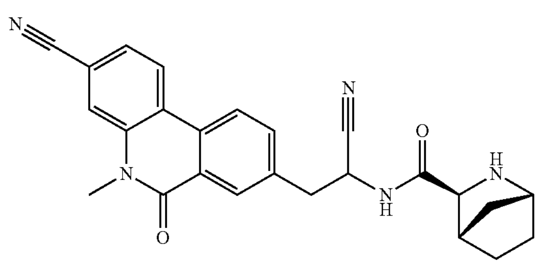 [SMILES: Cn1c(=O)c2cc(CC(C#N)NC(=O)[C@H]3N[C@@H]4CC[C@H]3C4)ccc2c2ccc(C#N)cc21] | I-18.2.13 | D1/TSA | 29 |
| 304 | 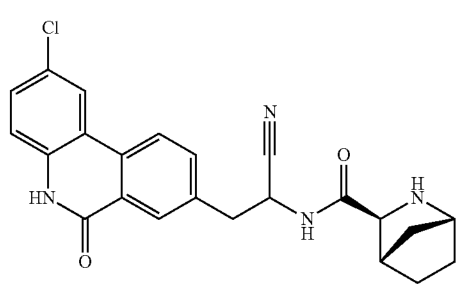 [SMILES: N#CC(Cc1ccc2c(c1)c(=O)[nH]c1ccc(Cl)cc12)NC(=O)[C@H]1N[C@@H]2CC[C@H]1C2] | I-18.2.14 | D1/SI | 32 |

TABLE 62-continued
| Example | Structure | Educt | Syn./Deprot. Method | Yield [%] |
|---|---|---|---|---|
| 305 | 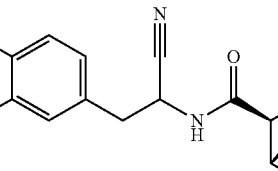 | I-18.2 | D1/MSA | 14 |
| 306 | 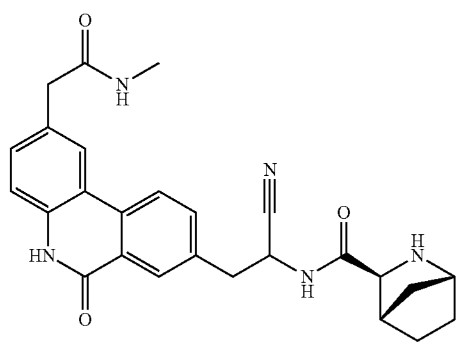 [SMILES: CNC(=O)Cc1ccc2[nH]c(=O)c3cc(CC(C#N)NC(=O)[C@H]4N[C@@H]5CC[C@H]4C5)ccc3c2c1] | I-18.2.15 | D1/MSA | 29 |
| 307 | 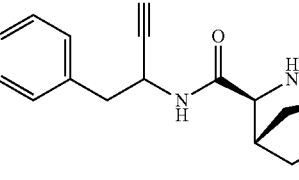 | I-18.2.16 | D1/SI | 36 |
| 308 | 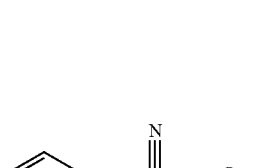 | I-18.2.17 | D1/SI | 37 |
| 309 | 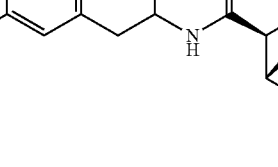 | I-18.2.18 | D1/MSA | 11 |

TABLE 62-continued
| Example | Structure | Educt | Syn./ Deprot. Method | Yield [%] |
|---|---|---|---|---|
| 310 | 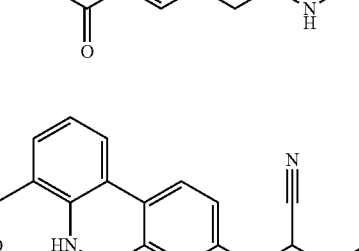 | I-18.2.19 | D1/SI | 63 |
| 311 | 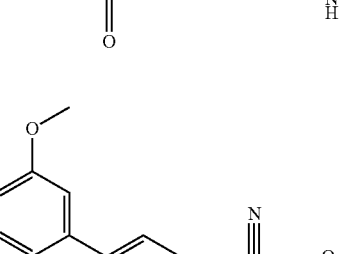 | I-18.2.20 | D1/SI | 13 |
| 312 | 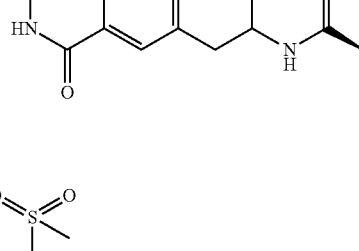 | I-18.2.21 | D1/SI | 28 |
| 313 | 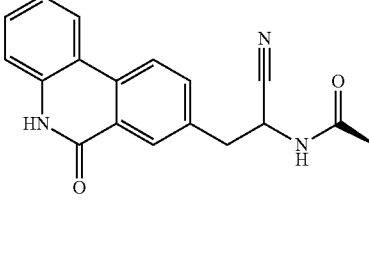 | I-18.2.22 | D1/SI | 7 |
| 314 | 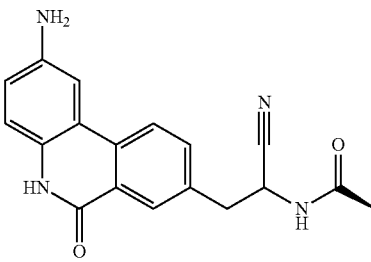 | I-18.2.23 | D1/MSA | 25 |

TABLE 62-continued

| Example | Structure | Educt | Syn./Deprot. Method | Yield [%] |
|---|---|---|---|---|
| 315 | 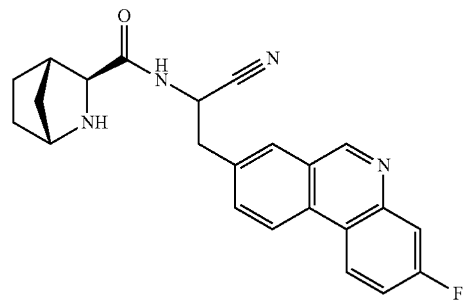 [SMILES: N#CC(Cc1ccc2c(cnc3cc(F)ccc32)c1)NC(=O)[C@H]1N[C@@H]2CC[C@H]1C2] | I-21.3 | Z/TSA | 60 |
| 316 | 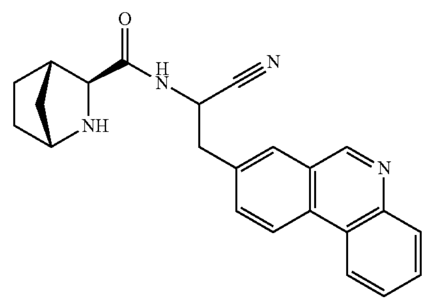 [SMILES: N#CC(Cc1ccc2c(cnc3ccccc32)c1)NC(=O)[C@H]1N[C@@H]2CC[C@H]1C2] | I-21.3.1 | Z/TSA | 51 |
| 317 | 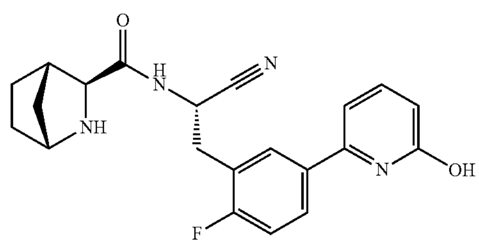 [SMILES: N#C[C@H](Cc1cc(-c2cccc(O)n2)ccc1F)NC(=O)[C@H]1N[C@@H]2CC[C@H]1C2] | I-3.2.77 | A2.1/TSA | 47 |
| 318 | 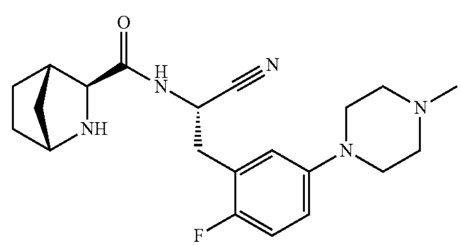 [SMILES: CN1CCN(c2ccc(F)c(C[C@@H](C#N)NC(=O)[C@H]3N[C@@H]4CC[C@H]3C4)c2)CC1] | I-3.2.102 | A2.2/TSA | 83 |
| 319 | 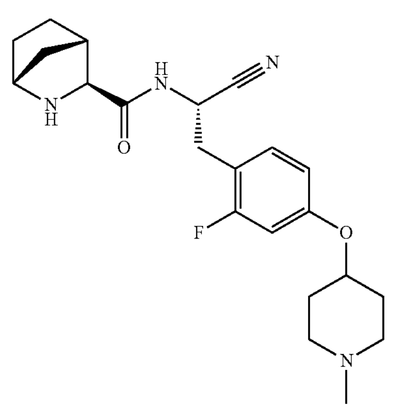 [SMILES: CN1CCC(Oc2ccc(C[C@@H](C#N)NC(=O)[C@H]3N[C@@H]4CC[C@H]3C4)c(F)c2)CC1] | I-19.1 | W/SI | 34 |

TABLE 62-continued

| Example | Structure | Educt | Syn./Deprot. Method | Yield [%] |
|---|---|---|---|---|
| 320 | 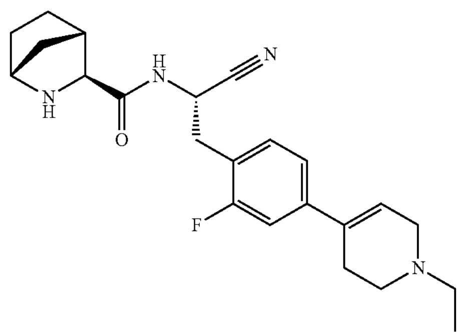 [SMILES: CCN1CC=C(c2ccc(C[C@@H](C#N)NC(=O)[C@H]3N[C@@H]4CC[C@H]3C4)c(F)c2)CC1] | I-3.3.13 | A2.1/SI | 74 |
| 321 | 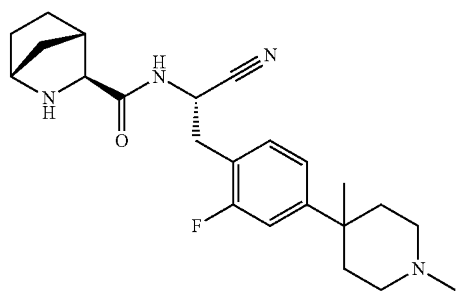 [SMILES: CN1CCC(C)(c2ccc(C[C@@H](C#N)NC(=O)[C@H]3N[C@@H]4CC[C@H]3C4)c(F)c2)CC1] | I-8.2.4 | C/TSA | 91 |
| 322 | 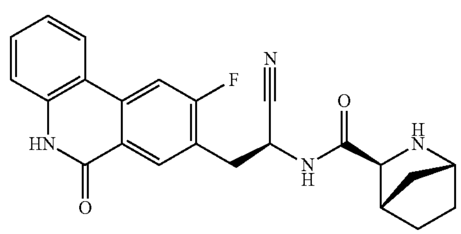 [SMILES: N#C[C@H](Cc1cc2c(=O)[nH]c3ccccc3c2cc1F)NC(=O)[C@H]1N[C@@H]2CC[C@H]1C2] | I-18.2.24 | D1/TSA | 30 |
| 323 | 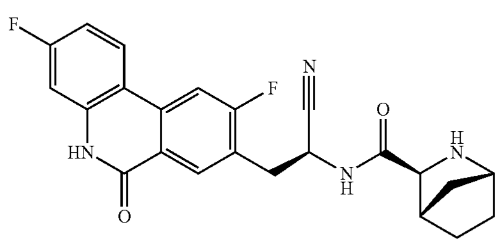 [SMILES: N#C[C@H](Cc1cc2c(=O)[nH]c3cc(F)ccc3c2cc1F)NC(=O)[C@H]1N[C@@H]2CC[C@H]1C2] | I-18.2.25 | D1/TSA | 32 |
| 324 | 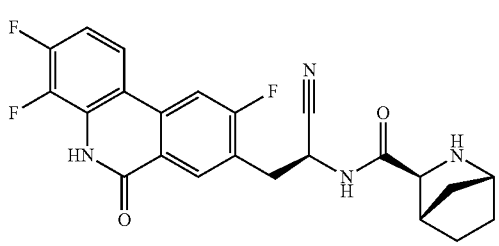 [SMILES: N#C[C@H](Cc1cc2c(=O)[nH]c3c(F)c(F)ccc3c2cc1F)NC(=O)[C@H]1N[C@@H]2CC[C@H]1C2] | I-18.2.26 | D1/TSA | 36 |

TABLE 62-continued

| Example | Structure | Educt | Syn./Deprot. Method | Yield [%] |
|---------|-----------|-------|---------------------|-----------|
| 325 | 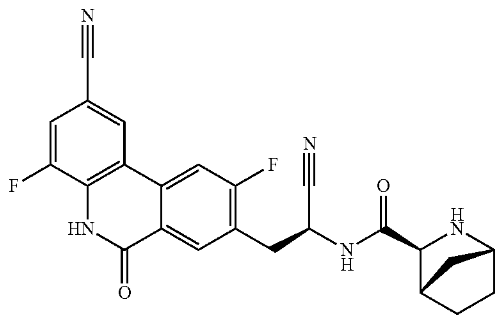 [SMILES: N#Cc1cc(F)c2[nH]c(=O)c3cc(C[C@@H](C#N)NC(=O)[C@H]4N[C@@H]5CC[C@H]4C5)c(F)cc3c2c1] | I-18.2.27 | D1/TSA | 9 |
| 326 | 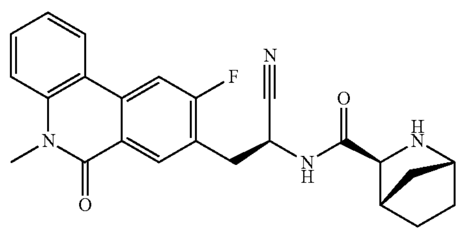 [SMILES: Cn1c(=O)c2cc(C[C@@H](C#N)NC(=O)[C@H]3N[C@@H]4CC[C@H]3C4)c(F)cc2c2ccccc21] | I-18.2.28 | D1/TSA | 30 |
| 327 | 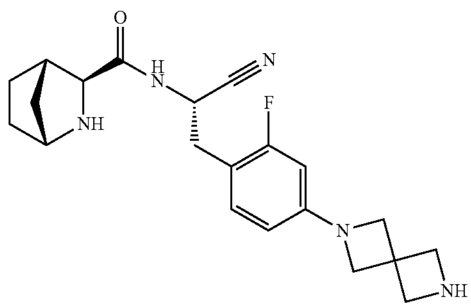 [SMILES: N#C[C@H](Cc1ccc(N2CC3(CNC3)C2)cc1F)NC(=O)[C@H]1N[C@@H]2CC[C@H]1C2] | I-3.2.103 | A2.2/TSA | 62 |
| 328 | 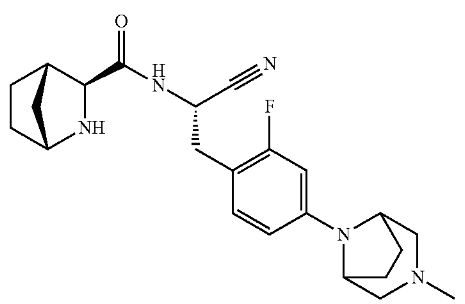 [SMILES: CN1CC2CCC(C1)N2c1ccc(C[C@@H](C#N)NC(=O)[C@H]2N[C@@H]3CC[C@H]2C3)c(F)c1] | I-3.2.104 | A2.2/TSA | 86 |
| 329 | 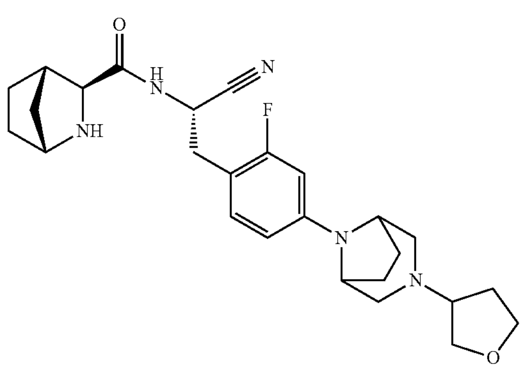 [SMILES: N#C[C@H](Cc1ccc(N2C3CCC2CN(C2CCOC2)C3)cc1F)NC(=O)[C@H]1N[C@@H]2CC[C@H]1C2] | I-3.2.105 | A2.2/TSA | 62 |

TABLE 62-continued

| Example | Structure | Educt | Syn./Deprot. Method | Yield [%] |
|---|---|---|---|---|
| 330 | 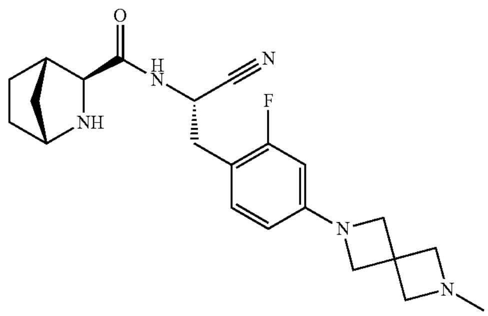 [SMILES: CN1CC2(C1)CN(c1ccc(C[C@@H](C#N)NC(=O)[C@H]3N[C@@H]4CC[C@H]3C4)c(F)c1)C2] | I-3.2.106 | A2.2/TSA | 59 |
| 331 | 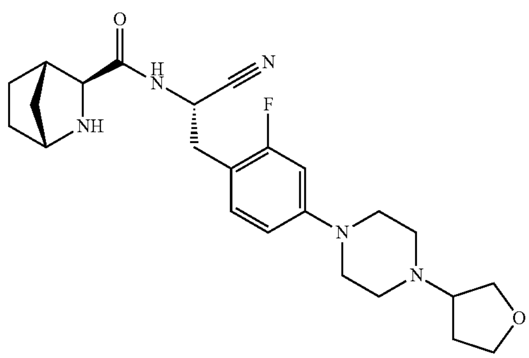 [SMILES: N#C[C@H](Cc1ccc(N2CCN(C3CCOC3)CC2)cc1F)NC(=O)[C@H]1N[C@@H]2CC[C@H]1C2] | I-3.2.107 | A2.2/TSA | 70 |
| 332 | 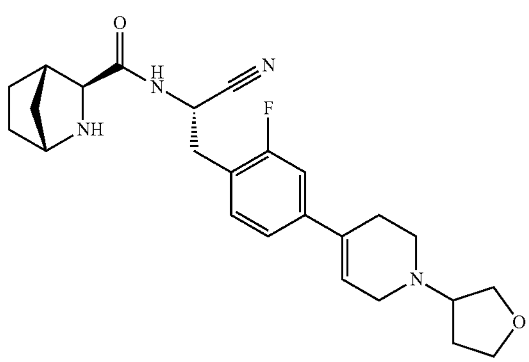 [SMILES: N#C[C@H](Cc1ccc(C2=CCN(C3CCOC3)CC2)cc1F)NC(=O)[C@H]1N[C@@H]2CC[C@H]1C2] | I-3.2.79 | A2.1/TSA | 64 |
| 333 | 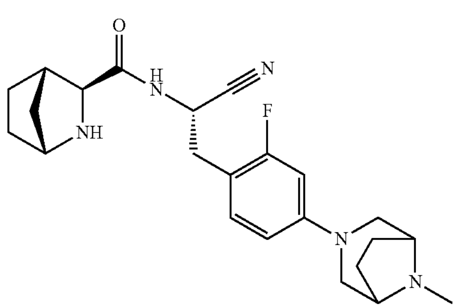 [SMILES: CN1C2CCC1CN(c1ccc(C[C@@H](C#N)NC(=O)[C@H]3N[C@@H]4CC[C@H]3C4)c(F)c1)C2] | I-3.2.108 | A2.2/TSA | 33 |

TABLE 62-continued
| Example | Structure | Educt | Syn./Deprot. Method | Yield [%] |
|---|---|---|---|---|
| 334 | 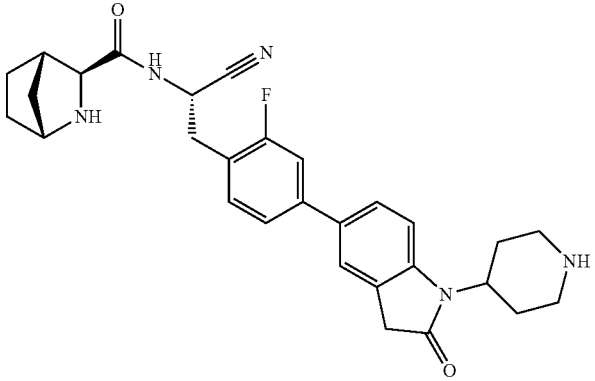 [SMILES: N#C[C@H](Cc1ccc(-c2ccc3c(c2)CC(=O)N3C2CCNCC2)cc1F)NC(=O)[C@H]1N[C@@H]2CC[C@H]1C2] | I-3.2.80 | A2.1/TSA | 11 |
| 335 | 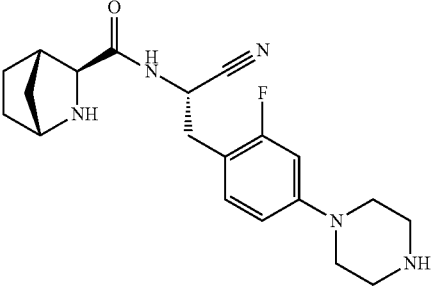 [SMILES: N#C[C@H](Cc1ccc(N2CCNCC2)cc1F)NC(=O)[C@H]1N[C@@H]2CC[C@H]1C2] | I-3.2.109 | A2.2/TSA | 90 |
| 336 | 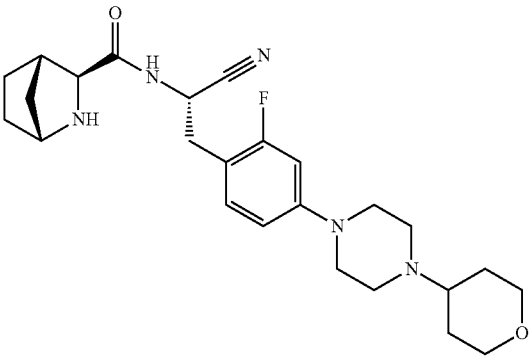 | I-3.2.110 | A2.2/TSA | 72 |
| 337 | 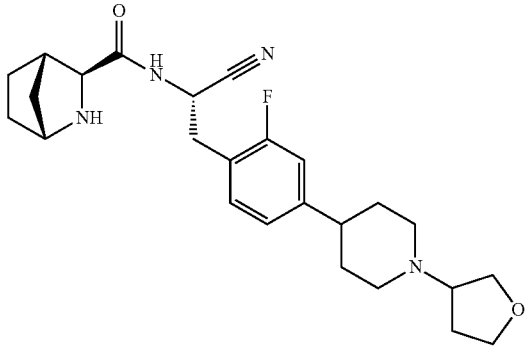 [SMILES: N#C[C@H](Cc1ccc(C2CCN(C3CCOC3)CC2)cc1F)NC(=O)[C@H]1N[C@@H]2CC[C@H]1C2] | I-3.3.14 | A2.1/TSA | 86 |

TABLE 62-continued

| Example | Structure | Educt | Syn./Deprot. Method | Yield [%] |
|---|---|---|---|---|
| 338 | 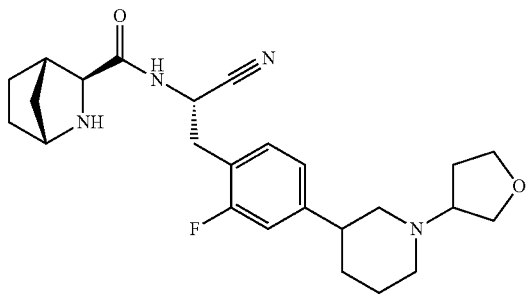 [SMILES: N#C[C@H](Cc1ccc(C2CCCN(C3CCOC3)C2)cc1F)NC(=O)[C@H]1N[C@@H]2CC[C@H]1C2] | I-3.3.15 | A2.1/TSA | 48 |
| 339 | 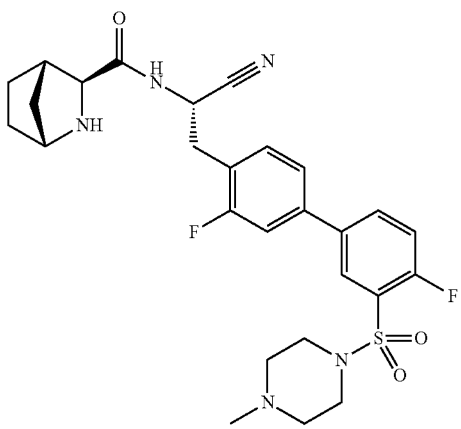 [SMILES: CN1CCN(S(=O)(=O)c2cc(-c3ccc(C[C@@H](C#N)NC(=O)[C@H]4N[C@@H]5CC[C@H]4C5)c(F)c3)ccc2F)CC1] | I-3.2.83 | A2.1/TSA | 54 |
| 340 | 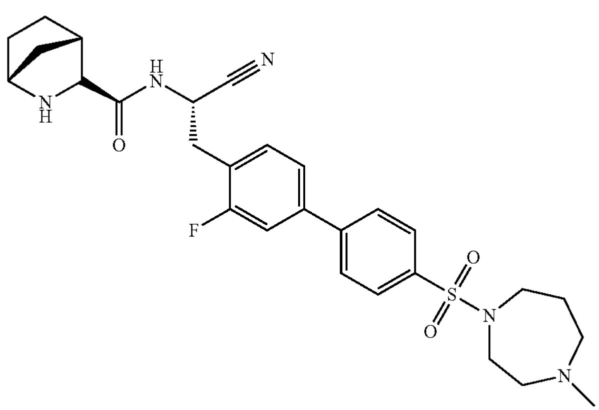 | I-3.2.84 | A2.1/TSA | 42 |
| 341 | 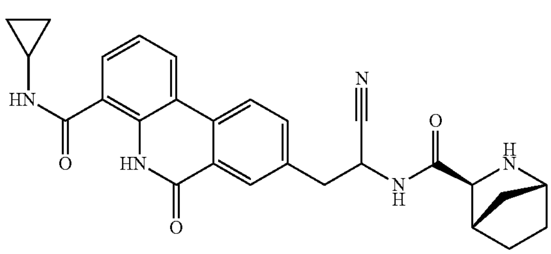 [SMILES: N#CC(Cc1ccc2c(c1)c(=O)[nH]c1c(C(=O)NC3CC3)cccc12)NC(=O)[C@H]1N[C@@H]2CC[C@H]1C2] | I-18.2.29 | D1/TSA | 17 |

TABLE 62-continued

| Example | Structure | Educt | Syn./Deprot. Method | Yield [%] |
|---|---|---|---|---|
| 342 | 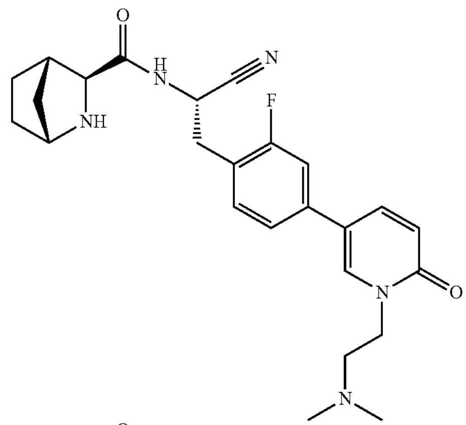 [SMILES: CN(C)CCn1cc(-c2ccc(C[C@@H](C#N)NC(=O)[C@H]3N[C@@H]4CC[C@H]3C4)c(F)c2)ccc1=O] | I-3.2.85 | A2.1/TSA | 68 |
| 343 | 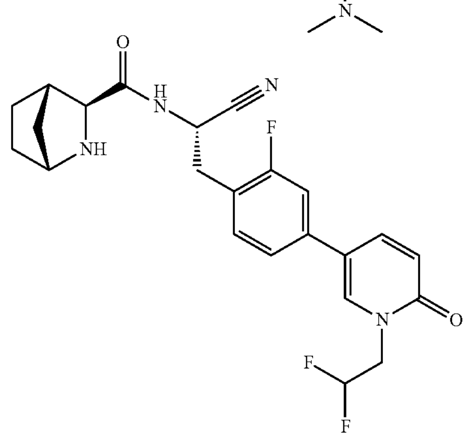 | I-3.2.86 | A2.1/TSA | 35 |
| 344 | 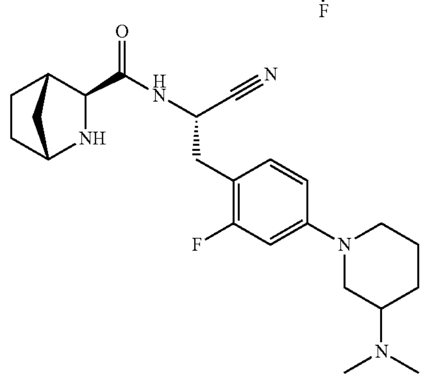 | I-20.1 | W1/TSA | 28 |
| 345 | 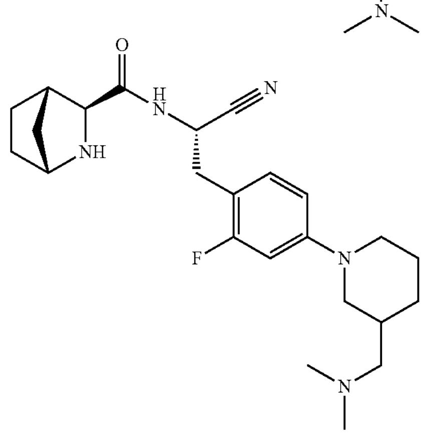 | I-3.2.111 | A2.2/TSA | 2 |

TABLE 62-continued

| Example | Structure | Educt | Syn./Deprot. Method | Yield [%] |
|---|---|---|---|---|
| 346 | 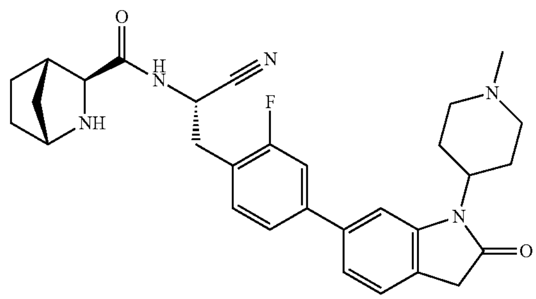 [SMILES: CN1CCC(N2C(=O)Cc3ccc(-c4ccc(C[C@@H](C#N)NC(=O)[C@H]5N[C@@H]6CC[C@H]5C6)c(F)c4)cc32)CC1] | I-3.2.87 | A2.1/TSA | 14 |
| 347 | 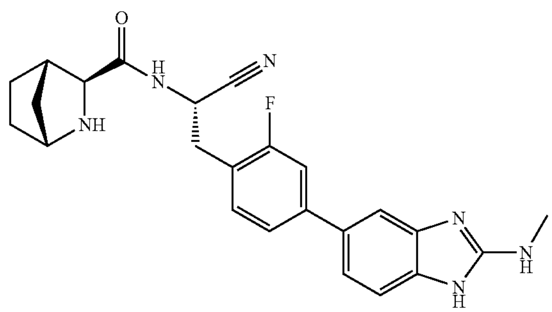 [SMILES: CNc1nc2cc(-c3ccc(C[C@@H](C#N)NC(=O)[C@H]4N[C@@H]5CC[C@H]4C5)c(F)c3)ccc2[nH]1] | I-3.2.88 | A2.1/TSA | 18 |
| 348 | 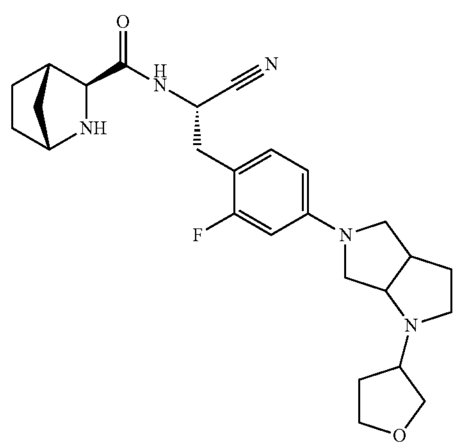 [SMILES: N#C[C@H](Cc1ccc(N2CC3CCN(C4CCOC4)C3C2)cc1F)NC(=O)[C@H]1N[C@@H]2CC[C@H]1C2] | I-3.3.16 | A2.1/TSA | 76 |
| 349 | 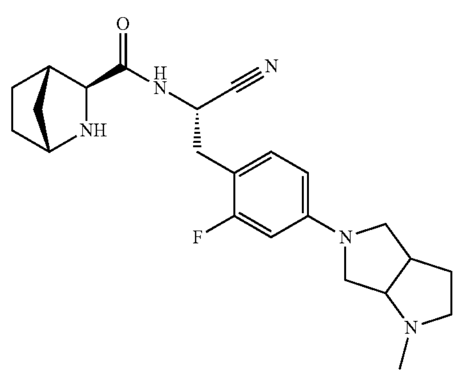 [SMILES: CN1CCC2CN(c3ccc(C[C@@H](C#N)NC(=O)[C@H]4N[C@@H]5CC[C@H]4C5)c(F)c3)CC21] | I-3.3.17 | A2.1/TSA | 73 |

TABLE 62-continued

| Example | Structure | Educt | Syn./Deprot. Method | Yield [%] |
|---------|-----------|-------|---------------------|-----------|
| 350 | 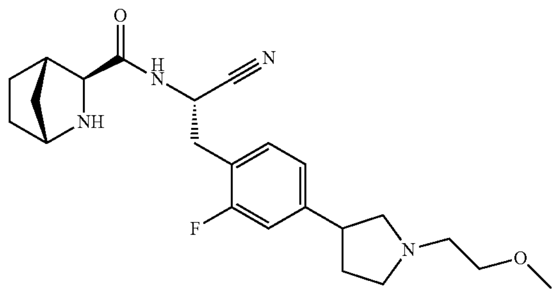 [SMILES: COCCN1CCC(c2ccc(C[C@@H](C#N)NC(=O)[C@H]3N[C@@H]4CC[C@H]3C4)c(F)c2)C1] | I-3.3.18 | A2.1/TSA | 65 |
| 351 | 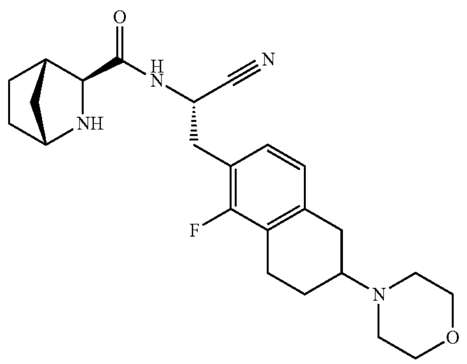 [SMILES: N#C[C@H](Cc1ccc2c(c1F)CCC(N1CCOCC1)C2)NC(=O)[C@H]1N[C@@H]2CC[C@H]1C2] | I-8.2.5 | C/TSA | 44 |
| 352 | 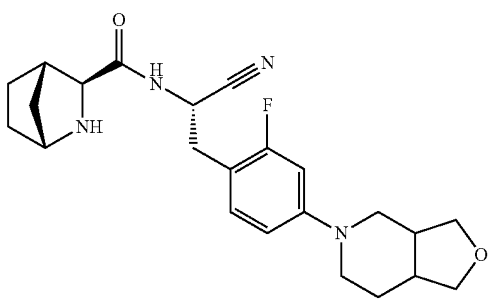 [SMILES: N#C[C@H](Cc1ccc(N2CCC3COCC3C2)cc1F)NC(=O)[C@H]1N[C@@H]2CC[C@H]1C2] | I-3.2.112 | A2.2/TSA | 78 |
| 353 | 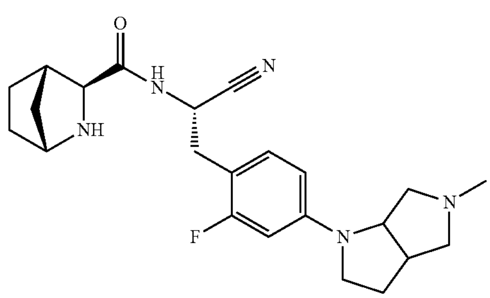 [SMILES: CN1CC2CCN(c3ccc(C[C@@H](C#N)NC(=O)[C@H]4N[C@@H]5CC[C@H]4C5)c(F)c3)C2C1] | I-3.3.19 | A2.1/TSA | 78 |
| 354 | 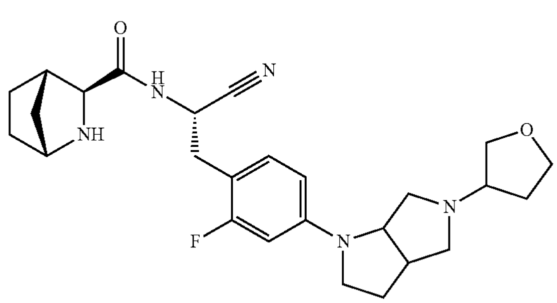 [SMILES: N#C[C@H](Cc1ccc(N2CCC3CN(C4CCOC4)CC32)cc1F)NC(=O)[C@H]1N[C@@H]2CC[C@H]1C2] | I-3.3.20 | A2.1/TSA | 62 |

TABLE 62-continued

| Example | Structure | Educt | Syn./Deprot. Method | Yield [%] |
|---------|-----------|-------|---------------------|-----------|
| 355 | 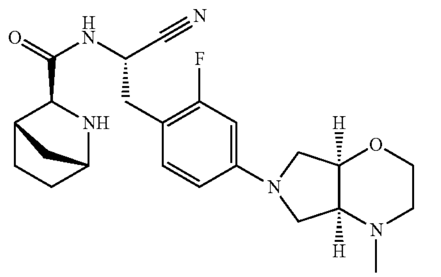 [SMILES: CN1CCO[C@@H]2CN(c3ccc(C[C@@H](C#N)NC(=O)[C@H]4N[C@@H]5CC[C@H]4C5)c(F)c3)C[C@@H]21] | I-3.2.114 | A2.2/TSA | 88 |
| 356 | 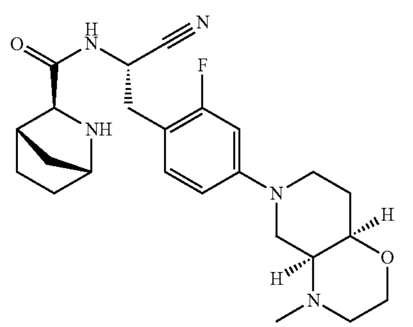 [SMILES: CN1CCO[C@@H]2CCN(c3ccc(C[C@@H](C#N)NC(=O)[C@H]4N[C@@H]5CC[C@H]4C5)c(F)c3)C[C@@H]21] | I-3.2.115 | A2.2/TSA | >95 |
| 357 | 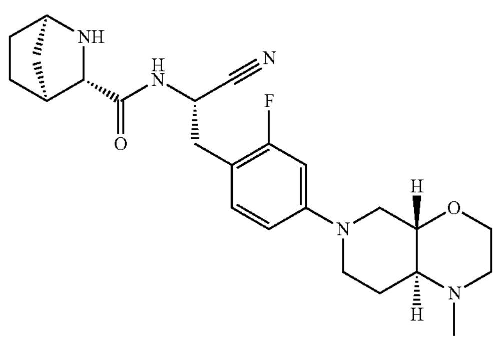 [SMILES: CN1CCO[C@H]2CN(c3ccc(C[C@@H](C#N)NC(=O)[C@H]4N[C@@H]5CC[C@H]4C5)c(F)c3)CC[C@@H]21] | I-3.2.116 | A2.2/TSA | 80 |
| 358 | 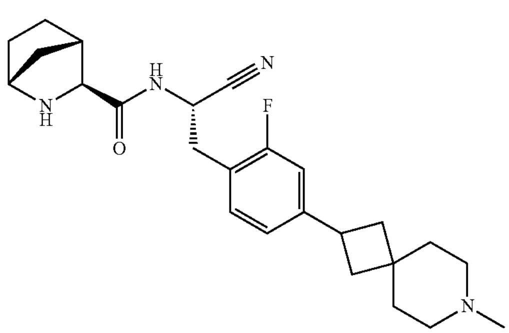 [SMILES: CN1CCC2(CC1)CC(c1ccc(C[C@@H](C#N)NC(=O)[C@H]3N[C@@H]4CC[C@H]3C4)c(F)c1)C2] | Ex 359 | A2.1 | 35 |

TABLE 62-continued

| Example | Structure | Educt | Syn./Deprot. Method | Yield [%] |
|---|---|---|---|---|
| 359 | 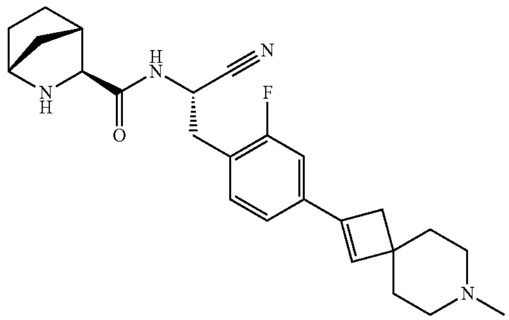 [SMILES: CN1CCC2(C=C(c3ccc(C[C@@H](C#N)NC(=O)[C@H]4N[C@@H]5CC[C@H]4C5)c(F)c3)C2)CC1] | I-3.2.136 | A2.1/TSA | 61 |

Analytical Data of Examples

TABLE 63

| Ex. | m/z [M + H]+ | rt [min] | LC-MS-Method |
|---|---|---|---|
| 1 | 419 | 1.16 | V011_S01 |
| 2 | 433 | 0.59 | X011_S01 |
| 3 | 420 | 0.41 | X016_S01 |
| 4 | 442 | 0.65 | Z018_S04 |
| 5 | 470 | 0.70 | Z018_S04 |
| 6 | 386 | 0.98 | V011_S01 |
| 7 | 410 | 0.96 | V018_S01 |
| 8 | 310 | 0.86 | V011_S01 |
| 9 | 387 | 0.39 | X012_S01 |
| 10 | 447 | 0.42 | X012_S01 |
| 11 | 420 | 0.41 | X012_S01 |
| 12 | 460 | 0.67 | Z018_S04 |
| 13 | 426 | 0.63 | Z018_S04 |
| 14 | 467 | 0.86 | V018_S01 |
| 15 | 433 | 1.04 | V001_007 |
| 16 | 442 | 0.65 | Z018_S04 |
| 17 | 428 | 0.81 | 004_CA01 |
| 18 | 370 | 0.80 | 004_CA01 |
| 19 | 467 | 0.86 | V018_S01 |
| 20 | 396 | 0.66 | Z018_S04 |
| 21 | 438 | 0.64 | Z018_S04 |
| 22 | 419 | 0.41 | Z001_002 |
| 23 | 410 | 0.78 | 004_CA01 |
| 24 | 451 | 0.69 | Z018_S04 |
| 25 | 385 | 0.64 | Z018_S04 |
| 26 | 382 | 0.68 | 004_CA01 |
| 27 | 368 | 0.82 | 004_CA01 |
| 28 | 452 | 0.70 | Z018_S04 |
| 29 | 419 | 0.41 | Z001_002 |
| 30 | 396 | 0.73 | 004_CA01 |
| 31 | 451 | 1.12 | V011_S01 |
| 32 | 448 | 1.28 | V011_S01 |
| 33 | 438 | 0.93 | 004_CA01 |
| 34 | 420 | 1.06 | V011_S01 |
| 35 | 407 | 1.10 | V001_007 |
| 36 | 370 | 0.80 | 004_CA01 |
| 37 | 443 | 0.62 | Z018_S04 |
| 38 | 439 | 0.60 | 004_CA01 |
| 39 | 382 | 0.64 | 004_CA01 |
| 40 | 407 | 0.72 | Z018_S04 |
| 41 | 419 | 0.61 | Z018_S04 |
| 42 | 447 | 1.09 | V011_S01 |
| 43 | 428 | 0.95 | V011_S01 |
| 44 | 412 | 0.63 | Z018_S04 |
| 45 | 421 | 0.90 | V012_S01 |
| 46 | 399 | 0.73 | 004_CA01 |
| 47 | 461 | 0.72 | Z018_S04 |
| 48 | 438 | 0.60 | X018_S01 |
| 49 | 433 | 1.13 | W018_S01 |
| 50 | 438 | 0.66 | Z018_S04 |
| 51 | 457 | 0.64 | Z018_S04 |
| 52 | n.d. | n.d. | n.d. |
| 53 | 407 | 0.61 | Z018_S04 |
| 54 | 442 | 0.63 | Z018_S04 |
| 55 | 493 | 0.64 | Z018_S04 |
| 56 | 443 | 0.60 | Z018_S04 |
| 57 | 452 | 0.69 | 004_CA01 |
| 58 | 368 | 0.79 | V018_S01 |
| 59 | 456 | 0.43 | X018_S01 |
| 60 | 418 | 0.80 | 004_CA01 |
| 61 | 451 | 0.88 | V018_S01 |
| 62 | 457 | 0.64 | Z018_S04 |
| 63 | 382 | 0.64 | 004_CA01 |
| 64 | 410 | 0.78 | 004_CA01 |
| 65 | 382 | 0.64 | 004_CA05 |
| 66 | 463 | 0.79 | Z011_S03 |
| 67 | 395 | 0.82 | Z011_S03 |
| 68 | 396 | 0.73 | 004_CA01 |
| 69 | 354 | 0.54 | 004_CA01 |
| 70 | 430 | 0.72 | Z018_S04 |
| 71 | 456 | 0.67 | Z018_S04 |
| 72 | 412 | 0.76 | 004_CA01 |
| 73 | 354 | 0.70 | Z018_S04 |
| 74 | 466 | 0.70 | Z018_S04 |
| 75 | 364 | 0.50 | X012_S01 |
| 76 | 433 | 0.65 | Z018_S04 |
| 77 | 491 | 0.86 | Z011_S03 |
| 78 | 430 | 0.85 | 004_CA01 |
| 79 | 419 | 0.62 | Z018_S04 |
| 80 | 399 | 0.62 | 004_CA01 |
| 81 | 449 | 0.90 | V012_S01 |
| 82 | 441 | 0.63 | Z018_S04 |
| 83 | 407 | 1.09 | W018_S01 |
| 84 | 471 | 0.92 | Z011_S03 |
| 85 | 395 | 0.50 | X018_S01 |
| 86 | 460 | 0.67 | Z018_S04 |
| 87 | 426 | 0.66 | Z018_S04 |
| 88 | 442 | 0.64 | Z018_S04 |
| 89 | 427 | 0.75 | Z011_S03 |
| 90 | 397 | 0.60 | Z018_S04 |
| 91 | 450 | 0.98 | V011_S01 |
| 92 | 368 | 0.81 | 004_CA01 |
| 93 | 397 | 0.65 | Z018_S04 |
| 94 | 461 | 0.90 | Z011_S03 |
| 95 | 419 | 0.82 | V012_S01 |
| 96 | 431 | 0.78 | Z018_S04 |
| 97 | 412 | 0.65 | 004_CA01 |
| 98 | 400 | 0.94 | V012_S01 |
| 99 | 468 | 0.73 | Z011_S03 |
| 100 | 436 | 0.82 | 004_CA01 |
| 101 | 413 | 0.70 | Z011_S03 |
| 102 | 400 | 0.92 | V012_S01 |

TABLE 63-continued

| Ex. | m/z [M + H]+ | rt [min] | LC-MS-Method |
|---|---|---|---|
| 103 | 354 | 0.76 | 004_CA01 |
| 104 | 368 | 0.79 | 004_CA05 |
| 105 | 413 | 0.79 | Z011_S03 |
| 106 | 482 | 0.81 | Z011_S03 |
| 107 | 435 | 1.25 | W018_S01 |
| 108 | 400 | 0.82 | V012_S01 |
| 109 | 441 | 0.80 | Z011_S03 |
| 110 | 382 | 0.67 | 004_CA01 |
| 111 | 399 | 0.58 | Z018_S04 |
| 112 | 443 | 0.75 | Z011_S03 |
| 113 | 411 | 0.70 | Z018_S04 |
| 114 | 354 | 0.59 | Z018_S04 |
| 115 | 414 | 0.68 | 004_CA01 |
| 116 | 438 | 0.68 | 004_CA01 |
| 117 | 385 | 0.65 | V012_S01 |
| 118 | 436 | 0.77 | 004_CA01 |
| 119 | 461 | 0.93 | Z011_S03 |
| 120 | 431 | 0.81 | V018_S01 |
| 121 | 383 | 0.71 | 004_CA01 |
| 122 | 521 | 0.97 | V018_S01 |
| 123 | 387 | 0.38 | X012_S01 |
| 124 | 427 | 0.83 | Z011_S03 |
| 125 | 400 | 0.83 | V011_S01 |
| 126 | 382 | 0.66 | 004_CA01 |
| 127 | 310 | 0.92 | V011_S01 |
| 128 | 387 | 0.35 | X012_S01 |
| 129 | 447 | 0.76 | 004_CA01 |
| 130 | 419 | 0.64 | 004_CA01 |
| 131 | 433 | 0.71 | 004_CA01 |
| 132 | 419 | 0.84 | 004_CA01 |
| 133 | 440 | 0.83 | 004_CA01 |
| 134 | 431 | 0.67 | 004_CA01 |
| 135 | 430 | 0.74 | 004_CA01 |
| 136 | 455 | 0.67 | 004_CA01 |
| 137 | 430 | 0.78 | 004_CA01 |
| 138 | 394 | 0.70 | 004_CA01 |
| 139 | 469 | 0.74 | 004_CA01 |
| 140 | 469 | 0.73 | 004_CA01 |
| 141 | 454 | 0.72 | 004_CA01 |
| 142 | 402 | 0.73 | 004_CA01 |
| 143 | 455 | 0.68 | 004_CA01 |
| 144 | 454 | 0.73 | 004_CA01 |
| 145 | 411 | 0.78 | 004_CA01 |
| 146 | 419 | 0.66 | 004_CA01 |
| 147 | 431 | 0.64 | 004_CA01 |
| 148 | 445 | 0.68 | 004_CA01 |
| 149 | 445 | 0.69 | 004_CA01 |
| 150 | 469 | 0.73 | 004_CA01 |
| 151 | 468 | 0.76 | 004_CA01 |
| 152 | 460 | 0.67 | Z018_S04 |
| 153 | 468 | 0.70 | Z018_S04 |
| 154 | 456 | 1.08 | V011_S01 |
| 155 | 526 | 0.80 | V012_S01 |
| 156 | 448 | 0.47 | X012_S01 |
| 157 | 413 | 0.61 | Z018_S04 |
| 158 | 477 | 0.87 | V012_S01 |
| 159 | 467 | 0.85 | V018_S01 |
| 160 | 382 | 0.64 | 004_CA05 |
| 161 | 427 | 0.64 | Z018_S04 |
| 162 | 379 | 0.76 | 004_CA05 |
| 163 | 368 | 0.61 | 004_CA05 |
| 164 | 455 | 0.71 | Z018_S04 |
| 165 | 467 | 0.70 | Z018_S04 |
| 166 | 448 | 0.48 | X12_S01 |
| 167 | 397 | 0.56 | 004_CA05 |
| 168 | 405 | 0.66 | 004_CA05 |
| 169 | 469 | 1.02 | V011_S01 |
| 170 | 441 | 0.67 | Z018_S04 |
| 171 | 430 | 0.83 | 004_CA05 |
| 172 | 415 | 0.87 | 004_CA05 |
| 173 | 411 | 0.78 | 004_CA05 |
| 174 | 405 | 0.63 | 004_CA05 |
| 175 | 412 | 0.74 | 004_CA05 |
| 176 | 460 | 0.67 | Z18_S04 |
| 177 | 511 | 1.05 | V012_S01 |
| 178 | 444 | 1.10 | V011_S01 |
| 179 | 442 | 0.86 | 004_CA05 |
| 180 | 354 | 0.36 | X018_S01 |
| 181 | 437 | 0.65 | Z018_S04 |
| 182 | 430 | 0.26 | X018_S01 |
| 183 | 485 | 0.67 | Z018_S04 |
| 184 | 435 | 0.67 | Z018_S04 |
| 185 | 490 | 0.55 | Z018_S04 |
| 186 | 421 | 0.63 | Z018_S04 |
| 187 | 412 | 0.26 | X018_S01 |
| 188 | 400 | 1.10 | V011_S01 |
| 189 | 416 | 0.88 | V011_S01 |
| 190 | 416 | 0.89 | V011_S01 |
| 191 | 458 | 1.14 | V011_S01 |
| 192 | 400 | 1.10 | V011_S01 |
| 193 | 456 | 1.00 | V011_S01 |
| 194 | 405 | 0.55 | 004_CA05 |
| 195 | 399 | 1.42 | V011_S01 |
| 196 | 414 | 0.65 | V018_S01 |
| 197 | 371 | 1.28 | V011_S01 |
| 198 | 442 | 0.84 | 004_CA05 |
| 199 | 461 | 1.24 | V012_S01 |
| 200 | 491 | 0.67 | Z018_S04 |
| 201 | 399 | 0.32 | X012_S02 |
| 202 | 477 | 0.66 | Z018_S04 |
| 203 | 359 | 0.46 | X12_S01 |
| 204 | 372 | 0.93 | V011_S01 |
| 205 | 373 | 1.05 | V011_S01 |
| 206 | 401 | 0.43 | X12_S01 |
| 207 | 405 | 0.41 | X12_S01 |
| 208 | 382 | 0.60 | 004_CA05 |
| 209 | 372 | 0.52 | X12_S01 |
| 210 | 475 | 0.74 | Z018_S04 |
| 211 | 435 | 0.67 | Z018_S04 |
| 212 | 360 | 0.48 | X12_S01 |
| 213 | 359 | 0.43 | X12_S01 |
| 214 | 467 | 1.02 | V011_S01 |
| 215 | 405 | 0.37 | X12_S01 |
| 216 | 461 | 0.70 | Z018_S04 |
| 217 | 513 | 0.92 | V012_S01 |
| 218 | 470 | 0.69 | Z018_S04 |
| 219 | 461 | 0.82 | V012_S01 |
| 220 | 320 | 0.39 | 001_CA07 |
| 221 | 394 | 0.59 | 004_CA05 |
| 222 | 466 | 0.65 | Z018_S04 |
| 223 | 383 | 0.31 | X012_S02 |
| 224 | 526 | 0.36 | X012_S01 |
| 225 | 496 | 0.54 | Z018_S04 |
| 226 | 519 | 1.17 | Z018_S04 |
| 227 | 524 | 0.56 | Z018_S04 |
| 228 | 540 | 0.83 | Z011_S03 |
| 229 | 522 | 0.9 | Z011_S03 |
| 230 | 483 | 0.8 | Z011_S03 |
| 231 | 524 | 0.77 | Z011_S03 |
| 232 | 564 | 1.31 | Z018_S04 |
| 233 | 510 | 0.76 | Z011_S03 |
| 234 | 538 | 0.95 | Z018_S04 |
| 235 | 497 | 0.82 | Z011_S03 |
| 236 | 413 | 0.60 | Z018_S04 |
| 237 | 519 | 0.68 | Z018_S04 |
| 238 | 522 | 0.66 | Z018_S04 |
| 239 | 397 | 0.37 | Z018_S04 |
| 240 | 503 | 0.64 | Z018_S04 |
| 241 | 480 | 0.53 | Z018_S04 |
| 242 | 425 | 0.64 | Z018_S04 |
| 243 | 494 | 0.74 | Z018_S04 |
| 244 | 407 | 0.73 | Z018_S04 |
| 245 | 490 | 0.56 | Z018_S04 |
| 246 | 547 | 1.05 | V012_S01 |
| 247 | 400 | 0.58 | X011_S03 |
| 248 | 440 | 0.97 | V011_S01 |
| 249 | 428 | 0.97 | V011_S01 |
| 250 | 428 | 0.97 | V011_S01 |
| 251 | 468 | 1.14 | V011_S01 |
| 252 | 522 | 0.61 | X011_S02 |
| 253 | 447 | 0.67 | X011_S03 |
| 254 | 395 | 0.56 | 004_CA05 |
| 255 | 395 | 0.55 | 004_CA05 |
| 256 | 452 | 0.60 | 004_CA05 |

TABLE 63-continued

| Ex. | m/z [M + H]+ | rt [min] | LC-MS-Method |
|---|---|---|---|
| 257 | 381 | 0.5 | 004_CA05 |
| 258 | 381 | 0.50 | 004_CA05 |
| 259 | 455 | 0.64 | n.d. |
| 260 | 438 | 0.66 | Z018_S04 |
| 261 | 438 | 0.65 | Z018_S04 |
| 262 | 438 | 0.65 | Z018_S04 |
| 263 | 466 | 0.65 | Z018_S04 |
| 264 | 525 | 1.19 | Z018_S04 |
| 265 | 461 | 0.59 | 003_CA04 |
| 266 | 459 | 0.6 | 003_CA04 |
| 267 | 428 | 0.61 | 004_CA07 |
| 268 | 427 | 0.59 | 004_CA07 |
| 269 | 442 | 0.78 | 003_CA04 |
| 270 | 412 | 0.82 | 003_CA04 |
| 271 | 426 | 0.65 | n.d. |
| 272 | 400 | 1.13 | V011_S01 |
| 273 | 438 | 0.73 | X011_S03 |
| 274 | 426 | 0.47 | 002_CA07 |
| 275 | 486 | 0.56 | 002_CA07 |
| 276 | 540 | 0.58 | 002_CA07 |
| 277 | 504 | 0.57 | Z020_S01 |
| 278 | 490 | 0.54 | n.d. |
| 279 | 490 | 0.53 | Z020_S01 |
| 280 | 413 | 0.35 | X012_S02 |
| 281 | 425 | 1.03 | V011_S01 |
| 282 | 425 | 1.02 | V011_S01 |
| 283 | 427 | 0.49 | 004_CA07 |
| 284 | 427 | 0.46 | 004_CA07 |
| 285 | 422 | 1.26 | V011_S01 |
| 286 | 425 | 0.58 | 004_CA05 |
| 287 | 467 | 0.57 | 004_CA05 |
| 288 | 467 | 0.64 | Z018_S04 |
| 289 | 480 | 0.53 | Z018_S04 |
| 290 | 394 | 1.28 | V011_S01 |
| 291 | 448 | 0.64 | Z011_S03 |
| 292 | 430 | 0.51 | 005_CA01 |
| 293 | 423 | 0.37 | 001_CA07 |
| 294 | 405 | 0.36 | 001_CA07 |
| 295 | 423 | 0.37 | 001_CA07 |
| 296 | 441 | 0.49 | X012_S02_ |
| 297 | 421 | 0.39 | 001_CA07 |
| 298 | 412 | 0.37 | X012_S01_ |
| 299 | 445 | 0.48 | 002_CA03 |
| 300 | 423 | 0.41 | X012_S01_ |
| 301 | 455 | 0.47 | X012_S01_ |
| 302 | 480 | 0.53 | 002_CA03 |
| 303 | 426 | 0.47 | X012_S02_ |
| 304 | 421 | 0.51 | 002_CA03 |
| 305 | 435 | 0.48 | X012_S01_ |
| 306 | 458 | 0.48 | 004_CA05 |
| 307 | 430 | 0.56 | 004_CA05 |
| 308 | 405 | 0.35 | 001_CA07 |
| 309 | 412 | 0.60 | 004_CA05 |
| 310 | 423 | 0.73 | 003_CA04 |
| 311 | 445 | 0.52 | 002_CA03 |
| 312 | 417 | 0.62 | 004_CA05 |
| 313 | 465 | 0.33 | X012_S01_ |
| 314 | 402 | 0.26 | X012_S01_ |
| 315 | 389 | 0.37 | X012_S01 |
| 316 | 371 | 0.31 | X012_S01 |
| 317 | 381 | 0.61 | 003_CA04 |
| 318 | 386 | 0.99 | V011_S01 |
| 319 | 401 | 0.31 | X012_S02 |
| 320 | 397 | 0.34 | X012_S02 |
| 321 | 399 | 1.10 | V011_S01 |
| 322 | 405 | 0.75 | 003_CA04 |
| 323 | 423 | 0.55 | 005_CA01 |
| 324 | 441 | 0.56 | 005_CA01 |
| 325 | 448 | 0.53 | 005_CA01 |
| 326 | 419 | 0.83 | 003_CA04 |
| 327 | 384 | 0.46 | 002_CA07 |
| 328 | 412 | 0.74 | 004_CA05 |
| 329 | 468 | 0.66 | X011_S03 |
| 330 | 398 | 0.8 | 003_CA04 |
| 331 | 442 | 0.72 | 003_CA04 |
| 332 | 439 | 0.62 | X011_S03 |
| 333 | 412 | 1.15 | V011_S01 |
| 334 | 502 | 0.54 | Z020_S01 |
| 335 | 372 | 0.93 | V011_S01 |
| 336 | 456 | 0.67 | 004_CA05 |
| 337 | 441 | 0.63 | X011_S03 |
| 338 | 441 | 0.29 | X018_S02 |
| 339 | 544 | 0.35 | X012_S01 |
| 340 | 540 | 0.83 | 003_CA04 |
| 341 | 470 | 0.40 | X012_S01_ |
| 342 | 452 | 0.47 | 004_CA07 |
| 343 | 445 | 0.48 | 004_CA07 |
| 344 | 414 | 0.74 | 004_CA05 |
| 345 | 428 | 0.30 | X012_S01 |
| 346 | 516 | 0.98 | Z011_S03 |
| 347 | 433 | 0.96 | V011_S01 |
| 348 | 468 | 1.09 | V011_S01 |
| 349 | 412 | 1.14 | V011_S01 |
| 350 | 415 | 0.79 | 003_CA04 |
| 351 | 427 | 0.57 | X011_S03 |
| 352 | 413 | 1.11 | V011_S01 |
| 353 | 412 | 0.78 | 004_CA05 |
| 354 | 468 | 0.81 | 003_CA04 |
| 355 | 428 | 0.90 | Z011_S03 |
| 356 | 442 | 0.91 | Z011_S03 |
| 357 | 442 | 0.93 | Z011_S03 |
| 358 | 425 | 0.71 | Z012_S04 |
| 359 | 423 | 1.06 | Z011_S03 |

Examples representing mixtures of stereoisomers can be detected and resolved into single stereoisomers through analytical and preparative chiral chromatography. Representatives of examples for this process are given in Table 64

TABLE 64

The abbreviation "Dist. example" refers to the distomer of the given example.

| | | Analytical SFC Data | | | | |
|---|---|---|---|---|---|---|
| Example | Methode | Stereoisomer 1 (Exampl No.). | rt [min] | Stereoisomer 2 (Example No.) | rt [min] | Prep. SFC Method |
| 15 | I_ASH_30_10MIN_SS4P.M | 2 | 3.94 | Dist.-2 | 5.67 | chiral SFC E |
| 22 | I_ADH_40_MEOH_DEA.M | 29 | 3.60 | Dist.-29 | 5.76 | chiral SFC D |
| 43 | I_ADH_15_MEOH_DEA.M | 249 | 7.43 | 250 | 8.72 | chiral SFC C |

TABLE 65

List of Abbreviations

| | |
|---|---|
| ACN | acetonitrile |
| AIBN | 2,2'-azobis(isobutyronitrile) |
| ALOX | aluminium oxide |
| aq. | aqueous |
| BOC | tert. butyloxycyrbonyle- |
| d | day |
| DBU | 1,8-diazabicyclo[5.4.0]undec-7-ene |
| DCM | dichloromethane |
| DEA | diethylamine |
| DIPEA | n,n-diisopropylethylamine |
| DIPE | diisopropyl ether |
| DMAP | 4-dimethylaminopyridine |
| DMF | n,n-dimethylformamide |
| DMSO | dimethyl sulfoxide |
| EA | ethyl acetate |
| FA | formic acid |
| h | hour |
| HATU | o-(7-azabenzotriazol-1-yl)-N,N,N',N'-tetramethyluronium hexafluoro-phosphate |
| LiOH | lithium hydroxide |
| MeOH | methanol |
| MSA | methanesulfonic acid |
| MeTHF | methyl tetrahydrofuran |
| NaH | sodium hydride |
| PE | petrol ether |
| RT, r.t. | room temperature, e.g. 15-25° C. |
| rt | retention time |
| SI | trimethylsilyl iodide |
| TBME | tert-butyl methyl ether |
| TBTU | o-(1H-benzo-1,2,3-triazol-1-yl)-N,N,N',N'-tetramethyluronium tetrafluoroborate |
| TEA | triethylamine |
| TFA | trifluoroacetic acid |
| THF | tetrahydrofuran |
| TSA | toluene sulfonic acid |

Pharmacological Data

Other features and advantages of the present invention will become apparent from the following more detailed examples which illustrate, by way of example, the principles of the invention.

Inhibition of Human DPPI (Cathepsin C)

Materials: Microtiterplates (Optiplate-384 F) were purchased from PerkinElmer (Prod. No. 6007270). The substrate Gly-Arg-AMC was from Biotrend (Prod.-No. 808756 Custom peptide). Bovine serum albumin (BSA; Prod. No. A3059) and Dithiothreitol (DTT; Prod. No D0632) were from Sigma. TagZyme buffer was from Riedel-de-Haen (Prod.-No. 04269), NaCl was from Merck (Prod.-No. 1.06404.1000) and morpholinoethane sulfonic acid (MES), was from Serva (Prod.-No. 29834). The DPP1 inhibitor Gly-Phe-DMK was purchased from MP Biomedicals (Prod.-No. 03DK00625). The recombinant human DPPI was purchased from Prozymex. All other materials were of highest grade commercially available.

The following buffers were used: MES buffer: 25 mM MES, 50 mM NaCl, 5 mM DTT, adjusted to pH 6.0, containing 0.1% BSA; TAGZyme Buffer: 20 mM $NaH_2PO_4$, 150 mM NaCl adjusted to pH 6.0 with HCl Assay conditions: The recombinant human DPPI was diluted in TAGZyme buffer to 1 U/ml (38.1 μg/ml, respectively), and then activated by mixing in a 1:2 ratio with a Cysteamine aqueous solution (2 mM) and incubating for 5 min at room temperature.

Five uL test compound (final concentration 0.1 nM to 100 μM) in aqua bidest (containing 4% DMSO, final DMSO concentration 1%) were mixed with 10 μL of DPPI in MES buffer (final concentration 0.0125 ng/μL) and incubated for 10 min. Then, 5 μL of substrate in MES buffer (final concentration 50 μM) were added. The microtiter plates were then incubated at room temperature for 30 min Then, the reaction was stopped by adding 10 μL of Gly-Phe-DMK in MES-buffer (final concentration 1 μM). The fluorescence in the wells was determined using a Molecular Devices SpectraMax M5 Fluorescence Reader (Ex 360 nm, Em 460 nm) or an Envision Fluorescence Reader (Ex 355 nm, Em 460 nm).

Each assay microtiter plate contained wells with vehicle controls (1% DMSO in bidest+0.075% BSA) as reference for non-inhibited enzyme activity (100% Ctl; high values) and wells with inhibitor (Gly-Phe-DMK, in bidest+1% DMSO+0.075% BSA, final concentration 1 μM) as controls for background fluorescence (0% Ctl; low values).

The analysis of the data was performed by calculating the percentage of fluorescence in the presence of test compound in comparison to the fluorescence of the vehicle control after subtracting the background fluorescence using the following formula:

(RFU(sample)−RFU(background))*100/(RFU(control)−RFU(background))

Data from these calculations were used to generate $IC_{50}$ values for inhibition of DPPI, respectively.

TABLE 66

| Example | Inhibition of DPPI IC50 [μM] |
|---|---|
| 1 | 0.0086 |
| 2 | 0.0020 |
| 3 | 0.0007 |
| 4 | 0.0014 |
| 5 | 0.0040 |
| 6 | 0.0107 |
| 7 | 0.0019 |
| 8 | 0.6794 |
| 9 | 0.0096 |
| 10 | 0.0015 |
| 11 | 0.0017 |
| 12 | 0.0019 |
| 13 | 0.0019 |
| 14 | 0.0020 |
| 15 | 0.0020 |
| 16 | 0.0026 |
| 17 | 0.0026 |
| 18 | 0.0027 |
| 19 | 0.0028 |
| 20 | 0.0031 |
| 21 | 0.0031 |
| 22 | 0.0033 |
| 23 | 0.0037 |
| 24 | 0.0037 |
| 25 | 0.0039 |
| 26 | 0.0040 |
| 27 | 0.0040 |
| 28 | 0.0041 |
| 29 | 0.0042 |
| 30 | 0.0042 |
| 31 | 0.0043 |
| 32 | 0.0045 |
| 33 | 0.0045 |
| 34 | 0.0046 |
| 35 | 0.0046 |
| 36 | 0.0047 |
| 37 | 0.0047 |
| 38 | 0.0048 |
| 39 | 0.0051 |
| 40 | 0.0051 |
| 41 | 0.0053 |
| 42 | 0.0053 |
| 43 | 0.0056 |

TABLE 66-continued

| Example | Inhibition of DPPI IC50 [μM] |
|---|---|
| 44 | 0.0059 |
| 45 | 0.0063 |
| 46 | 0.0069 |
| 47 | 0.0072 |
| 48 | 0.0072 |
| 49 | 0.0073 |
| 50 | 0.0074 |
| 51 | 0.0075 |
| 52 | 0.0076 |
| 53 | 0.0079 |
| 54 | 0.0082 |
| 55 | 0.0082 |
| 56 | 0.0083 |
| 57 | 0.0083 |
| 58 | 0.0084 |
| 59 | 0.0085 |
| 60 | 0.0087 |
| 61 | 0.0087 |
| 62 | 0.0091 |
| 63 | 0.0093 |
| 64 | 0.0093 |
| 65 | 0.0094 |
| 66 | 0.0094 |
| 67 | 0.0096 |
| 68 | 0.0097 |
| 69 | 0.0099 |
| 70 | 0.0102 |
| 71 | 0.0108 |
| 72 | 0.0108 |
| 73 | 0.0112 |
| 74 | 0.0114 |
| 75 | 0.0114 |
| 76 | 0.0117 |
| 77 | 0.0119 |
| 78 | 0.0120 |
| 79 | 0.0120 |
| 80 | 0.0124 |
| 81 | 0.0131 |
| 82 | 0.0131 |
| 83 | 0.0133 |
| 84 | 0.0137 |
| 85 | 0.0140 |
| 86 | 0.0141 |
| 87 | 0.0142 |
| 88 | 0.0152 |
| 89 | 0.0156 |
| 90 | 0.0160 |
| 91 | 0.0170 |
| 92 | 0.0177 |
| 93 | 0.0183 |
| 94 | 0.0187 |
| 95 | 0.0192 |
| 96 | 0.0198 |
| 97 | 0.0199 |
| 98 | 0.0203 |
| 99 | 0.0211 |
| 100 | 0.0223 |
| 101 | 0.0239 |
| 102 | 0.0248 |
| 103 | 0.0249 |
| 104 | 0.0249 |
| 105 | 0.0250 |
| 106 | 0.0259 |
| 107 | 0.0259 |
| 108 | 0.0264 |
| 109 | 0.0269 |
| 110 | 0.0286 |
| 111 | 0.0318 |
| 112 | 0.0333 |
| 113 | 0.0364 |
| 114 | 0.0367 |
| 115 | 0.0378 |
| 116 | 0.0391 |
| 117 | 0.0396 |
| 118 | 0.0443 |
| 119 | 0.0512 |
| 120 | 0.0556 |
| 121 | 0.1565 |
| 122 | 0.1817 |
| 123 | 0.1866 |
| 124 | 0.1869 |
| 125 | 0.2060 |
| 126 | 0.2751 |
| 127 | 0.8597 |
| 128 | 2.3930 |
| 129 | 0.0827 |
| 130 | 0.0435 |
| 131 | 0.1387 |
| 132 | 0.0189 |
| 133 | 0.0161 |
| 134 | 0.0178 |
| 135 | 0.2857 |
| 136 | 0.0102 |
| 137 | 0.0597 |
| 138 | 0.0145 |
| 139 | 0.0117 |
| 140 | 0.0215 |
| 141 | 0.0366 |
| 142 | 0.0631 |
| 143 | 0.0067 |
| 144 | 0.0263 |
| 145 | 0.0538 |
| 146 | 0.0305 |
| 147 | 0.0062 |
| 148 | 0.0304 |
| 149 | 0.0387 |
| 150 | 0.0386 |
| 151 | 0.0369 |
| 152 | 0.0021 |
| 153 | 0.0038 |
| 154 | 0.0135 |
| 155 | 0.0008 |
| 156 | 0.0006 |
| 157 | 0.0009 |
| 158 | 0.0015 |
| 159 | 0.0016 |
| 160 | 0.0017 |
| 161 | 0.0019 |
| 162 | 0.002 |
| 163 | 0.0021 |
| 164 | 0.0023 |
| 165 | 0.0027 |
| 166 | 0.0033 |
| 167 | 0.0034 |
| 168 | 0.0037 |
| 169 | 0.0041 |
| 170 | 0.0042 |
| 171 | 0.005 |
| 172 | 0.0052 |
| 173 | 0.0055 |
| 174 | 0.0056 |
| 175 | 0.0063 |
| 176 | 0.0066 |
| 177 | 0.0074 |
| 178 | 0.0074 |
| 179 | 0.0075 |
| 180 | 0.0077 |
| 181 | 0.0086 |
| 182 | 0.0088 |
| 183 | 0.0088 |
| 184 | 0.0088 |
| 185 | 0.009 |
| 186 | 0.0096 |
| 187 | 0.0098 |
| 188 | 0.0098 |
| 189 | 0.0104 |
| 190 | 0.0109 |
| 191 | 0.0112 |
| 192 | 0.0113 |
| 193 | 0.0123 |

TABLE 66-continued

| Example | Inhibition of DPPI IC50 [μM] |
|---|---|
| 194 | 0.0133 |
| 195 | 0.0147 |
| 196 | 0.0151 |
| 197 | 0.0156 |
| 198 | 0.0158 |
| 199 | 0.016 |
| 200 | 0.0165 |
| 201 | 0.0201 |
| 202 | 0.0229 |
| 203 | 0.0233 |
| 204 | 0.0245 |
| 205 | 0.0259 |
| 206 | 0.0263 |
| 207 | 0.0291 |
| 208 | 0.0298 |
| 209 | 0.0458 |
| 210 | 0.0494 |
| 211 | 0.0611 |
| 212 | 0.2955 |
| 213 | 0.619 |
| 214 | 0.8148 |
| 215 | 0.8819 |
| 216 |  |
| 217 | 0.0037 |
| 218 | 0.0189 |
| 219 | 0.0374 |
| 220 | 0.253 |
| 221 | 0.0037 |
| 222 | 0.0022 |
| 223 | 0.0059 |
| 224 | 0.0012 |
| 225 | 0.0008 |
| 226 | 0.0009 |
| 227 | 0.0010 |
| 228 | 0.0016 |
| 229 | 0.0017 |
| 230 | 0.0018 |
| 231 | 0.0022 |
| 232 | 0.0022 |
| 233 | 0.0022 |
| 234 | 0.0038 |
| 235 | 0.0047 |
| 236 | 0.0016 |
| 237 | 0.0046 |
| 238 | 0.0143 |
| 239 | 0.0034 |
| 240 | 0.0061 |
| 241 | 0.0068 |
| 242 | 0.0109 |
| 243 | 0.0048 |
| 244 | 0.0037 |
| 245 | 0.0059 |
| 246 | 0.0059 |
| 247 | 0.0084 |
| 248 | 0.0180 |
| 249 | 0.0063 |
| 250 | 0.0042 |
| 251 | 0.0115 |
| 252 | 0.0038 |
| 253 | 0.0110 |
| 254 | 0.0020 |
| 255 | 0.0109 |
| 256 | 0.0263 |
| 257 | 0.0399 |
| 258 | 0.0079 |
| 259 | 0.0060 |
| 260 | 0.0035 |
| 261 | 0.0042 |
| 262 | 0.0064 |
| 263 | 0.0118 |
| 264 | 0.0170 |
| 265 | 0.0627 |
| 266 | 0.0437 |
| 267 | 0.0105 |
| 268 | 0.0111 |

TABLE 66-continued

| Example | Inhibition of DPPI IC50 [μM] |
|---|---|
| 269 | 0.0094 |
| 270 | 0.0063 |
| 271 | 0.0059 |
| 272 | 0.0068 |
| 273 | 0.0289 |
| 274 | 0.0065 |
| 275 | 0.0330 |
| 276 | 0.0141 |
| 277 | 0.0030 |
| 278 | 0.0010 |
| 279 | 0.0055 |
| 280 | 0.0212 |
| 281 | 0.0033 |
| 282 | 0.0037 |
| 283 | 0.0097 |
| 284 | 0.0138 |
| 285 | 0.0093 |
| 286 | 0.0389 |
| 287 | 0.0397 |
| 288 | 0.0023 |
| 289 | 0.0025 |
| 290 | 0.0206 |
| 291 | 0.0059 |
| 292 | 0.0009 |
| 293 | 0.0013 |
| 294 | 0.0016 |
| 295 | 0.0021 |
| 296 | 0.0029 |
| 297 | 0.0032 |
| 298 | 0.0032 |
| 299 | 0.0032 |
| 300 | 0.0038 |
| 301 | 0.0045 |
| 302 | 0.0047 |
| 303 | 0.0050 |
| 304 | 0.0060 |
| 305 | 0.0069 |
| 306 | 0.0070 |
| 307 | 0.0072 |
| 308 | 0.0083 |
| 309 | 0.0091 |
| 310 | 0.0094 |
| 311 | 0.0099 |
| 312 | 0.0110 |
| 313 | 0.0136 |
| 314 | 0.0140 |
| 315 | 0.0135 |
| 316 | 0.0424 |
| 317 | 0.0520 |
| 318 | 0.2120 |
| 319 | 0.0175 |
| 320 | 0.0096 |
| 321 | 0.0568 |
| 322 | 0.0008 |
| 323 | 0.0008 |
| 324 | 0.0010 |
| 325 | 0.0013 |
| 326 | 0.0019 |
| 327 | 0.0034 |
| 328 | 0.0042 |
| 329 | 0.0070 |
| 330 | 0.0078 |
| 331 | 0.0093 |
| 332 | 0.0129 |
| 333 | 0.0153 |
| 334 | 0.0220 |
| 335 | 0.0245 |
| 336 | 0.0245 |
| 337 | 0.0282 |
| 338 | 0.0443 |
| 339 | 0.0013 |
| 340 | 0.0018 |
| 341 | 0.0076 |
| 342 | 0.0013 |
| 343 | 0.0045 |

TABLE 66-continued

| Example | Inhibition of DPPI IC50 [μM] |
|---|---|
| 344 | 0.0100 |
| 345 | 0.0184 |
| 346 | 0.0010 |
| 347 | 0.0085 |
| 348 | 0.0176 |
| 349 | 0.0206 |
| 350 | 0.0386 |
| 351 | 0.0828 |
| 352 | 0.0173 |
| 353 | 0.0065 |
| 354 | 0.0068 |
| 355 | 0.0224 |
| 356 | 0.0200 |
| 357 | 0.0338 |
| 358 | 0.0220 |
| 359 | 0.0088 |
| WO09074829; Example 56 | 0.0441 |

Determination of Neutrophil Elastase Activity in U937 Cytosolic Lysate Preparation after Incubation with Test Compound Materials:

Optiplate 384F were purchased from PerkinElmer (Prod. No. #6007270). 24 well Nunclon cell culture plates (No. 142475) and 96 well plates (No. 267245) were from Nunc. Dimethylsulfoxid (DMSO) was from Sigma (Prod. No. D8418). Nonidet-P40 (NP40) was from USBiological (Prod. No. N3500)

Substrate, specific for Neutrophil elastase, was from Bachem (MeOSuc-Ala-Ala-Pro-Val-AMC; Prod. No. I-1270).

Human neutrophil elastase was from Calbiochem (Prod. No. 324681)

Buffers:

Tris-buffer (100 mM Tris; 1M NaCL; pH 7.5)

Tris-buffer+HSA 0.1%; Human Serum Albumin from Calbiochem (Cat#. 126658)

Serine-protease buffer (20 mM Tris; 100 mM NaCL; pH 7.5)+0.1% HSA

Serine protease lysis buffer: 20 mM Tris-HCL; 100 mM NaCl pH 7.5; +0.2% Nonidet-P40;

PBS: phosphate buffered saline, without Ca and Mg, from Gibco

Cell Culture:

U937 from ECACC (Cat. No. 85011440) cultured in suspension at 37° C. and 5% CO2.

Cell density: 0.2-1 Mio. Cells/ml.

Medium: RPMI1640 GlutaMAX (No. 61870) with 10% FCS from Gibco

Cell Seeding and Treatment:

Compounds in 100% DMSO were diluted in Medium (-FCS) with 10% DMSO and further diluted according to the experiment planned.

20 μl of the compound solution was transferred in the respective wells of the 24 well plate and diluted with 2 ml cell suspension/well containing 1'105 cells/ml (final concentration of DMSO=0.1%). Compound dilution factor=100

Compounds (up to 7 concentrations) were tested in triplicates with 3 wells for the DMSO 0.1% control, incubated for 48 hours without medium change at 37° C., 5% CO2 and 95% relative humidity.

Cell Harvesting and Cell Lysate:

Transfer the cell suspension in 2,2 ml Eppendorf cups. Separate cells from medium by centrifugation (400×g; 5 min; RT); discard the supernatant. Resuspend in 1 ml PBS; centrifugation (400×g; 5 min; RT); wash cells twice with PBS. Add 100 μl Serin lysis buffer (ice cold) to the cell pellet; resuspend the pellet and store on ice for 15 minutes. Remove debris by centrifugation at 15000×g for 10 min at 4° C. Transfer 80-100 μl lysate supernatant in 96 well plate and store immediately at −80° C.

Neutrophil Elastase Activity Assay:

Frozen lysates were thawn at 37° C. for 10 minutes and stored on ice. Protein content was determined with Bradford protein assay. Lysates were diluted to 0.2-0.5 mg/ml protein in serine protease buffer+HSA.

Standard: NE (100 μg/ml stocksolution in Tris-buffer; stored at −80° C.) was diluted in Tris-buffer+HSA to 750 ng/ml, and further serially diluted 1:2 for the standard curve.

Buffer, blank, standard and lysate samples were transferred into 384 well plate

Pipetting Plan

Blank: 5 μl Tris-buffer+10 μl Tris-buffer+HSA+5 μl Substrate

Standard: 5 μl Tris-buffer+10 μl NE (diff. conc.)+5 μl Substrate

Lysate: 5 μl Tris-buffer+10 μl Lysat+5 μl Substrate

The increase in fluorescence (Ex360 nm/Em 460 nm) is determined over 30 minutes with a Molecular Device Spectramax M5 Fluorescence Reader. Kinetic Reduction (Vmax units/sec); 4 vmax points. The amount of neutrophil elastase (ng/ml) is calculated using the standard curve and the Spectramax software. The result is interpolated to ng/mg lysate protein using excel formula functions. Percent inhibition in the compound-treated lysate samples is calculated relative to the DMSO-treated control-sample (100−(compound-sample*100)/control-sample)

A test compound will give values between 0% and 100% inhibition of neutrophil elastase. I050 is calculated using Graphpad Prism; nonlinear fitting (log(inhibitor) vs. response—Variable slope). The IC50 value is interpolated as the concentration of test compound which leads to a neutrophil elastase activity reduction of 50% (relative to the DMSO-treated control).

TABLE 67

| Example | Reduction of NE-activity in U937 cells IC50 [μM] |
|---|---|
| 1 | 0.0023 |
| 2 | 0.0062 |
| 3 | 0.0029 |
| 4 | 0.0064 |
| 6 | 0.0024 |
| 11 | 0.0087 |
| 16 | 0.0145 |
| 29 | 0.0088 |
| 42 | 0.0083 |
| 43 | 0.0092 |
| 154 | 0.0046 |
| 155 | 0.0005 |
| 156 | 0.0023 |
| 158 | 0.0088 |
| 169 | 0.0091 |
| 177 | 0.0092 |
| 178 | 0.0036 |
| 182 | 0.0081 |
| 185 | 0.0039 |
| 187 | 0.0073 |
| 188 | 0.0044 |
| 191 | 0.0033 |
| 192 | 0.0041 |
| 193 | 0.0065 |
| 196 | 0.0053 |

TABLE 67-continued

| Example | Reduction of NE-activity in U937 cells IC50 [µM] |
|---|---|
| 217 | 0.0075 |
| 223 | 0.0030 |
| 224 | 0.0010 |
| 225 | 0.0028 |
| 226 | 0.0018 |
| 227 | 0.0009 |
| 228 | 0.0046 |
| 229 | 0.0029 |
| 232 | 0.0052 |
| 234 | 0.0069 |
| 237 | 0.0096 |
| 241 | 0.0053 |
| 245 | 0.0038 |
| 247 | 0.0080 |
| 249 | 0.0165 |
| 250 | 0.0115 |
| 253 | 0.0055 |
| 254 | 0.0305 |
| 267 | 0.0027 |
| 268 | 0.0007 |
| 269 | 0.0055 |
| 270 | 0.0014 |
| 271 | 0.0017 |
| 272 | 0.0024 |
| 277 | 0.0036 |
| 278 | 0.0010 |
| 279 | 0.0019 |
| 281 | 0.0019 |
| 282 | 0.0034 |
| 283 | 0.0045 |
| 284 | 0.0053 |
| 289 | 0.0039 |
| 293 | 0.0046 |
| 294 | 0.0078 |
| 295 | 0.0086 |
| 300 | 0.0089 |
| 303 | 0.0083 |
| 319 | 0.0093 |
| 320 | 0.0037 |
| 322 | 0.0021 |
| 323 | 0.0014 |
| 324 | 0.0013 |
| 325 | 0.0047 |
| 326 | 0.0019 |
| 328 | 0.0012 |
| 329 | 0.0025 |
| 330 | 0.0377 |
| 331 | 0.0060 |
| 332 | 0.0058 |
| 333 | 0.0047 |
| 339 | 0.0006 |
| 340 | 0.0008 |
| 342 | 0.0247 |
| 343 | 0.0169 |
| 344 | 0.0041 |
| 345 | 0.0069 |
| 346 | 0.0068 |
| 348 | 0.0020 |
| 349 | 0.0028 |
| 358 | 0.0037 |
| 359 | 0.0029 |
| WO09074829; Example 56 | 0.1067 |

Inhibition of Human Cathepsin K

Materials: Microtiterplates (Optiplate-384 F were purchased from PerkinElmer (Prod. No. 6007270). The substrate Z-Gly-Pro-Arg-AMC was from Biomol (Prod.-No. P-142). L-Cysteine (Prod. No. 168149) was from Sigma. Sodium acetate was from Merck (Prod.-No. 6268.0250), EDTA was from Fluka (Prod.-No. 03680). The inhibitor E-64 was purchased from Sigma (Prod.-No. E3132). The recombinant human Cathepsin K proenzyme was purchased from Biomol (Prod. No. SE-367). All other materials were of highest grade commercially available.

The following buffers were used: Activation buffer: 32.5 mM sodium acetate, adjusted to pH 3.5 with HCl; Assay buffer: 150 mM sodium acetate, 4 mM EDTA, 20 mM L-Cysteine, adjusted to pH 5.5 with HCl, Assay conditions: To activate the proenzyme, 5 µl pro-cathepsin K were mixed with 1 ul activation buffer, and incubated at room temperature for 30 min.

5 µL test compound (final concentration 0.1 nM to 100 µM) in aqua bidest (containing 4% DMSO, final DMSO concentration 1%) were mixed with 10 uL of Cathepsin K in assay buffer (final concentration 2 ng/µL) and incubated for 10 min. Then 5 µL of substrate in assay buffer (final concentration 12.5 µM) were added. The plates were then incubated at room temperature for 60 min. Then, the reaction was stopped by adding 10 µL of E64 in assay buffer (final concentration 1 µM). The fluorescence in the wells was determined using a Molecular Devices SpectraMax M5 Fluorescence Reader (Ex 360 nm, Em 460 nm).

Each assay microtiter plate contains wells with vehicle controls (1% DMSO in bidest) as reference for non-inhibited enzyme activity (100% Ctl; high values) and wells with inhibitor (E64 in bidest+1% DMSO, final concentration 1 µM) as controls for background fluorescence (0% Ctl; low values). The analysis of the data was performed by calculating the percentage of fluorescence in the presence of test compound in comparison to the fluorescence of the vehicle control after subtracting the background fluorescence:

$$(RFU(sample)-RFU(background))*100/(RFU(control)-RFU(background))$$

Data from these calculations were used to generate $IC_{50}$ values for inhibition of Cathepsin K, respectively.

TABLE 68

| Example | Inhibition of Cathepsin K IC50 [µM] |
|---|---|
| 2 | 2.8 |
| 3 | 2.1 |
| 4 | 2.6 |
| 5 | 2.6 |
| 6 | 2.5 |
| 7 | 8.0 |
| 10 | 2.7 |
| 11 | 2.6 |
| 12 | 2.1 |
| 13 | 3.4 |
| 14 | 2.7 |
| 15 | 3.2 |
| 16 | 2.1 |
| 17 | 6.1 |
| 18 | 3.0 |
| 19 | 5.4 |
| 20 | 2.9 |
| 21 | 4.9 |
| 22 | 3.2 |
| 23 | 3.8 |
| 24 | 13.3 |
| 25 | 6.3 |
| 26 | 3.6 |
| 27 | 3.2 |
| 28 | 2.7 |
| 29 | 1.4 |
| 30 | 3.1 |
| 31 | 7.3 |
| 32 | 3.9 |
| 33 | 4.8 |
| 34 | 2.5 |
| 35 | 4.4 |
| 36 | 3.0 |
| 37 | 5.1 |
| 38 | 2.9 |
| 39 | 7.8 |

TABLE 68-continued

| Example | Inhibition of Cathepsin K IC50 [μM] |
|---|---|
| 40 | 7.8 |
| 41 | 4.7 |
| 42 | 2.9 |
| 43 | 2.2 |
| 44 | 4.0 |
| 45 | 4.4 |
| 46 | 4.0 |
| 47 | 3.4 |
| 48 | 3.3 |
| 49 | 6.5 |
| 50 | 3.6 |
| 51 | 4.9 |
| 52 | 17.0 |
| 53 | 4.1 |
| 54 | 4.5 |
| 55 | 3.9 |
| 56 | 4.0 |
| 57 | 2.3 |
| 58 | 11.1 |
| 59 | 2.5 |
| 60 | 12.3 |
| 61 | 10.9 |
| 62 | 3.9 |
| 63 | 6.2 |
| 64 | 4.2 |
| 65 | 11.7 |
| 66 | 4.8 |
| 67 | 4.6 |
| 68 | 7.3 |
| 69 | 2.4 |
| 70 | 12.0 |
| 71 | 4.8 |
| 72 | 7.3 |
| 73 | 3.1 |
| 74 | 2.5 |
| 75 | 5.3 |
| 76 | 5.3 |
| 77 | 5.3 |
| 78 | 6.7 |
| 79 | 3.5 |
| 80 | 4.1 |
| 81 | 4.5 |
| 82 | 5.4 |
| 83 | 5.1 |
| 84 | 4.9 |
| 85 | 3.0 |
| 86 | 6.8 |
| 88 | 8.8 |
| 89 | 5.4 |
| 90 | 3.5 |
| 91 | 2.5 |
| 92 | 8.2 |
| 93 | 6.9 |
| 94 | 4.9 |
| 95 | 3.6 |
| 96 | 5.5 |
| 97 | 7.9 |
| 98 | 8.4 |
| 99 | 2.9 |
| 100 | 8.2 |
| 101 | 6.5 |
| 102 | 4.3 |
| 103 | 5.9 |
| 104 | 10.3 |
| 105 | 5.2 |
| 106 | 5.3 |
| 107 | 4.7 |
| 108 | 9.4 |
| 109 | 4.5 |
| 110 | 9.8 |
| 111 | 4.3 |
| 112 | 5.6 |
| 113 | 8.3 |
| 114 | 6.8 |
| 115 | 2.3 |
| 116 | 7.7 |
| 117 | 2.7 |
| 118 | 3.9 |
| 119 | 4.5 |
| 121 | 5.2 |
| 130 | 10.2 |
| 132 | 12.2 |
| 133 | 19.4 |
| 134 | 6.7 |
| 136 | 6.2 |
| 138 | 6.4 |
| 139 | 4.8 |
| 140 | 8.4 |
| 141 | 8.8 |
| 143 | 5.1 |
| 144 | 11.1 |
| 145 | 7.4 |
| 146 | 9.6 |
| 147 | 9.7 |
| 148 | 14.6 |
| 149 | 7.6 |
| 150 | 9.3 |
| 151 | 4.8 |
| 152 | 6.1 |
| 153 | 4.4 |
| 154 | 4.6 |
| 155 | 1.0 |
| 156 | 7.8 |
| 157 | 7.4 |
| 158 | 9.4 |
| 159 | 3.3 |
| 161 | 10.7 |
| 167 | 6.3 |
| 169 | 5.2 |
| 176 | 13.9 |
| 181 | 9.7 |
| 182 | 3.5 |
| 185 | 1.7 |
| 186 | 3.5 |
| 190 | 3.7 |
| 193 | 2.2 |
| 199 | 11.7 |
| 200 | 3.3 |
| 201 | 2.5 |
| 203 | 8.4 |
| 218 | 26.0 |
| 222 | 1.7 |
| 228 | 2.0 |
| 229 | 1.6 |
| 230 | 5.9 |
| 231 | 2.4 |
| 233 | 3.0 |
| 234 | 2.9 |
| 235 | 3.0 |
| 236 | 1.7 |
| 237 | 1.9 |
| 238 | 9.3 |
| 239 | 2.0 |
| 240 | 9.4 |
| 241 | 2.5 |
| 242 | 2.5 |
| 244 | 2.0 |
| 245 | 1.2 |
| 247 | 4.5 |
| 249 | 3.6 |
| 250 | 3.1 |
| 252 | 3.3 |
| 253 | 5.7 |
| 254 | 4.5 |
| 259 | 3.7 |
| 260 | 3.9 |
| 261 | 3.8 |
| 262 | 2.8 |
| 263 | 2.1 |
| 267 | 4.7 |
| 268 | 3.8 |
| 269 | 1.7 |
| 270 | 6.1 |
| 274 | 3.5 |

TABLE 68-continued

| Example | Inhibition of Cathepsin K IC50 [µM] |
|---|---|
| 276 | 5.5 |
| 278 | 1.2 |
| 281 | 1.9 |
| 282 | 1.8 |
| 283 | 3.6 |
| 285 | 8.7 |
| 288 | 2.2 |
| 293 | 2.7 |
| 294 | 2.2 |
| 295 | 4.7 |
| 296 | >30.0 |
| 297 | 12.4 |
| 298 | 17.6 |
| 300 | 23.1 |
| 301 | 19.5 |
| 303 | 22.2 |
| 315 | >30.0 |
| 319 | 4.5 |
| 322 | 1.1 |
| 323 | 0.9 |
| 324 | 0.8 |
| 325 | 2.3 |
| 326 | 1.1 |
| 328 | 7.7 |
| 330 | 6.6 |
| 331 | 1.5 |
| 332 | 6.2 |
| 333 | 2.4 |
| 343 | 5.3 |
| 344 | 6.2 |
| 345 | 9.2 |
| 346 | 4.0 |
| 348 | 4.3 |
| 349 | 5.0 |
| 358 | 9.6 |
| 359 | 6.3 |
| WO09074829; Example 56 | 0.4 |

Determination of Metabolic Stability with Human Liver Microsomes

The metabolic degradation of the test compound is assayed at 37° C. with pooled human liver microsomes. The final incubation volume of 100 µl per time point contains TRIS buffer pH 7.6 (0.1 M), magnesium chloride (5 mM), microsomal protein (1 mg/ml) and the test compound at a final concentration of 1 µM. Following a short preincubation period at 37° C., the reactions are initiated by addition of beta-nicotinamide adenine dinucleotide phosphate, reduced form (NADPH, 1 mM) and terminated by transferring an aliquot into acetonitrile after different time points. Additionally, the NADPH-independent degradation is monitored in incubations without NADPH, terminated at the last time point. The [%] remaining test compound after NADPH independent incubation is reflected by the parameter c (control) (metabolic stability). The quenched incubations are pelleted by centrifugation (10,000 g, 5 min) An aliquot of the supernatant is assayed by LC-MS/MS for the amount of parent compound.

The half-life (t½ INVITRO) is determined by the slope of the semilogarithmic plot of the concentration-time profile. The intrinsic clearance (CL_INTRINSIC) is calculated by considering the amount of protein in the incubation:

CL_INTRINSIC [µl/min/mg protein]=(ln 2/(half-life [min]*protein content [mg/ml]))*1,000.

The half-life (t½ INVITRO) values of selected compounds in the metabolic stability assay described above are listed in the following table

TABLE 69

| Example | In vitro stability in human liver microsome incubations t½ [min] |
|---|---|
| 2 | >125 |
| 3 | 57 |
| 4 | >130 |
| 5 | 92 |
| 6 | >130 |
| 9 | >120 |
| 10 | >130 |
| 12 | >130 |
| 14 | >130 |
| 15 | 130 |
| 16 | >130 |
| 19 | >130 |
| 21 | >130 |
| 22 | >130 |
| 24 | 110 |
| 28 | >130 |
| 29 | >130 |
| 31 | 90 |
| 33 | >130 |
| 35 | >130 |
| 40 | >130 |
| 41 | >130 |
| 42 | >130 |
| 43 | >130 |
| 44 | >130 |
| 47 | 84 |
| 49 | >130 |
| 50 | >130 |
| 52 | >130 |
| 53 | >130 |
| 54 | >130 |
| 55 | >130 |
| 57 | 95 |
| 58 | >130 |
| 62 | >130 |
| 67 | 89 |
| 71 | >120 |
| 76 | 84 |
| 77 | >130 |
| 78 | 130 |
| 82 | >130 |
| 83 | >130 |
| 86 | >130 |
| 88 | >130 |
| 89 | >130 |
| 90 | >130 |
| 91 | >130 |
| 95 | >130 |
| 96 | 82 |
| 97 | >130 |
| 98 | >130 |
| 99 | >130 |
| 100 | >130 |
| 102 | >130 |
| 105 | >130 |
| 106 | >130 |
| 108 | >130 |
| 109 | >130 |
| 110 | >130 |
| 111 | >130 |
| 112 | >130 |
| 114 | >130 |
| 116 | >130 |
| 117 | >130 |
| 125 | >130 |
| 132 | >130 |
| 136 | >130 |
| 139 | >130 |
| 143 | >130 |
| 147 | >130 |
| 152 | >130 |
| 153 | 110 |
| 154 | >130 |
| 155 | 62 |
| 156 | 95 |
| 157 | >130 |

TABLE 69-continued

| Example | In vitro stability in human liver microsome incubations t½ [min] |
|---|---|
| 158 | >130 |
| 159 | >130 |
| 162 | >130 |
| 166 | 94 |
| 167 | >130 |
| 169 | >130 |
| 171 | 83 |
| 176 | >130 |
| 178 | >130 |
| 180 | >120 |
| 181 | >130 |
| 182 | >130 |
| 183 | >130 |
| 184 | >130 |
| 185 | >130 |
| 188 | 97 |
| 189 | >130 |
| 190 | >130 |
| 191 | 91 |
| 192 | >130 |
| 193 | >130 |
| 194 | 85 |
| 196 | >130 |
| 199 | 88 |
| 200 | >130 |
| 201 | >130 |
| 204 | >130 |
| 205 | >130 |
| 218 | >130 |
| 221 | >130 |
| 222 | >130 |
| 223 | >130 |
| 230 | >130 |
| 231 | >130 |
| 233 | >130 |
| 235 | >130 |
| 236 | >130 |
| 238 | 110 |
| 239 | >130 |
| 240 | 110 |
| 241 | 84 |
| 242 | >130 |
| 244 | 92 |
| 245 | >130 |
| 247 | >130 |
| 248 | >130 |
| 249 | >130 |
| 250 | >130 |
| 252 | 130 |
| 253 | >130 |
| 254 | >130 |
| 255 | >130 |
| 258 | >130 |
| 259 | >130 |
| 260 | >130 |
| 261 | >130 |
| 262 | >120 |
| 263 | >130 |
| 266 | >130 |
| 267 | >130 |
| 268 | >130 |
| 269 | >130 |
| 270 | >130 |
| 271 | 130 |
| 272 | >130 |
| 274 | >125 |
| 276 | 130 |
| 277 | >130 |
| 278 | >130 |
| 281 | >130 |
| 282 | >130 |
| 283 | >130 |
| 284 | 58 |
| 285 | >130 |
| 288 | >130 |
| 289 | 110 |
| 291 | >130 |
| 292 | 94 |
| 293 | >130 |
| 294 | >130 |
| 295 | >130 |
| 296 | >130 |
| 298 | 105 |
| 300 | >130 |
| 301 | 100 |
| 303 | >130 |
| 305 | 91 |
| 306 | >130 |
| 307 | >130 |
| 308 | >130 |
| 310 | >130 |
| 313 | >130 |
| 314 | >130 |
| 315 | 92 |
| 319 | >130 |
| 320 | >130 |
| 321 | >130 |
| 322 | >130 |
| 323 | >130 |
| 324 | >130 |
| 325 | >130 |
| 327 | >130 |
| 328 | >130 |
| 330 | >130 |
| 331 | >120 |
| 332 | 100 |
| 333 | >130 |
| 335 | >130 |
| 341 | >130 |
| 342 | >130 |
| 343 | >130 |
| 344 | 110 |
| 345 | >130 |
| 346 | >130 |
| 347 | >130 |
| 348 | 130 |
| 349 | >130 |
| 358 | >130 |
| 359 | >130 |
| WO09074829; Example 56 | 120 |

Combinations

The compounds of general formula I may be used on their own or combined with other active substances of formula I according to the invention. The compounds of general formula I may optionally also be combined with other pharmacologically active substances. These include, β2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, Non-steroidal anti-inflammatory agents (NSAIDs), CRTH2 antagonists, DPI-receptor modulators, Thromboxane receptor antagonists, CCR3 antagonists, CCR4 antagonists, CCR1 antagonists, CCR5 antagonists, CCR6 antagonists, CCR7 antagonists, CCR8 antagonists, CCR9 antagonists, CCR30 antagonists, $CXCR^3$ antagonists, $CXCR^4$ antagonists, $CXCR^2$ antagonists, $CXCR^1$ antagonists, CXCR5 antagonists, CXCR6 antagonists, $CX3CR^3$ antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic receptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Matriptase-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, NE-inhibitors, MMP9 inhibitors, MMP12 inhibitors, but also combinations of two or three active substances.

Preferred are betamimetics, anticholinergics, corticosteroids, PDE4-inhibitors, LTD4-antagonists, EGFR-inhibitors, CRTH2 inhibitors, 5-LO-inhibitors, Histamine receptor antagonists and SYK-inhibitors, NE-inhibitors, MMP9 inhibitors, MMP12 inhibitors, but also combinations of two or three active substances, i.e.:

Betamimetics with corticosteroids, PDE4-inhibitors, CRTH2-inhibitors or LTD4-antagonists,
Anticholinergics with betamimetics, corticosteroids, PDE4-inhibitors, CRTH2-inhibitors or LTD4-antagonists,
Corticosteroids with PDE4-inhibitors, CRTH2-inhibitors or LTD4-antagonists
PDE4-inhibitors with CRTH2-inhibitors or LTD4-antagonists
CRTH2-inhibitors with LTD4-antagonists.

Indications

The compounds of the invention and their pharmaceutically acceptable salts have activity as pharmaceuticals, in particular as inhibitors of dipeptidyl peptidase I activity, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1-antitrypsin deficiency, bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, polyangiitis (Wegener Granulomatosis) and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and *mycobacterium avium*, leprosy; other infectious diseases, such as fungal diseases, *chlamydia, Candida, aspergillus*, cryptococcal meningitis, *Pneumocystis carnii*, cryptosporidiosis, histoplasmosis, toxoplasmosis, trypanosome infection and leishmaniasis.

9. pain: Recent literature data from Cathepsin C-deficient mice point to a modulatory role of Cathepsin C in pain sensation. Accordingly, inhibitors of Cathepsin C may also be useful in the clinical setting of various form of chronic pain, e.g. inflammatory or neuropathic pain.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

The invention claimed is:

1. A method of treating pulmonary emphysema comprising administering to a patient a therapeutically effective amount of a compound of formula 1

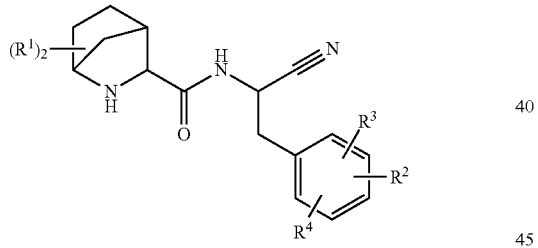

wherein
R$^1$ is independently selected from H, C$_{1-6}$-alkyl-, halogen, HO—, C$_{1-6}$-alkyl-O—, H$_2$N—, C$_{1-6}$-alkyl-HN—, C$_{1-6}$-alkyl)$_2$N— and C$_{1-6}$-alkyl-C(O)HN—; or two R$^1$ are together C$_{1-4}$-alkylene;
R$^2$ is selected from

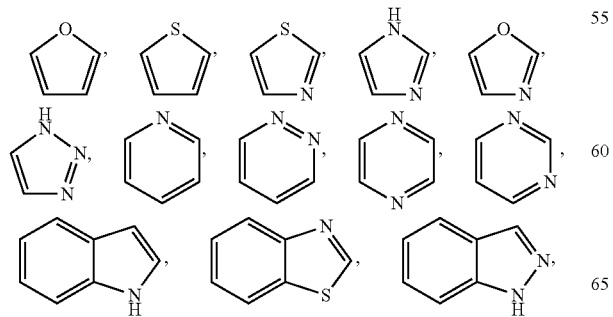

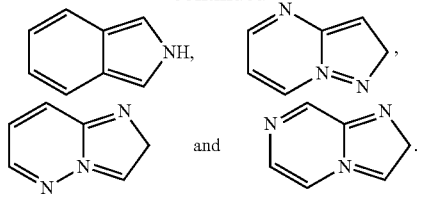

wherein carbon atoms of the ring are optionally and independently from each other substituted with one, two or three R$^{2.1}$; wherein possibly available nitrogen atoms of the ring are optionally and independently from each other substituted with R$^{2.2}$; and
R$^{2.1}$ is independently selected from H, halogen, NC—, O=, HO—, H-A-, H-A-C$_{1-4}$-alkylene-, R$^{2.1.1}$-A-, C$_{1-4}$-alkyl-A-, C$_{3-6}$-cycloalkyl-A-, C$_{1-4}$-haloalkyl-A-, R$^{2.1.1}$—C$_{1-4}$-alkylene-A-, C$_{1-4}$-alkyl-A-C$_{1-4}$-alkylene-, C$_{3-6}$-cycloalkyl-A-C$_{1-4}$-alkylene-, C$_{1-4}$-haloalkyl-A-C$_{1-4}$-alkylene-, R$^{2.1.1}$—C$_{1-4}$-alkylene-A-C$_{1-4}$-alkylene-, R$^{2.1.1}$-A-C$_{1-4}$-alkylene, HO—C$_{1-4}$-alkylene-A-, HO—C$_{1-4}$-alkylene-A-C$_{1-4}$-alkylene-, C$_{1-4}$-alkyl-O—C$_{1-4}$-alkylene-A- and C$_{1-4}$-alkyl-O—C$_{1-4}$-alkylene-A-C$_{1-4}$-alkylene-; and
R2.1.1 is independently selected from
aryl-; optionally substituted independently from each other with one, two or three R$^{2.1.1.1}$;
C$_{5-10}$-heteroaryl-; containing one, two, three or four heteroatoms independently selected from S, S(O), S(O)$_2$, O and N, wherein carbon atoms of the ring are optionally and independently from each other substituted with one, two or three R$^{2.1.1.1}$; wherein nitrogen atoms of the ring are optionally and independently from each other substituted with one, two or three R$^{2.1.1.2}$; and
C$_{5-10}$-heterocyclyl-; containing one, two, three or four heteroatoms independently selected from S, S(O), S(O)$_2$, O and N, wherein the ring is fully or partially saturated, wherein carbon atoms of the ring are optionally and independently from each other substituted with one, two or three or four R$^{2.1.1.1}$; wherein nitrogen atoms of the ring are optionally and independently from each other substituted with one, two or three R$^{2.1.1.2}$;
R2.1.1.1 is independently selected from halogen, HO—, O=, C$_{1-4}$-alkyl-, C$_{1-4}$-alkyl-O—, C$_{1-4}$-haloalkyl-, C$_{1-4}$-haloalkyl-O— and C$_{3-6}$-cycloalkyl-; and
R2.1.1.2 is independently selected from C$_{1-4}$-alkyl-, C$_{1-4}$-haloalkyl-; C$_{3-6}$-cycloalkyl-, C$_{1-4}$-alkyl-O—C$_{1-4}$-alkyl-, H(O)C—, C$_{1-4}$-alkyl-(O)C—, tetrahydrofuranylmethyl- and tetrahydropyranylmethyl-; and
R2.2 is independently selected from H-A-C$_{1-4}$-alkylene-, C$_{3-6}$-cycloalkyl-, C$_{1-4}$-alkyl-A-C$_{1-4}$-alkylene-, C$_{3-6}$-cycloalkyl-A-C$_{1-4}$-alkylene-, C$_{1-4}$-haloalkyl-A-C$_{1-4}$-alkylene-, R$^{2.1.1}$-A-, C$_{1-4}$-alkyl-S(O)$_2$— and C$_{1-4}$-alkyl-C(O)—, R2.1.1-A-;
R$^{2.3}$ and R$^4$ are together selected from —O—, —S—, —N(R$^{2.3.1}$)—, —C(O)N(R$^{2.3.1}$)—, —N(R$^{2.3.1}$)C(O)—, —S(O)$_2$N(R$^{2.3.1}$)—, —N(R$^{2.3.1}$)S(O)$_2$—, —C(O)O—, —OC(O)—, —C(O)—, —S(O)—, —S(O)$_2$—, R$^{2.3}$, R$^{2.3}$, —C(R$^{2.3.2}$)=C(R$^{2.3.2}$)—, —C=N—, —N=C—, —C($R^{2.3.2}$)$_2$—O—, —O—C($R^{2.3.2}$)$_2$—, —C($R^{2.3.2}$)$_2$N($R^{2.3.1}$)—, and —N($R^{2.3.1}$)C($R^{2.3.2}$)$_2$— and —C$_{1-4}$-alkylene-;

$R^{2.3.1}$ is independently selected from H, C$_{1-6}$-alkyl-, C$_{1-6}$-haloalkyl-; C$_{3-8}$-cycloalkyl-, HO—C$_{1-4}$-alkylene-, (C$_{1-4}$-alkyl)-O—C$_{1-4}$-alkylene-, H$_2$N—C$_{1-4}$-alkylene-, (C$_{1-4}$-alkyl)HN—C$_{1-4}$-alkylene- and (C$_{1-4}$-alkyl)$_2$N—C$_{1-4}$-alkylene-;

$R^{2.3.2}$ is independently selected from H, C$_{1-6}$-alkyl-, C$_{1-6}$-haloalkyl-; C$_{3-8}$-cycloalkyl-, HO—C$_{1-4}$-alkylene-, (C$_{1-4}$-alkyl)-O—C$_{1-4}$-alkylene-, H$_2$N—C$_{1-4}$-alkylene-, (C$_{1-4}$-alkyl)HN—C$_{1-4}$-alkylene- and (C$_{1-4}$-alkyl)$_2$N—C$_{1-4}$-alkylene-;

$R^{2.4}$ and $R^4$ are together selected from —N($R^{2.4.1}$)—, —C(O)N($R^{2.4.1}$)—, —N($R^{2.4.1}$)C(O)—, —S(O)$_2$N($R^{2.4.1}$)—, —N($R^{2.4.1}$)S(O)$_2$—, —C(O)—, —S(O)—, —S(O)$_2$—, —C($R^{2.4.2}$)=C($R^{2.4.2}$)—, —C=N—, —N=C—, —C($R^{2.4.2}$)$_2$N($R^{2.4.1}$)— and —N($R^{2.4.1}$)C($R^{2.4.2}$)$_2$—, —C$_{1-4}$-alkylene-; and $R^{2.4.1}$ is independently selected from H, C$_{1-6}$-alkyl-, C$_{1-6}$-haloalkyl-; C$_{3-8}$-cycloalkyl-, HO—C$_{1-4}$-alkylene-, (C$_{1-4}$-alkyl)-O—C$_{1-4}$-alkylene-, H$_2$N—C$_{1-4}$-alkylene-, (C$_{1-4}$-alkyl)HN—C$_{1-4}$-alkylene- and (C$_{1-4}$-alkyl)$_2$N—C$_{1-4}$-alkylene-;

$R^{2.4.2}$ is independently selected from H, C$_{1-6}$-alkyl-, C$_{1-6}$-haloalkyl-; C$_{3-8}$-cycloalkyl-, HO—C$_{1-4}$-alkylene-, (C$_{1-4}$-alkyl)-O—C$_{1-4}$-alkylene-, H$_2$N—C$_{1-4}$-alkylene-, (C$_{1-4}$-alkyl)HN—C$_{1-4}$-alkylene- and (C$_{1-4}$-alkyl)$_2$N—C$_{1-4}$-alkylene-;

$R^{2.5}$ and $R^4$ are together selected from —C($R^{2.5.1}$)=, =C($R^{2.5.1}$)—, —N=; and $R^{2.5.1}$ is independently selected from H, C$_{1-6}$-alkyl-, C$_{1-6}$-haloalkyl-; C$_{3-8}$ cycloalkyl, HO—C$_{1-4}$-alkylene-, (C$_{1-4}$-alkyl)-O—C$_{1-4}$-alkylene-, H$_2$N—C$_{1-4}$-alkylene-, (C$_{1-4}$-alkyl)HN—C$_{1-4}$-alkylene- and (C$_{1-4}$-alkyl)$_2$N—C$_{1-4}$-alkylene-;

$R^3$ is H or F;

$R^4$ is independently selected from F, Cl, phenyl-H$_2$C—O—, HO—, C$_{1-6}$-alkyl-, C$_{1-6}$-haloalkyl-, C$_{3-8}$-cycloalkyl-, C$_{1-6}$-alkyl-O—, C$_{1-6}$-haloalkyl-O—, C$_{1-6}$-alkyl-HN—, (C$_{1-6}$-alkyl)$_2$-HN—, C$_{1-6}$-alkyl-HN—C$_{1-4}$-alkylene- and (C$_{1-6}$-alkyl)$_2$-HN—C$_{1-4}$-alkylene-;

A is a bond or independently selected from —O—, —S—, —N($R^5$)—, —C(O)N($R^5$)—, —N($R^5$)C(O)—, —S(O)$_2$N($R^5$)—, —N($R^5$)S(O)$_2$—, —S(O)(=N$R^5$)—N($R^5$)—, —N($R^5$)(N$R^5$=)S(O)—, —S(=N$R^5$)$_2$—N($R^5$)—, —N($R^5$)(N$R^5$=)$_2$S—, —C($R^5$)=C($R^5$)—, C=C—, —C(O)O—, —OC(O)—, —C(O)—, —S(O)—, —S(O)$_2$—, —S(=N$R^5$)—, —S(O)(=N$R^5$)—, —S(=N$R^5$)$_2$—, —($R^5$)(O)S=N—, —($R^5$N=)(O)S—, and —N=(O)($R^5$)S—;

$R^5$ is independently selected from H, C$_{1-6}$-alkyl- and NC—;

or a salt thereof.

2. The method according to claim 1, wherein $R^1$ is $R^{1.a}$ and $R^{1.a}$ is independently selected from H, C$_{1-4}$-alkyl-, F and HO—.

3. The method according to claim 1, wherein $R^4$ is $R^{4.a}$ and $R^{4.a}$ is F, Cl, phenyl-H$_2$C—O—, HO—, C$_{1-4}$-alkyl-, C$_{1-4}$-haloalkyl-, C$_{3-6}$-cycloalkyl-, C$_{1-4}$-alkyl-O— and C$_{1-4}$-haloalkyl-O—.

4. The method according to claim 1, wherein $R^4$ is $R^{4.b}$ and $R^{4.b}$ is F.

5. The method according to claim 1, wherein A is $A^a$ and $A^a$ is a bond or independently selected from —O—, —C(O) N($R^5$)—, —N($R^5$)C(O)—, —S(O)$_2$N($R^5$)—, —N($R^5$) S(O)$_2$—, —C(O)O—, —OC(O)—, —C(O)—, —S(O)$_2$—, —($R^5$)(O)S=N—, —($R^5$N=)(O)S—, —N=(O)($R^5$)S— and $R^5$ is $R^{5.a}$ and $R^{5.a}$ is independently selected from H, C$_{1-4}$-alkyl- and NC—.

6. The method according to claim 1, wherein $R^2$ is $R^{2.1}$ and $R^{2.1}$ is $R^{2.1.a}$ and $R^{2.1.a}$ is selected from H, halogen, NC—, O=, HO—, H-A-, H-A-C$_{1-4}$-alkylene-, $R^{2.1.1}$-A-, C$_{1-4}$-alkyl-A-, C$_{3-6}$-cycloalkyl-A-, C$_{1-4}$-haloalkyl-A-, $R^{2.1.1}$—C$_{1-4}$-alkylene-A-, C$_{1-4}$-alkyl-A-C$_{1-4}$-alkylene-, C$_{3-6}$-cycloalkyl-A-C$_{1-4}$-alkylene-, C$_{1-4}$-haloalkyl-A-C$_{1-4}$-alkylene-, $R^{2.1.1}$—C$_{1-4}$-alkylene-A-C$_{1-4}$-alkylene-, $R^{2.1.1}$-A-C$_{1-4}$-alkylene-, HO—C$_{1-4}$-alkylene-A-, HO—C$_{1-4}$-alkylene-A-C$_{1-4}$-alkylene-, C$_{1-4}$-alkyl-O—C$_{1-4}$-alkylene-A- and C$_{1-4}$-alkyl-O—C$_{1-4}$-alkylene-A-C$_{1-4}$-alkylene-; and $R^{2.1.1}$ is $R^{2.1.1.a}$ and $R^{2.1.1.a}$ is selected from aryl-, optionally substituted independently from each other with one, two or three residues independently selected from $R^{2.1.1.1}$;

C$_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and C$_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from halogen, HO—, O=, C$_{1-4}$-alkyl-, C$_{1-4}$-alkyl-O—, C$_{1-4}$-haloalkyl-, C$_{1-4}$-haloalkyl-O— and C$_{3-6}$-cycloalkyl-; and $R^{2.1.1.2}$ is independently selected from O=, C$_{1-4}$-alkyl-, C$_{1-4}$-haloalkyl-; C$_{3-6}$-cycloalkyl-, C$_{1-4}$-alkyl-O—C$_{1-4}$-alkyl, H(O)C—, C$_{1-4}$-alkyl-(O)C—, tetrahydrofuranylmethyl- and tetrahydropyranylmethyl.

7. The method according to claim 1, wherein $R^2$ is $R^{2.d}$ and $R^{2.d}$ is phenyl; optionally substituted with one, two or three residues independently selected from $R^{2.1}$ and $R^{2.1}$ is $R^{2.1.a}$ and $R^{2.1.a}$ is selected from H, halogen, NC—, O=, HO—, H-A-, H-A-C$_{1-4}$-alkylene-, $R^{2.1.1}$-A-, C$_{1-4}$-alkyl-A-, C$_{3-6}$-cycloalkyl-A-, C$_{1-4}$-haloalkyl-A-, $R^{2.1.1}$—C$_{1-4}$-alkylene-A-, C$_{1-4}$-alkyl-A-C$_{1-4}$-alkylene-, C$_{3-6}$-cycloalkyl-A-C$_{1-4}$-alkylene-, C$_{1-4}$-haloalkyl-A-C$_{1-4}$-alkylene-, $R^{2.1.1}$—C$_{1-4}$-alkylene-A-C$_{1-4}$-alkylene-, $R^{2.1.1}$-A-C$_{1-4}$-alkylene-, HO—C$_{1-4}$-alkylene-A-, HO—C$_{1-4}$-alkylene-A-C$_{1-4}$-alkylene-, C$_{1-4}$-alkyl-O—C$_{1-4}$-alkylene-A- and C$_{1-4}$-alkyl-O—C$_{1-4}$-alkylene-A-C$_{1-4}$-alkylene-; and $R^{2.1.1}$ is $R^{2.1.1.a}$ and $R^{2.1.1.a}$ is selected from aryl-, optionally substituted independently from each other with one, two or three residues independently selected from $R^{2.1.1.1}$;

C$_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl.

8. The method according to claim 1, wherein $R^2$ is $R^{2.j}$ and $R^{2.j}$ is selected from

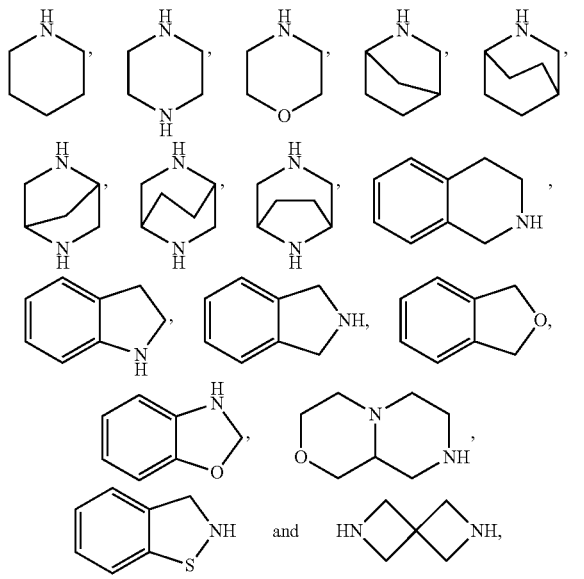

wherein carbon atoms of the ring are optionally and independently from each other substituted with one, two or three $R^{2.1}$; wherein possibly available nitrogen atoms of the ring are optionally and independently from each other substituted with $R^{2.2}$; and $R^{2.1}$ is $R^{2.1.a}$ and $R^{2.1.a}$ is selected from H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from aryl-, optionally substituted independently from each other with one, two or three residues independently selected from $R^{2.1.1.1}$;

$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from halogen, HO—, O=, $C_{1-4}$-alkyl-, $C_{1-4}$-alkyl-O—, $C_{1-4}$-haloalkyl- and $C_{1-4}$-haloalkyl-O—, $C_{3-6}$-cycloalkyl-; and $R^{2.1.1.2}$ is independently selected from O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl; and $R^{2.1.2}$ is $R^{2.2.a}$ and $R^{2.2.a}$ is independently selected from H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$—, $C_{1-4}$-alkyl-C(O)— and $R^{2.1.1}$-A-.

9. The method according to claim 1, wherein $R^2$ is $R^{2.m}$ and $R^{2.m}$ is together with $R^4$ and two adjacent carbon atoms of the phenyl ring a 5- or 6-membered aryl or heteroaryl, containing one, two or three heteroatoms independently selected from S, S(O), S(O)$_2$, O and N, wherein carbon atoms of the ring are optionally and independently from each other substituted with one, two or three $R^{2.1}$, wherein possibly available nitrogen atoms of the ring are optionally and independently from each other substituted with one, two or three $R^{2.2}$; and $R^{2.1}$ is $R^{2.1.a}$ and $R^{2.1.a}$ is selected from H, halogen, NC—, O=, HO—, H-A-, H-A-$C_{1-4}$-alkylene-, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from aryl-, optionally substituted independently from each other with one, two or three residues independently selected from $R^{2.1.1.1}$;

$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$;

wherein nitrogen atoms of the ring are optionally and independently from each other substituted with one, two or three $R^{2.1.1.2}$; and $R^{2.1.1.1}$ is independently selected from halogen, HO—, O=, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$—, $C_{1-4}$-alkyl-C(O)— and $R^{2.1.1}$-A-.

10. The method according to claim 1, wherein $R^2$ is $R^{2.n}$ and $R^{2.n}$ is selected from aryl-, pyrazole, thiophene, furane; wherein carbon atoms of the ring are optionally and independently from each other substituted with one, two, three or four $R^{2.1}$; wherein possibly available nitrogen atoms of the ring are optionally and independently from each other substituted with $R^{2.2}$; wherein a carbon atom of the ring is optionally substituted with one $R^{2.3}$; a nitrogen atom of the ring is optionally substituted with one $R^{2.4}$; or $R^{2.n}$ is selected from

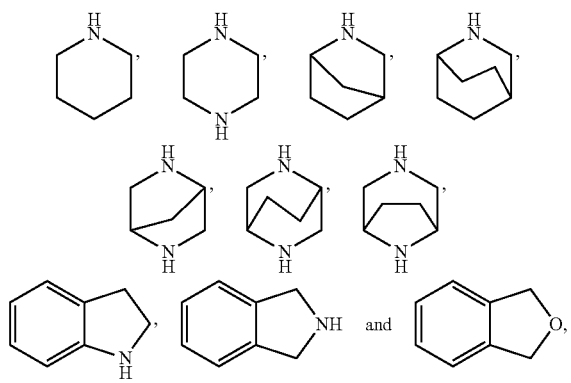

wherein carbon atoms of the ring are optionally and independently from each other substituted with one, two, three or four $R^{2.1}$; wherein possibly available nitrogen atoms of the ring are optionally and independently from each other substituted with $R^{2.2}$; wherein a carbon atom of the ring is optionally substituted with one $R^{2.3}$ or one $R^{2.5}$; a nitrogen atom of the ring is optionally substituted with one $R^{2.4}$; and $R^{2.1}$ is $R^{2.1.a}$ and $R^{2.1.a}$ is selected from H, halogen, NC—, O=, HO—, H-A-, H-A-$C_{1-4}$-alkylene-, $R^{2.1.1}$-A-, $C_{1-4}$-alkyl-A, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ is selected from aryl-, optionally substituted independently from each other with one, two or three residues independently selected from $R^{2.1.1.1}$;

$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $C_{5-10}$-heterocyclyl-, containing one, two, three or four heteroatoms selected independently from S, S(O), S(O)$_2$, O and N and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl; and $R^{2.2}$ is $R^{2.2.a}$ and $R^{2.2.a}$ is independently selected from H-A-$C_{1-4}$-alkylene-, $C_{3-6}$-cycloalkyl-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$-A-$C_{1-4}$-alkylene-, $C_{1-4}$-alkyl-S(O)$_2$—, $C_{1-4}$-alkyl-C(O)— and $R^{2.1.1}$-A-; and $R^{2.3}$ is together with $R^4$ a group $R^{2.3.a}$ and $R^{2.3.a}$ is selected from —O—, —S—, —N($R^{2.3.1}$)—, —C(O)N($R^{2.3.1}$)—, —N($R^{2.3.1}$)C(O)—, —S(O)$_2$N($R^{2.3.1}$)—, —N($R^{2.3.1}$)S(O)$_2$—, —C(O)O—, —OC(O)—, —C(O)—, —S(O)—, —S(O)$_2$—, —C($R^{2.3.2}$)=C($R^{2.3.2}$)—, —C=N—, —N=C—, —C($R^{2.3.2}$)$_2$—O—, —O—C($R^{2.3.2}$)$_2$—, —C($R^{2.3.2}$)$_2$N($R^{2.3.1}$)—, —N($R^{2.3.1}$)C($R^{2.3.2}$)$_2$— and —$C_{1-4}$-alkylene-; and $R^{2.3.1}$ is independently selected from H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.3.2}$ is independently selected from H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-; and $R^{2.4}$ is together with $R^4$ a group $R^{2.4.a}$ and $R^{2.4.a}$ is selected from —N($R^{2.4.1}$)—, —C(O)N($R^{2.4.1}$)—, —N($R^{2.4.1}$)C(O)—, —S(O)$_2$N($R^{2.4.1}$)—, —N($R^{2.4.1}$)S(O)$_2$—, —C(O)—, —S(O)—, —S(O)$_2$—, —C($R^{2.4.2}$)=C($R^{2.4.2}$)—, —C=N—, —N=C—, —C($R^{2.4.2}$)$_2$N($R^{2.4.1}$)—, and —N($R^{2.4.1}$)C($R^{2.4.2}$)$_2$—, —$C_{1-4}$-alkylene-; and $R^{2.4.1}$ is independently selected from H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-;

$R^{2.4.2}$ is independently selected from H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, H$_2$N—$C_{1-4}$-alkylene-, ($C_{1-4}$-alkyl)HN—$C_{1-4}$-alkylene- and ($C_{1-4}$-alkyl)$_2$N—$C_{1-4}$-alkylene-; and $R^{2.5}$ is together with $R^4$ a group $R^{2.5.a}$ and $R^{2.5.a}$ is selected from $-C(R^{2.5.1})=$, $=C(R^{2.5.1})-$ and $-N=$; and $R^{2.5.1}$ is independently selected from H, $C_{1-4}$-alkyl-, $C_{1-4}$-haloalkyl-, $C_{3-6}$-cycloalkyl-, HO—$C_{1-4}$-alkylene-, ($C_{1-4}$-alkyl)-O—$C_{1-4}$-alkylene-, $H_2N$—$C_{1-4}$-alkylene-, ($C_{1-4}$-alkyl)HN—$C_{1-4}$-alkylene- and ($C_{1-4}$-alkyl)$_2$N—$C_{1-4}$-alkylene-.

11. The method according to claim 1, wherein $R^1$ is $R^{1.b}$ and $R^{1.b}$ is H;

$R^2$ is $R^{2.q}$ and $R^{2.q}$ is selected from among the substituents (a1) to (q1)

wherein carbon atoms of the ring are optionally and independently from each other substituted with one, two, three or four $R^{2.1}$; wherein possibly available nitrogen atoms of the ring are optionally and independently from each other are substituted with $R^{2.2}$;

or a salt thereof.

12. The method according to claim 1, wherein $R^2$ is $R^{2.s}$ and $R^{2.s}$ is Phenyl-$R^{2.3}$, wherein the phenyl ring is optionally substituted with one or two residues $R^{2.1}$, wherein $R^{2.1}$ is $R^{2.1.a}$ and $R^{2.1.a}$ is selected from H, halogen, NC—, O=, HO—, H-A-, H-A-$C_{1-4}$-alkylene, $R^{2.1.1}$-A-, $C_{1-4}$-alkyl-A-, $C_{3-6}$-cycloalkyl-A-, $C_{1-4}$-haloalkyl-A-, $R^{2.1.1}$—$C_{1-4}$-alkylene-A-, $C_{1-4}$-alkyl-A-$C_{1-4}$-alkylene-, $C_{3-6}$-cycloalkyl-A-$C_{1-4}$-alkylene-, $C_{1-4}$-haloalkyl-A-$C_{1-4}$-alkylene-, $R^{2.1.1}$—$C_{1-4}$-alkylene-A-$C_{1-4}$-alkylene-, $R^{2.1.1}$-A-$C_{1-4}$-alkylene-, HO—$C_{1-4}$-alkylene-A-, HO—$C_{1-4}$-alkylene-A-$C_{1-4}$-alkylene-, $C_{1-4}$-alkyl-O—$C_{1-4}$-alkylene-A- and $C_{1-4}$-alkyl-O—$C_{1-4}$-alkylene-A-$C_{1-4}$-alkylene-; and $R^{2.1.1}$ is $R^{2.1.1.a}$ and $R^{2.1.1.a}$ selected from aryl-, optionally substituted independently from each other with one, two or three residues independently selected from $R^{2.1.1.1}$;

$C_{5-10}$-heteroaryl-, containing one, two, three or four heteroatoms selected independently from S, S(O), S(O)$_2$, O and N, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$;

$C_{5-10}$-heterocyclyl-, containing one, two, three or four heteroatoms selected independently from S, S(O), S(O)$_2$, O and N, and the ring is fully or partially saturated, wherein carbon atoms of the ring are optionally and independently from each other substituted with one, two or three $R^{2.1.1.1}$; wherein nitrogen atoms of the ring are optionally and independently from each other substituted with one, two or three $R^{2.1.1.2}$; and $R^{2.1.1.1}$ is independently selected from halogen, HO—, O=, $C_{1-4}$-alkyl-, $C_{1-4}$-alkyl-O—, $C_{1-4}$-haloalkyl-, $C_{1-4}$-haloalkyl-O— and $C_{3-6}$-cycloalkyl-; and $R^{2.1.1.2}$ is independently selected from O=, $C_{1-4}$-alkyl-, $C_{1-4}$-haloalkyl-; $C_{3-6}$-cycloalkyl-, $C_{1-4}$-alkyl-O—$C_{1-4}$-alkyl-, H(O)C—, $C_{1-4}$-alkyl-(O)C—, tetrahydrofuranylmethyl- and tetrahydropyranylmethyl;

and $R^{2.s}$ and $R^4$ together denote a group (r1),

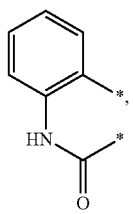

(r1)

wherein the N-atom is optionally substituted with —$R^{2.2}$, wherein $R^{2.2}$ is independently selected from H-A-$C_{1-6}$-alkylene-, $C_{3-8}$-cycloalkyl-, $C_{1-6}$-alkyl-A-$C_{1-6}$-alkylene-, $C_{3-8}$-cycloalkyl-A-$C_{1-6}$-alkylene-, $C_{1-6}$-haloalkyl-A-$C_{1-6}$-alkylene-, $R^{2.1.1}$-A-$C_{1-6}$-alkylene-, $C_{1-6}$-alkyl-S(O)$_2$—, $C_{1-6}$-alkyl-C(O)— and $R^{2.1.1}$-A-;

or a salt thereof.

13. A method of treating pulmonary emphysema comprising administering to a patient a therapeutically effective amount of a compound of formula 1'

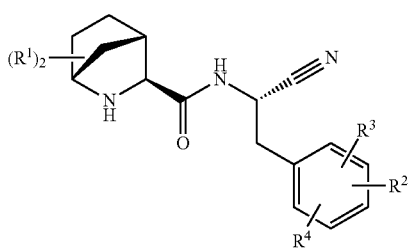

1' wherein $R^1$, $R^2$, $R^3$ and $R^4$ have the meaning of claim 1, or a pharmaceutically acceptable salt thereof.

14. The method according to claim 1 comprising administering a pharmaceutical composition comprising a compound of formula 1 or a pharmaceutically acceptable salt thereof.

15. The method according to claim 14 wherein the pharmaceutical composition further comprises a pharmaceutically active compound selected from the group consisting of betamimetics, anticholinergics, corticosteroids, PDE4-inhibitors, LTD4-antagonists, EGFR-inhibitors, CRTH2 inhibitors, 5-LO-inhibitors, Histamine receptor antagonists, CCR9 antagonists and SYK-inhibitors, NE-inhibitors, MMP9 inhibitors and MMP12 inhibitors, or combinations of two or three the pharmaceutically active compound.

16. The method according to claim 1 wherein the compound is

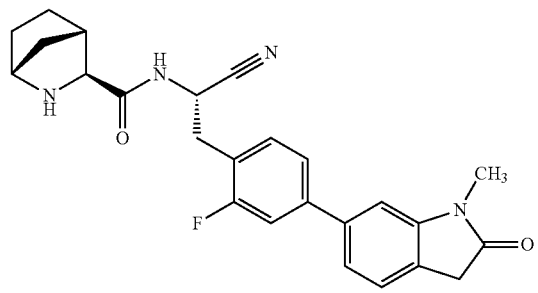 [SMILES: CN1C(=O)Cc2ccc(-c3ccc(C[C@@H](C#N)NC(=O)[C@H]4N[C@@H]5CC[C@H]4C5)c(F)c3)cc21]

or a pharmaceutically acceptable salt thereof.

17. The method according to claim 1 wherein the compound is

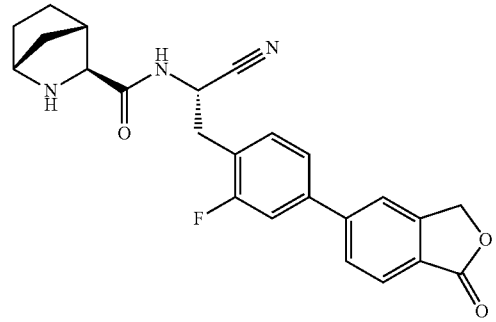 [SMILES: N#C[C@H](Cc1ccc(-c2ccc3c(c2)COC3=O)cc1F)NC(=O)[C@H]1N[C@@H]2CC[C@H]1C2]

or a pharmaceutically acceptable salt thereof.

18. The method according to claim 1 wherein the compound is

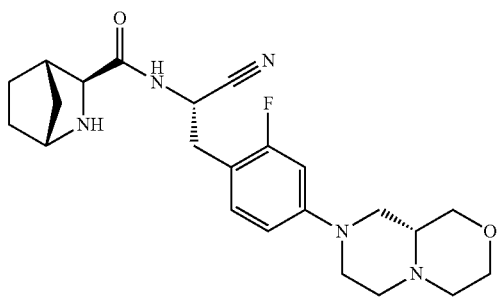 [SMILES: N#C[C@H](Cc1ccc(N2CCN3CCOC[C@H]3C2)cc1F)NC(=O)[C@H]1N[C@@H]2CC[C@H]1C2]

or a pharmaceutically acceptable salt thereof.

19. The method according to claim 1 wherein the compound is

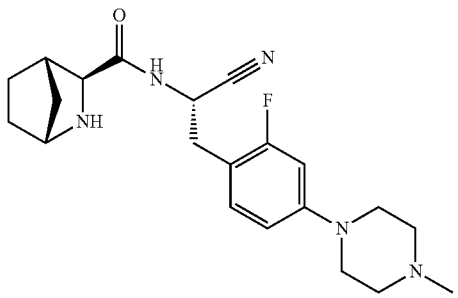 [SMILES: CN1CCN(c2ccc(C[C@@H](C#N)NC(=O)[C@H]3N[C@@H]4CC[C@H]3C4)c(F)c2)CC1]

or a pharmaceutically acceptable salt thereof.

20. The method according to claim 1 wherein the compound is

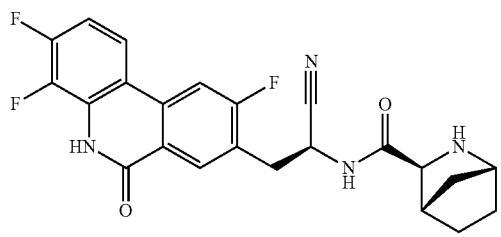 [SMILES: N#C[C@H](Cc1cc2c(=O)[nH]c3c(F)c(F)ccc3c2cc1F)NC(=O)[C@H]1N[C@@H]2CC[C@H]1C2]

or a pharmaceutically acceptable salt thereof.

21. The method according to claim 1 wherein the compound is

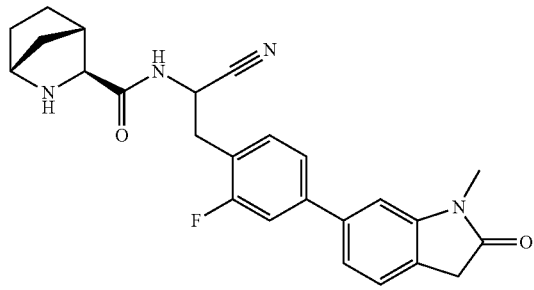 [SMILES: CN1C(=O)Cc2ccc(-c3ccc(CC(C#N)NC(=O)[C@H]4N[C@@H]5CC[C@H]4C5)c(F)c3)cc21]

or a pharmaceutically acceptable salt thereof.

22. The method according to claim 1 wherein the compound is

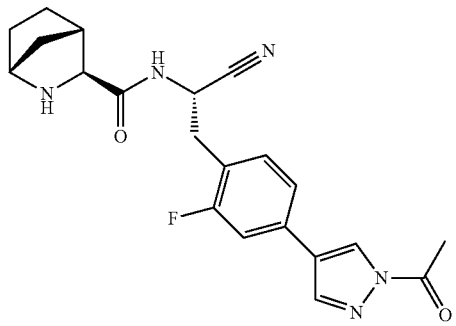 [SMILES: CC(=O)n1cc(-c2ccc(C[C@@H](C#N)NC(=O)[C@H]3N[C@@H]4CC[C@H]3C4)c(F)c2)cn1]

or a pharmaceutically acceptable salt thereof.

23. The method according to claim 1 wherein the compound is

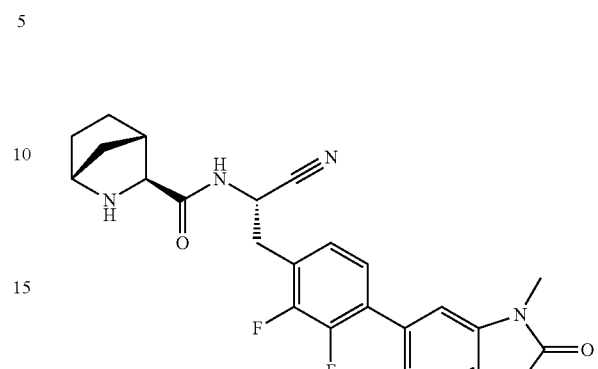

or a pharmaceutically acceptable salt thereof.

24. The method according to claim 1 wherein the compound is

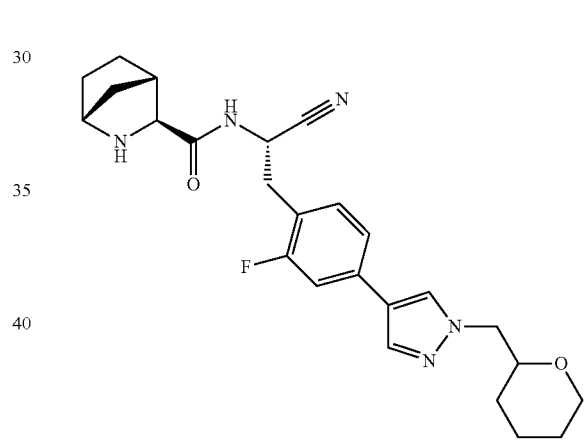

or a pharmaceutically acceptable salt thereof.

25. The method according to claim 1 wherein the compound is

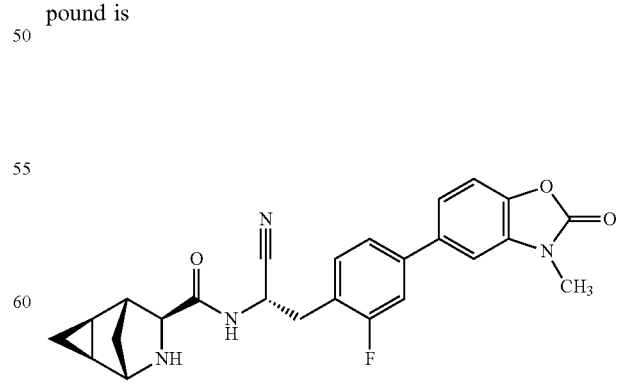

or a pharmaceutically acceptable salt thereof.

* * * * *